United States Patent
Ajemba et al.

(10) Patent No.: US 11,311,217 B2
(45) Date of Patent: Apr. 26, 2022

(54) METHODS, SYSTEMS, AND DEVICES FOR CALIBRATION AND OPTIMIZATION OF GLUCOSE SENSORS AND SENSOR OUTPUT

(71) Applicant: MEDTRONIC MINIMED, INC., Northridge, CA (US)

(72) Inventors: Peter Ajemba, Canyon Country, CA (US); Keith Nogueira, Mission Hills, CA (US); Brian T. Kannard, Northridge, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 895 days.

(21) Appl. No.: 16/117,617

(22) Filed: Aug. 30, 2018

(65) Prior Publication Data

US 2019/0076067 A1 Mar. 14, 2019

Related U.S. Application Data

(60) Provisional application No. 62/558,248, filed on Sep. 13, 2017.

(51) Int. Cl.
*A61B 5/1495* (2006.01)
*A61B 5/145* (2006.01)
(Continued)

(52) U.S. Cl.
CPC .......... *A61B 5/1495* (2013.01); *A61B 5/1468* (2013.01); *A61B 5/14532* (2013.01);
(Continued)

(58) Field of Classification Search
None
See application file for complete search history.

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

| JP | 2017-504008 A | 2/2017 |
| WO | 2010/065067 A1 | 6/2010 |
| WO | 2017/116503 A1 | 7/2017 |

OTHER PUBLICATIONS

Patent Cooperation Treaty International Searching Authority, "Invitation to Pay Additional Fees and, Where Applicable, Protest Fee", re application PCT/US2018/049190 of Medtronic Minimed, Inc. dated Dec. 10, 2018; 18 pages.

(Continued)

*Primary Examiner* — Jay B Shah
(74) *Attorney, Agent, or Firm* — Carter, DeLuca & Farrell LLP

(57) ABSTRACT

A continuous glucose monitoring system may utilize externally sourced information regarding the physiological state and ambient environment of its user for externally calibrating sensor glucose measurements. Externally sourced factory calibration information may be utilized, where the information is generated by comparing metrics obtained from the data used to generate the sensor's glucose sensing algorithm to similar data obtained from each batch of sensors to be used with the algorithm in the future. The output sensor glucose value of a glucose sensor may also be estimated by analytically optimizing input sensor signals to accurately correct for changes in sensitivity, run-in time, glucose current dips, and other variable sensor wear effects. Correction actors, fusion algorithms, EIS, and advanced ASICs may be used to implement the foregoing, thereby achieving the goal of improved accuracy and reliability (Continued)

without the need for blood-glucose calibration, and providing a calibration-free, or near calibration-free, sensor.

15 Claims, 160 Drawing Sheets

(51) Int. Cl.
| | |
|---|---|
| A61B 5/00 | (2006.01) |
| G06N 5/02 | (2006.01) |
| G01N 27/02 | (2006.01) |
| A61B 5/1468 | (2006.01) |
| A61B 5/1455 | (2006.01) |
| A61B 5/1486 | (2006.01) |
| G16H 50/30 | (2018.01) |
| G16H 20/17 | (2018.01) |
| G16H 50/70 | (2018.01) |
| G16H 40/40 | (2018.01) |
| A61B 5/0205 | (2006.01) |
| A61B 5/021 | (2006.01) |
| A61B 5/024 | (2006.01) |
| A61B 5/11 | (2006.01) |

(52) U.S. Cl.
CPC .......... *A61B 5/14865* (2013.01); *A61B 5/686* (2013.01); *A61B 5/6849* (2013.01); *G01N 27/026* (2013.01); *G06N 5/022* (2013.01); *G16H 20/17* (2018.01); *G16H 40/40* (2018.01); *G16H 50/30* (2018.01); *G16H 50/70* (2018.01); *A61B 5/0075* (2013.01); *A61B 5/021* (2013.01); *A61B 5/024* (2013.01); *A61B 5/02055* (2013.01); *A61B 5/1118* (2013.01); *A61B 5/1455* (2013.01); *A61B 5/14546* (2013.01); *A61B 5/7203* (2013.01); *A61B 5/7221* (2013.01); *A61B 5/7267* (2013.01); *A61B 5/742* (2013.01); *A61B 2505/07* (2013.01); *A61B 2560/0223* (2013.01); *A61B 2560/0252* (2013.01); *A61B 2560/0257* (2013.01); *A61B 2562/028* (2013.01); *A61B 2562/029* (2013.01); *A61B 2562/164* (2013.01)

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 2,942,844 A1 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0160861 A1 | 6/2010 | Causey, III et al. |
| 2012/0262298 A1 | 10/2012 | Bohm et al. |
| 2014/0184422 A1 | 7/2014 | Mensinger et al. |
| 2015/0164387 A1* | 6/2015 | Varsavsky ............ G01N 27/026 702/182 |

OTHER PUBLICATIONS

Patent Cooperation Treaty International Searching Authority, "Notification of Transmittal of the International Search Report and the Written Opinion of the International Searching Authority, or the Declaration", re application PCT/US2018/049190 of Medtronic Minimed, Inc. dated Feb. 1, 2019; 22 pages.

Japanese Patent Office, "Notice of Reasons for Refusal" re Japanese Patent Application No. 2019-563152, dated: Nov. 19, 2020, 4 pages.

* cited by examiner

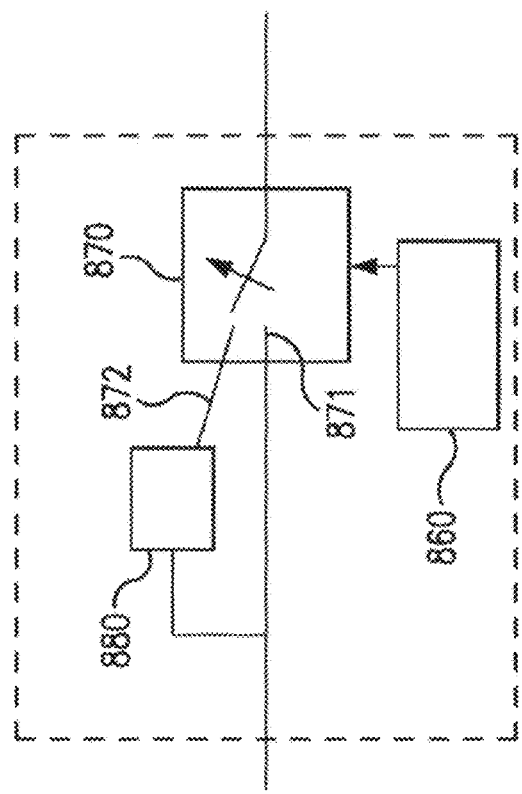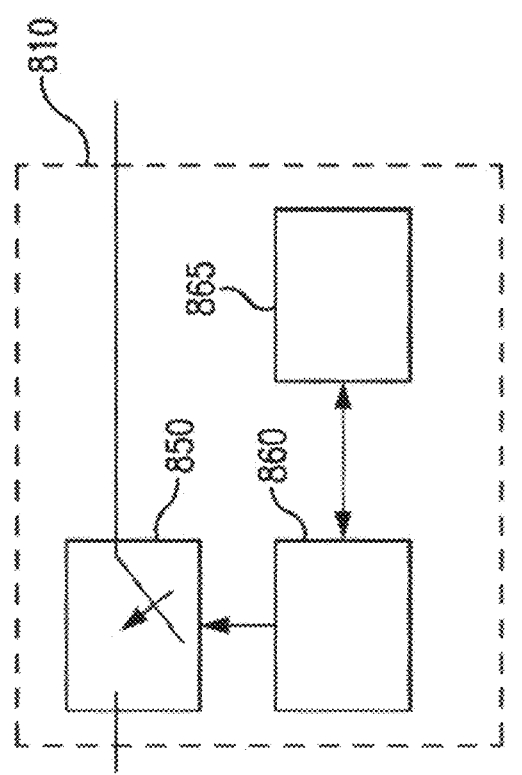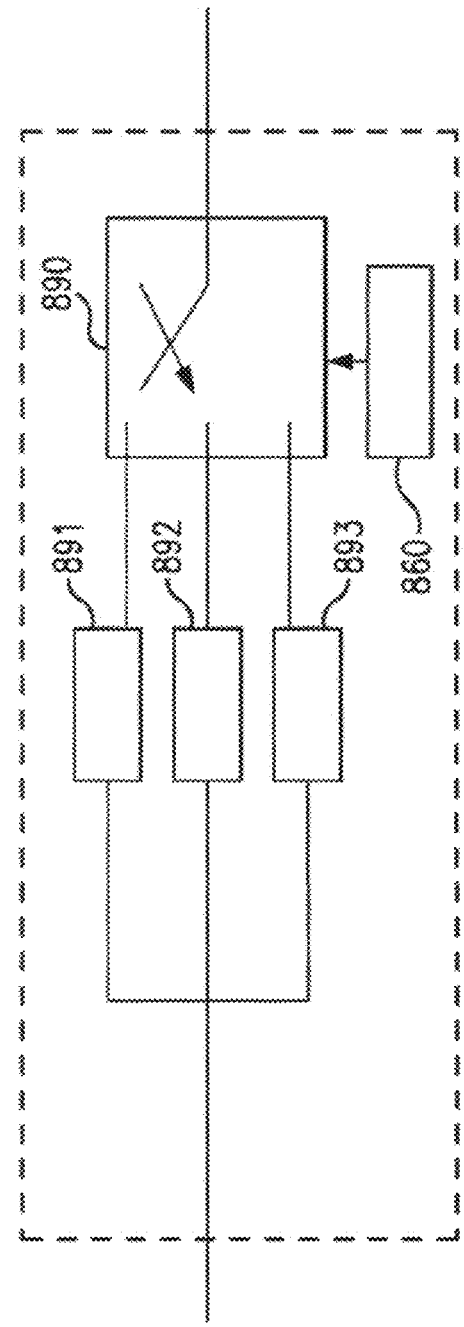

Relationship to Nyquist Plots
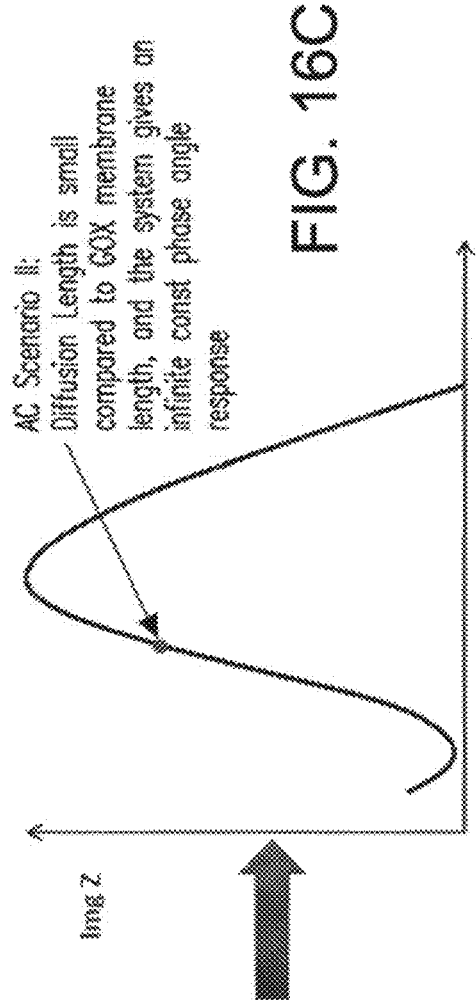
AC Scenario II: Low Diffusivity
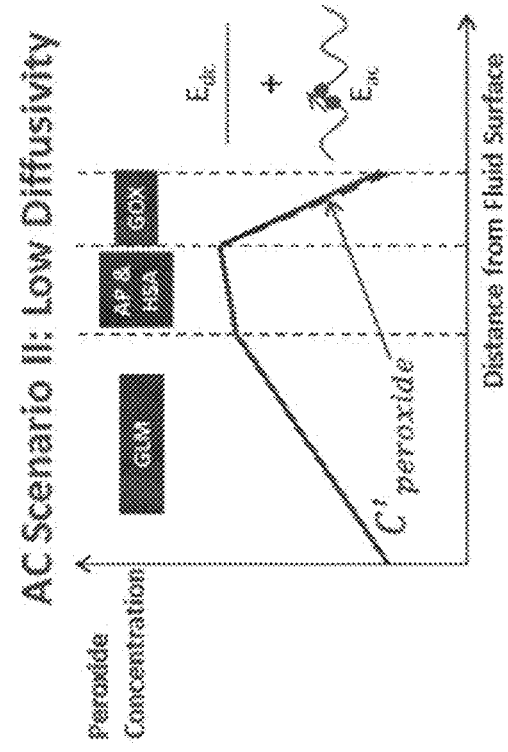
AC Scenario II: Diffusion Length is small compared to GOX membrane length, and the system gives an infinite const phase angle response
FIG. 16C
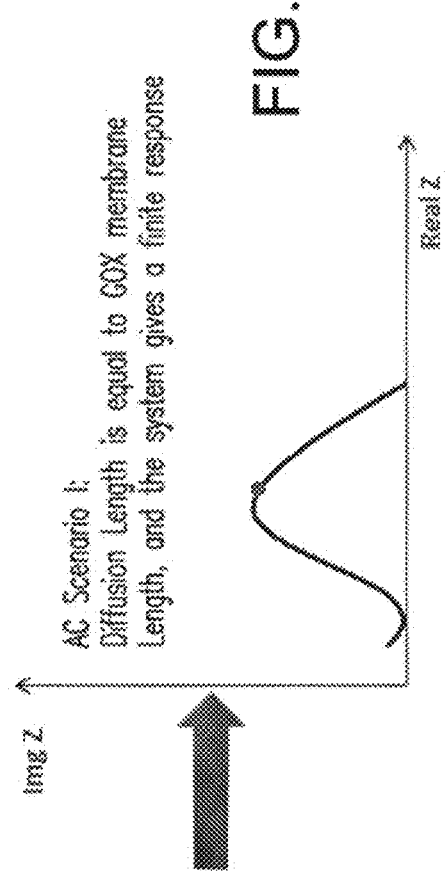
AC Scenario I: High Diffusivity
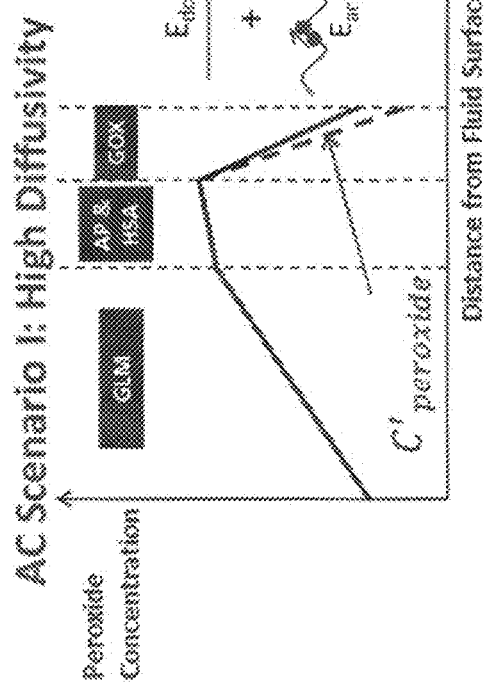
AC Scenario I: Diffusion Length is equal to GOX membrane Length, and the system gives a finite response
FIG. 16D

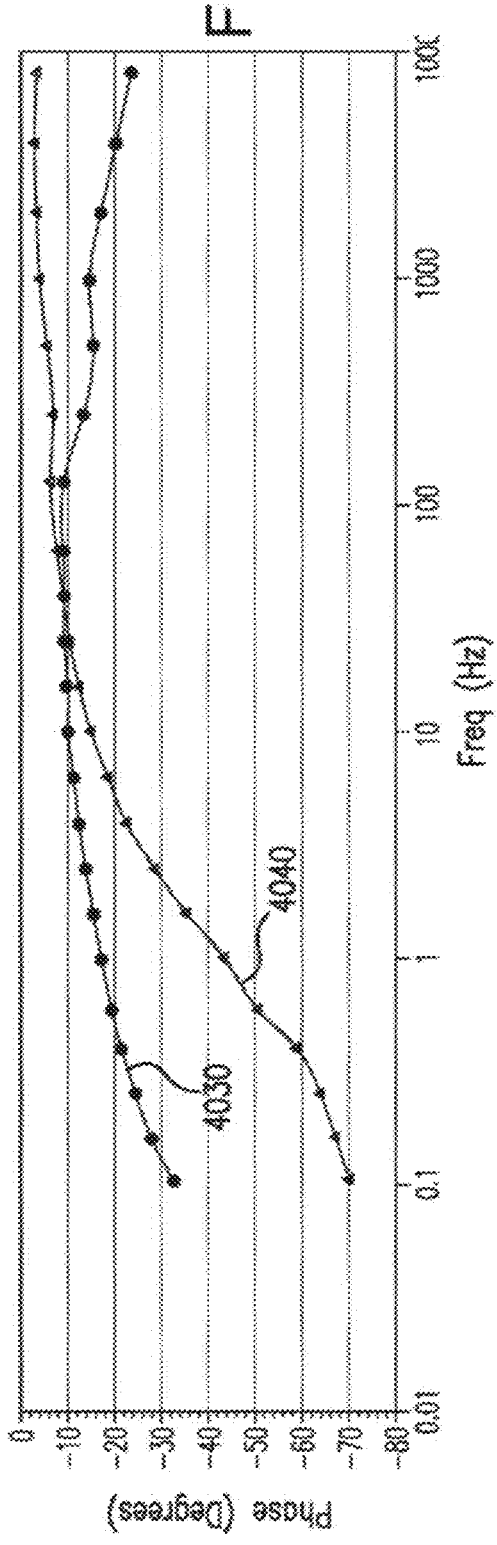
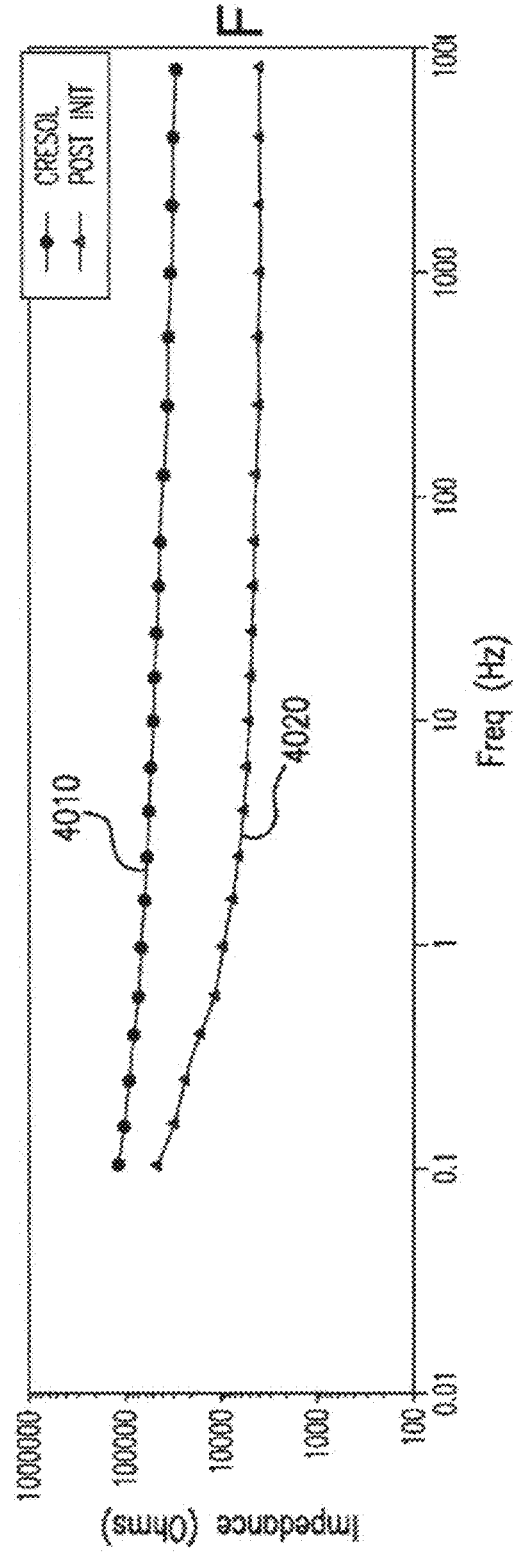

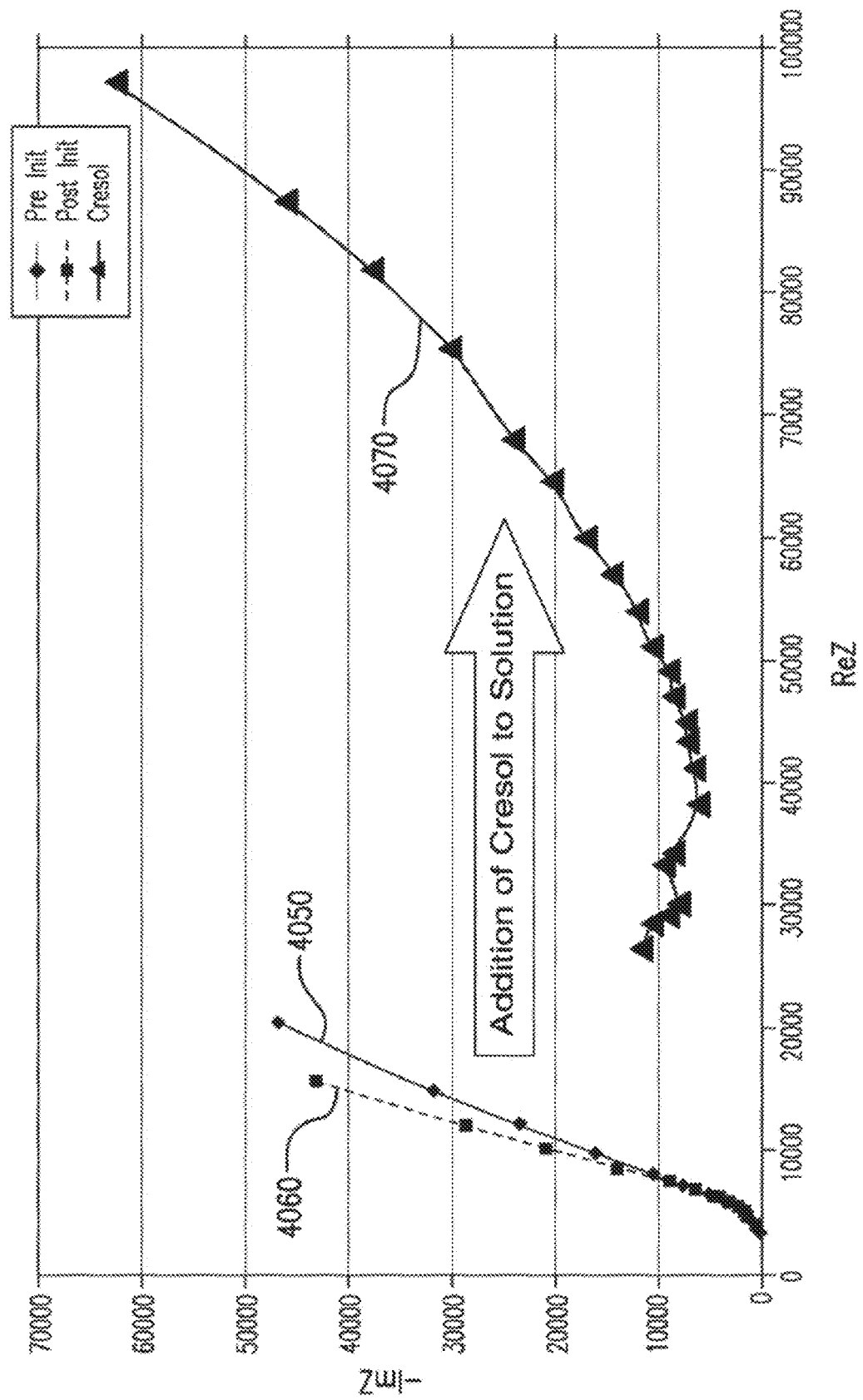

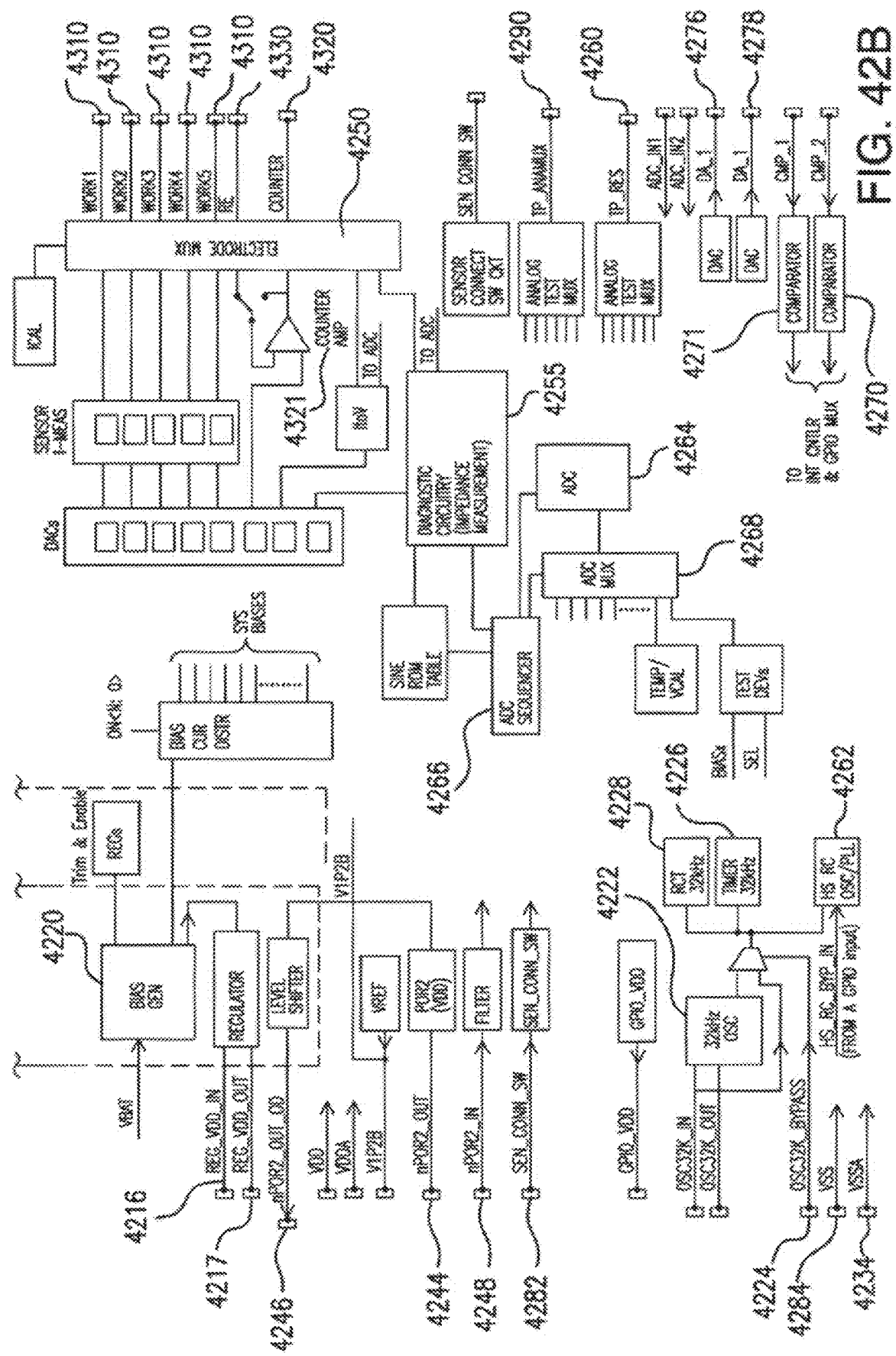

POTENTIOSTAT CONFIGURATION

FIG. 67A
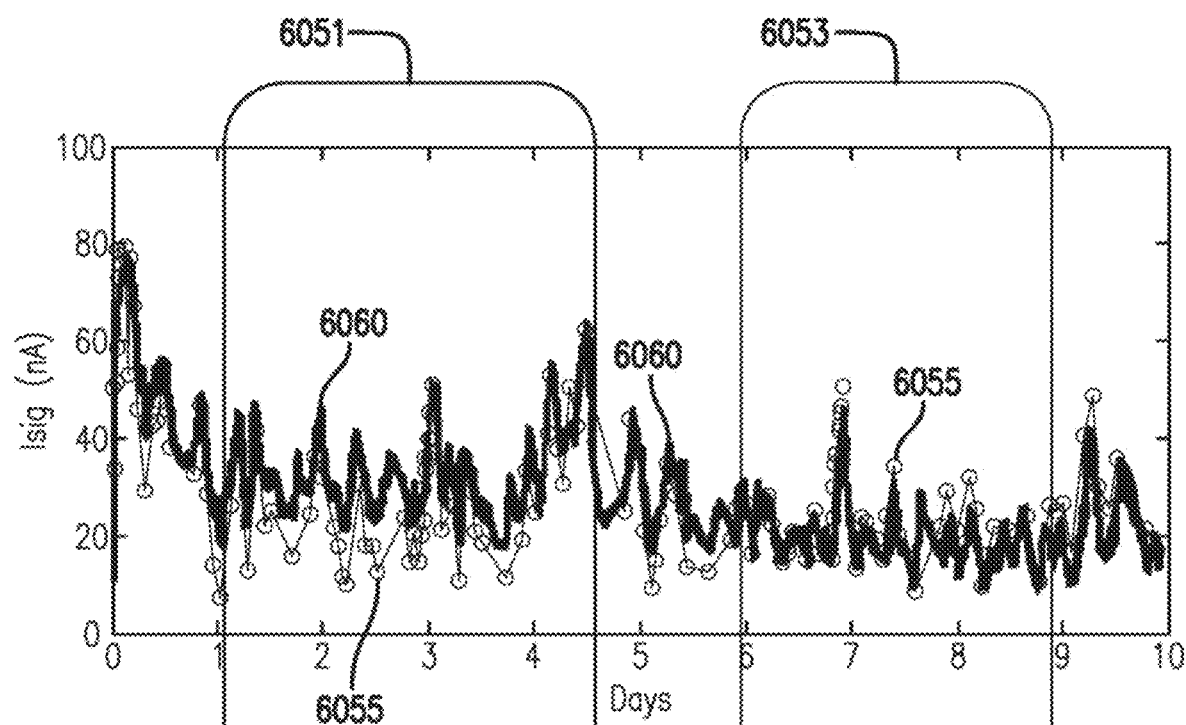
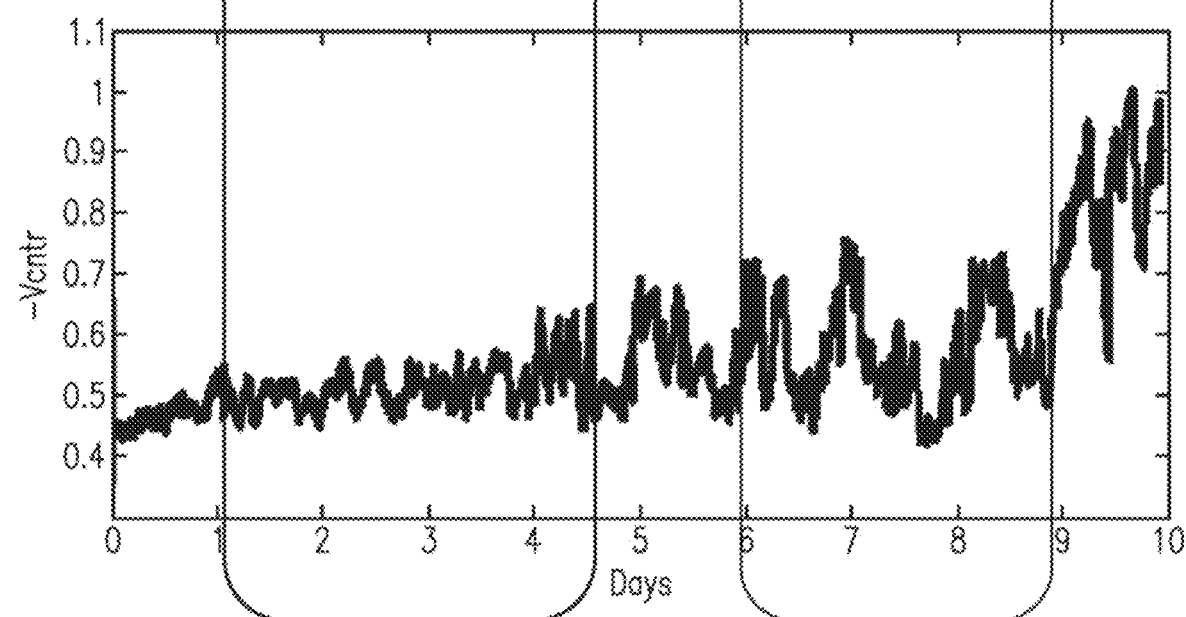
FIG. 67B

\* MARD over all valid BGs in first ~8 hours

| First Calibration Time | No adjustment | With adjustment | With Modified adjustment | Approx No. of eval points |
|---|---|---|---|---|
| 1 hour | 22.23 | 16.98 | 15.89 | 1380 |
| 1.5 hours | 17.83 | 15.26 | 14.83 | 1100 |
| 2 hours | 19.34 | 15.42 | 16.01 | 795 |

FIG. 91A

\* Median ARD over all valid BGs in first ~8 hours

| First Calibration Time | No adjustment | With adjustment | With Modified adjustment | Approx No. of eval points |
|---|---|---|---|---|
| 1 hour | 15.15 | 13.68 | 11.87 | 1380 |
| 1.5 hours | 10.71 | 10.95 | 9.96 | 1100 |
| 2 hours | 11.98 | 10.00 | 10.09 | 795 |

FIG. 91B

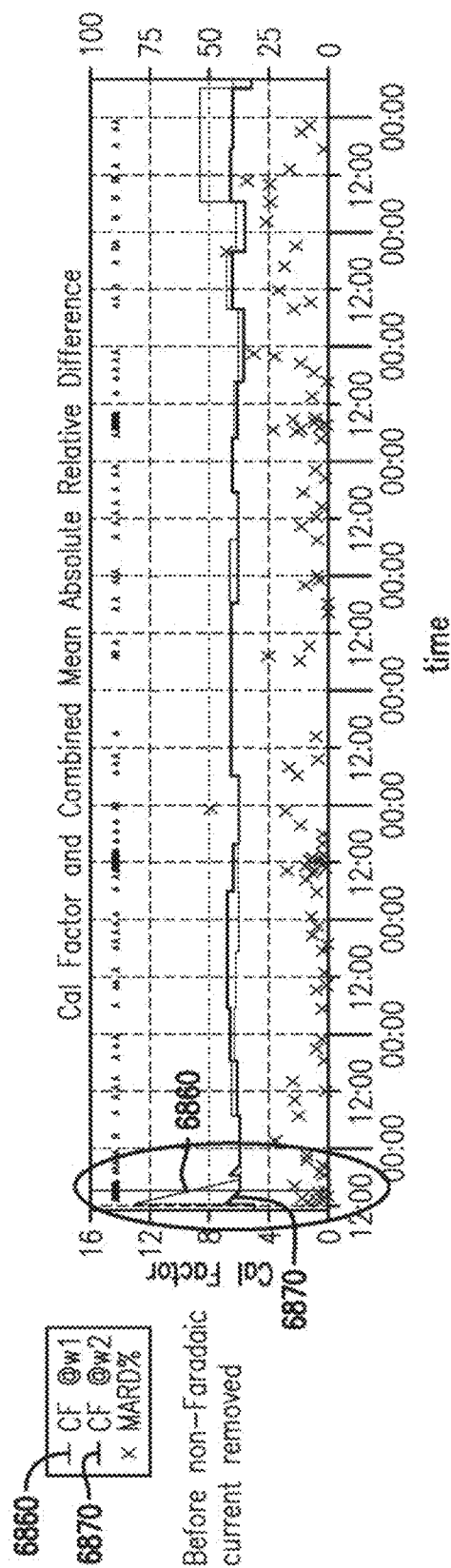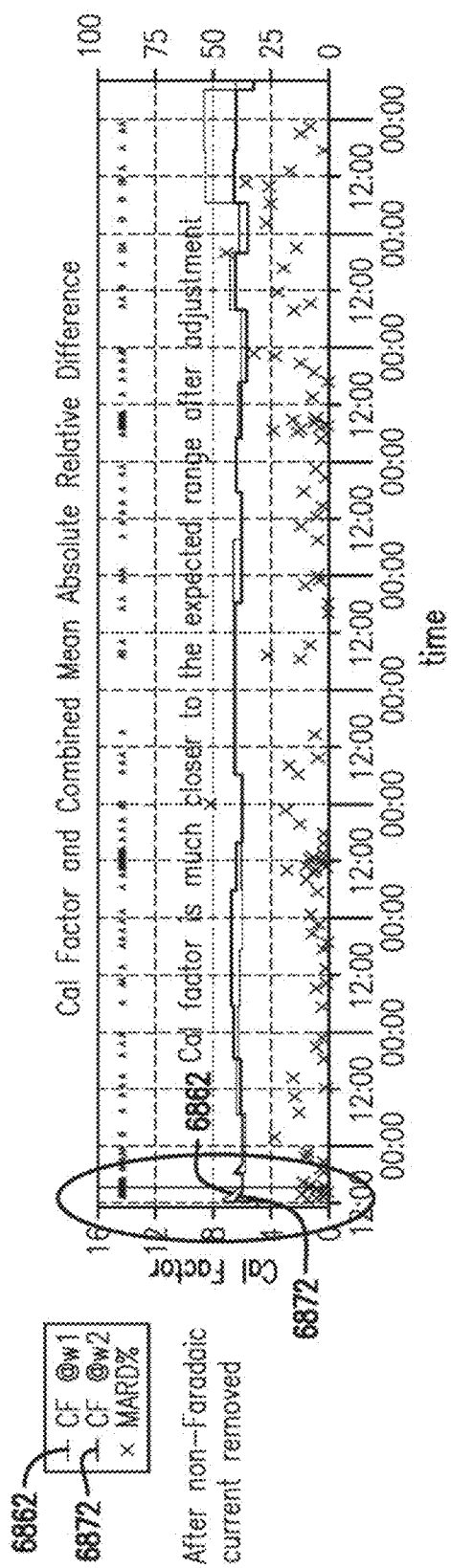

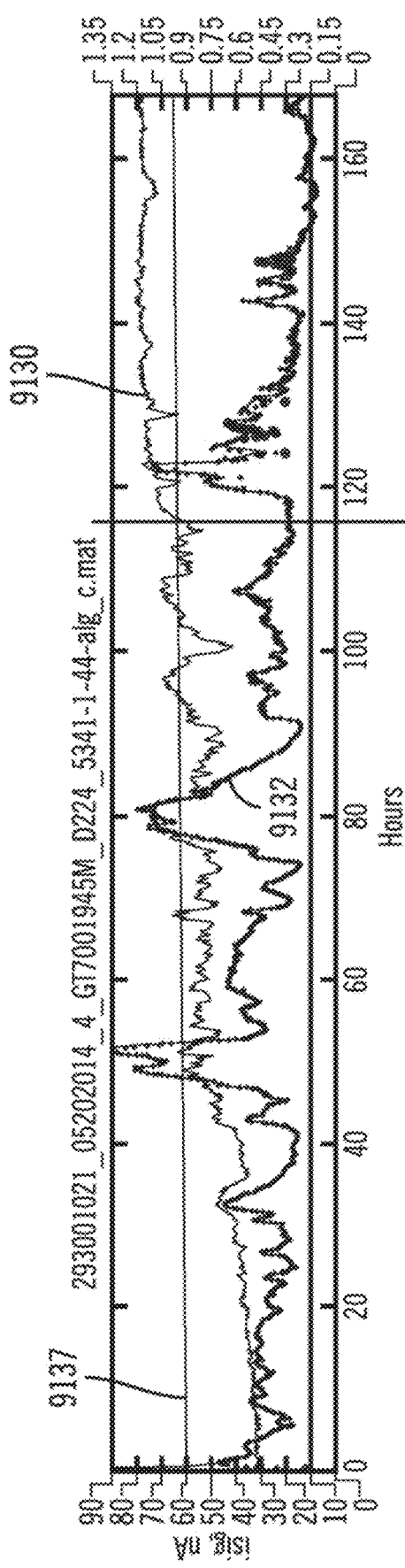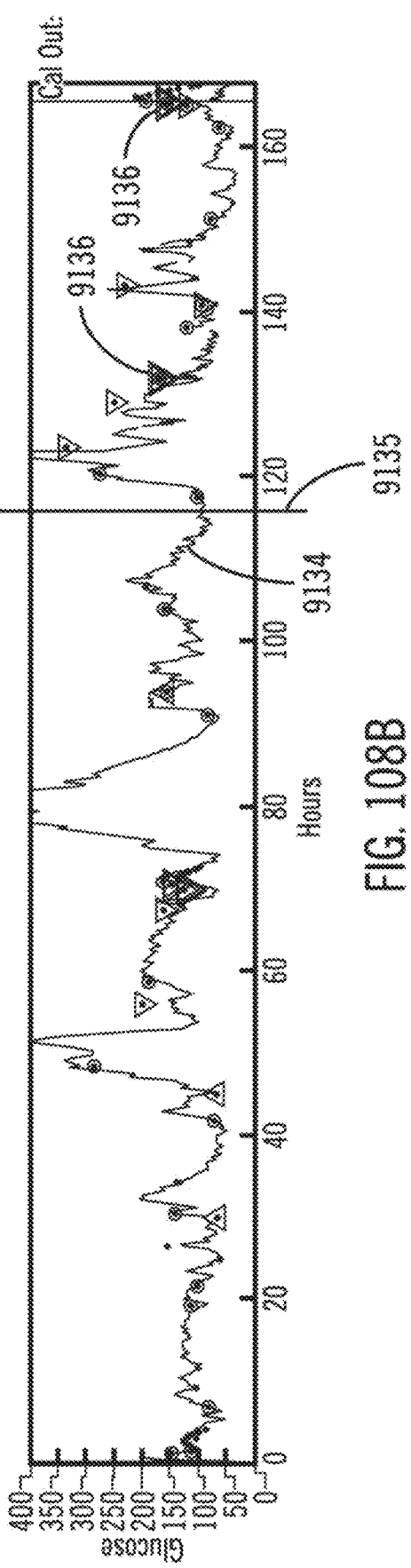
FIG. 108A
FIG. 108B

| Parameter | Weight | Directional | Rationale/Believed Effect |
|---|---|---|---|
| Isig | -0.060 | No | Low Isig sign of low sensitivity |
| Noise Level | 72.230 | No | Higher noise causes variability in SG |
| Vcntr Deviation | 7.509 | No | Deviation from expected value sign of early sensor degradation |
| Vcntr Rail Time | 0.023 | No | Cumulative time spent at the railed Vcntr correlates to higher noise and sensitivity loss |
| Isig Rate of Change | 0.467 | Yes | High rate of change causes directional error due to lag |
| Lifetime | -0.293 | Yes | Sensor typically degrades during wear, causing sensitivity loss |
| Sg Rate of Change | -1.805 | Yes | High rate of change causes direction error due to lag |
| Cal Ratio Deviation | -2.746 | Yes | Deviation from the expected cal ratio in either direction relates to underreads |
| Real 6.3Hz Impedance | 0.001 | Yes | Large value for real impedance usually sign of start up issues and pull out |
| Imag 1k Impedance | 0.040 | Yes | High imaginary impedance corresponds to sensitivity loss |
| Imag 8k Impedance | -0.009 | Yes | Very negative 8k imaginary impedance corresponds to sensitivity loss and overreads |
| Constant | 8.759 | No | Background Error not attributable to any of the parameters |

FIG. 116

| | Mean-ARD | Eval Points | %Sensor pck Display | Day1Mard | Day 1 Eval Points | Mean Abs Hypo Bias | Hypo Eval Points | Consensus A+B |
|---|---|---|---|---|---|---|---|---|
| DT | 11.55 | 2139 | 98.6 | 14.78 | 381 | 12.27 | 101 | 99.72 |
| GP | 11.64 | 1984 | 95.16 | 14.16 | 323 | 9.84 | 89 | 99.9 |
| Fusion | 11.44 | 2139 | 98.6 | 14.37 | 381 | 9.92 | 101 | 99.72 |
| Filtered | 11.32 | 2121 | 98.14 | 14.45 | 382 | 10 | 101 | 99.81 |
| Blanked | 11.14 | 2106 | 97.7 | 14.3 | 381 | 10 | 101 | 100 |

FIG. 117

| Concept | Model | Sensitivity Map | Key Assumptions |
|---|---|---|---|
| A non-linear complex field of exact values | Genetic Programming (GP) | | The training algorithm can infer the correct structure of the sensitivity map from the available exemplars. |
| A non-linear complex field whose values represent corrections to an initial constant calibration-factor/offset model | Analytical Modeling (AM) | | Starting with a base sensor model, appropriate adjustments could be made to account for changes in oxygen, foreign body response, etc. |
| A non-linear complex map where each point is an integer cal-factor value | Bag of Trees Model (BT) | | Sensor response at each point can be expressed using a fixed offset and variable calibration factor value. |
| A piecewise linear map where adjacent regions belong to stable linear regions | Decision Trees Model (DT) | | There exists distinct regions of the sensitivity map wherein calibration factor and bias change linearly. |

Figure 120

| Foreign body response | Oxygen | Dips, hypoglycemia | Day 1 stabilization |
|---|---|---|---|
| Input: High freq. imaginary impedance<br>Basis<br>• Post explant experiments, literature, historical data<br>Max Adjustment: 30%<br>$c_1 e^{imag1000 \times c_2} + c_3$ | Input: Counter voltage<br>Basis<br>• Reaction requires $O_2$<br>• $H_2O_2$ gradient affected by $O_2$ concentration<br>• Vcntr is proxy for $O_2$<br>Max Adjustment: 12%<br>$c_1 Vcntr^2 + c_2 Vcntr + c_3$ | Input: Long term Isig trend<br>Basis<br>• Unexpected dips in signal, might be related to hypoglycemia<br>Max Adjustment: 15%<br>$c_1 e^{IsigTrend \times c_2} + c_3$ | Input: Counter voltage<br>Basis:<br>• Theory: Pt oxidation, capacitance. In-vivo exp<br>Max Adjustment: 5%<br>$Adj = c_1 Vcntr + c_2$<br>Consider Isig, low freq imag, real high low freq |

Calibration Factor Adjustment

Figure 139

METHODS, SYSTEMS, AND DEVICES FOR CALIBRATION AND OPTIMIZATION OF GLUCOSE SENSORS AND SENSOR OUTPUT

RELATED APPLICATION DATA

This application claims the benefit of the filing date of U.S. Provisional Application Ser. No. 62/558,248, filed Sep. 13, 2017, which is incorporated herein by reference in its entirety.

FIELD

The present technology is generally related to sensor technology, including sensors used for sensing a variety of physiological parameters, e.g., glucose concentration, and to enabling elimination of the need for blood glucose (BG) calibration in calibration-free or near-calibration-free glucose sensing systems, devices, and methods.

BACKGROUND

Over the years, a variety of sensors have been developed for detecting and/or quantifying specific agents or compositions in a patient's blood, which enable patients and medical personnel to monitor physiological conditions within the patient's body. Illustratively, subjects may wish to monitor blood glucose levels in a subject's body on a continuing basis. Thus, glucose sensors have been developed for use in obtaining an indication of blood glucose levels in a diabetic patient. Such readings are useful in monitoring and/or adjusting a treatment regimen which typically includes the regular administration of insulin to the patient.

Presently, a patient can measure his/her blood glucose (BG) using a BG measurement device (i.e., glucose meter), such as a test strip meter, a continuous glucose measurement system (or a continuous glucose monitor), or a hospital hemacue. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device.

Current continuous glucose measurement systems include subcutaneous (or short-term) sensors and implantable (or long-term) sensors. Sensors have been applied in a telemetered characteristic monitor system. As described, e.g., in commonly-assigned U.S. Pat. No. 6,809,653, the entire contents of which are incorporated herein by reference, a telemetered system using an electrochemical sensor includes a remotely located data receiving device, a sensor for producing signals indicative of a characteristic of a user, and a transmitter device for processing signals received from the sensor and for wirelessly transmitting the processed signals to the remotely located data receiving device. The data receiving device may be a characteristic monitor, a data receiver that provides data to another device, an RF programmer, a medication delivery device (such as an infusion pump), or the like.

Regardless of whether the data receiving device (e.g., a glucose monitor), the transmitter device, and the sensor (e.g., a glucose sensor) communicate wirelessly or via an electrical wire connection, a characteristic monitoring system of the type described above is of practical use only after it has been calibrated based on the unique characteristics of the individual user. According to the current state of the art, the user is required to externally calibrate the sensor. More specifically, and in connection with the illustrative example of a diabetic patient, the latter is required to utilize a finger-stick blood glucose meter reading an average of two-four times per day for the duration that the characteristic monitor system is used. Each time, blood is drawn from the user's finger and analyzed by the blood glucose meter to provide a real-time blood sugar level for the user. The user then inputs this data into the glucose monitor as the user's current blood sugar level which is used to calibrate the glucose monitoring system.

Such external calibrations, however, are disadvantageous for various reasons. For example, blood glucose meters are not perfectly accurate and include inherent margins of error. Moreover, even if completely accurate, blood glucose meters are susceptible to improper use; for example, if the user has handled candy or other sugar-containing substance immediately prior to performing the finger stick, with some of the sugar sticking to the user's fingers, the blood sugar analysis will result in an inaccurate blood sugar level indication. Furthermore, there is a cost, not to mention pain and discomfort, associated with each application of the finger stick.

The current state of the art in continuous glucose monitoring (CGM) is largely adjunctive, meaning that the readings provided by a CGM device (including, e.g., an implantable or subcutaneous sensor) cannot be used without a reference value in order to make a clinical decision. The reference value, in turn, must be obtained from a finger stick using, e.g., a BG meter. The reference value is needed because there is a limited amount of information that is available from the sensor/sensing component. Specifically, the only pieces of information that are currently provided by the sensing component for processing are the raw sensor value (i.e., the sensor current or Isig) and the counter voltage. Therefore, during analysis, if it appears that the raw sensor signal is abnormal (e.g., if the signal is decreasing), the only way one can distinguish between a sensor failure and a physiological change within the user/patient (i.e., glucose level changing in the body) is by acquiring a reference glucose value via a finger stick. As is known, the reference finger stick is also used for calibrating the sensor.

The art has searched for ways to eliminate or, at the very least, minimize, the number of finger sticks that are necessary for calibration and for assessing sensor health. However, given the number and level of complexity of the multitude of sensor failure modes, no satisfactory solution has been found. At most, diagnostics have been developed that are based on either direct assessment of the Isig, or on comparison of multiple Isigs, e.g., from redundant and/or orthogonally redundant, sensors and/or electrodes. In either case, because the Isig tracks the level of glucose in the body, by definition, it is not analyte independent. As such, by itself, the Isig is not a reliable source of information for sensor diagnostics, nor is it a reliable predictor for continued sensor performance.

Another limitation that has existed in the art thus far has been the lack of sensor electronics that can not only run the sensor, but also perform real-time sensor and electrode diagnostics, and do so for redundant electrodes, all while managing the sensor's power supply. To be sure, the concept of electrode redundancy has been around for quite some time. However, up until now, there has been little to no success in using electrode redundancy not only for obtaining more than one reading at a time, but also for assessing the relative health of the redundant electrodes, the overall reliability of the sensor, and the frequency of the need, if at all, for calibration reference values.

The art has also searched for more accurate and reliable means for providing self-calibrating sensors, and for performing sensor diagnostics by developing a variety of circuit models. In such models, an attempt is generally made to correlate circuit elements to parameters that may be used in intelligent diagnostics, gross failure analysis, and real-time self-calibrations. However, most such models have had limited success thus far.

SUMMARY

In one aspect, the present disclosure provides a method for external calibration of a glucose sensor used for measuring the level of glucose in the body of a user, the sensor including physical sensor electronics, a microcontroller, and a working electrode, the method comprising periodically measuring, by the physical sensor electronics, electrode current (Isig) signals for the working electrode; performing, by the microcontroller, an Electrochemical Impedance Spectroscopy (EIS) procedure to generate EIS-related data for the working electrode; based on the Isig signals and EIS-related data and a plurality of calibration-free sensor glucose (SG)-predictive models, calculating, by the microcontroller, a respective SG value for each of the SG-predictive models; calculating, by the microcontroller, a modification factor based on respective values of a physiological calibration factor (PCF), an environmental calibration factor (ECF), or both, and determining, by the microcontroller, whether the calculated modification factor is valid; when the modification factor is valid, calculating, by the microcontroller, a calibrated respective SG value for each of the SG-predictive models based on the modification factor and the respective SG values; fusing, by the microcontroller, the calibrated respective SG values to calculate a single, calibrated, fused SG value; performing, by the microcontroller, error detection diagnostics on the calibrated, fused SG value to determine whether a correctable error exists in the calibrated, fused, SG value; correcting, by the microcontroller, the correctable error; and displaying a corrected, calibrated, fused SG value to the user.

In another aspect, the disclosure provides a method for external calibration of a glucose sensor used for measuring the level of glucose in the body of a user, the sensor including physical sensor electronics, a microcontroller, and a working electrode, the method comprising periodically measuring, by the physical sensor electronics, electrode current (Isig) signals for the working electrode; performing, by the microcontroller, an Electrochemical Impedance Spectroscopy (EIS) procedure to generate EIS-related data for the working electrode; based on the Isig signals and EIS-related data and a plurality of calibration-free sensor glucose (SG)-predictive models, calculating, by the microcontroller, a respective SG value for each of the SG-predictive models; fusing, by the microcontroller, the respective SG values to calculate a single, fused SG value; calculating, by the microcontroller, a modification factor based on respective values of a physiological calibration factor (PCF), an environmental calibration factor (ECF), or both, and determining, by the microcontroller, whether the calculated modification factor is valid; when the modification factor is valid, calculating, by the microcontroller, a single, calibrated, fused SG value based on the modification factor and the single, fused SG value; performing, by the microcontroller, error detection diagnostics on the calibrated, fused SG value to determine whether a correctable error exists in the calibrated, fused, SG value; correcting, by the microcontroller, the correctable error; and displaying a corrected, calibrated, fused SG value to the user.

In a further aspect, the disclosure provides a method for using factory calibration to correct for manufacturing batch variations in one or more sensor parameters of a glucose sensor used for measuring the level of glucose in the body of a user, the sensor including physical sensor electronics, a microcontroller, and a working electrode, the method comprising periodically measuring, by the physical sensor electronics, electrode current (Isig) signal values for the working electrode; performing, by the microcontroller, an Electrochemical Impedance Spectroscopy (EIS) procedure to generate values of one or more EIS-related parameters for the working electrode; calculating, by the microcontroller, values of counter voltage (Vcntr) for the sensor; applying, by the microcontroller, a factory calibration factor to the Isig, EIS parameter, and Vcntr values to generate respective modified Isig, EIS parameter, and Vcntr values; based on the modified Isig, EIS parameter, and Vcntr values and a plurality of calibration-free sensor glucose (SG)-predictive models, calculating, by the microcontroller, a respective SG value for each of the SG-predictive models; fusing, by the microcontroller, the respective SG values to calculate a single, fused SG value; performing, by the microcontroller, error detection diagnostics on the calibrated, fused SG value to determine whether a correctable error exists in the calibrated, fused, SG value; correcting, by the microcontroller, the correctable error; and displaying a corrected, calibrated, fused SG value to the user.

In yet another aspect, the disclosure provides a method of optimizing glucose sensor estimation for a glucose sensor used for measuring the level of glucose in the body of a user, the sensor including physical sensor electronics, a microcontroller, and a working electrode, the method comprising periodically measuring, by the physical sensor electronics, electrode current (Isig) signals for the working electrode; performing, by the microcontroller, an Electrochemical Impedance Spectroscopy (EIS) procedure to generate EIS-related data for the working electrode; calculating, by the microcontroller, an adjusted calibration factor for the sensor based on the EIS-related data; calculating, by the microcontroller, an adjusted offset value for the sensor based on at least one of a stabilization time adjustment and a non-linear sensor response adjustment; and calculating, by the microcontroller, an optimized measured glucose value (SG) based on the adjusted calibration factor and the adjusted offset value, wherein SG=(adjusted calibration factor)×(Isig+adjusted offset value).

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A detailed description of embodiments of the invention will be made with reference to the accompanying drawings, wherein like numerals designate corresponding parts in the figures.

FIG. 8B illustrates a voltage generation device to implement this embodiment of the invention.

FIG. 8C illustrates a voltage generation device to generate two voltage values according to an embodiment of the invention.

FIG. 8D illustrates a voltage generation device having three voltage generation systems, according to embodiments of the invention.

FIGS. 16C and 16D show, respectively, infinite and finite glucose sensor response to a sinusoidal working potential.

FIGS. 40A and 40B show Bode plots for phase and impedance, respectively, for the simulation shown in FIG. 39.

FIG. 40C shows a Nyquist plot for the simulation shown in FIG. 39.

FIGS. 42A and 42B illustrate an ASIC block diagram in accordance with embodiments of the invention.

FIGS. 67A-67B show sensor drift in accordance with embodiments of the invention.

FIG. 91A is a chart showing in-vivo results for MARD over all valid BGs in approximately the first 8 hours of sensor life, in accordance with embodiments of the invention.

FIG. 91B is a chart showing median ARD numbers over all valid BGs in approximately the first 8 hours of sensor life, in accordance with embodiments of the invention.

FIG. 96 shows the effects on Isig of removal of the non-Faradaic current, in accordance with embodiments of the invention.

FIG. 97A shows the Calibration Factor before removal of the non-Faradaic current for two working electrodes, in accordance with embodiments of the invention.

FIG. 97B shows the Calibration Factor after removal of the non-Faradaic current for two working electrodes, in accordance with embodiments of the invention.

FIGS. 98A and 98B show the effect on MARD of the removal of the non-Faradaic current, in accordance with embodiments of the invention.

FIG. 99 is an illustration of double layer capacitance over time, in accordance with embodiments of the invention.

FIG. 100 shows a shift in Rmem+Rsol and the appearance of the higher-frequency semicircle during sensitivity loss, in accordance with embodiments of the invention.

FIG. 101A shows a flow diagram for detection of sensitivity loss using combinatory logic, in accordance with an embodiment of the invention.

FIG. 101B shows a flow diagram for detection of sensitivity loss using combinatory logic, in accordance with another embodiment of the invention.

FIG. 102 shows an illustrative method for using Nyquist slope as a marker to differentiate between new and used sensors, in accordance with embodiments of the invention.

FIGS. 103A-103C show an illustrative example of Nyquist plots having different lengths for different sensor configurations, in accordance with embodiments of the invention.

FIG. 104 shows Nyquist plot length as a function of time, for the sensors of FIGS. 103A-103C.

FIG. 105 shows a flow diagram for blanking sensor data or terminating a sensor in accordance with an embodiment of the invention.

Figure 106:
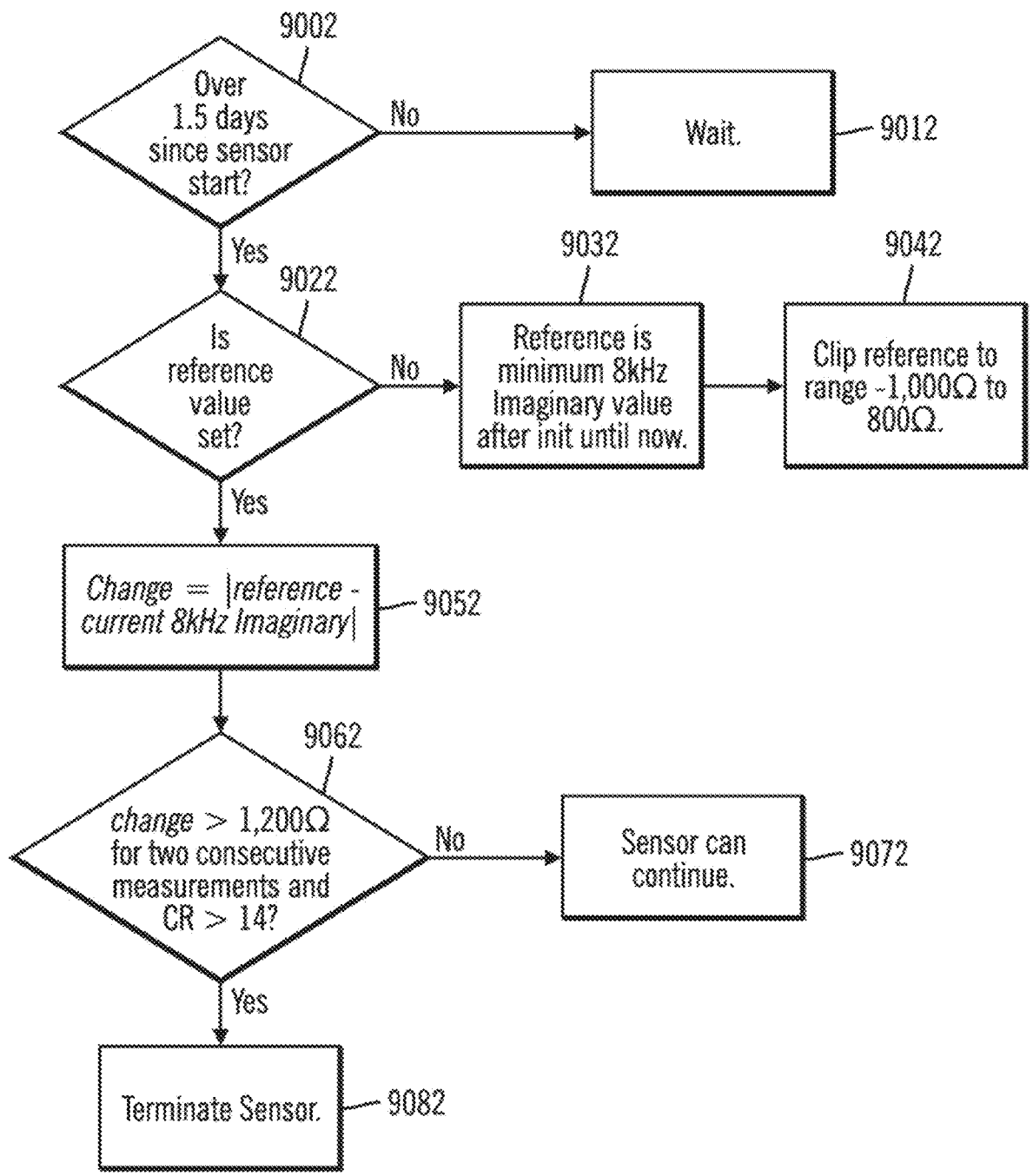

FIG. 106 shows a flow diagram for sensor termination in accordance with an embodiment of the invention.

Figure 107:
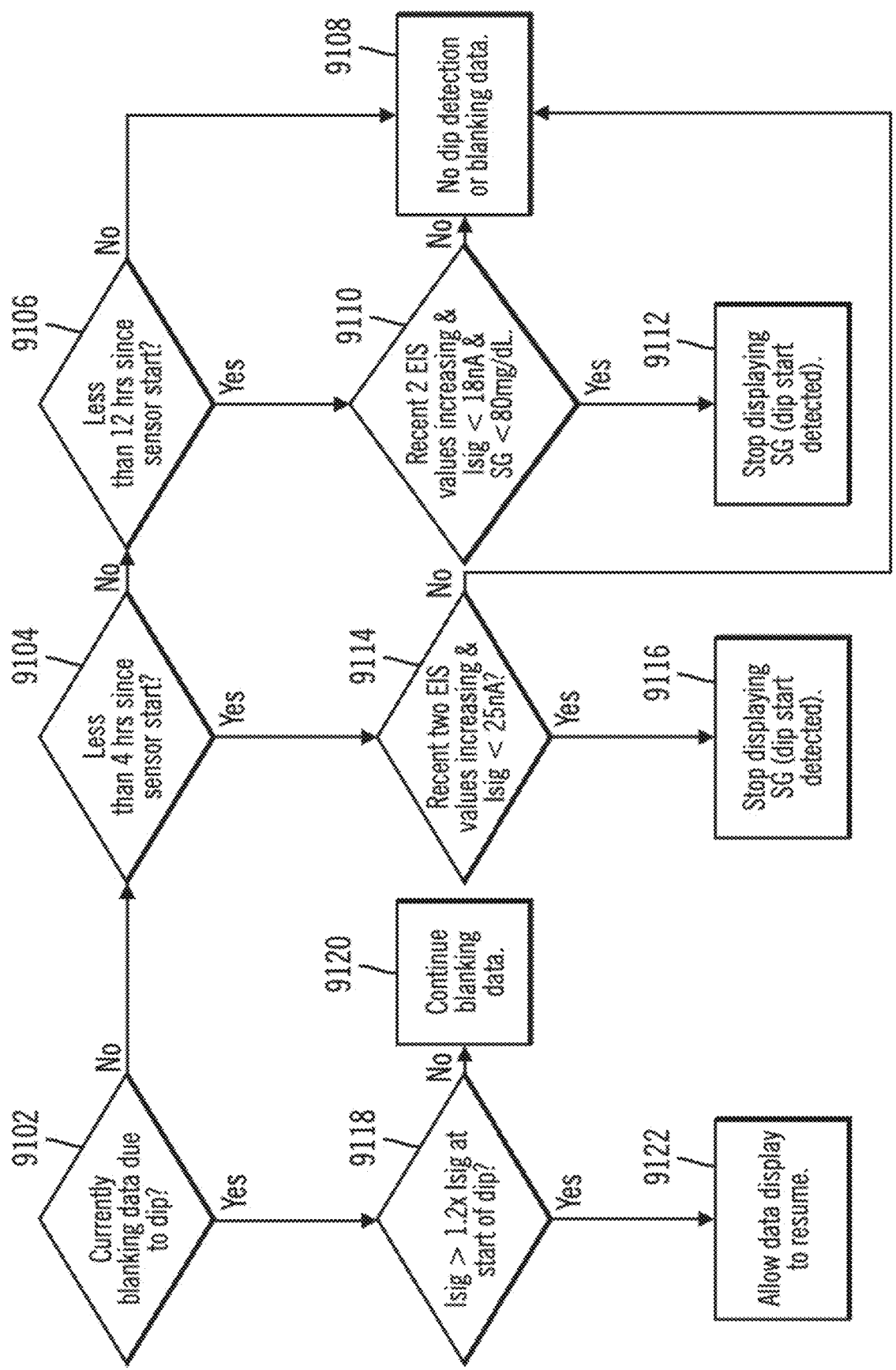

FIG. 107 shows a flow diagram for signal dip detection in accordance with an embodiment of the invention.

FIG. 108A shows Isig and Vcntr as a function of time, and FIG. 108B shows glucose as a function of time, in accordance with an embodiment of the invention.

Figure 109A:
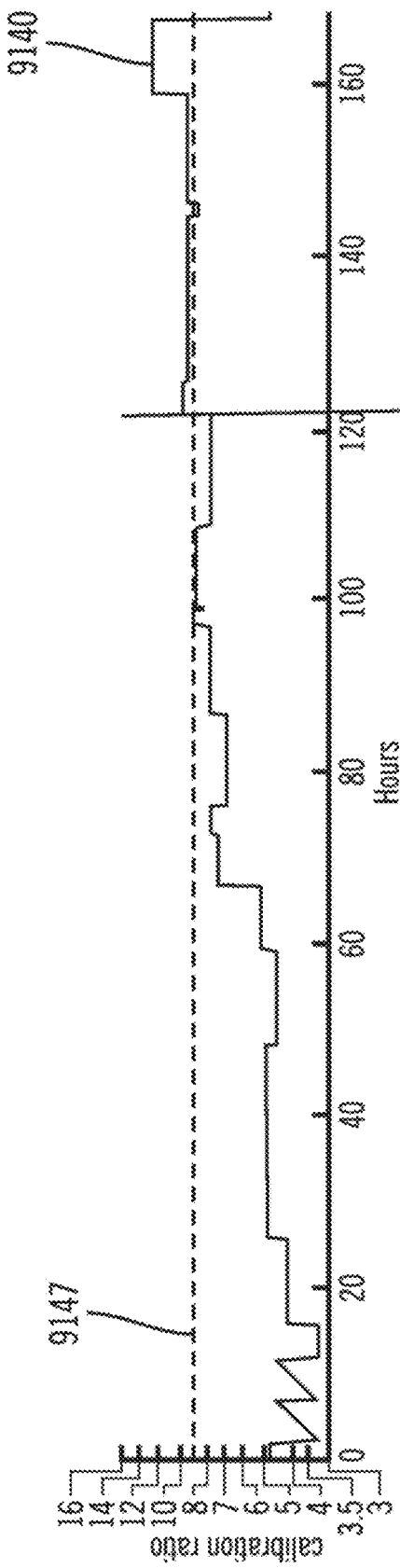
Figure 109B:
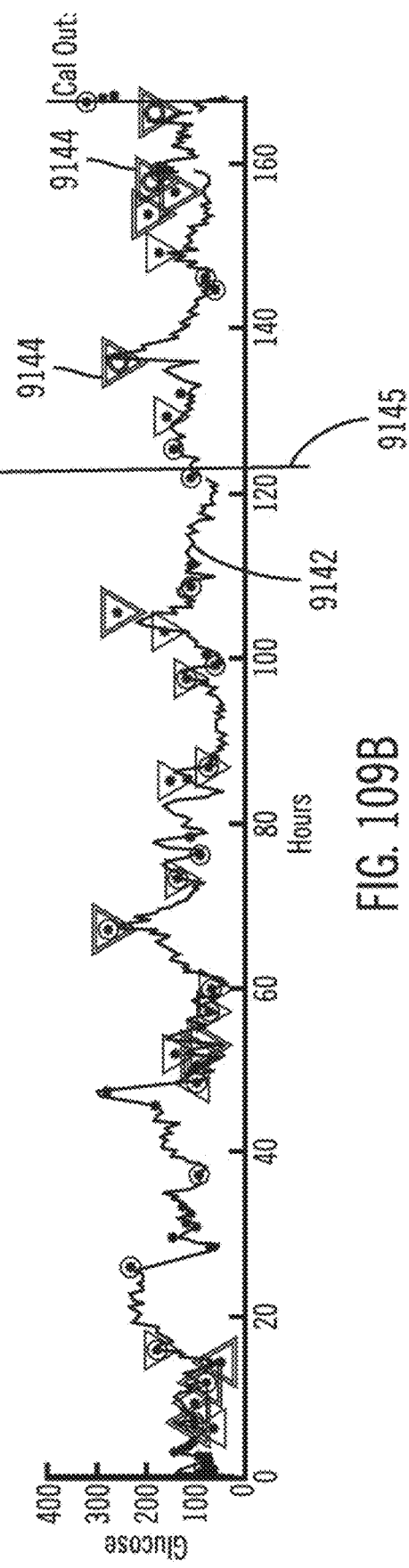

FIG. 109A calibration ratio as a function of time, and FIG. 109B show glucose as a function of time, in accordance with an embodiment of the invention.

Figure 110A:
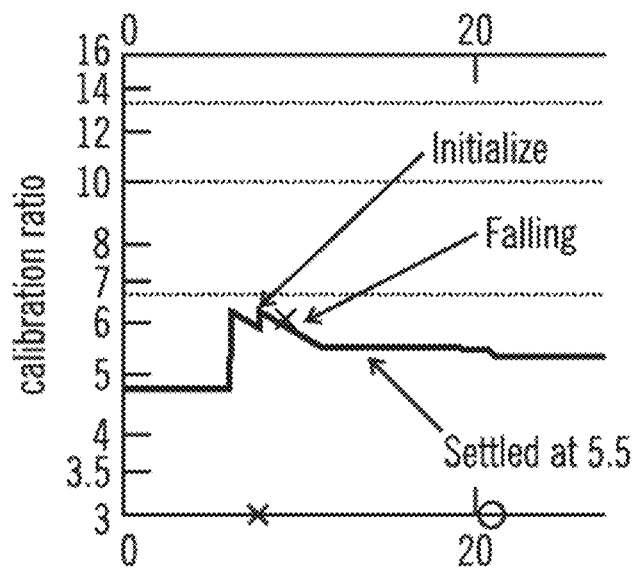
Figure 110B:
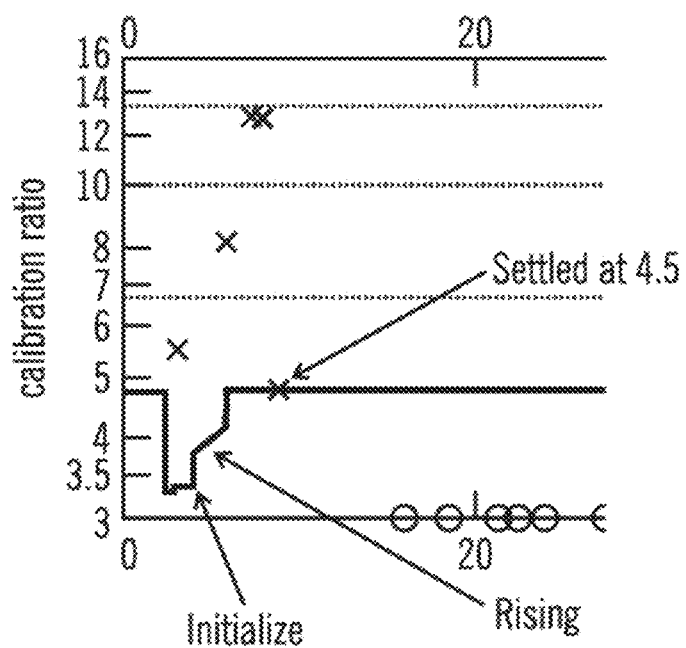

FIGS. 110A and 110B show calibration factor trends as a function of time in accordance with embodiments of the invention.

Figure 111:
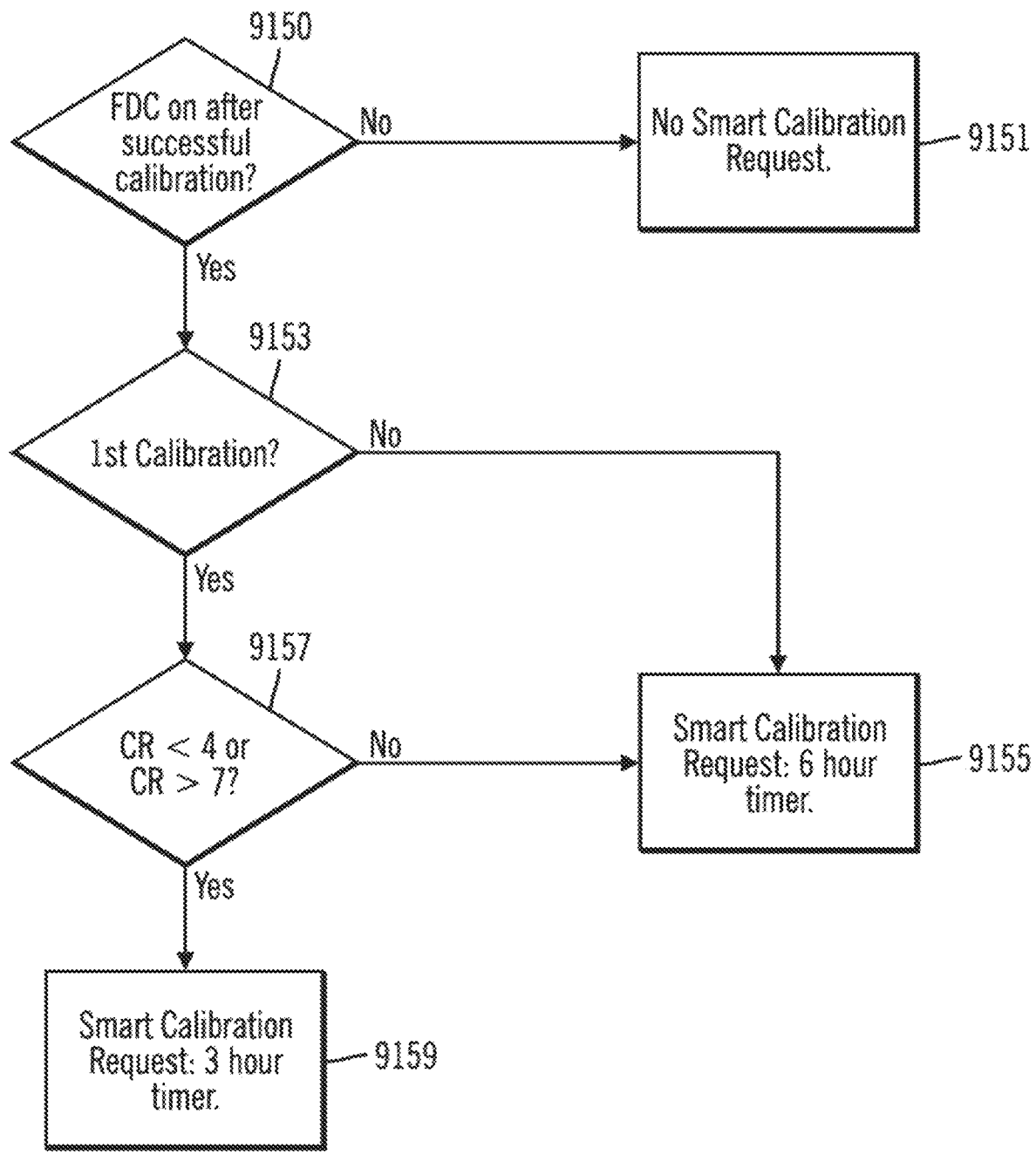

FIG. 111 shows a flow diagram for First Day Calibration (FDC) in accordance with an embodiment of the invention.

Figure 112:
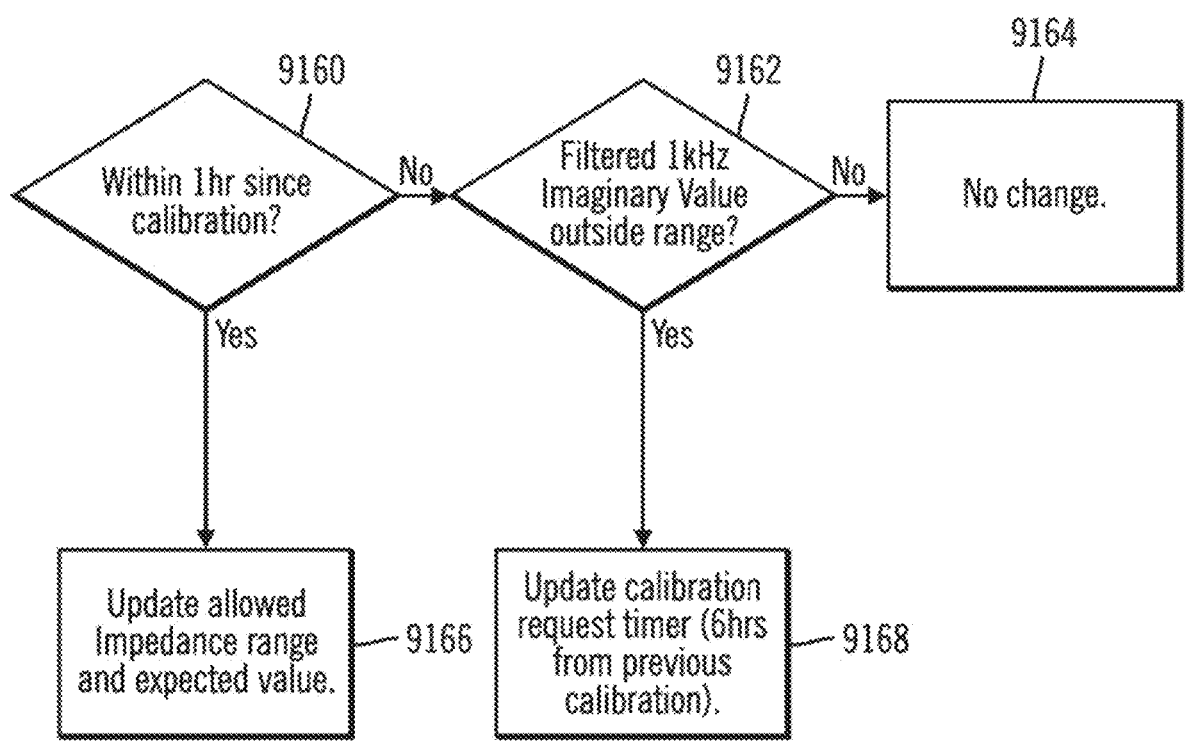

FIG. 112 shows a flow diagram for EIS-based calibration in accordance with an embodiment of the invention.

Figure 113:
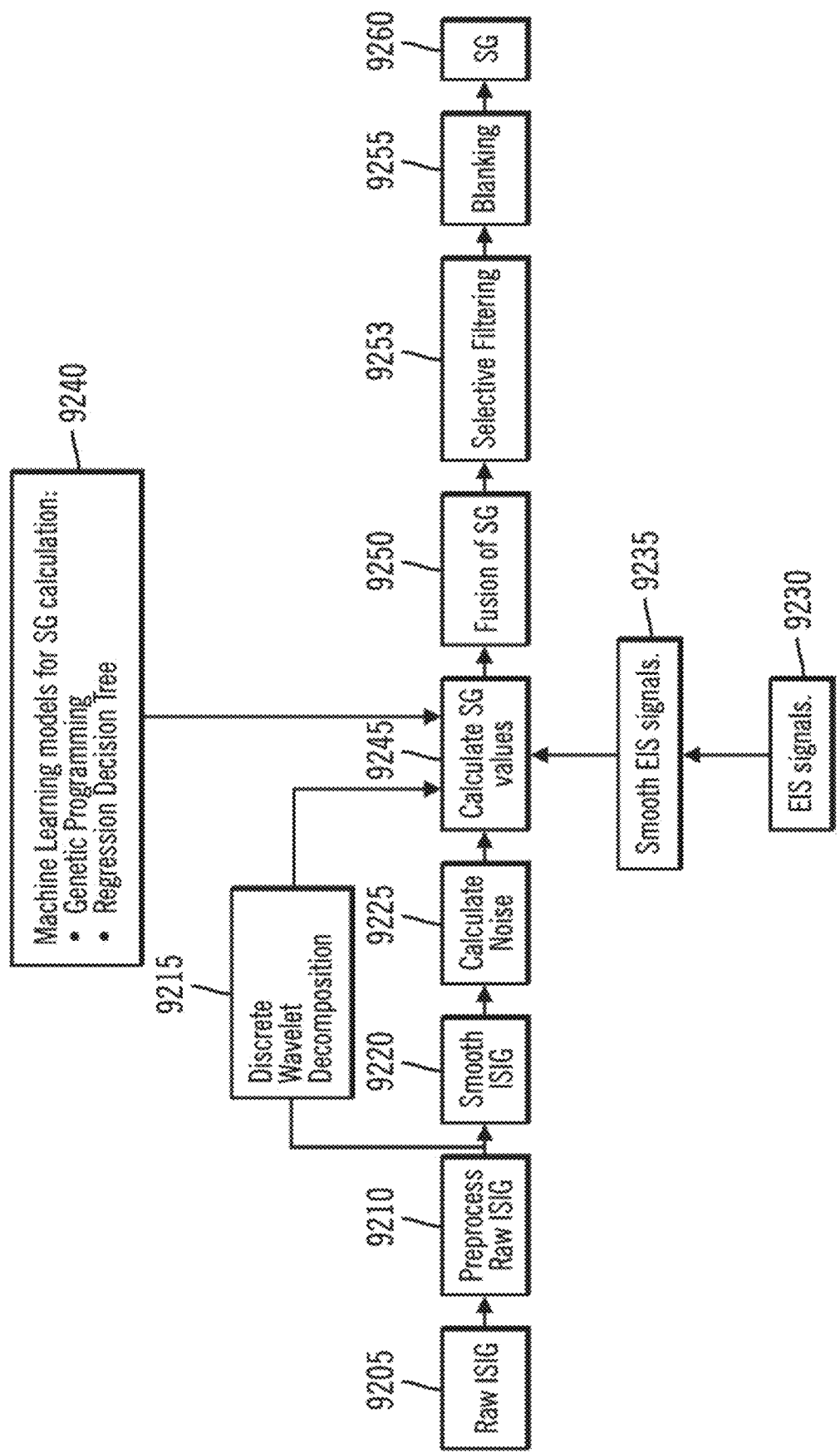

FIG. 113 shows a flow diagram of a calibration-free retrospective algorithm in accordance with an embodiment of the invention.

Figure 114:
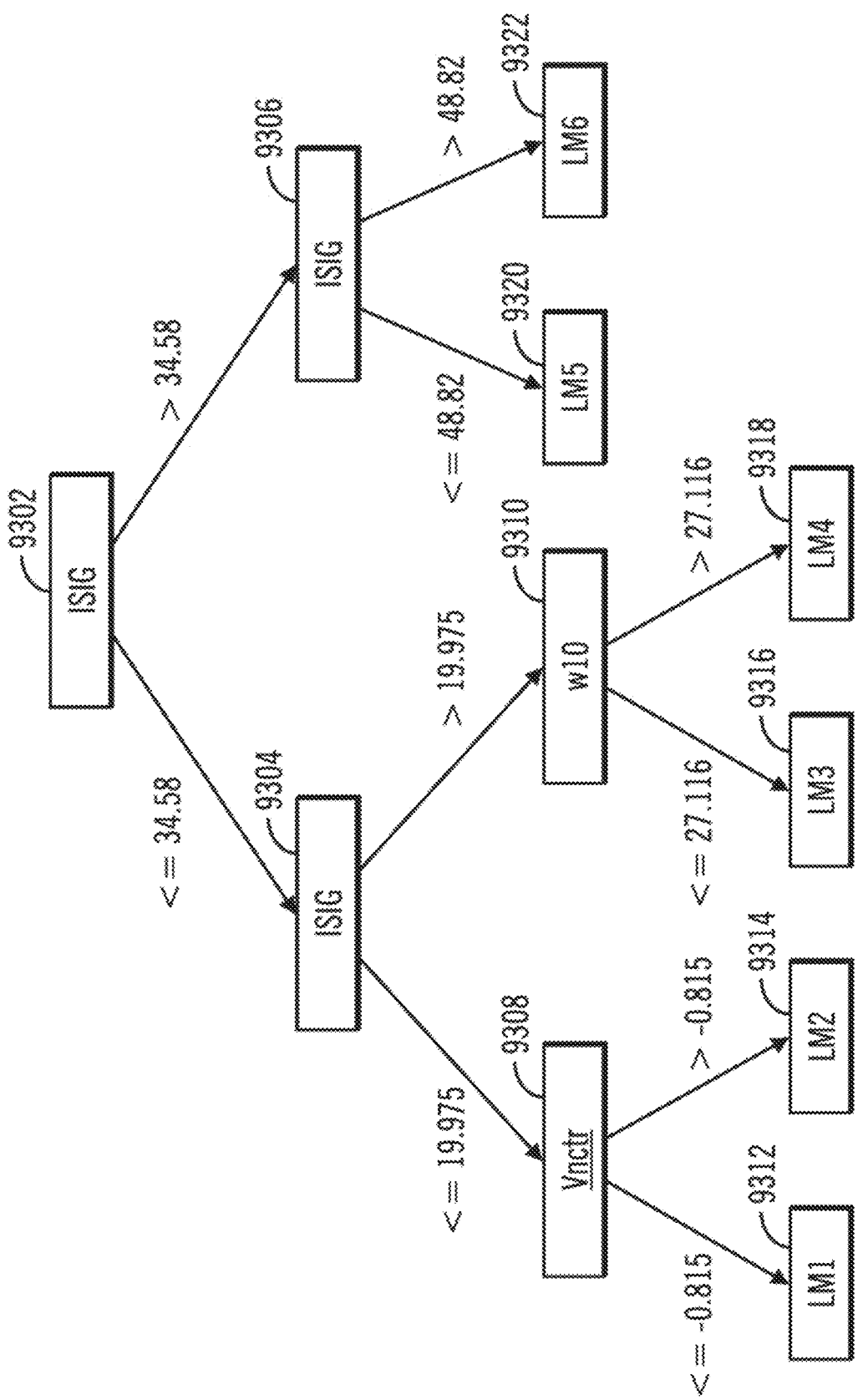

FIG. 114 shows a decision tree model in accordance with embodiments of the invention.

Figure 115:
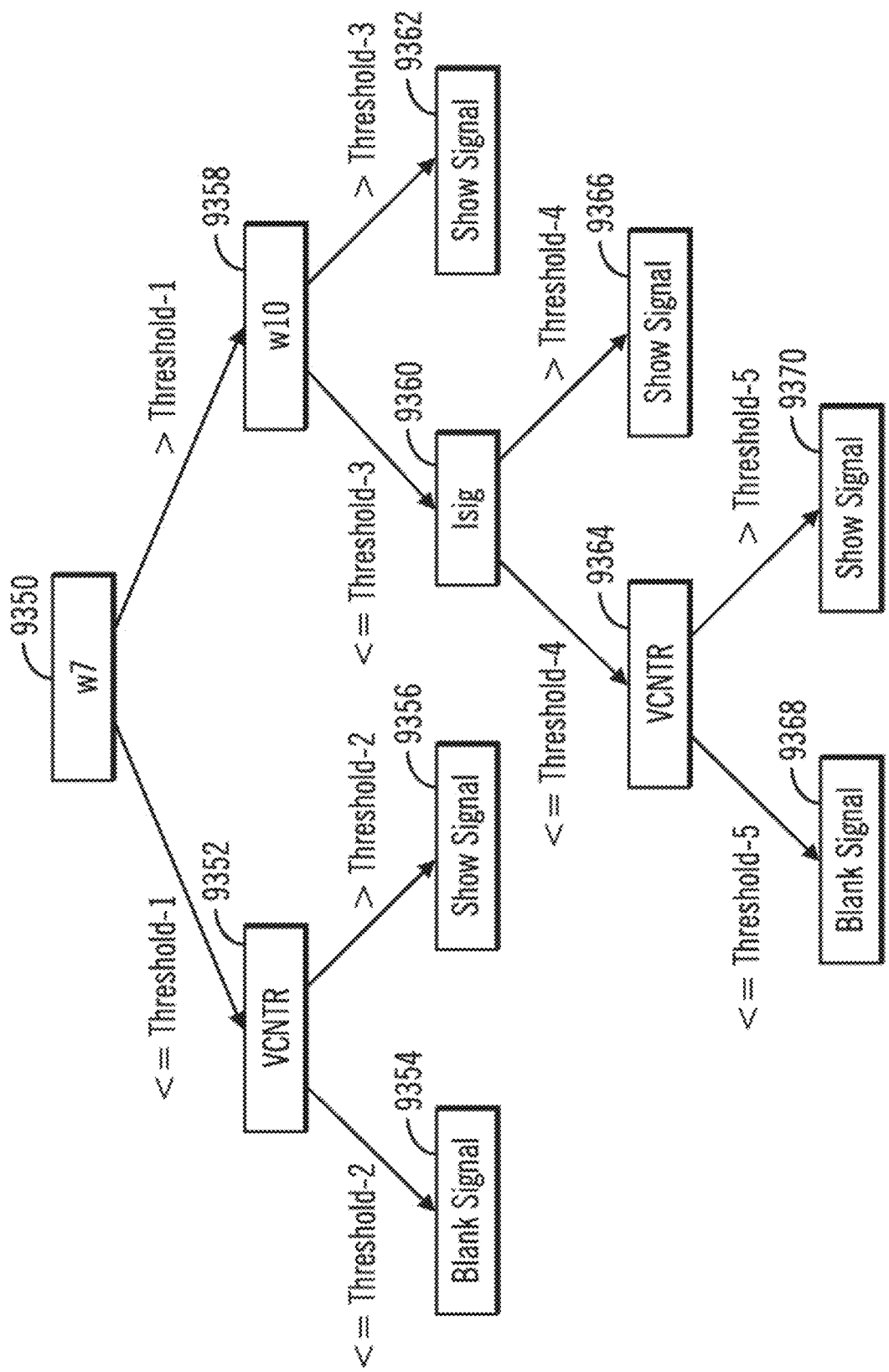

FIG. 115 shows a decision tree model for blanking data in accordance with an embodiment of the invention.

FIG. 116 is a table showing examples of parameters for a blanking algorithm in accordance with embodiments of the invention.

FIG. 117 shows fusion, filtering, and blanking results in accordance with embodiments of the invention.

Figure 118:
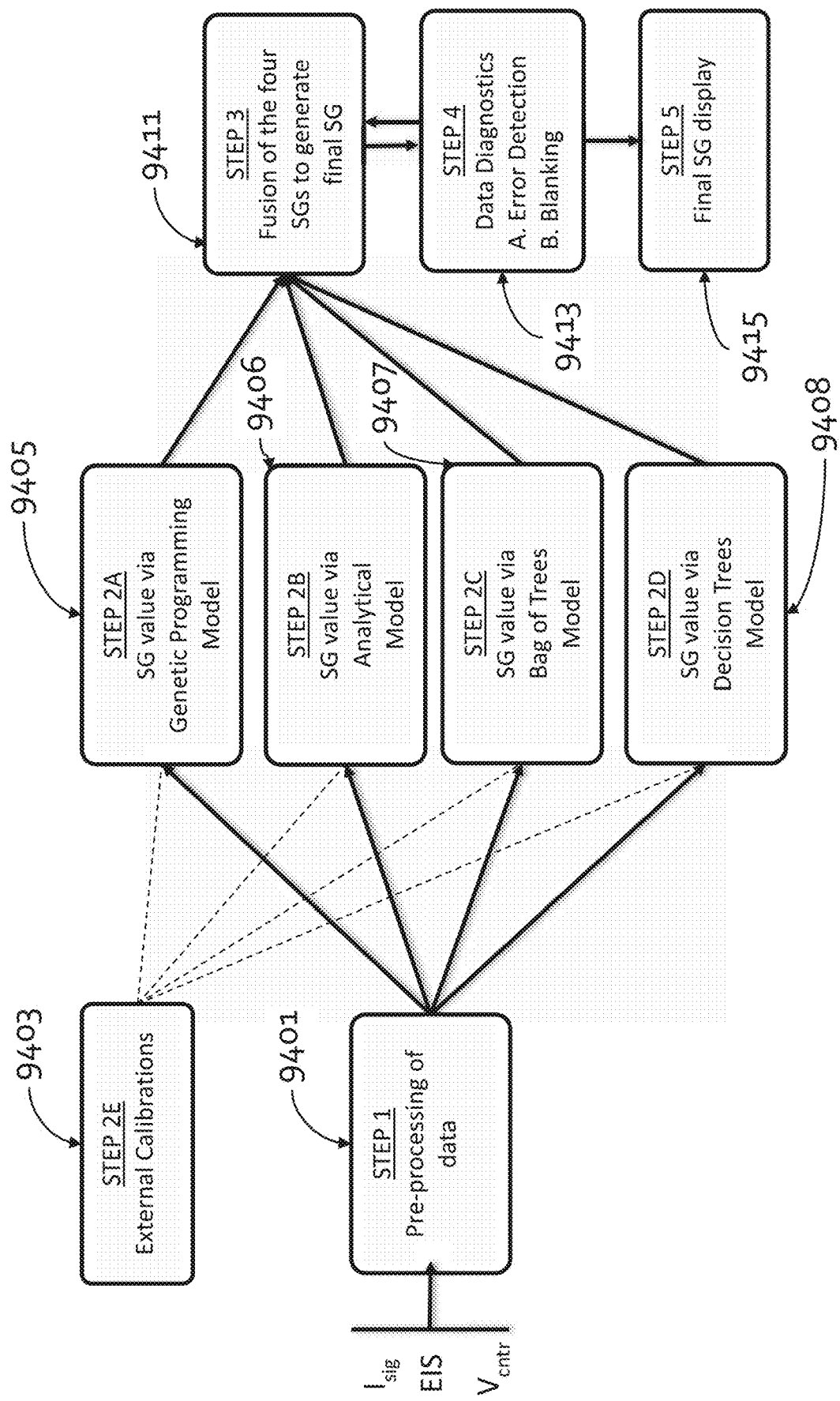

FIG. 118 shows a flow diagram and schematic of modules of an algorithm for correcting for the time varying error between sensor glucose (SG) and blood glucose (BG) calculation, in accordance with an embodiment of the invention.

Figure 119:
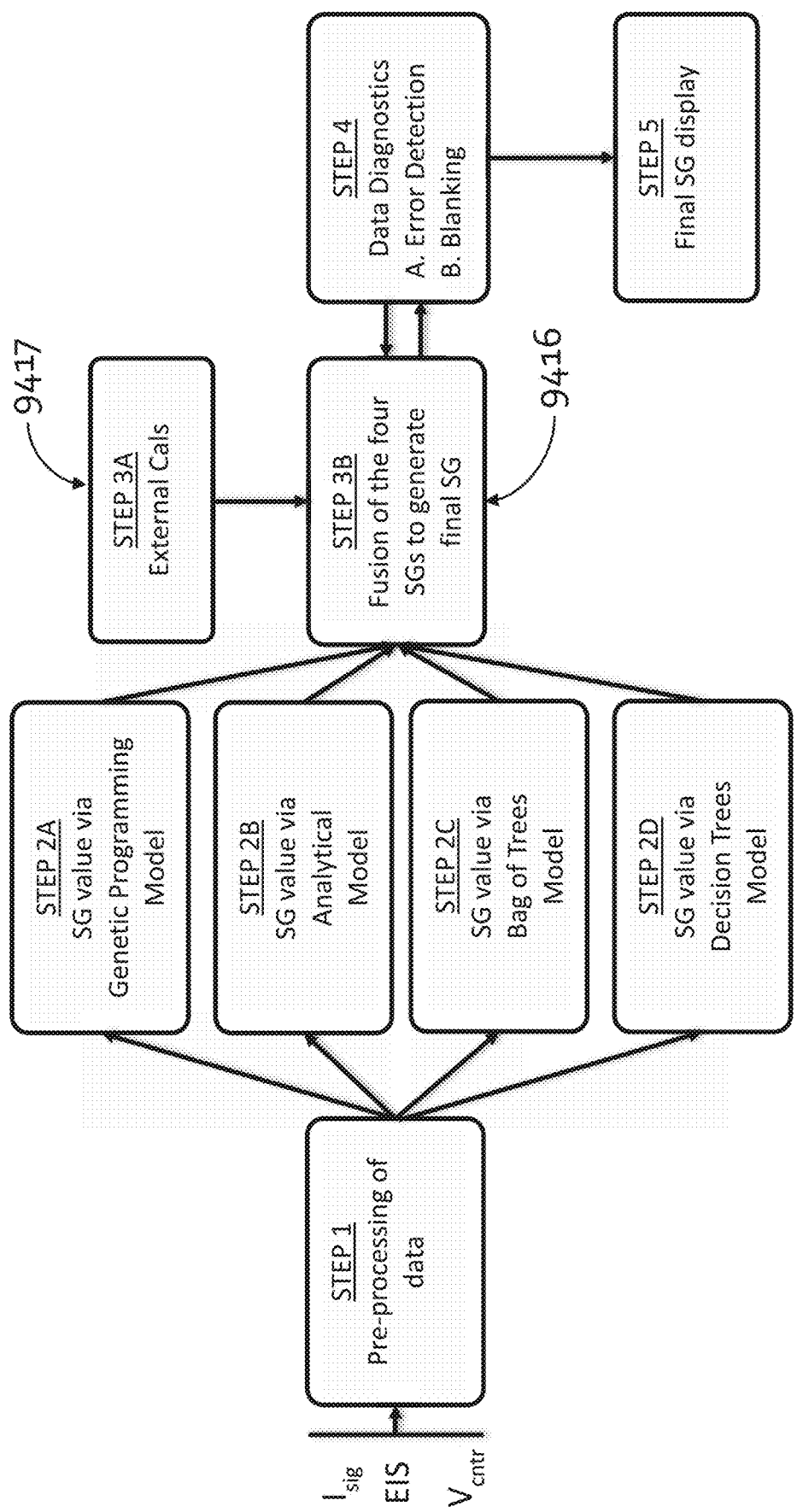

FIG. 119 shows a flow diagram and schematic of modules of an algorithm for correcting for the time varying error between sensor glucose (SG) and blood glucose (BG) calculation, in accordance with another embodiment of the invention.

FIG. 120 is a table of various models that may be used in embodiments of the invention.

Figure 121:
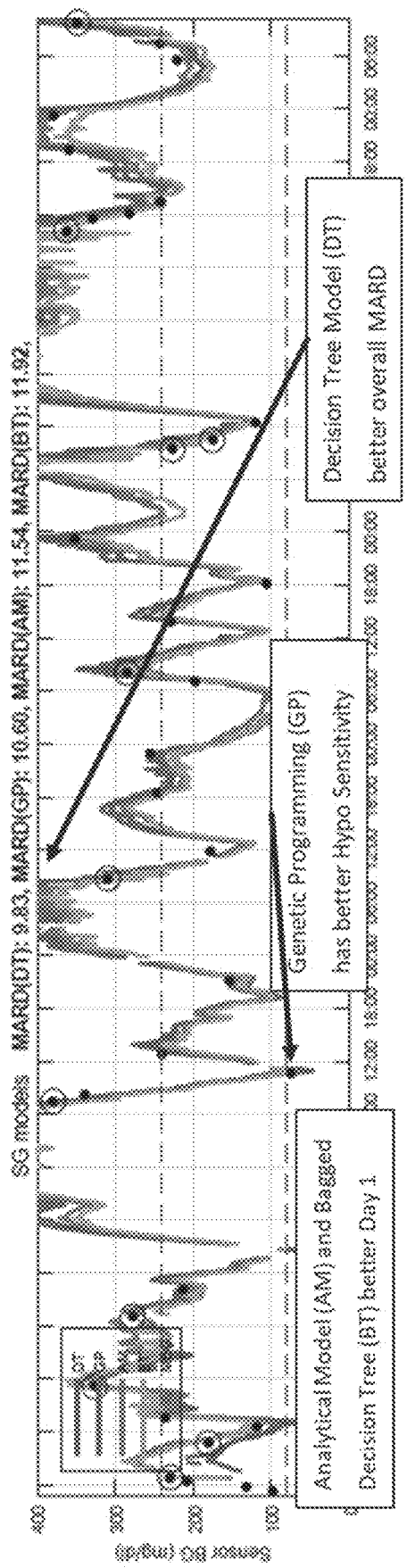

FIG. 121 is a plot of model performance in accordance with embodiments of the invention.

Figure 122:
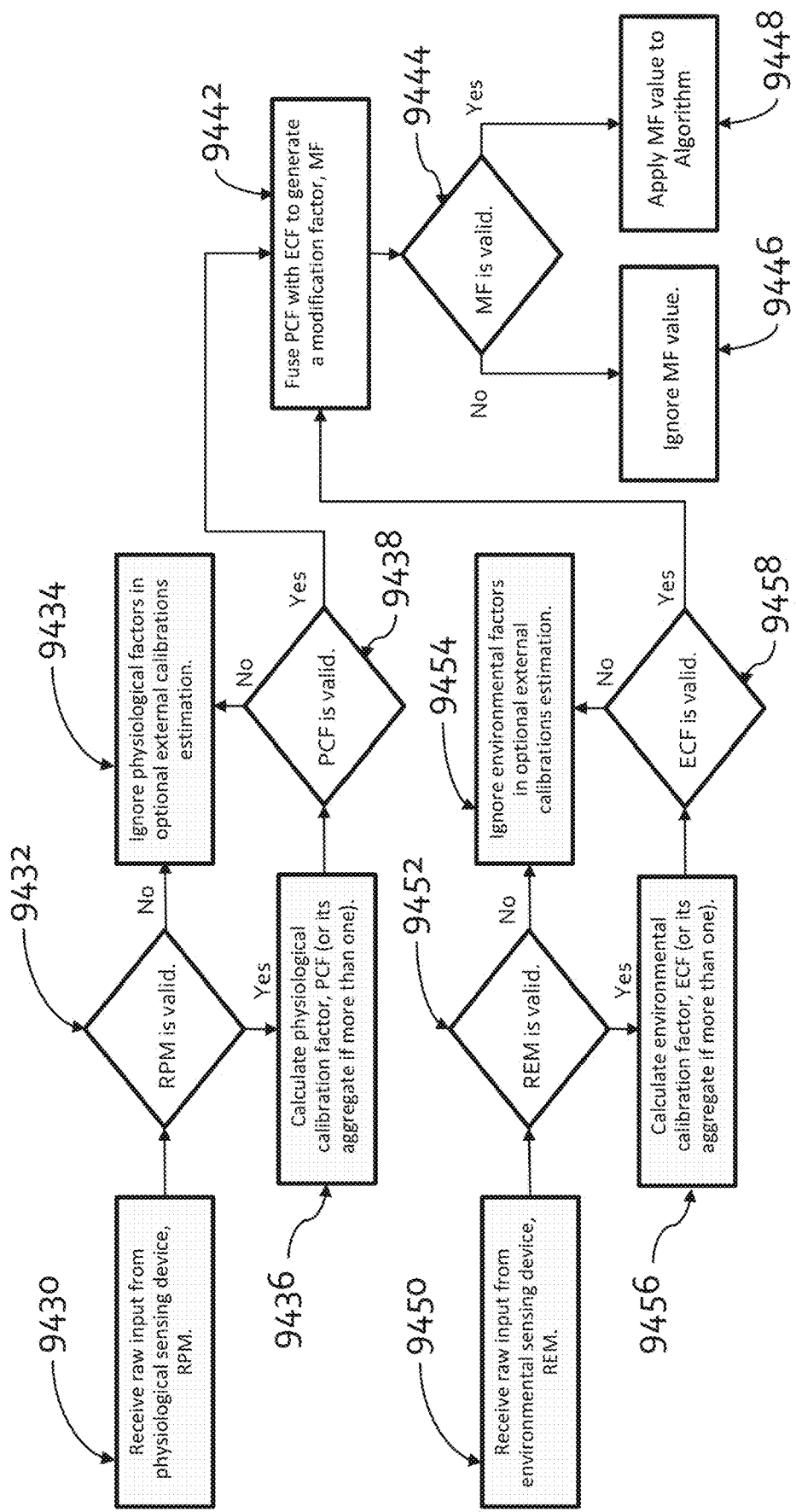

FIG. 122 shows a flow diagram for operationalizing an optional external calibration algorithm in accordance with embodiments of the invention.

Figure 123A:
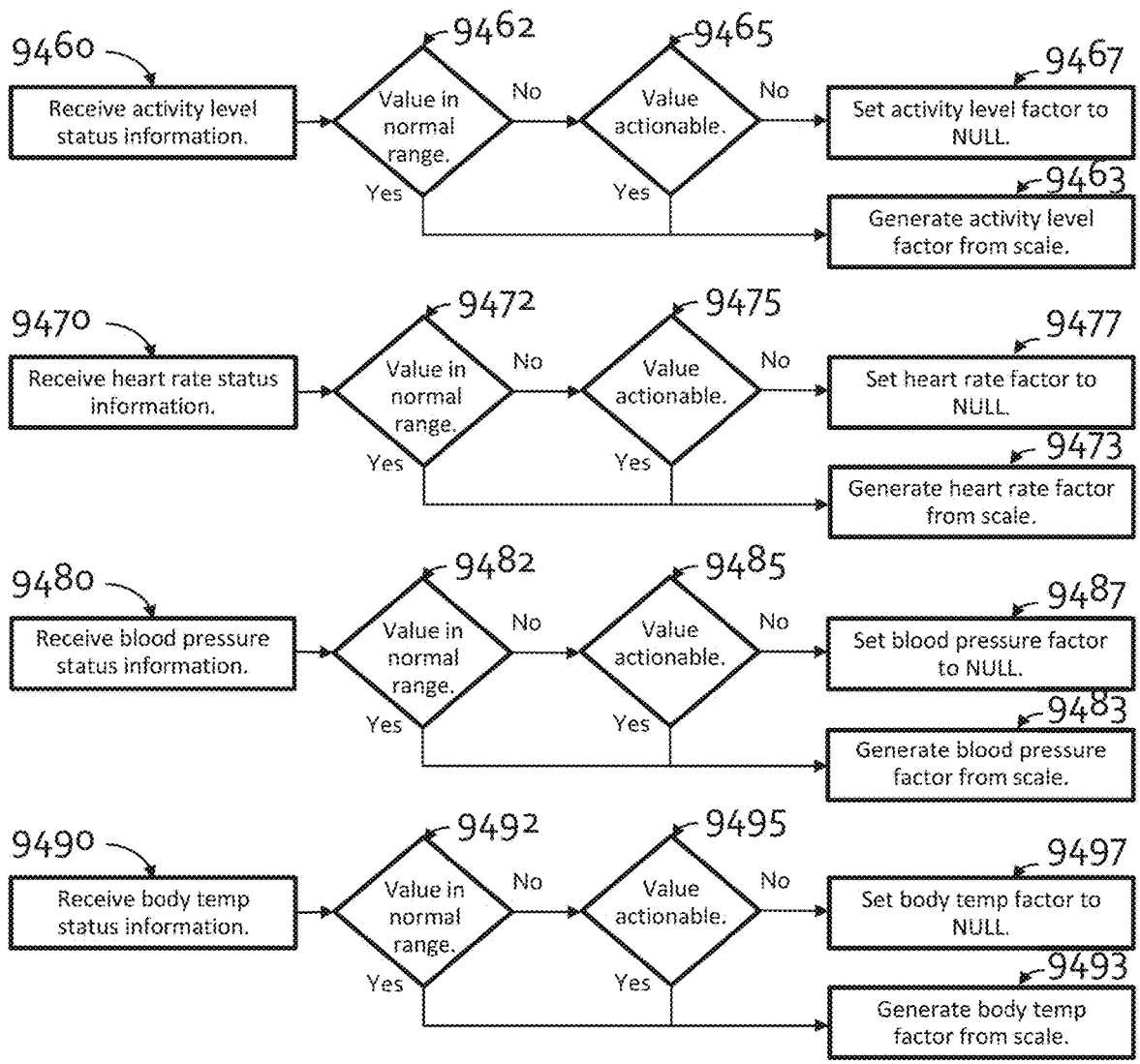
Figure 123B:
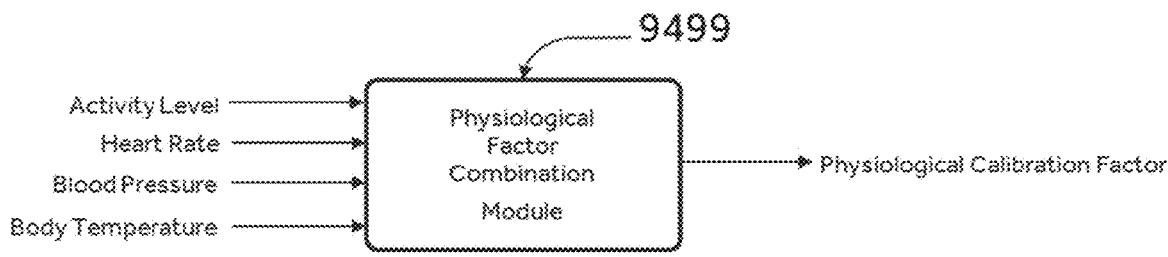

FIGS. 123A and 123B show flow diagrams for generating a Physiological Calibration Factor in accordance with embodiments of the invention.

Figure 124A:
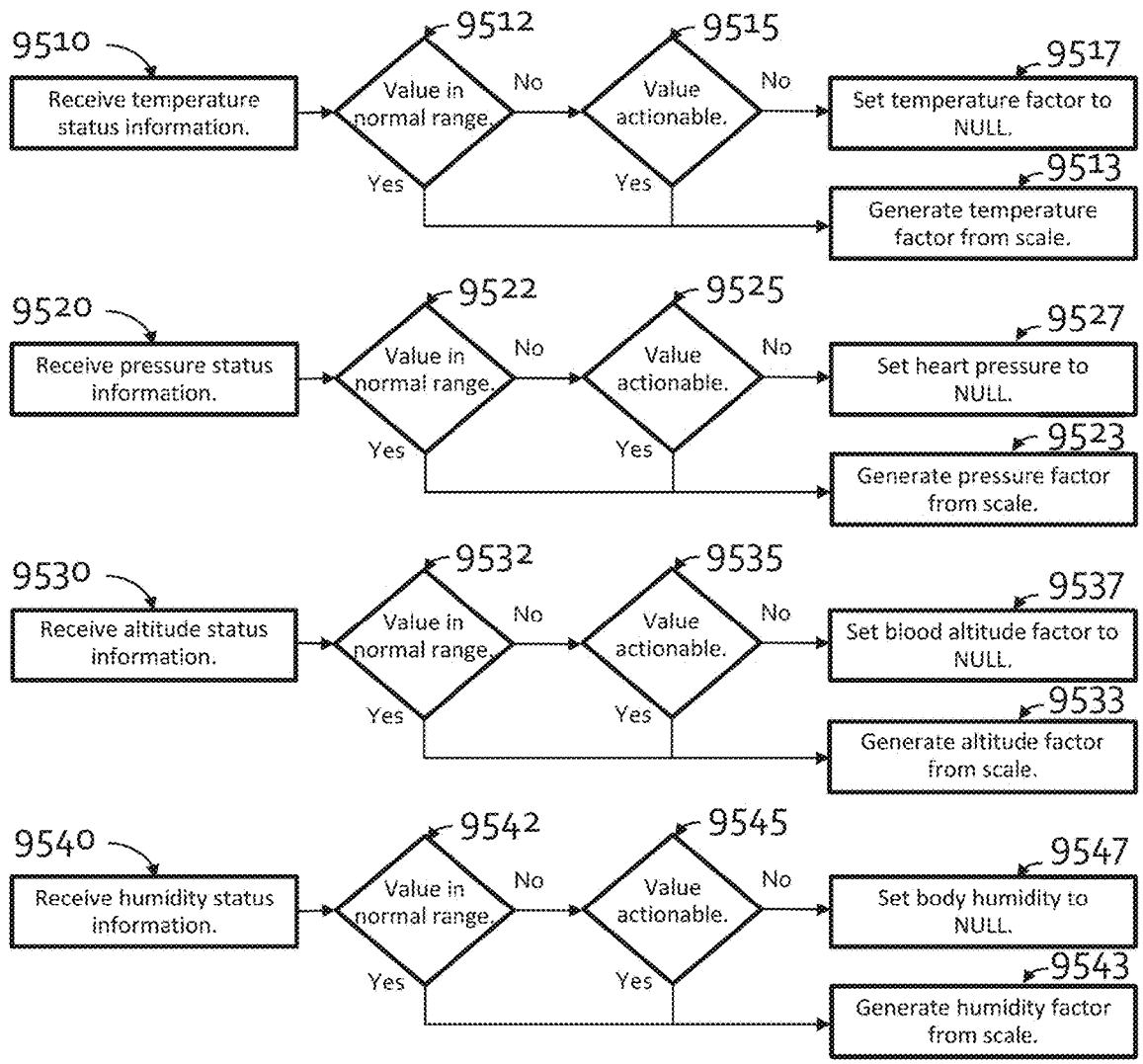
Figure 124B:
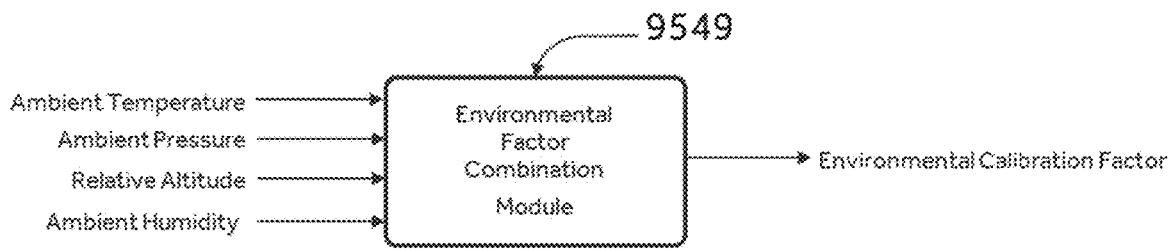

FIGS. 124A and 124B show flow diagrams for generating an Environmental Calibration Factor in accordance with embodiments of the invention.

Figure 125:
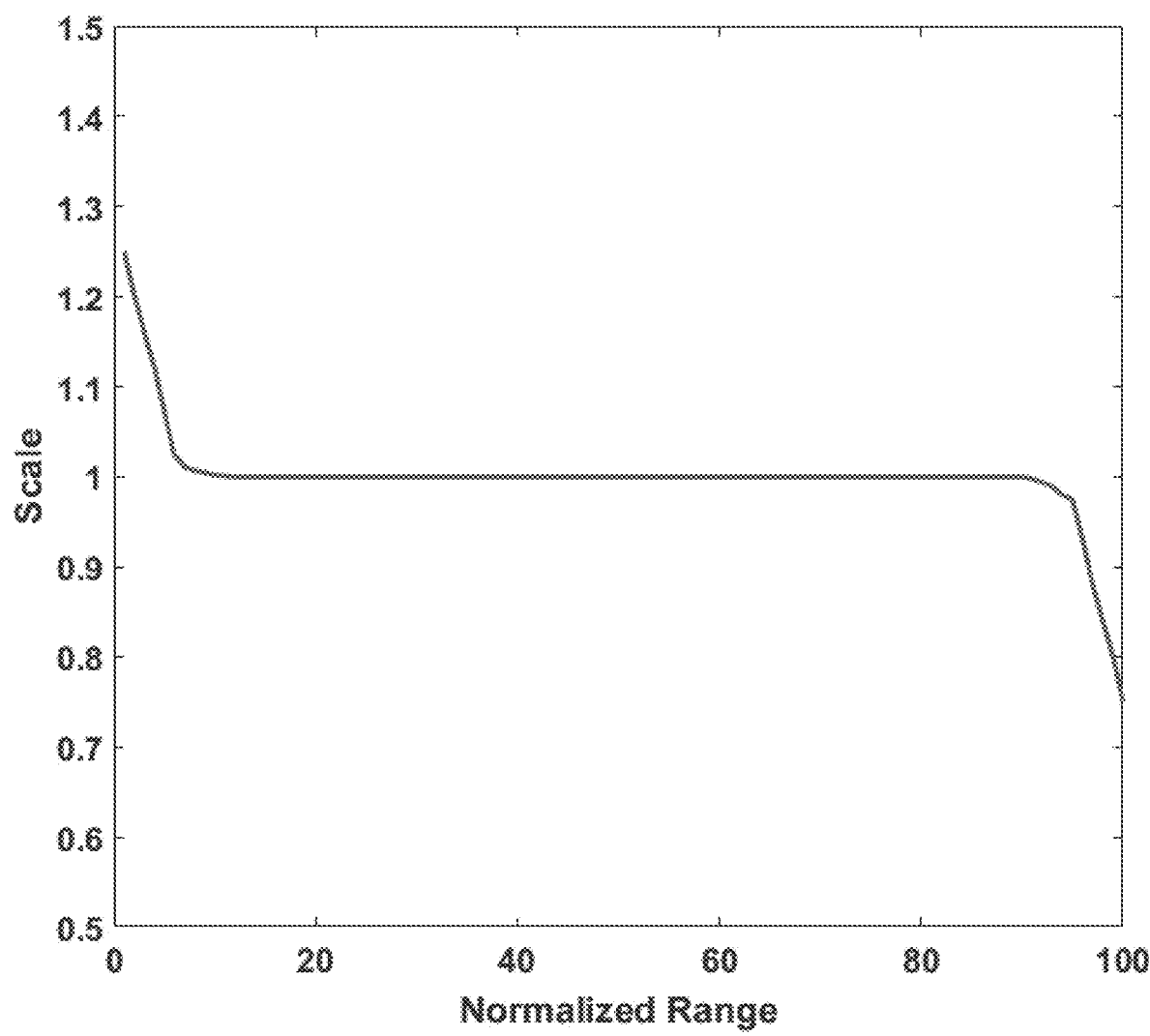

FIG. 125 shows an idealized boosting conversion scale for physiological and environmental factors in accordance with embodiments of the invention.

Figure 126:
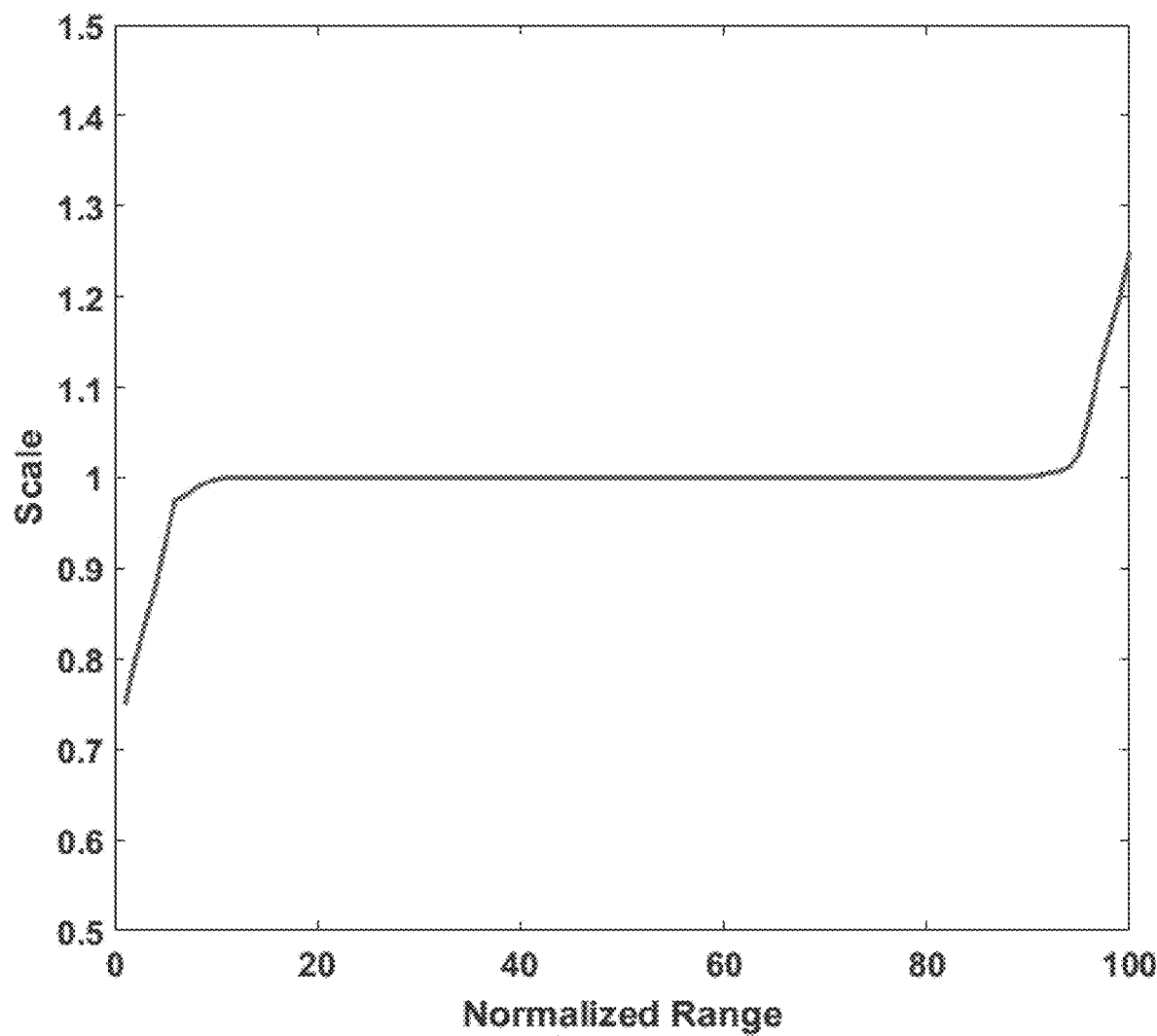

FIG. 126 shows an idealized suppression conversion scale for physiological and environmental factors in accordance with embodiments of the invention.

FIGS. 127A-127D show variance estimates across glycemic ranges for 1821 sensors worn by 537 subjects for Day 1, Day 3, Day 5 and Day 7 of sensor wear, calculated for eight distinct sensor glucose calculating units.

Figure 128A:
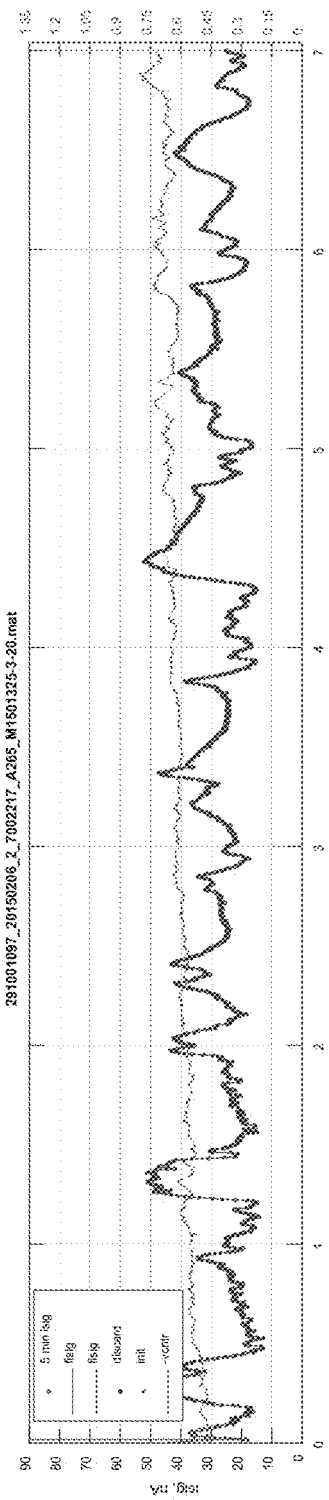
Figure 128B:
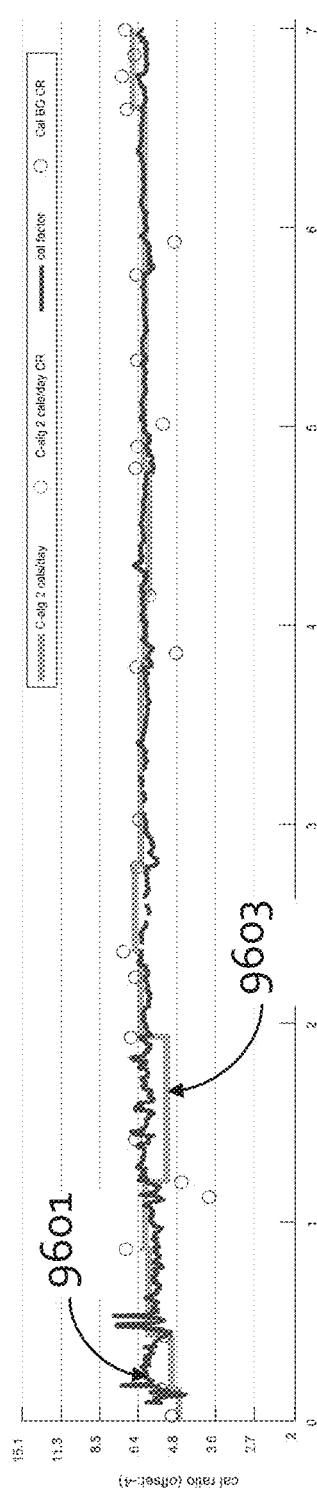
Figure 128C:
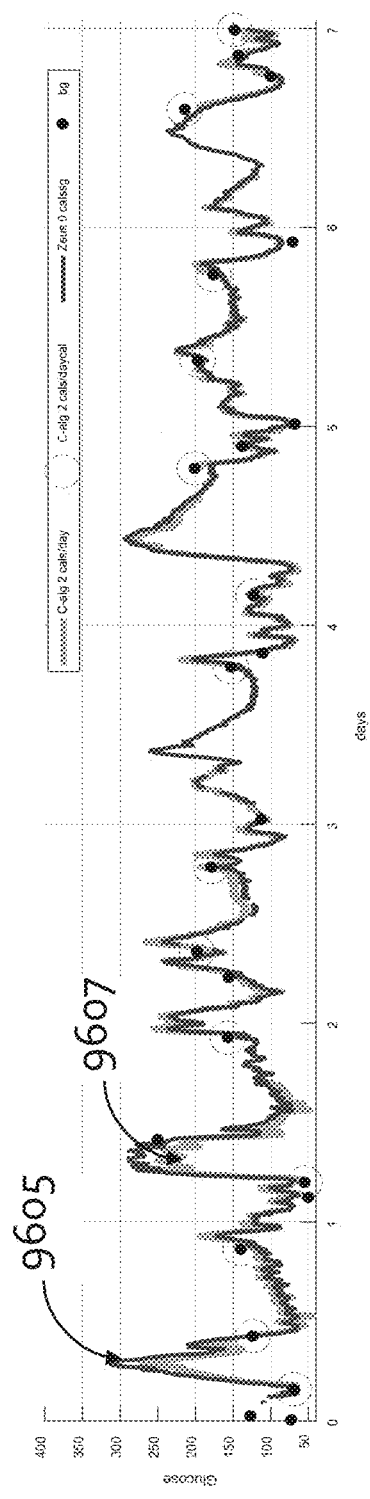

FIGS. 128A-128C show data for a typical sensor trace-set in accordance with embodiments of the invention.

Figure 129A:
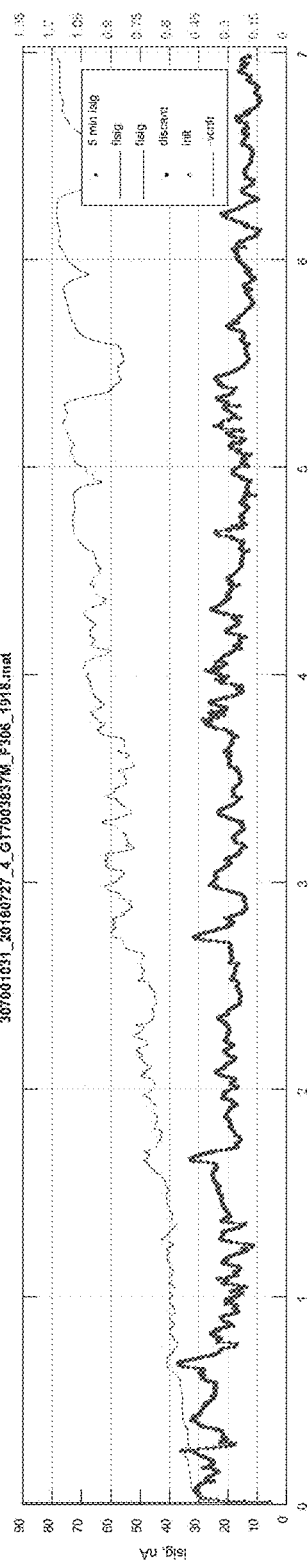
Figure 129B:
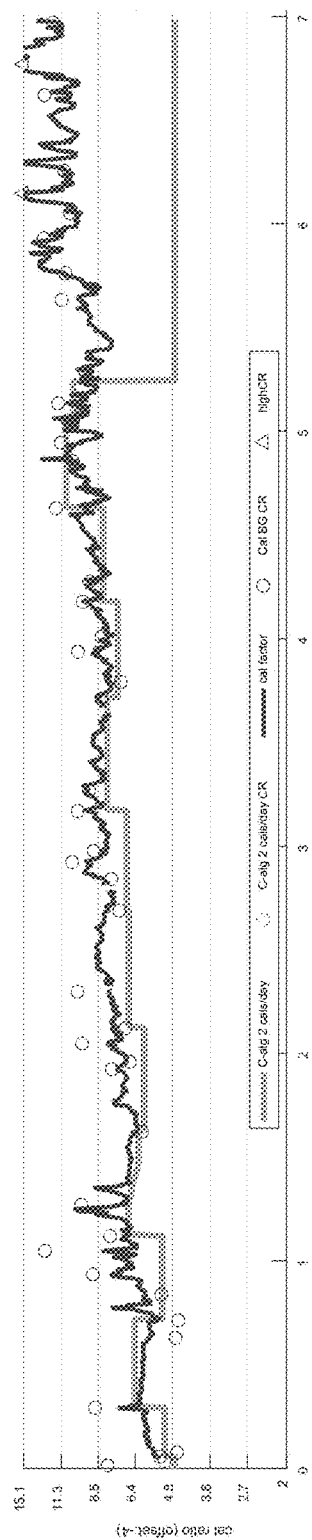
Figure 129C:
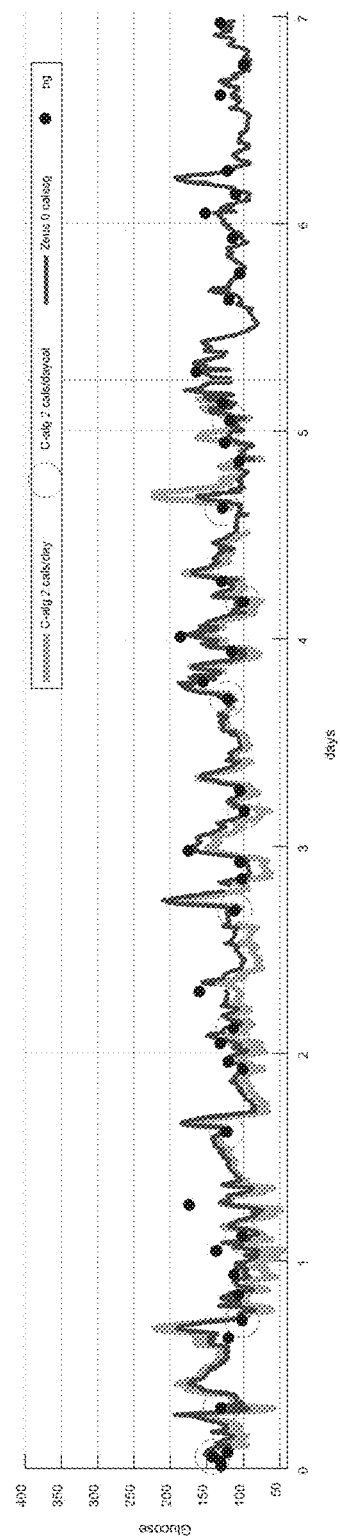

FIGS. 129A-129C show sensor trace-set data for a sensor that exhibits a decrease in sensitivity during a 7-day sensor wear in accordance with embodiments of the invention.

Figure 130A:
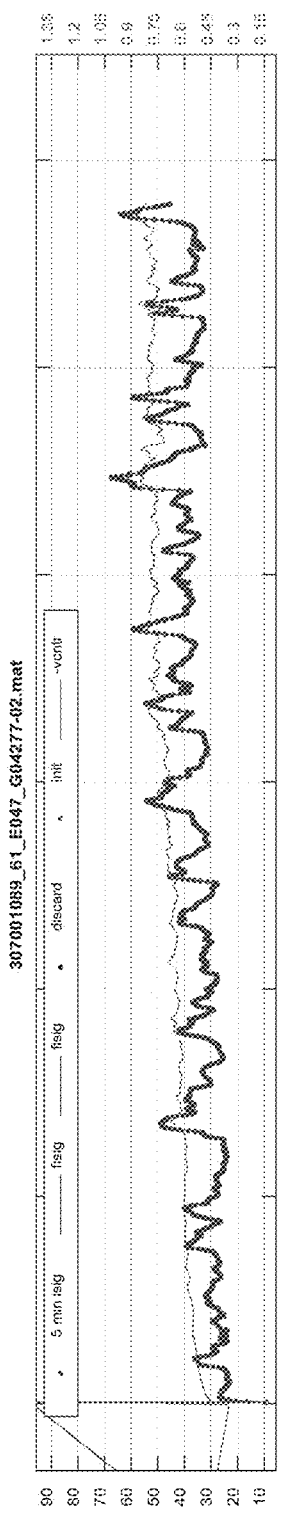
Figure 130B:
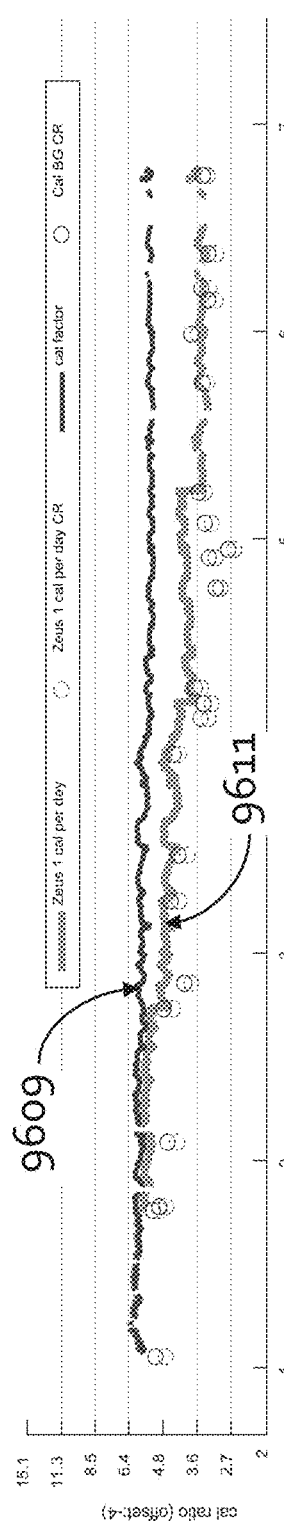
Figure 130C:
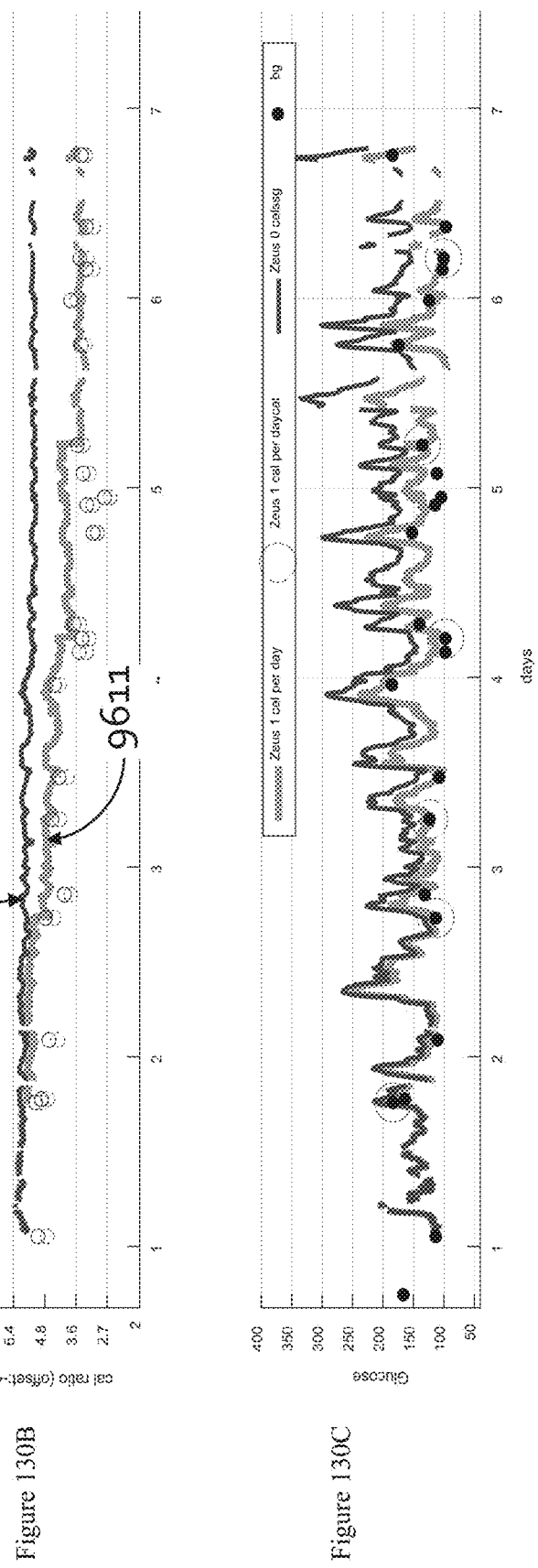

FIGS. 130A-130C show sensor trace-set data for a sensor that exhibits sensitivity increase during a 7-day sensor wear in accordance with embodiments of the invention.

Figure 131:
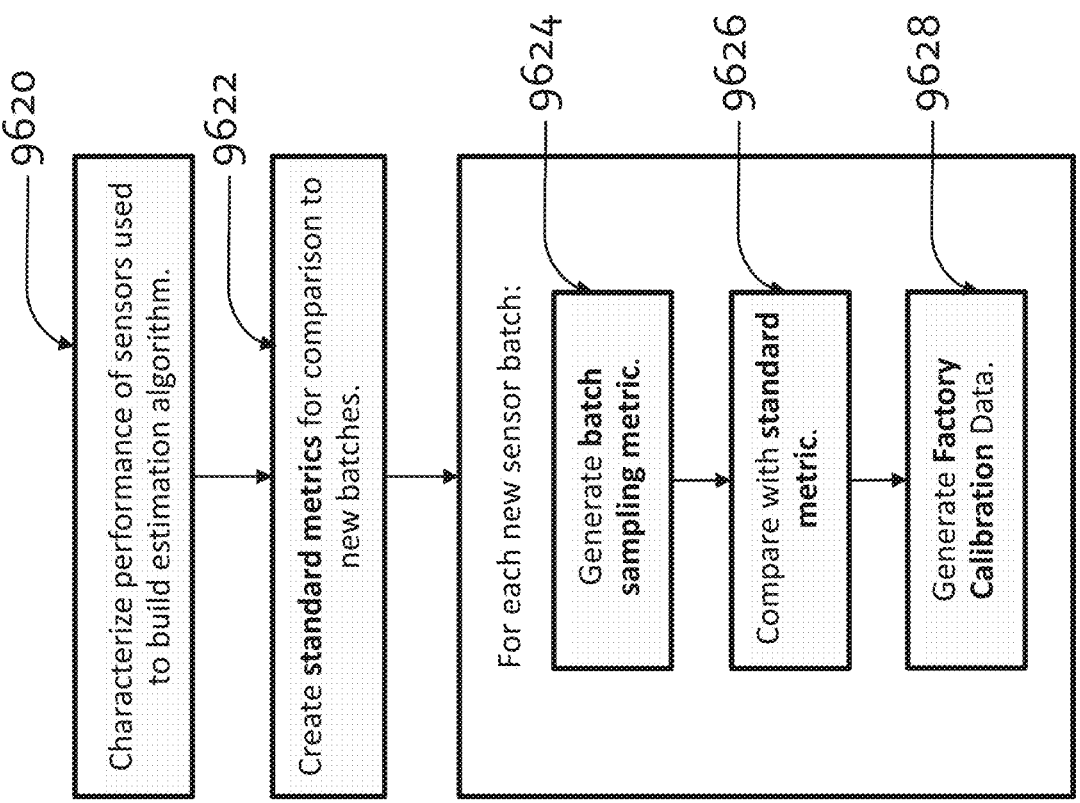

FIG. 131 shows a flow diagram for generating factory calibration metrics for sensors produced after a sensor glucose estimation algorithm has been trained and deployed, in accordance with embodiments of the invention.

Figure 132:
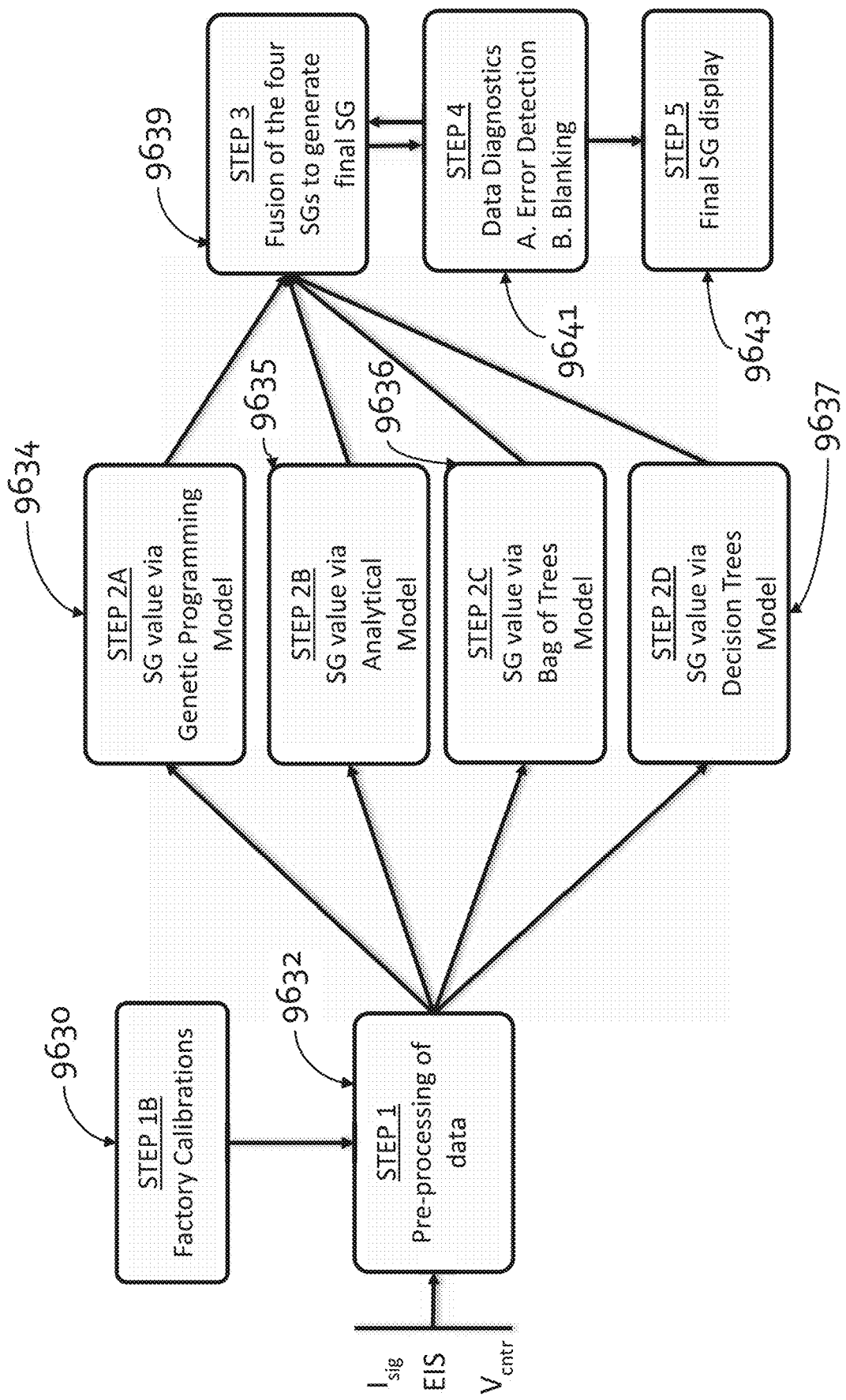

FIG. 132 shows a flow diagram and schematic of various modules of an algorithm, in accordance with embodiments of the invention, for correcting for the time varying change in sensor sensitivity using an optional factory calibration mechanism.

Figure 133:
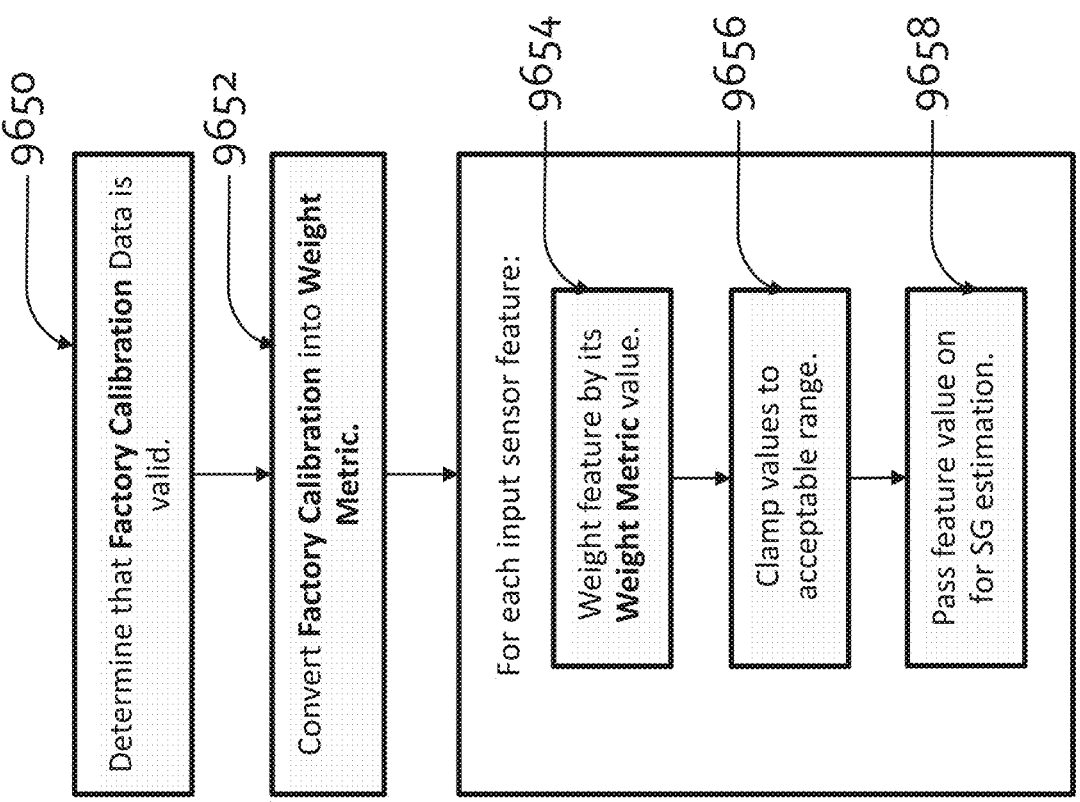

FIG. 133 shows the logic flow within the optional factory calibration block of FIG. 132.

Figure 134:
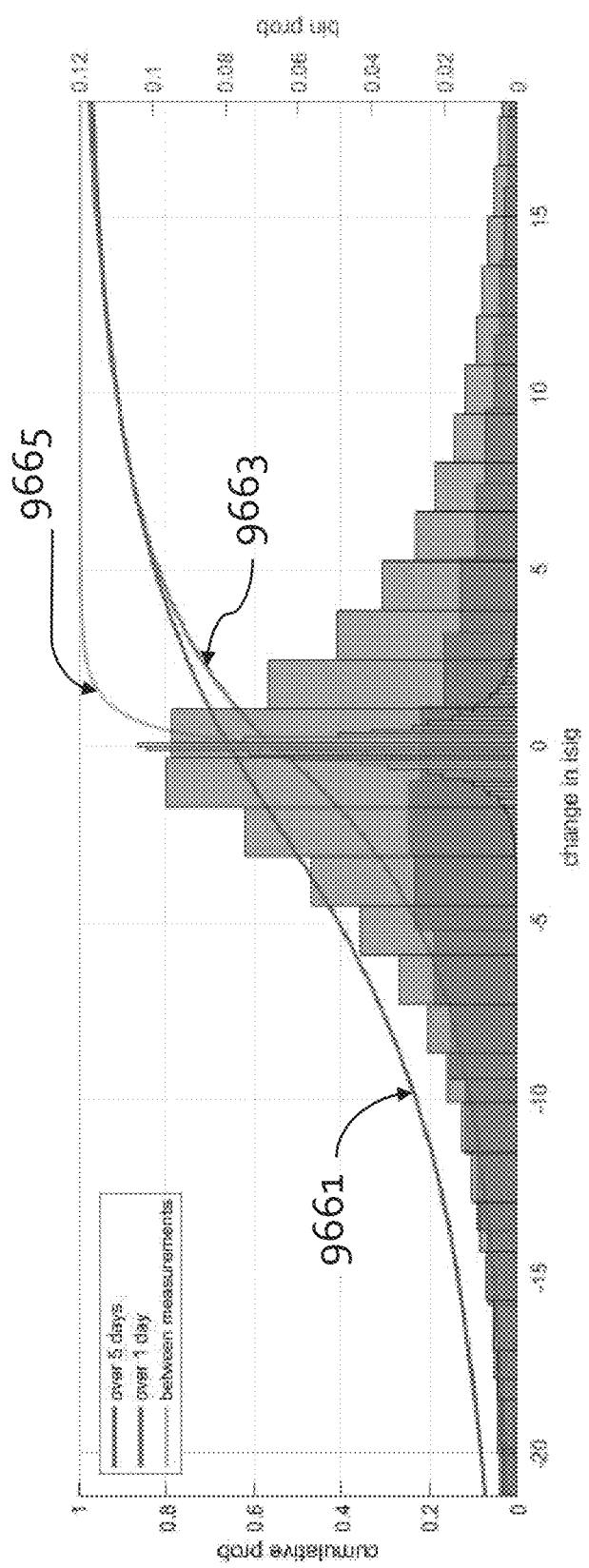

FIG. 134 shows histograms of changes in the value of a sensor characteristic feature with consistent distributions, in accordance with embodiments of the invention.

Figure 135:
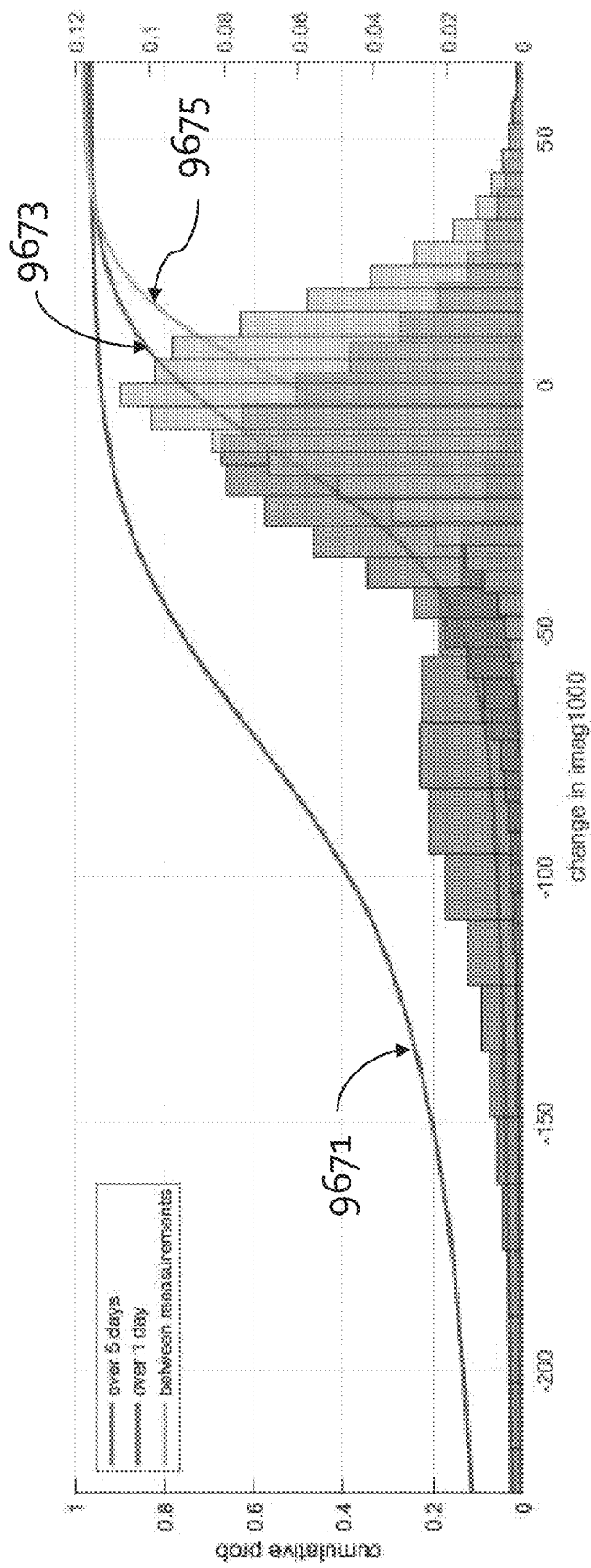

FIG. 135 shows histograms of changes in the value of a sensor characteristic feature with inconsistent distributions, in accordance with embodiments of the invention.

Figure 136:
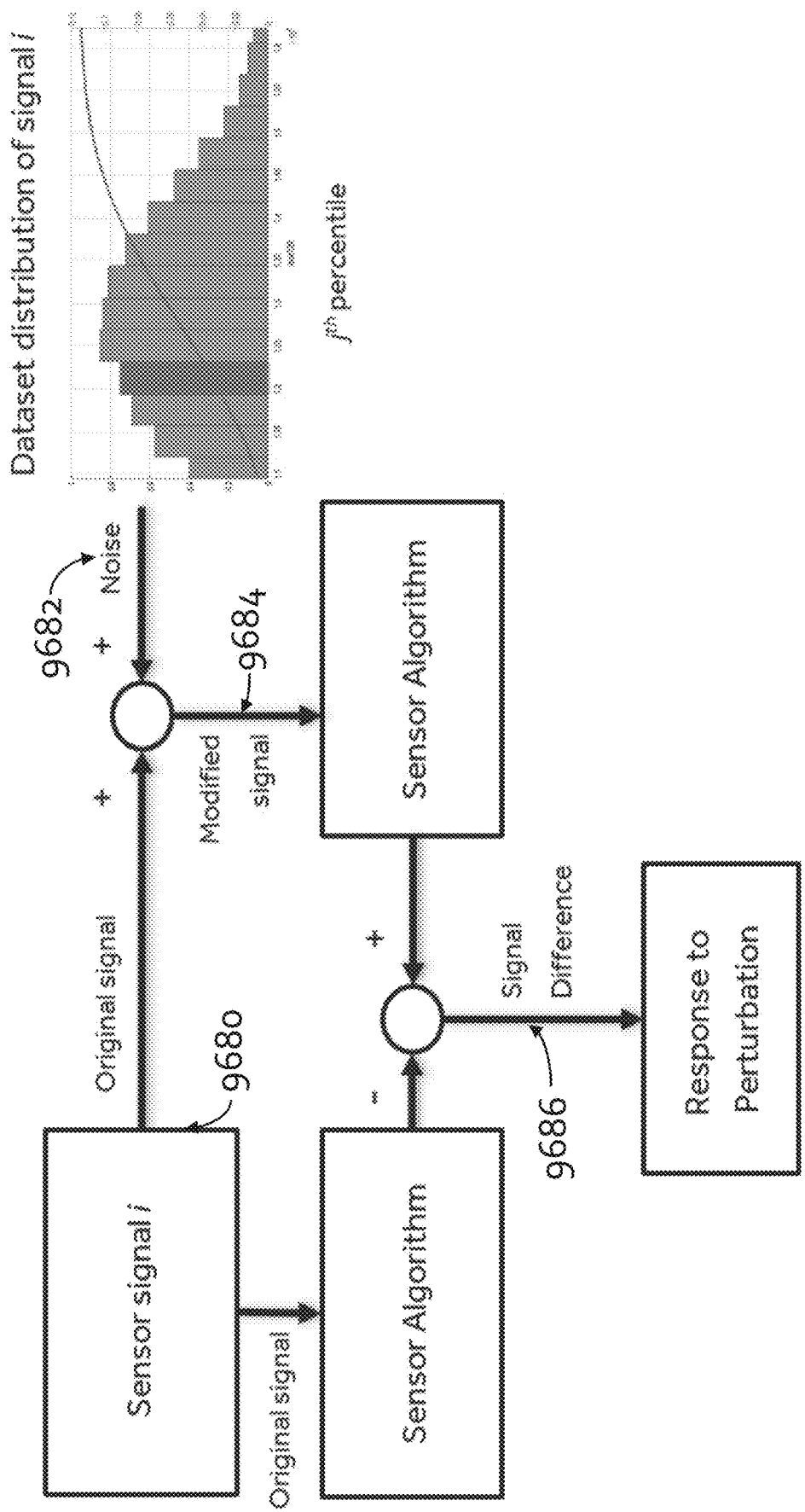

FIG. 136 shows a perturbation analysis in accordance with an embodiment of the invention.

Figure 137:
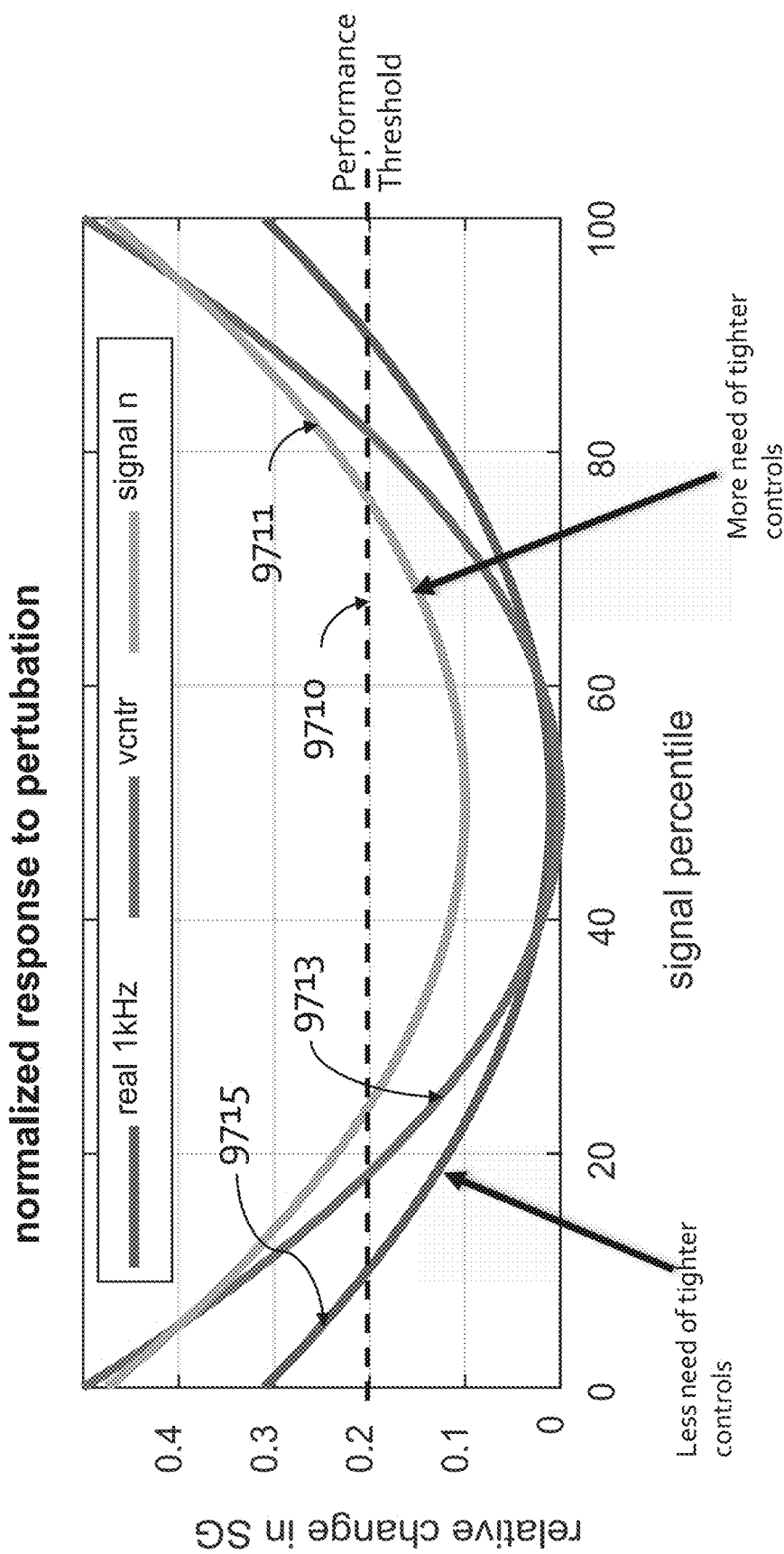

FIG. 137 shows an idealized, or normalized, response to perturbation for various features that may be used as factory calibration input, in accordance with embodiments of the invention.

Figure 138:
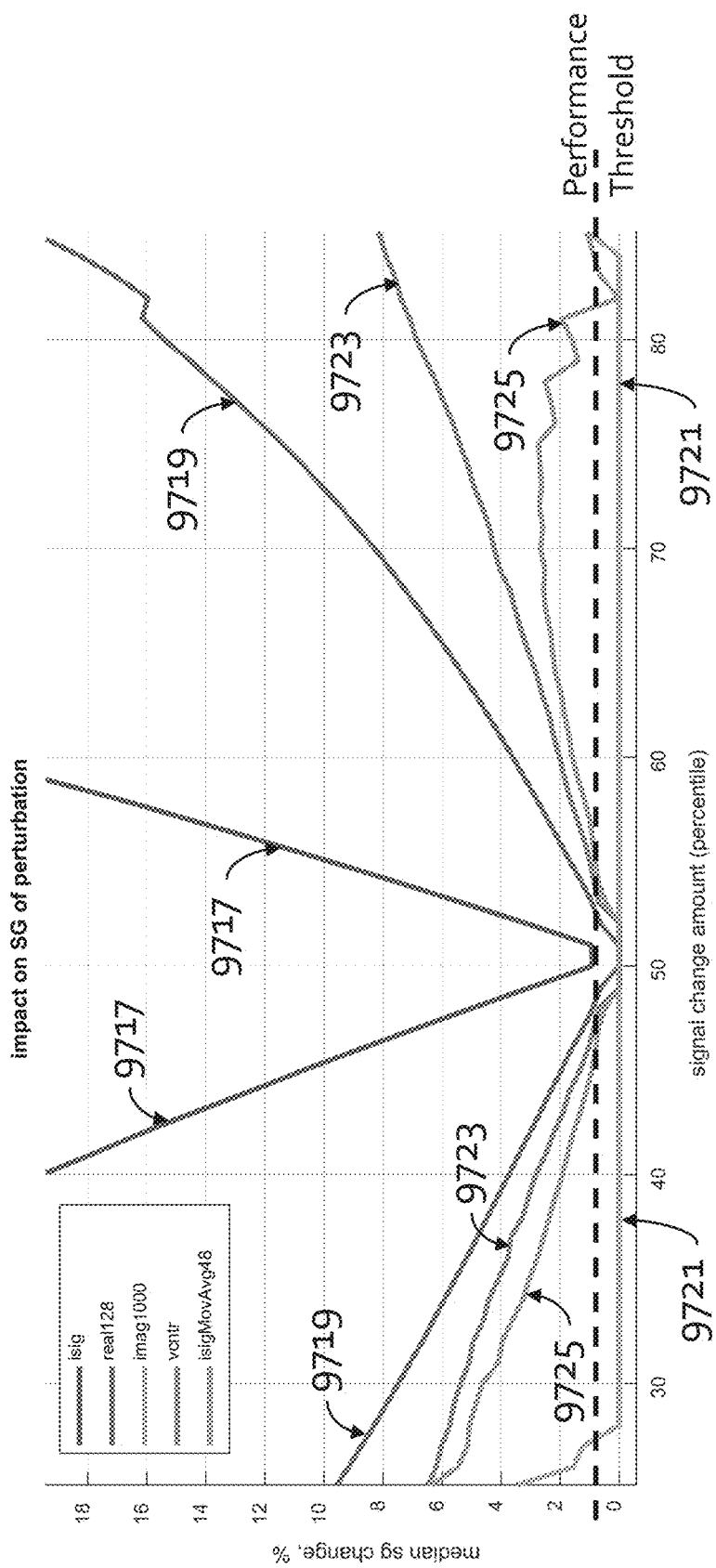

FIG. 138 shows actual results of perturbation analysis to determine the best features to be use for factory calibration, in accordance with embodiments of the invention.

FIG. 139 shows components of the calibration factor adjustment of an analytical sensor glucose estimation optimization model in accordance with embodiments of the invention.

Figure 140:
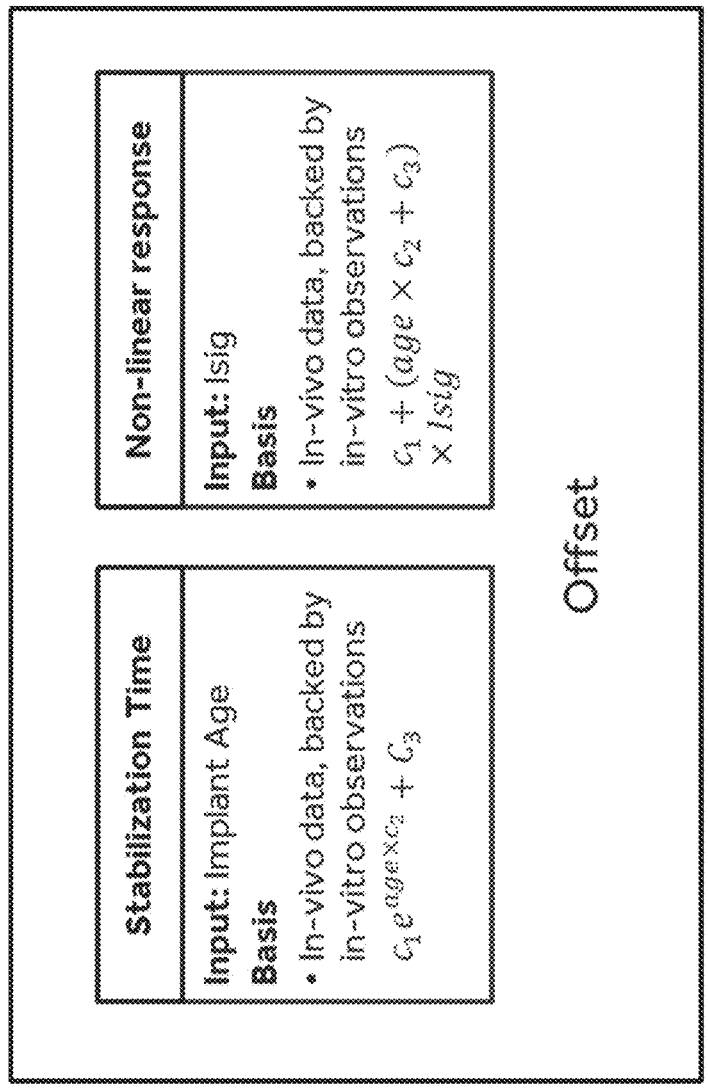

FIG. 140 shows components of the offset adjustment of an analytical optimization sensor glucose estimation model in accordance with embodiments of the invention.

DETAILED DESCRIPTION

In the following description, reference is made to the accompanying drawings which form a part hereof and which illustrate several embodiments of the present inventions. It is understood that other embodiments may be utilized, and structural and operational changes may be made without departing from the scope of the present inventions.

The inventions herein are described below with reference to flowchart illustrations of methods, systems, devices, apparatus, and programming and computer program products. It will be understood that each block of the flowchart illustrations, and combinations of blocks in the flowchart illustrations, can be implemented by programing instructions, including computer program instructions (as can any menu screens described in the figures). These computer program instructions may be loaded onto a computer or other programmable data processing apparatus (such as a controller, microcontroller, or processor in a sensor electronics device) to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein. Programming instructions may also be stored in and/or implemented via electronic circuitry, including integrated circuits (ICs) and Application Specific Integrated Circuits (ASICs) used in conjunction with sensor devices, apparatuses, and systems.

Figure 1:
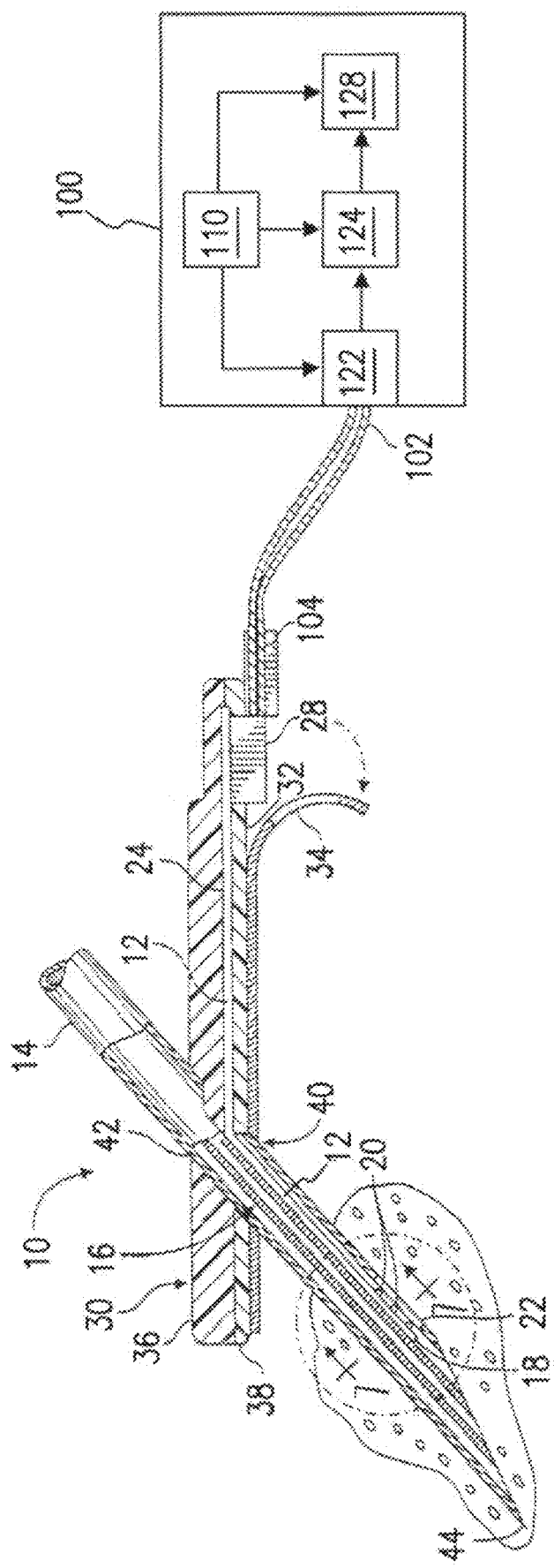
FIG. 1 is a perspective view of a subcutaneous sensor insertion set and block diagram of a sensor electronics device according to an embodiment of the invention.

FIG. 1 is a perspective view of a subcutaneous sensor insertion set and a block diagram of a sensor electronics device according to an embodiment of the invention. As illustrated in FIG. 1, a subcutaneous sensor set 10 is provided for subcutaneous placement of an active portion of a flexible sensor 12 (see, e.g., FIG. 2), or the like, at a selected site in the body of a user. The subcutaneous or percutaneous portion of the sensor set 10 includes a hollow, slotted insertion needle 14, and a cannula 16. The needle 14 is used to facilitate quick and easy subcutaneous placement of the cannula 16 at the subcutaneous insertion site. Inside the cannula 16 is a sensing portion 18 of the sensor 12 to expose one or more sensor electrodes 20 to the user's bodily fluids through a window 22 formed in the cannula 16. In an embodiment of the invention, the one or more sensor electrodes 20 may include a counter electrode, a reference electrode, and one or more working electrodes. After insertion, the insertion needle 14 is withdrawn to leave the cannula 16 with the sensing portion 18 and the sensor electrodes 20 in place at the selected insertion site.

In particular embodiments, the subcutaneous sensor set 10 facilitates accurate placement of a flexible thin film electrochemical sensor 12 of the type used for monitoring specific blood parameters representative of a user's condition. The sensor 12 monitors glucose levels in the body and may be used in conjunction with automated or semi-automated medication infusion pumps of the external or implantable type as described, e.g., in U.S. Pat. Nos. 4,562,751; 4,678,408; 4,685,903 or 4,573,994, to control delivery of insulin to a diabetic patient.

Particular embodiments of the flexible electrochemical sensor 12 are constructed in accordance with thin film mask techniques to include elongated thin film conductors embedded or encased between layers of a selected insulative material such as polyimide film or sheet, and membranes. The sensor electrodes 20 at a tip end of the sensing portion 18 are exposed through one of the insulative layers for direct contact with patient blood or other body fluids, when the sensing portion 18 (or active portion) of the sensor 12 is subcutaneously placed at an insertion site. The sensing portion 18 is joined to a connection portion 24 that terminates in conductive contact pads, or the like, which are also exposed through one of the insulative layers. In alternative embodiments, other types of implantable sensors, such as chemical based, optical based, or the like, may be used.

As is known in the art, the connection portion 24 and the contact pads are generally adapted for a direct wired electrical connection to a suitable monitor or sensor electronics device 100 for monitoring a user's condition in response to signals derived from the sensor electrodes 20. Further description of flexible thin film sensors of this general type are be found in U.S. Pat. No. 5,391,250, entitled METHOD OF FABRICATING THIN FILM SENSORS, which is herein incorporated by reference. The connection portion 24 may be conveniently connected electrically to the monitor or sensor electronics device 100 or by a connector block 28 (or the like) as shown and described in U.S. Pat. No. 5,482,473, entitled FLEX CIRCUIT CONNECTOR, which is also herein incorporated by reference. Thus, in accordance with embodiments of the present invention, subcutaneous sensor sets 10 may be configured or formed to work with either a wired or a wireless characteristic monitor system.

The sensor electrodes 20 may be used in a variety of sensing applications and may be configured in a variety of ways. For example, the sensor electrodes 20 may be used in physiological parameter sensing applications in which some type of biomolecule is used as a catalytic agent. For example, the sensor electrodes 20 may be used in a glucose and oxygen sensor having a glucose oxidase (GOx) enzyme catalyzing a reaction with the sensor electrodes 20. The sensor electrodes 20, along with a biomolecule or some other catalytic agent, may be placed in a human body in a vascular or non-vascular environment. For example, the sensor electrodes 20 and biomolecule may be placed in a vein and be subjected to a blood stream or may be placed in a subcutaneous or peritoneal region of the human body.

The monitor 100 may also be referred to as a sensor electronics device 100. The monitor 100 may include a power source 110, a sensor interface 122, processing electronics 124, and data formatting electronics 128. The monitor 100 may be coupled to the sensor set 10 by a cable 102 through a connector that is electrically coupled to the connector block 28 of the connection portion 24. In an alternative embodiment, the cable may be omitted. In this embodiment of the invention, the monitor 100 may include an appropriate connector for direct connection to the connection portion 104 of the sensor set 10. The sensor set 10 may be modified to have the connector portion 104 positioned at a different location, e.g., on top of the sensor set to facilitate placement of the monitor 100 over the sensor set.

In embodiments of the invention, the sensor interface 122, the processing electronics 124, and the data formatting electronics 128 are formed as separate semiconductor chips, however, alternative embodiments may combine the various semiconductor chips into a single, or multiple customized semiconductor chips. The sensor interface 122 connects with the cable 102 that is connected with the sensor set 10.

The power source 110 may be a battery. The battery can include three series silver oxide 357 battery cells. In alternative embodiments, different battery chemistries may be utilized, such as lithium-based chemistries, alkaline batteries, nickel metalhydride, or the like, and a different number of batteries may be used. The monitor 100 provides power to the sensor set via the power source 110, through the cable 102 and cable connector 104. In an embodiment of the invention, the power is a voltage provided to the sensor set 10. In an embodiment of the invention, the power is a current provided to the sensor set 10. In an embodiment of the invention, the power is a voltage provided at a specific voltage to the sensor set 10.

Figure 2A:
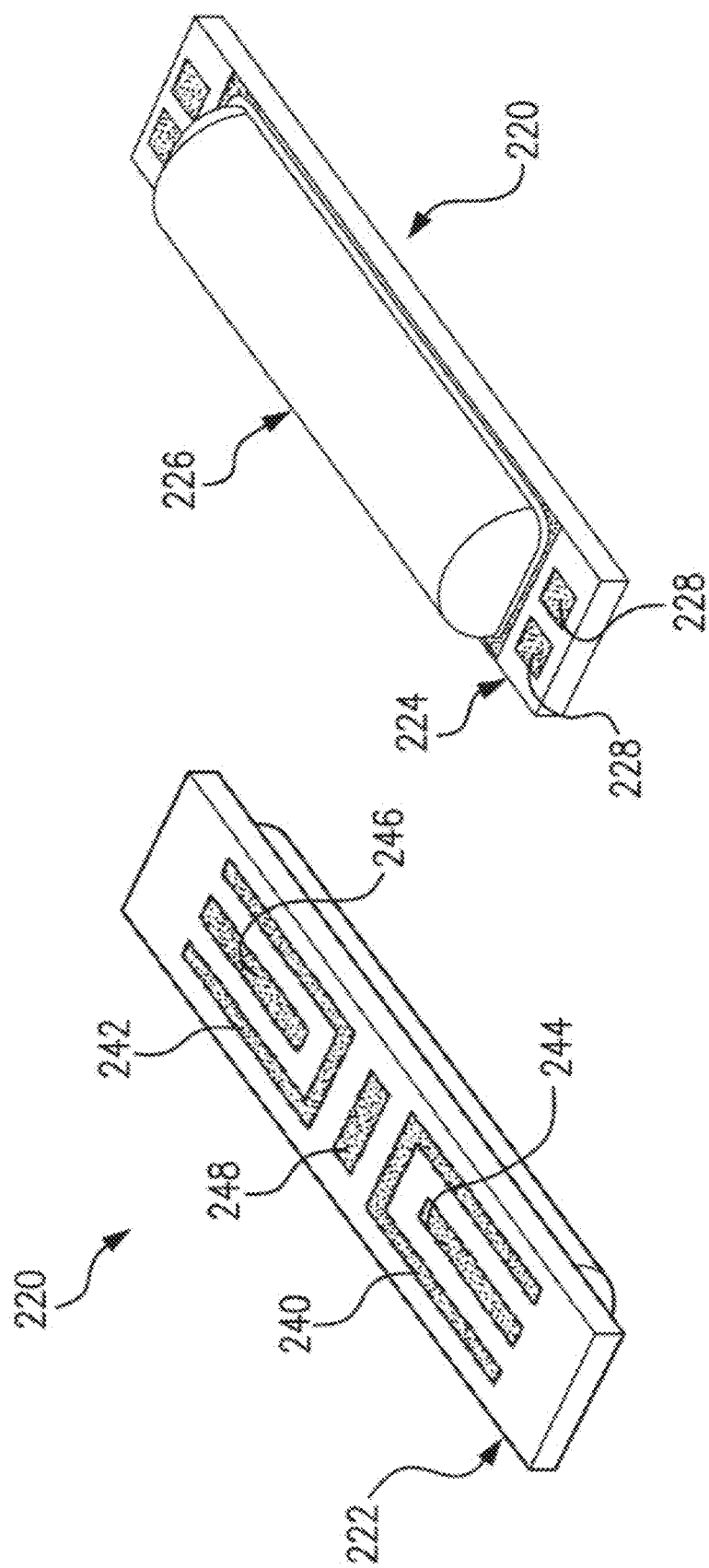
FIG. 2A illustrates a substrate having two sides, a first side which contains an electrode configuration and a second side which contains electronic circuitry.
Figure 2B:
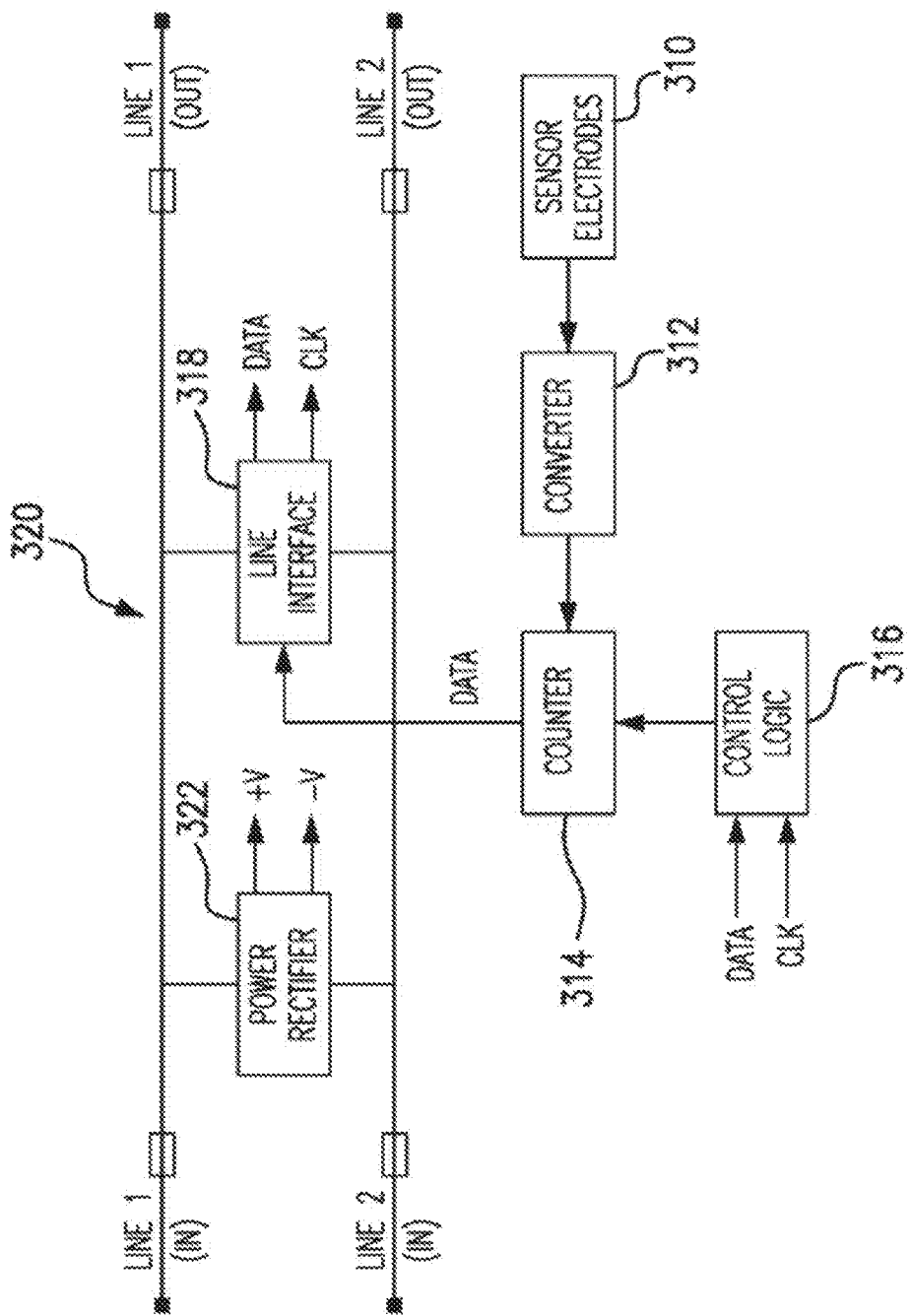
FIG. 2B illustrates a general block diagram of an electronic circuit for sensing an output of a sensor.

FIGS. 2A and 2B illustrate an implantable sensor, and electronics for driving the implantable sensor according to an embodiment of the present invention. FIG. 2A shows a substrate 220 having two sides, a first side 222 of which contains an electrode configuration and a second side 224 of which contains electronic circuitry. As may be seen in FIG. 2A, a first side 222 of the substrate comprises two counter electrode-working electrode pairs 240, 242, 244, 246 on opposite sides of a reference electrode 248. A second side 224 of the substrate comprises electronic circuitry. As shown, the electronic circuitry may be enclosed in a hermetically sealed casing 226, providing a protective housing for the electronic circuitry. This allows the sensor substrate 220 to be inserted into a vascular environment or other environment which may subject the electronic circuitry to fluids. By sealing the electronic circuitry in a hermetically sealed casing 226, the electronic circuitry may operate without risk of short circuiting by the surrounding fluids. Also shown in FIG. 2A are pads 228 to which the input and output lines of the electronic circuitry may be connected. The electronic circuitry itself may be fabricated in a variety of ways. According to an embodiment of the present invention, the electronic circuitry may be fabricated as an integrated circuit using techniques common in the industry.

FIG. 2B illustrates a general block diagram of an electronic circuit for sensing an output of a sensor according to an embodiment of the present invention. At least one pair of sensor electrodes 310 may interface to a data converter 312, the output of which may interface to a counter 314. The counter 314 may be controlled by control logic 316. The output of the counter 314 may connect to a line interface 318. The line interface 318 may be connected to input and output lines 320 and may also connect to the control logic 316. The input and output lines 320 may also be connected to a power rectifier 322.

The sensor electrodes 310 may be used in a variety of sensing applications and may be configured in a variety of ways. For example, the sensor electrodes 310 may be used in physiological parameter sensing applications in which some type of biomolecule is used as a catalytic agent. For example, the sensor electrodes 310 may be used in a glucose and oxygen sensor having a glucose oxidase (GOx) enzyme catalyzing a reaction with the sensor electrodes 310. The sensor electrodes 310, along with a biomolecule or some other catalytic agent, may be placed in a human body in a vascular or non-vascular environment. For example, the sensor electrodes 310 and biomolecule may be placed in a vein and be subjected to a blood stream.

Figure 3:
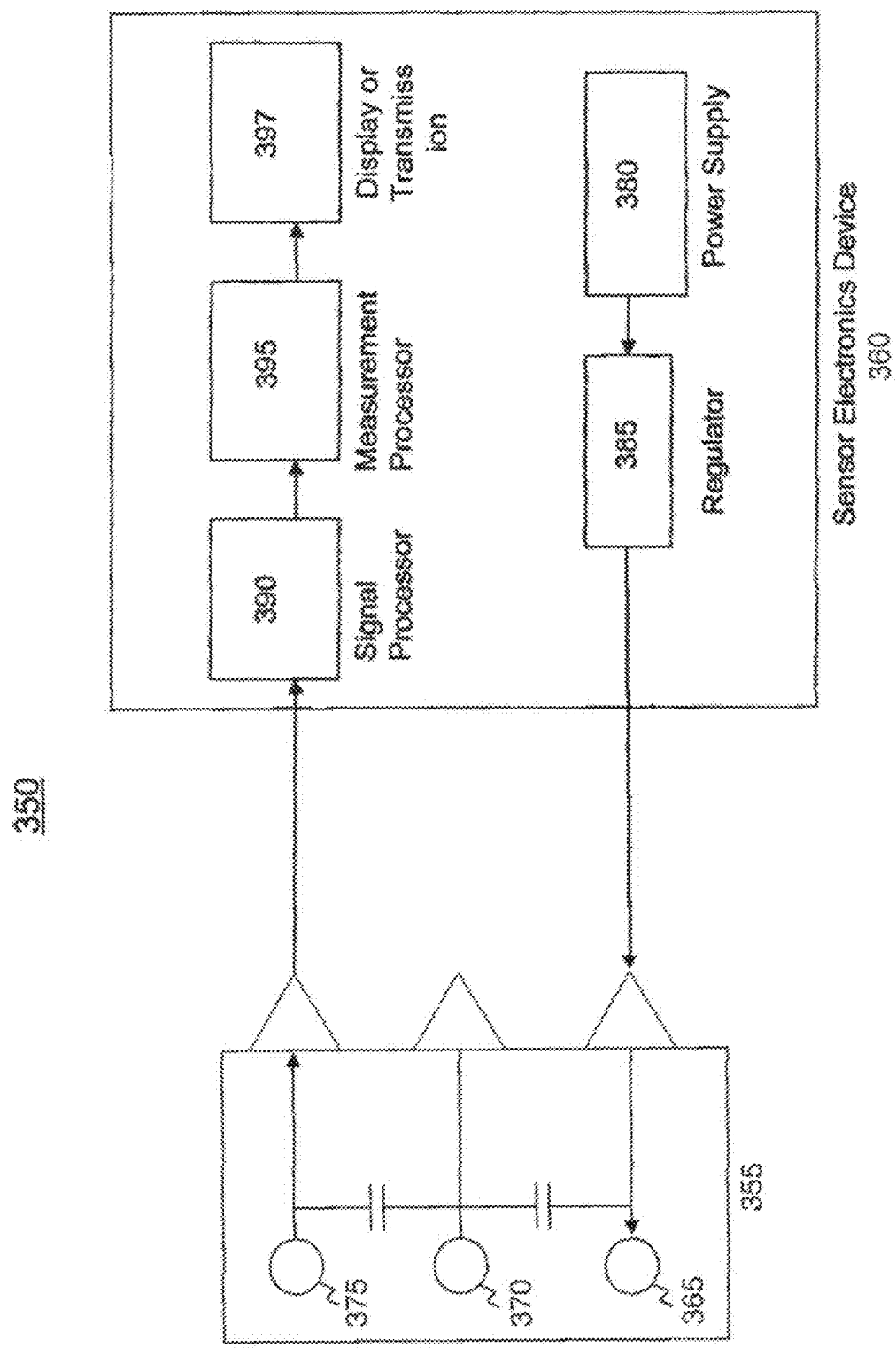
FIG. 3 illustrates a block diagram of a sensor electronics device and a sensor including a plurality of electrodes according to an embodiment of the invention.

FIG. 3 illustrates a block diagram of a sensor electronics device and a sensor including a plurality of electrodes according to an embodiment of the invention. The sensor set or system 350 includes a sensor 355 and a sensor electronics device 360. The sensor 355 includes a counter electrode 365, a reference electrode 370, and a working electrode 375. The sensor electronics device 360 includes a power supply 380, a regulator 385, a signal processor 390, a measurement processor 395, and a display/transmission module 397. The power supply 380 provides power (in the form of either a voltage, a current, or a voltage including a current) to the regulator 385. The regulator 385 transmits a regulated voltage to the sensor 355. In an embodiment of the invention, the regulator 385 transmits a voltage to the counter electrode 365 of the sensor 355.

The sensor 355 creates a sensor signal indicative of a concentration of a physiological characteristic being measured. For example, the sensor signal may be indicative of a blood glucose reading. In an embodiment of the invention utilizing subcutaneous sensors, the sensor signal may represent a level of hydrogen peroxide in a subject. In an embodiment of the invention where blood or cranial sensors are utilized, the amount of oxygen is being measured by the sensor and is represented by the sensor signal. In an embodiment of the invention utilizing implantable or long-term sensors, the sensor signal may represent a level of oxygen in the subject. The sensor signal is measured at the working electrode 375. In an embodiment of the invention, the sensor signal may be a current measured at the working electrode. In an embodiment of the invention, the sensor signal may be a voltage measured at the working electrode.

The signal processor 390 receives the sensor signal (e.g., a measured current or voltage) after the sensor signal is measured at the sensor 355 (e.g., the working electrode). The signal processor 390 processes the sensor signal and generates a processed sensor signal. The measurement processor 395 receives the processed sensor signal and calibrates the processed sensor signal utilizing reference values. In an embodiment of the invention, the reference values are stored in a reference memory and provided to the measurement processor 395. The measurement processor 395 generates sensor measurements. The sensor measurements may be stored in a measurement memory (not shown). The sensor measurements may be sent to a display/transmission device to be either displayed on a display in a housing with the sensor electronics or transmitted to an external device.

The sensor electronics device 360 may be a monitor which includes a display to display physiological characteristics readings. The sensor electronics device 360 may also be installed in a desktop computer, a pager, a television including communications capabilities, a laptop computer, a server, a network computer, a personal digital assistant (PDA), a portable telephone including computer functions, an infusion pump including a display, a glucose sensor including a display, and/or a combination infusion pump/glucose sensor. The sensor electronics device 360 may be housed in a blackberry, a network device, a home network device, or an appliance connected to a home network.

Figure 4:
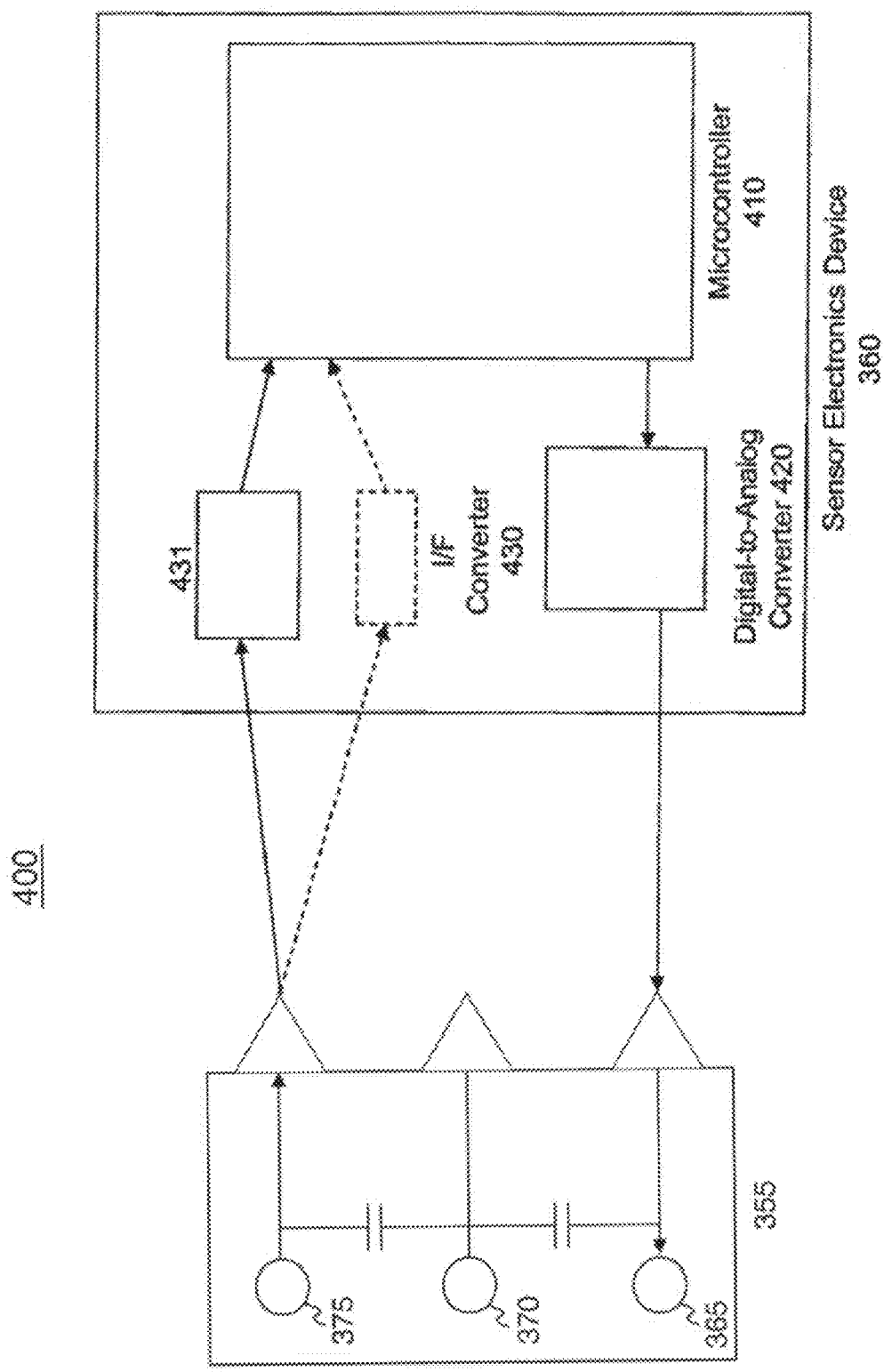
FIG. 4 illustrates an alternative embodiment of the invention including a sensor and a sensor electronics device according to an embodiment of the invention.

FIG. 4 illustrates an alternative embodiment of the invention including a sensor and a sensor electronics device according to an embodiment of the invention. The sensor set or sensor system 400 includes a sensor electronics device 360 and a sensor 355. The sensor includes a counter electrode 365, a reference electrode 370, and a working electrode 375. The sensor electronics device 360 includes a microcontroller 410 and a digital-to-analog converter (DAC) 420. The sensor electronics device 360 may also include a current-to-frequency converter (I/F converter) 430.

The microcontroller 410 includes software program code, which when executed, or programmable logic which, causes the microcontroller 410 to transmit a signal to the DAC 420, where the signal is representative of a voltage level or value that is to be applied to the sensor 355. The DAC 420 receives the signal and generates the voltage value at the level instructed by the microcontroller 410. In embodiments of the invention, the microcontroller 410 may change the representation of the voltage level in the signal frequently or infrequently. Illustratively, the signal from the microcontroller 410 may instruct the DAC 420 to apply a first voltage value for one second and a second voltage value for two seconds.

The sensor 355 may receive the voltage level or value. In an embodiment of the invention, the counter electrode 365 may receive the output of an operational amplifier which has as inputs the reference voltage and the voltage value from the DAC 420. The application of the voltage level causes the sensor 355 to create a sensor signal indicative of a concentration of a physiological characteristic being measured. In an embodiment of the invention, the microcontroller 410 may measure the sensor signal (e.g., a current value) from the working electrode. Illustratively, a sensor signal measurement circuit 431 may measure the sensor signal. In an embodiment of the invention, the sensor signal measurement circuit 431 may include a resistor and the current may be passed through the resistor to measure the value of the sensor signal. In an embodiment of the invention, the sensor signal may be a current level signal and the sensor signal measurement circuit 431 may be a current-to-frequency (I/F) converter 430. The current-to-frequency converter 430 may measure the sensor signal in terms of a current reading, convert it to a frequency-based sensor signal, and transmit the frequency-based sensor signal to the microcontroller 410. In embodiments of the invention, the microcontroller 410 may be able to receive frequency-based sensor signals easier than non-frequency-based sensor signals. The microcontroller 410 receives the sensor signal, whether frequency-based or non-frequency-based, and determines a value for the physiological characteristic of a subject, such as a blood glucose level. The microcontroller 410 may include program code, which when executed or run, is able to receive the sensor signal and convert the sensor signal to a physiological characteristic value. In an embodiment of the invention, the microcontroller 410 may convert the sensor signal to a blood glucose level. In an embodiment of the invention, the microcontroller 410 may utilize measurements stored within an internal memory in order to determine the blood glucose level of the subject. In an embodiment of the invention, the microcontroller 410 may utilize measurements stored within a memory external to the microcontroller 410 to assist in determining the blood glucose level of the subject.

After the physiological characteristic value is determined by the microcontroller 410, the microcontroller 410 may store measurements of the physiological characteristic values for a number of time periods. For example, a blood glucose value may be sent to the microcontroller 410 from the sensor every second or five seconds, and the microcontroller may save sensor measurements for five minutes or ten minutes of BG readings. The microcontroller 410 may transfer the measurements of the physiological characteristic values to a display on the sensor electronics device 360. For example, the sensor electronics device 360 may be a monitor which includes a display that provides a blood glucose reading for a subject. In an embodiment of the invention, the microcontroller 410 may transfer the measurements of the physiological characteristic values to an output interface of the microcontroller 410. The output interface of the microcontroller 410 may transfer the measurements of the physiological characteristic values, e.g., blood glucose values, to an external device, e.g., an infusion pump, a combined infusion pump/glucose meter, a computer, a personal digital assistant, a pager, a network appliance, a server, a cellular phone, or any computing device.

Figure 5:
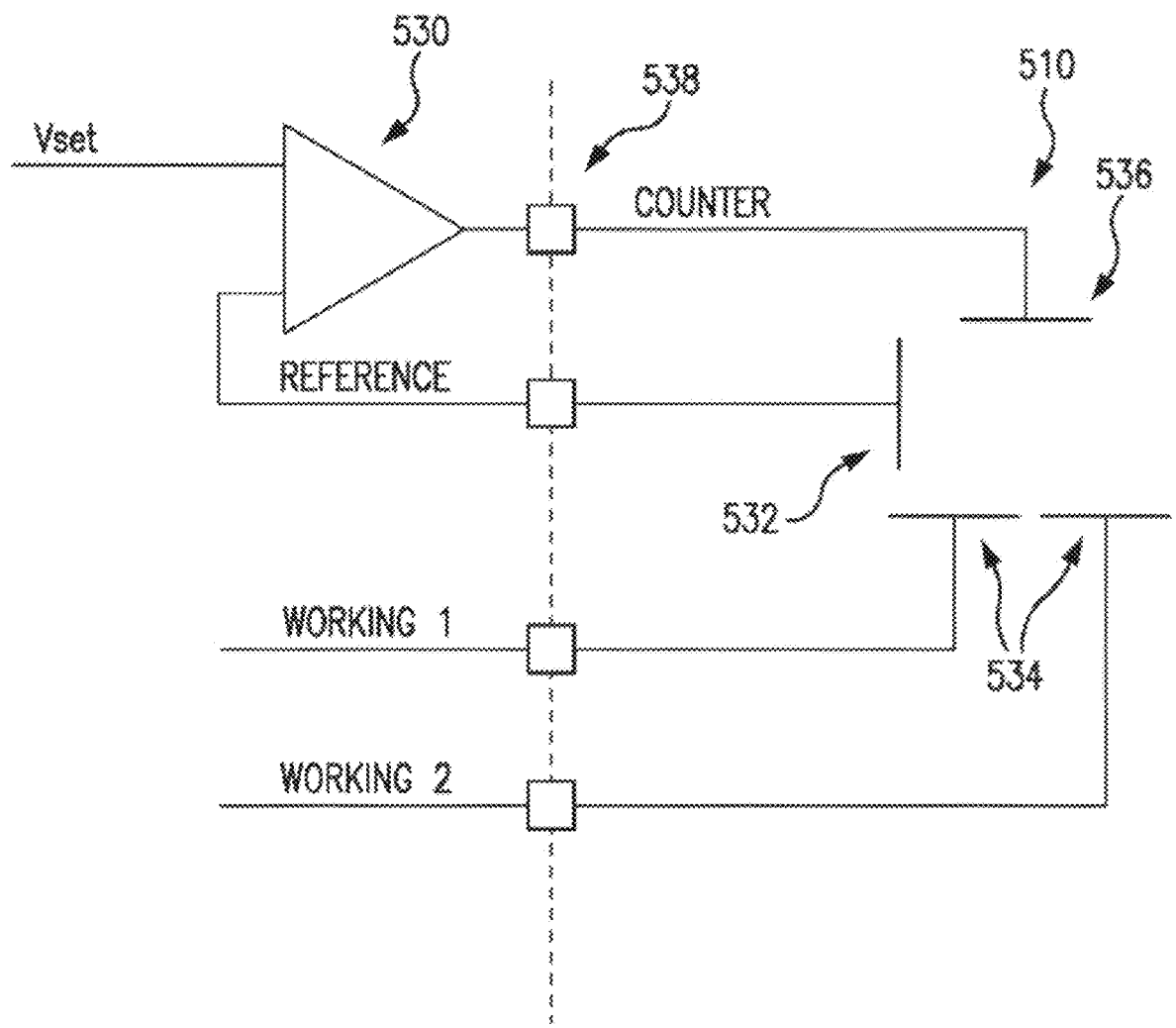
FIG. 5 illustrates an electronic block diagram of the sensor electrodes and a voltage being applied to the sensor electrodes according to an embodiment of the invention.

FIG. 5 illustrates an electronic block diagram of the sensor electrodes and a voltage being applied to the sensor electrodes according to an embodiment of the present invention. In the embodiment of the invention illustrated in FIG. 5, an op amp 530 or other servo-controlled device may connect to sensor electrodes 510 through a circuit/electrode interface 538. The op amp 530, utilizing feedback through the sensor electrodes, attempts to maintain a prescribed voltage (what the DAC may desire the applied voltage to be) between a reference electrode 532 and a working electrode 534 by adjusting the voltage at a counter electrode 536. Current may then flow from a counter electrode 536 to a working electrode 534. Such current may be measured to ascertain the electrochemical reaction between the sensor electrodes 510 and the biomolecule of a sensor that has been placed in the vicinity of the sensor electrodes 510 and used as a catalyzing agent. The circuitry disclosed in FIG. 5 may be utilized in a long-term or implantable sensor or may be utilized in a short-term or subcutaneous sensor.

In a long-term sensor embodiment, where a glucose oxidase (GOx) enzyme is used as a catalytic agent in a sensor, current may flow from the counter electrode 536 to a working electrode 534 only if there is oxygen in the vicinity of the enzyme and the sensor electrodes 510. Illustratively, if the voltage set at the reference electrode 532 is maintained at about 0.5 volts, the amount of current flowing from the counter electrode 536 to a working electrode 534 has a fairly linear relationship with unity slope to the amount of oxygen present in the area surrounding the enzyme and the electrodes. Thus, increased accuracy in determining an amount of oxygen in the blood may be achieved by maintaining the reference electrode 532 at about 0.5 volts and utilizing this region of the current-voltage curve for varying levels of blood oxygen. Different embodiments of the present invention may utilize different sensors having biomolecules other than a glucose oxidase enzyme and may, therefore, have voltages other than 0.5 volts set at the reference electrode.

As discussed above, during initial implantation or insertion of the sensor 510, the sensor 510 may provide inaccurate readings due to the adjusting of the subject to the sensor and also electrochemical byproducts caused by the catalyst utilized in the sensor. A stabilization period is needed for many sensors in order for the sensor 510 to provide accurate readings of the physiological parameter of the subject. During the stabilization period, the sensor 510 does not provide accurate blood glucose measurements. Users and manufacturers of the sensors may desire to improve the stabilization timeframe for the sensor so that the sensors can be utilized quickly after insertion into the subject's body or a subcutaneous layer of the subject.

Figure 6A:
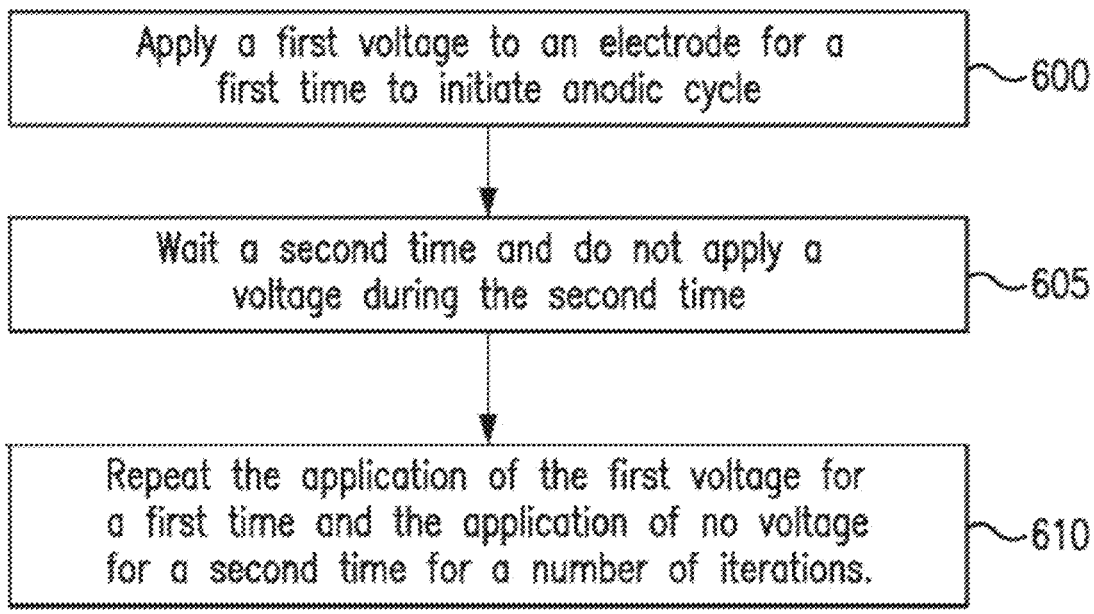
FIG. 6A illustrates a method of applying pulses during a stabilization timeframe in order to reduce the stabilization timeframe according to an embodiment of the invention.

In previous sensor electrode systems, the stabilization period or timeframe was one hour to three hours. In order to decrease the stabilization period or timeframe and increase the timeliness of accuracy of the sensor, a sensor (or electrodes of a sensor) may be subjected to a number of pulses rather than the application of one pulse followed by the application of another voltage. FIG. 6A illustrates a method of applying pulses during a stabilization timeframe in order to reduce the stabilization timeframe according to an embodiment of the present invention. In this embodiment of the invention, a voltage application device applies 600 a first voltage to an electrode for a first time or time period. In an embodiment of the invention, the first voltage may be a DC constant voltage. This results in an anodic current being generated. In an alternative embodiment of the invention, a digital-to-analog converter or another voltage source may supply the voltage to the electrode for a first time period. The anodic current means that electrons are being driven towards the electrode to which the voltage is applied. In an embodiment of the invention, an application device may apply a current instead of a voltage. In an embodiment of the invention where a voltage is applied to a sensor, after the application of the first voltage to the electrode, the voltage regulator may wait (i.e., not apply a voltage) for a second time, timeframe, or time period 605. In other words, the voltage application device waits until a second time period elapses. The non-application of voltage results in a cathodic current, which results in the gaining of electrons by the electrode to which the voltage is not applied. The application of the first voltage to the electrode for a first time period followed by the non-application of voltage for a second time period is repeated 610 for a number of iterations. This may be referred to as an anodic and cathodic cycle. In an embodiment of the invention, the number of total iterations of the stabilization method is three, i.e., three applications of the voltage for the first time period, each followed by no application of the voltage for the second time period. In an embodiment of the invention, the first voltage may be 1.07 volts. In an embodiment of the invention, the first voltage may be 0.535 volts. In an embodiment of the invention, the first voltage may be approximately 0.7 volts.

The repeated application of the voltage and the non-application of the voltage results in the sensor (and thus the electrodes) being subjected to an anodic-cathodic cycle. The anodic-cathodic cycle results in the reduction of electrochemical byproducts which are generated by a patient's body reacting to the insertion of the sensor or the implanting of the sensor. In an embodiment of the invention, the electrochemical byproducts cause generation of a background current, which results in inaccurate measurements of the physiological parameter of the subject. In an embodiment of the invention, the electrochemical byproduct may be eliminated. Under other operating conditions, the electrochemical byproducts may be reduced or significantly reduced. A successful stabilization method results in the anodic-cathodic cycle reaching equilibrium, electrochemical byproducts being significantly reduced, and background current being minimized.

In an embodiment of the invention, the first voltage being applied to the electrode of the sensor may be a positive voltage. In an embodiment of the invention, the first voltage being applied may be a negative voltage. In an embodiment of the invention, the first voltage may be applied to a working electrode. In an embodiment of the invention, the first voltage may be applied to the counter electrode or the reference electrode.

In embodiments of the invention, the duration of the voltage pulse and the non-application of voltage may be equal, e.g., such as three minutes each. In embodiments of the invention, the duration of the voltage application or voltage pulse may be different values, e.g., the first time and the second time may be different. In an embodiment of the invention, the first time period may be five minutes and the waiting period may be two minutes. In an embodiment of the invention, the first time period may be two minutes and the waiting period (or second timeframe) may be five minutes. In other words, the duration for the application of the first voltage may be two minutes and there may be no voltage applied for five minutes. This timeframe is only meant to be illustrative and should not be limiting. For example, a first timeframe may be two, three, five or ten minutes and the second timeframe may be five minutes, ten minutes, twenty minutes, or the like. The timeframes (e.g., the first time and the second time) may depend on unique characteristics of different electrodes, the sensors, and/or the patient's physiological characteristics.

In embodiments of the invention, more or less than three pulses may be utilized to stabilize the glucose sensor. In other words, the number of iterations may be greater than 3 or less than three. For example, four voltage pulses (e.g., a high voltage followed by no voltage) may be applied to one of the electrodes or six voltage pulses may be applied to one of the electrodes.

Illustratively, three consecutive pulses of 1.07 volts (followed by respective waiting periods) may be sufficient for a sensor implanted subcutaneously. In an embodiment of the invention, three consecutive voltage pulses of 0.7 volts may be utilized. The three consecutive pulses may have a higher or lower voltage value, either negative or positive, for a sensor implanted in blood or cranial fluid, e.g., the long-term or permanent sensors. In addition, more than three pulses (e.g., five, eight, twelve) may be utilized to create the anodic-cathodic cycling between anodic and cathodic currents in any of the subcutaneous, blood, or cranial fluid sensors.

Figure 6B:
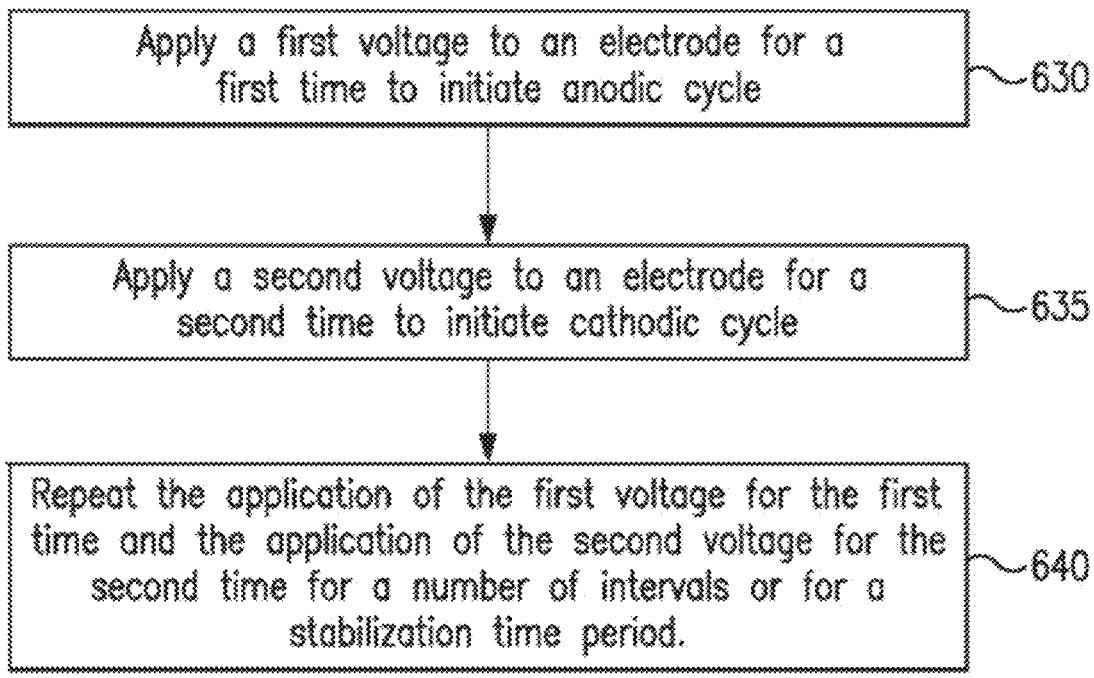
FIG. 6B illustrates a method of stabilizing sensors according to an embodiment of the invention.

FIG. 6B illustrates a method of stabilizing sensors according to an embodiment of the invention. In the embodiment of the invention illustrated in FIG. 6B, a voltage application device may apply 630 a first voltage to the sensor for a first time to initiate an anodic cycle at an electrode of the sensor. The voltage application device may be a DC power supply, a digital-to-analog converter, or a voltage regulator. After the first time period has elapsed, a second voltage is applied 635 to the sensor for a second time to initiate a cathodic cycle at an electrode of the sensor. Illustratively, rather than no voltage being applied, as is illustrated in the method of FIG. 6A, a different voltage (from the first voltage) is applied to the sensor during the second timeframe. In an embodiment of the invention, the application of the first voltage for the first time and the application of the second voltage for the second time is repeated 640 for a number of iterations. In an embodiment of the invention, the application of the first voltage for the first time and the application of the second voltage for the second time may each be applied for a stabilization timeframe, e.g., 10 minutes, 15 minutes, or 20 minutes rather than for a number of iterations. This stabilization timeframe is the entire timeframe for the stabilization sequence, e.g., until the sensor (and electrodes) are stabilized. The benefit of this stabilization methodology is a faster run-in of the sensors, less background current (in other words a suppression of some the background current), and a better glucose response.

In an embodiment of the invention, the first voltage may be 0.535 volts applied for five minutes, the second voltage may be 1.070 volts applied for two minutes, the first voltage of 0.535 volts may be applied for five minutes, the second voltage of 1.070 volts may be applied for two minutes, the first voltage of 0.535 volts may be applied for five minutes, and the second voltage of 1.070 volts may be applied for two minutes. In other words, in this embodiment, there are three iterations of the voltage pulsing scheme. The pulsing methodology may be changed in that the second timeframe, e.g., the timeframe of the application of the second voltage may be lengthened from two minutes to five minutes, ten minutes, fifteen minutes, or twenty minutes. In addition, after the three iterations are applied in this embodiment of the invention, a nominal working voltage of 0.535 volts may be applied.

The 1.070 and 0.535 volts are illustrative values. Other voltage values may be selected based on a variety of factors. These factors may include the type of enzyme utilized in the sensor, the membranes utilized in the sensor, the operating period of the sensor, the length of the pulse, and/or the magnitude of the pulse. Under certain operating conditions, the first voltage may be in a range of 1.00 to 1.09 volts and the second voltage may be in a range of 0.510 to 0.565 volts. In other operating embodiments, the ranges that bracket the first voltage and the second voltage may have a higher range, e.g., 0.3 volts, 0.6 volts, 0.9 volts, depending on the voltage sensitivity of the electrode in the sensor. Under other operating conditions, the voltage may be in a range of 0.8 volts to 1.34 volts and the other voltage may be in a range of 0.335 to 0.735. Under other operating conditions, the range of the higher voltage may be smaller than the range of the lower voltage. Illustratively, the higher voltage may be in a range of 0.9 to 1.09 volts and the lower voltage may be in a range of 0.235 to 0.835 volts.

In an embodiment of the invention, the first voltage and the second voltage may be positive voltages, or alternatively in other embodiments of the invention, negative voltages. In an embodiment of the invention, the first voltage may be positive, and the second voltage may be negative, or alternatively, the first voltage may be negative and the second voltage may be positive. The first voltage may be different voltage levels for each of the iterations. In an embodiment of the invention, the first voltage may be a D.C. constant voltage. In other embodiments of the invention, the first voltage may be a ramp voltage, a sinusoid-shaped voltage, a stepped voltage, or other commonly utilized voltage waveforms. In an embodiment of the invention, the second voltage may be a D.C. constant voltage, a ramp voltage, a sinusoid-shaped voltage, a stepped voltage, or other commonly utilized voltage waveforms. In an embodiment of the invention, the first voltage or the second voltage may be an AC signal riding on a DC waveform. In an embodiment of the invention, the first voltage may be one type of voltage, e.g., a ramp voltage, and the second voltage may be a second type of voltage, e.g., a sinusoid-shaped voltage. In an embodiment of the invention, the first voltage (or the second voltage) may have different waveform shapes for each of the iterations. For example, if there are three cycles in a stabilization method, in a first cycle, the first voltage may be a ramp voltage, in the second cycle, the first voltage may be a constant voltage, and in the third cycle, the first voltage may be a sinusoidal voltage.

In an embodiment of the invention, a duration of the first timeframe and a duration of the second timeframe may have the same value, or alternatively, the duration of the first timeframe and the second timeframe may have different values. For example, the duration of the first timeframe may be two minutes and the duration of the second timeframe may be five minutes and the number of iterations may be three. As discussed above, the stabilization method may include a number of iterations. In embodiments of the invention, during different iterations of the stabilization method, the duration of each of the first timeframes may change and the duration of each of the second timeframes may change. Illustratively, during the first iteration of the anodic-cathodic cycling, the first timeframe may be 2 minutes and the second timeframe may be 5 minutes. During the second iteration, the first timeframe may be 1 minute, and the second timeframe may be 3 minutes. During the third iteration, the first timeframe may be 3 minutes and the second timeframe may be 10 minutes.

In an embodiment of the invention, a first voltage of 0.535 volts is applied to an electrode in a sensor for two minutes to initiate an anodic cycle, then a second voltage of 1.07 volts is applied to the electrode for five minutes to initiate a cathodic cycle. The first voltage of 0.535 volts is then applied again for two minutes to initiate the anodic cycle and a second voltage of 1.07 volts is applied to the sensor for five minutes. In a third iteration, 0.535 volts is applied for two minutes to initiate the anodic cycle and then 1.07 volts is applied for five minutes. The voltage applied to the sensor is then 0.535 during the actual working timeframe of the sensor, e.g., when the sensor provides readings of a physiological characteristic of a subject.

Shorter duration voltage pulses may be utilized in the embodiment of FIGS. 6A and 6B. The shorter duration voltage pulses may be utilized to apply the first voltage, the second voltage, or both. In an embodiment of the present invention, the magnitude of the shorter duration voltage pulse for the first voltage is −1.07 volts and the magnitude of the shorter duration voltage pulse for the second voltage is approximately half of the high magnitude, e.g., −0.535 volts. Alternatively, the magnitude of the shorter duration pulse for the first voltage may be 0.535 volts and the magnitude of the shorter duration pulse for the second voltage is 1.07 volts.

In embodiments of the invention utilizing short duration pulses, the voltage may not be applied continuously for the entire first time period. Instead, the voltage application device may transmit a number of short duration pulses during the first time period. In other words, a number of mini-width or short duration voltage pulses may be applied to the electrodes of the sensor over the first time period. Each mini-width or short duration pulse may have a width of a number of milliseconds. Illustratively, this pulse width may be 30 milliseconds, 50 milliseconds, 70 milliseconds or 200 milliseconds. These values are meant to be illustrative and not limiting. In an embodiment of the invention, such as the embodiment illustrated in FIG. 6A, these short duration pulses are applied to the sensor (electrode) for the first time period and then no voltage is applied for the second time period.

In an embodiment of the invention, each short duration pulse may have the same time duration within the first time period. For example, each short duration voltage pulse may have a time width of 50 milliseconds and each pulse delay between the pulses may be 950 milliseconds. In this example, if two minutes is the measured time for the first timeframe, then 120 short duration voltage pulses may be applied to the sensor. In an embodiment of the invention, each of the short duration voltage pulses may have different time durations. In an embodiment of the invention, each of the short duration voltage pulses may have the same amplitude values. In an embodiment of the invention, each of the short duration voltage pulses may have different amplitude values. By utilizing short duration voltage pulses rather than a continuous application of voltage to the sensor, the same anodic and cathodic cycling may occur and the sensor (e.g., electrodes) is subjected to less total energy or charge over time. The use of short duration voltage pulses utilizes less power as compared to the application of continuous voltage to the electrodes because there is less energy applied to the sensors (and thus the electrodes).

Figure 6C:
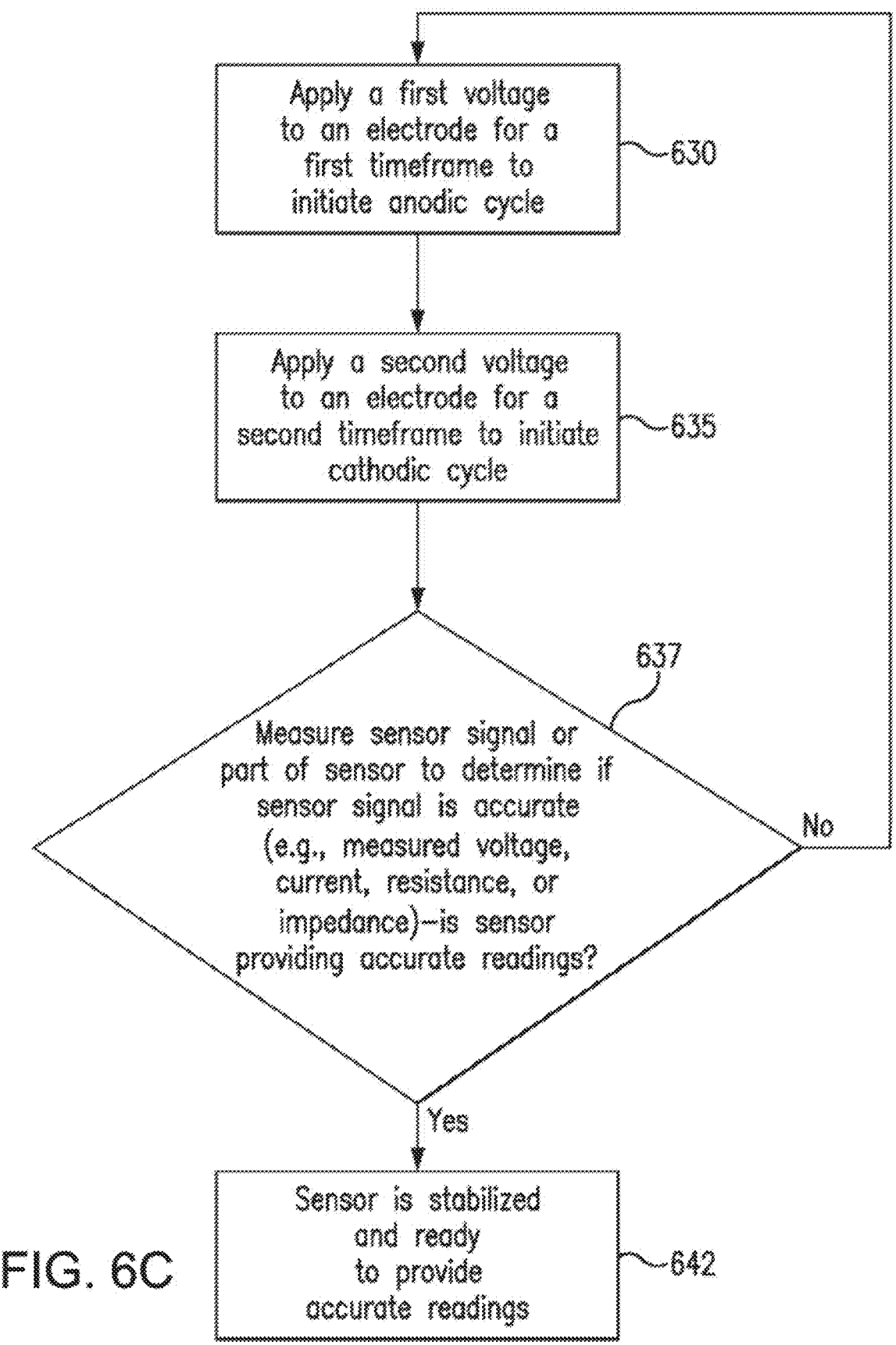
FIG. 6C illustrates utilization of feedback in stabilizing the sensors according to an embodiment of the invention.

FIG. 6C illustrates utilization of feedback in stabilizing the sensor according to an embodiment of the present invention. The sensor system may include a feedback mechanism to determine if additional pulses are needed to stabilize a sensor. In an embodiment of the invention, a sensor signal generated by an electrode (e.g., a working electrode) may be analyzed to determine if the sensor signal is stabilized. A first voltage is applied 630 to an electrode for a first timeframe to initiate an anodic cycle. A second voltage is applied 635 to an electrode for a second timeframe to initiate a cathodic cycle. In an embodiment of the invention, an analyzation module may analyze a sensor signal (e.g., the current emitted by the sensor signal, a resistance at a specific point in the sensor, an impedance at a specific node in the sensor) and determine if a threshold measurement has been reached 637 (e.g., determining if the sensor is providing accurate readings by comparing against the threshold measurement). If the sensor readings are determined to be accurate, which represents that the electrode (and thus the sensor) is stabilized 642, no additional application of the first voltage and/or the second voltage may be generated. If stability was not achieved, in an embodiment of the invention, then an additional anodic/cathodic cycle is initiated by the application 630 of a first voltage to an electrode for a first time period and then the application 635 of the second voltage to the electrode for a second time period.

In embodiments of the invention, the analyzation module may be employed after an anodic/cathodic cycle of three applications of the first voltage and the second voltage to an electrode of the sensor. In an embodiment of the invention, an analyzation module may be employed after one application of the first voltage and the second voltage, as is illustrated in FIG. 6C.

In an embodiment of the invention, the analyzation module may be utilized to measure a voltage emitted after a current has been introduced across an electrode or across two electrodes. The analyzation module may monitor a voltage level at the electrode or at the receiving level. In an embodiment of the invention, if the voltage level is above a certain threshold, this may mean that the sensor is stabilized. In an embodiment of the invention, if the voltage level falls below a threshold level, this may indicate that the sensor is stabilized and ready to provide readings. In an embodiment of the invention, a current may be introduced to an electrode or across a couple of electrodes. The analyzation module may monitor a current level emitted from the electrode. In this embodiment of the invention, the analyzation module may be able to monitor the current if the current is different by an order of magnitude from the sensor signal current. If the current is above or below a current threshold, this may signify that the sensor is stabilized.

In an embodiment of the invention, the analyzation module may measure an impedance between two electrodes of the sensor. The analyzation module may compare the impedance against a threshold or target impedance value and if the measured impedance is lower than the target or threshold impedance, the sensor (and hence the sensor signal) may be stabilized. In an embodiment of the invention, the analyzation module may measure a resistance between two electrodes of the sensor. In this embodiment of the invention, if the analyzation module compares the resistance against a threshold or target resistance value and the measured resistance value is less than the threshold or target resistance value, then the analyzation module may determine that the sensor is stabilized and that the sensor signal may be utilized.

Figure 7:
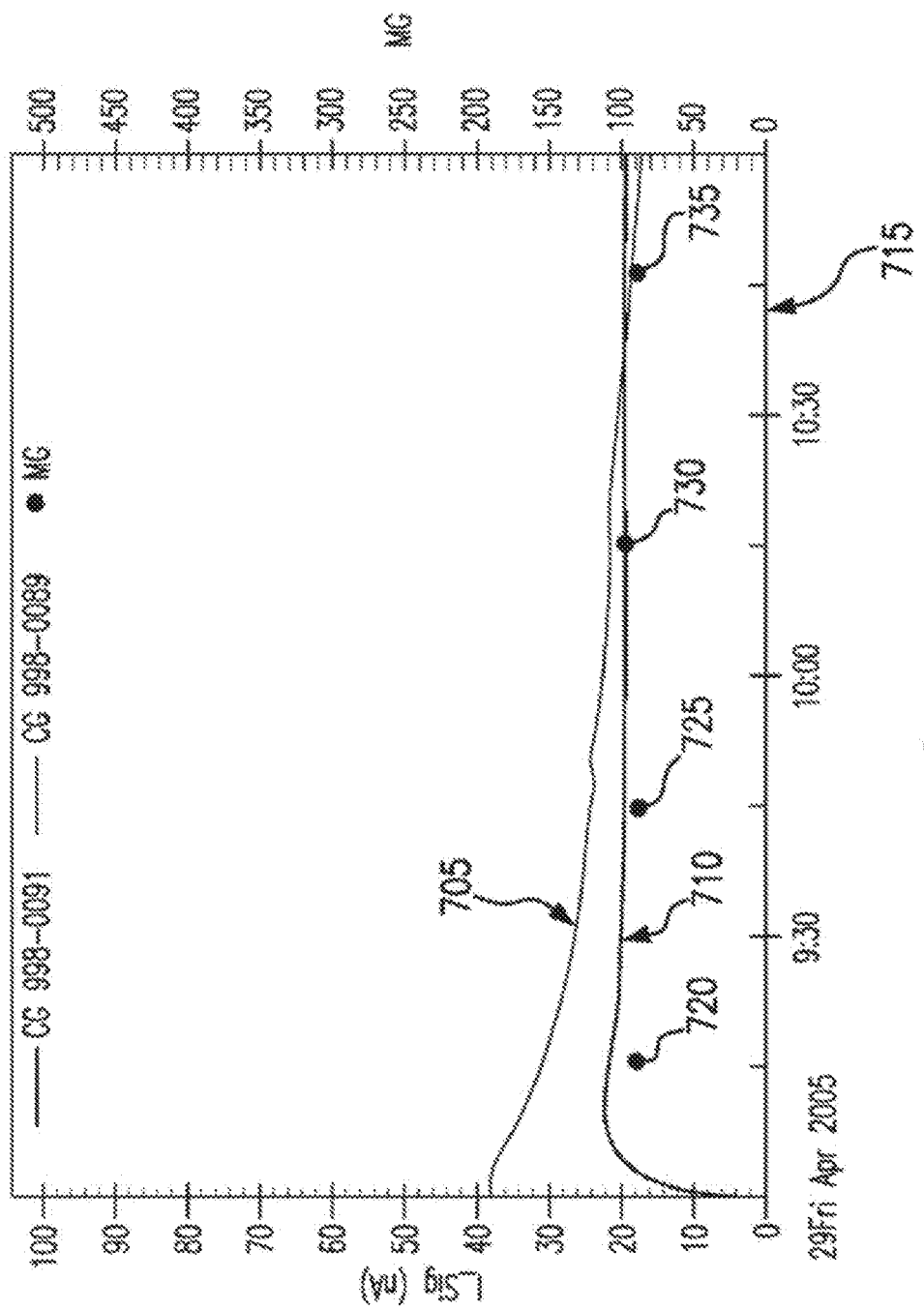
FIG. 7 illustrates an effect of stabilizing a sensor according to an embodiment of the invention.

FIG. 7 illustrates an effect of stabilizing a sensor according to an embodiment of the invention. Line 705 represents blood glucose sensor readings for a glucose sensor where a previous single pulse stabilization method was utilized. Line 710 represents blood glucose readings for a glucose sensor where three voltage pulses are applied (e.g., 3 voltage pulses having a duration of 2 minutes each followed by 5 minutes of no voltage being applied). The x-axis 715 represents an amount of time. The dots 720, 725, 730, and 735 represent measured glucose readings, taken utilizing a finger stick and then input into a glucose meter. As illustrated by the graph, the previous single pulse stabilization method took approximately 1 hour and 30 minutes in order to stabilize to the desired glucose reading, e.g., 100 units. In contrast, the three-pulse stabilization method took only approximately 15 minutes to stabilize the glucose sensor and results in a drastically improved stabilization timeframe.

Figure 8A:
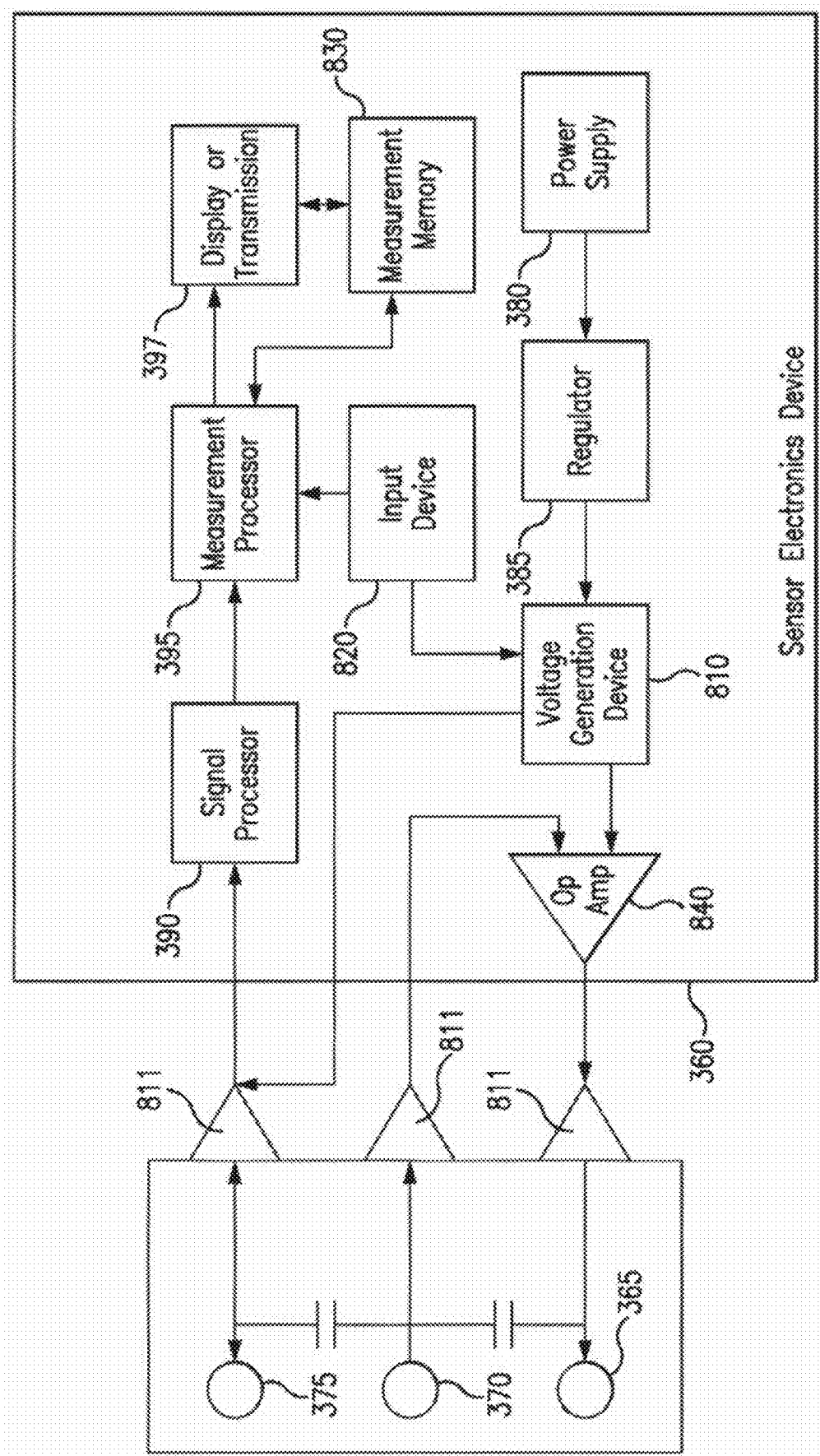
FIG. 8A illustrates a block diagram of a sensor electronics device and a sensor including a voltage generation device according to an embodiment of the invention.

FIG. 8A illustrates a block diagram of a sensor electronics device and a sensor including a voltage generation device according to an embodiment of the invention. The voltage generation or application device 810 includes electronics, logic, or circuits which generate voltage pulses. The sensor electronics device 360 may also include an input device 820 to receive reference values and other useful data. In an embodiment of the invention, the sensor electronics device may include a measurement memory 830 to store sensor measurements. In this embodiment of the invention, the power supply 380 may supply power to the sensor electronics device. The power supply 380 may supply power to a regulator 385, which supplies a regulated voltage to the voltage generation or application device 810. The connection terminals 811 represent that in the illustrated embodiment of the invention, the connection terminal couples or connects the sensor 355 to the sensor electronics device 360.

In an embodiment of the invention illustrated in FIG. 8A, the voltage generation or application device 810 supplies a voltage, e.g., the first voltage or the second voltage, to an input terminal of an operational amplifier 840. The voltage generation or application device 810 may also supply the voltage to a working electrode 375 of the sensor 355. Another input terminal of the operational amplifier 840 is coupled to the reference electrode 370 of the sensor. The application of the voltage from the voltage generation or application device 810 to the operational amplifier 840 drives a voltage measured at the counter electrode 365 to be close to or equal to the voltage applied at the working electrode 375. In an embodiment of the invention, the voltage generation or application device 810 could be utilized to apply the desired voltage between the counter electrode and the working electrode. This may occur by the application of the fixed voltage to the counter electrode directly.

In an embodiment of the invention as illustrated in FIGS. 6A and 6B, the voltage generation device 810 generates a first voltage that is to be applied to the sensor during a first timeframe. The voltage generation device 810 transmits this first voltage to an op amp 840 which drives the voltage at a counter electrode 365 of the sensor 355 to the first voltage. In an embodiment of the invention, the voltage generation device 810 also could transmit the first voltage directly to the counter electrode 365 of the sensor 355. In the embodiment of the invention illustrated in FIG. 6A, the voltage generation device 810 then does not transmit the first voltage to the sensor 355 for a second timeframe. In other words, the voltage generation device 810 is turned off or switched off. The voltage generation device 810 may be programmed to continue cycling between applying the first voltage and not applying a voltage for either a number of iterations or for a stabilization timeframe, e.g., for twenty minutes. FIG. 8B illustrates a voltage generation device to implement this embodiment of the invention. The voltage regulator 385 transfers the regulated voltage to the voltage generation device 810. A control circuit 860 controls the closing and opening of a switch 850. If the switch 850 is closed, the voltage is applied. If the switch 850 is opened, the voltage is not applied. The timer 865 provides a signal to the control circuit 860 to instruct the control circuit 860 to turn on and off the switch 850. The control circuit 860 includes logic which can instruct the circuit to open and close the switch 850 a number of times (to match the necessary iterations). In an embodiment of the invention, the timer 865 may also transmit a stabilization signal to identify that the stabilization sequence is completed, i.e., that a stabilization timeframe has elapsed.

In an embodiment of the invention, the voltage generation device generates a first voltage for a first timeframe and generates a second voltage for a second timeframe. FIG. 8C illustrates a voltage generation device to generate two voltage values to implement this embodiment of the invention. In this embodiment of the invention, a two-position switch 870 is utilized. Illustratively, if the first switch position 871 is turned on or closed by the timer 865 instructing the control circuit 860, then the voltage generation device 810 generates a first voltage for the first timeframe. After the first voltage has been applied for the first timeframe, the timer sends a signal to the control circuit 860 indicating the first timeframe has elapsed and the control circuit 860 directs the switch 870 to move to the second position 872. When the switch 870 is at the second position 872, the regulated voltage is directed to a voltage step-down or buck converter 880 to reduce the regulated voltage to a lesser value. The lesser value is then delivered to the op amp 840 for the second timeframe. After the timer 865 has sent a signal to the control circuit 860 that the second timeframe has elapsed, the control circuit 860 moves the switch 870 back to the first position. This continues until the desired number of iterations has been completed or the stabilization timeframe has elapsed. In an embodiment of the invention, after the sensor stabilization timeframe has elapsed, the sensor transmits a sensor signal 350 to the signal processor 390.

FIG. 8D illustrates a voltage application device 810 utilized to perform more complex applications of voltage to the sensor. The voltage application device 810 may include a control device 860, a switch 890, a sinusoid voltage generation device 891, a ramp voltage generation device 892, and a constant voltage generation device 893. In other embodiments of the invention, the voltage application may generate an AC wave on top of a DC signal or other various voltage pulse waveforms. In the embodiment of the invention illustrated in FIG. 8D, the control device 860 may cause the switch to move to one of the three voltage generation systems 891 (sinusoid), 892 (ramp), 893 (constant DC). This results in each of the voltage generation systems generating the identified voltage waveform. Under certain operating conditions, e.g., where a sinusoidal pulse is to be applied for three pulses, the control device 860 may cause the switch 890 to connect the voltage from the voltage regulator 385 to the sinusoid voltage generator 891 in order for the voltage application device 810 to generate a sinusoidal voltage. Under other operating conditions, e.g., when a ramp voltage is applied to the sensor as the first voltage for a first pulse of three pulses, a sinusoid voltage is applied to the sensor as the first voltage for a second pulse of the three pulses, and a constant DC voltage is applied to the sensor as the first voltage for a third pulse of the three pulses, the control device 860 may cause the switch 890, during the first timeframes in the anodic/cathodic cycles, to move between connecting the voltage from the voltage generation or application device 810 to the ramp voltage generation system 892, then to the sinusoidal voltage generation system 891, and then to the constant DC voltage generation system 893. In this embodiment of the invention, the control device 860 may also be directing or controlling the switch to connect certain ones of the voltage generation subsystems to the voltage from the regulator 385 during the second timeframe, e.g., during application of the second voltage.

Figure 9A:
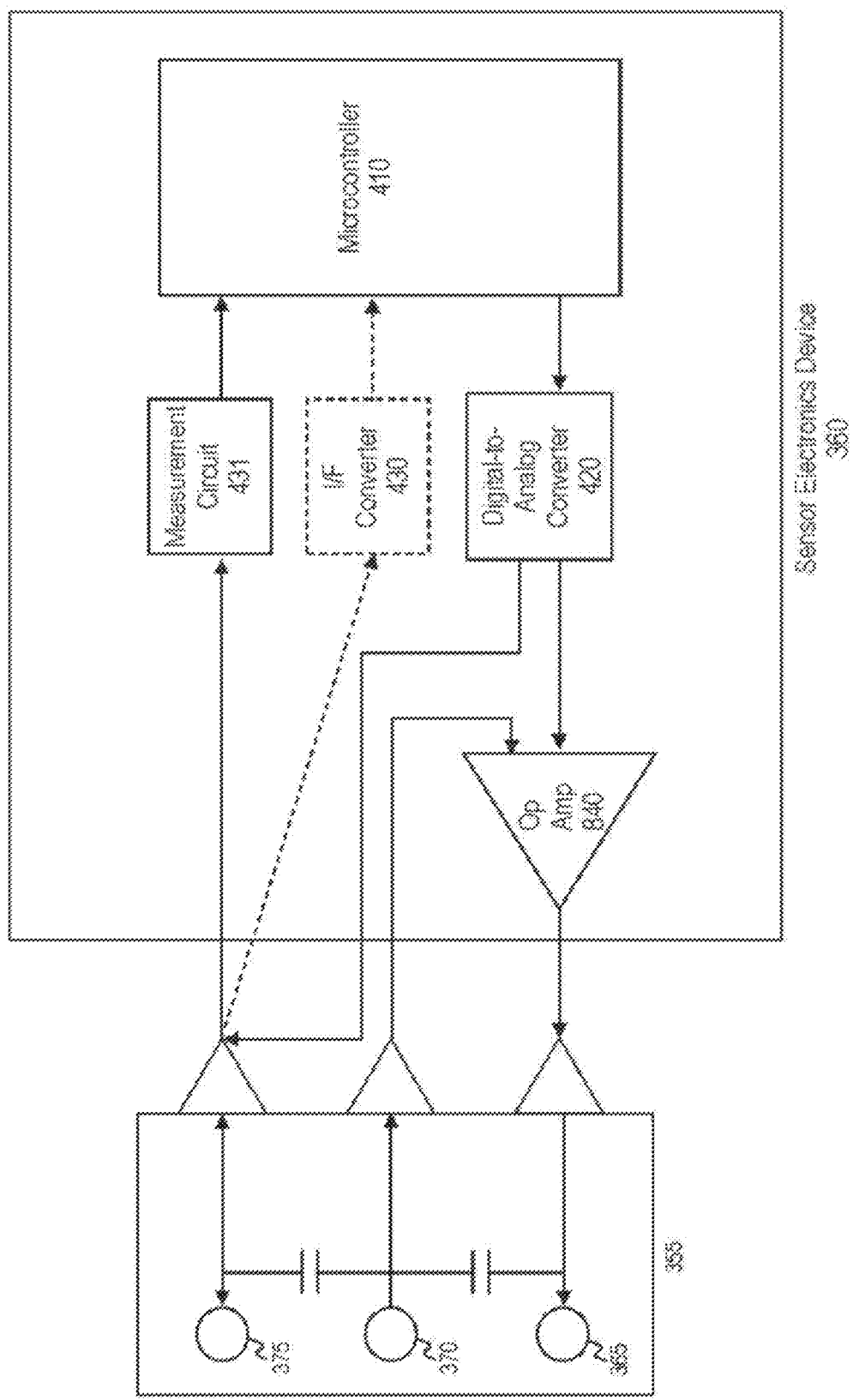
FIG. 9A illustrates a sensor electronics device including a microcontroller for generating voltage pulses according to an embodiment of the invention.

FIG. 9A illustrates a sensor electronics device including a microcontroller for generating voltage pulses according to an embodiment of the invention. The advanced sensor electronics device may include a microcontroller 410 (see FIG. 4), a digital-to-analog converter (DAC) 420, an op amp 840, and a sensor signal measurement circuit 431. In an embodiment of the invention, the sensor signal measurement circuit may be a current-to-frequency (I/F) converter 430. In the embodiment of the invention illustrated in FIG. 9A, software or programmable logic in the microcontroller 410 provides instructions to transmit signals to the DAC 420, which in turn instructs the DAC 420 to output a specific voltage to the operational amplifier 840. The microcontroller 410 may also be instructed to output a specific voltage to the working electrode 375, as is illustrated by line 911 in FIG. 9A. As discussed above, the application of the specific voltage to operational amplifier 840 and the working electrode 375 may drive the voltage measured at the counter electrode to the specific voltage magnitude. In other words, the microcontroller 410 outputs a signal which is indicative of a voltage or a voltage waveform that is to be applied to the sensor 355 (e.g., the operational amplifier 840 coupled to the sensor 355). In an alternative embodiment of the invention, a fixed voltage may be set by applying a voltage directly from the DAC 420 between the reference electrode and the working electrode 375. A similar result may also be obtained by applying voltages to each of the electrodes with the difference equal to the fixed voltage applied between the reference and working electrode. In addition, the fixed voltage may be set by applying a voltage between the reference and the counter electrode. Under certain operating conditions, the microcontroller 410 may generate a pulse of a specific magnitude which the DAC 420 understands represents that a voltage of a specific magnitude is to be applied to the sensor. After a first timeframe, the microcontroller 410 (via the program or programmable logic) outputs a second signal which either instructs the DAC 420 to output no voltage (for a sensor electronics device 360 operating according to the method described in FIG. 6A) or to output a second voltage (for a sensor electronics device 360 operating according to the method described in FIG. 6B). The microcontroller 410, after the second timeframe has elapsed, then repeats the cycle of sending the signal indicative of a first voltage to be applied (for the first timeframe) and then sending the signal to instruct no voltage is to be applied or that a second voltage is to be applied (for the second timeframe).

Under other operating conditions, the microcontroller 410 may generate a signal to the DAC 420 which instructs the DAC to output a ramp voltage. Under other operating conditions, the microcontroller 410 may generate a signal to the DAC 420 which instructs the DAC 420 to output a voltage simulating a sinusoidal voltage. These signals could be incorporated into any of the pulsing methodologies discussed above in the preceding paragraph or earlier in the application. In an embodiment of the invention, the microcontroller 410 may generate a sequence of instructions and/or pulses, which the DAC 420 receives and understands to mean that a certain sequence of pulses is to be applied. For example, the microcontroller 410 may transmit a sequence of instructions (via signals and/or pulses) that instruct the DAC 420 to generate a constant voltage for a first iteration of a first timeframe, a ramp voltage for a first iteration of a second timeframe, a sinusoidal voltage for a second iteration of a first timeframe, and a squarewave having two values for a second iteration of the second timeframe.

The microcontroller 410 may include programmable logic or a program to continue this cycling for a stabilization timeframe or for several iterations. Illustratively, the microcontroller 410 may include counting logic to identify when the first timeframe or the second timeframe has elapsed. Additionally, the microcontroller 410 may include counting logic to identify that a stabilization timeframe has elapsed. After any of the preceding timeframes have elapsed, the counting logic may instruct the microcontroller to either send a new signal or to stop transmission of a signal to the DAC 420.

The use of the microcontroller 410 allows a variety of voltage magnitudes to be applied in several sequences for several time durations. In an embodiment of the invention, the microcontroller 410 may include control logic or a program to instruct the digital-to-analog converter 420 to transmit a voltage pulse having a magnitude of approximately 1.0 volt for a first time period of 1 minute, to then transmit a voltage pulse having a magnitude of approximately 0.5 volts for a second time period of 4 minutes, and to repeat this cycle for four iterations. In an embodiment of the invention, the microcontroller 420 may be programmed to transmit a signal to cause the DAC 420 to apply the same magnitude voltage pulse for each first voltage in each of the iterations. In an embodiment of the invention, the microcontroller 410 may be programmed to transmit a signal to cause the DAC to apply a different magnitude voltage pulse for each first voltage in each of the iterations. In this embodiment of the invention, the microcontroller 410 may also be programmed to transmit a signal to cause the DAC 420 to apply a different magnitude voltage pulse for each second voltage in each of the iterations. Illustratively, the microcontroller 410 may be programmed to transmit a signal to cause the DAC 420 to apply a first voltage pulse of approximately 1.0 volt in the first iteration, to apply a second voltage pulse of approximately 0.5 volts in the first iteration, to apply a first voltage of 0.7 volts and a second voltage of 0.4 volts in the second iteration, and to apply a first voltage of 1.2 volts and a second voltage of 0.8 volts in the third iteration.

The microcontroller 410 may also be programmed to instruct the DAC 420 to provide a number of short duration voltage pulses for a first timeframe. In this embodiment of the invention, rather than one voltage being applied for the entire first timeframe (e.g., two minutes), a number of shorter duration pulses may be applied to the sensor. In this embodiment, the microcontroller 410 may also be programmed to instruct the DAC 420 to provide a number of short duration voltage pulses for the second timeframe to the sensor. Illustratively, the microcontroller 410 may send a signal to cause the DAC to apply a number of short duration voltage pulses where the short duration is 50 milliseconds or 100 milliseconds. In between these short duration pulses the DAC may apply no voltage, or the DAC may apply a minimal voltage. The microcontroller may cause the DAC 420 to apply the short duration voltage pulses for the first timeframe, e.g., two minutes. The microcontroller 410 may then send a signal to cause the DAC to either not apply any voltage or to apply the short duration voltage pulses at a magnitude of a second voltage for a second timeframe to the sensor, e.g., the second voltage may be 0.75 volts and the second timeframe may be 5 minutes. In an embodiment of the invention, the microcontroller 410 may send a signal to the DAC 420 to cause the DAC 420 to apply a different magnitude voltage for each of the short duration pulses in the first timeframe and/or in the second timeframe. In an embodiment of the invention, the microcontroller 410 may send a signal to the DAC 420 to cause the DAC 420 to apply a pattern of voltage magnitudes to the short durations voltage pulses for the first timeframe or the second timeframe. For example, the microcontroller may transmit a signal or pulses instructing the DAC 420 to apply thirty 20-millisecond pulses to the sensor during the first timeframe. Each of the thirty 20-millisecond pulses may have the same magnitude or may have a different magnitude. In this embodiment of the invention, the microcontroller 410 may instruct the DAC 420 to apply short duration pulses during the second timeframe or may instruct the DAC 420 to apply another voltage waveform during the second timeframe.

Although the disclosures in FIGS. 6-8 disclose the application of a voltage, a current may also be applied to the sensor to initiate the stabilization process. Illustratively, in the embodiment of the invention illustrated in FIG. 6B, a first current may be applied during a first timeframe to initiate an anodic or cathodic response and a second current may be applied during a second timeframe to initiate the opposite anodic or cathodic response. The application of the first current and the second current may continue for a number of iterations or may continue for a stabilization timeframe. In an embodiment of the invention, a first current may be applied during a first timeframe and a first voltage may be applied during a second timeframe. In other words, one of the anodic or cathodic cycles may be triggered by a current being applied to the sensor and the other of the anodic or cathodic cycles may be triggered by a voltage being applied to the sensor. As described above, a current applied may be a constant current, a ramp current, a stepped pulse current, or a sinusoidal current. Under certain operating conditions, the current may be applied as a sequence of short duration pulses during the first timeframe.

Figure 9B:
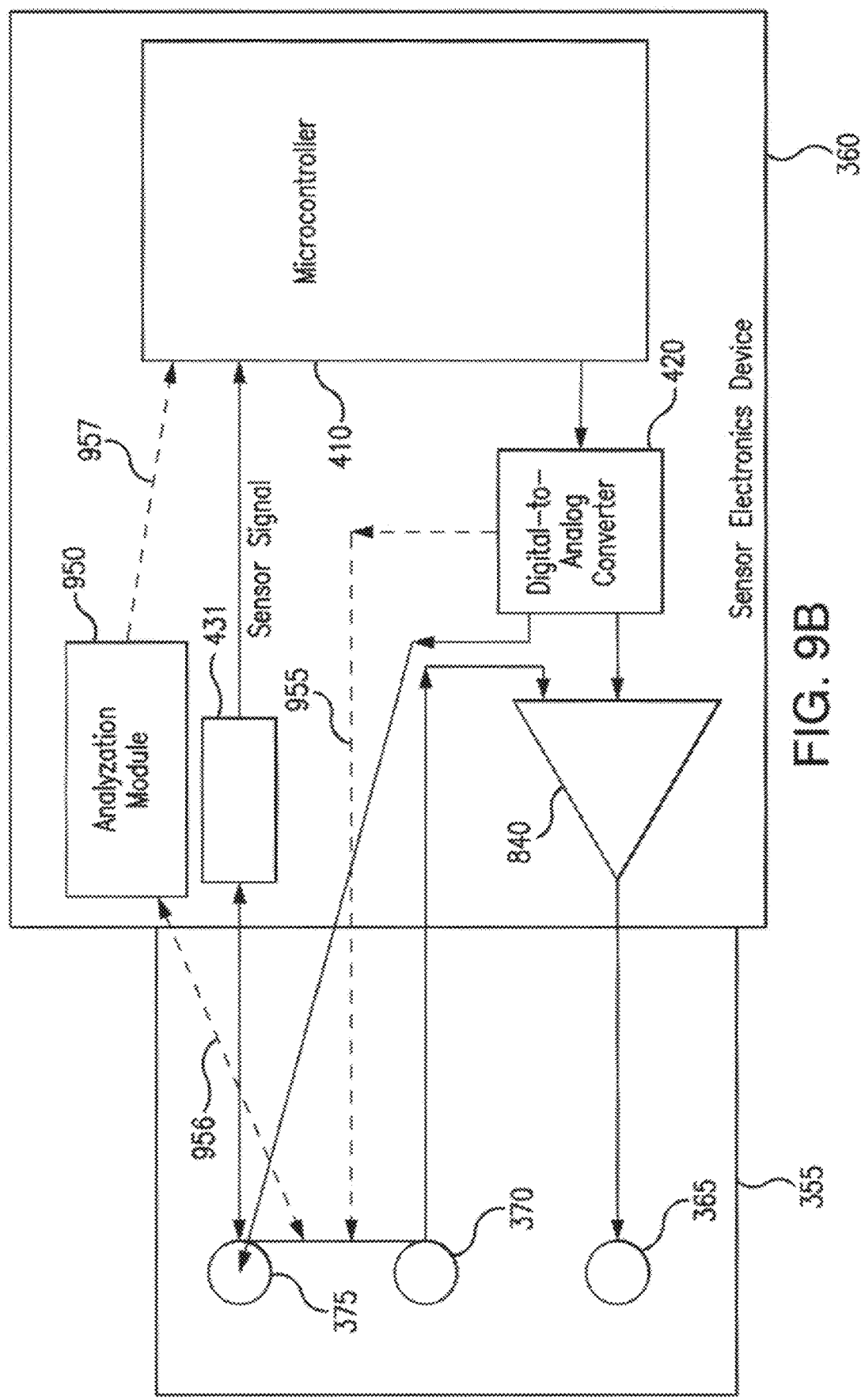
FIG. 9B illustrates a sensor electronics device including an analyzation module according to an embodiment of the invention.

FIG. 9B illustrates a sensor, and sensor electronics utilizing an analyzation module for feedback in a stabilization period according to an embodiment of the present invention. FIG. 9B introduces an analyzation module 950 to the sensor electronics device 360. The analyzation module 950 utilizes feedback from the sensor to determine whether the sensor is stabilized or not. In an embodiment of the invention, the microcontroller 410 may include instructions or commands to control the DAC 420 so that the DAC 420 applies a voltage or current to a part of the sensor 355. FIG. 9B illustrates that a voltage or current could be applied between a reference electrode 370 and a working electrode 375. However, the voltage or current can be applied in between electrodes or directly to one of the electrodes and the invention should not be limited by the embodiment illustrated in FIG. 9B. The application of the voltage or current is illustrated by dotted line 955. The analyzation module 950 may measure a voltage, a current, a resistance, or an impedance in the sensor 355. FIG. 9B illustrates that the measurement occurs at the working electrode 375, but this should not limit the invention because other embodiments of the invention may measure a voltage, a current, a resistance, or an impedance in between electrodes of the sensor or directly at either the reference electrode 370 or the counter electrode 365. The analyzation module 950 may receive the measured voltage, current, resistance, or impedance and may compare the measurement to a stored value (e.g., a threshold value). Dotted line 956 represents the analyzation module 950 reading or taking a measurement of the voltage, current, resistance, or impedance. Under certain operating conditions, if the measured voltage, current, resistance, or impedance is above the threshold, the sensor is stabilized, and the sensor signal is providing accurate readings of a physiological condition of a patient. Under other operating conditions, if the measured voltage, current, resistance, or impedance is below the threshold, the sensor is stabilized. Under other operating conditions, the analyzation module 950 may verify that the measured voltage, current, resistance, or impedance is stable for a specific timeframe, e.g., one minute or two minutes. This may represent that the sensor 355 is stabilized and that the sensor signal is transmitting accurate measurements of a subject's physiological parameter, e.g., blood glucose level. After the analyzation module 950 has determined that the sensor is stabilized, and the sensor signal is providing accurate measurements, the analyzation module 950 may transmit a signal (e.g., a sensor stabilization signal) to the microcontroller 410 indicating that the sensor is stabilized and that the microcontroller 410 can start using or receiving the sensor signal from the sensor 355. This is represented by dotted line 957.

Figure 10:
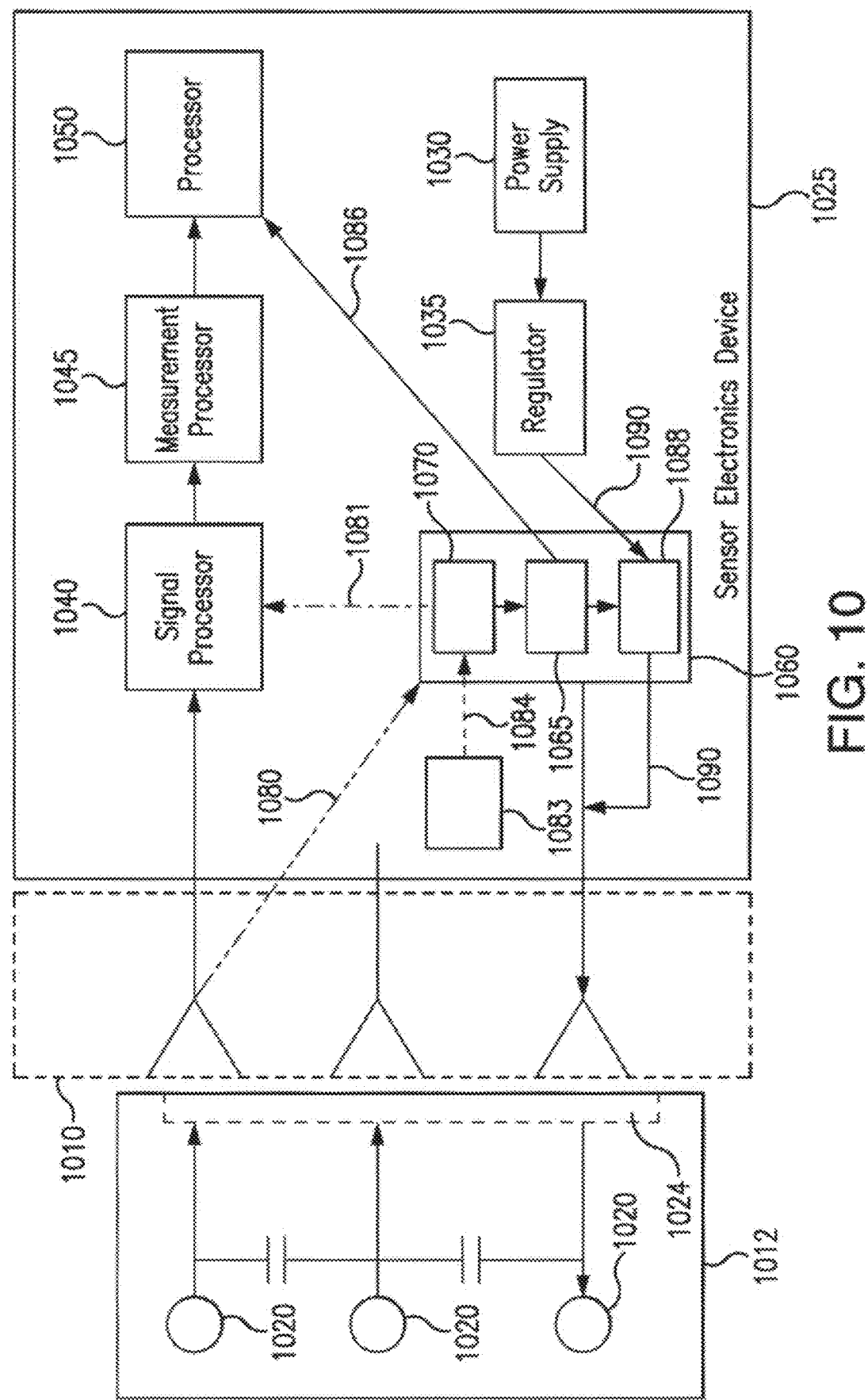
FIG. 10 illustrates a block diagram of a sensor system including hydration electronics according to an embodiment of the invention.

FIG. 10 illustrates a block diagram of a sensor system including hydration electronics according to an embodiment of the invention. The sensor system includes a connector 1010, a sensor 1012, and a monitor or sensor electronics device 1025. The sensor 1012 includes electrodes 1020 and a connection portion 1024. In an embodiment of the invention, the sensor 1012 may be connected to the sensor electronics device 1025 via a connector 1010 and a cable. In other embodiments of the invention, the sensor 1012 may be directly connected to the sensor electronics device 1025. In other embodiments of the invention, the sensor 1012 may be incorporated into the same physical device as the sensor electronics device 1025. The monitor or sensor electronics device 1025 may include a power supply 1030, a regulator 1035, a signal processor 1040, a measurement processor 1045, and a processor 1050. The monitor or sensor electronics device 1025 may also include a hydration detection circuit 1060. The hydration detection circuit 1060 interfaces with the sensor 1012 to determine if the electrodes 1020 of the sensor 1012 are sufficiently hydrated. If the electrodes 1020 are not sufficiently hydrated, the electrodes 1020 do not provide accurate glucose readings, so it is important to know when the electrodes 1020 are sufficiently hydrated. Once the electrodes 1020 are sufficiently hydrated, accurate glucose readings may be obtained.

In an embodiment of the invention illustrated in FIG. 10, the hydration detection circuit 1060 may include a delay or timer module 1065 and a connection detection module 1070. In an embodiment of the invention utilizing the short-term sensor or the subcutaneous sensor, after the sensor 1012 has been inserted into the subcutaneous tissue, the sensor electronics device or monitor 1025 is connected to the sensor 1012. The connection detection module 1070 identifies that the sensors electronics device 1025 has been connected to the sensor 1012 and sends a signal to the timer module 1065. This is illustrated in FIG. 10 by the arrow 1084 which represents a detector 1083 detecting a connection and sending a signal to the connection detection module 1070 indicating the sensor 1012 has been connected to the sensor electronics device 1025. In an embodiment of the invention where implantable or long-term sensors are utilized, a connection detection module 1070 identifies that the implantable sensor has been inserted into the body. The timer module 1065 receives the connection signal and waits a set or established hydration time. Illustratively, the hydration time may be two minutes, five minutes, ten minutes, or 20 minutes. These examples are meant to be illustrative and not to be limiting. The timeframe does not have to be a set number of minutes and can include any number of seconds. In an embodiment of the invention, after the timer module 1065 has waited for the set hydration time, the timer module 1065 may notify the processor 1050 that the sensor 1012 is hydrated by sending a hydration signal, which is illustrated by line 1086.

In this embodiment of the invention, the processor 1050 may receive the hydration signal and only start utilizing the sensor signal (e.g., sensor measurements) after the hydration signal has been received. In another embodiment of the invention, the hydration detection circuit 1060 may be coupled between the sensor (the sensor electrodes 1020) and the signal processor 1040. In this embodiment of the invention, the hydration detection circuit 1060 may prevent the sensor signal from being sent to signal processor 1040 until the timer module 1065 has notified the hydration detection circuit 1060 that the set hydration time has elapsed. This is illustrated by the dotted lines labeled with reference numerals 1080 and 1081. Illustratively, the timer module 1065 may transmit a connection signal to a switch (or transistor) to turn on the switch and let the sensor signal proceed to the signal processor 1040. In an alternative embodiment of the invention, the timer module 1065 may transmit a connection signal to turn on a switch 1088 (or close the switch 1088) in the hydration detection circuit 1060 to allow a voltage from the regulator 1035 to be applied to the sensor 1012 after the hydration time has elapsed. In other words, in this embodiment of the invention, the voltage from the regulator 1035 is not applied to the sensor 1012 until after the hydration time has elapsed.

Figure 11:
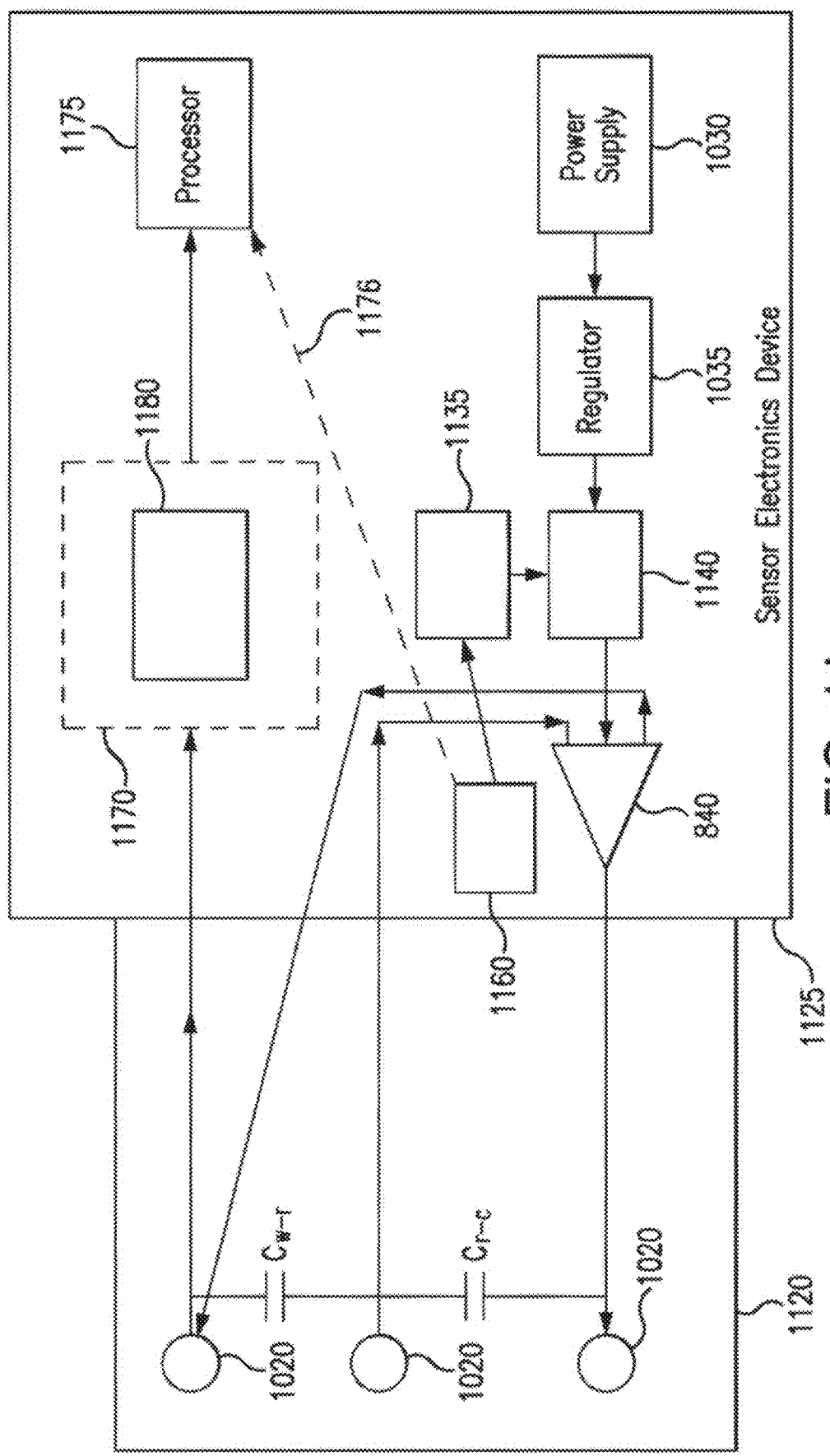
FIG. 11 illustrates an embodiment of the invention including a mechanical switch to assist in determining a hydration time.

FIG. 11 illustrates an embodiment of the invention including a mechanical switch to assist in determining a hydration time. In an embodiment of the invention, a single housing may include a sensor assembly 1120 and a sensor electronics device 1125. In an embodiment of the invention, the sensor assembly 1120 may be in one housing and the sensor electronics device 1125 may be in a separate housing, but the sensor assembly 1120 and the sensor electronics device 1125 may be connected together. In this embodiment of the invention, a connection detection mechanism 1160 may be a mechanical switch. The mechanical switch may detect that the sensor 1120 is physically connected to the sensor electronics device 1125. In an embodiment of the invention, a timer circuit 1135 may also be activated when the mechanical switch 1160 detects that the sensor 1120 is connected to the sensor electronics device 1125. In other words, the mechanical switch may close, and a signal may be transferred to a timer circuit 1135. Once a hydration time has elapsed, the timer circuit 1135 transmits a signal to the switch 1140 to allow the regulator 1035 to apply a voltage to the sensor 1120. In other words, no voltage is applied until the hydration time has elapsed. In an embodiment of the invention, current may replace voltage as what is being applied to the sensor once the hydration time elapses. In an alternative embodiment of the invention, when the mechanical switch 1160 identifies that a sensor 1120 has been physically connected to the sensor electronics device 1125, power may initially be applied to the sensor 1120. Power being sent to the sensor 1120 results in a sensor signal being output from the working electrode in the sensor 1120. The sensor signal may be measured and sent to a processor 1175. The processor 1175 may include a counter input. Under certain operating conditions, after a set hydration time has elapsed from when the sensor signal was input into the processor 1175, the processor 1175 may start processing the sensor signal as an accurate measurement of the glucose in a subject's body. In other words, the processor 1170 has received the sensor signal from the potentiostat circuit 1170 for a certain amount of time but will not process the signal until receiving an instruction from the counter input of the processor identifying that a hydration time has elapsed. In an embodiment of the invention, the potentiostat circuit 1170 may include a current-to-frequency converter 1180. In this embodiment of the invention, the current-to-frequency converter 1180 may receive the sensor signal as a current value and may convert the current value into a frequency value, which is easier for the processor 1175 to handle.

In an embodiment of the invention, the mechanical switch 1160 may also notify the processor 1175 when the sensor 1120 has been disconnected from the sensor electronics device 1125. This is represented by dotted line 1176 in FIG. 11. This may result in the processor 1170 powering down or reducing power to a number of components, chips, and/or circuits of the sensor electronics device 1125. If the sensor 1120 is not connected, the battery or power source may be drained if the components or circuits of the sensor electronics device 1125 are in a power on state. Accordingly, if the mechanical switch 1160 detects that the sensor 1120 has been disconnected from the sensor electronics device 1125, the mechanical switch may indicate this to the processor 1175, and the processor 1175 may power down or reduce power to one or more of the electronic circuits, chips, or components of the sensor electronics device 1125.

Figure 12:
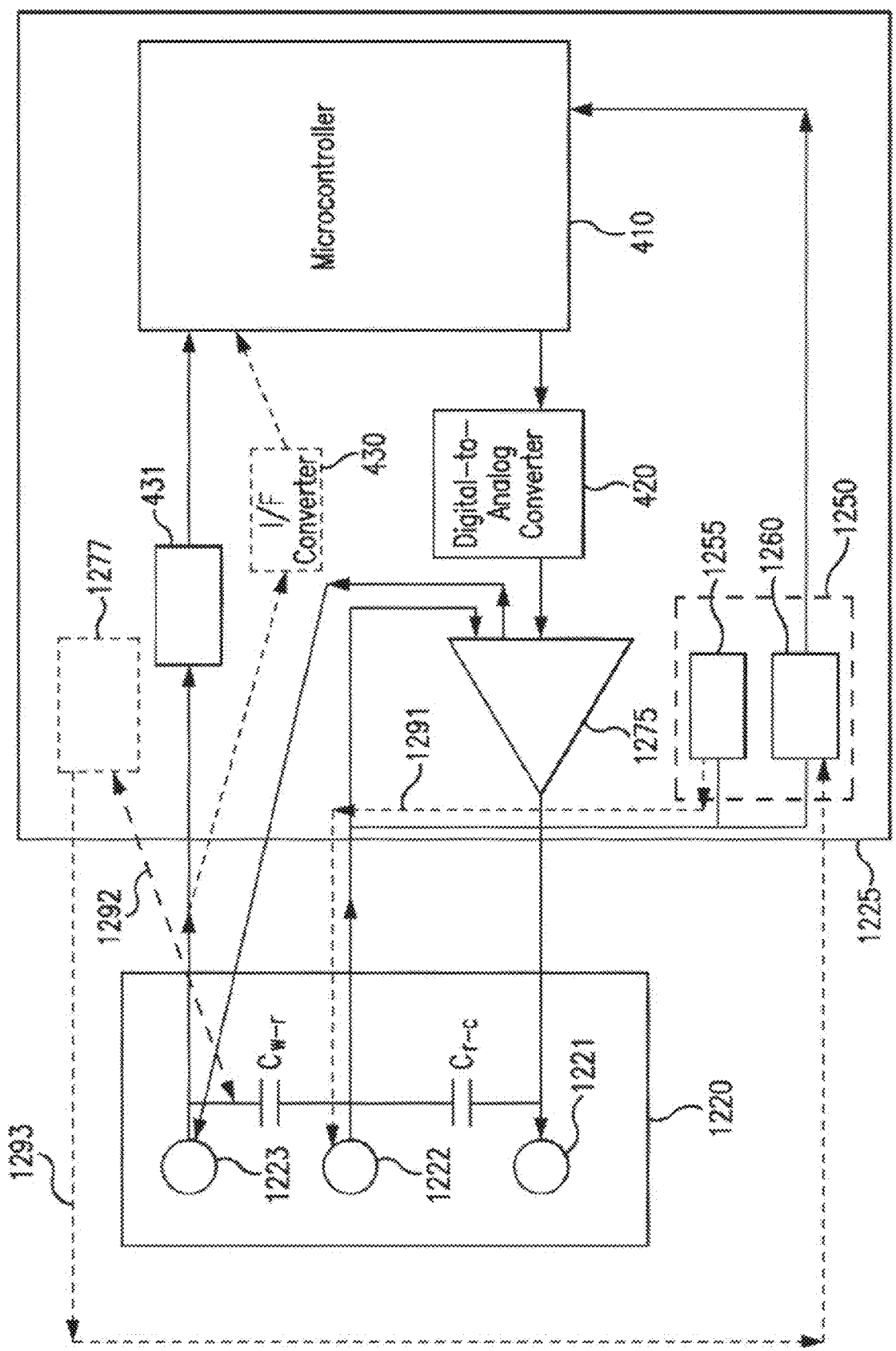
FIG. 12 illustrates a method of detection of hydration according to an embodiment of the invention.

FIG. 12 illustrates an electrical method of detection of hydration according to an embodiment of the invention. In an embodiment of the invention, an electrical detecting mechanism for detecting connection of a sensor may be utilized. In this embodiment of the invention, the hydration detection electronics 1250 may include an AC source 1255 and a detection circuit 1260. The hydration detection electronics 1250 may be located in the sensor electronics device 1225. The sensor 1220 may include a counter electrode 1221, a reference electrode 1222, and a working electrode 1223. As illustrated in FIG. 12, the AC source 1255 is coupled to a voltage setting device 1275, the reference electrode 1222, and the detection circuit 1260. In this embodiment of the invention, an AC signal from the AC source is applied to the reference electrode connection, as illustrated by dotted line 1291 in FIG. 12. In an embodiment of the invention, the AC signal is coupled to the sensor 1220 through an impedance and the coupled signal is attenuated significantly if the sensor 1220 is connected to the sensor electronics device 1225. Thus, a low-level AC signal is present at an input to the detection circuit 1260. This may also be referred to as a highly attenuated signal or a signal with a high level of attenuation. Under certain operating conditions, the voltage level of the AC signal may be Vapplied*(Ccoupling)/(Ccoupling+Csensor). If the detection circuit 1260 detects that a high-level AC signal (lowly attenuated signal) is present at an input terminal of the detection circuit 1260, no interrupt is sent to the microcontroller 410 because the sensor 1220 has not been sufficiently hydrated or activated. For example, the input of the detection circuit 1260 may be a comparator. If the sensor 1220 is sufficiently hydrated (or wetted), an effective capacitance forms between the counter electrode and the reference electrode (e.g., capacitance $C_{r\text{-}c}$ in FIG. 12), and an effective capacitance forms between the reference electrode and the working electrode (e.g., capacitance $C_{w\text{-}r}$ in FIG. 12). In other words, an effective capacitance relates to capacitance being formed between two nodes and does not represent that an actual capacitor is placed in a circuit between the two electrodes. In an embodiment of the invention, the AC signal from the AC source 1255 is sufficiently attenuated by capacitances $C_{r\text{-}c}$ and $C_{w\text{-}r}$ and the detection circuit 1260 detects the presence of a low level or highly attenuated AC signal from the AC source 1255 at the input terminal of the detection circuit 1260. This embodiment of the invention is significant because the utilization of the existing connections between the sensor 1120 and the sensor electronics device 1125 reduces the number of connections to the sensor. In other words, the mechanical switch, disclosed in FIG. 11, requires a switch and associated connections between the sensor 1120 and the sensor electronics device 1125. It is advantageous to eliminate the mechanical switch because the sensor 1120 is continuously shrinking in size and the elimination of components helps achieve this size reduction. In alternative embodiments of the invention, the AC signal may be applied to different electrodes (e.g., the counter electrode or the working electrode) and the invention may operate in a similar fashion.

As noted above, after the detection circuit 1260 has detected that a low-level AC signal is present at the input terminal of the detection circuit 1260, the detection circuit 1260 may later detect that a high-level AC signal, with low attenuation, is present at the input terminal. This represents that the sensor 1220 has been disconnected from the sensor electronics device 1225 or that the sensor is not operating properly. If the sensor has been disconnected from the sensor electronics device 1225, the AC source may be coupled with little or low attenuation to the input of the detection circuit 1260. As noted above, the detection circuit 1260 may generate an interrupt to the microcontroller. This interrupt may be received by the microcontroller and the microcontroller may reduce or eliminate power to one or a number of components or circuits in the sensor electronics device 1225. This may be referred to as the second interrupt. Again, this helps reduce power consumption of the sensor electronics device 1225, specifically when the sensor 1220 is not connected to the sensor electronics device 1225.

In an alternative embodiment of the invention illustrated in FIG. 12, the AC signal may be applied to the reference electrode 1222, as is illustrated by reference numeral 1291, and an impedance measuring device 1277 may measure the impedance of an area in the sensor 1220. Illustratively, the area may be an area between the reference electrode and the working electrode, as illustrated by dotted line 1292 in FIG. 12. Under certain operating conditions, the impedance measuring device 1277 may transmit a signal to the detection circuit 1260 if a measured impedance has decreased to below an impedance threshold or other set criteria. This represents that the sensor is sufficiently hydrated. Under other operating conditions, the impedance measuring device 1277 may transmit a signal to the detection circuit 1260 once the impedance is above an impedance threshold. The detection circuit 1260 then transmits the interrupt to the microcontroller 410. In another embodiment of the invention, the impedance measuring device 1277 may transmit an interrupt or signal directly to the microcontroller.

In an alternative embodiment of the invention, the AC source 1255 may be replaced by a DC source. If a DC source is utilized, then a resistance measuring element may be utilized in place of an impedance measuring element 1277. In an embodiment of the invention utilizing the resistance measuring element, once the resistance drops below a resistance threshold or a set criterion, the resistance measuring element may transmit a signal to the detection circuit 1260 (represented by dotted line 1293) or directly to the microcontroller indicating that the sensor is sufficiently hydrated and that power may be applied to the sensor.

In the embodiment of the invention illustrated in FIG. 12, if the detection circuit 1260 detects a low level or highly attenuated AC signal from the AC source, an interrupt is generated to the microcontroller 410. This interrupt indicates that sensor is sufficiently hydrated. In this embodiment of the invention, in response to the interrupt, the microcontroller 410 generates a signal that is transferred to a digital-to-analog converter 420 to instruct or cause the digital-to-analog converter 420 to apply a voltage or current to the sensor 1220. Any of the different sequence of pulses or short duration pulses described above in FIG. 6A, 6B, or 6C or the associated text describing the application of pulses, may be applied to the sensor 1220. Illustratively, the voltage from the DAC 420 may be applied to an op-amp 1275, the output of which is applied to the counter electrode 1221 of the sensor 1220. This results in a sensor signal being generated by the sensor, e.g., the working electrode 1223 of the sensor. Because the sensor is sufficiently hydrated, as identified by the interrupt, the sensor signal created at the working electrode 1223 is accurately measuring glucose. The sensor signal is measured by a sensor signal measuring device 431 and the sensor signal measuring device 431 transmits the sensor signal to the microcontroller 410 where a parameter of a subject's physiological condition is measured. The generation of the interrupt represents that a sensor is sufficiently hydrated and that the sensor 1220 is now supplying accurate glucose measurements. In this embodiment of the invention, the hydration period may depend on the type and/or the manufacturer of the sensor and on the sensor's reaction to insertion or implantation in the subject. Illustratively, one sensor 1220 may have a hydration time of five minutes and one sensor 1220 may have a hydration time of one minute, two minutes, three minutes, six minutes, or 20 minutes. Again, any amount of time may be an acceptable amount of hydration time for the sensor, but smaller amounts of time are preferable.

If the sensor 1220 has been connected, but is not sufficiently hydrated or wetted, the effective capacitances $C_{r\text{-}c}$ and $C_{w\text{-}r}$ may not attenuate the AC signal from the AC source 1255. The electrodes in the sensor 1120 are dry before insertion and because the electrodes are dry, a good electrical path (or conductive path) does not exist between the two electrodes. Accordingly, a high-level AC signal or lowly attenuated AC signal may still be detected by the detection circuit 1260 and no interrupt may be generated. Once the sensor has been inserted, the electrodes become immersed in the conductive body fluid. This results in a leakage path with lower DC resistance. Also, boundary layer capacitors form at the metal/fluid interface. In other words, a rather large capacitance forms between the metal/fluid interface and this large capacitance looks like two capacitors in series between the electrodes of the sensor. This may be referred to as an effective capacitance. In practice, a conductivity of an electrolyte above the electrode is being measured. In some embodiments of the invention, the glucose limiting membrane (GLM) also illustrates impedance blocking electrical efficiency. An unhydrated GLM results in high impedance, whereas a high moisture GLM results in low impedance. Low impedance is desired for accurate sensor measurements.

Figure 13A:
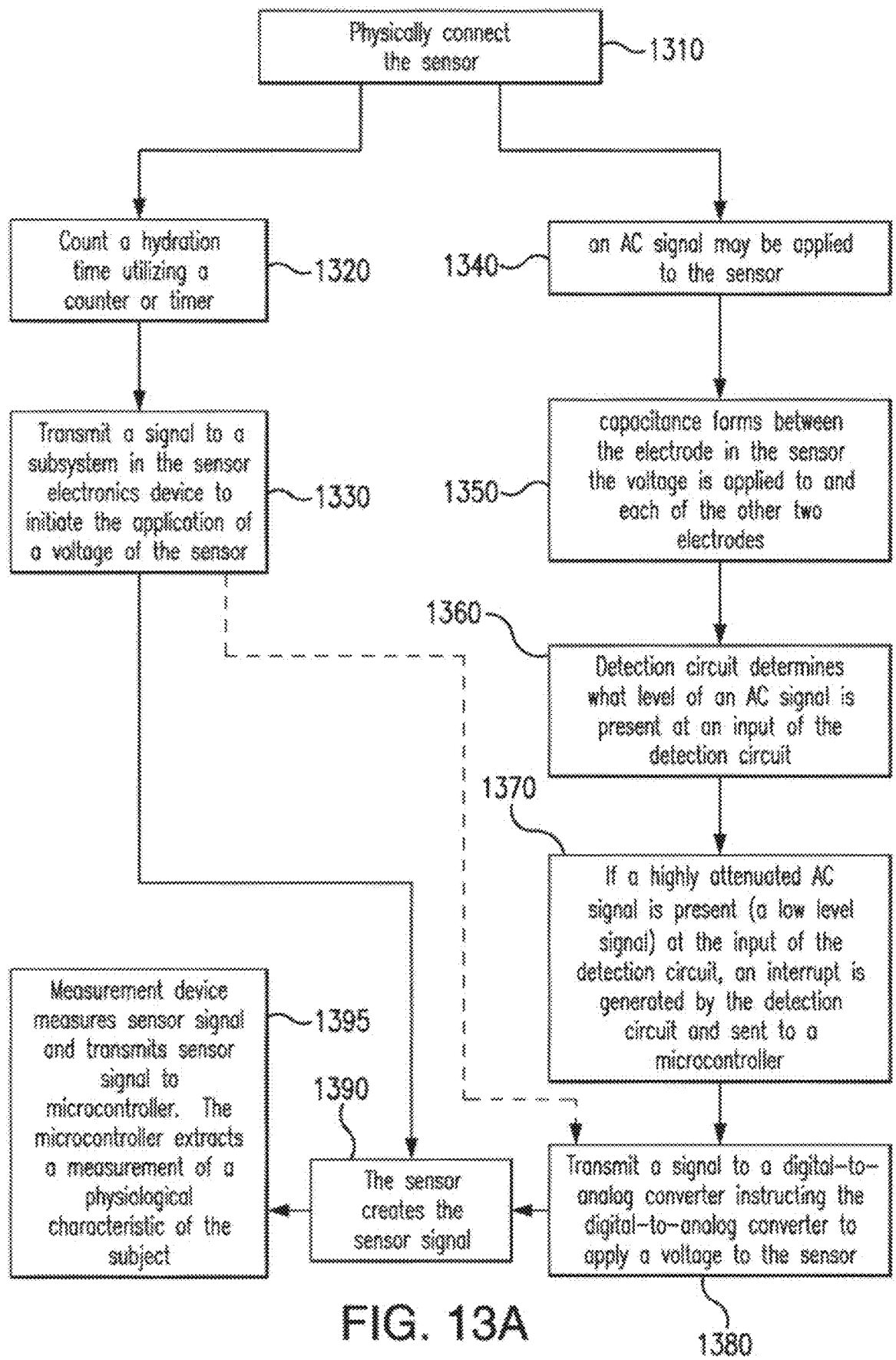
FIG. 13A illustrates a method of hydrating a sensor according to an embodiment of the present invention.

FIG. 13A illustrates a method of hydrating a sensor according to an embodiment of the present invention. In an embodiment of the invention, the sensor may be physically connected 1310 to the sensor electronics device. After the connection, in one embodiment of the invention, a timer or counter may be initiated to count 1320 a hydration time. After the hydration time has elapsed, a signal may be transmitted 1330 to a subsystem in the sensor electronics device to initiate the application of a voltage to the sensor. As discussed above, in an embodiment of the invention, a microcontroller may receive the signal and instruct the DAC to apply a voltage to the sensor or in another embodiment of the invention, a switch may receive a signal which allows a regulator to apply a voltage to the sensor. The hydration time may be five minutes, two minutes, ten minutes and may vary depending on the subject and also on the type of sensor.

In an alternative embodiment of the invention, after the connection of the sensor to the sensor electronics device, an AC signal (e.g., a low voltage AC signal) may be applied 1340 to the sensor, e.g., the reference electrode of the sensor. The AC signal may be applied because the connection of the sensor to the sensor electronics device allows the AC signal to be applied to the sensor. After application of the AC signal, an effective capacitance forms 1350 between the electrode in the sensor that the voltage is applied to and the other two electrodes. A detection circuit determines 1360 what level of the AC signal is present at the input of the detection circuit. If a low-level AC signal (or highly attenuated AC signal) is present at the input of the detection circuit, due to the effective capacitance forming a good electrical conduit between the electrodes and the resulting attenuation of the AC signal, an interrupt is generated 1370 by the detection circuit and sent to a microcontroller.

The microcontroller receives the interrupt generated by the detection circuit and transmits 1380 a signal to a digital-to-analog converter instructing or causing the digital-to-analog converter to apply a voltage to an electrode of the sensor, e.g., the counter electrode. The application of the voltage to the electrode of the sensor results in the sensor creating or generating a sensor signal 1390. A sensor signal measurement device 431 measures the generated sensor signal and transmits the sensor signal to the microcontroller. The microcontroller receives 1395 the sensor signal from the sensor signal measurement device, which is coupled to the working electrode, and processes the sensor signal to extract a measurement of a physiological characteristic of the subject or patient.

Figure 13B:
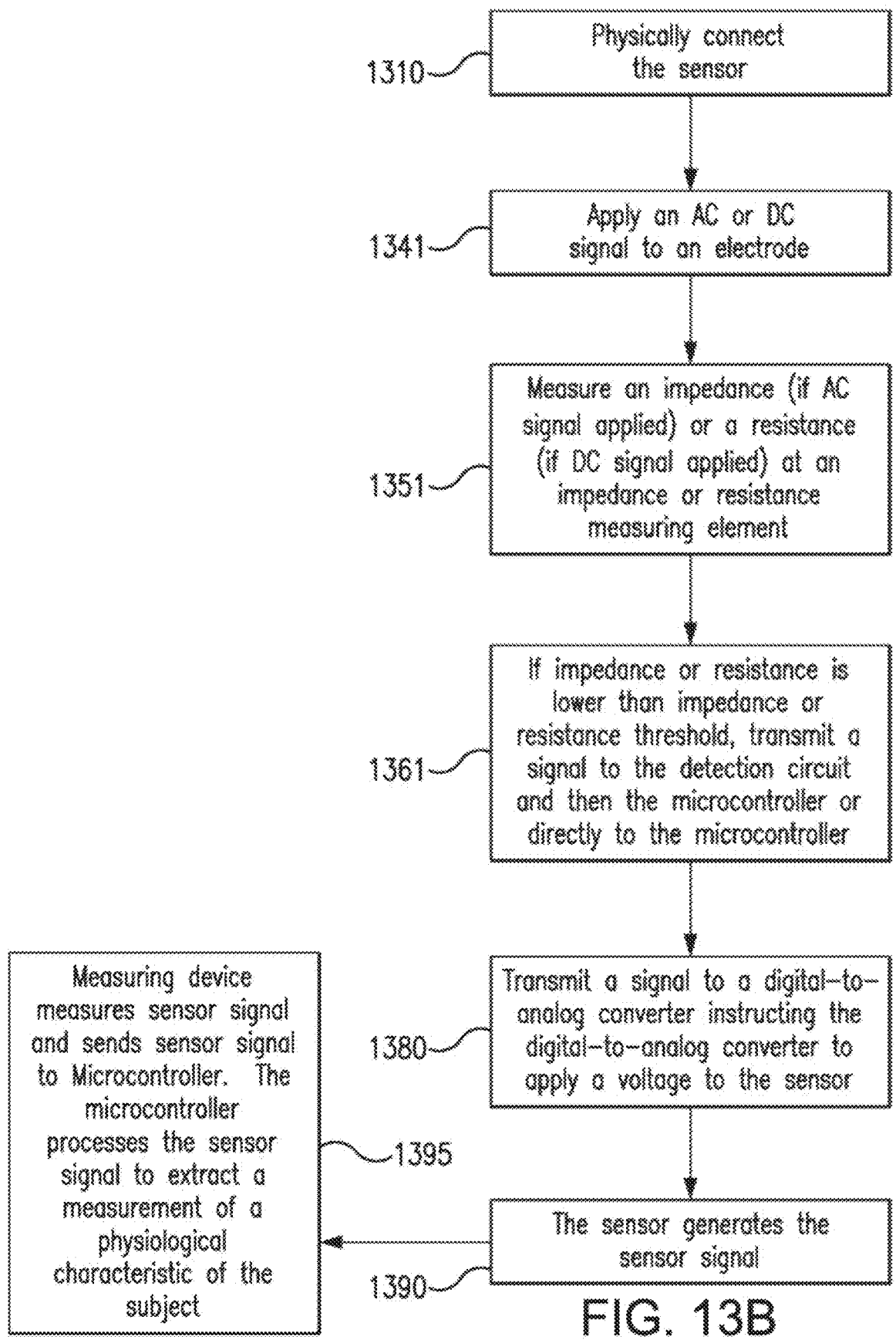
FIG. 13B illustrates an additional method for verifying hydration of a sensor according to an embodiment of the invention.

FIG. 13B illustrates an additional method for verifying hydration of a sensor according to an embodiment of the present invention. In the embodiment of the invention illustrated in FIG. 13B, the sensor is physically connected 1310 to the sensor electronics device. In an embodiment of the invention, an AC signal is applied 1341 to an electrode, e.g., a reference electrode, in the sensor. Alternatively, in an embodiment of the invention, a DC signal is applied 1341 to an electrode in the sensor. If an AC signal is applied, an impedance measuring element measures 1351 an impedance at a point within the sensor. Alternatively, if a DC signal is applied, a resistance measuring element measures 1351 a resistance at a point within the sensor. If the resistance or impedance is lower than a resistance threshold or an impedance threshold, respectively, (or other set criteria), then the impedance (or resistance) measuring element transmits 1361 (or allows a signal to be transmitted) to the detection circuit, and the detection circuit transmits an interrupt to the microcontroller identifying that the sensor is hydrated. The reference numbers 1380, 1390, and 1395 are the same in FIGS. 13A and 13B because they represent the same action.

The microcontroller receives the interrupt and transmits 1380 a signal to a digital-to-analog converter to apply a voltage to the sensor. In an alternative embodiment of the invention, the digital-to-analog converter can apply a current to the sensor, as discussed above. The sensor, e.g., the working electrode, creates 1390 a sensor signal, which represents a physiological parameter of a patient. The microcontroller receives 1395 the sensor signal from a sensor signal measuring device, which measures the sensor signal at an electrode in the sensor, e.g., the working electrode. The microcontroller processes the sensor signal to extract a measurement of the physiological characteristic of the subject or patient, e.g., the blood glucose level of the patient.

Figure 14A:
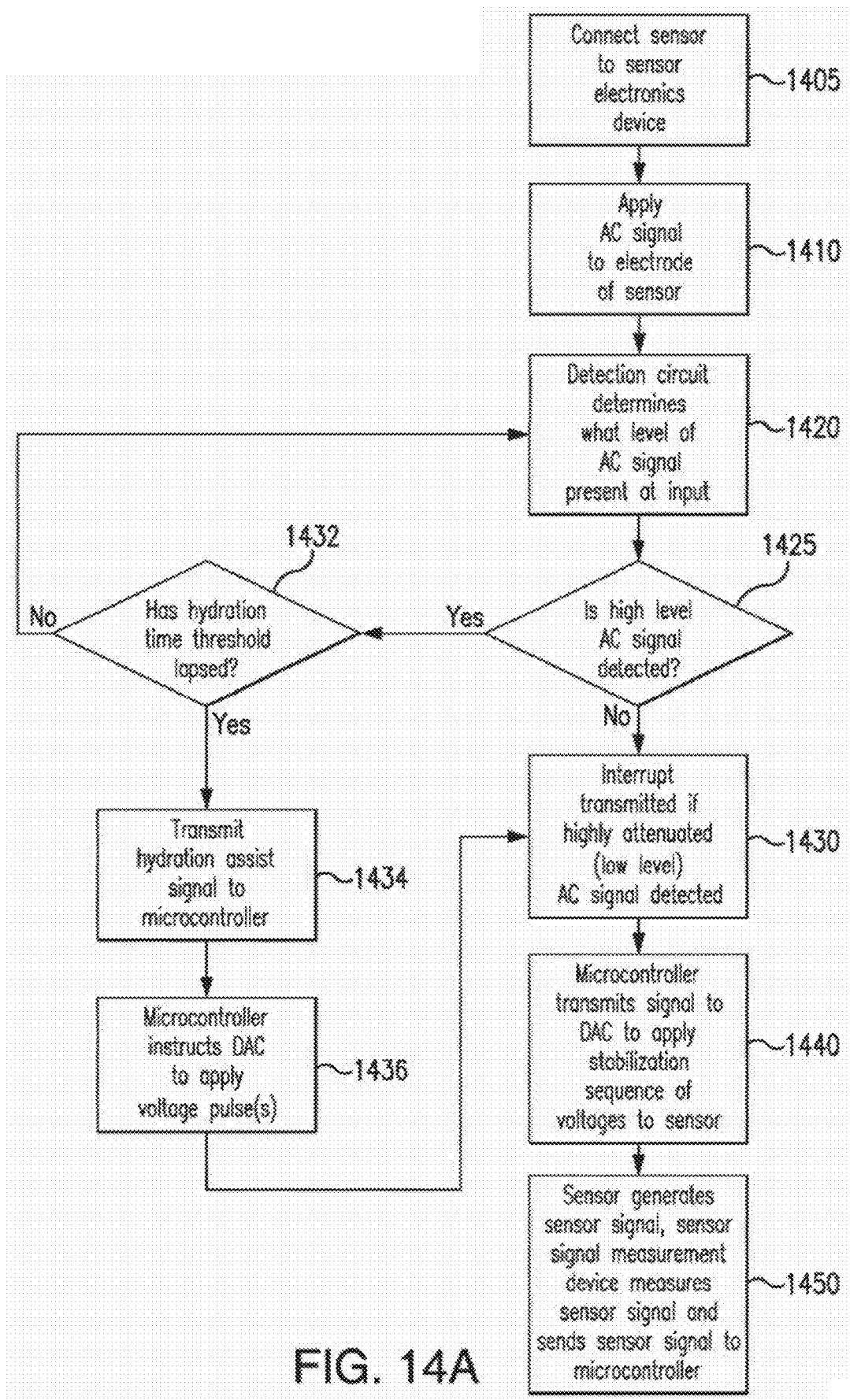
FIGS. 14A, 14B, and 14C illustrate methods of combining hydrating of a sensor with stabilizing a sensor according to an embodiment of the invention.
Figure 14B:
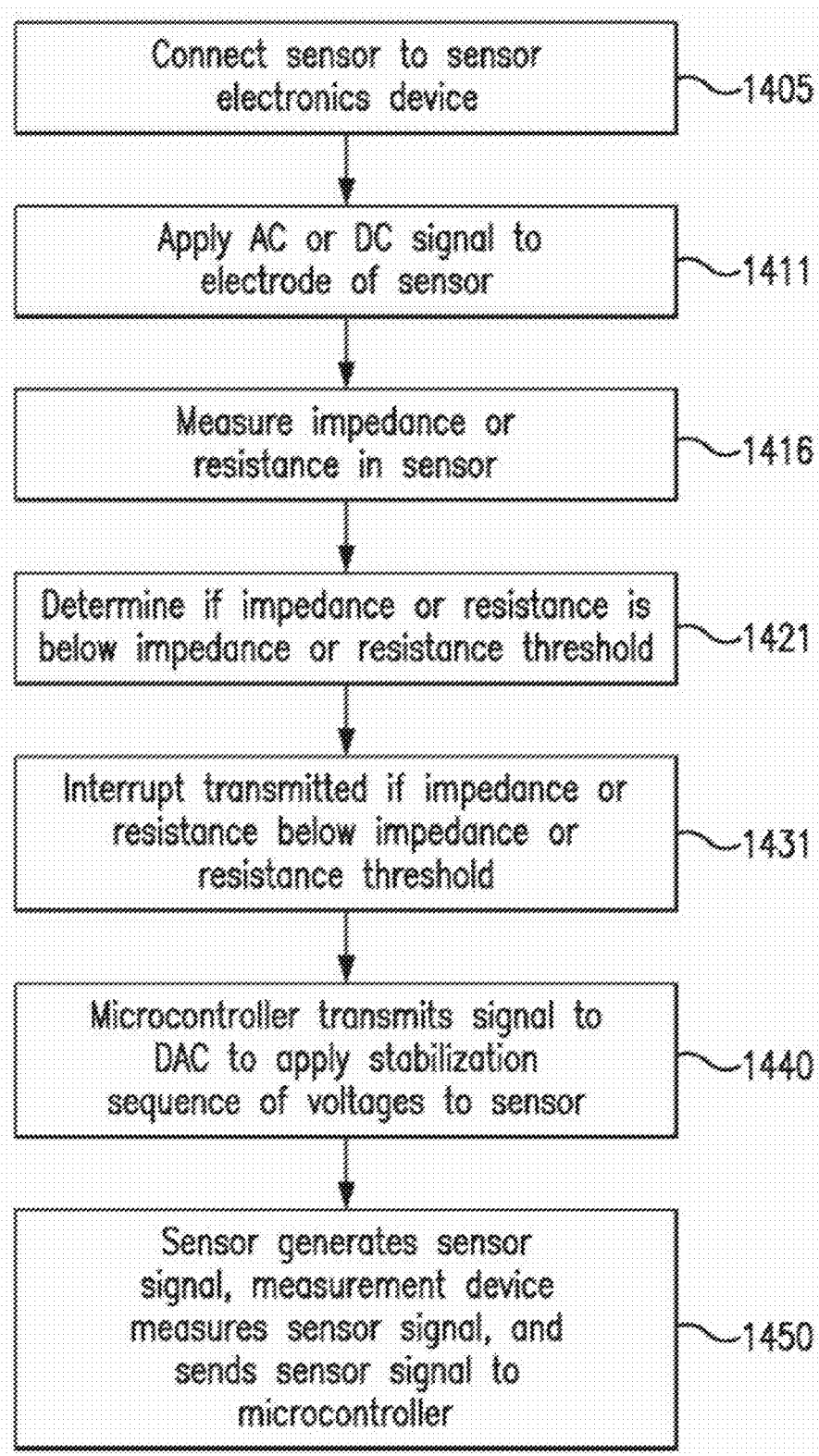

FIGS. 14A and 14B illustrate methods of combining hydrating of a sensor with stabilizing of a sensor according to an embodiment of the present invention. In an embodiment of the invention illustrated in FIG. 14A, the sensor is connected 1405 to the sensor electronics device. The AC signal is applied 1410 to an electrode of the sensor. The detection circuit determines 1420 what level of the AC signal is present at an input of the detection circuit. If the detection circuit determines that a low level of the AC signal is present at the input (representing a high level of attenuation to the AC signal), an interrupt is sent 1430 to microcontroller. Once the interrupt is sent to the microcontroller, the microcontroller knows to begin or initiate 1440 a stabilization sequence, i.e., the application of a number of voltage pulses to an electrode of the sensors, as described above. For example, the microcontroller may cause a digital-to-analog converter to apply three voltage pulses (having a magnitude of +0.535 volts) to the sensor with each of the three voltage pulses followed by a period of three voltage pulses (having a magnitude of 1.07 volts to be applied). This may be referred to transmitting a stabilization sequence of voltages. The microcontroller may cause this by the execution of a software program in a read-only memory (ROM) or a random-access memory. After the stabilization sequence has finished executing, the sensor may generate 1450 a sensor signal, which is measured and transmitted to a microcontroller.

In an embodiment of the invention, the detection circuit may determine 1432 that a high-level AC signal has continued to be present at the input of the detection circuit (e.g., an input of a comparator), even after a hydration time threshold has elapsed. For example, the hydration time threshold may be 10 minutes. After 10 minutes has elapsed, the detection circuit may still be detecting that a high-level AC signal is present. At this point in time, the detection circuit may transmit 1434 a hydration assist signal to the microcontroller. If the microcontroller receives the hydration assist signal, the microcontroller may transmit 1436 a signal to cause a DAC to apply a voltage pulse or a series of voltage pulses to assist the sensor in hydration. In an embodiment of the invention, the microcontroller may transmit a signal to cause the DAC to apply a portion of the stabilization sequence or other voltage pulses to assist in hydrating the sensor. In this embodiment of the invention, the application of voltage pulses may result in the low-level AC signal (or highly attenuated signal) being detected 1438 at the detection circuit. At this point, the detection circuit may transmit an interrupt, as is disclosed in step 1430, and the microcontroller may initiate a stabilization sequence.

FIG. 14B illustrates a second embodiment of a combination of a hydration method and a stabilization method where feedback is utilized in the stabilization process. A sensor is connected 1405 to a sensor electronics device. An AC signal (or a DC signal) is applied 1411 to the sensor. In an embodiment of the invention, the AC signal (or the DC signal) is applied to an electrode of the sensor, e.g. the reference electrode. An impedance measuring device (or resistance measuring device) measures 1416 the impedance (or resistance) within a specified area of the sensor. In an embodiment of the invention, the impedance (or resistance) may be measured between the reference electrode and the working electrode. The measured impedance (or resistance) may be compared 1421 to an impedance or resistance value to see if the impedance (or resistance) is low enough in the sensor, which indicates the sensor is hydrated. If the impedance (or resistance) is below the impedance (or resistance) value or other set criteria, (which may be a threshold value), an interrupt is transmitted 1431 to the microcontroller. After receiving the interrupt, the microcontroller transmits 1440 a signal to the DAC instructing the DAC to apply a stabilization sequence of voltages (or currents) to the sensor. After the stabilization sequence has been applied to the sensor, a sensor signal is created in the sensor (e.g., at the working electrode), is measured by a sensor signal measuring device, is transmitted by the sensor signal measuring device, and is received 1450 by the microcontroller. Because the sensor is hydrated, and the stabilization sequence of voltages has been applied to the sensor, the sensor signal is accurately measuring a physiological parameter (i.e., blood glucose).

Figure 14C:
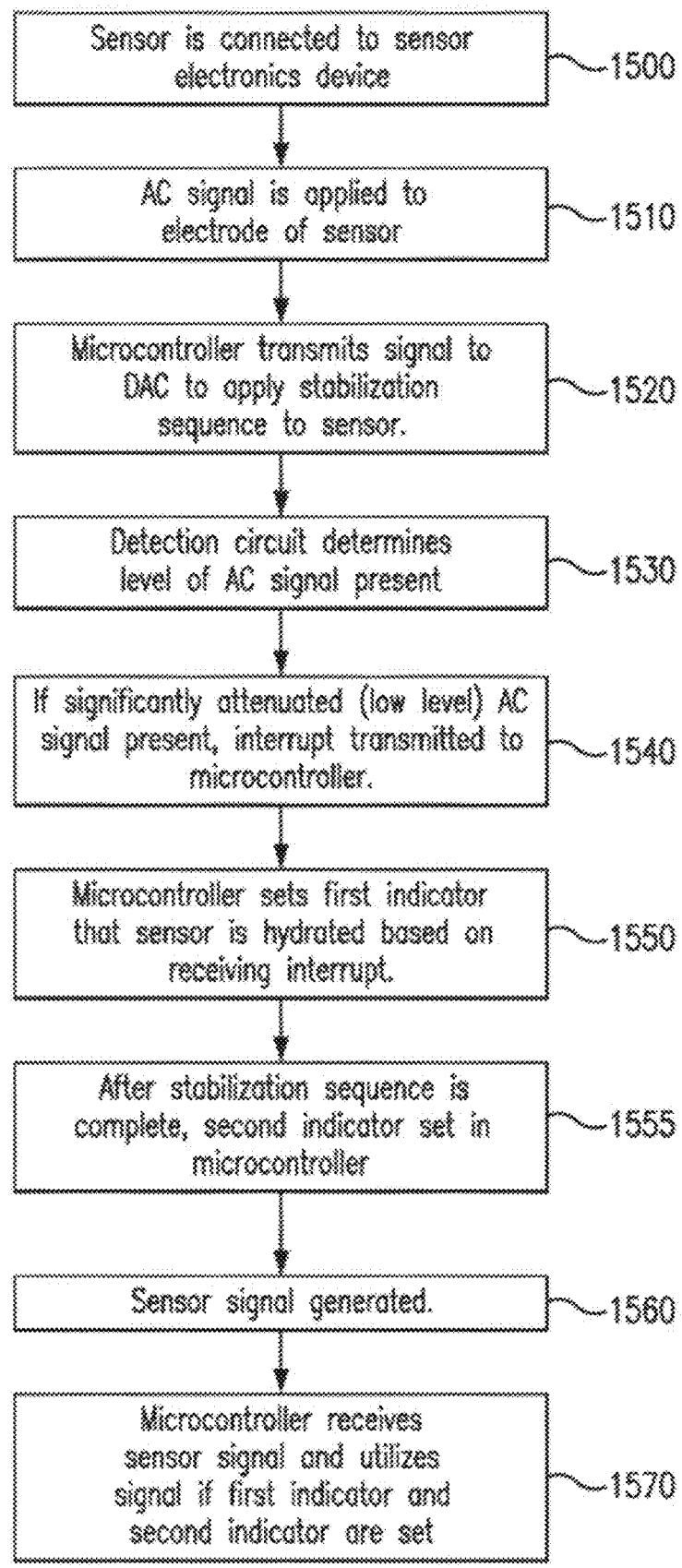

FIG. 14C illustrates a third embodiment of the invention where a stabilization method and hydration method are combined. In this embodiment of the invention, the sensor is connected 1500 to the sensor electronics device. After the sensor is physically connected to the sensor electronics device, an AC signal (or DC signal) is applied 1510 to an electrode (e.g., reference electrode) of the sensor. At the same time, or around the same time, the microcontroller transmits a signal to cause the DAC to apply 1520 a stabilization voltage sequence to the sensor. In an alternative embodiment of the invention, a stabilization current sequence may be applied to the sensor instead of a stabilization voltage sequence. The detection circuit determines 1530 what level of an AC signal (or DC signal) is present at an input terminal of the detection circuit. If there is a low-level AC signal (or DC signal), representing a highly attenuated AC signal (or DC signal), present at the input terminal of the detection circuit, an interrupt is transmitted 1540 to the microcontroller. Because the microcontroller has already initiated the stabilization sequence, the microcontroller receives the interrupt and sets 1550 a first indicator that the sensor is sufficiently hydrated. After the stabilization sequence is complete, the microcontroller sets 1555 a second indicator indicating the completion of the stabilization sequence. The application of the stabilization sequence voltages results in the sensor, e.g., the working electrode, creating 1560 a sensor signal, which is measured by a sensor signal measuring circuit, and sent to the microcontroller. If the second indicator that the stabilization sequence is complete is set and the first indicator that the hydration is complete is set, the microcontroller is able to utilize 1570 the sensor signal. If one or both of the indicators are not set, the microcontroller may not utilize the sensor signal because the sensor signal may not represent accurate measurements of the physiological measurements of the subject.

The above-described hydration and stabilization processes may be used, in general, as part of a larger continuous glucose monitoring (CGM) methodology. The current state of the art in continuous glucose monitoring is largely adjunctive, meaning that the readings provided by a CGM device (including, e.g., an implantable or subcutaneous sensor) cannot be used without a reference value in order to make a clinical decision. The reference value, in turn, must be obtained from a finger stick using, e.g., a BG meter. The reference value is needed because there is a limited amount of information that is available from the sensor/sensing component. Specifically, the only pieces of information that are currently provided by the sensing component for processing are the raw sensor value (i.e., the sensor current or Isig) and the counter voltage, which is the voltage between the counter electrode and the reference electrode (see, e.g., FIG. 5). Therefore, during analysis, if it appears that the raw sensor signal is abnormal (e.g., if the signal is decreasing), the only way one can distinguish between a sensor failure and a physiological change within the user/patient (i.e., glucose level changing in the body) is by acquiring a reference glucose value via a finger stick. As is known, the reference finger stick is also used for calibrating the sensor.

Embodiments of the inventions described herein are directed to advancements and improvements in continuous glucose monitoring resulting in a more autonomous system, as well as related devices and methodologies, wherein the requirement of reference finger sticks may be minimized, or eliminated, and whereby clinical decisions may be made based on information derived from the sensor signal alone, with a high level of reliability. From a sensor-design standpoint, in accordance with embodiments of the invention, such autonomy may be achieved through electrode redundancy, sensor diagnostics, and Isig and/or sensor glucose (SG) fusion.

As will be explored further hereinbelow, redundancy may be achieved through the use of multiple working electrodes (e.g., in addition to a counter electrode and a reference electrode) to produce multiple signals indicative of the patient's blood glucose (BG) level. The multiple signals, in turn, may be used to assess the relative health of the (working) electrodes, the overall reliability of the sensor, and the frequency of the need, if at all, for calibration reference values.

Sensor diagnostics includes the use of additional (diagnostic) information which can provide a real-time insight into the health of the sensor. In this regard, it has been discovered that Electrochemical Impedance Spectroscopy (EIS) provides such additional information in the form of sensor impedance and impedance-related parameters at different frequencies. Moreover, advantageously, it has been further discovered that, for certain ranges of frequencies, impedance and/or impedance-related data are substantially glucose independent. Such glucose independence enables the use of a variety of EIS-based markers or indicators for not only producing a robust, highly-reliable sensor glucose value (through fusion methodologies), but also assessing the condition, health, age, and efficiency of individual electrode(s) and of the overall sensor substantially independently of the glucose-dependent Isig.

For example, analysis of the glucose-independent impedance data provides information on the efficiency of the sensor with respect to how quickly it hydrates and is ready for data acquisition using, e.g., values for 1 kHz real-impedance, 1 kHz imaginary impedance, and Nyquist Slope (to be described in more detail hereinbelow). Moreover, glucose-independent impedance data provides information on potential occlusion(s) that may exist on the sensor membrane surface, which occlusion(s) may temporarily block passage of glucose into the sensor and thus cause the signal to dip (using, e.g., values for 1 kHz real impedance). In addition, glucose-independent impedance data provides information on loss of sensor sensitivity during extended wear—potentially due to local oxygen deficit at the insertion site—using, e.g., values for phase angle and/or imaginary impedance at 1 kHz and higher frequencies.

Within the context of electrode redundancy and EIS, as well as other contexts, as will be described in further detail hereinbelow, a fusion algorithm may be used to take the diagnostic information provided by EIS for each redundant electrode and assess the reliability of each electrode independently. Weights, which are a measure of reliability, may then be added for each independent signal, and a single fused signal may be calculated that can be used to generate sensor glucose values as seen by the patient/subject.

As can be seen from the above, the combined use of redundancy, sensor diagnostics using EIS, and EIS-based fusion algorithms allows for an overall CGM system that is more reliable than what is currently available. Redundancy is advantageous in at least two respects. First, redundancy removes the risk of a single point of failure by providing multiple signals. Second, providing multiple (working) electrodes where a single electrode may be sufficient allows the output of the redundant electrode to be used as a check against the primary electrode, thereby reducing, and perhaps eliminating, the need for frequent calibrations. In addition, EIS diagnostics scrutinize the health of each electrode autonomously without the need for a reference glucose value (finger stick), thereby reducing the number of reference values required. However, the use of EIS technology and EIS diagnostic methods is not limited to redundant systems, i.e., those having more than one working electrode. Rather, as is discussed below in connection with embodiments of the invention, EIS may be advantageously used in connection with single- and/or multiple-electrode sensors.

Figure 15A:
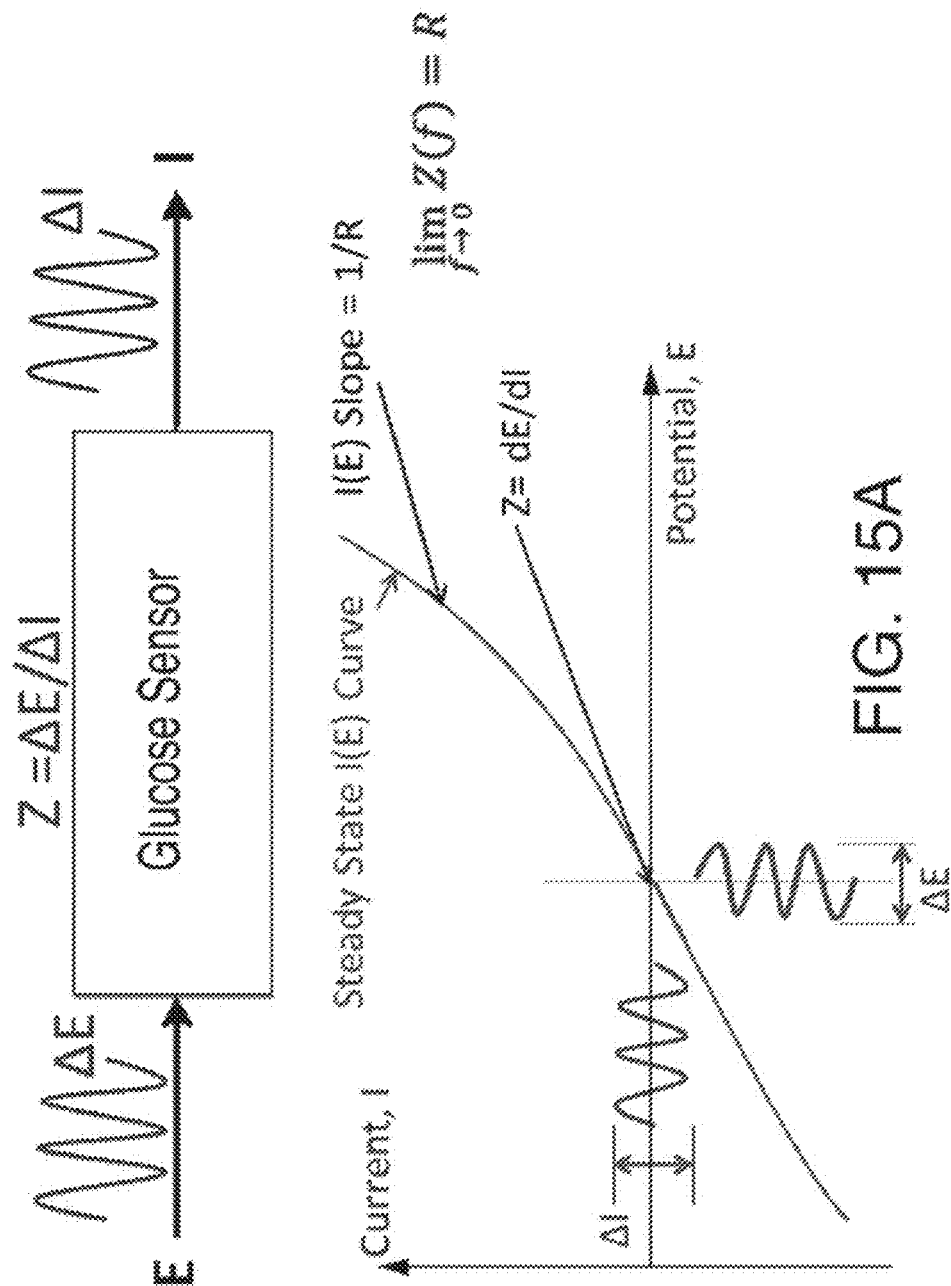
FIG. 15A illustrates EIS-based analysis of system response to the application of a periodic AC signal in accordance with embodiments of the invention.

EIS, or AC impedance methods, study the system response to the application of a periodic small amplitude AC signal. This is shown illustratively in FIG. 15A, where E is the applied potential, I is the current, and impedance (Z) is defined as $\Delta E/\Delta I$. However, although impedance, per se, may be mathematically simply defined as $\Delta E/\Delta I$, heretofore, there has been no commercialization success in application of EIS technology to continuous glucose monitoring. This has been due, in part, to the fact that glucose sensors are very complicated systems and, so far, no mathematical models have been developed which can completely explain the complexity of the EIS output for a glucose sensor.

Figure 15B:
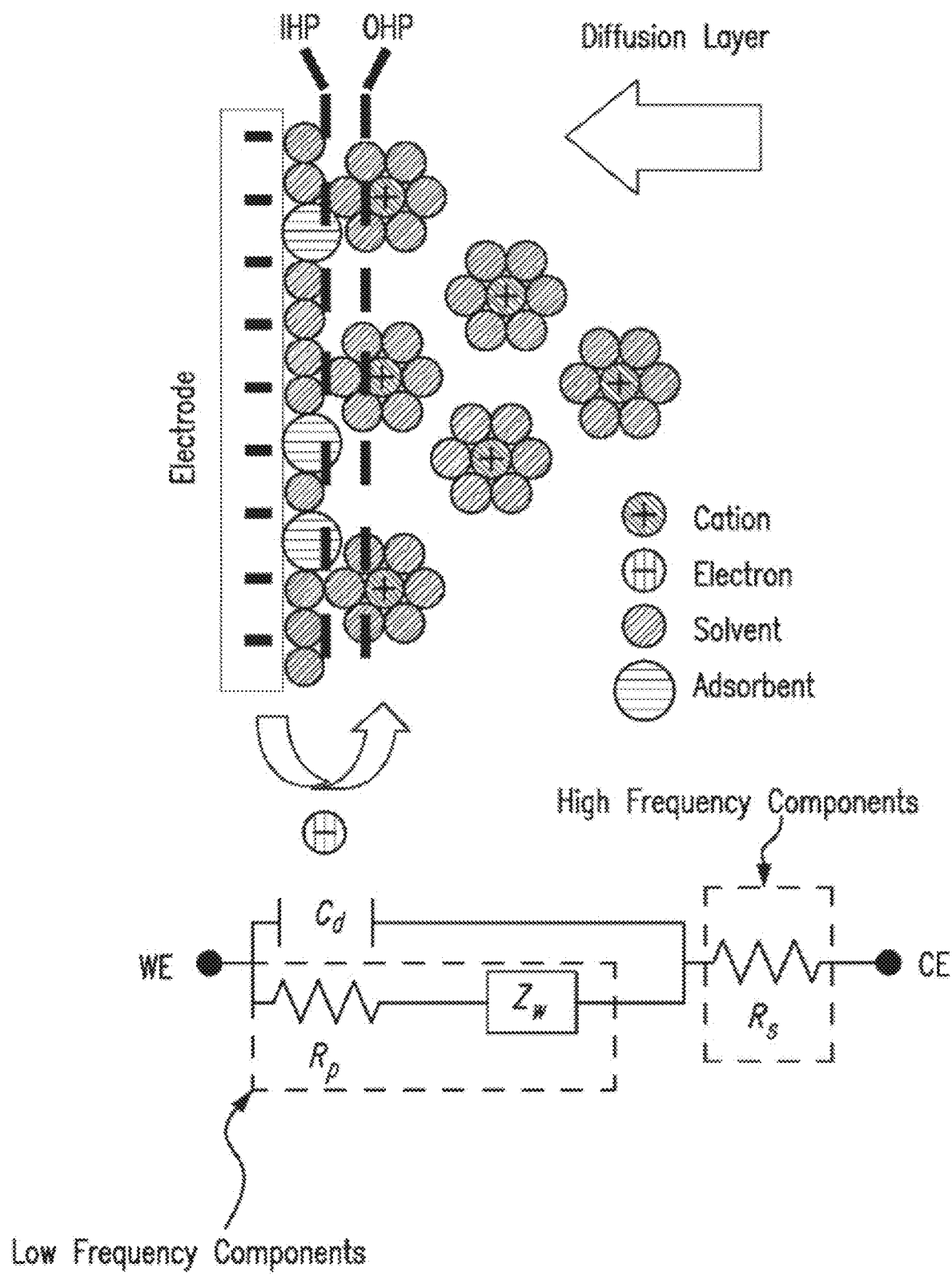
FIG. 15B illustrates a known circuit model for electrochemical impedance spectroscopy.

One simplified electrical circuit model that has been used to describe electrochemical impedance spectroscopy is shown in FIG. 15B. In this illustration, IHP stands for Inner Helmholtz Plane, OHP stands for Outer Helmholtz Plane, CE is the counter electrode, WE is the working electrode, $C_d$ is double layer capacitance, $R_p$ is polarization resistance, $Z_w$ is Warburg impedance, and $R_s$ is solution resistance. Each of the latter four components—double layer capacitance ($C_d$), Warburg impedance ($Z_w$), polarization resistance ($R_p$), and solution resistance ($R_s$)—may play a significant role in sensor performance and can be measured separately by applying low- or high-frequency alternating working potential. For example, Warburg impedance is closely related to diffusional impedance of electrochemical systems—which is primarily a low-frequency impedance—and, as such, exists in all diffusion-limited electrochemical sensors. Thus, by correlating one or more of these components with one or more components and/or layers of a glucose sensor, one may use EIS technology as a sensor-diagnostics tool.

As is known, impedance may be defined in terms of its magnitude and phase, where the magnitude (|Z|) is the ratio of the voltage difference amplitude to the current amplitude, and the phase (θ) is the phase shift by which the current is ahead of the voltage. When a circuit is driven solely with direct current (DC), the impedance is the same as the resistant, i.e., resistance is a special case of impedance with zero phase angle. However, as a complex quantity, impedance may also be represented by its real and imaginary parts. In this regard, the real and imaginary impedance can be derived from the impedance magnitude and phase using the following equations:

Real Impedance(ω)=Magnitude(ω)×cos(Phase(ω)/180×π)

Imaginary Impedance(ω)=Magnitude(ω)×sin(Phase(ω)/180×π)

where ω represents the input frequency at which the magnitude (in ohms) and the phase (in degrees) are measured. The relationship between impedance, on the one hand, and current and voltage on the other—including how the former may be calculated based on measurement of the latter—will be explored more fully below in connection with the sensor electronics, including the Application Specific Integrated Circuit (ASIC), that has been developed for use in embodiments of the invention.

Continuing with the circuit model shown in FIG. 15B, total system impedance may be simplified as:

$$Z_t(\omega) = Z_w(\omega) + R_s + \frac{R_p}{1+\omega^2 R_p^2 C_d^2} - j\frac{\omega R_p^2 C_d}{1+\omega^2 R_p^2 C_d^2}$$

where $Z_w(\omega)$ is the Warburg impedance, ω is the angular velocity, j is the imaginary unit (used instead of the traditional "i" so as not to be confused with electric current), and $C_d$, $R_p$, and $R_s$ are the double layer capacitance, the polarization resistance, and the solution resistance, respectively (as defined previously). Warburg impedance can be calculated as $$Z_w(\omega) = Z_0 \frac{\tanh((js)^m)}{(js)^m}$$

$$s = \frac{L^2}{\omega/D} = \left(\frac{\text{Membrane Thickness}}{\text{Frequency Dependent Diffusion Length}}\right)^2$$

$$Z_0 = \frac{RTL}{n^2 F^2 DC}$$

where D is diffusivity, L is the sensor membrane thickness, C is Peroxide concentration, and m: ½ corresponds to a 45° Nyquist slope.

Figure 16A:
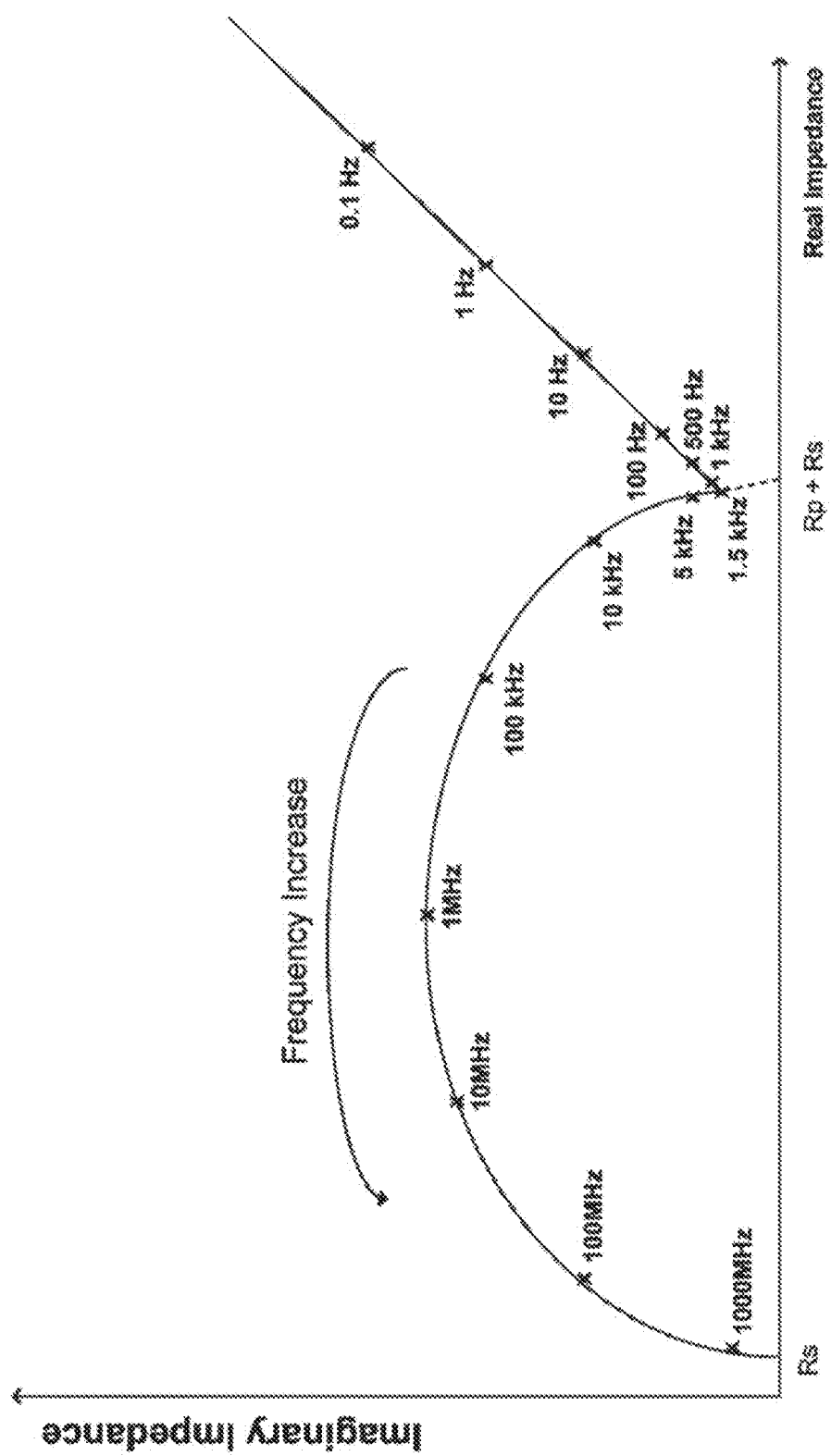
FIG. 16A illustrates an example of a Nyquist plot where, for a selected frequency spectrum from 0.1 Hz to 1000 Mhz, AC voltages plus a DC voltage (DC bias) are applied to the working electrode in accordance with embodiments of the invention.

A Nyquist plot is a graphical representation, wherein the real part of impedance (Real Z) is plotted against its imaginary part (Img Z) across a spectrum of frequencies. FIG. 16A shows a generalized example of a Nyquist Plot, where the X value is the real part of the impedance and the Y value is the imaginary part of the impedance. The phase angle is the angle between the impedance point (X, Y)—which defines a vector having magnitude |Z|—and the X axis.

The Nyquist plot of FIG. 16A is generated by applying AC voltages plus a DC voltage (DC bias) between the working electrode and the counter electrode at selected frequencies from 0.1 Hz to 1000 MHz (i.e., a frequency sweep). Starting from the right, the frequency increases from 0.1 Hz. With each frequency, the real and imaginary impedance can be calculated and plotted. As shown, a typical Nyquist plot of an electrochemical system may look like a semicircle joined with a straight line at an inflection point, wherein the semicircle and the line indicate the plotted impedance. In certain embodiments, the impedance at the inflection point is of particular interest since it is easiest to identify in the Nyquist plot and may define an intercept. Typically, the inflection point is close to the X axis, and the X value of the inflection point approximates the sum of the polarization resistance and solution resistance ($R_p+R_s$).

Figure 16B:
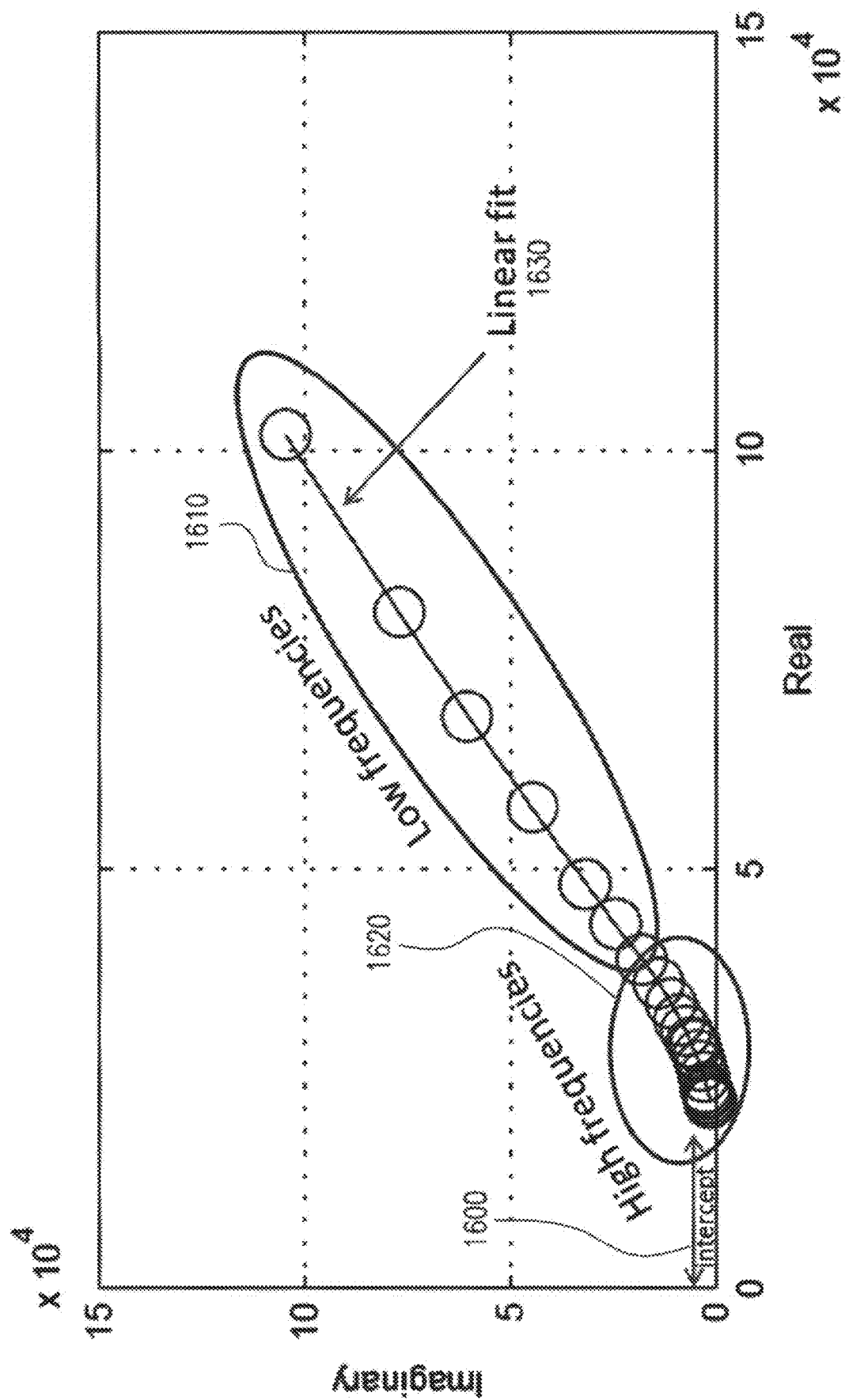
FIG. 16B shows another example of a Nyquist plot with a linear fit for the relatively-lower frequencies and the intercept approximating the value of real impedance at the relatively-higher frequencies.

With reference to FIG. 16B, a Nyquist plot may typically be described in terms of a lower-frequency region 1610 and a higher-frequency region 1620, where the labels "higher frequency" and "lower frequency" are used in a relative sense and are not meant to be limiting. Thus, for example, the lower-frequency region 1610 may illustratively include data points obtained for a frequency range between about 0.1 Hz and about 100 Hz (or higher), and the higher-frequency region 1620 may illustratively include data points obtained for a frequency range between about 1 kHz (or lower) and about 8 kHz (and higher). In the lower-frequency region 1610, the Nyquist slope represents the gradient of the linear fit 1630 of the lower-frequency data points in the Nyquist plot. As shown, in the higher-frequencies region 1620, the value of imaginary impedance is minimal, and may become negligible. As such, the intercept 1600 is essentially the value of the real impedance at the higher frequencies (e.g., approximately in the 1 kHz to 8 kHz range in this case). In FIG. 16B, the intercept 1600 is at about 25 kOhms.

FIGS. 16C and 16D demonstrate how a glucose sensor responds to a sinusoidal (i.e., alternating) working potential. In these figures, GLM is the sensor's glucose limiting membrane, AP is the adhesion promoter, HSA is human serum albumin, GOX is glucose oxidase enzyme (layer), $E_{dc}$ is DC potential, $E_{ac}$ is AC potential, and $C'_{peroxide}$ is peroxide concentration during AC application. As shown in FIG. 16C, if the sensor diffusion length, which is a function of AC potential frequency, molecular diffusivity, and membrane thickness, is small compared to the membrane (GOX) length, the system gives a relatively linear response with a constant phase angle (i.e., infinite). In contrast, if the diffusion length is equal to the membrane (GOX) length, the system response will become finite, resulting in a semi-circle Nyquist plot, as shown in FIG. 16D. The latter usually holds true for low-frequency EIS, where the non-Faradaic process is negligible.

In performing an EIS analysis, an AC voltage of various frequencies and a DC bias may be applied between, e.g., the working and reference electrodes. In this regard, EIS is an improvement over previous methodologies that may have limited the application to a simple DC current or an AC voltage of single frequency. Although, generally, EIS may be performed at frequencies in the μHz to MHz range, in embodiments of the invention, a narrower range of frequencies (e.g., between about 0.1 Hz and about 8 kHz) may be sufficient. Thus, in embodiments of the invention, AC potentials may be applied that fall within a frequency range of between about 0.1 Hz and about 8 kHz, with a programmable amplitude of up to at least 100 mV, and preferably at about 50 mV.

Figure 16E:
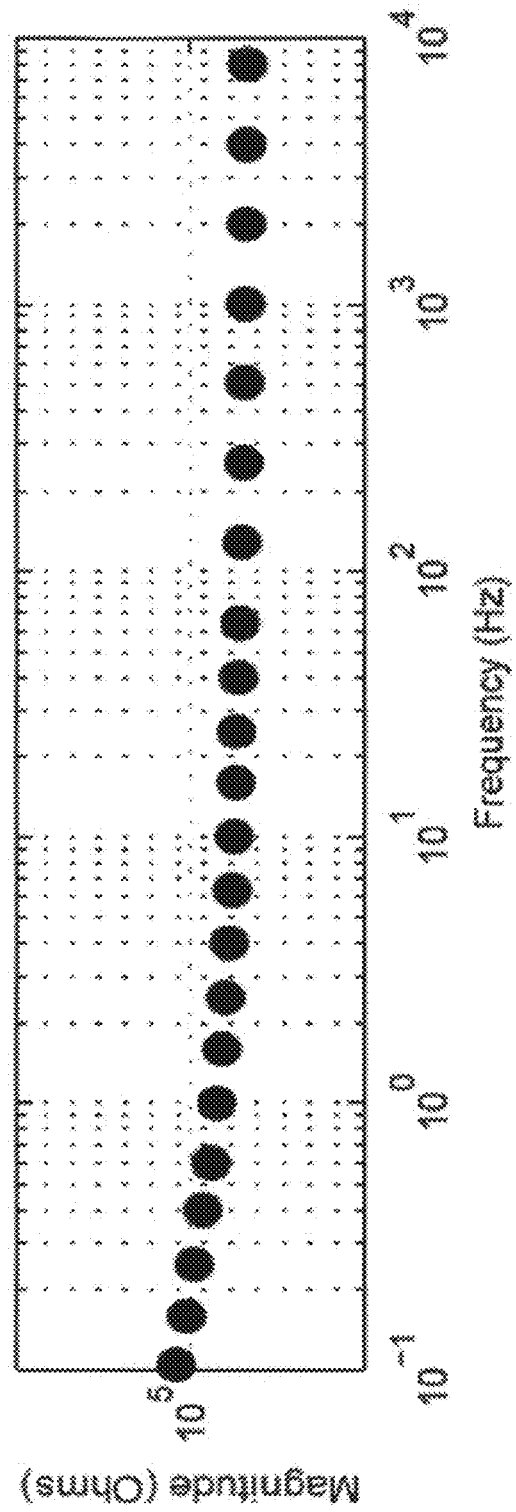
FIG. 16E shows a Bode plot for magnitude in accordance with embodiments of the invention.
Figure 16F:
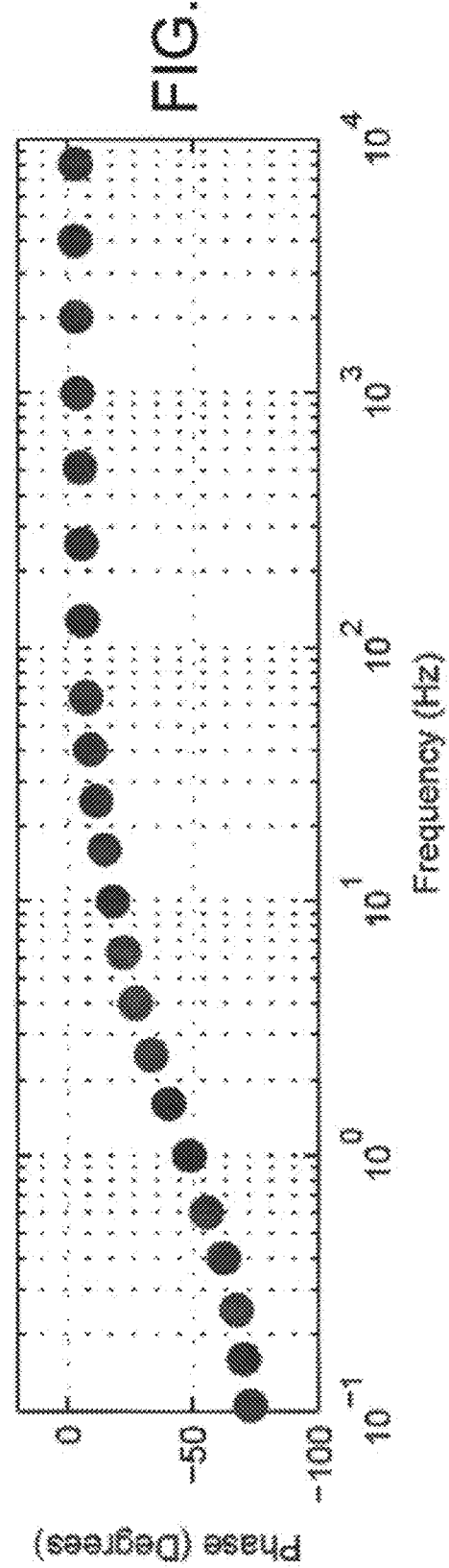
FIG. 16F shows a Bode plot for phase in accordance with embodiments of the invention.

Within the above-mentioned frequency range, the relatively-higher frequencies—i.e., those that fall generally between about 1 kHz and about 8 kHz—are used to scrutinize the capacitive nature of the sensor. Depending on the thickness and permeability of membranes, a typical range of impedance at the relatively-higher frequencies may be, e.g., between about 500 Ohms and 25 kOhms, and a typical range for the phase may be, e.g., between 0 degrees and −40 degrees. The relatively-lower frequencies—i.e., those that fall generally between about 0.1 Hz and about 100 Hz—on the other hand, are used to scrutinize the resistive nature of the sensor. Here, depending on electrode design and the extent of metallization, a typical functioning range for output real impedance may be, e.g., between about 50 kOhms and 300 kOhms, and a typical range for the phase may be between about −50 degrees to about −90 degrees. The above illustrative ranges are shown, e.g., in the Bode plots of FIGS. 16E and 16F.

As noted previously, the phrases "higher frequencies" and "lower frequencies" are meant to be used relative to one another, rather than in an absolute sense, and they, as well as the typical impedance and phase ranges mentioned above, are meant to be illustrative, and not limiting. Nevertheless, the underlying principle remains the same: the capacitive and resistive behavior of a sensor can be scrutinized by analyzing the impedance data across a frequency spectrum, wherein, typically, the lower frequencies provide information about the more resistive components (e.g., the electrode, etc.), while the higher frequencies provide information about the capacitive components (e.g., membranes). However, the actual frequency range in each case is dependent on the overall design, including, e.g., the type(s) of electrode(s), the surface area of the electrode(s), membrane thickness, the permeability of the membrane, and the like. See also FIG. 15B regarding general correspondence between high-frequency circuit components and the sensor membrane, as well as between low-frequency circuit components and the Faradaic process, including, e.g., the electrode(s).

Figure 17:
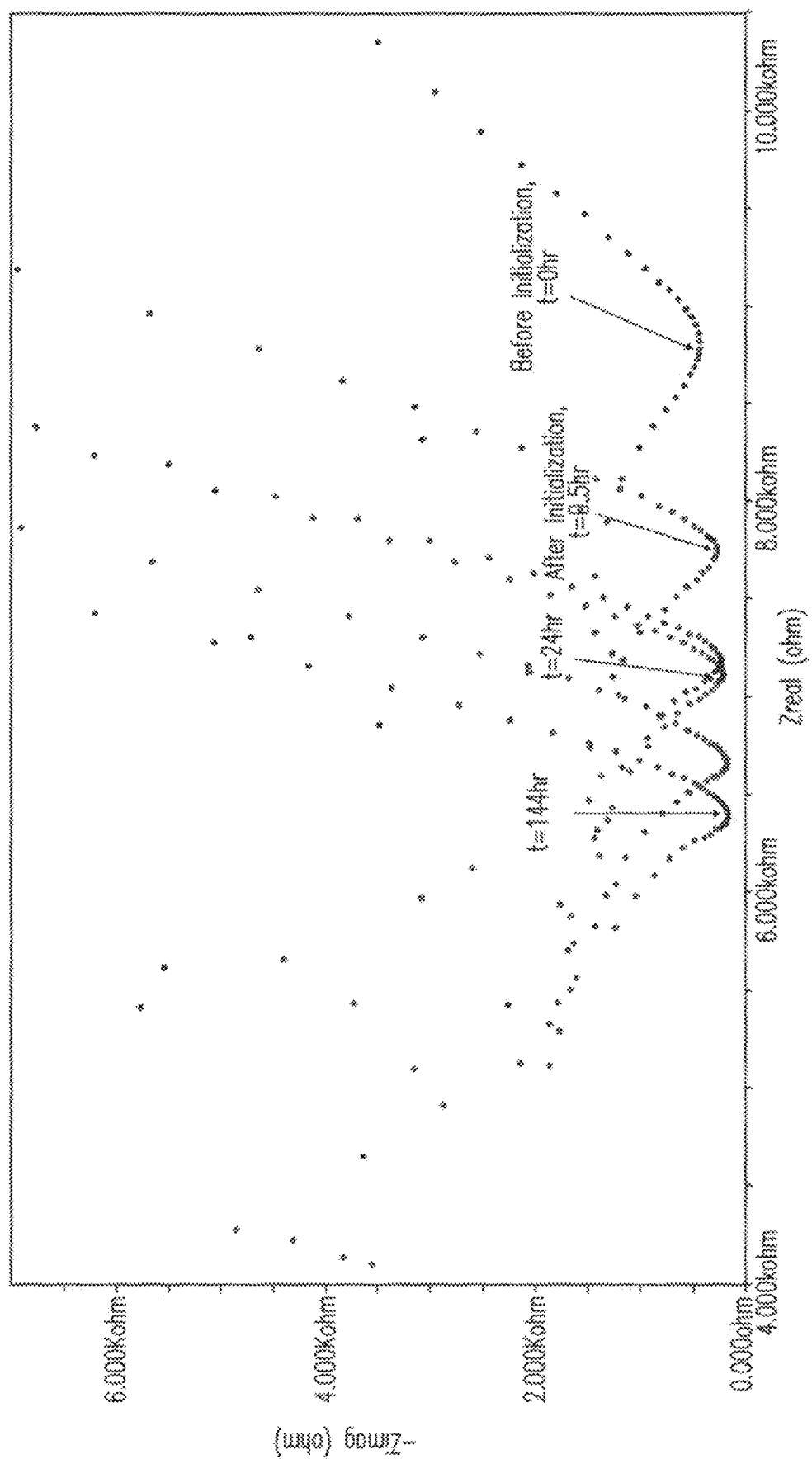
FIG. 17 illustrates the changing Nyquist plot of sensor impedance as the sensor ages in accordance with embodiments of the invention.

EIS may be used in sensor systems where the sensor includes a single working electrode, as well those in which the sensor includes multiple (redundant) working electrodes. In one embodiment, EIS provides valuable information regarding the age (or aging) of the sensor. Specifically, at different frequencies, the magnitude and the phase angle of the impedance vary. As seen in FIG. 17, the sensor impedance—in particular, the sum of Rp and Rs—reflects the sensor age as well as the sensor's operating conditions. Thus, a new sensor normally has higher impedance than a used sensor as seen from the different plots in FIG. 17. In this way, by considering the X-value of the sum of Rp and Rs, a threshold can be used to determine when the sensor's age has exceeded the specified operating life of the sensor. It is noted that, although for the illustrative examples shown in FIGS. 17-21 and discussed below, the value of real impedance at the inflection point (i.e., Rp+Rs) is used to determine the aging, status, stabilization, and hydration of the sensor, alternative embodiments may use other EIS-based parameters, such as, e.g., imaginary impedance, phase angle, Nyquist slope, etc. in addition to, or in place of, real impedance.

FIG. 17 illustrates an example of a Nyquist plot over the life time of a sensor. The points indicated by arrows are the respective inflection points for each of the sweeps across the frequency spectrum. For example, before initialization (at time t=0), Rs+Rp is higher than 8.5 kOhms, and after initialization (at time t=0.5 hr), the value of Rs+Rp dropped to below 8 kOhms. Over the next six days, Rs+Rp continues to decrease, such that, at the end of the specified sensor life, Rs+Rp dropped to below 6.5 kOhms. Based on such examples, a threshold value can be set to specify when the Rs+Rp value would indicate the end of the specified operating life of the sensor. Therefore, the EIS technique allows closure of the loophole of allowing a sensor to be re-used beyond the specified operating time. In other words, if the patient attempts to re-use a sensor after the sensor has reached its specified operating time by disconnecting and then re-connecting the sensor again, the EIS will measure abnormally-low impedance, thereby enabling the system to reject the sensor and prompt the patient for a new sensor.

Additionally, EIS may enable detection of sensor failure by detecting when the sensor's impedance drops below a low impedance threshold level indicating that the sensor may be too worn to operate normally. The system may then terminate the sensor before the specified operating life. As will be explored in more detail below, sensor impedance can also be used to detect other sensor failure (modes). For example, when a sensor goes into a low-current state (i.e., sensor failure) due to any variety of reasons, the sensor impedance may also increase beyond a certain high impedance threshold. If the impedance becomes abnormally high during sensor operation, due, e.g., to protein or polypeptide fouling, macrophage attachment or any other factor, the system may also terminate the sensor before the specified sensor operating life.

Figure 18:
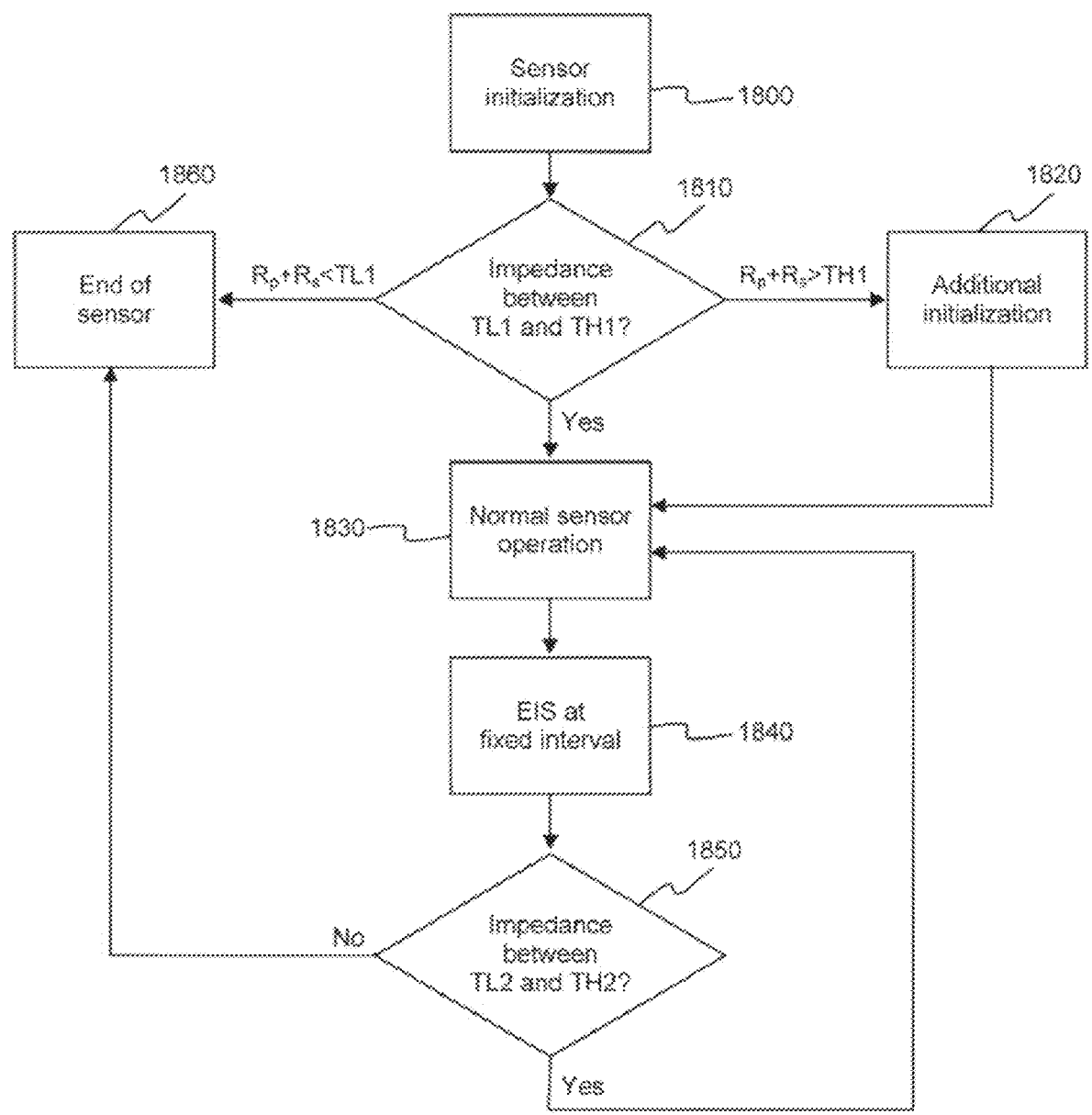
FIG. 18 illustrates methods of applying EIS technique in stabilizing and detecting the age of the sensor in accordance with embodiments of the invention.

FIG. 18 illustrates how the EIS technique can be applied during sensor stabilization and in detecting the age of the sensor in accordance with embodiments of the invention. The logic of FIG. 18 begins at 1800 after the hydration procedure and sensor initialization procedure described previously has been completed. In other words, the sensor has been deemed to be sufficiently hydrated, and the first initialization procedure has been applied to initialize the sensor. The initialization procedure may preferably be in the form of voltage pulses as described previously in the detailed description. However, in alternative embodiments, different waveforms can be used for the initialization procedure. For example, a sine wave can be used, instead of the pulses, to accelerate the wetting or conditioning of the sensor. In addition, it may be necessary for some portion of the waveform to be greater than the normal operating voltage of the sensor, i.e., 0.535 volt.

At block 1810, an EIS procedure is applied and the impedance is compared to both a first high and a first low threshold. An example of a first high and first low threshold value would be 7 kOhms and 8.5 kOhms, respectively, although the values can be set higher or lower as needed. If the impedance, for example, Rp+Rs, is higher than the first high threshold, the sensor undergoes an additional initialization procedure (e.g., the application of one or more additional pulses) at block 1820. Ideally, the number of total initialization procedures applied to initialize the sensor would be optimized to limit the impact on both the battery life of the sensor and the overall amount of time needed to stabilize a sensor. Thus, by applying EIS, fewer initializations can be initially performed, and the number of initializations can be incrementally added to give just the right amount of initializations to ready the sensor for use. Similarly, in an alternative embodiment, EIS can be applied to the hydration procedure to minimize the number of initializations needed to aid the hydration process as described in FIGS. 13-14.

On the other hand, if the impedance, for example, Rp+Rs, is below the first low threshold, the sensor will be determined to be faulty and would be terminated immediately at block 1860. A message will be given to the user to replace the sensor and to begin the hydration process again. If the impedance is within the high and low thresholds, the sensor will begin to operate normally at block 1830. The logic then proceeds to block 1840 where an additional EIS is performed to check the age of the sensor. The first time the logic reaches block 1840, the microcontroller will perform an EIS to gauge the age of the sensor to close the loophole of the user being able to plug in and plug out the same sensor. In future iterations of the EIS procedure as the logic returns to block 1840, the microprocessor will perform an EIS at fixed intervals during the specified life of the sensor. In one preferred embodiment, the fixed interval is set for every 2 hours, however, longer or shorter periods of time can easily be used.

At block 1850, the impedance is compared to a second set of high and low thresholds. An example of such second high and low threshold values may be 5.5 kOhms and 8.5 kOhms, respectively, although the values can be set higher or lower as needed. As long as the impedance values stay within a second high and low threshold, the logic proceeds to block 1830, where the sensor operates normally until the specified sensor life, for example, 5 days, is reached. Of course, as described with respect to block 1840, EIS will be performed at the regularly scheduled intervals throughout the specified sensor life. However, if, after the EIS is performed, the impedance is determined to have dropped below a second lower threshold or risen above a second higher threshold at block 1850, the sensor is terminated at block 1860. In further alternative embodiments, a secondary check can be implemented of a faulty sensor reading. For example, if the EIS indicates that the impedance is out of the range of the second high and low thresholds, the logic can perform a second EIS to confirm that the second set of thresholds is indeed not met (and confirm that the first EIS was correctly performed) before determining the end of sensor at block 1860.

Figure 19:
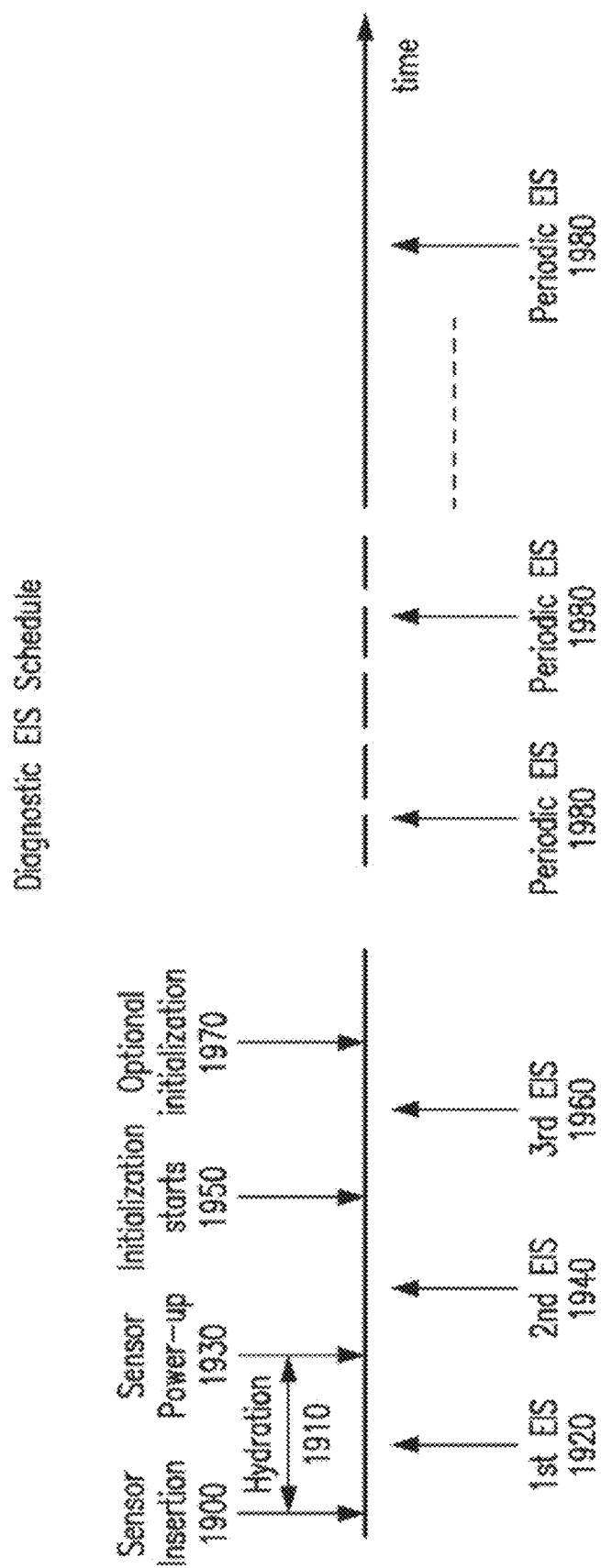
FIG. 19 illustrates a schedule for performing the EIS procedure in accordance with embodiments of the invention.

FIG. 19 builds upon the above description and details a possible schedule for performing diagnostic EIS procedures in accordance with preferred embodiments of the present invention. Each diagnostic EIS procedure is optional and it is possible to not schedule any diagnostic EIS procedure or to have any combination of one or more diagnostic EIS procedures, as deemed needed. The schedule of FIG. 19 begins at sensor insertion at point 1900. Following sensor insertion, the sensor undergoes a hydration period 1910. This hydration period is important because a sensor that is not sufficiently hydrated may give the user inaccurate readings, as described previously. The first optional diagnostic EIS procedure at point 1920 is scheduled during this hydration period 1910 to ensure that the sensor is sufficiently hydrated. The first diagnostic EIS procedure 1920 measures the sensor impedance value to determine if the sensor has been sufficiently hydrated. If the first diagnostic EIS procedure 1920 determines impedance is within a set high and low threshold, indicating sufficient hydration, the sensor controller will allow the sensor power-up at point 1930. Conversely, if the first diagnostic EIS procedure 1920 determines impedance is outside a set high and low threshold, indicating insufficient hydration, the sensor hydration period 1910 may be prolonged. After prolonged hydration, once a certain capacitance has been reached between the sensor's electrodes, meaning the sensor is sufficiently hydrated, power-up at point 1930 can occur.

A second optional diagnostic EIS procedure 1940 is scheduled after sensor power-up at point 1930, but before sensor initialization starts at point 1950. Scheduled here, the second diagnostic EIS procedure 1940 can detect if a sensor is being re-used prior to the start of initialization at 1950. The test to determine if the sensor is being reused was detailed in the description of FIG. 18. However, unlike the previous description with respect to FIG. 18, where the aging test is performed after initialization is completed, the aging test is shown in FIG. 19 as being performed before initialization. It is important to appreciate that the timeline of EIS procedures described in FIG. 19 can be rearranged without affecting the overall teaching of the application, and that the order of some of the steps can be interchanged. As explained previously, the second diagnostic EIS procedure 1940 detects a re-used sensor by determining the sensor's impedance value and then comparing it to a set high and low threshold. If impedance falls outside of the set threshold, indicating the sensor is being re-used, the sensor may then be rejected, and the user prompted to replace it with a new sensor. This prevents the complications that may arise out of re-use of an old sensor. Conversely, if impedance falls within a set threshold, sensor initialization 1950 can start with the confidence that a new sensor is being used.

A third optional diagnostic EIS procedure 1960 is scheduled after initialization starts at point 1950. The third diagnostic EIS procedure 1960 tests the sensor's impedance value to determine if the sensor is fully initialized. The third diagnostic EIS procedure 1960 should be performed at the minimum amount of time needed for any sensor to be fully initialized. When performed at this time, sensor life is maximized by limiting the time a fully initialized sensor goes unused, and over-initialization is averted by confirming full initialization of the sensor before too much initialization occurs. Preventing over-initialization is important because over-initialization results in a suppressed current which can cause inaccurate readings. However, under-initialization is also a problem, so if the third diagnostic EIS procedure 1960 indicates the sensor is under-initialized, an optional initialization at point 1970 may be performed in order to fully initialize the sensor. Under-initialization is disadvantageous because it results in an excessive current that does not relate to the actual glucose concentration. Because of the danger of under- and over-initialization, the third diagnostic EIS procedure plays an important role in ensuring the sensor functions properly when used.

In addition, optional periodic diagnostic EIS procedures 1980 can be scheduled for the time after the sensor is fully initialized. The EIS procedures 1980 can be scheduled at any set interval. As will be discussed in more detail below, EIS procedures 1980 may also be triggered by other sensor signals, such as an abnormal current or an abnormal counter electrode voltage. Additionally, as few or as many EIS procedures 1980 can be scheduled as desired. In preferred embodiments, the EIS procedure used during the hydration process, sensor life check, initialization process, or the periodic diagnostic tests is the same procedure. In alternative embodiments, the EIS procedure can be shortened or lengthened (i.e., fewer or more ranges of frequencies checked) for the various EIS procedures depending on the need to focus on specific impedance ranges. The periodic diagnostic EIS procedures 1980 monitor impedance values to ensure that the sensor is continuing to operate at an optimal level.

The sensor may not be operating at an optimal level if the sensor current has dropped due to polluting species, sensor age, or a combination of polluting species and sensor age. A sensor that has aged beyond a certain length is no longer useful, but a sensor that has been hampered by polluting species can possibly be repaired. Polluting species can reduce the surface area of the electrode or the diffusion pathways of analytes and reaction byproducts, thereby causing the sensor current to drop. These polluting species are charged and gradually gather on the electrode or membrane surface under a certain voltage. Previously, polluting species would destroy the usefulness of a sensor. Now, if periodic diagnostic EIS procedures 1980 detect impedance values which indicate the presence of polluting species, remedial action can be taken. When remedial action is to be taken is described with respect to FIG. 20. Periodic diagnostic EIS procedures 1980 therefore become extremely useful because they can trigger sensor remedial action which can possibly restore the sensor current to a normal level and prolong the life of the sensor. Two possible embodiments of sensor remedial actions are described below in the descriptions of FIGS. 21A and 21B.

Additionally, any scheduled diagnostic EIS procedure 1980 may be suspended or rescheduled when certain events are determined imminent. Such events may include any circumstance requiring the patient to check the sensor reading, including for example when a patient measures his or her BG level using a test strip meter in order to calibrate the sensor, when a patient is alerted to a calibration error and the need to measure his or her BG level using a test strip meter a second time, or when a hyperglycemic or hypoglycemic alert has been issued but not acknowledged.

Figure 20:
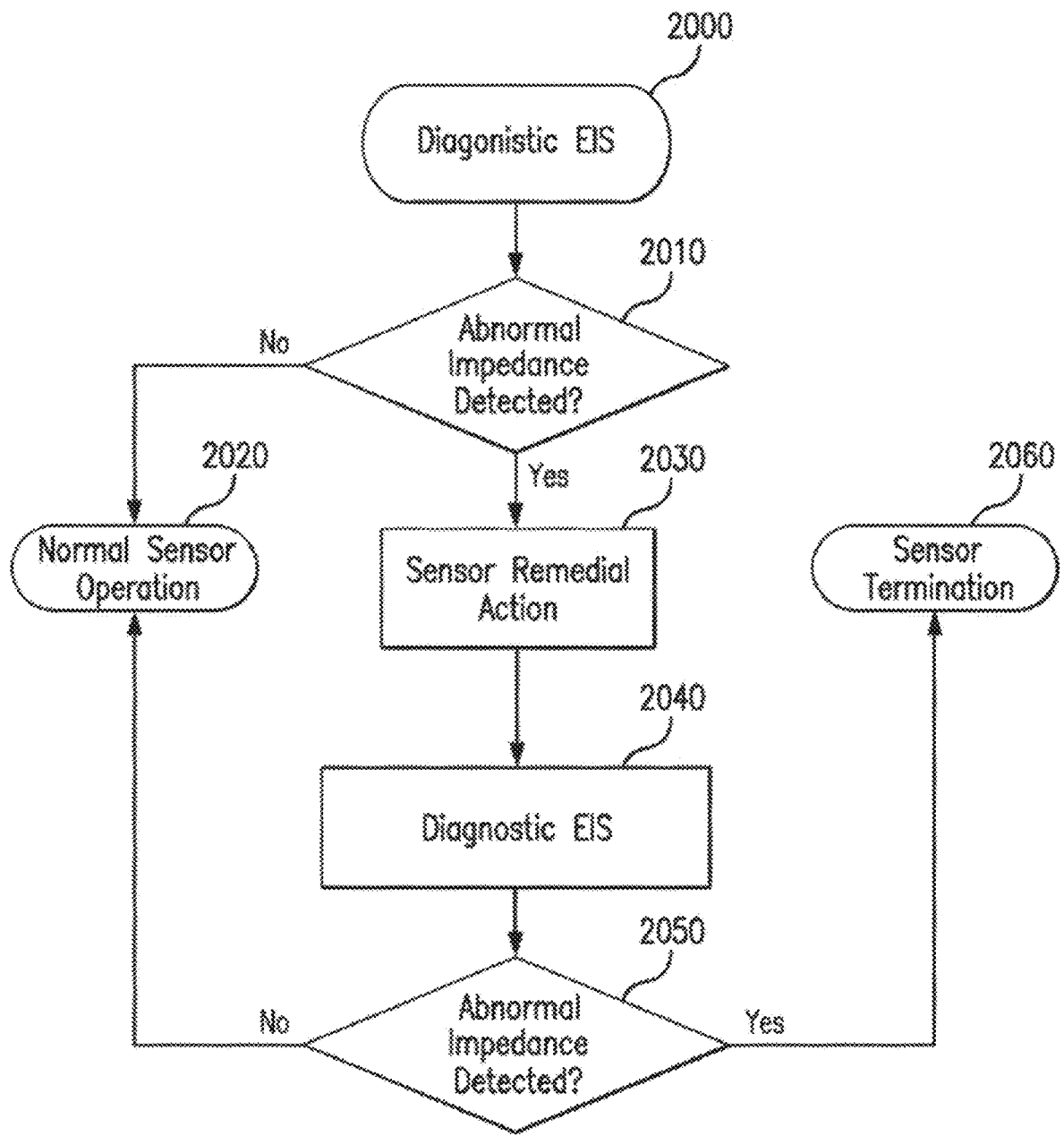
FIG. 20 illustrates a method of detecting and repairing a sensor using EIS procedures in conjunction with remedial action in accordance with embodiments of the invention.

FIG. 20 illustrates a method of combining diagnostic EIS procedures with sensor remedial action in accordance with embodiments of the present invention. The block 2000 diagnostic procedure may be any of the periodic diagnostic EIS procedures 1980 as detailed in FIG. 19. The logic of this method begins when a diagnostic EIS procedure is performed at block 2000 in order to detect the sensor's impedance value. As noted, in specific embodiments, the EIS procedure applies a combination of a DC bias and an AC voltage of varying frequencies wherein the impedance detected by performing the EIS procedure is mapped on a Nyquist plot, and an inflection point in the Nyquist plot approximates a sum of polarization resistance and solution resistance (i.e., the real impedance value). After the block 2000 diagnostic EIS procedure detects the sensor's impedance value, the logic moves to block 2010.

At block 2010, the impedance value is compared to a set high and low threshold to determine if it is normal. If impedance is within the set boundaries of the high and low thresholds at block 2010, normal sensor operation is resumed at block 2020 and the logic of FIG. 20 will end until a time when another diagnostic EIS procedure is scheduled. Conversely, if impedance is determined to be abnormal (i.e., outside the set boundaries of the high and low thresholds) at block 2010, remedial action at block 2030 is triggered. An example of a high and low threshold value that would be acceptable during a sensor life would be 5.5 kOhms and 8.5 kOhms, respectively, although the values can be set higher or lower as needed.

The block 2030 remedial action is performed to remove any of the polluting species, which may have caused the abnormal impedance value. In preferred embodiments, the remedial action is performed by applying a reverse current, or a reverse voltage between the working electrode and the reference electrode. The specifics of the remedial action will be described in more detail with respect to FIG. 21. After the remedial action is performed at block 2030, impedance value is again tested by a diagnostic EIS procedure at block 2040. The success of the remedial action is then determined at block 2050 when the impedance value from the block 2040 diagnostic EIS procedure is compared to the set high or low threshold. As in block 2010, if impedance is within the set thresholds, it is deemed normal, and if impedance is outside the set thresholds, it is deemed abnormal.

If the sensor's impedance value is determined to have been restored to normal at block 2050, normal sensor operation at block 2020 will occur. If impedance is still not normal, indicating that either sensor age is the cause of the abnormal impedance or the remedial action was unsuccessful in removing the polluting species, the sensor is then terminated at block 2060. In alternative embodiments, instead of immediately terminating the sensor, the sensor may generate a sensor message initially requesting the user to wait and then perform further remedial action after a set period of time has elapsed. This alternative step may be coupled with a separate logic to determine if the impedance values are getting closer to being within the boundary of the high and low threshold after the initial remedial action is performed. For example, if no change is found in the sensor impedance values, the sensor may then decide to terminate. However, if the sensor impedance values are getting closer to the preset boundary, yet still outside the boundary after the initial remedial action, an additional remedial action could be performed. In yet another alternative embodiment, the sensor may generate a message requesting the user to calibrate the sensor by taking a finger stick meter measurement to further confirm whether the sensor is truly failing. All of the above embodiments work to prevent a user from using a faulty sensor that produces inaccurate readings.

Figure 21A:
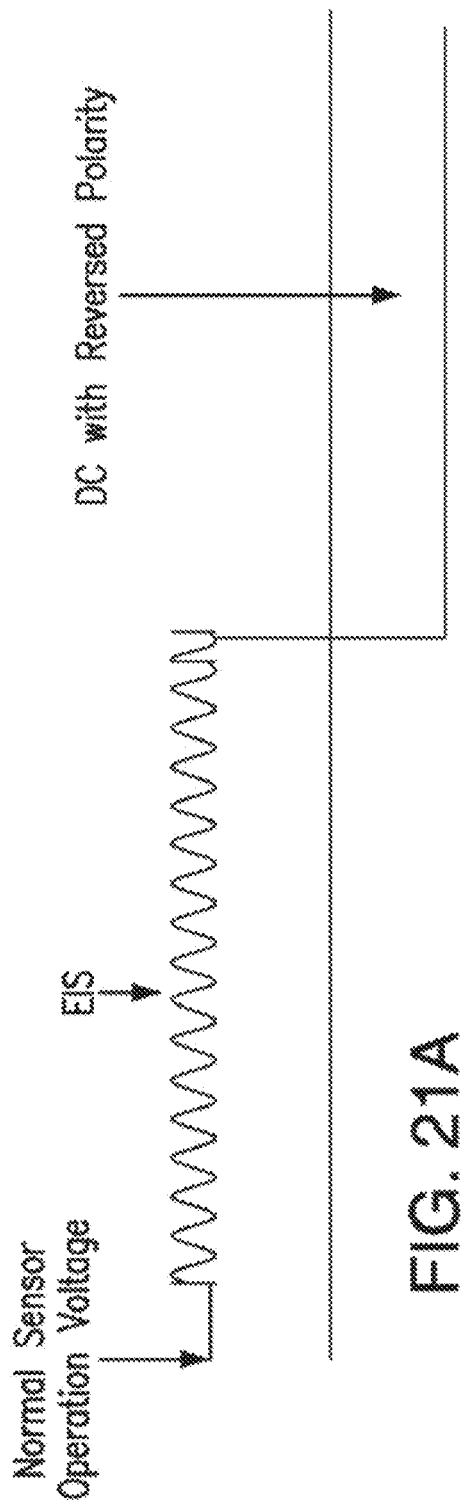
FIGS. 21A and 21B illustrate examples of a sensor remedial action in accordance with embodiments of the invention.

FIG. 21A illustrates one embodiment of the sensor remedial action previously mentioned. In this embodiment, blockage created by polluting species is removed by reversing the voltage being applied to the sensor between the working electrode and the reference electrode. The reversed DC voltage lifts the charged, polluting species from the electrode or membrane surface, clearing diffusion pathways. With cleared pathways, the sensor's current returns to a normal level and the sensor can give accurate readings. Thus, the remedial action saves the user the time and money associated with replacing an otherwise effective sensor.

Figure 21B:
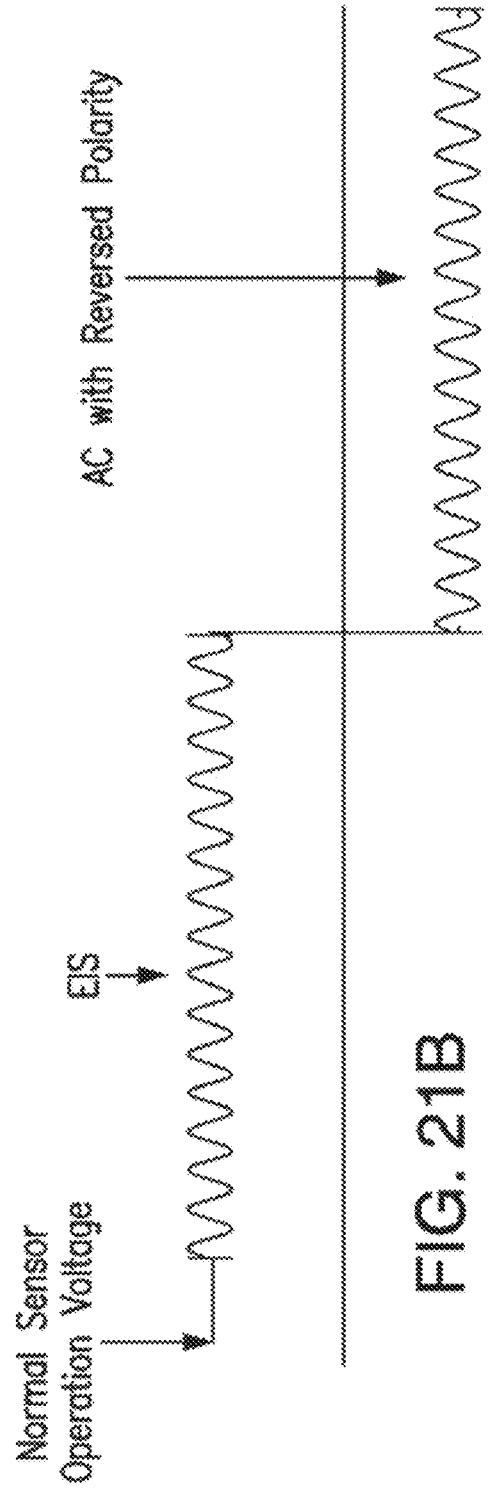

FIG. 21B illustrates an alternative embodiment of the sensor remedial action previously mentioned. In this embodiment, the reversed DC voltage applied between the working electrode and the reference electrode is coupled with an AC voltage. By adding the AC voltage, certain tightly absorbed species or species on the superficial layer can be removed since the AC voltage can extend its force further from the electrode and penetrate all layers of the sensor. The AC voltage can come in any number of different waveforms. Some examples of waveforms that could be used include square waves, triangular waves, sine waves, or pulses. As with the previous embodiment, once polluting species are cleared, the sensor can return to normal operation, and both sensor life and accuracy are improved.

While the above examples illustrate the use, primarily, of real impedance data in sensor diagnostics, embodiments of the invention are also directed to the use of other EIS-based, and substantially analyte-independent, parameters (in addition to real impedance) in sensor diagnostic procedures. For example, as mentioned previously, analysis of (substantially) glucose-independent impedance data, such as, e.g., values for 1 kHz real impedance and 1 kHz imaginary impedance, as well as Nyquist slope, provide information on the efficiency of the sensor with respect to how quickly it hydrates and is ready for data acquisition. Moreover, (substantially) glucose-independent impedance data, such as, e.g., values for 1 kHz real impedance, provides information on potential occlusion(s) that may exist on the sensor membrane surface, which occlusion(s) may temporarily block passage of glucose into the sensor and thus cause the signal to dip.

In addition, (substantially) glucose-independent impedance data, such as, e.g., values for higher-frequency phase angle and/or imaginary impedance at 1 kHz and higher frequencies, provides information on loss of sensor sensitivity during extended wear, which sensitivity loss may potentially be due to local oxygen deficit at the insertion site. In this regard, the underlying mechanism for oxygen deficiency-led sensitivity loss may be described as follows: when local oxygen is deficient, sensor output (i.e., Isig and SG) will be dependent on oxygen rather than glucose and, as such, the sensor will lose sensitivity to glucose. Other markers, including 0.1 Hz real impedance, the counter electrode voltage (Vcntr), and EIS-induced spikes in the Isig may also be used for the detection of oxygen deficiency-led sensitivity loss. Moreover, in a redundant sensor system, the relative differences in 1 kHz real impedance, 1 kHz imaginary impedance, and 0.1 Hz real impedance between two or more working electrodes may be used for the detection of sensitivity loss due to biofouling.

In accordance with embodiments of the invention, EIS-based sensor diagnostics entails consideration and analysis of EIS data relating to one or more of at least three primary factors, i.e., potential sensor failure modes: (1) signal start-up; (2) signal dip; and (3) sensitivity loss. Significantly, the discovery herein that a majority of the impedance-related parameters that are used in such diagnostic analyses and procedures can be studied at a frequency, or within a range of frequencies, where the parameter is substantially analyte-independent allows for implementation of sensor-diagnostic procedures independently of the level of the analyte in a patient's body. Thus, while EIS-based sensor diagnostics may be triggered by, e.g., large fluctuations in Isig, which is analyte-dependent, the impedance-related parameters that are used in such sensor diagnostic procedures are themselves substantially independent of the level of the analyte. As will be explored in more detail below, it has also been found that, in a majority of situations where glucose may be seen to have an effect on the magnitude (or other characteristic) of an EIS-based parameter, such effect is usually small enough—e.g., at least an order of magnitude difference between the EIS-based measurement and the glucose effect thereon—such that it can be filtered out of the measurement, e.g., via software in the IC.

By definition, "start-up" refers to the integrity of the sensor signal during the first few hours (e.g., t=0-6 hours) after insertion. For example, in current devices, the signal during the first 2 hours after insertion is deemed to be unreliable and, as such, the sensor glucose values are blinded to the patient/user. In situations where the sensor takes an extended amount of time to hydrate, the sensor signal is low for several hours after insertion. With the use of EIS, additional impedance information is available (by running an EIS procedure) right after the sensor has been inserted. In this regard, the total impedance equation may be used to explain the principle behind low-startup detection using 1 kHz real impedance. At relatively higher frequencies—in this case, 1 kHz and above-imaginary impedance is very small (as confirmed with in-vivo data), such that total impedance reduces to:

$$Z_t(\omega) = R_s + \frac{R_p}{1 + \omega^2 R_p^2 C_d^2}$$

As sensor wetting is gradually completed, the double layer capacitance ($C_d$) increases. As a result, the total impedance will decrease because, as indicated in the equation above, total impedance is inversely proportional to $C_d$. This is illustrated in the form of the intercept 1600 on the real impedance axis shown, e.g., in FIG. 16B. Importantly, the 1 kHz imaginary impedance can also be used for the same purpose, as it also includes, and is inversely proportional to, a capacitance component.

Figure 22:
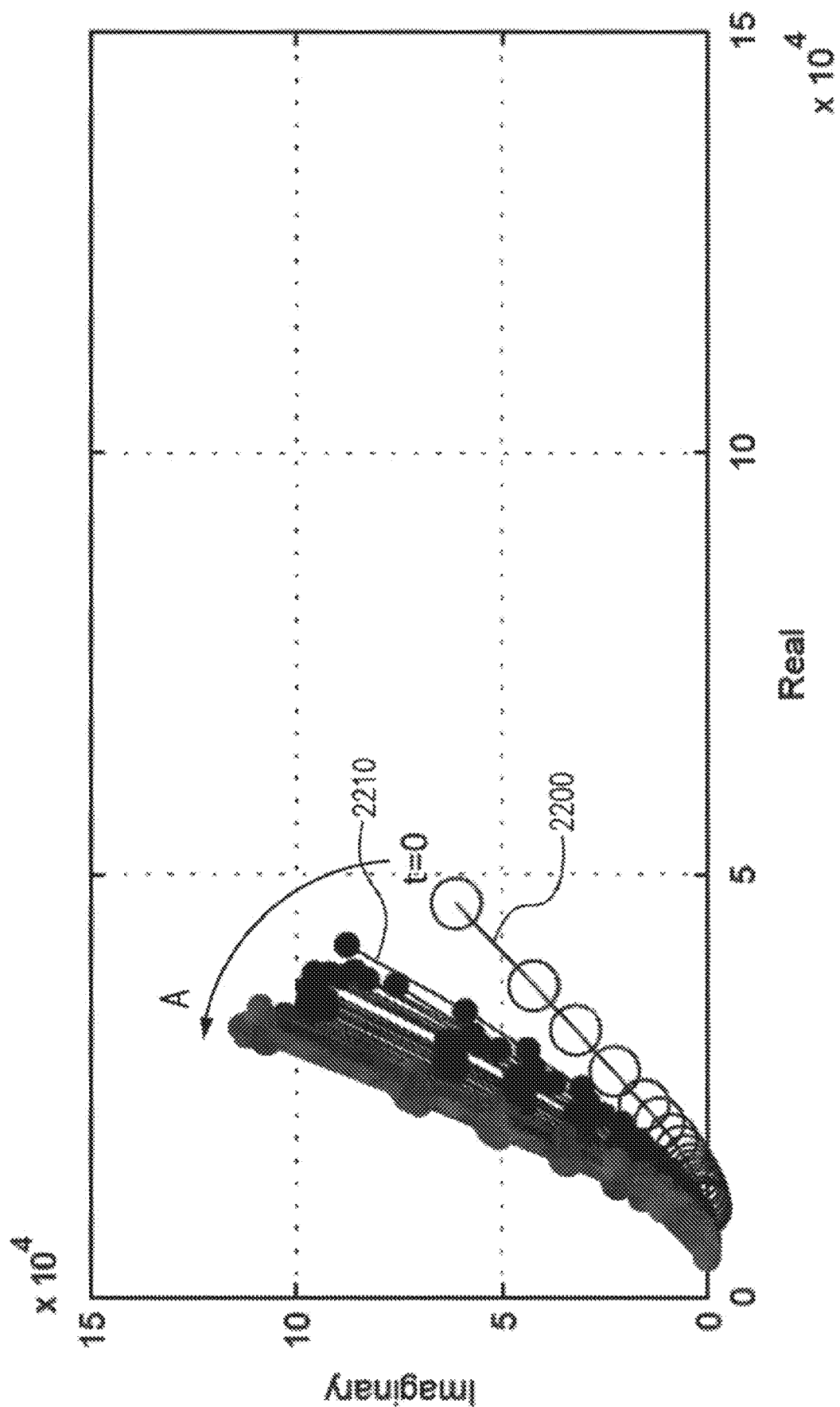
FIG. 22 shows a Nyquist plot for a normally-functioning sensor where the Nyquist slope gradually increases, and the intercept gradually decreases, as the sensor wear-time progresses.

Another marker for low startup detection is Nyquist slope, which relies solely on the relatively lower-frequency impedance which, in turn, corresponds to the Warburg impedance component of total impedance (see, e.g., FIG. 15B). FIG. 22 shows a Nyquist plot for a normally-functioning sensor, where Arrow A is indicative of the progression of time, i.e., sensor wear time, starting from t=0. Thus, EIS at the relatively-lower frequencies is performed right after sensor insertion (time t=0), which generates real and imaginary impedance data that is plotted with a first linear fit 2200 having a first (Nyquist) slope. At a time-interval after t=0, a second (lower) frequency sweep is run that produces a second linear fit 2210 having a second (Nyquist) slope larger than the first Nyquist slope, and so on. As the sensor becomes more hydrated, the Nyquist slope increases, and the intercept decrease, as reflected by the lines 2200, 2210, etc. becoming steeper and moving closer to the Y-axis. In connection with low startup detection, clinical data indicates that there is typically a dramatic increase of Nyquist slope after sensor insertion and initialization, which is then stabilized to a certain level. One explanation for this is that, as the sensor is gradually wetted, the species diffusivity as well as concentration undergo dramatic change, which is reflected in Warburg impedance.

Figure 23A:
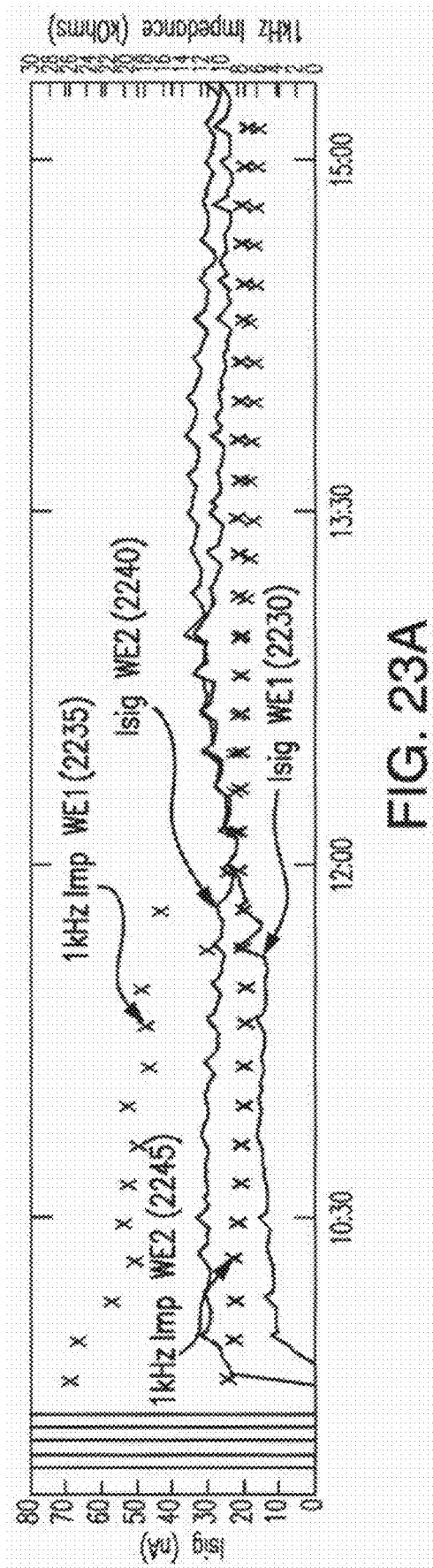
FIG. 23A shows raw current signal (Isig) from two redundant working electrodes, and the electrodes' respective real impedances at 1 kHz, in accordance with embodiments of the invention.
Figure 23B:
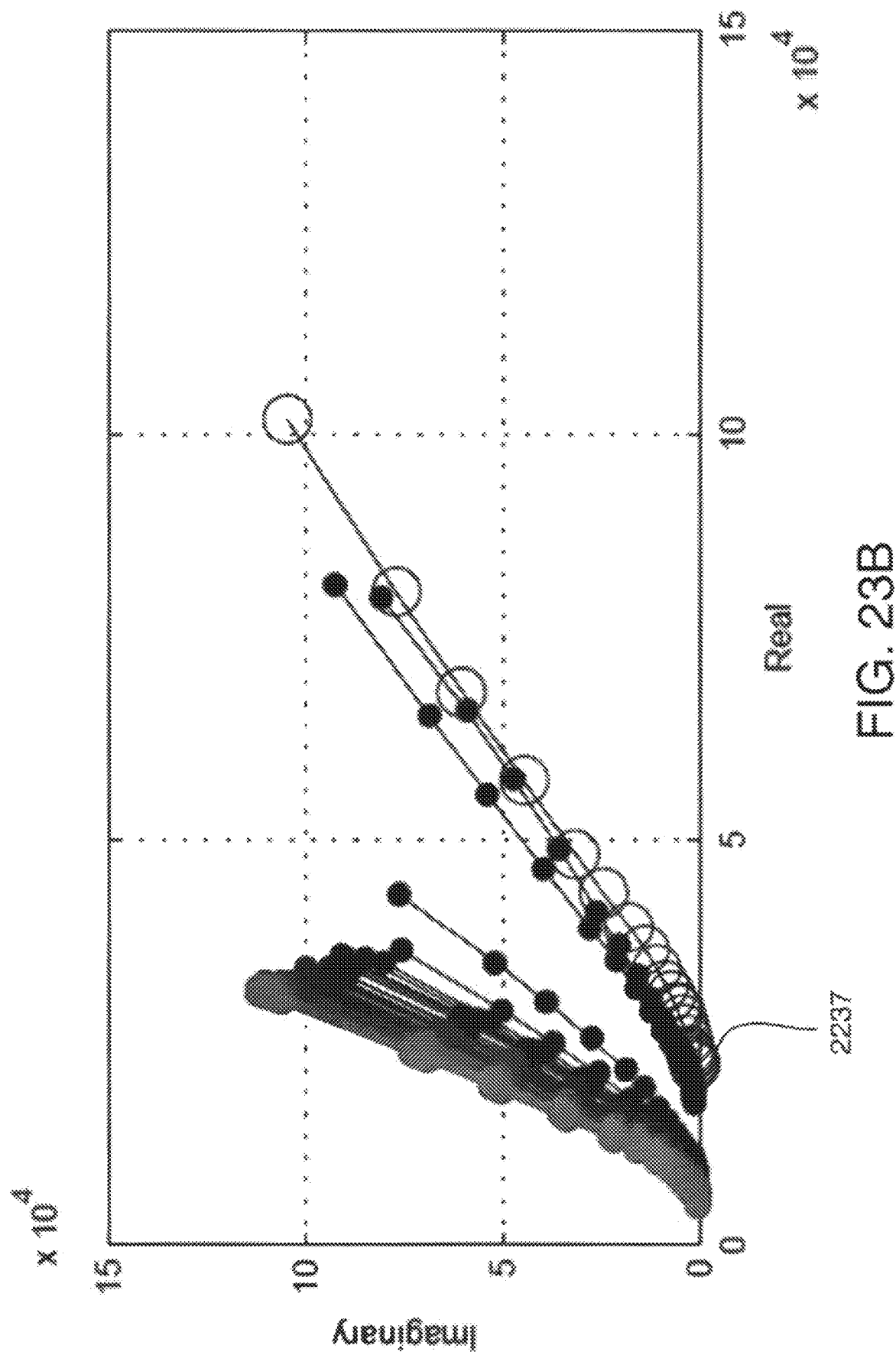
FIG. 23B shows the Nyquist plot for the first working electrode (WE1) of FIG. 23A.
Figure 23C:
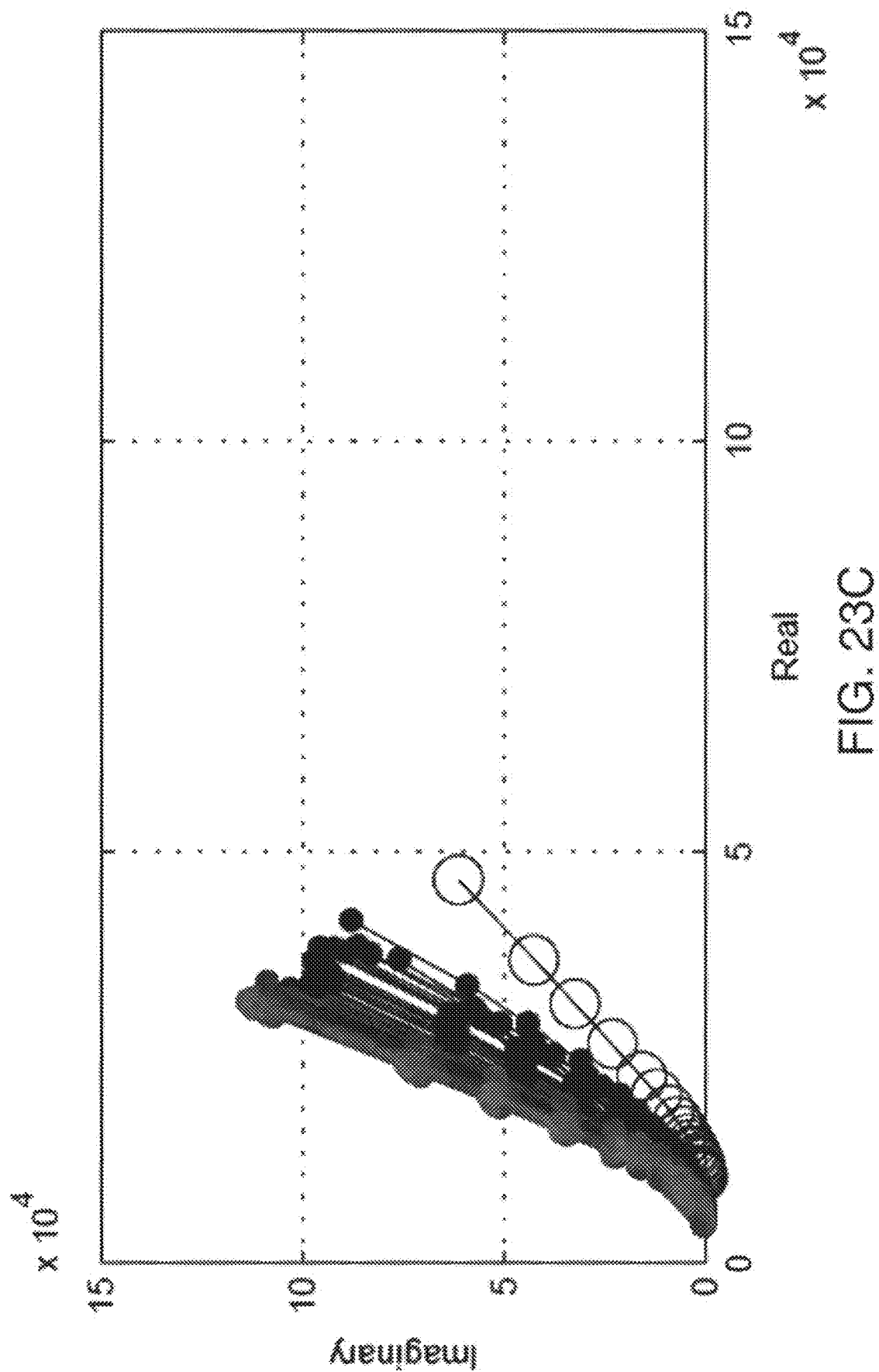
FIG. 23C shows the Nyquist plot for the second working electrode (WE2) of FIG. 23A.

In FIG. 23A, the Isig 2230 for a first working electrode WE1 starts off lower than expected (at about 10 nA) and takes some time to catch up with the Isig 2240 for a second working electrode WE2. Thus, in this particular example, WE1 is designated as having a low start-up. The EIS data reflects this low start-up in two ways. First, as shown in FIG. 23A, the real impedance at 1 kHz (2235) of WE1 is much higher than the 1 kHz real impedance 2245 of WE2. Second, when compared to the Nyquist slope for WE2 (FIG. 23C), the Nyquist slope for WE1 (FIG. 23B) starts out lower, has a larger intercept 2237, and takes more time to stabilize. As will be discussed later, these two signatures—the 1 kHz real impedance and the Nyquist slope—can be used as diagnostic inputs in a fusion algorithm to decide which of the two electrodes can carry a higher weight when the fused signal is calculated. In addition, one or both of these markers may be used in a diagnostic procedure to determine whether the sensor, as a whole, is acceptable, or whether it should be terminated and replaced.

By definition, signal (or Isig) dips refer to instances of low sensor signal, which are mostly temporary in nature, e.g., on the order of a few hours. Such low signals may be caused, for example, by some form of biological occlusion on the sensor surface, or by pressure applied at the insertion site (e.g., while sleeping on the side). During this period, the sensor data is deemed to be unreliable; however, the signal does recover eventually. In the EIS data, this type of signal dip—as opposed to one that is caused by a glycemic change in the patient's body—is reflected in the 1 kHz real impedance data, as shown in FIG. 24.

Figure 24:
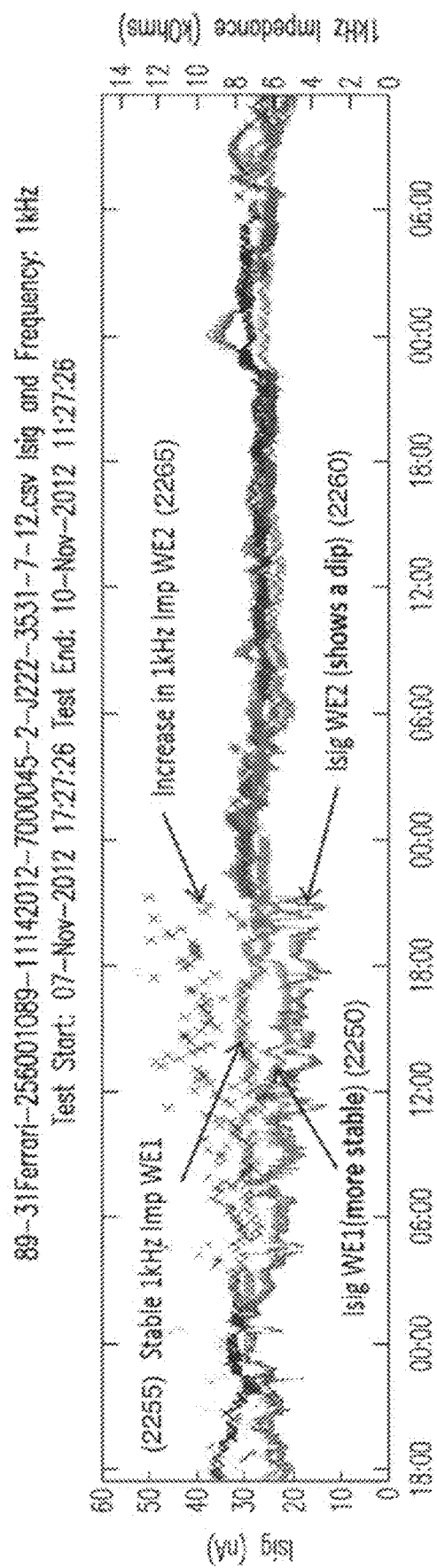
FIG. 24 illustrates examples of signal dip for two redundant working electrodes, and the electrodes' respective real impedances at 1 kHz, in accordance with embodiments of the invention.

Specifically, in FIG. 24, both the Isig 2250 for the first working electrode WE1 and the Isig 2260 for the second working electrode WE2 start out at about 25 nA at the far-left end (i.e., at 6 pm). As time progresses, both Isigs fluctuate, which is reflective of glucose fluctuations in the vicinity of the sensor. For about the first 12 hours or so (i.e., until about 6 am), both Isigs are fairly stable, as are their respective 1 kHz real impedances 2255, 2265. However, between about 12 and 18 hours—i.e., between 6 am and noon—the Isig 2260 for WE2 starts to dip and continues a downward trend for the next several hours, until about 9 pm. During this period, the Isig 2250 for WE1 also exhibits some dipping, but Isig 2250 is much more stable, and dips quite a bit less, than Isig 2260 for WE2. The behavior of the Isigs for WE1 and WE2 is also reflected in their respective 1 kHz real impedance data. Thus, as shown in FIG. 24, during the time period noted above, while the 1 kHz real impedance for WE1 (2255) remains fairly stable, there is a marked increase in the 1 kHz real impedance for WE2 (2265).

By definition, sensitivity loss refers to instances where the sensor signal (Isig) becomes low and non-responsive for an extended period of time and is usually unrecoverable. Sensitivity loss may occur for a variety of reasons. For example, electrode poisoning drastically reduces the active surface area of the working electrode, thereby severely limiting current amplitude. Sensitivity loss may also occur due to hypoxia, or oxygen deficit, at the insertion site. In addition, sensitivity loss may occur due to certain forms of extreme surface occlusion (i.e., a more permanent form of the signal dip caused by biological or other factors) that limit the passage of both glucose and oxygen through the sensor membrane, thereby lowering the number/frequency of the chemical reactions that generate current in the electrode and, ultimately, the sensor signal (Isig). It is noted that the various causes of sensitivity loss mentioned above apply to both short-term (7 to 10-day wear) and long term (6-month wear) sensors.

Figure 25A:
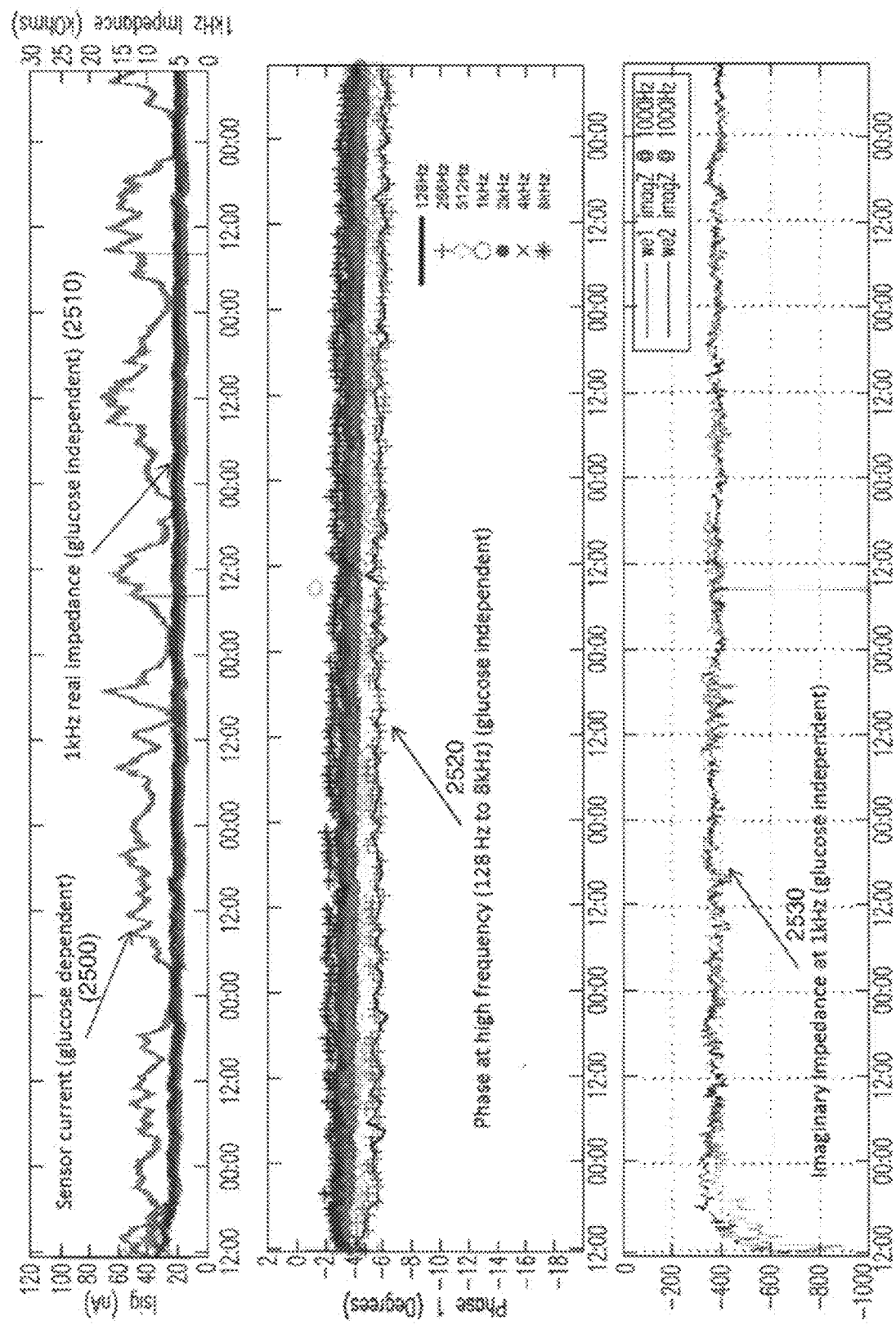
FIG. 25A illustrates substantial glucose independence of real impedance, imaginary impedance, and phase at relatively-higher frequencies for a normally-functioning glucose sensor in accordance with embodiments of the invention.

In the EIS data, sensitivity loss is often preceded by an increase in the absolute value of phase (|phase|) and of the imaginary impedance (|imaginary impedance|) at the relatively higher frequency ranges (e.g., 128 Hz and above, and 1 kHz and above, respectively). FIG. 25A shows an example of a normally-functioning glucose sensor where the sensor current 2500 is responsive to glucose—i.e., Isig 2500 tracks glucose fluctuations—but all relevant impedance outputs, such as, e.g., 1 kHz real impedance 2510, 1 kHz imaginary impedance 2530, and phase for frequencies at or above about 128 Hz (2520), remain steady, as they are substantially glucose-independent.

Specifically, the top graph in FIG. 25A shows that, after the first few hours, the 1 kHz real impedance 2510 holds fairly steady at about 5 kOhms (and the 1 kHz imaginary impedance 2530 holds fairly steady at about −400 Ohms). In other words, at 1 kHz, the real impedance data 2510 and the imaginary impedance data 2530 are substantially glucose-independent, such that they can be used as signatures for, or independent indicators of, the health, condition, and ultimately, reliability of the specific sensor under analysis. However, as mentioned previously, different impedance-related parameters may exhibit glucose-independence at different frequency ranges, and the range, in each case, may depend on the overall sensor design, e.g., electrode type, surface area of electrode, thickness of membrane, permeability of membrane, etc.

Figure 25B:
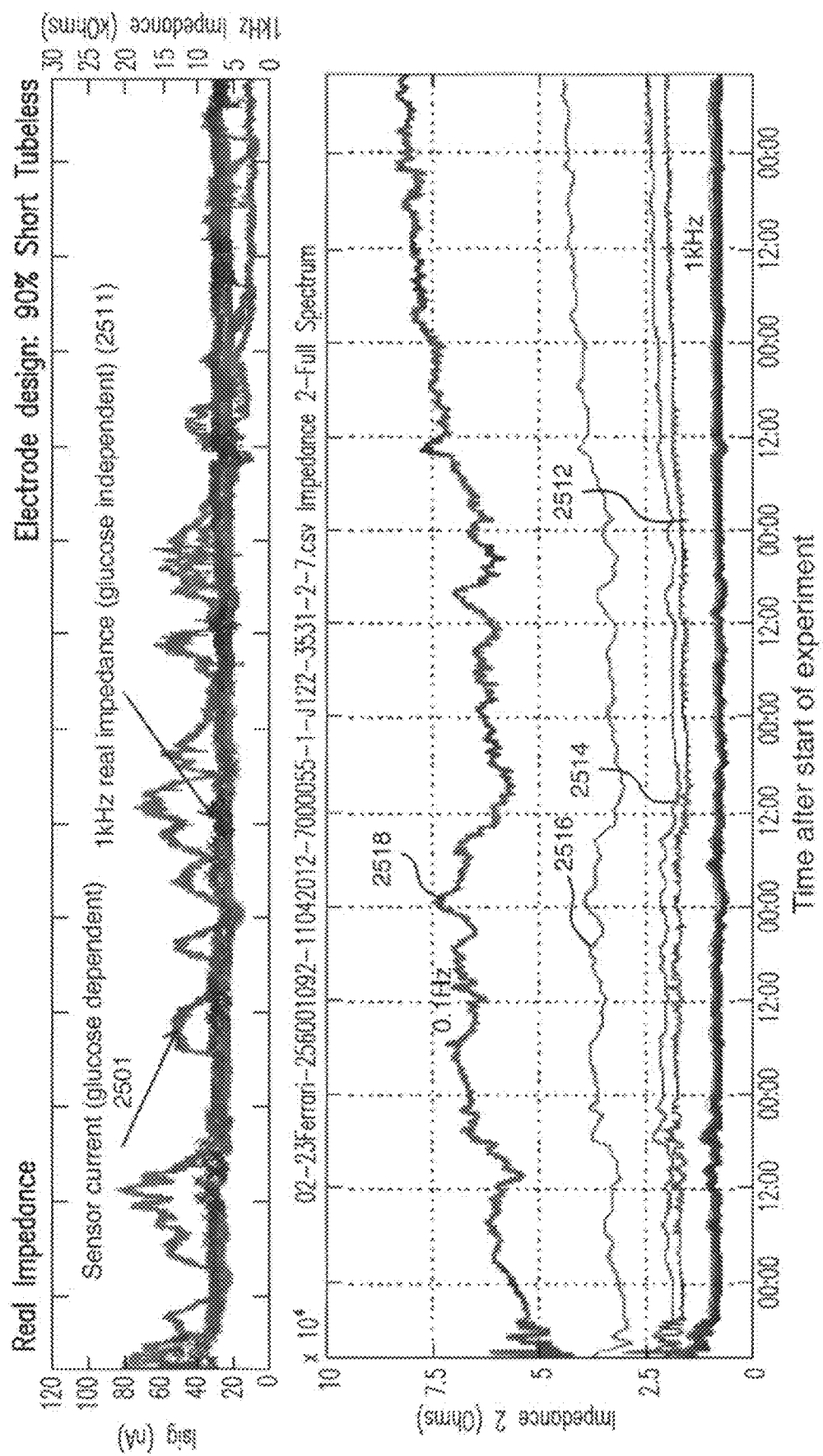
FIG. 25B shows illustrative examples of varying levels of glucose dependence of real impedance at the relatively-lower frequencies in accordance with embodiments of the invention.

Thus, in the example FIG. 25B—for a 90% short tubeless electrode design—the top graph again shows that sensor current 2501 is responsive to glucose, and that, after the first few hours, the 1 kHz real impedance 2511 holds fairly steady at about 7.5 kOhms. The bottom graph in FIG. 25B shows real impedance data for frequencies between 0.1 Hz (2518) and 1 kHz (2511). As can be seen, the real impedance data at 0.1 Hz (2518) is quite glucose-dependent. However, as indicated by reference numerals 2516, 2514, and 2512, real impedance becomes more and more glucose-independent as the frequency increases from 0.1 Hz to 1 kHz, i.e., for impedance data measured at frequencies closer to 1 kHz.

Figure 25C:
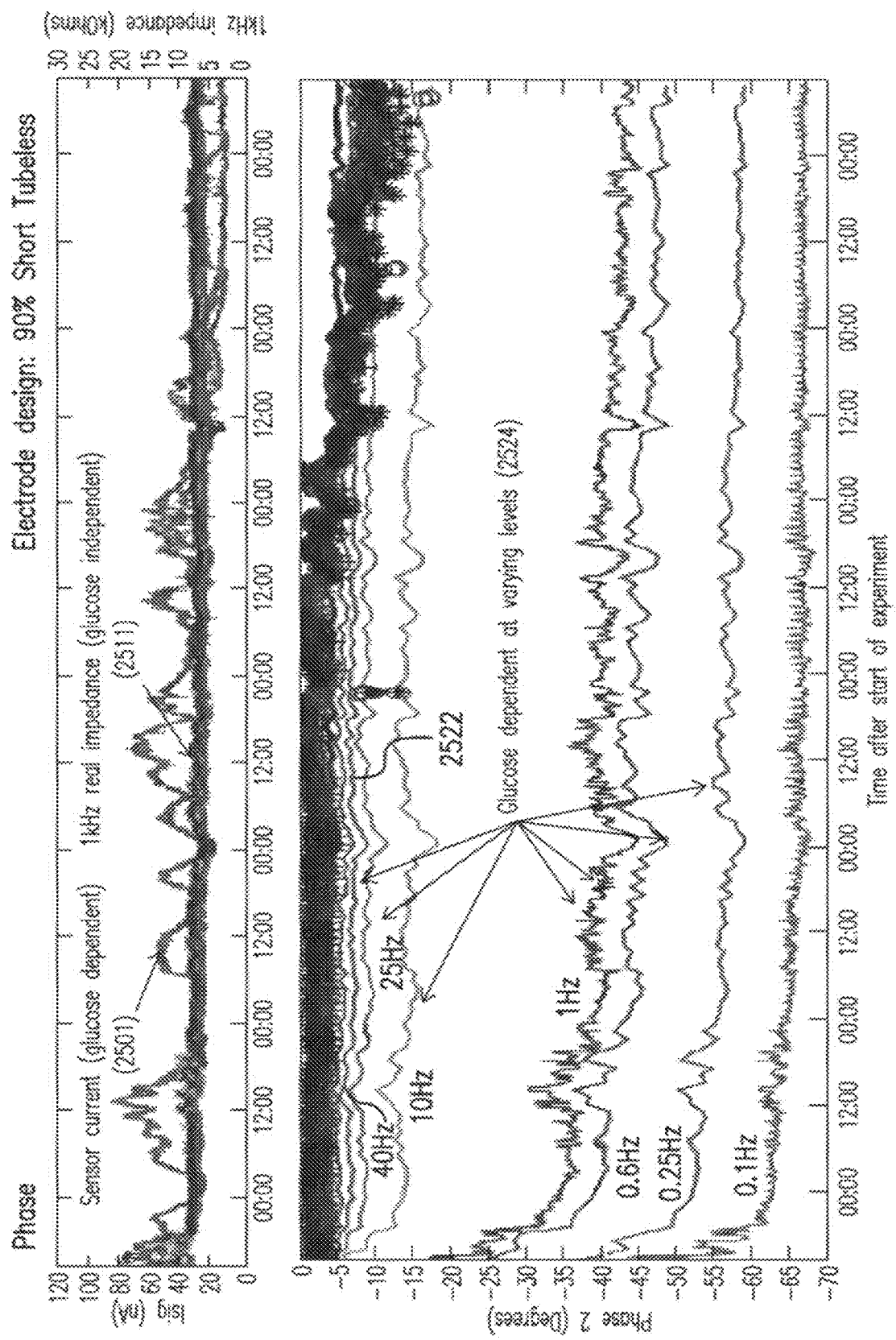
FIG. 25C shows illustrative examples of varying levels of glucose dependence of phase at the relatively-lower frequencies in accordance with embodiments of the invention.

Returning to FIG. 25A, the middle graph shows that the phase 2520 at the relatively-higher frequencies is substantially glucose-independent. It is noted, however, that "relatively-higher frequencies" in connection with this parameter (phase) for the sensor under analysis means frequencies of 128 Hz and above. In this regard, the graph shows that the phase for all frequencies between 128 Hz and 8 kHz is stable throughout the period shown. On the other hand, as can be seen in the bottom graph of FIG. 25C, while the phase 2522 at 128 Hz (and above) is stable, the phase 2524 fluctuates— i.e., it becomes more and more glucose-dependent, and to varying degrees—at frequencies that are increasingly smaller than 128 Hz. It is noted that the electrode design for the example of FIG. 25C is the same as that used in FIG. 25B, and that the top graph in the former is identical to the top graph in the latter.

Figure 26:
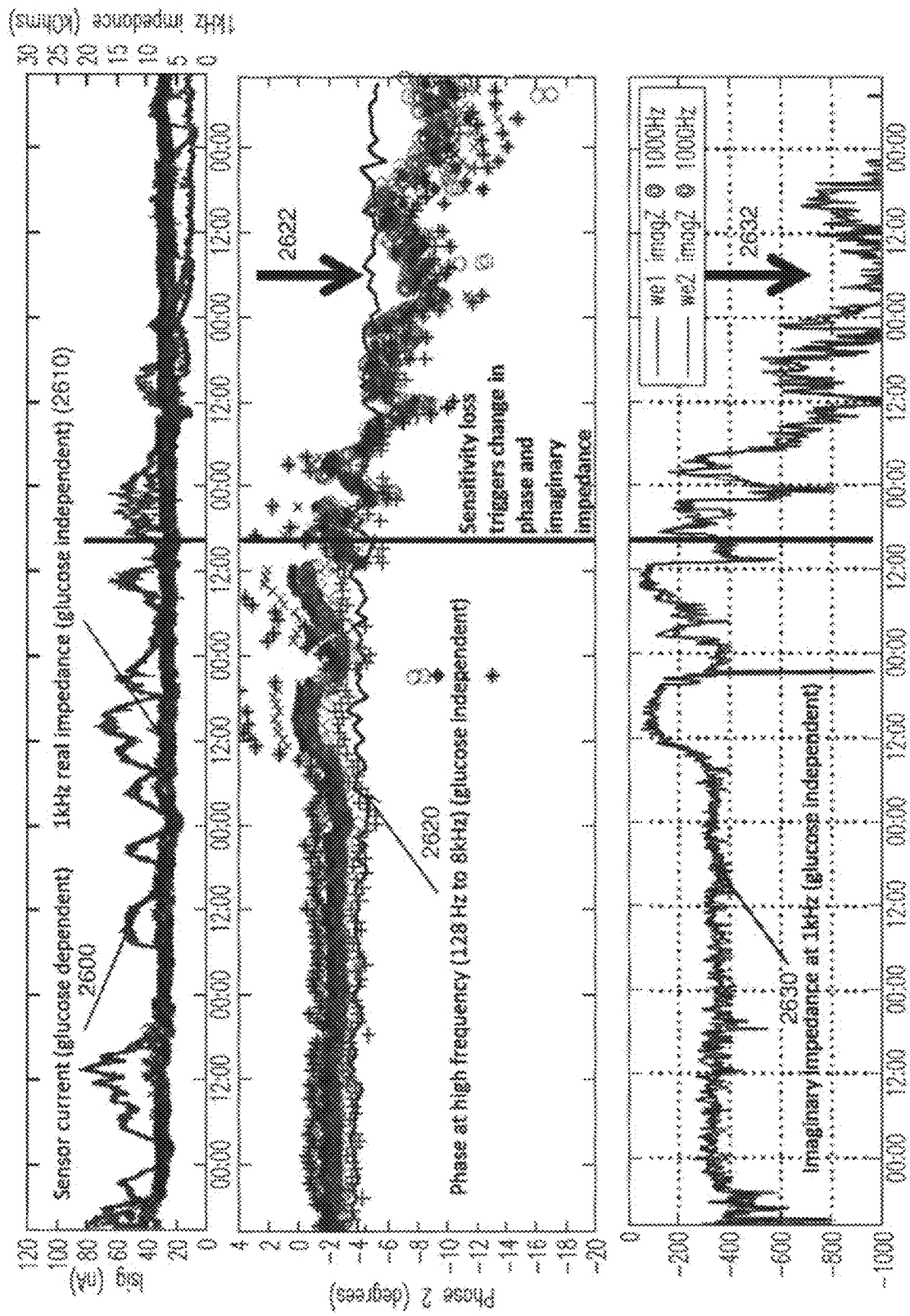
FIG. 26 shows the trending for 1 kHz real impedance, 1 kHz imaginary impedance, and relatively-higher frequency phase as a glucose sensor loses sensitivity as a result of oxygen deficiency at the sensor insertion site, according to embodiments of the invention.

FIG. 26 shows an example of sensitivity loss due to oxygen deficiency at the insertion site. In this case, the insertion site becomes oxygen deprived just after day 4 (designated by dark vertical line in FIG. 26), causing the sensor current 2600 to become low and non-responsive. The 1 kHz real impedance 2610 remains stable, indicating no physical occlusion on the sensor. However, as shown by the respective downward arrows, changes in the relatively higher-frequency phase 2622 and 1 kHz imaginary impedance 2632 coincide with loss in sensitivity, indicating that this type of loss is due to an oxygen deficit at the insertion site. Specifically, FIG. 26 shows that the phase at higher frequencies (2620) and the 1 kHz imaginary impedance (2630) become more negative prior to the sensor losing sensitivity—indicated by the dark vertical line—and continue their downward trend as the sensor sensitivity loss continues. Thus, as noted above, this sensitivity loss is preceded, or predicted, by an increase in the absolute value of phase (|phase|) and of the imaginary impedance (|imaginary impedance|) at the relatively higher frequency ranges (e.g., 128 Hz and above, and 1 kHz and above, respectively).

Figure 27:
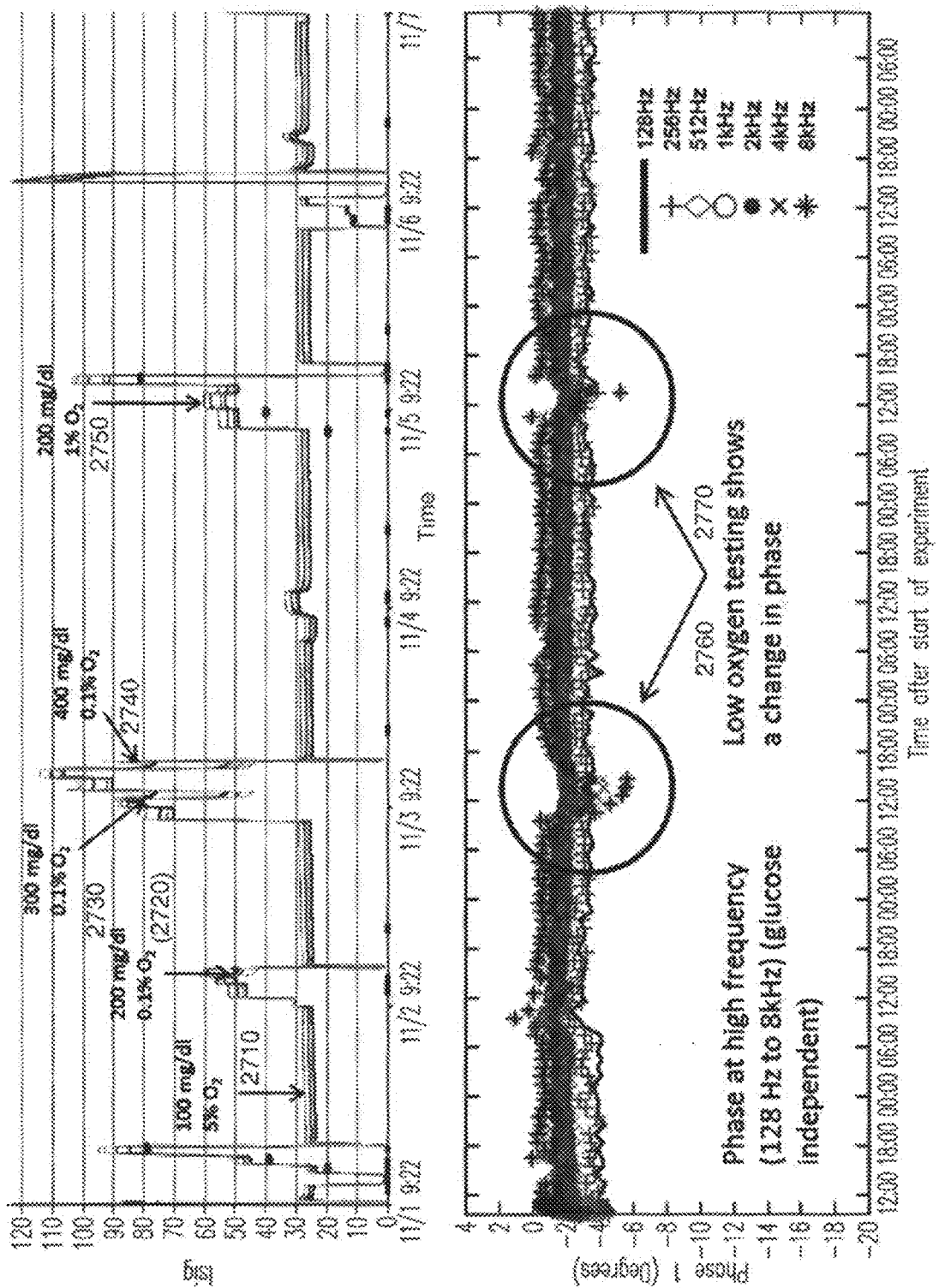
FIG. 27 shows Isig and phase for an in-vitro simulation of oxygen deficit at different glucose concentrations in accordance with embodiments of the invention.

The above-described signatures may be verified by in-vitro testing, an example of which is shown in FIG. 27. FIG. 27 shows the results of in-vitro testing of a sensor, where oxygen deficit at different glucose concentrations is simulated. In the top graph, the Isig fluctuates with the glucose concentration as the latter is increased from 100 mg/dl (2710) to 200 mg/dl (2720), 300 mg/dl (2730), and 400 mg/dl (2740), and then decreased back down to 200 and/dl (2750). In the bottom graph, the phase at the relatively-higher frequencies is generally stable, indicating that it is glucose-independent. However, at very low oxygen concentrations, such as, e.g., at 0.1% $O_2$, the relatively high-frequency phase fluctuates, as indicated by the encircled areas and arrows 2760, 2770. It is noted that the magnitude and/or direction (i.e., positive or negative) of fluctuation depend on various factors. For example, the higher the ratio of glucose concentration to oxygen concentration, the higher the magnitude of the fluctuation in phase. In addition, the specific sensor design, as well as the age of the sensor (i.e., as measured by time after implant), affect such fluctuations. Thus, e.g., the older a sensor is, the more susceptible it is to perturbations.

Figure 28A:
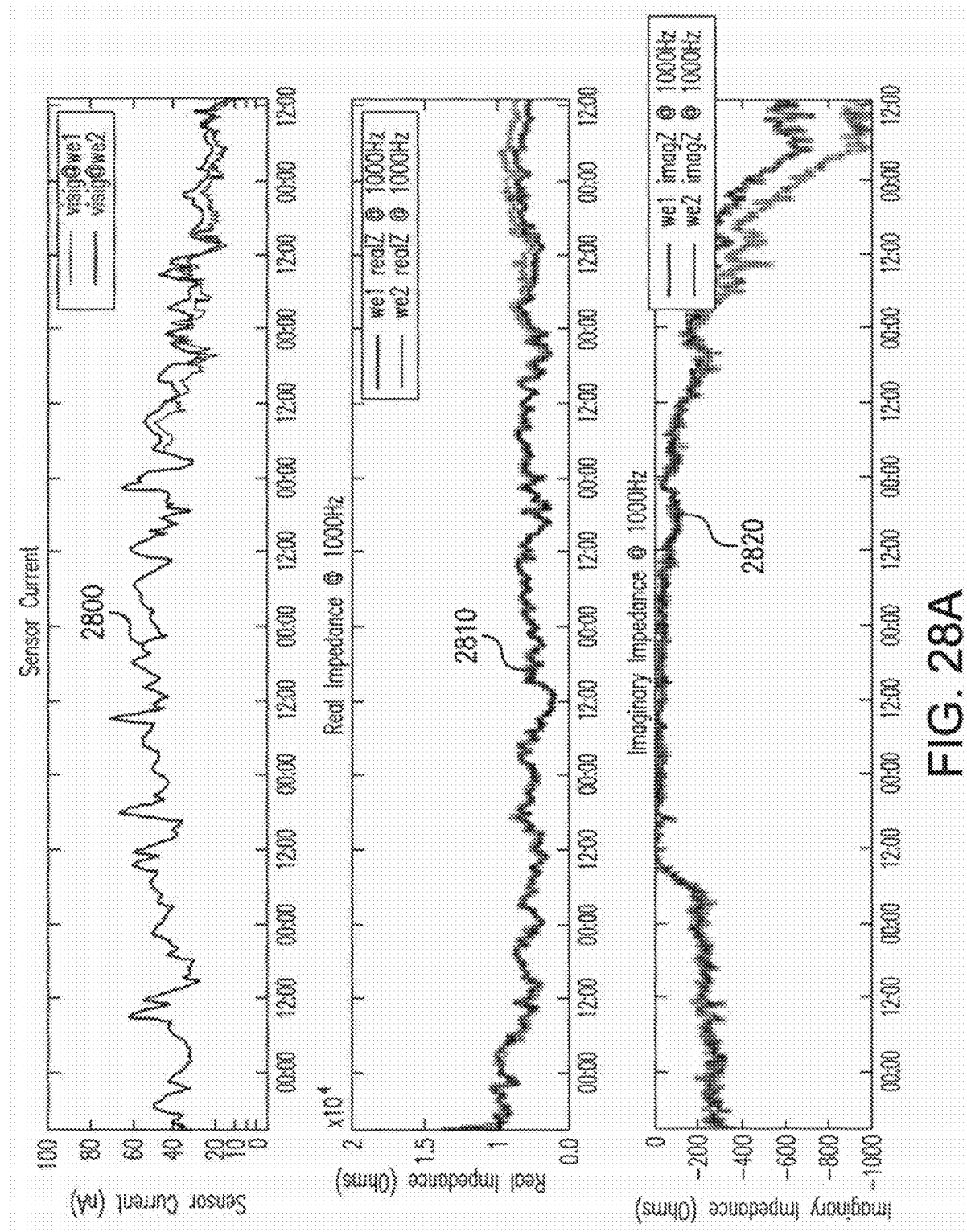
FIGS. 28A-28C show an example of oxygen deficiency-led sensitivity loss with redundant working electrodes WE1 and WE2, as well as the electrodes' EIS-based parameters, in accordance with embodiments of the invention.
Figure 28B:
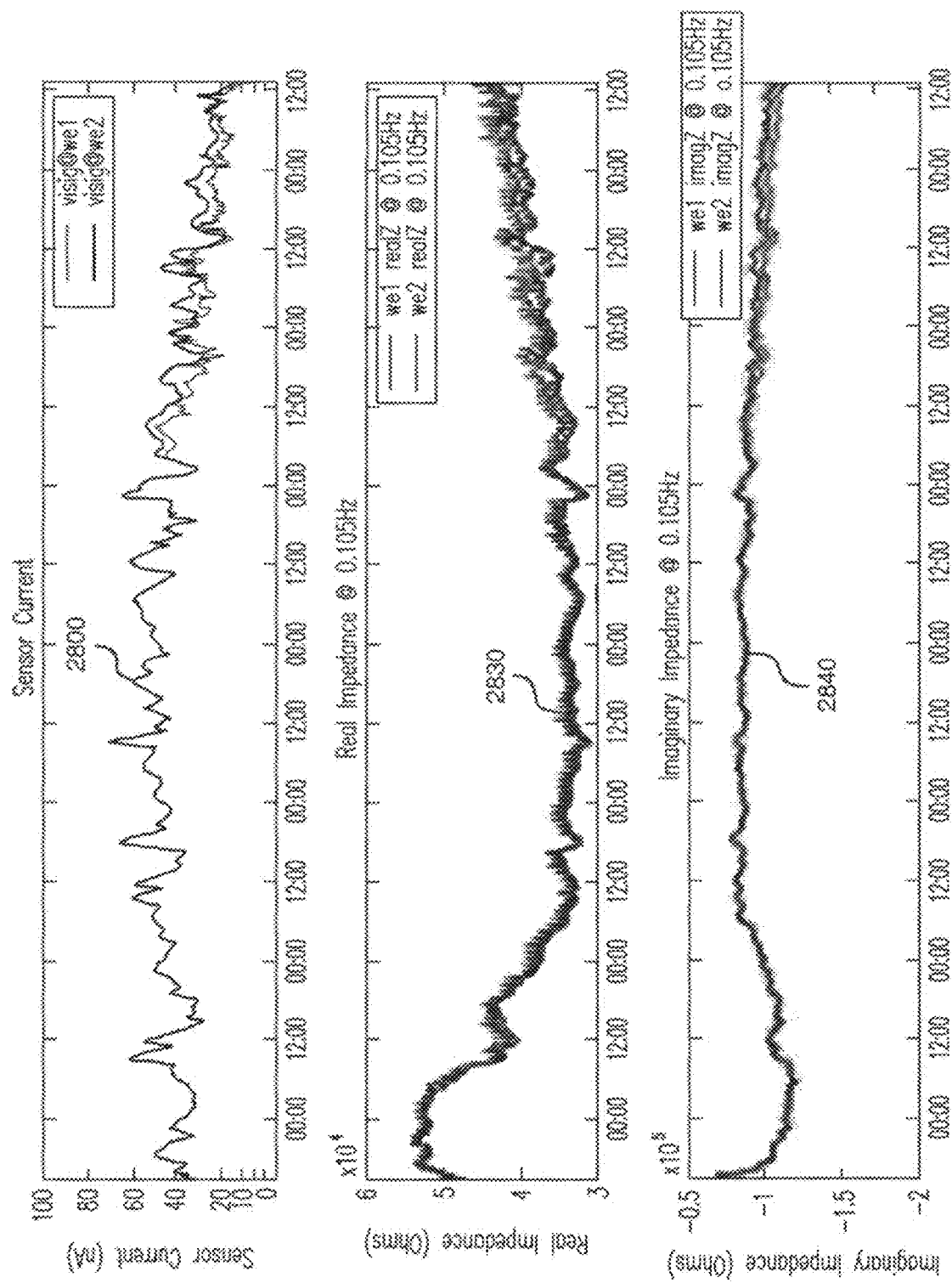
Figure 28C:
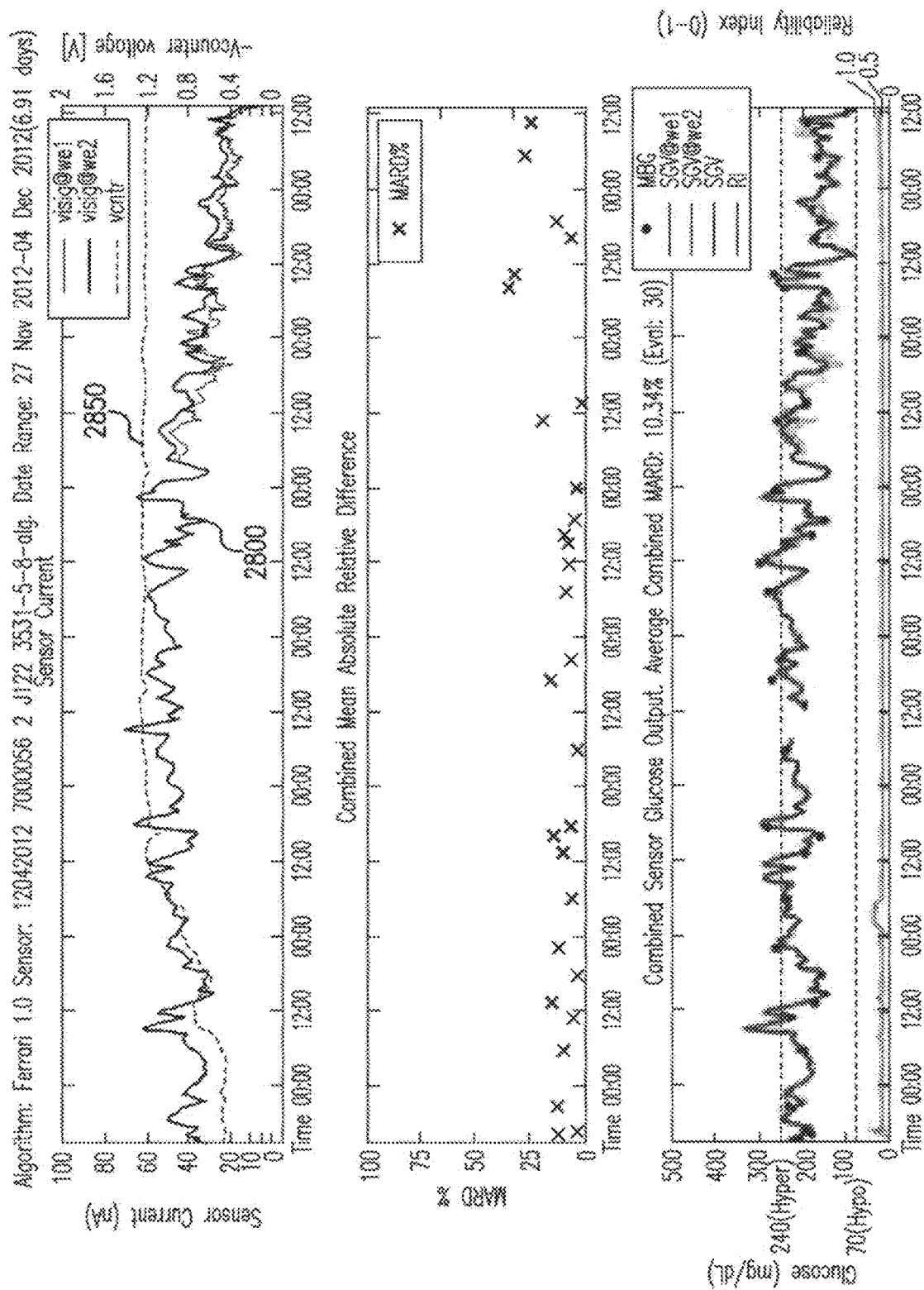

FIGS. 28A-28D show another example of oxygen deficiency-led sensitivity loss with redundant working electrodes WE1 and WE2. As shown in FIG. 28A, the 1 kHz real impedance 2810 is steady, even as sensor current 2800 fluctuates and eventually becomes non-responsive. Also, as before, the change in 1 kHz imaginary impedance 2820 coincides with the sensor's loss of sensitivity. In addition, however, FIG. 28B shows real impedance data and imaginary impedance data (2830 and 2840, respectively) at 0.105 Hz. The latter, which may be more commonly referred to as "0.1 Hz data", indicates that, whereas imaginary impedance at 0.1 Hz appears to be fairly steady, 0.1 Hz real impedance 2830 increases considerably as the sensor loses sensitivity. Moreover, as shown in FIG. 28C, with loss of sensitivity due to oxygen deficiency, $V_{cntr}$ 2850 rails to 1.2 Volts.

In short, the diagrams illustrate the discovery that oxygen deficiency-led sensitivity loss is coupled with lower 1 kHz imaginary impedance (i.e., the latter becomes more negative), higher 0.105 Hz real impedance (i.e., the latter becomes more positive), and $V_{cntr}$ rail. Moreover, the oxygen-deficiency process and $V_{cntr}$-rail are often coupled with the increase of the capacitive component in the electrochemical circuit. It is noted that, in some of the diagnostic procedures to be described later, the 0.105 Hz real impedance may not be used, as it appears that this relatively lower-frequency real impedance data may be analyte-dependent.

Figure 28D:
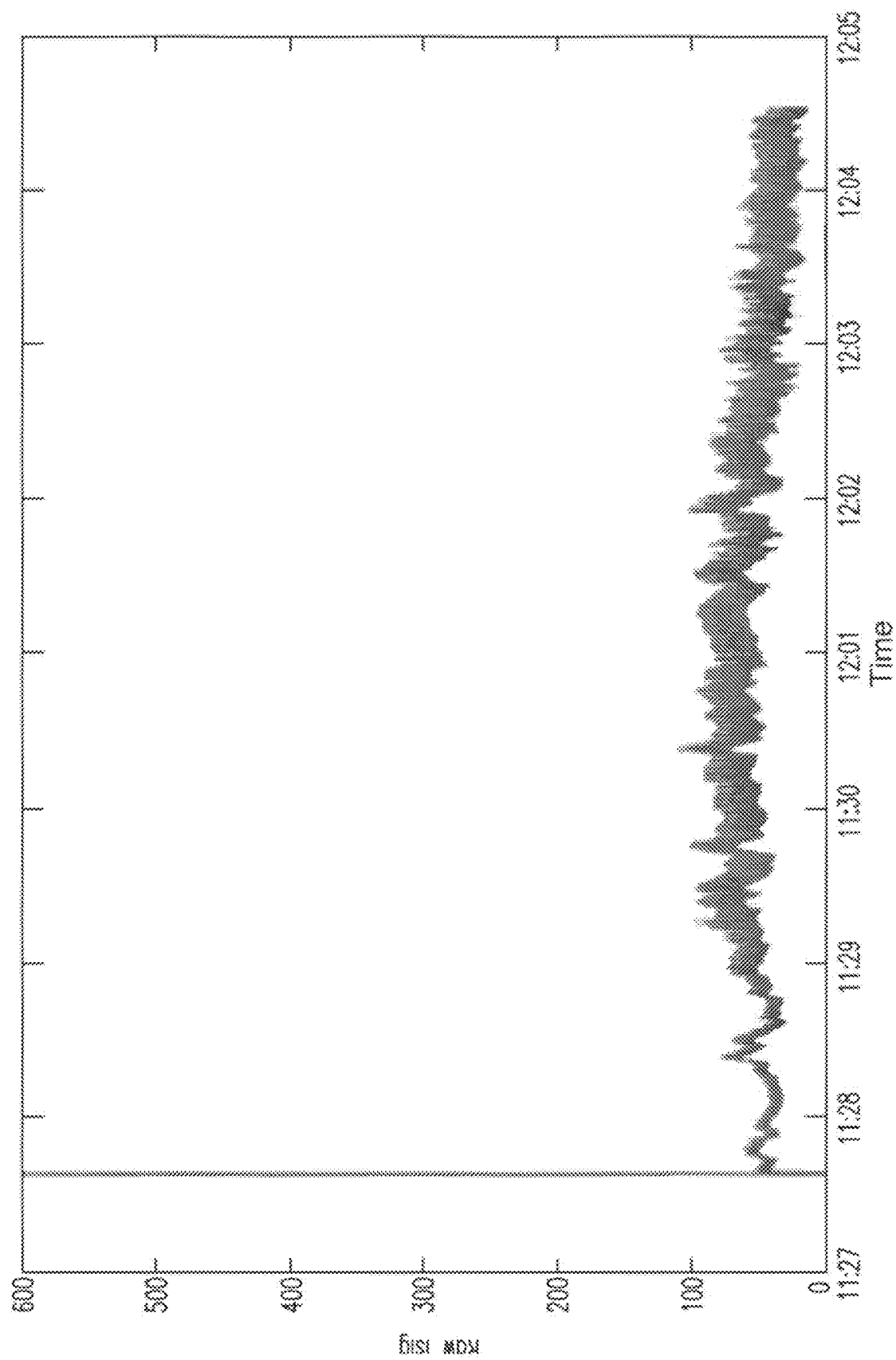
FIG. 28D shows EIS-induced spikes in the raw Isig for the example of FIGS. 28A-28C.

Finally, in connection with the example of FIGS. 28A-28D, it is noted that 1 kHz or higher-frequency impedance measurement typically causes EIS-induced spikes in the Isig. This is shown in FIG. 28D, where the raw Isig for WE2 is plotted against time. The drastic increase of Isig when the spike starts is a non-Faradaic process, due to double-layer capacitance charge. Thus, oxygen deficiency-led sensitivity loss may also be coupled with higher EIS-induced spikes, in addition to lower 1 kHz imaginary impedance, higher 0.105 Hz real impedance, and $V_{cntr}$ rail, as discussed above.

Figure 29:
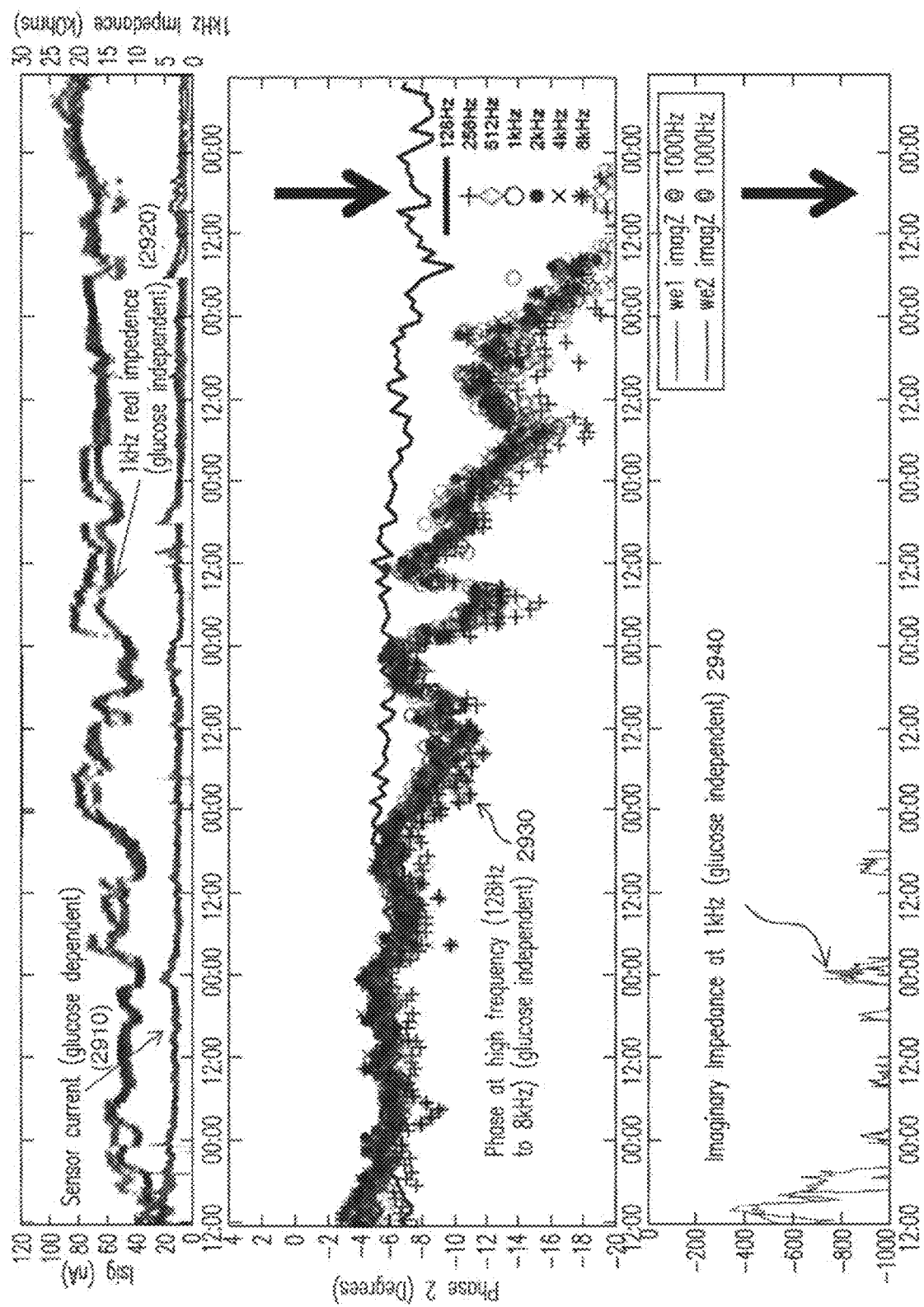
FIG. 29 shows an example of sensitivity loss due to oxygen deficiency that is caused by an occlusion, in accordance with embodiments of the invention.

FIG. 29 illustrates another example of sensitivity loss. This case may be thought of as an extreme version of the Isig dip described above in connection with FIG. 24. Here, the sensor current 2910 is observed to be low from the time of insertion, indicating that there was an issue with an insertion procedure resulting in electrode occlusion. The 1 kHz real-impedance 2920 is significantly higher, while the relatively higher-frequency phase 2930 and the 1 kHz imaginary impedance 2940 are both shifted to much more negative values, as compared to the same parameter values for the normally-functioning sensor shown in FIG. 25A. The shift in the relatively higher-frequency phase 2930 and 1 kHz imaginary impedance 2940 indicates that the sensitivity loss may be due to an oxygen deficit which, in turn, may have been caused by an occlusion on the sensor surface.

Figure 30A:
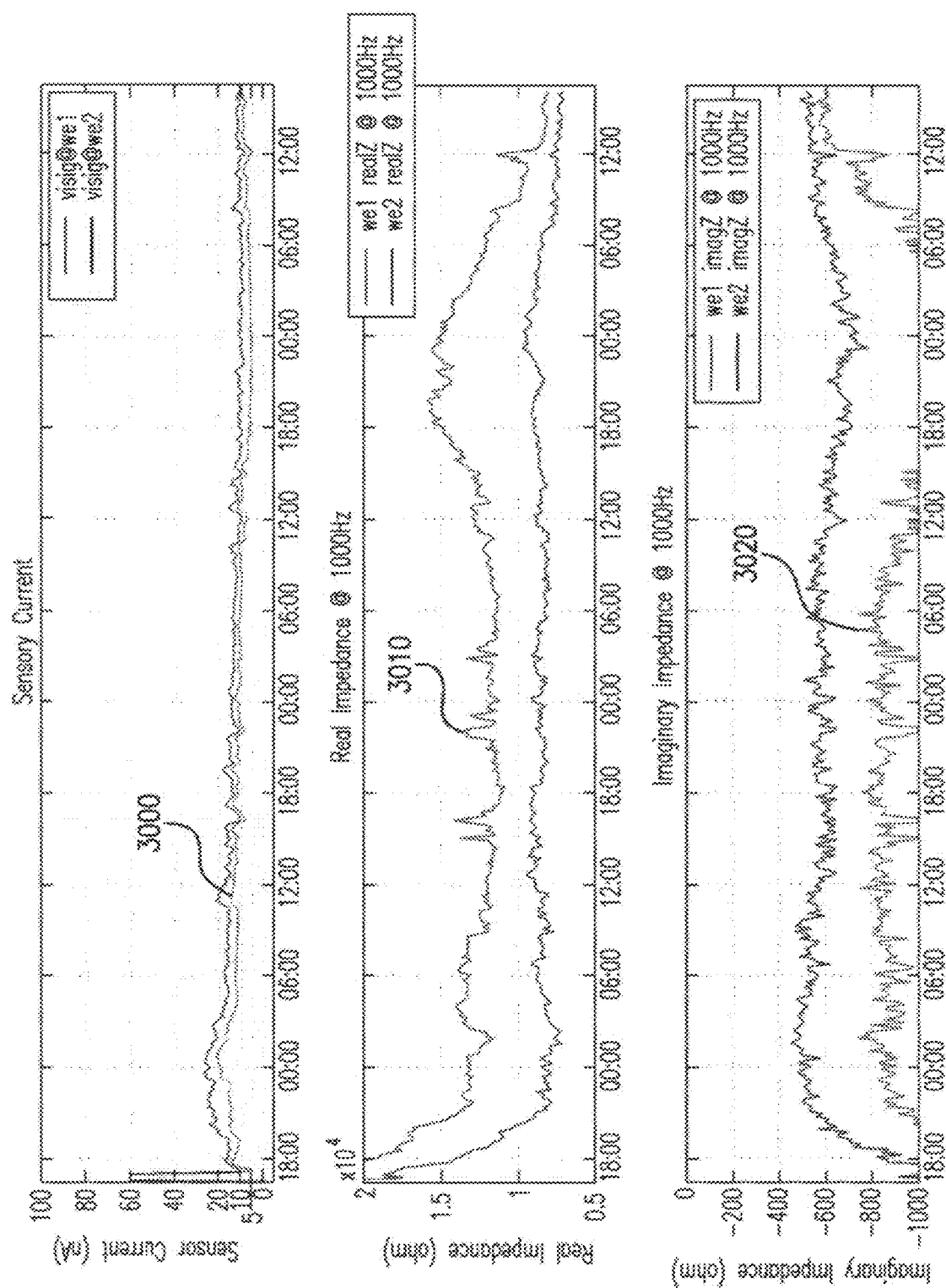
FIGS. 30A-30C show an example of sensitivity loss due to bio-fouling, with redundant working electrodes WE1 and WE2, as well as the electrodes' EIS-based parameters, in accordance with embodiments of the invention.
Figure 30B:
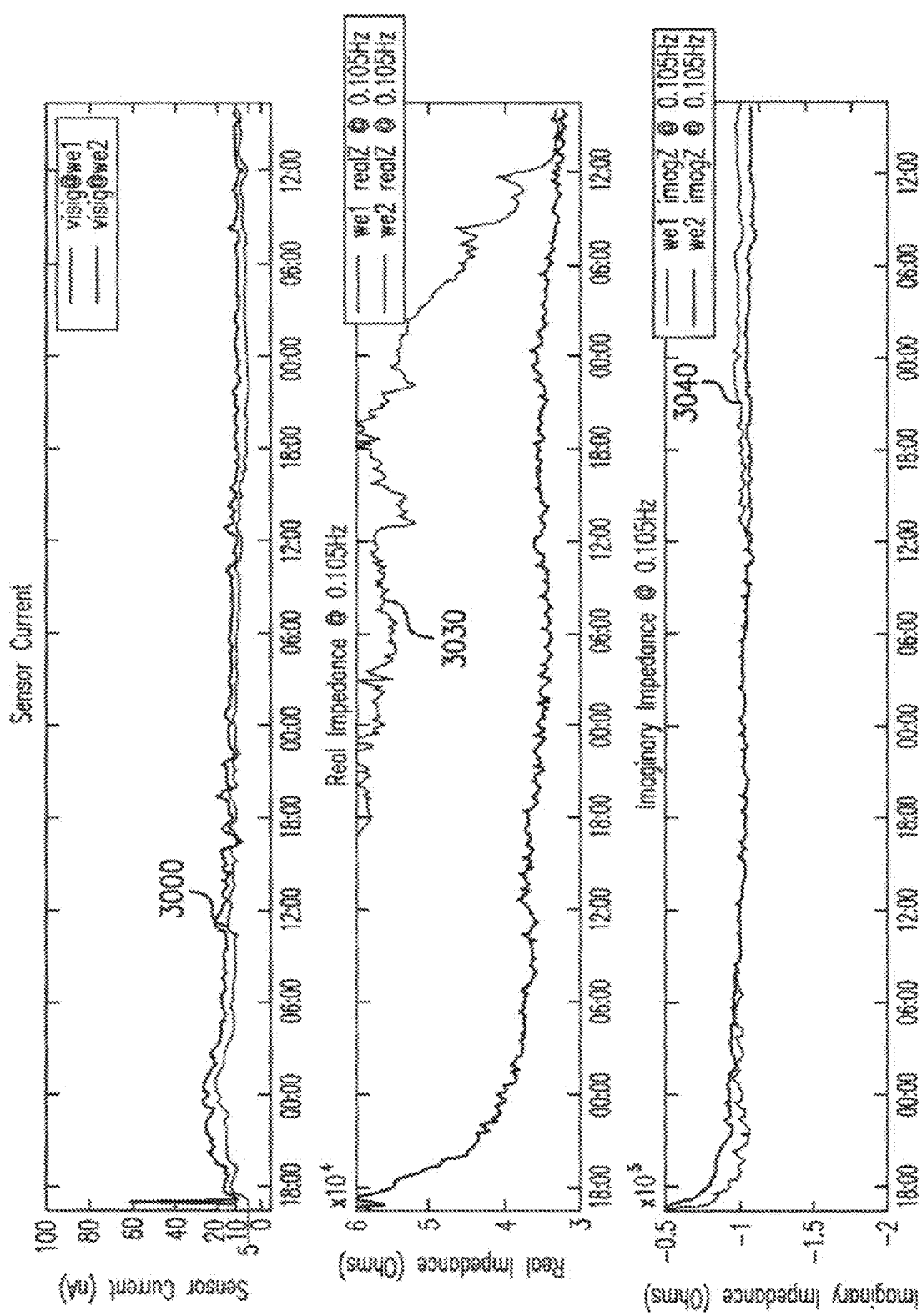
Figure 30C:
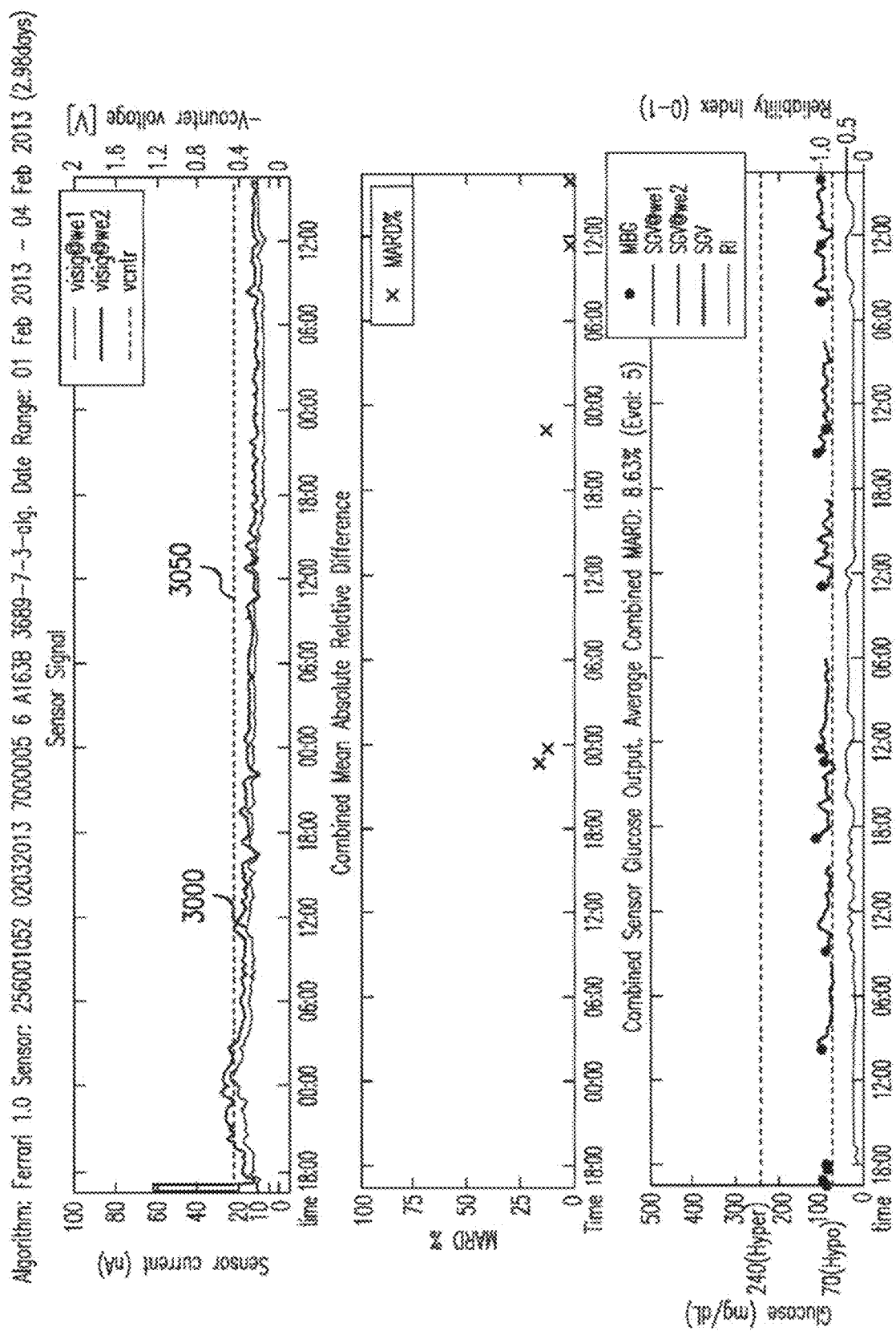
Figure 30D:
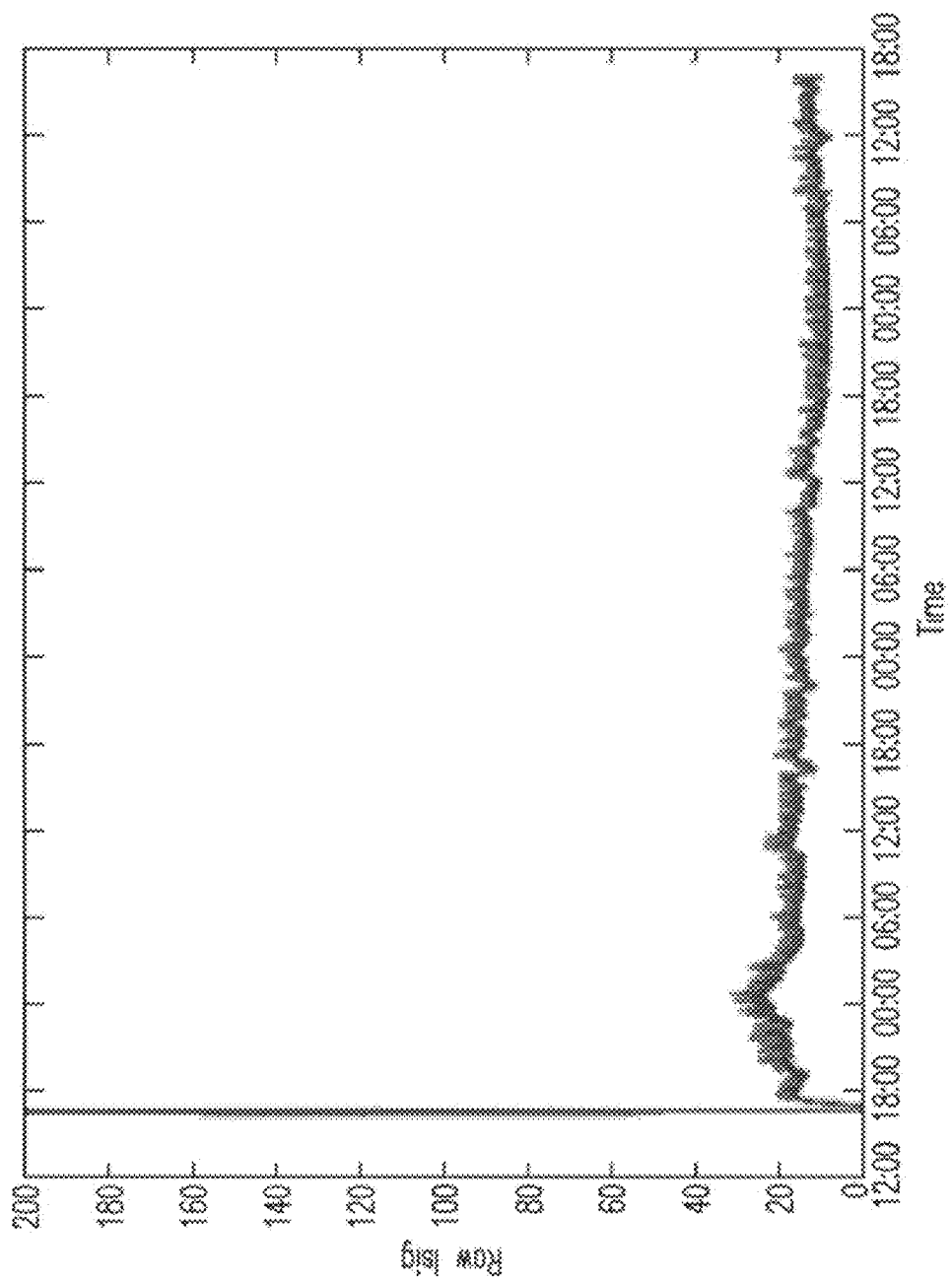
FIG. 30D shows EIS-induced spikes in the raw Isig for the example of FIGS. 30A-30C.

FIGS. 30A-30D show data for another redundant sensor, where the relative differences in 1 kHz real impedance and 1 kHz imaginary impedance, as well as 0.1 Hz real impedance, between two or more working electrodes may be used for the detection of sensitivity loss due to biofouling. In this example, WE1 exhibits more sensitivity loss than WE2, as is evident from the higher 1 kHz real impedance 3010, lower 1 kHz imaginary impedance 3020, and much higher real impedance at 0.105 kHz (3030) for WE2. In addition, however, in this example, $V_{cntr}$ 3050 does not rail. Moreover, as shown in FIG. 30D, the height of the spikes in the raw Isig data does not change much as time progresses. This indicates that, for sensitivity loss due to biofouling, $V_{cntr}$-rail and the increase in spike height are correlated. In addition, the fact that the height of the spikes in the raw Isig data does not change much with time indicates that the capacitive component of the circuit does not change significantly with time, such that sensitivity loss due to biofouling is related to the resistance component of the circuit (i.e., diffusion).

Various of the above-described impedance-related parameters may be used, either individually or in combination, as inputs into: (1) EIS-based sensor diagnostic procedures; and/or (2) fusion algorithms for generating more reliable sensor glucose values. With regard to the former, FIG. 31 illustrates how EIS-based data—i.e., impedance-related parameters, or characteristics—may be used in a diagnostic procedure to determine, in real time, whether a sensor is behaving normally, or whether it should be replaced.

Figure 31:
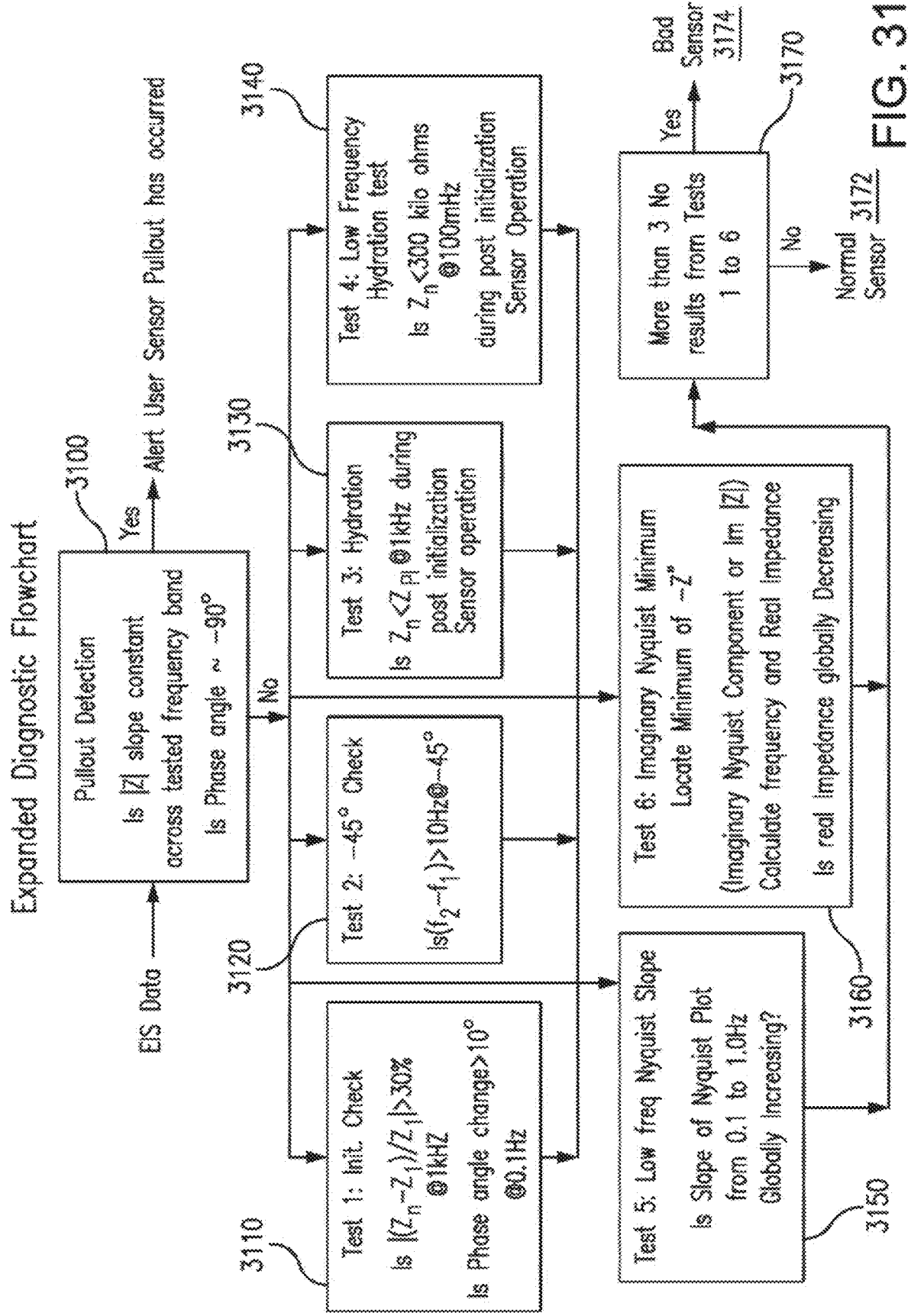
FIG. 31 shows a diagnostic procedure for sensor fault detection in accordance with embodiments of the invention.

The diagnostic procedure illustrated in the flow diagram of FIG. 31 is based on the collection of EIS data on a periodic basis, such as, e.g., hourly, every half hour, every 10 minutes, or at any other interval—including continuously—as may be appropriate for the specific sensor under analysis. At each such interval, EIS may be run for an entire frequency spectrum (i.e., a "full sweep"), or it may be run for a selected frequency range, or even at a single frequency. Thus, for example, for an hourly data collection scheme, EIS may be performed at frequencies in the µHz to MHz range, or it may be run for a narrower range of frequencies, such as, e.g., between about 0.1 Hz and about 8 kHz, as discussed hereinabove. In embodiments of the invention, EIS data acquisition may be implemented alternatingly between a full sweep and a narrower-range spectrum, or in accordance with other schemes.

The temporal frequency of EIS implementation and data collection may be dictated by various factors. For example, each implementation of EIS consumes a certain amount of power, which is typically provided by the sensor's battery, i.e., the battery running the sensor electronics, including the ASIC which is described later. As such, battery capacity, as well as the remaining sensor life, may help determine the number of times EIS is run, as well as the breadth of frequencies sampled for each such run. In addition, embodiments of the invention envision situations that may require that an EIS parameter at a specific frequency (e.g., real impedance at 1 kHz) be monitored based on a first schedule (e.g., once every few seconds, or minutes), while other parameters, and/or the same parameter at other frequencies, can be monitored based on a second schedule (e.g., less frequently). In these situations, the diagnostic procedure can be tailored to the specific sensor and requirements, such that battery power may be preserved, and unnecessary and/or redundant EIS data acquisition may be avoided.

It is noted that, in embodiments of the invention, a diagnostic procedure, such as the one shown in FIG. 31, entails a series of separate "tests" which are implemented in order to perform real-time monitoring of the sensor. The multiple tests, or markers—also referred to as "multi markers"—are implemented because each time EIS is run (i.e., each time an EIS procedure is performed), data may be gathered about a multiplicity of impedance-based parameters, or characteristics, which can be used to detect sensor condition or quality, including, e.g., whether the sensor has failed or is failing. In performing sensor diagnostics, sometimes, there can be a diagnostic test that may indicate a failure, whereas other diagnostic(s) may indicate no failure. Therefore, the availability of multiple impedance-related parameters, and the implementation of a multi-test procedure, are advantageous, as some of the multiplicity of tests may act as validity checks against some of the other tests. Thus, real-time monitoring using a multi-marker procedure may include a certain degree of built-in redundancy.

With the above in mind, the logic of the diagnostic procedure shown in FIG. 31 begins at 3100, after the sensor has been inserted/implanted, and an EIS run has been made, so as to provide the EIS data as input. At 3100, using the EIS data as input, it is first determined whether the sensor is still in place. Thus, if the |Z|slope is found to be constant across the tested frequency band (or range), and/or the phase angle is about −90°, it is determined that the sensor is no longer in place, and an alert is sent, e.g., to the patient/user, indicating that sensor pullout has occurred. The specific parameters (and their respective values) described herein for detecting sensor pullout are based on the discovery that, once the sensor is out of the body and the membrane is no longer hydrated, the impedance spectrum response appears just like a capacitor.

If it is determined that the sensor is still in place, the logic moves to step 3110 to determine whether the sensor is properly initialized. As shown, the "Init. Check" is performed by determining: (i) whether $|(Z_n-Z_1)/Z_1|>30\%$ at 1 kHz, where $Z_1$ is the real impedance measured at a first time, and $Z_n$ is the measured impedance at the next interval, at discussed above; and (2) whether the phase angle change is greater than 10° at 0.1 Hz. If the answer to either one of the questions is "yes", then the test is satisfactory, i.e., the Test 1 is not failed. Otherwise, the Test 1 is marked as a failure.

At step 3120, Test 2 asks whether, at a phase angle of −45°, the difference in frequency between two consecutive EIS runs $(f_2-f_1)$ is greater than 10 Hz. Again, a "No" answer is marked as a fail; otherwise, Test 2 is satisfactorily met.

Test 3 at step 3130 is a hydration test. Here, the inquiry is whether the current impedance $Z_n$ is less than the post-initialization impedance $Z_{pi}$ at 1 kHz. If it is, then this test is satisfied; otherwise, Test 3 is marked as a fail. Test 4 at step 3140 is also a hydration test, but this time at a lower frequency. Thus, this test asks whether $Z_n$ is less than 300 kOhms at 0.1 Hz during post-initialization sensor operation. Again, a "No" answer indicates that the sensor has failed Test 4.

At step 3150, Test 5 inquires whether the low-frequency Nyquist slope is globally increasing from 0.1 Hz to 1 Hz. As discussed previously, for a normally-operating sensor, the relatively lower-frequency Nyquist slope should be increasing over time. Thus, this test is satisfied if the answer to the inquiry is "yes"; otherwise, the test is marked as failed.

Step 3160 is the last test for this embodiment of the diagnostic procedure. Here, the inquiry is whether real impedance is globally decreasing. Again, as was discussed previously, in a normally-operating sensor, it is expected that, as time goes by, the real impedance should be decreasing. Therefore, a "Yes" answer here would mean that the sensor is operating normally; otherwise, the sensor fails Test 6.

Once all 6 tests have been implemented, a decision is made at 3170 as to whether the sensor is operating normally, or whether it has failed. In this embodiment, a sensor is determined to be functioning normally (3172) if it passes at least 3 out of the 6 tests. Put another way, in order to be determined to have failed (3174), the sensor must fail at least 4 out of the 6 tests. In alternative embodiments, a different rule may be used to assess normal operation versus sensor failure. In addition, in embodiments of the invention, each of the tests may be weighted, such that the assigned weight reflects, e.g., the importance of that test, or of the specific parameter(s) queried for that test, in determining overall sensor operation (normal vs. failed). For example, one test may be weighted twice as heavily as another, but only half as heavily as a third test, etc.

Figure 32A:
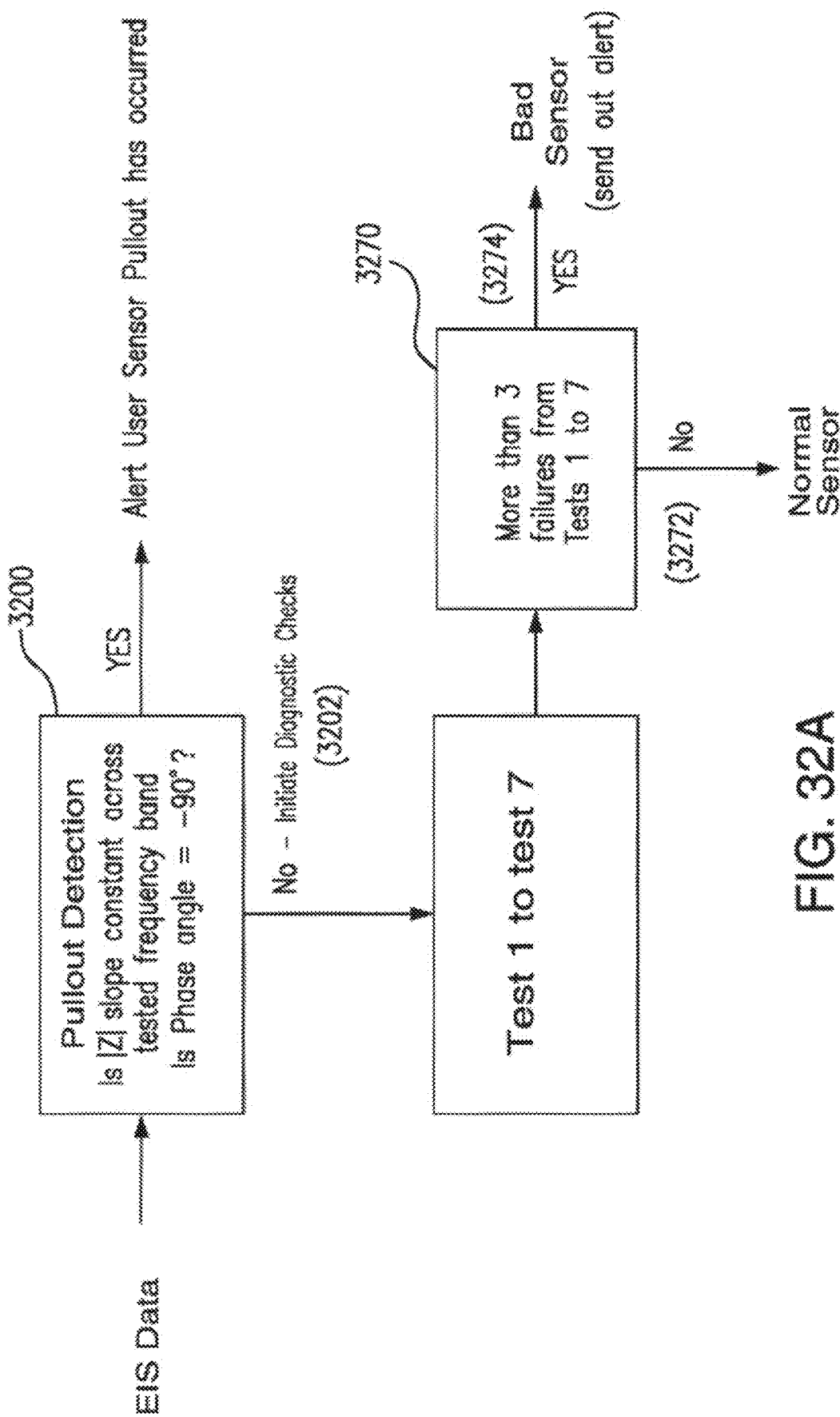
FIGS. 32A and 32B show another diagnostic procedure for sensor fault detection in accordance with embodiments of the invention.
Figure 32B:
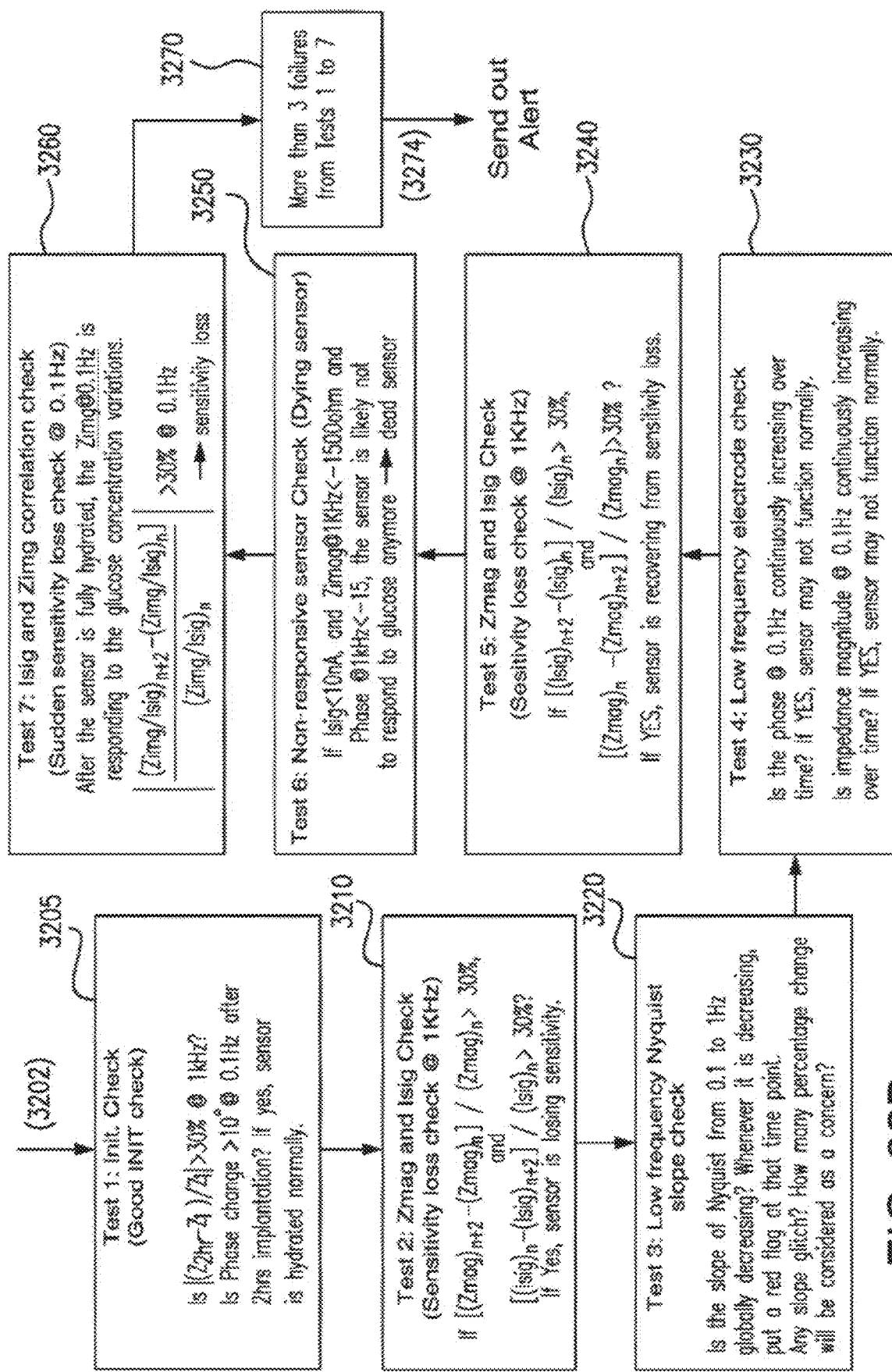

In other alternative embodiments, a different number of tests and/or a different set of EIS-based parameters for each test may be used. FIGS. 32A and 32B show an example of a diagnostic procedure for real-time monitoring that includes 7 tests. Referring to FIG. 32A, the logic begins at 3200, after the sensor has been inserted/implanted, and an EIS procedure has been performed, so as to provide the EIS data as input. At 3200, using the EIS data as input, it is first determined whether the sensor is still in place. Thus, if the |Z| slope is found to be constant across the tested frequency band (or range), and/or the phase angle is about −90°, it is determined that the sensor is no longer in place, and an alert is sent, e.g., to the patient/user, indicating that sensor pullout has occurred. If, on the other hand, the sensor is determined to be in place, the logic moves to initiation of diagnostic checks (3202).

At 3205, Test 1 is similar to Test 1 of the diagnostic procedure discussed above in connection with FIG. 31, except that the instant Test 1 specifies that the later measurement $Z_n$ is taken 2 hours after the first measurement. As such, in this example, $Z_n=Z_{2hr}$. More specifically, Test 1 compares the real impedance 2 hours after (sensor implantation and) initialization to the pre-initialization value. Similarly, the second part of Test 1 asks whether the difference between the phase 2 hours after initialization and the pre-initialization phase is greater than 10° at 0.1 Hz. As before, if the answer to either one of the inquiries is affirmative, then it is determined that the sensor is hydrated normally and initialized, and Test 1 is satisfied; otherwise, the sensor fails this test. It should be noted that, even though the instant test inquires about impedance and phase change 2 hours after initialization, the time interval between any two consecutive EIS runs may be shorter or longer, depending on a variety of factors, including, e.g., sensor design, the level of electrode redundancy, the degree to which the diagnostic procedure includes redundant tests, battery power, etc.

Moving to 3210, the logic next performs a sensitivity-loss check by inquiring whether, after a 2-hour interval (n+2), the percentage change in impedance magnitude at 1 kHz, as well as that in the Isig, is greater than 30%. If the answer to both inquiries is "yes", then it is determined that the sensor is losing sensitivity and, as such, Test 2 is determined to be failed. It is noted that, although Test 2 is illustrated herein based on a preferred percentage difference of 30%, in other embodiments, the percentage differences in the impedance magnitude at 1 kHz and in the Isig may fall within the range 10%-50% for purposes of conducting this test.

Test 3 (at 3220) is similar to Test 5 of the algorithm illustrated in FIG. 31. Here, as before, the question is whether the low-frequency Nyquist slope is globally increasing from 0.1 Hz to 1 Hz. If it is, then this test is passed; otherwise, the test is failed. As shown in 3220, this test is also amenable to setting a threshold, or an acceptable range, for the percent change in the low-frequency Nyquist slope, beyond which the sensor may be deemed to be failed or, at the very least, may trigger further diagnostic testing. In embodiments of the invention, such threshold value/acceptable range for the percent change in low-frequency Nyquist slope may fall within a range of about 2% to about 20%. In some preferred embodiments, the threshold value may be about 5%.

The logic next moves to 3230, which is another low-frequency test, this time involving the phase and the impedance magnitude. More specifically, the phase test inquires whether the phase at 0.1 Hz is continuously increasing over time. If it is, then the test is failed. As with other tests where the parameter's trending is monitored, the low-frequency phase test of Test 4 is also amenable to setting a threshold, or an acceptable range, for the percent change in the low-frequency phase, beyond which the sensor may be deemed to be failed or, at the very least, raise a concern. In embodiments of the invention, such threshold value/acceptable range for the percent change in low-frequency phase may fall within a range of about 5% to about 30%. In some preferred embodiments, the threshold value may be about 10%.

As noted, Test 4 also includes a low-frequency impedance magnitude test, where the inquiry is whether the impedance magnitude at 0.1 Hz is continuously increasing over time. If it is, then the test is failed. It is noted that Test 4 is considered "failed" if either the phase test or the impedance magnitude test is failed. The low-frequency impedance magnitude test of Test 4 is also amenable to setting a threshold, or an acceptable range, for the percent change in the low-frequency impedance magnitude, beyond which the sensor may be deemed to be failed or, at the very least, raise a concern. In embodiments of the invention, such threshold value/acceptable range for the percent change in low-frequency impedance magnitude may fall within a range of about 5% to about 30%. In some preferred embodiments, the threshold value may be about 10%, where the range for impedance magnitude in normal sensors is generally between about 100 KOhms and about 200 KOhms.

Test 5 (at 3240) is another sensitivity loss check that may be thought of as supplemental to Test 2. Here, if both the percentage change in the Isig and the percentage change in the impedance magnitude at 1 kHz are greater than 30%, then it is determined that the sensor is recovering from sensitivity loss. In other words, it is determined that the sensor had previously undergone some sensitivity loss, even if the sensitivity loss was not, for some reason, detected by Test 2. As with Test 2, although Test 5 is illustrated based on a preferred percentage difference of 30%, in other embodiments, the percentage differences in the Isig and the impedance magnitude at 1 kHz may fall within the range 10%-50% for purposes of conducting this test.

Moving to 3250, Test 6 provides a sensor functionality test with specific failure criteria that have been determined based on observed data and the specific sensor design. Specifically, in one embodiment, a sensor may be determined to have failed and, as such, to be unlikely to respond to glucose, if at least two out of the following three criteria are met: (1) Isig is less than 10 nA; and (2) the imaginary impedance at 1 kHz is less than −1500 Ohm; and (3) the phase at 1 kHz is less than −15°. Thus, Test 6 is determined to have been passed if any two of (1)-(3) are not met. It is noted that, in other embodiments, the Isig prong of this test may be failed if the Isig is less than about 5 nA to about 20 nA. Similarly, the second prong may be failed if the imaginary impedance at 1 kHz is less than about −1000 Ohm to about −2000 Ohms. Lastly, the phase prong may be failed if the phase at 1 kHz is less than about −10° to about −20°.

Lastly, step 3260 provides another sensitivity check, wherein the parameters are evaluated at low frequency. Thus, Test 7 inquires whether, at 0.1 Hz, the magnitude of the difference between the ratio of the imaginary impedance to the Isig (n+2), on the one hand, and the pervious value of the ratio, on the other, is larger than 30% of the magnitude of the previous value of the ratio. If it is, then the test is failed; otherwise, the test is passed. Here, although Test 7 is illustrated based on a preferred percentage difference of 30%, in other embodiments, the percentage difference may fall within the range 10%-50% for purposes of conducting this test.

Once all 7 tests have been implemented, a decision is made at 3270 as to whether the sensor is operating normally, or whether an alert should be sent out, indicating that the sensor has failed (or may be failing). As shown, in this embodiment, a sensor is determined to be functioning normally (3272) if it passes at least 4 out of the 7 tests. Put another way, in order to be determined to have failed, or to at least raise a concern (3274), the sensor must fail at least 4 out of the 7 tests. If it is determined that the sensor is "bad" (3274), an alert to that effect may be sent, e.g., to the patient/user. As noted previously, in alternative embodiments, a different rule may be used to assess normal operation versus sensor failure/concern. In addition, in embodiments of the invention, each of the tests may be weighted, such that the assigned weight reflects, e.g., the importance of that test, or of the specific parameter(s) queried for that test, in determining overall sensor operation (normal vs. failed).

As was noted previously, in embodiments of the invention, various of the above-described impedance-related parameters may be used, either individually or in combination, as inputs into one or more fusion algorithms for generating more reliable sensor glucose values. Specifically, it is known that, unlike a single-sensor (i.e., a single-working-electrode) system, multiple sensing electrodes provide higher-reliability glucose readouts, as a plurality of signals, obtained from two or more working electrodes, may be fused to provide a single sensor glucose value. Such signal fusion utilizes quantitative inputs provided by EIS to calculate the most reliable output sensor glucose value from the redundant working electrodes. It is noted that, while the ensuing discussion may describe various fusion algorithms in terms of a first working electrode (WE1) and a second working electrode (WE2) as the redundant electrodes, this is by way of illustration, and not limitation, as the algorithms and their underlying principles described herein are applicable to, and may be used in, redundant sensor systems having more than 2 working electrodes.

Figures 33A, 33B:
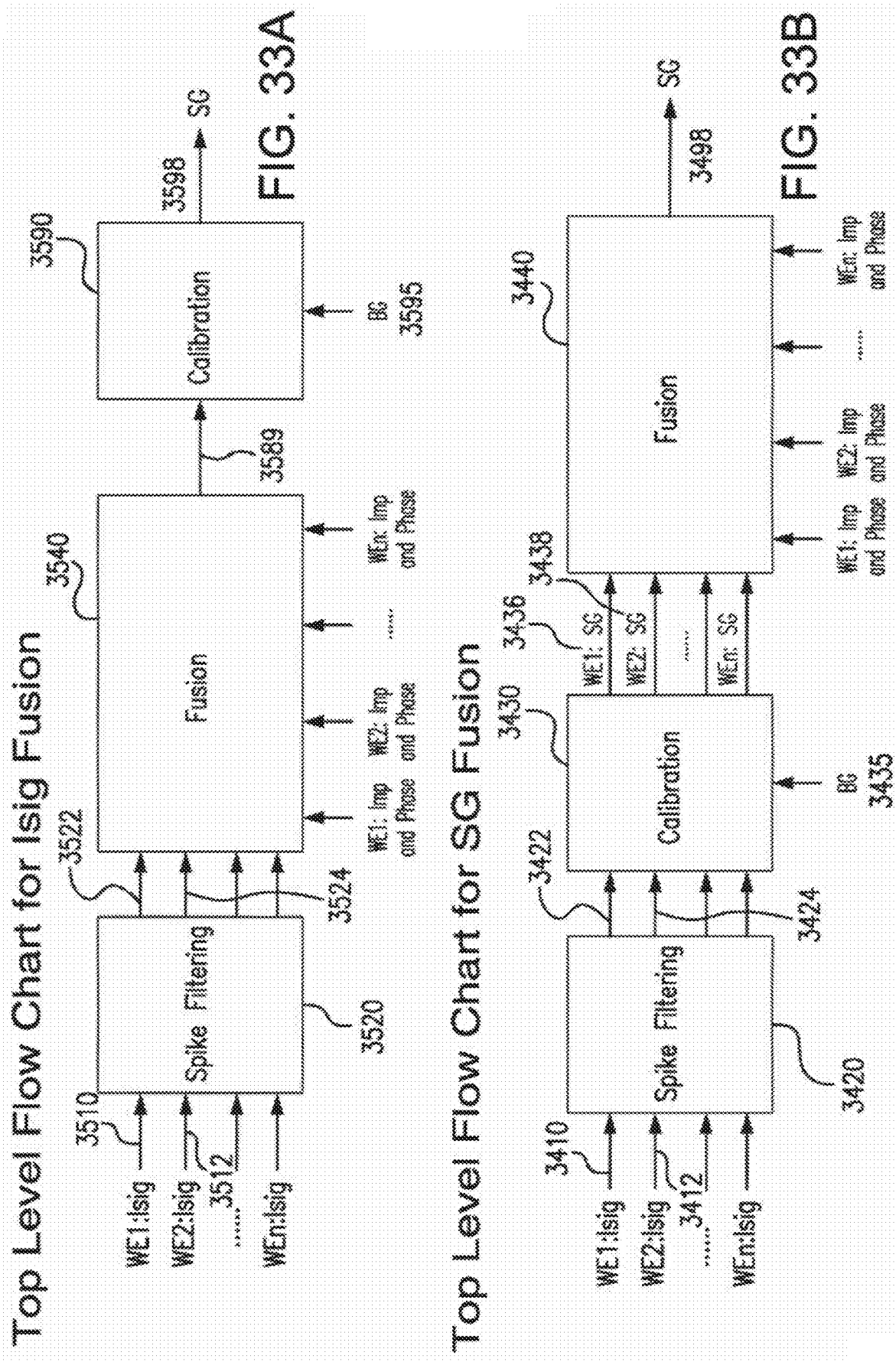
FIG. 33A shows a top-level flowchart involving a current (Isig)-based fusion algorithm in accordance with embodiments of the invention.
FIG. 33B shows a top-level flowchart involving a sensor glucose (SG)-based fusion algorithm in accordance with embodiments of the invention.

FIGS. 33A and 33B show top-level flowcharts for two alternative methodologies, each of which includes a fusion algorithm. Specifically, FIG. 33A is a flowchart involving a current (Isig)-based fusion algorithm, and FIG. 33B is a flowchart directed to sensor glucose (SG) fusion. As may be seen from the diagrams, the primary difference between the two methodologies is the time of calibration. Thus, FIG. 33A shows that, for Isig fusion, calibration 3590 is performed after the fusion 3540 is completed. That is, redundant Isigs from WE1 to WEn are fused into a single Isig 3589, which is then calibrated to produce a single sensor glucose value 3598. For SG fusion, on the other hand, calibration 3435 is completed for each individual Isig from WE1 to WEn to produce calibrated SG values (e.g., 3436, 3438) for each of the working electrodes. Thus, SG fusion algorithms provide for independent calibration of each of the plurality of Isigs, which may be preferred in embodiments of the invention. Once calibrated, the plurality of calibrated SG values is fused into a single SG value 3498.

It is important to note that each of flowcharts shown in FIGS. 33A and 33B includes a spike filtering process (3520, 3420). As was described above in the discussion relating to sensitivity loss, 1 kHz or higher-frequency impedance measurements typically cause EIS-induced spikes in the Isig. Therefore, once an EIS procedure has been performed for each of the electrodes WE1 to WEn, for both SG fusion and Isig fusion, it is preferable to first filter the Isigs 3410, 3412, etc. and 3510, 3512, etc. to obtain respective filtered Isigs 3422, 3424, etc. and 3522, 3524, etc. The filtered Isigs are then either used in Isig fusion, or first calibrated and then used in SG fusion, as detailed below. As will become apparent in the ensuing discussion, both fusion algorithms entail calculation and assignment of weights based on various factors.

Figure 34:
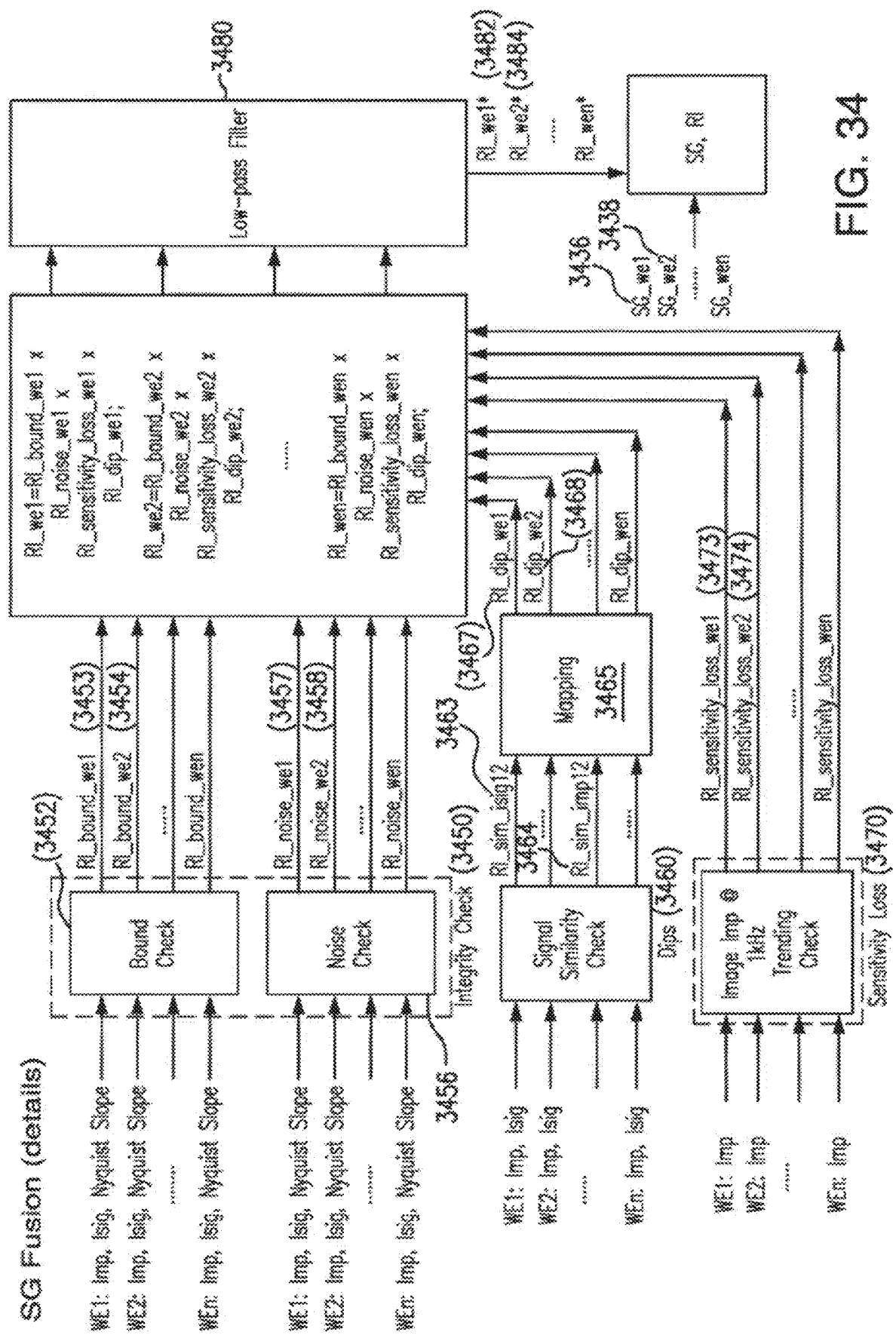
FIG. 34 shows details of the sensor glucose (SG)-based fusion algorithm of FIG. 33B in accordance with embodiments of the invention.

FIG. 34 shows the details of the fusion algorithm 3440 for SG fusion. Essentially, there are four factors that need to be checked before the fusion weights are determined. First, integrity check 3450 involves determining whether each of the following parameters is within specified ranges for normal sensor operation (e.g., predetermined lower and upper thresholds): (i) Isig; (ii) 1 kHz real and imaginary impedances; (iii) 0.105 Hz real and imaginary impedances; and (iv) Nyquist slope. As shown, integrity check 3450 includes a Bound Check 3452 and a Noise Check 3456, wherein, for each of the Checks, the above-mentioned parameters are used as input parameters. It is noted that, for brevity, real and/or imaginary impedances, at one or more frequencies, appear on FIGS. 33A-35 simply as "Imp" for impedance. In addition, both real and imaginary impedances may be calculated using impedance magnitude and phase (which is also shown as an input on FIGS. 33A and 33B).

The output from each of the Bound Check 3452 and the Noise Check 3458 is a respective reliability index (RI) for each of the redundant working electrodes. Thus, the output from the Bound Check includes, e.g., RI_bound_We$_1$ (3543) and RI_bound_We$_2$ (3454). Similarly, for the Noise Check, the output includes, e.g., RI_noise_We$_1$ (3457) and RI_noise_We$_2$ (3458). The bound and noise reliability indices for each working electrode are calculated based on compliance with the above-mentioned ranges for normal sensor operation. Thus, if any of the parameters falls outside the specified ranges for a particular electrode, the reliability index for that particular electrode decreases.

It is noted that the threshold values, or ranges, for the above-mentioned parameters may depend on various factors, including the specific sensor and/or electrode design. Nevertheless, in one preferred embodiment, typical ranges for some of the above-mentioned parameters may be, e.g., as follows: Bound threshold for 1 kHz real impedance=[0.3e+4 2e+4]; Bound threshold for 1 kHz imaginary impedance= [−2e+3, 0]; Bound threshold for 0.105 Hz real impedance= [2e+4 7e+4]; Bound threshold for 0.105 Hz imaginary impedance=[−2e+5-0.25e+5]; and Bound threshold for Nyquist slope=[25]. Noise may be calculated, e.g., using second order central difference method where, if noise is above a certain percentage (e.g., 30%) of median value for each variable buffer, it is considered to be out of noise bound.

Second, sensor dips may be detected using sensor current (Isig) and 1 kHz real impedance. Thus, as shown in FIG. 34, Isig and "Imp" are used as inputs for dips detection 3460. Here, the first step is to determine whether there is any divergence between Isigs, and whether any such divergence is reflected in 1 kHz real impedance data. This may be accomplished by using mapping 3465 between the Isig similarity index (RI_sim_isig12) 3463 and the 1 kHz real impedance similarity index (RI_sim_imp12) 3464. This mapping is critical, as it helps avoid false positives in instances where a dip is not real. Where the Isig divergence is real, the algorithm will select the sensor with the higher Isig.

In accordance with embodiments of the invention, the divergence/convergence of two signals (e.g., two Isigs, or two 1 kHz real impedance data points) can be calculated as follows:

$$\text{diff\_va1} = \text{abs}(\text{va1} - (\text{va1} + \text{va2})/2);$$

$$\text{diff\_va2} = \text{abs}(\text{va2} - (\text{va1} + \text{va2})/2);$$

$$\text{RI\_sim} = 1 - (\text{diff\_va1} + \text{diff\_va2})/(\text{mean}(\text{abs}(\text{va1} + \text{va2}))/4)$$

where va1 and va2 are two variables, and RI_sim (similarity index) is the index to measure the convergence or divergence of the signals. In this embodiment, RI_sim must be bound between 0 and 1. Therefore, if RI_sim as calculated above is less than 0, it will be set to 0, and if it is higher than 1, it will be set to 1.

The mapping 3465 is performed by using ordinary linear regression (OLR). However, when OLR does not work well, a robust median slope linear regression (RMSLR) can be used. For Isig similarity index and 1 kHz real impedance index, for example, two mapping procedures are needed: (i) Map Isig similarity index to 1 kHz real impedance similarity index; and (ii) map 1 kHz real impedance similarity index to Isig similarity index. Both mapping procedures will generate two residuals: res12 and res21. Each of the dip reliability indices 3467, 3468 can then be calculated as:

$$\text{RI\_dip} = 1 - (\text{res12} + \text{res21})/(\text{RI\_sim\_isig} + \text{RI\_sim\_1K\_real\_impedance}).$$

The third factor is sensitivity loss 3470, which may be detected using 1 kHz imaginary impedance trending in, e.g., the past 8 hours. If one sensor's trending turns negative, the algorithm will rely on the other sensor. If both sensors lose sensitivity, then a simple average is taken. Trending may be calculated by using a strong low-pass filter to smooth over the 1 kHz imaginary impedance, which tends to be noisy, and by using a correlation coefficient or linear regression with respect to time during, e.g., the past 8 hours to determine whether the correlation coefficient is negative or the slope is negative. Each of the sensitivity loss reliability indices 3473, 3474 is then assigned a binary value of 1 or 0.

The total reliability index (RI) for each of we1, we2, . . . wen is calculated as follows:

$$RI\_we_1 = RI\_dip\_we_1 \times RI\_sensitivity\_loss\_we_1 \times RI\_bound\_we_1 \times RI\_noise\_we_1$$

$$RI\_we_2 = RI\_dip\_we_2 \times RI\_sensitivity\_loss\_we_2 \times RI\_bound\_we_2 \times RI\_noise\_we_2$$

$$RI\_we_3 = RI\_dip\_we_3 \times RI\_sensitivity\_loss\_we_3 \times RI\_bound\_we_3 \times RI\_noise\_we_3$$

$$RI\_we_4 = RI\_dip\_we_4 \times RI\_sensitivity\_loss\_we_4 \times RI\_bound\_we_4 \times RI\_noise\_we_4$$

$$\vdots$$

$$RI\_we_n = RI\_dip\_we_n \times RI\_sensitivity\_loss\_we_n \times RI\_bound\_we_n \times RI\_noise\_we_n$$

Having calculated the respective reliability indices of the individual working electrodes, the weight for each of the electrodes may be calculated as follow:

$$weight\_we_1 = RI\_we_1/(RI\_we_1 + RI\_we_2 + RI\_we_3 + RI\_we_4 + \ldots + RI\_we_n)$$

$$weight\_we_2 = RI\_we_2/(RI\_we_1 + RI\_we_2 + RI\_we_3 + RI\_we_4 + \ldots + RI\_we_n)$$

$$weight\_we_3 = RI\_we_3/(RI\_we_1 + RI\_we_2 + RI\_we_3 + RI\_we_4 + \ldots + RI\_we_n)$$

$$weight\_we_4 = RI\_we_4/(RI\_we_1 + RI\_we_2 + RI\_we_3 + RI\_we_4 + \ldots + RI\_we_n)$$

$$\vdots$$

$$weight\_we_n = RI\_we_n/(RI\_we_1 + RI\_we_2 + RI\_we_3 + RI\_we_4 + \ldots + RI\_we_n)$$

Based on the above, the fused SG 3498 is then calculated as follows:

SG=weight_$we_1$×SG_$we_1$+weight_$we_2$×SG_$we_2$+weight_$we_3$×SG_$we_3$+weight_$we_4$×SG_$we_4$+ . . . +weight_$we_n$×SG_$we_n$ The last factor relates to artifacts in the final sensor readout, such as may be caused by instant weight change of sensor fusion. This may be avoided by either applying a low-pass filter 3480 to smooth the RI for each electrode, or by applying a low-pass filter to the final SG. When the former is used, the filtered reliability indices—e.g., RI_We1* and RI_We2* (3482, 3484)—are used in the calculation of the weight for each electrode and, therefore, in the calculation of the fused SG 3498.

Figure 35:
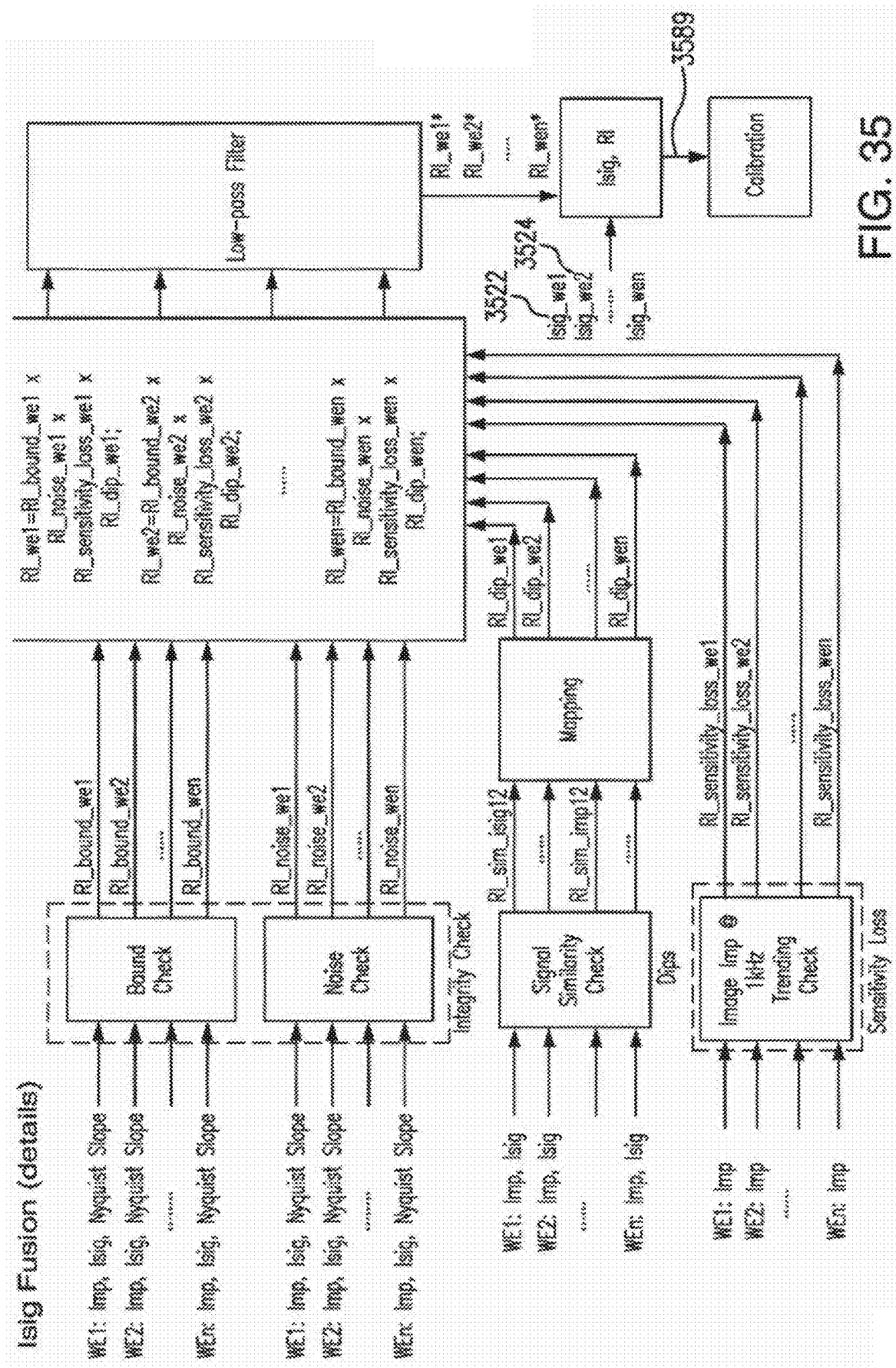
FIG. 35 shows details of the current (Isig)-based fusion algorithm of FIG. 33A in accordance with embodiments of the invention.

FIG. 35 shows the details of the fusion algorithm 3540 for Isig fusion. As can be seen, this algorithm is substantially similar to the one shown in FIG. 34 for SG fusion, with two exceptions. First, as was noted previously, for Isig fusion, calibration constitutes the final step of the process, where the single fused Isig 3589 is calibrated to generate a single sensor glucose value 3598. See also FIG. 33B. Second, whereas SG fusion uses the SG values for the plurality of electrodes to calculate the final SG value 3498, the fused Isig value 3589 is calculated using the filtered Isigs (3522, 3524, and so on) for the plurality of electrodes.

In one closed-loop study involving a non-diabetic population, it was found that the above-described fusion algorithms provided considerable improvements in the Mean Absolute Relative Difference (MARD) both on Day 1, when low start-up issues are most significant and, as such, may have a substantial impact on sensor accuracy and reliability, and overall (i.e., over a 7-day life of the sensor). The study evaluated data for an 88% distributed layout design with high current density (nominal) plating using three different methodologies: (1) calculation of one sensor glucose value (SG) via fusion using Medtronic Minimed's Ferrari Algorithm 1.0 (which is a SG fusion algorithm as discussed above); (2) calculation of one SG by identifying the better ISIG value using 1 kHz EIS data (through the Isig fusion algorithm discussed above); and (3) calculation of one SG by using the higher ISIG value (i.e., without using EIS). The details of the data for the study are presented below:

(1) SG Based on Ferrari 1.0 Alg for 88% Distributed Layout with High Current Density (Nominal) Plating

| Mean-ARD Percentage | | | | | | | | |
|---|---|---|---|---|---|---|---|---|
| | Day | | | | | | | |
| | 1 | 2 | 3 | 4 | 5 | 6 | 7 | Total |
| 040-080 | 19.39 | 17.06 | | 22.27 | 17.50 | 37.57 | 11.43 | 19.69 |
| 080-120 | 19.69 | 09.18 | 09.34 | 08.64 | 10.01 | 08.31 | 11.33 | 11.56 |
| 120-240 | 19.01 | 17.46 | 12.44 | 07.97 | 11.75 | 08.82 | 12.15 | 12.92 |
| 240-400 | | 10.25 | 08.36 | 14.09 | 10.86 | 12.84 | 22.70 | 12.88 |
| Total | 19.52 | 11.71 | 10.14 | 09.30 | 10.83 | 09.49 | 11.89 | 12.28 |

| Mean-Absolute Bias (sg-bg) | | | | | | | | |
|---|---|---|---|---|---|---|---|---|
| | Day | | | | | | | |
| | 1 | 2 | 3 | 4 | 5 | 6 | 7 | Total |
| 040-080 | 14.86 | 11.78 | | 15.81 | 11.07 | 29.00 | 07.26 | 14.05 |
| 080-120 | 19.53 | 09.37 | 09.49 | 08.78 | 09.88 | 08.44 | 11.61 | 11.62 |
| 120-240 | 30.04 | 29.73 | 19.34 | 14.45 | 18.25 | 12.66 | 18.89 | 20.60 |
| 240-400 | | 26.75 | 22.23 | 39.82 | 29.00 | 33.00 | 61.36 | 35.19 |
| Total | 21.62 | 15.20 | 12.79 | 13.21 | 12.04 | 10.84 | 15.04 | 14.79 |

| Mean-Signed Bias (sg-bg) | | | | | | | | |
|---|---|---|---|---|---|---|---|---|
| | Day | | | | | | | |
| | 1 | 2 | 3 | 4 | 5 | 6 | 7 | Total |
| 040-080 | 12.15 | 09.78 | | 15.81 | 11.07 | 29.00 | 07.26 | 13.01 |
| 080-120 | −04.45 | −04.92 | −00.90 | 00.18 | 01.21 | 00.85 | 00.03 | −01.44 |
| 120-240 | −10.18 | −27.00 | −16.89 | −02.91 | −05.40 | −01.24 | −11.58 | −10.71 |
| 240-400 | | 11.25 | 02.23 | −00.07 | −27.00 | −33.00 | −61.36 | −10.29 |
| Total | −04.81 | −09.77 | −05.09 | −00.23 | −00.22 | 00.67 | −04.98 | −03.56 |

| Eval Points | | | | | | | | |
|---|---|---|---|---|---|---|---|---|
| | Day | | | | | | | |
| | 1 | 2 | 3 | 4 | 5 | 6 | 7 | Total |
| 040-080 | 007 | 004 | 000 | 002 | 006 | 003 | 004 | 026 |
| 080-120 | 090 | 064 | 055 | 055 | 067 | 056 | 047 | 434 |
| 120-240 | 028 | 025 | 022 | 021 | 016 | 032 | 026 | 170 |
| 240-400 | 000 | 002 | 004 | 008 | 003 | 001 | 002 | 020 |
| Total | 125 | 095 | 081 | 086 | 092 | 092 | 079 | 650 |

| Eval Points | | | | | | | | |
|---|---|---|---|---|---|---|---|---|
| | Day | | | | | | | |
| | 1 | 2 | 3 | 4 | 5 | 6 | 7 | Total |
| 040-080 | 007 | 004 | 000 | 001 | 006 | 002 | 004 | 024 |
| 080-120 | 082 | 053 | 044 | 045 | 058 | 043 | 041 | 366 |
| 120-240 | 030 | 022 | 023 | 019 | 015 | 030 | 022 | 161 |
| 240-400 | 000 | 002 | 004 | 006 | 003 | 001 | 001 | 017 |
| Total | 119 | 081 | 071 | 071 | 082 | 076 | 068 | 568 |

(2) SG Based on Better ISIG Using 1 kHz EIS for 88% Distributed Layout with High Current Density (Nominal) Plating (3) SG Based on Higher ISIG for 88% Distributed Layout with High Current Density (Nominal) Plating

| Mean-ARD Percentage | | | | | | | | |
|---|---|---|---|---|---|---|---|---|
| | Day | | | | | | | |
| | 1 | 2 | 3 | 4 | 5 | 6 | 7 | Total |
| 040-080 | 16.66 | 18.78 | | 21.13 | 16.21 | 43.68 | 09.50 | 18.14 |
| 080-120 | 16.22 | 11.96 | 08.79 | 10.49 | 09.75 | 08.04 | 10.34 | 11.36 |
| 120-240 | 15.08 | 17.50 | 12.68 | 07.72 | 08.74 | 08.84 | 13.02 | 12.16 |
| 240-400 | | 07.66 | 06.42 | 11.10 | 07.52 | 15.95 | 21.13 | 09.84 |
| Total | 15.96 | 13.70 | 09.92 | 09.95 | 09.96 | 09.40 | 11.31 | 11.83 |

| Mean-ARD Percentage | | | | | | | | |
|---|---|---|---|---|---|---|---|---|
| | Day | | | | | | | |
| | 1 | 2 | 3 | 4 | 5 | 6 | 7 | Total |
| 040-080 | 17.24 | 19.13 | | 21.13 | 17.31 | 43.68 | 10.38 | 18.79 |
| 080-120 | 17.69 | 11.77 | 09.36 | 10.70 | 10.19 | 08.34 | 10.68 | 11.86 |
| 120-240 | 16.80 | 17.63 | 13.04 | 07.38 | 09.04 | 08.52 | 13.25 | 12.50 |
| 240-400 | | 07.47 | 06.02 | 10.85 | 07.52 | 15.95 | 21.13 | 09.63 |
| Total | 17.44 | 13.60 | 10.37 | 10.00 | 10.40 | 09.36 | 11.66 | 12.26 |

| Mean-Absolute Bias (sg-bg) | | | | | | | | |
|---|---|---|---|---|---|---|---|---|
| | Day | | | | | | | |
| | 1 | 2 | 3 | 4 | 5 | 6 | 7 | Total |
| 040-080 | 12.71 | 13.00 | | 15.00 | 10.17 | 33.50 | 06.00 | 12.83 |
| 080-120 | 15.70 | 12.17 | 08.57 | 10.89 | 09.62 | 08.26 | 10.49 | 11.32 |
| 120-240 | 24.43 | 29.82 | 19.43 | 13.79 | 14.60 | 12.97 | 20.27 | 19.58 |
| 240-400 | | 20.00 | 17.00 | 32.50 | 20.00 | 41.00 | 60.00 | 27.29 |
| Total | 17.72 | 17.20 | 12.56 | 13.55 | 10.95 | 11.21 | 14.12 | 14.20 |

| Mean-Absolute Bias (sg-bg) | | | | | | | | |
|---|---|---|---|---|---|---|---|---|
| | Day | | | | | | | |
| | 1 | 2 | 3 | 4 | 5 | 6 | 7 | Total |
| 040-080 | 13.14 | 13.25 | | 15.00 | 11.00 | 33.50 | 06.50 | 13.29 |
| 080-120 | 17.23 | 11.98 | 09.22 | 11.02 | 10.08 | 08.59 | 10.86 | 11.85 |
| 120-240 | 27.40 | 30.09 | 19.75 | 13.26 | 14.93 | 12.45 | 20.65 | 20.09 |
| 240-400 | | 19.50 | 16.00 | 32.00 | 20.00 | 41.00 | 60.00 | 26.82 |
| Total | 19.53 | 17.09 | 13.00 | 13.35 | 11.37 | 11.18 | 14.53 | 14.67 |

| Mean-Signed Bias (sg-bg) | | | | | | | | |
|---|---|---|---|---|---|---|---|---|
| | Day | | | | | | | |
| | 1 | 2 | 3 | 4 | 5 | 6 | 7 | Total |
| 040-080 | 08.71 | 13.00 | | 15.00 | 10.17 | 33.50 | 06.00 | 11.67 |
| 080-120 | −04.30 | −08.62 | −01.11 | −03.64 | 02.52 | 00.40 | −01.56 | −02.52 |
| 120-240 | −11.30 | −29.64 | −17.09 | −08.74 | −10.87 | −07.23 | −15.09 | −14.05 |
| 240-400 | | 20.00 | 00.50 | 09.50 | −17.33 | −41.00 | −60.00 | −03.18 |
| Total | −05.30 | −12.56 | −06.20 | −03.63 | −00.10 | −02.29 | −06.35 | −05.21 |

| Mean-Signed Bias (sg-bg) | | | | | | | | |
|---|---|---|---|---|---|---|---|---|
| | Day | | | | | | | |
| | 1 | 2 | 3 | 4 | 5 | 6 | 7 | Total |
| 040-080 | 08.29 | 12.75 | | 15.00 | 11.00 | 33.50 | 06.50 | 11.79 |
| 080-120 | −04.72 | −08.83 | −02.35 | −01.56 | 01.75 | −00.18 | −01.52 | −02.70 |
| 120-240 | −15.13 | −29.73 | −17.67 | −08.42 | −11.47 | −07.03 | −15.43 | −14.86 |
| 240-400 | | 19.50 | 01.50 | 06.33 | −17.33 | −41.00 | −60.00 | −04.12 |
| Total | −06.57 | −12.70 | −07.11 | −02.46 | −00.63 | −02.56 | −06.47 | −05.57 |

| Eval Points | | | | | | | | |
|---|---|---|---|---|---|---|---|---|
| | Day | | | | | | | |
| | 1 | 2 | 3 | 4 | 5 | 6 | 7 | Total |
| 040-080 | 007 | 004 | 000 | 001 | 006 | 002 | 004 | 024 |
| 080-120 | 083 | 054 | 046 | 048 | 060 | 044 | 042 | 377 |
| 120-240 | 030 | 022 | 024 | 019 | 015 | 031 | 023 | 164 |
| 240-400 | 000 | 002 | 004 | 006 | 003 | 001 | 001 | 017 |
| Total | 120 | 082 | 074 | 074 | 084 | 078 | 070 | 582 |

With the above data, it was found that, with the first approach, the MARD (%) on Day 1 was 19.52%, with an overall MARD of 12.28%. For the second approach, the Day-1 MARD was 15.96% and the overall MARD was 11.83%. Lastly, for the third approach, the MARD was 17.44% on Day 1, and 12.26% overall. Thus, for this design with redundant electrodes, it appears that calculation of SG based on the better ISIG using 1 kHz EIS (i.e., the second methodology) provides the greatest advantage. Specifically, the lower Day-1 MARD may be attributable, e.g., to better low start-up detection using EIS. In addition, the overall MARD percentages are more than 1% lower than the overall average MARD of 13.5% for WE1 and WE2 in this study. It is noted that, in the above-mentioned approaches, data transitions may be handled, e.g., by a filtering method to minimize the severity of the transitions, such as by using a low-pass filter 3480 as discussed above in connection with FIGS. 33A-35.

It bears repeating that sensor diagnostics, including, e.g., assessment of low start-up, sensitivity-loss, and signal-dip events depends on various factors, including the sensor design, number of electrodes (i.e., redundancy), electrode distribution/configuration, etc. As such, the actual frequency, or range of frequencies, for which an EIS-based parameter may be substantially glucose-independent, and therefore, an independent marker, or predictor, for one or more of the above-mentioned failure modes may also depend on the specific sensor design. For example, while it has been discovered, as described hereinabove, that sensitivity loss may be predicted using imaginary impedance at the relatively higher frequencies—where imaginary impedance is substantially glucose-independent—the level of glucose dependence, and, therefore, the specific frequency range for using imaginary impedance as a marker for sensitivity loss, may shift (higher or lower) depending on the actual sensor design.

More specifically, as sensor design moves more and more towards the use of redundant working electrodes, the latter must be of increasingly smaller sizes in order to maintain the overall size of the sensor. The size of the electrodes, in turn, affects the frequencies that may be queried for specific diagnostics. In this regard, it is important to note that the fusion algorithms described herein and shown in FIGS. 33A-35 are to be regarded as illustrative, and not limiting, as each algorithm can be modified as necessary to use EIS-based parameters at frequencies that exhibit the least amount of glucose dependence, based on the type of sensor under analysis.

In addition, experimental data indicates that human tissue structure may also affect glucose dependence at different frequencies. For example, in children, real impedance at 0.105 Hz has been found to be a substantially glucose-independent indicator for low start-up detection. It is believed that this comes about as a result of a child's tissue structure changing, e.g., the Warburg impedance, which relates mostly to the resistive component. See also the subsequent discussion relating to interferent detection.

Figure 36:
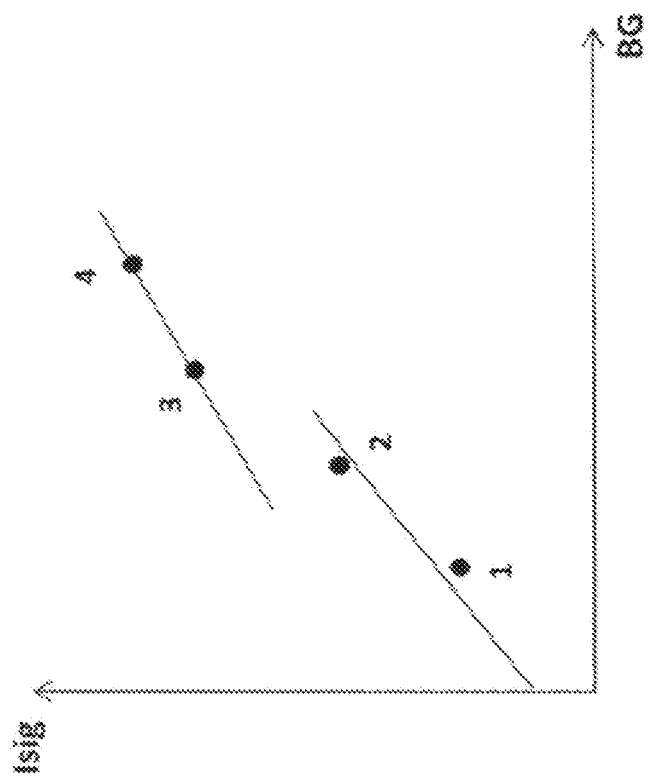
FIG. 36 is an illustration of calibration for a sensor in steady state, in accordance with embodiments of the invention.

Embodiments of the invention herein are also directed to the use of EIS in optimizing sensor calibration. By way of background, in current methodologies, the slope of a BG vs. Isig plot, which may be used to calibrate subsequent Isig values, is calculated as follows:

$$\text{slope} = \frac{\sum \alpha\beta(isig - \text{offset})bg}{\sum \alpha\beta(isig - \text{offset})^2}$$

where $\alpha$ is an exponential function of a time constant, $\beta$ is a function of blood glucose variance, and offset is a constant. For a sensor in steady condition, this method provides fairly accurate results. As shown, e.g., in FIG. 36, BG and Isig follow a fairly linear relationship, and offset can be taken as a constant.

Figure 37:
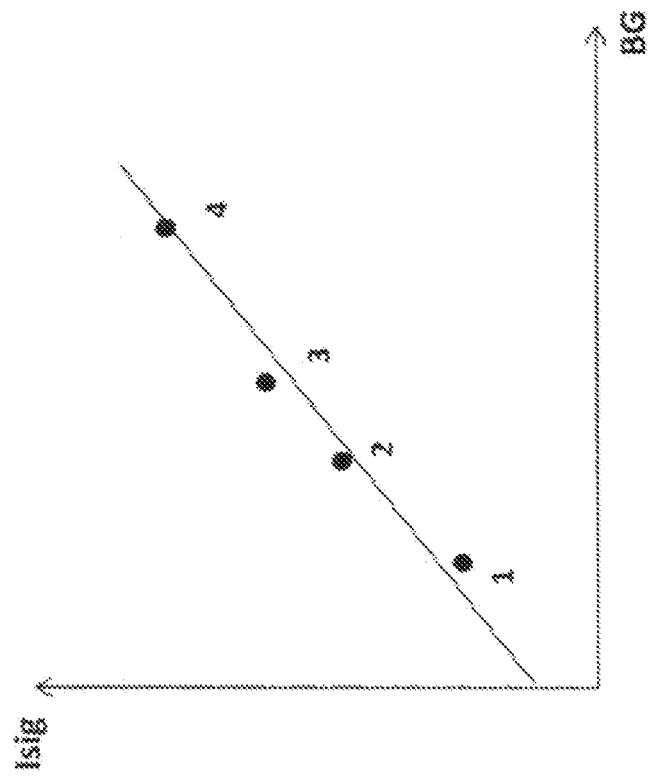
FIG. 37 is an illustration of calibration for a sensor in transition, in accordance with embodiments of the invention.

However, there are situations in which the above-mentioned linear relationship does not hold true, such as, e.g., during periods in which the sensor experiences a transition. As shown in FIG. 37, it is clear that Isig-BG pairs 1 and 2 are significantly different from pairs 3 and 4 in terms of Isig and BG relationship. For these types of conditions, use of a constant offset tends to produce inaccurate results.

To address this issue, one embodiment of the invention is directed to the use of an EIS-based dynamic offset, where EIS measurements are used to define a sensor status vector as follows:

$$V = \{\text{real\_}imp\_1\text{K}, \text{img\_}imp\_1\text{K}, \text{Nyquist\_slope}, \text{Nyquist\_}R\_\text{square}\}$$

where all of the elements in the vector are substantially BG independent. It is noted that Nyquist_R_square is the R square of linear regression used to calculate the Nyquist slope, i.e., the square of the correlation coefficient between real and imaginary impedances at relatively-lower frequencies, and a low R square indicates abnormality in sensor performance. For each Isig-BG pair, a status vector is assigned. If a significant difference in status vector is detected—e.g., |V2−V3| for the example shown in FIG.

37—a different offset value is assigned for 3 and 4 when compared to 1 and 2. Thus, by using this dynamic offset approach, it is possible to maintain a linear relationship between Isig and BG.

In a second embodiment, an EIS-based segmentation approach may be used for calibration. Using the example of FIG. 37 and the vector V, it can be determined that sensor state during 1 and 2 is signficantly different from sensor state during 3 and 4. Therefore, the calibration buffer can be divided into two segments, as follows:

Isig_buffer1=[Isig1,Isig2];BG_buffer1=[BG1,BG2]

Isig_buffer2=[Isig3,Isig3];BG_buffer2=[BG3,BG3]

Thus, when the sensor operates during 1 and 2, Isig_buffer1 and BG_buffer1 would be used for calibration. However, when the sensor operates during 3 and 4, i.e., during a transition period, Isig_buffer2 and BG_buffer2 would be used for calibration.

Figure 38A:
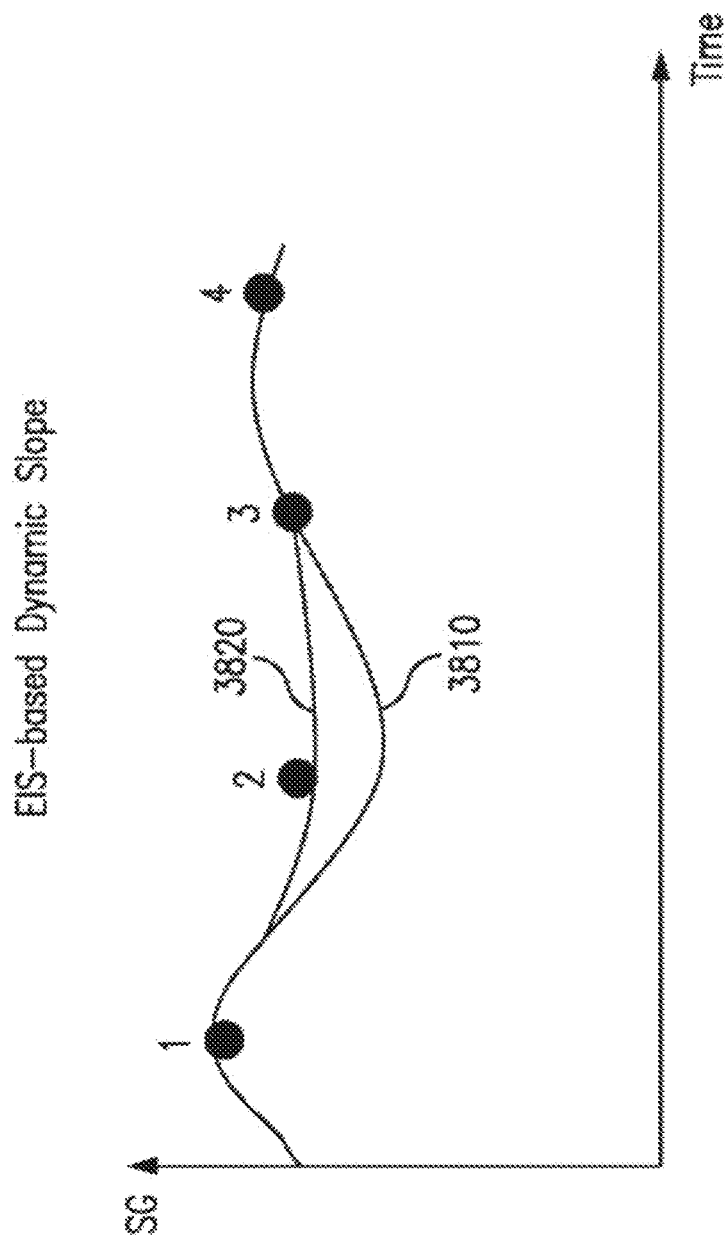
FIG. 38A is an illustration of EIS-based dynamic slope (with slope adjustment) in accordance with embodiments of the invention for sensor calibration.

In yet another embodiment, an EIS-based dynamic slope approach, where EIS is used to adjust slope, may be used for calibration purposes. FIG. 38A shows an example of how this method can be used to improve sensor accuracy. In this diagram, the data points 1-4 are discrete blood glucose values. As can be seen from FIG. 38A, there is a sensor dip 3810 between data points 1 and 3, which dip can be detected using the sensor state vector V described above. During the dip, slope can be adjusted upward to reduce the underreading, as shown by reference numeral 3820 in FIG. 38A.

In a further embodiment, EIS diagnostics may be used to determine the timing of sensor calibrations, which is quite useful for, e.g, low-startup events, sensitivity-loss events, and other similar situations. As is known, most current methodologies require regular calibrations based on a preset schedule, e.g., 4 times per day. Using EIS diagnostics, however, calibrations become event-driven, such that they may be performed only as often as necessary, and when they would be most productive. Here, again, the status vector V may be used to determine when the sensor state has changed, and to request calibration if it has, indeed, changed.

Figure 38B:
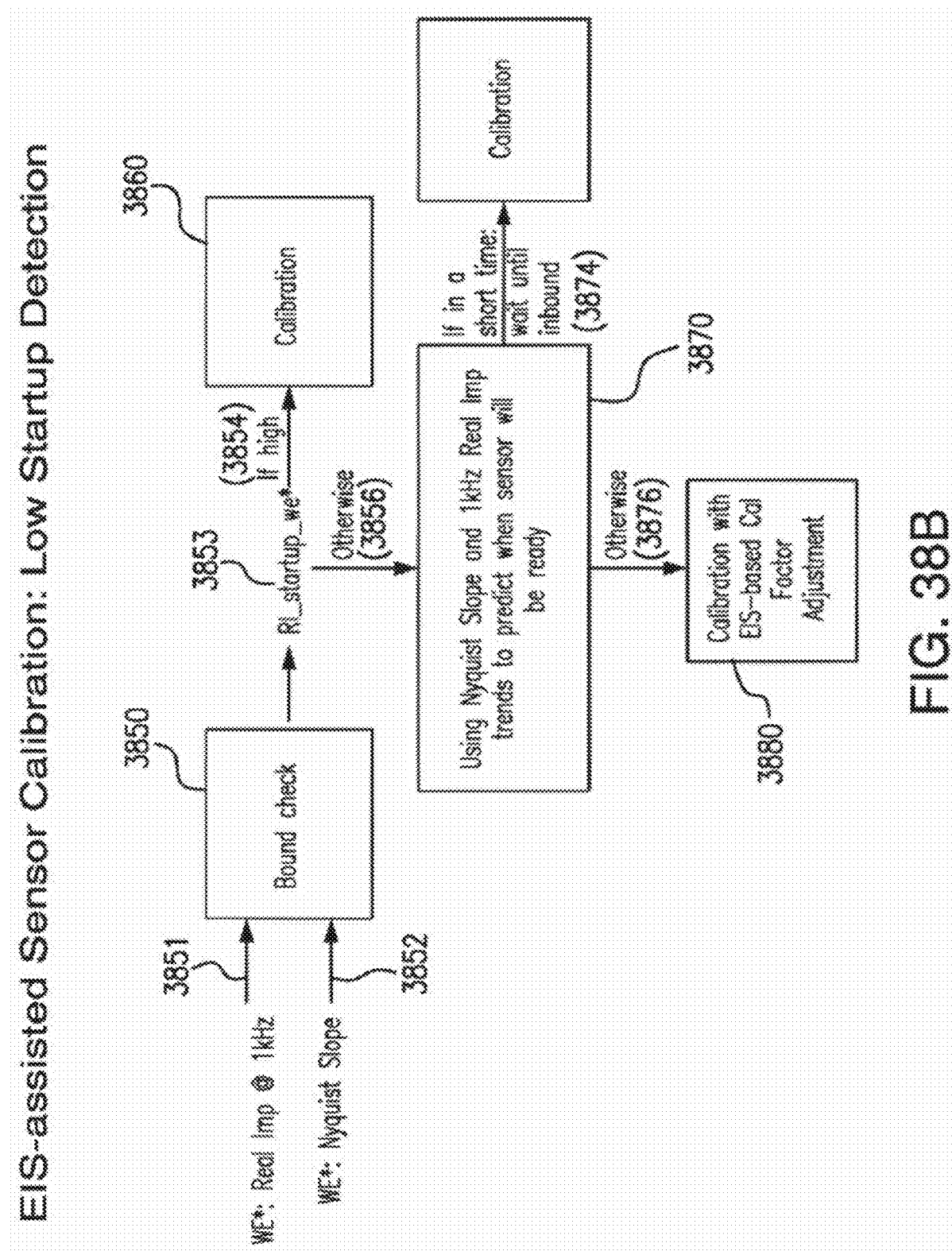
FIG. 38B shows an EIS-assisted sensor calibration flowchart involving low start-up detection in accordance with embodiments of the invention.

More specifically, in an illustrative example, FIG. 38B shows a flowchart for EIS-assisted sensor calibration involving low start-up detection. Using Nyquist slope, 1 kHz real impedance, and a bound check 3850 (see, e.g., the previously-described bound check and associated threshold values for EIS-based parameters in connection with the fusion algorithms of FIGS. 33A-35), a reliability index 3853 can be developed for start-up, such that, when the 1 kHz real impedance 3851 and the Nyquist slope 3852 are lower than their corresponding upper bounds, RI_startup=1, and sensor is ready for calibration. In other words, the reliability index 3853 is "high" (3854), and the logic can proceed to calibration at 3860.

When, on the other hand, the 1 kHz real impedance and the Nyquist slope are higher than their corresponding upper bounds (or threshold values), RI_startup=0 (i.e., it is "low"), and the sensor is not ready for calibration (3856), i.e., a low start-up issue may exist. Here, the trend of 1 kHz real impedance and the Nyquist slope can be used to predict when both parameters will be in range (3870). If it is estimated that this will only take a very short amount of time (e.g., less than one hour), then the algorithm waits until the sensor is ready, i.e., until the above-mentioned EIS-based parameters are in-bound (3874), at which point the algorithm proceeds to calibration. If, however, the wait time would be relatively long (3876), then the sensor can be calibrated now, and then the slope or offset can be gradually adjusted according to the 1 kHz real impedance and the Nyquist slope trend (3880). It is noted that by performing the adjustment, serious over- or under-reading caused by low start-up can be avoided. As noted previously, the EIS-based parameters and related information that is used in the instant calibration algorithm is substantially glucose-independent.

It is noted that, while the above description in connection with FIG. 38B shows a single working electrode, as well as the calculation of a reliability index for start-up of that working electrode, this is by way of illustration, and not limitation. Thus, in a redundant sensor including two or more working electrodes, a bound check can be performed, and a start-up reliability index calculated, for each of the plurality of (redundant) working electrodes. Then, based on the respective reliability indices, at least one working electrode can be identified that can proceed to obtain glucose measurements. In other words, in a sensor having a single working electrode, if the latter exhibits low start-up, actual use of the sensor (for measuring glucose) may have to be delayed until the low start-up period is over. This period may typically be on the order of one hour or more, which is clearly disadvantageous. In contrast, in a redundant sensor, utilizing the methodology described herein allows an adaptive, or "smart", start-up, wherein an electrode that can proceed to data gathering can be identified in fairly short order, e.g., on the order of a few minutes. This, in turn, reduces MARD, because low start-up generally provides about a ½% increase in MARD.

In yet another embodiment, EIS can aid in the adjustment of the calibration buffer. For existing calibration algorithms, the buffer size is always 4, i.e., 4 Isig-BG pairs, and the weight is based upon a which, as noted previously, is an exponential function of a time constant, and β, which is a function of blood glucose variance. Here, EIS can help to determine when to flush the buffer, how to adjust buffer weight, and what the appropriate buffer size is.

Embodiments of the invention are also directed to the use of EIS for interferent detection. Specifically, it may be desirable to provide a medication infusion set that includes a combination sensor and medication-infusion catheter, where the sensor is placed within the infusion catheter. In such a system, the physical location of the infusion catheter relative to the sensor may be of some concern, due primarily to the potential impact on (i.e., interference with) sensor signal that may be caused by the medication being infused and/or an inactive component thereof.

For example, the diluent used with insulin contains m-cresol as a preservative. In in-vitro studies, m-cresol has been found to negatively impact a glucose sensor if insulin (and, therefore, m-cresol) is being infused in close proximity to the sensor. Therefore, a system in which a sensor and an infusion catheter are to be combined in a single needle must be able to detect, and adjust for, the effect of m-cresol on the sensor signal. Since m-cresol affects the sensor signal, it would be preferable to have a means of detecting this interferent independently of the sensor signal itself.

Experiments have shown that the effect of m-cresol on the sensor signal is temporary and, thus, reversible. Nevertheless, when insulin infusion occurs too close to the sensor, the m-cresol tends to "poison" the electrode(s), such that the latter can no longer detect glucose, until the insulin (and m-cresol) have been absorbed into the patient's tissue. In this regard, it has been found that there is typically about a 40-minute time period between initiation of insulin infusion and when the sensor has re-gained the ability to detect glucose again. However, advantageously, it has also been discovered that, during the same time period, there is a large increase in 1 kHz impedance magnitude quite independently of the glucose concentration.

Figure 39:
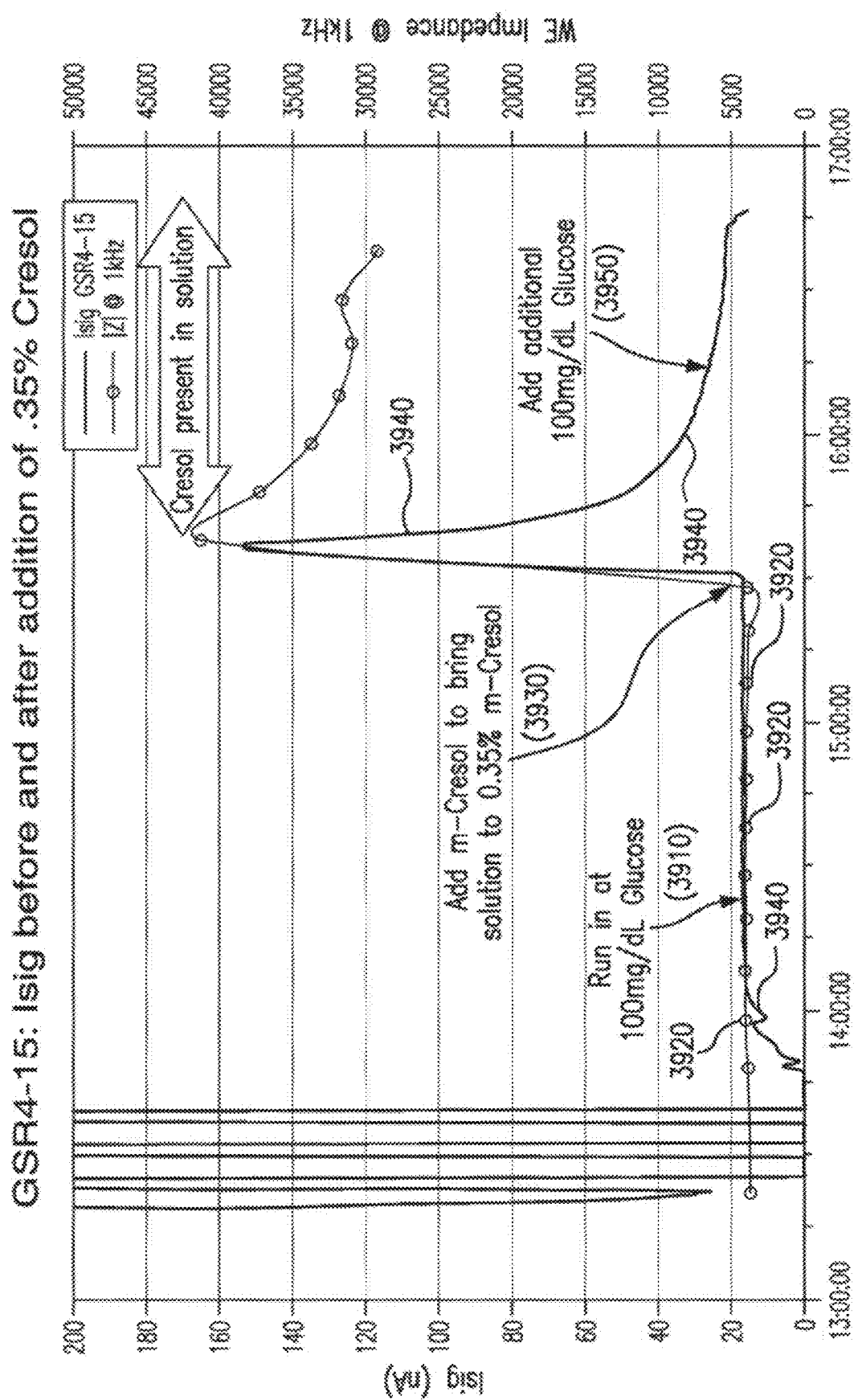
FIG. 39 shows sensor current (Isig) and 1 kHz impedance magnitude for an in-vitro simulation of an interferent being in close proximity to a sensor in accordance with embodiments of the invention.

Specifically, FIG. 39 shows Isig and impedance data for an in-vitro experiment, wherein the sensor was placed in a 100 mg/dL glucose solution, and 1 kHz impedance was measured every 10 minutes, as shown by encircled data points 3920. m-cresol was then added to bring the solution to 0.35% m-cresol (3930). As can be seen, once m-cresol has been added, the Isig 3940 initially increases dramatically, and then begins to drift down. The concentration of glucose in the solution was then doubled, by adding an addition 100 mg/dL glucose. This, however, had no effect on the Isig 3940, as the electrode was unable to detect the glucose.

On the other hand, the m-cresol had a dramatic effect on both impedance magnitude and phase. FIG. 40A shows a Bode plot for the phase, and FIG. 40B shows a Bode plot for impedance magnitude, for both before and after the addition of m-cresol. As can be seen, after the m-cresol was added, the impedance magnitude 4010 increased from its post-initialization value 4020 by at least an order of magnitude across the frequency spectrum. At the same time, the phase 4030 changed completely as compared to its post-initialization value 4040. On the Nyquist plot of FIG. 40C. Here, the pre-initialization curve 4050 and the post-initialization curve 4060 appear as expected for a normally-functioning sensor. However, after the addition of m-cresol, the curve 4070 becomes drastically different.

The above experiment identifies an important practical pitfall of continuing to rely on the Isig after m-cresol has been added. Referring back to FIG. 39, a patient/user monitoring the sensor signal may be put under the mistaken impression that his glucose level has just spiked, and that he should administer a bolus. The user then administers the bolus, at which the Isig has already started to drift back down. In other words, to the patient/user, everything may look normal. In reality, however, what has really happened is that the patient just administered an unneeded dose of insulin which, depending on the patient's glucose level prior to administration of the bolus, may put the patient at risk of experiencing a hypoglycemic event. This scenario reinforces the desirability of a means of detecting interferents that is as glucose-independent as possible.

Figure 41:
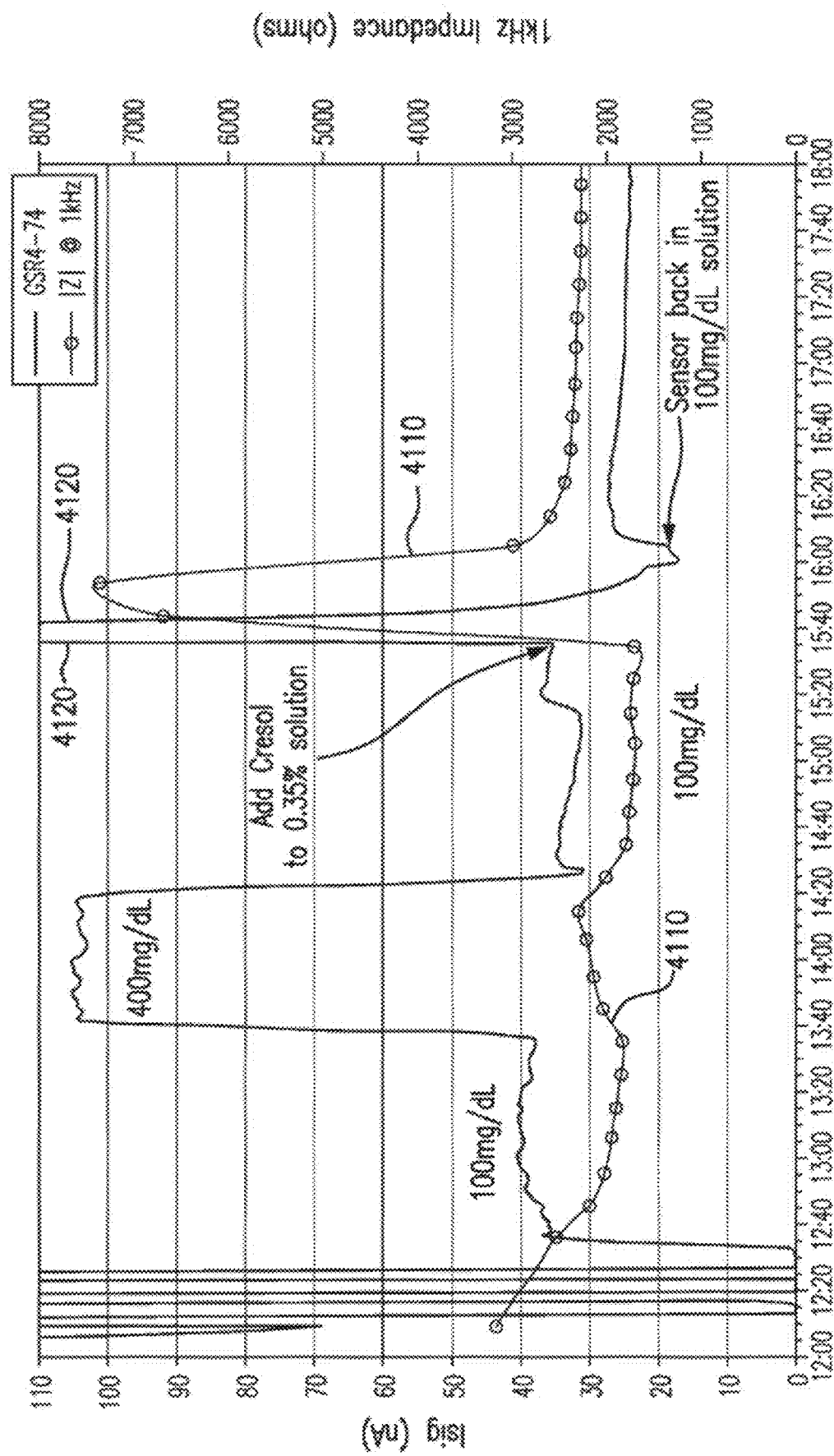
FIG. 41 shows another in-vitro simulation with an interferent in accordance to embodiments of the invention.

FIG. 41 shows another experiment, where a sensor was initialized a 100 mg/dL glucose solution, after which glucose was raised to 400 mg/dL for one hour, and then returned to 100 mg/dL. m-cresol was then added to raise the concentration to 0.35%, with the sensor remaining in this solution for 20 minutes. Finally, the sensor was placed in a 100 mg/dL glucose solution to allow Isig to recover after exposure to m-cresol. As can be seen, after initialization, the 1 kHz impedance magnitude 4110 was at about 2 kOhms. When m-cresol was added, the Isig 4120 spiked, as did impedance magnitude 4110. Moreover, when the sensor was returned to a 100 md/dL glucose solution, the impedance magnitude 4110 also returned to near normal level.

As can be seen from the above experiments, EIS can be used to detect the presence of an interfering agent—in this case, m-cresol. Specifically, since the interferent affects the sensor in such a way as to increase the impedance magnitude across the entire frequency spectrum, the impedance magnitude may be used to detect the interference. Once the interference has been detected, either the sensor operating voltage can be changed to a point where the interferent is not measured, or data reporting can be temporarily suspended, with the sensor indicating to the patient/user that, due to the administration of medication, the sensor is unable to report data (until the measured impedance returns to the pre-infusion level). It is noted that, since the impact of the interferent is due to the preservative that is contained in insulin, the impedance magnitude will exhibit the same behavior as described above regardless of whether the insulin being infused is fast-acting or slow.

Importantly, as mentioned above, the impedance magnitude, and certainly the magnitude at 1 kHz, is substantially glucose-independent. With reference to FIG. 41, it can be seen that, as the concentration of glucose is raised from 100 mg/dL to 400 mg/dL—a four-fold increase—the 1 kHz impedance magnitude increase from about 2000 Ohms to about 2200 Ohms, or about a 10% increase. In other words, the effect of glucose on the impedance magnitude measurement appears to be about an order of magnitude smaller compared to the measured impedance. This level of "signal-to-noise" ratio is typically small enough to allow the noise (i.e., the glucose effect) to be filtered out, such that the resultant impedance magnitude is substantially glucose-independent. In addition, it should be emphasized that the impedance magnitude exhibits an even higher degree of glucose-independence in actual human tissue, as compared to the buffer solution that was used for the in-vitro experiments described above.

Embodiments of the invention are also directed to an Analog Front End Integrated Circuit (AFE IC), which is a custom Application Specific Integrated Circuit (ASIC) that provides the necessary analog electronics to: (i) support multiple potentiostats and interface with multi-terminal glucose sensors based on either Oxygen or Peroxide; (ii) interface with a microcontroller so as to form a micropower sensor system; and (iii) implement EIS diagnostics, fusion algorithms, and other EIS-based processes based on measurement of EIS-based parameters. More specifically, the ASIC incorporates diagnostic capability to measure the real and imaginary impedance parameters of the sensor over a wide range of frequencies, as well as digital interface circuitry to enable bidirectional communication with a microprocessor chip. Moreover, the ASIC includes power control circuitry that enables operation at very low standby and operating power, and a real-time clock and a crystal oscillator so that an external microprocessor's power can be turned off.

Figure 42A:
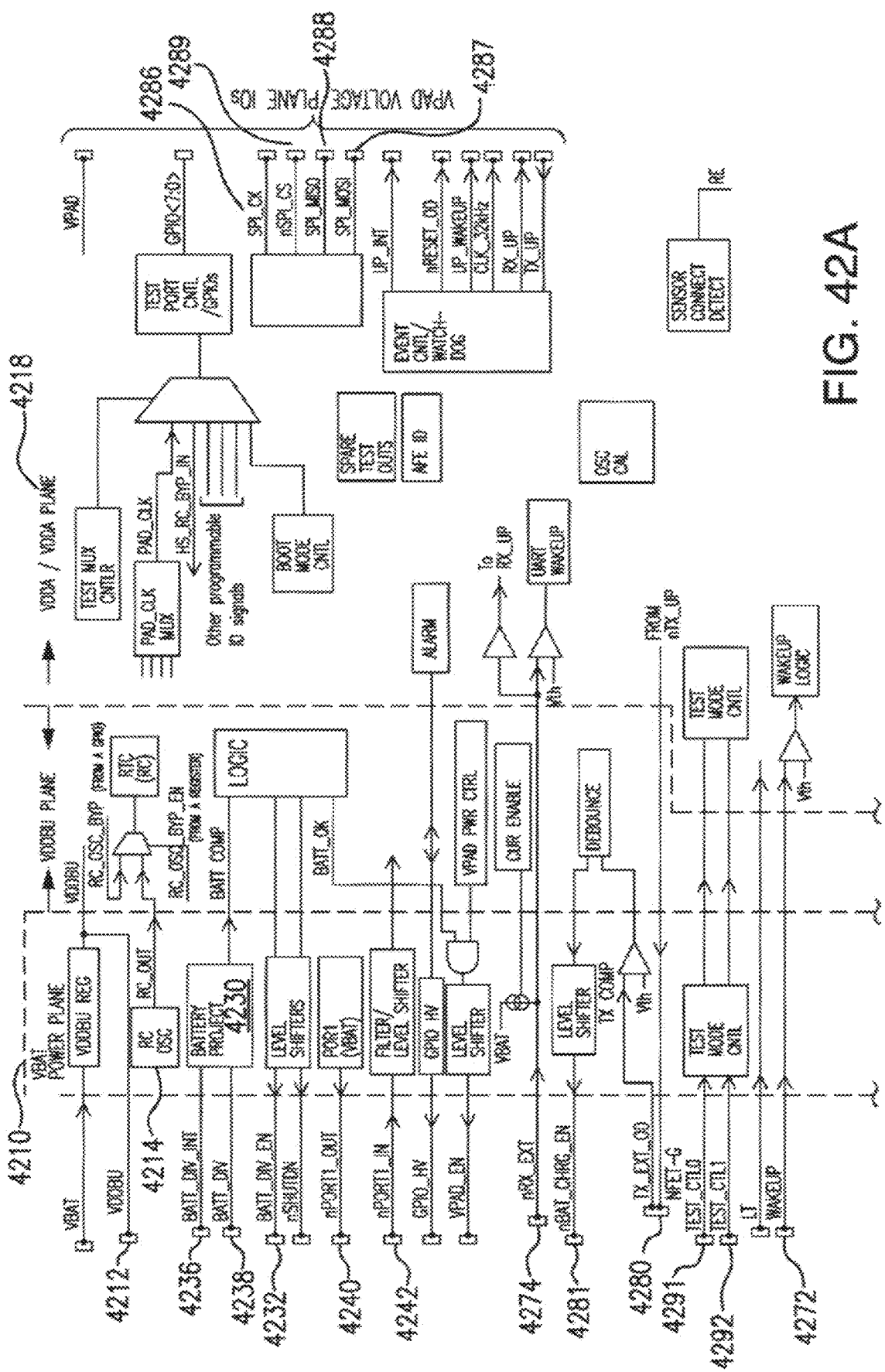

FIGS. 42A and 42B show a block diagram of the ASIC, and Table 1 below provides pad signal descriptions (shown on the left-hand side of FIGS. 42A and 42B), with some signals being multiplexed onto a single pad.

TABLE 1

Pad signal descriptions

| Pad Name | Functional Description | Power plane |
|---|---|---|
| VBAT | Battery power input 2.0 V to 4.5 V | VBAT |
| VDDBU | Backup logic power 1.4 to 2.4 V | VDDBU |
| VDD | Logic power -- 1.6-2.4 V | VDD |
| VDDA | Analog power - 1.6-2.4 V | VDDA |
| VPAD | Pad I/O power -- 1.8 V-3.3 V | VPAD |
| VSS | Logic ground return and digital pad return | |
| VSSA | Analog ground return and analog pad return | |
| ADC_IN1, 2 | ADC Inputs, VDDA max input | VDDA |
| V1P2B | 1.2 volt reference Bypass capacitor | VDDA |
| nSHUTDN | External VDD regulator control signal. Goes low when battery is low. | VBAT |
| VPAD_EN | Goes high when VPAD IOs are active. Can control external regulator. | VBAT |

TABLE 1-continued

Pad signal descriptions

| Pad Name | Functional Description | Power plane |
|---|---|---|
| DA1, 2 | DAC outputs | VDDA |
| TP_ANA_MUX | Mux of analog test port -- output or input | VDDA |
| TP_RES | External 1 meg ohm calibration resistor & analog test port | VDDA |
| WORK1-5 | Working Electrodes of Sensor | VDDA |
| RE | Reference Electrode of Sensor | VDDA |
| COUNTER | Counter Electrode of Sensor | VDDA |
| CMP1_IN | General purpose Voltage comparator | VDDA |
| CMP2_IN | General purpose Voltage comparator | VDDA |
| WAKEUP | Debounced interrupt input | VBAT |
| XTALI, XTALO | 32.768 kHz Crystal Oscillator pads | VDDA |
| OSC_BYPASS | Test clock control | VDDA |
| SEN_CONN_SW | Sensor connection switch input. Pulled to VSSA = connection | VDDA |
| VPAD_EN | Enable the VPAD power and VPAD power plane logic | VBAT |
| nRESET_OD | Signal to reset external circuitry such as a microprocessor | |
| SPI_CK, nSPI_CS, SPI_MOIS, SPI_MISO | SPI interface signals to microprocessor | VPAD |
| UP_WAKEUP | Microprocessor wakeup signal | VPAD |
| CLK_32KHZ | Gated Clock output to external circuitry microprocessor | VPAD |
| UP_INT | Interrupt signal to microprocessor | VPAD |
| nPOR1_OUT | Backup Power on reset, output from analog | VBAT |
| nPOR1_IN | VBAT power plane reset, input to digital in battery plane (VDDBU) | VBAT |
| nPOR2_OUT | VDD POR signal, output from analog | VDD |
| nPOR2_OUT_OD | VDD POR signal open drain (nfet out only), stretched output from digital | VBAT |
| nPOR2_IN | VDD power plane logic reset. Is level shifted to VDD inside the chip, input to digital VDD logic. | VDD |

The ASIC will now be described with reference to FIGS. 42A and 42B and Table 1.

Power Planes

The ASIC has one power plane that is powered by the supply pad VBAT (4210), which has an operating input range from 2.0 volts to 4.5 volts. This power plane has a regulator to lower the voltage for some circuits in this plane. The supply is called VDDBU (4212) and has an output pad for test and bypassing. The circuits on the VBAT supply include an RC oscillator, real time clock (RC osc) 4214, battery protection circuit, regulator control, power on reset circuit (POR), and various inputs/outputs. The pads on the VBAT power plane are configured to draw less than 75 nA at 40° C. and VBAT=3.50V.

The ASIC also has a VDD supply to supply logic. The VDD supply voltage range is programmable from at least 1.6 volts to 2.4 volts. The circuits on the VDD power plane include most of the digital logic, timer (32 khz), and real time clock (32 khz). The VDD supply plane includes level shifters interfacing to the other voltage planes as necessary. The level shifters, in turn, have interfaces conditioned so that any powered power plane does not have an increase in current greater than 10 nA if another power plane is unpowered.

The ASIC includes an onboard regulator (with shutdown control) and an option for an external VDD source. The regulator input is a separate pad, REG_VDD_IN (4216), which has electrostatic discharge (ESD) protection in common with other I/Os on VBAT. The onboard regulator has an output pad, REG_VDD_OUT (4217). The ASIC also has an input pad for the VDD, which is separate from the REG_VDD_OUT pad.

The ASIC includes an analog power plane, called VDDA (4218), which is powered by either the VDD onboard regulator or an external source, and is normally supplied by a filtered VDD. The VDDA supplied circuits are configured to operate within 0.1 volt of VDD, thereby obviating the need for level shifting between the VDDA and VDD power planes. The VDDA supply powers the sensor analog circuits, the analog measurement circuits, as well as any other noise-sensitive circuitry.

The ASIC includes a pad supply, VPAD, for designated digital interface signals. The pad supply has an operating voltage range from at least 1.8 V to 3.3 V. These pads have separate supply pad(s) and are powered from an external source. The pads also incorporate level shifters to other onboard circuits to allow the flexible pad power supply range independently of the VDD logic supply voltage. The ASIC can condition the VPAD pad ring signals such that, when the VPAD supply is not enabled, other supply currents will not increase by more than 10 nA.

Bias Generator

The ASIC has a bias generator circuit, BIAS_GEN (4220), which is supplied from the VBAT power, and which generates bias currents that are stable with supply voltage for the system. The output currents have the following specifications: (i) Supply sensitivity: <±2.5% from a supply voltage of 1.6 v to 4.5V; and (ii) Current accuracy: <±3% after trimming.

The BIAS_GEN circuit generates switched and unswitched output currents to supply circuits needing a bias current for operation. The operating current drain of the BIAS_GEN circuit is less than 0.3 uA at 25° C. with VBAT from 2.5V-4.5V (excluding any bias output currents). Lastly, the temperature coefficient of the bias current is generally between 4,000 ppm/° C. and 6,000 ppm/° C.

Voltage Reference

The ASIC, as described herein is configured to have a low power voltage reference, which is powered from the VBAT power supply. The voltage reference has an enable input which can accept a signal from logic powered by VBAT or VDDBU. The ASIC is designed such that the enable signal does not cause any increase in current in excess of 10 nA from any supply from this signal interface when VBAT is powered.

The reference voltage has the following specifications: (i) Output voltage: 1.220±3 mV after trimming; (ii) Supply sensitivity: <±6 mV from 1.6 V to 4.5V input; (iii) Temperature sensitivity: <±5 mV from 0° C. to 60° C.; and (iv) Output voltage default accuracy (without trim): 1.220 V±50 mV. In addition, the supply current is to be less than 800 nA at 4.5V, 40° C. In this embodiment, the reference output will be forced to VSSA when the reference is disabled so as to keep the VDD voltage regulator from overshooting to levels beyond the breakdown voltage of the logic.

32 kHz Oscillator

The ASIC includes a low power 32.768 kHz crystal oscillator 4222 which is powered with power derived from the VDDA supply and can trim the capacitance of the crystal oscillator pads (XTALI, XTALO) with software. Specifically, the frequency trim range is at least −50 ppm to +100 ppm with a step size of 2 ppm max throughout the trim range. Here, a crystal may be assumed with a load capacitance of 7 pF, Ls=6.9512 kH, Cs=3.3952 fF, Rs=70 k, shunt capacitance=1 pF, and a PC Board parasitic capacitance of 2 pF on each crystal terminal.

The ASIC has a VPAD level output available on a pad, CLK_32 kHZ, where the output can be disabled under software and logic control. The default is driving the 32 kHz oscillator out. An input pin, OSC32K_BYPASS (4224), can disable the 32 kHz oscillator (no power drain) and allows for digital input to the XTALI pad. The circuits associated with this function are configured so as not add any ASIC current in excess of 10 nA in either state of the OSC32K_BYPASS signal other than the oscillator current when OSC32K_BYPASS is low.

The 32 kHZ oscillator is required to always be operational when the VDDA plane is powered, except for the bypass condition. If the OSC32K_BYPASS is true, the 32 KHZ oscillator analog circuitry is put into a low power state, and the XTALI pad is configured to accept a digital input whose level is from 0 to VDDA. It is noted that the 32 kHz oscillator output has a duty cycle between 40% and 60%.

Timer

The ASIC includes a Timer 4226 that is clocked from the 32 kHz oscillator divided by 2. It is pre-settable and has two programmable timeouts. It has 24 programmable bits giving a total time count to 17 minutes, 4 seconds. The Timer also has a programmable delay to disable the clock to the CLK_32 KHz pad and set the microprocessor (uP) interface signals on the VPAD plane to a predetermined state (See section below on Microprocessor Wakeup Control Signals). This will allow the microprocessor to go into suspend mode without an external clock. However, this function may be disabled by software with a programmable bit.

The Timer also includes a programmable delay to wakeup the microprocessor by enabling the CLK_32 KHZ clock output and setting UP_WAKEUP high. A transition of the POR2 (VDD POR) from supply low state to supply OK state will enable the 32 kHz oscillator, the CLK_32 KHZ clock output and set UP_WAKEUP high. The power shutdown and power up are configured to be controlled with programmable control bits.

Real Time Clock (RTC)

The ASIC also has a 48-bit readable/writeable binary counter that operates from the ungated, free running 32 kHz oscillator. The write to the real time clock 4228 requires a write to an address with a key before the clock can be written. The write access to the clock is configured to terminate between 1 msec and 20 msec after the write to the key address.

The real time clock 4228 is configured to be reset by a power on reset either by POR1_IN (the VBAT POR) or POR2_IN (the VDD_POR) to half count (MSB=1, all other bits 0). In embodiments of the invention, the real time clock has programmable interrupt capability, and is designed to be robust against single event upsets (SEUs), which may be accomplished either by layout techniques or by adding capacitance to appropriate nodes, if required.

RC Oscillator

The ASIC further includes an RC clock powered from the VBAT supply or VBAT derived supply. The RC Oscillator is always running, except that the oscillator can be bypassed by writing to a register bit in analog test mode (see section on Digital Testing) and applying a signal to the GPIO_VBAT with a 0 to VBAT level. The RC oscillator is not trimmable, and includes the following specifications: (i) a frequency between 750 Hz and 1500 Hz; (ii) a duty cycle between 50%±10%; (iii) current consumption of less than 200 nA at 25° C.; (iv) frequency change of less than ±2% from 1V to 4.5V VBAT supply and better than 1% from 1.8V to 4.5V VBAT supply; and (v) frequency change of less than +2, −2% from a temperature of 15° C. to 40° C. with VBAT=3.5V. The RC frequency can be measured with the 32 kHz crystal oscillator or with an external frequency source (See Oscillator Calibration Circuit).

Real Time RC Clock (RC Oscillator Based)

The ASIC includes a 48-bit readable/writeable binary ripple counter based on the RC oscillator. A write to the RC real time clock requires a write to an address with a key before the clock can be written. The write access to the clock terminates between 1 msec and 20 msec after the write to the key address, wherein the time for the protection window is configured to be generated with the RC clock.

The real time RC clock allows for a relative time stamp if the crystal oscillator is shutdown and is configured to be reset on POR1_IN (the BAT POR) to half count (MSB=1, all others 0). The real time RC clock is designed to be robust against single event upsets (SEUs) either by layout techniques or by adding capacitance to appropriate nodes, where required. On the falling edge of POR2_IN, or if the ASIC goes into Battery Low state, the RT real time clock value may be captured into a register that can be read via the SPI port. This register and associated logic are on the VBAT or VDDBU power plane.

Battery Protection Circuit

The ASIC includes a battery protection circuit 4230 that uses a comparator to monitor the battery voltage and is powered with power derived from the VBAT power plane. The battery protection circuit is configured to be always running with power applied to the VBAT supply. The battery protection circuit may use the RC oscillator for clocking signals and have an average current drain that is less than 30 nA, including a 3 MOhm total resistance external voltage divider.

The battery protection circuit uses an external switched voltage divider having a ratio of 0.421 for a 2.90V battery threshold. The ASIC also has an internal voltage divider with the ratio of 0.421±0.5%. This divider is connected between BATT_DIV_EN (4232) and VSSA (4234), and the divider output is a pin called BATT_DIV_INT (4236). To save pins in the packaged part, the BATT_DIV_INT in this embodiment is connected to BATT_DIV internally in the package. Also, in this configuration, BATT_DIV_EN does not need to come out of the package, saving two package pins.

The battery protection circuit is configured to sample the voltage on an input pin, BATT_DIV (4238), at approximately 2 times per second, wherein the sample time is generated from the RC Oscillator. The ASIC is able to adjust the divider of the RC Oscillator to adjust the sampling time interval to 0.500 sec±5 msec with the RC oscillator operating within its operating tolerance. In a preferred embodiment, the ASIC has a test mode which allows more frequent sampling intervals during test.

The comparator input is configured to accept an input from 0 to VBAT volts. The input current to the comparator input, BATT_DIV, is less than 10 nA for inputs from 0 to VBAT volts. The comparator sampling circuit outputs to a pad, BATT_DIV_EN, a positive pulse which can be used by external circuitry to enable an off-chip resistor divider only during the sampling time to save power. The voltage high logic level is the VBAT voltage and the low level is VSS level.

The output resistance of the BATT_DIV_EN pad shall be less than 2 kOhms at VBAT=3.0V. This allows the voltage divider to be driven directly from this output. After a programmable number of consecutive samples indicating a low battery condition, the comparator control circuitry triggers an interrupt to the interrupt output pad, UP_INT. The default number of samples is 4, although the number of consecutive samples is programmable from 4 to 120.

After a programmable number of consecutive samples indicating a low battery after the generation of the UP_INT above, the comparator control circuitry is configured to generate signals that will put the ASIC into a low power mode: The VDD regulator will be disabled and a low signal will be asserted to the pad, VPAD_EN. This will be called the Battery Low state. Again, the number of consecutive samples is programmable from 4 to 120 samples, with the default being 4 samples.

The comparator has individual programmable thresholds for falling and rising voltages on BATT_DIV. This is implemented in the digital logic to multiplex the two values to the circuit depending on the state of the Battery Low state. Thus, if Battery Low state is low, the falling threshold applies, and if the Battery Low state is high, the rising threshold applies. Specifically, the comparator has 16 programmable thresholds from 1.22 to 1.645±3%, wherein the DNL of the programmable thresholds is set to be less than 0.2 LSB.

The comparator threshold varies less than +/−1% from 20° C. to 40° C. The default threshold for falling voltage is 1.44V (VBAT threshold of 3.41V with nominal voltage divider), and the default threshold for rising voltage is 1.53V (VBAT threshold of 3.63V with nominal voltage divider). After the ASIC has been put into the Battery Low state, if the comparator senses 4 consecutive indications of battery OK, then the ASIC will initiate the microprocessor startup sequence.

Battery Power Plane Power on Reset

A power on reset (POR) output is generated on pad nPOR1_OUT (4240) if the input VBAT slews more than 1.2 volt in a 50 usec period or if the VBAT voltage is below 1.6±0.3 volts. This POR is stretched to a minimum pulse width of 5 milliseconds. The output of the POR circuit is configured to be active low and go to a pad, nPOR1_OUT, on the VBAT power plane.

The IC has an input pad for the battery power plane POR, nPOR1_IN (4242). This input pad has RC filtering such that pulses shorter than 50 nsec will not cause a reset to the logic. In this embodiment, nPOR1_OUT is externally connected to the nPOR1_IN in normal operation, thereby separating the analog circuitry from the digital circuitry for testing. The nPOR1_IN causes a reset of all logic on any of the power planes and initializes all registers to their default value. Thus, the reset status register POR bit is set, and all other reset status register bits are cleared. The POR reset circuitry is configured so as not to consume more than 0.1 uA from VBAT supply for time greater than 5 seconds after power up.

VDD Power on Reset (POR)

The ASIC also has a voltage comparator circuit which generates a VDD voltage plane reset signal upon power up, or if the VDD drops below a programmable threshold. The range is programmable with several voltage thresholds. The default value is 1.8V-15% (1.53V). The POR2 has a programmable threshold for rising voltage, which implements hysteresis. The rising threshold is also programmable, with a default value of 1.60V±3%.

The POR signal is active low and has an output pad, nPOR2_OUT (4244), on the VDD power plane. The ASIC also has an active low POR open drain output, nPOR2_OUT_OD (4246), on the VBAT power plane. This could be used for applying POR to other system components.

The VDD powered logic has POR derived from the input pad, nPOR2_IN (4248). The nPOR2_IN pad is on the VDD power plane and has RC filtering such that pulses shorter than 50 nsec will not cause a reset to the logic. The nPOR2_OUT is configured be externally connected to the nPOR2_IN input pad under normal usage, thereby separating the analog circuitry from the digital circuitry.

The reset which is generated is stretched to at least 700 msec of active time after VDD goes above the programmable threshold to assure that the crystal oscillator is stable. The POR reset circuitry is to consume no more than 0.1 uA from the VDD supply for time greater than 5 seconds after power up, and no more than 0.1 uA from VBAT supply for time greater than 5 seconds after power up. The register that stores the POR threshold value is powered from the VDD power plane.

Sensor Interface Electronics

Figure 43:
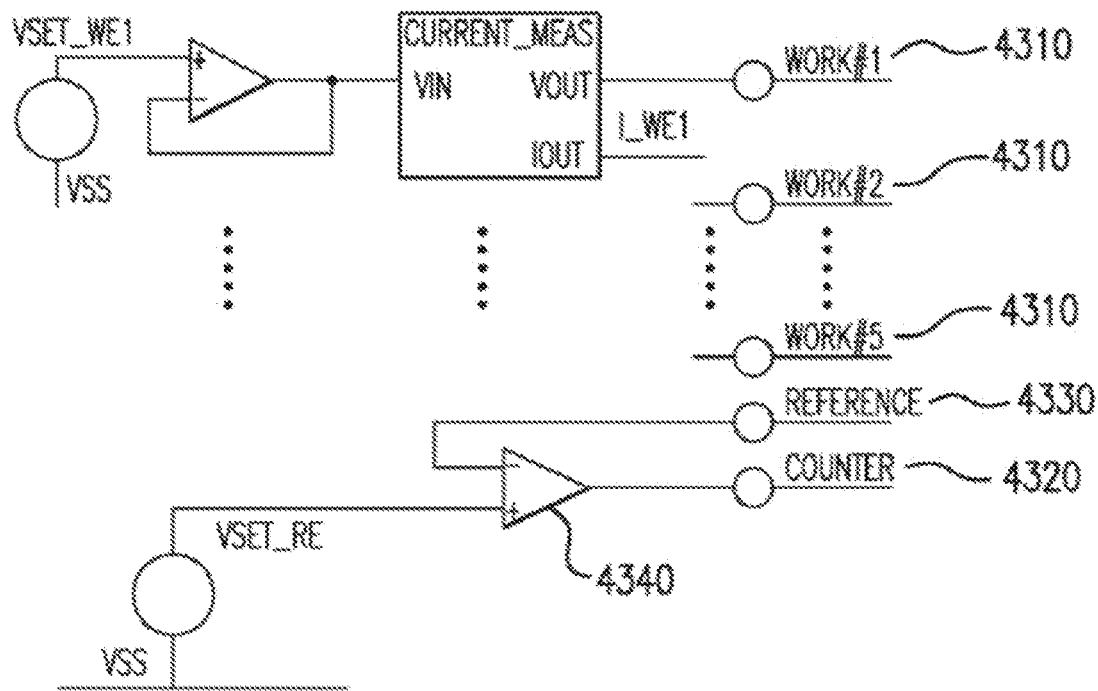
FIG. 43 shows a potentiostat configuration for a sensor with redundant working electrodes in accordance with embodiments of the invention.

In an embodiment of the invention, the sensor circuitry supports up to five sensor WORK electrodes (4310) in any combination of peroxide or oxygen sensors, although, in additional embodiments, a larger number of such electrodes may also be accommodated. While the peroxide sensor WORK electrodes source current, the oxygen sensor WORK electrodes sink current. For the instant embodiment, the sensors can be configured in the potentiostat configuration as shown in FIG. 43.

The sensor electronics have programmable power controls for each electrode interface circuit to minimize current drain by turning off current to unused sensor electronics. The sensor electronics also include electronics to drive a COUNTER electrode 4320 that uses feedback from a RE (reference) electrode 4330. The current to this circuitry may be programmed off when not in use to conserve power. The interface electronics include a multiplexer 4250 so that the COUNTER and RE electrodes may be connected to any of the (redundant) WORK electrodes.

The ASIC is configured to provide the following Sensor Interfaces: (i) RE: Reference electrode, which establishes a reference potential of the solution for the electronics for setting the WORK voltages; (ii) WORK1-WORK5: Working sensor electrodes where desired reduction/oxidation (redox) reactions take place; and (iii) COUNTER: Output from this pad maintains a known voltage on the RE electrode relative to the system VSS. In this embodiment of the invention, the ASIC is configured so as to be able to individually set the WORK voltages for up to 5 WORK electrodes with a resolution and accuracy of better than or equal to 5 mV.

The WORK voltage(s) are programmable between at least 0 and 1.22V relative to VSSA in the oxygen mode. In the peroxide mode, the WORK voltage(s) are programmable between at least 0.6 volt and 2.054 volts relative to VSSA. If the VDDA is less than 2.15V, the WORK voltage is operational to VDDA −0.1V. The ASIC includes current measuring circuits to measure the WORK electrode currents in the peroxide sensor mode. This may be implemented, e.g., with current-to-voltage or current-to-frequency converters, which may have the following specifications: (i) Current Range: 0-300 nA; (ii) Voltage output range: Same as WORK electrode in peroxide/oxygen mode; (iii) Output offset voltage: ±5 mV max; and (iv) Uncalibrated resolution: ±0.25 nA.

Current Measurement Accuracy after applying a calibration factor to the gain and assuming an acquisition time of 10 seconds or less is:

5 pA–1 nA: ±3%±20 pA 1 nA–10 nA: ±3%±20 pA 10 nA–300 nA: ±3%±0.2 nA

For current-to-frequency converters (ItoFs) only, the frequency range may be between 0 Hz and 50 kHz. The current converters must operate in the specified voltage range relative to VSS of WORK electrodes in the peroxide mode. Here, the current drain is less than 2 uA from a 2.5V supply with WORK electrode current less than 10 nA per converter including digital-to-analog (DAC) current.

The current converters can be enabled or disabled by software control. When disabled, the WORK electrode will exhibit a very high impedance value, i.e., greater than 100 Mohm. Again, for ItoFs only, the output of the I-to-F converters will go to 32-bit counters, which can be read, written to, and cleared by the microprocessor and test logic. During a counter read, clocking of the counter is suspended to ensure an accurate read.

In embodiments of the invention, the ASIC also includes current measuring circuits to measure the WORK electrode currents in the oxygen sensor mode. The circuit may be implemented as a current-to-voltage or a current-to-frequency converter, and a programmable bit may be used to configure the current converters to operate in the oxygen mode. As before, the current converters must operate in the specified voltage range of the WORK electrodes relative to VSS in the oxygen mode. Here, again, the current range is 3.7 pA-300 nA, the voltage output range is the same as WORK electrode in oxygen mode, the output offset voltage is ±5 mV max, and the uncalibrated resolution is 3.7 pA±2 pA.

Current Measurement Accuracy after applying a calibration factor to the gain and assuming an acquisition time of 10 seconds or less is:

5 pA–1 nA: ±3%±20 pA 1 nA–10 nA: ±3%±20 pA 10 nA–300 nA: ±3%±0.2 nA

For current-to-frequency converters (ItoFs) only, the frequency range may be between 0 Hz and 50 kHz, and the current drain is less than 2 uA from a 2.5V supply with WORK electrode current less than 10 nA per converter, including DAC current. The current converters can be enabled or disabled by software control. When disabled, the WORK electrode will exhibit a very high impedance value, i.e., greater than 100 Mohm. Also, for ItoFs only, the output of the I-to-F converters will go to 32-bit counters, which can be read, written to, and cleared by the microprocessor and test logic. During a counter read, clocking of the counter is suspended to ensure an accurate read.

In embodiments of the invention, the Reference electrode (RE) 4330 has an input bias current of less than 0.05 nA at 40° C. The COUNTER electrode adjusts its output to maintain a desired voltage on the RE electrode. This is accomplished with an amplifier 4340 whose output to the COUNTER electrode 4320 attempts to minimize the difference between the actual RE electrode voltage and the target RE voltage, the latter being set by a DAC.

The RE set voltage is programmable between at least 0 and 1.80V, and the common mode input range of the COUNTER amplifier includes at least 0.20 to (VDD −0.20) V. A register bit may be used to select the common mode input range, if necessary, and to provide for programming the mode of operation of the COUNTER. The WORK voltage is set with a resolution and accuracy of better than or equal to 5 mV. It is noted that, in the normal mode, the COUNTER voltage seeks a level that maintains the RE voltage to the programmed RE target value. In the force counter mode, however, the COUNTER electrode voltage is forced to the programmed RE target voltage.

Figure 44:
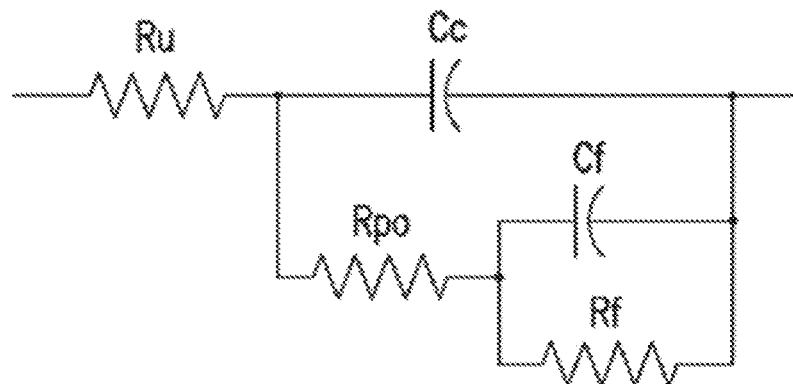
FIG. 44 shows an equivalent AC inter-electrode circuit for a sensor with the potentiostat configuration shown in FIG. 43.

All electrode driving circuits are configured to be able to drive the electrode to electrode load and be free from oscillation for any use scenario. FIG. 44 shows the equivalent ac inter-electrode circuit according to the embodiment of the invention with the potentiostat configuration as shown in FIG. 43. The equivalent circuit shown in FIG. 44 may be between any of the electrodes, i.e., WORK1-WORK5, COUNTER and RE, with value ranges as follows for the respective circuit components:

$Ru$=[200-5k] Ohms $Cc$=[10-2000] pF $Rpo$=[1-20] kOhms $Rf$=[200-2000] kOhms $Cf$=[2-30] uF During initialization, the drive current for WORK electrodes and the COUNTER electrode need to supply higher currents than for the normal potentiostat operation described previously. As such, programmable register bits may be used to program the electrode drive circuits to a higher power state if necessary for extra drive. It is important to achieve low power operation in the normal potentiostat mode, where the electrode currents are typically less than 300 nA.

In preferred embodiments, during initialization, the WORK1 through WORK5 electrodes are programmable in steps equal to, or less than, 5 mV from 0 to VDD volts, and their drive or sink current output capability is a minimum of 20 uA, from 0.20V to (VDD −0.20V). Also, during initialization, the ASIC is generally configured to be able to measure the current of one WORK electrode up to 20 uA with an accuracy of ±2%±40 nA of the measurement value. Moreover, during initialization, the RE set voltage is programmable as described previously, the COUNTER DRIVE CIRCUIT output must be able to source or sink 50 uA minimum with the COUNTER electrode from 0.20V to (VDD −0.20V), and the supply current (VDD and VDDA) to the initialization circuitry is required to be less than 50 uA in excess of any output current sourced.

Current Calibrator

In embodiments of the invention, the ASIC has a current reference that can be steered to any WORK electrode for the purpose of calibration. In this regard, the calibrator includes a programmable bit that causes the current output to sink current or source current. The programmable currents include at least 10 nA, 100 nA, and 300 nA, with an accuracy of better than ±1%±1 nA, assuming a 0-tolerance external precision resistor. The calibrator uses a 1 MegOhm precision resistor connected to the pad, TP_RES (4260), for a reference resistance. In addition, the current reference can be steered to the COUNTER or RE electrodes for the purpose of initialization and/or sensor status. A constant current may be applied to the COUNTER or the RE electrodes and the electrode voltage may be measured with the ADC.

High Speed RC Oscillator

With reference back to FIG. 42, the ASIC further includes a high-speed RC oscillator 4262 which supplies the analog-to-digital converter (ADC) 4264, the ADC sequencer 4266, and other digital functions requiring a higher speed clock than 32 kHz. The high-speed RC oscillator is phased locked to the 32 kHz clock (32.768 kHz) to give an output frequency programmable from 524.3 kHz to 1048 kHz. In addition, the high-speed RC oscillator has a duty cycle of 50%±10%, a phase jitter of less than 0.5% rms, a current of less than 10 uA, and a frequency that is stable through the VDD operating range (voltage range of 1.6 to 2.5V). The default of the high-speed RC oscillator is "off" (i.e., disabled), in which case the current draw is less than 10 nA. However, the ASIC has a programmable bit to enable the High-Speed RC oscillator.

Analog to Digital Converter

The ASIC includes a 12-bit ADC (4264) with the following characteristics: (i) capability to effect a conversion in less than 1.5 msec with running from a 32 kHz clock; (ii) ability to perform faster conversions when clocked from the high speed RC oscillator; (iii) have at least 10 bits of accuracy (12 bit±4 counts); (iv) have a reference voltage input of 1.220V, with a temperature sensitivity of less than 0.2 mV/° C. from 20° C. to 40° C.; (v) full scale input ranges of 0 to 1.22V, 0 to 1.774V, 0 to 2.44V, and 0-VDDA, wherein the 1.774 and 2.44V ranges have programmable bits to reduce the conversion range to lower values to accommodate lower VDDA voltages; (vi) have current consumption of less than 50 uA from its power supply; (vi) have a converter capable of operating from the 32 kHz clock or the High Speed RC clock; (vii) have a DNL of less than 1 LSB; and (viii) issue an interrupt at the end of a conversion.

As shown in FIGS. 42A and 42B, the ASIC has an analog multiplexer 4268 at the input of the ADC 4264, both of which are controllable by software. In a preferred embodiment, at least the following signals are connected to the multiplexer:

(i) VDD—Core Voltage and regulator output
(ii) VBAT—Battery source
(iii) VDDA—Analog supply
(iv) RE—Reference Electrode of Sensor
(v) COUNTER—Counter Electrode of Sensor
(vi) WORK1-WORK5—Working Electrodes of Sensor
(vii) Temperature sensor
(viii) At least two external pin analog signal inputs
(ix) EIS integrator outputs
(x) I to V current converter output.

The ASIC is configured such that the loading of the ADC will not exceed±0.01 nA for the inputs COUNTER, RE, WORK1-WORK5, the temperature sensor, and any other input that would be adversely affected by loading. The multiplexer includes a divider for any inputs that have higher voltage than the input voltage range of the ADC, and a buffer amplifier that will decrease the input resistance of the divided inputs to less than 1 nA for load sensitive inputs. The buffer amplifier, in turn, has a common mode input range from at least 0.8V to VDDA voltage, and an offset less than 3 mV from the input range from 0.8V to VDDA −0.1V.

In a preferred embodiment, the ASIC has a mode where the ADC measurements are taken in a programmed sequence. Thus, the ASIC includes a programmable sequencer 4266 that supervises the measurement of up to 8 input sources for ADC measurements with the following programmable parameters:

(i) ADC MUX input
(ii) ADC range
(iii) Delay time before measurement, wherein the delays are programmable from 0 to 62 msec in 0.488 msec steps
(iv) Number of measurements for each input from 0 to 255
(v) Number of cycles of measurements: 0-255, wherein the cycle of measurements refers to repeating the sequence of up to 8 input measurements multiple times (e.g., as an outer loop in a program)
(vi) Delay between cycles of measurement, wherein the delays are programmable from 0 to 62 msec in 0.488 msec steps.

The sequencer 4266 is configured to start upon receiving an auto-measure start command, and the measurements may be stored in the ASIC for retrieval over the SPI interface. It is noted that the sequencer time base is programmable between the 32 kHz clock and the High-Speed RC oscillator 4262.

Sensor Diagnostics

As was previously described in detail, embodiments of the invention are directed to use of impedance and impedance-related parameters in, e.g., sensor diagnostic procedures and Isig/SG fusion algorithms. To that end, in preferred embodiments, the ASIC described herein has the capability of measuring the impedance magnitude and phase angle of any WORK sensor electrode to the RE and COUNTER electrode when in the potentiostat configuration. This is done, e.g., by measuring the amplitude and phase of the current waveform in response to a sine-like waveform superimposed on the WORK electrode voltage. See, e.g., Diagnostic Circuitry 4255 in FIG. 42B.

The ASIC has the capability of measuring the resistive and capacitive components of any electrode to any electrode via, e.g., the Electrode Multiplexer 4250. It is noted that such measurements may interfere with the sensor equilibrium and may require settling time or sensor initialization to record stable electrode currents. As discussed previously, although the ASIC may be used for impedance measurements across a wide spectrum of frequencies, for purposes of the embodiments of the invention, a relatively narrower frequency range may be used. Specifically, the ASIC's sine wave measurement capability may include test frequencies from about 0.10 Hz to about 8192 Hz. In making such measurements, the minimum frequency resolution in accordance with an embodiment of the invention may be limited as shown in Table 2 below:

TABLE 2

| Frequency [Hz] | Min step [Hz] |
| --- | --- |
| .1 to 15 | <1 |
| 16 to 31 | 1 |
| 32 to 63 | 2 |
| 64 to 127 | 4 |
| 128 to 255 | 8 |
| 256 to 511 | 16 |
| 512 to 1023 | 32 |
| 1024 to 2047 | 64 |
| 2048 to 4095 | 128 |
| 4096 to 8192 | 256 |

The sinewave amplitude is programmable from at least 10 mVp-p to 50 mVp-p in 5 mV steps, and from 60 mVp-p to 100 mVp-p in 10 mV steps. In a preferred embodiment, the amplitude accuracy is better than ±5% or ±5 mV, whichever is larger. In addition, the ASIC may measure the electrode impedance with accuracies specified in Table 3 below:

TABLE 3

| Frequency Range | Impedance Range | Impedance Measurement Accuracy | Phase Measurement Accuracy |
|---|---|---|---|
| .1-10 Hz | 2k to 1 MegΩ | ±5% | ±0.5° |
| 10-100 Hz | 1k to 100 kΩ | ±5% | ±0.5° |
| 100 to 8000 Hz | .5k to 201 kΩ | ±5% | ±1.0° |

In an embodiment of the invention, the ASIC can measure the input waveform phase relative to a time base, which can be used in the impedance calculations to increase the accuracy. The ASIC may also have on-chip resistors to calibrate the above electrode impedance circuit. The on-chip resistors, in turn, may be calibrated by comparing them to the known 1 MegOhm off-chip precision resistor.

Data sampling of the waveforms may also be used to determine the impedances. The data may be transmitted to an external microprocessor with the serial peripheral interface (SPI) for calculation and processing. The converted current data is sufficiently buffered to be able to transfer 2000 ADC conversions of data to an external device through the SPI interface without losing data. This assumes a latency time of 8 msec maximum for servicing a data transfer request interrupt.

In embodiments of the invention, rather than, or in addition to, measuring electrode impedance with a sine wave, the ASIC may measure electrode current with a step input. Here, the ASIC can supply programmable amplitude steps from 10 to 200 mV with better than 5 mV resolution to an electrode and sample (measure) the resulting current waveform. The duration of the sampling may be programmable to at least 2 seconds in 0.25 second steps, and the sampling interval for measuring current may include at least five programmable binary weighted steps approximately 0.5 msec to 8 msec.

The resolution of the electrode voltage samples is smaller than 1 mV with a range up to ±0.25 volt. This measurement can be with respect to a suitable stable voltage in order to reduce the required dynamic range of the data conversion. Similarly, the resolution of the electrode current samples is smaller than 0.04 uA with a range up to 20 uA. The current measurements can be unipolar if the measurement polarity is programmable.

In embodiments of the invention, the current measurement may use an I-to-V converter. Moreover, the ASIC may have on-chip resistors to calibrate the current measurement. The on-chip resistors, in turn, may be calibrated by comparing them to the known 1 MegOhm off-chip precision resistor. The current measurement sample accuracy is better than ±3% or ±10 nA, whichever is greater. As before, the converted current data is sufficiently buffered to be able to transfer 2000 ADC conversions of data to an external device through the SPI interface without losing data. This assumes a latency time of 8 msec maximum for servicing a data transfer request interrupt.

Calibration Voltage

The ASIC includes a precision voltage reference to calibrate the ADC. The output voltage is 1.000V±3% with less than ±1.5% variation in production, and stability is better than ±3 mV over a temperature range of 20° C. to 40° C. This precision calibration voltage may be calibrated, via the on-chip ADC, by comparing it to an external precision voltage during manufacture. In manufacturing, a calibration factor may be stored in a system non-volatile memory (not on this ASIC) to achieve higher accuracy.

The current drain of the calibration voltage circuit is preferably less than 25 uA. Moreover, the calibration voltage circuit is able to power down to less than 10 nA to conserve battery power when not in use.

Temperature Sensor

The ASIC has a temperature transducer having a sensitivity between 9 and 11 mV per degree Celsius between the range −10° C. to 60° C. The output voltage of the Temperature Sensor is such that the ADC can measure the temperature-related voltage with the 0 to 1.22V ADC input range. The current drain of the Temperature Sensor is preferably less than 25 uA, and the Temperature Sensor can power down to less than 10 nA to conserve battery power when not in use.

VDD Voltage Regulator

The ASIC has a VDD voltage regulator with the following characteristics:
 (i) Minimum input Voltage Range: 2.0V-4.5V.
 (ii) Minimum output Voltage: 1.6-2.5V±5%, with a default of 2.0V.
 (iii) Dropout voltage: Vin−Vout<0.15V at Iload=100 uA, Vin=2.0V.
 (iv) The output voltage is programmable, with an accuracy within 2% of the indicated value per Table 4 below:

TABLE 4

| Hex | vout | hex | vout |
|---|---|---|---|
| 0 | 1.427 | 10 | 1.964 |
| 1 | 1.460 | 11 | 1.998 |
| 2 | 1.494 | 12 | 2.032 |
| 3 | 1.528 | 13 | 2.065 |
| 4 | 1.561 | 14 | 2.099 |
| 5 | 1.595 | 15 | 2.132 |
| 6 | 1.628 | 16 | 2.166 |
| 7 | 1.662 | 17 | 2.200 |
| 8 | 1.696 | 18 | 2.233 |
| 9 | 1.729 | 19 | 2.267 |
| A | 1.763 | 1A | 2.300 |
| B | 1.796 | 1B | 2.334 |
| C | 1.830 | 1C | 2.368 |
| D | 1.864 | 1D | 2.401 |
| E | 1.897 | 1E | 2.435 |
| F | 1.931 | 1F | 2.468 |

(v) The regulator can supply output of 1 mA at 2.5V with an input voltage of 2.8V.
 (vi) The regulator also has input and output pads that may be open circuited if an external regulator is used. The current draw of the regulator circuit is preferably less than 100 nA in this non-operational mode.
 (vii) The change of output voltage from a load of 10 uA to 1 mA is preferably less than 25 mV.
 (viii) Current Drain excluding output current @ 1 mA load is less than 100 uA from source.
 (ix) Current Drain excluding output current @ 0.1 mA load is less than 10 uA from source.
 (x) Current Drain excluding output current @ 10 uA load is less than 1 uA from source.

General Purpose Comparators

The ASIC includes at least two comparators 4270, 4271 powered from VDDA. The comparators use 1.22V as a reference to generate the threshold. The output of the comparators can be read by the processor and will create a maskable interrupt on the rising or falling edge determined by configuration registers.

The comparators have power control to reduce power when not in use, and the current supply is less than 50 nA per comparator. The response time of the comparator is preferably less than 50 usec for a 20 mV overdrive signal, and the offset voltage is less than ±8 mV.

The comparators also have programmable hysteresis, wherein the hysteresis options include threshold=1.22V+ Vhyst on a rising input, threshold=1.22−Vhyst on a falling input, or no hysteresis (Vhyst=25±10 mV). The output from either comparator is available to any GPIO on any power plane. (See GPIO section).

Sensor Connection Sensing Circuitry on RE

An analog switched capacitor circuit monitors the impedance of the RE connection to determine if the sensor is connected. Specifically, a capacitor of about 20 pF is switched at a frequency of 16 Hz driven by an inverter with an output swing from VSS to VDD. Comparators will sense the voltage swing on the RE pad and, if the swing is less than a threshold, the comparator output will indicate a connection. The above-mentioned comparisons are made on both transitions of the pulse. A swing below threshold on both transitions is required to indicate a connect, and a comparison indicating high swing on either phase will indicate a disconnect. The connect signal/disconnect signal is debounced such that a transition of its state requires a stable indication to the new state for at least ½ second.

The circuit has six thresholds defined by the following resistances in parallel with a 20 pF capacitor: 500 k, 1 Meg, 2 MEG, 4 Meg, 8 Meg, and 16 Meg ohms. This parallel equivalent circuit is between the RE pad and a virtual ground that can be at any voltage between the power rails. The threshold accuracy is better than ±30%.

The output of the Sensor Connect sensing circuitry is able to programmably generate an interrupt or processor startup if a sensor is connected or disconnected. This circuit is active whenever the nPOR2_IN is high and the VDD and VDDA are present. The current drain for this circuit is less than 100 nA average.

WAKEUP Pad

The WAKEUP circuitry is powered by the VDD supply, with an input having a range from 0V to VBAT. The WAKEUP pad 4272 has a weak pulldown of 80±40 nA. This current can be derived from an output of the BIAS_GEN 4220. The average current consumed by the circuit is less than 50 nA with 0 v input.

The WAKEUP input has a rising input voltage threshold, Vih, of 1.22±0.1 V, and the falling input threshold is −25 mV±12 mV that of the rising threshold. In preferred embodiments, the circuit associated with the WAKEUP input draws no more than 100 nA for any input whose value is from −0.2 to VBAT voltage (this current excludes the input pulldown current). The WAKEUP pad is debounced for at least ½ second.

The output of the WAKEUP circuit is able to programmably generate an interrupt or processor startup if the WAKEUP pad changes state. (See the Event Handler section). It is important to note that the WAKEUP pad circuitry is configured to assume a low current, <1 nA, if the Battery Protection Circuit indicates a low battery state.

UART Wakeup

The ASIC is configured to monitor the nRX_EXT pad 4274. If the nRX_EXT level is continuously high (UART BREAK) for longer than ½ second, a UART WAKEUP event will be generated. The due to sampling the UART WAKEUP event could be generated with a continuous high as short as ¼ second. The UART WAKEUP event can programmably generate an interrupt, WAKEUP and/or a microprocessor reset (nRESET_OD). (See the Event Handler section).

In preferred embodiments, the circuit associated with the UART WAKEUP input draws no more than 100 nA, and the UART WAKEUP pad circuitry is configured to assume a low current, <1 nA, if the Battery Protection circuitry indicates a Battery Low state. The UART Wakeup input has a rising input voltage threshold, Vih, of 1.22±0.1 V. The falling input threshold is −25 mV±12 mV that of the rising threshold.

Microprocessor Wakeup Control Signals

The ASIC is able to generate signals to help control the power management of a microprocessor. Specifically, the ASIC may generate the following signals:

(i) nSHUTDN-nSHUTDN may control the power enable of an off chip VDD regulator. The nSHUTDN pad is on the VBAT power rail. nSHUTDN shall be low if the Battery Protection circuitry indicates a Battery Low state, otherwise nSHUTDN shall be high.

(ii) VPAD_EN-VPAD_EN may control the power enable of an external regulator that supplies VPAD power. An internal signal that corresponds to this external signal ensures that inputs from the VPAD pads will not cause extra current due to floating inputs when the VPAD power is disabled. The VPAD_EN pad is an output on the VBAT power rail. The VPAD_EN signal is low if the Battery Protection signal indicates a low battery. The VPAD_EN signal may be set low by a software command that starts a timer; the terminal count of the timer forces VPAD_EN low. The following events may cause the VPAD_EN signal to go high if the Battery Protection signal indicates a good battery (see Event Handler for more details): nPOR2_IN transitioning from low to high; SW/Timer (programmable); WAKEUP transition; low to high, and/or high to low, (programmable); Sensor Connect transition; low to high, and/or high to low, (programmable); UART Break; and RTC Time Event (programmable).

(iii) UP_WAKEUP-UP_WAKEUP may connect to a microprocessor wakeup pad. It is intended to wakeup the microprocessor from a sleep mode or similar power down mode. The UP_WAKEUP pad is an output on the VPAD power rail. The UP_WAKEUP signal can be programmed to be active low, active high or a pulse. The UP_WAKEUP signal may be set low by a software command that starts a timer; the terminal count of the timer forces UP_WAKEUP low. The following events may cause the UP_WAKEUP signal to go high if the Battery Protection signal indicates a good battery (see Event Handler for more details): nPOR2_IN transitioning from low to high; SW/Timer (programmable); WAKEUP transition; low to high, and/or high to low, (programmable); Sensor Connect transition; low to high, and/or high to low, (programmable); UART Break; and RTC Time Event (programmable). The WAKEUP signal may be delayed by a programmable amount. If WAKEUP is programmed to be a pulse, the pulse width may be programmed.

(iv) CLK_32 KHZ-CLK_32 KHZ pad may connect to a microprocessor to supply a low speed clock. The clock is on-off programmable and programmably turns on to wakeup events. The CLK_32 KHZ pad is an output on the VPAD power rail. The CLK_32 KHZ signal is low if the Battery Protection signal indicates a low battery. The CLK_32 KHZ output may be programmed off by a programmable bit. The default is ON. The CLK_32 KHZ signal may be disabled by a software command that starts a timer; The terminal count of the timer forces CLK_32 KHZ low. The following events may cause the CLK_32 KHZ signal to be enabled if the Battery Protection signal indicates a good battery (see Event Handler for more details): nPOR2_IN transitioning from low to high; SW/Timer (programmable); WAKEUP transition; low to high, and/or high to low, (programmable); Sensor Connect transition; low to high, and/or high to low, (programmable); UART Break; RTC Time Event (programmable); and Detection of low battery by Battery Protection Circuit.

(v) nRESET_OD-nRESET_OD may connect to a microprocessor to cause a microprocessor reset. The nRESET_OD is programmable to wakeup events. The nRESET_OD pad is an output on the VPAD power rail. This pad is open drain (nfet output). The nRESET_OD signal is low if the Battery Protection signal indicates a low battery. The nRESET_OD active time is programmable from 1 to 200 msec. The default is 200 ms. The following events may cause the nRESET_OD signal to be asserted low (see Event Handler for more details): nPOR2_IN; SW/Timer (programmable); WAKEUP transition; low to high, and/or high to low, (programmable); Sensor Connect transition; low to high, and/or high to low, (programmable); UART Break; and RTC Time Event (programmable).

(vi) UP_INT-UP_INT may connect to a microprocessor to communicate interrupts. The UP_INT is programmable to wakeup events. The UP_INT pad is an output on the VPAD power rail. The UP_INT signal is low if the Battery Protection signal indicates a low battery. The UP_INT signal may be set high by a software command that starts a timer; the terminal count of the timer forces UP_INT high. The following events may cause the UP_INT signal to be asserted high if the Battery Protection signal indicates a good battery (see Event Handler for more details): SW/Timer (programmable); WAKEUP transition; low to high, and/or high to low, (programmable); Sensor Connect transition; low to high and/or high to low, (programmable); UART Break; RTC Time Event (programmable); Detection of low battery by Battery Protection Circuit; and any of the ASIC interrupts when unmasked.

The ASIC has GPIO1 and GPIO0 pads able to act as boot mode control for a microprocessor. A POR2 event will reset a 2 bit counter whose bits map to GPIO1 & GPIO0 (MSB, LSB respectively). A rising edge of UART break increments the counter by one, wherein the counter counts by modulo 4, and goes to zero if it is incremented in state 11. The boot mode counter is pre-settable via SPI.

Event Handler/Watchdog

The ASIC incorporates an event handler to define the responses to events, including changes in system states and input signals. Events include all sources of interrupts (e.g. UART_BRK, WAKE_UP, Sensor Connect, etc. . . . ). The event handler responses to stimuli are programmable by the software through the SPI interface. Some responses, however, may be hardwired (non-programmable).

The event handler actions include enable/disable VPAD_EN, enable/disable CLK_32 KHZ, assert nRESET_OD, assert UP_WAKEUP, and assert UP_INT. The Event Watchdog Timer 1 through Timer 5 are individually programmable in 250 msec increments from 250 msec to 16,384 seconds. The timeouts for Event Watchdog timers 6 through 8 are hardcoded. The timeout for Timer6 and Timer7 are 1 minute; timeout for Timer8 is 5 minutes.

The ASIC also has a watchdog function to monitor the microprocessor's responses when triggered by an event. The event watchdog is activated when the microprocessor fails to acknowledge the event induced activities. The event watchdog, once activated, performs a programmable sequence of actions, Event Watchdog Timer 1-5, and followed by a hard-wired sequence of actions, Event Watchdog Timer 6-8, to re-gain the response of the microprocessor. The sequence of actions includes interrupt, reset, wake up, assert 32 KHz clock, power down and power up to the microprocessor.

During the sequences of actions, if the microprocessor regains its ability to acknowledge the activities that had been recorded, the event watchdog is reset. If the ASIC fails to obtain an acknowledgement from the microprocessor, the event watchdog powers down the microprocessor in a condition that will allow UART_BRK to reboot the microprocessor and it will activate the alarm. When activated, the alarm condition generates a square wave with a frequency of approximately 1 kHz on the pad ALARM with a programmable repeating pattern. The programmable pattern has two programmable sequences with programmable burst on and off times. The alarm has another programmable pattern that may be programmed via the SPI port. It will have two programmable sequences with programmable burst on and off times.

Digital to Analog (D/A)

In a preferred embodiment, the ASIC has two 8 bit D/A converters 4276, 4278 with the following characteristics:
 (i) The D/A settles in less than 1 msec with less than 50 pF load.
 (ii) The D/A has at least 8 bits of accuracy.
 (iii) The output range is programmable to either 0 to 1.22V or 0 to VDDA.
 (iv) Temperature sensitivity of the D/A voltage reference is less than 1 mV/° C.
 (v) The DNL is less than 1 LSB.
 (vi) Current consumed by the D/A is less than 2 uA from the VDDA supply.
 (vii) Each D/A has an output 1 to a pad.
 (viii) The D/A outputs are high impedance. Loading current must be less than 1 nA.
 (ix) The D/A pads can be programmed to output a digital signal from a register. The output swing is from VSSA to VDDA.

Charger/Data Downloader Interface

The TX_EXT_OD 4280 is an open drain output whose input is the signal on the TX_UP input pad. This will allow the TX_EXT_OD pad to be open in the UART idle condition. The TX_EXT_OD pad has a comparator monitoring its voltage. If the voltage is above the comparator threshold voltage for a debounce period (¼ second), the output, nBAT_CHRG_EN (4281), will go low. This comparator and other associated circuitry with this function are on the VBAT and/or VDDBU planes.

The circuitry associated with this function must allow lows on TX_EXT_OD pad that result from normal communication with an external device without disabling the assertion of nBAT_CHRG_EN. If POR1 is active, nBAT_CHRG_EN will be high (not asserted). The comparator's threshold voltage is between 0.50V and 1.2V. The comparator will have hysteresis; The falling threshold is approximately 25 mV lower than the rising threshold.

The nRX_EXT pad inverts the signal on this pad and output it to RX_UP. In this way, the nRX_EXT signal will idle low. The nRX_EXT must accept inputs up to VBAT voltage. The nRX_EXT threshold is 1.22V±3%. The output of this comparator will be available over the SPI bus for a microprocessor to read.

The nRX_EXT pad also incorporates a means to programmably source a current, which will be 80±30 nA, with the maximum voltage being VBAT. The ASIC layout has mask programmable options to adjust this current from 30 nA to 200 nA in less than 50 nA steps with a minimal number of mask layer changes. A programmable bit will be available to block the UART break detection and force the RX_UP high. In normal operation, this bit will be set high before enabling the current sourcing to nRX_EXT and then set low after the current sourcing is disabled to ensure that no glitches are generated on RX_UP or that a UART break event is generated. Note to implement a wet connector detector, while the current source into nRX_EXT is active, an RX comparator output indicating a low input voltage would indicate leakage current. The ASIC includes a pull-down resistor approximately 100 k ohms on the nRX_EXT pad. This pulldown will be disconnected when the current source is active.

Sensor Connect Switch

The ASIC shall have a pad, SEN_CONN_SW (4282), which is able to detect a low resistance to VSS (4284). The SEN_CONN_SW sources a current from 5 to 25 uA with SEN_CONN_SW=0V and has a maximum open circuit voltage of 0.4V. The ASIC layout has mask programmable options to adjust this current from 1 uA to 20 uA in less than 5 uA steps with a minimal number of mask layer changes. The SEN_CONN_SW has associated circuitry that detects the presence of a resistance between SEN_CONN_SW and VSSA (4234) whose threshold is between 2 k and 15 k ohms. The average current drain of this circuit is 50 nA max. Sampling must be used to achieve this low current.

Oscillator Calibration Circuit

The ASIC has counters whose inputs can be steered to internal or external clock sources. One counter generates a programmable gating interval for the other counter. The gating intervals include 1 to 15 seconds from the 32 kHz oscillator. The clocks that can be steered to either counter are 32 kHz, RC oscillator, High Speed RC oscillator, and an input from any GPIO pad.

Oscillator Bypassing

The ASIC can substitute external clocks for each of the oscillators' outputs. The ASIC has a register that can be written only when a specific TEST_MODE is asserted. This register has bits to enable the external input for the RC Oscillator, and may be shared with other analog test control signals. However, this register will not allow any oscillator bypass bits to be active if the TEST_MODE is not active.

The ASIC also has an input pad for an external clock to bypass the RC Oscillator. The pad, GPIO_VBAT, is on the VBAT power plane. The ASIC further includes a bypass enable pad for the 32 KHZ oscillator, OSC32K_BYPASS. When high, the 32 KHZ oscillator output is supplied by driving the OSC32 KHZ_IN pad. It is noted that, normally, the OSC32 KHZ_IN pad is connected to a crystal.

The ASIC has inputs for an external clock to bypass the HS_RC_OSC. The bypass is enabled by a programmable register bit. The HS_RC_OSC may be supplied programmably by either the GPIO on the VDD plane or by GPIOs on the VPAD plane.

SPI Slave Port

The SPI slave port includes an interface consisting of a chip select input (SPI_nCS) 4289, a clock input (SPI_CK) 4286, a serial data input (SPI_MOSI) 4287, and a serial data output (SPI_MISO) 4288. The chip select input (SPI_nCS) is an active low input, asserted by an off-chip SPI master to initiate and qualify an SPI transaction. When SPI_nCS is asserted low, the SPI slave port configures itself as a SPI slave and performs data transactions based on the clock input (SPI_CK). When SPI_nCS is inactive, the SPI slave port resets itself and remains in reset mode. As this SPI interface supports block transfers, the master should keep SPI_nCS low until the end of a transfer.

The SPI clock input (SPI_CK) will always be asserted by the SPI master. The SPI slave port latches the incoming data on the SPI_MOSI input using the rising edge of SPI_CK and driving the outgoing data on the SPI_MISO output using the falling edge of SPI_CK. The serial data input (SPI_MOSI) is used to transfer data from the SPI master to the SPI slave. All data bits are asserted following the falling edge of SPI_CK. The serial data output (SPI_MISO) is used to transfer data from the SPI slave to the SPI master. All data bits are asserted following the falling edge of SPI_CK.

SPI_nCS, SPI_CK and SPI_MOSI are always driven by the SPI master, unless the SPI master is powered down. If VPAD_EN is low, these inputs are conditioned so that the current drain associated with these inputs is less than 10 nA and the SPI circuitry is held reset or inactive. SPI_MISO is only driven by the SPI slave port when SPI_nCS is active, otherwise, SPI_MISO is tri-stated.

The chip select (SPI_nCS) defines and frames the data transfer packet of an SPI data transaction. The data transfer packet consists of three parts. There is a 4-bit command section followed by a 12-bit address section, which is then followed by any number of 8-bit data bytes. The command bit 3 is used as the direction bit. A "1" indicates a write operation, and a "0" indicates a read operation. The combinations of command bit 2, 1 and 0 have the following definitions. Unused combinations are undefined.

(i) 0000: read data and increment address.
(ii) 0001: read data, no change to address
(iii) 0010: read data, decrement address
(iv) 1000: write data and increment address
(v) 1001: write data, no change to address
(vi) 1010: write data, decrement address
(vii) x011: Test Port Addressing The 12-bit address section defines the starting byte address. If SPI_nCS stays active after the first data byte, to indicate a multi-byte transfer, the address is incremented by one after each byte is transferred. Bit<11> of the address (of address<11:0>) indicates the highest address bit. The address wraps around after reaching the boundary.

Data is in the byte format, and a block transfer can be performed by extending SPI_nCS to allow all bytes to be transferred in one packet.

Microprocessor Interrupt

The ASIC has an output at the VPAD logic level, UP_INT, for the purpose of sending interrupts to a host microprocessor. The microprocessor interrupt module consists of an interrupt status register, an interrupt mask register, and a function to logically OR all interrupt statuses into one microprocessor interrupt. The interrupt is implemented to support both edge sensitive and level sensitive styles. The polarity of the interrupt is programmable. The default interrupt polarity is TBD.

In a preferred embodiment, all interrupt sources on the AFE ASIC will be recorded in the interrupt status register. Writing a "1" to the corresponding interrupt status bit clears the corresponding pending interrupt. All interrupt sources on the AFE ASIC are mask-able through the interrupt mask register. Writing a "1" to the corresponding interrupt mask bit enables the masking of the corresponding pending interrupt. Writing a "0" to the corresponding interrupt mask bit disables the masking of the corresponding interrupt. The default state of the interrupt mask register is TBD.

General Purpose Input/Outputs (GPIOs)/Parallel Test Port

In embodiments of the invention, the ASIC may have eight GPIOs that operate on VPAD level signals. The ASIC has one GPIO that operates on a VBAT level signal, and one GPIO that operates on a VDD level signal. All off the GPIOs have at least the following characteristics:
(i) Register bits control the selection and direction of each GPIO.
(ii) The ASIC has a means to configure the GPIOs as inputs that can be read over the SPI interface.
(iii) The ASIC has a means to configure the GPIOs as input to generate an interrupt.
(iv) The ASIC has a means to configure each GPIO as an output to be controlled by a register bit that can be written over the SPI interface.
(v) Programmably, the ASIC is able to output an input signal applied to GPIO_VBAT or GPIO_VDD to a GPIO (on the VPAD power plane). (Level shifting function).
(vi) The ASIC has a means to configure each GPIO as an input to the oscillator calibration circuit.
(vii) The ASIC has a means to configure each general-purpose comparator output to at least one GPIO on each power plane. The polarity of the comparator output is programmable by a programmable bit.
(viii) The GPIOs have microprocessor interrupt generating capability.
(ix) The GPIOs are programmable to open drain outputs.
(x) The GPIOs on the VPAD power plane are configurable to implement boot control of a microprocessor.

A Parallel Test Port shares the 8-bit GPIOs on the VPAD voltage plane. The test port will be used for observing register contents and various internal signals. The outputs of this port are controlled by the port configuration register in the normal mode. Writing 8'hFF to both GPIO_O1S_REG & GPIO_O2S_REG registers will steer the test port data on the GPIO outputs, while writing 8'h00 to the GPIO_ON_REG register will disable the test port data and enable the GPIO data onto the GPIO outputs.

Registers and pre-grouped internal signals can be observed over this test port by addressing the target register through the SPI slave port. The SPI packet has the command bits set to 4'b0011 followed by the 12-bit target register address. The parallel test port continues to display the content of the addressed register until the next Test Port Addressing command is received.

Analog Test Ports

The IC has a multiplexer feeding the pad, TP_ANAMUX (4290), which will give visibility to internal analog circuit nodes for testing. The IC also has a multiplexer feeding the pad, TP_RES (4260), which will give visibility to internal analog circuit nodes for testing. This pad will also accommodate a precision 1 meg resistor in usual application to perform various system calibrations.

Chip ID

The ASIC includes a 32-bit mask programmable ID. A microprocessor using the SPI interface will be able to read this ID. This ID is to be placed in the analog electronics block so that changing the ID does not require a chip reroute. The design should be such that only one metal or one contact mask change is required to change the ID.

Spare Test Outputs

The ASIC has 16 spare digital output signals that can be multiplexed to the 8-bit GPIO under commands sent over the SPI interface. These signals will be organized as two 8-bit bytes and will be connected to VSS if not used.

Digital Testing

The ASIC has a test mode controller that uses two input pins, TEST_CTL0 (4291) and TEST_CTL1 (4292). The test controller generates signals from the combination of the test control signals that have the following functionality (TEST_CTL<1:0>):
(i) 0 is normal operating mode;
(ii) 1 is Analog Test Mode;
(iii) 2 is Scan Mode;
(iv) 3 is Analog Test mode with the VDD_EN controlled by an input to GPIO_VBAT.

The test controller logic is split between the VDD and VDDBU power planes. During scan mode, testing LT_VBAT should be asserted high to condition the analog outputs to the digital logic. The ASIC has a scan chain implemented in as much digital logic as reasonably possible for fast digital testing.

Leakage Test Pin

The ASIC has a pin called LT_VBAT that, when high, will put all the analog blocks into an inactive mode so that only leakage currents will be drawn from the supplies. LT_VBAT causes all digital outputs from analog blocks to be in a stable high or low state as to not affect interface logic current drain. The LT_VBAT pad is on the VBAT plane with a pulldown with a resistance between 10 k and 40 k ohms.

Power Requirements

In embodiments of the invention, the ASIC includes a low power mode where, at a minimum, the microprocessor clock is off, the 32 kHz real time clock runs, and circuitry is active to detect a sensor connection, a change of level of the WAKE_UP pin, or a BREAK on the nRX_EXT input. This mode has a total current drain from VBAT (VDDBU), VDD, and VDDA of 4.0 uA maximum. When the Battery Protection Circuit detects a low battery (see Battery Protection Circuit description), the ASIC goes to a mode with only the VBAT and VDDBU power planes active. This is called Low Battery state. The VBAT current in this mode is less than 0.3 uA.

With the ASIC programmed to the potentiostat configuration with any one WORK electrode active in the H2O2 (peroxide) mode with its voltage set to 1.535V, the COUNTER amplifier on with the VSET RE set to 1.00V, a 20 MEG load resistor connected between WORK and the COUNTER, the COUNTER and RE connected together and assuming one WORK electrode current measurement per minute, the average current drain of all power supplies is less than 7 uA. The measured current after calibration should be 26.75 nA±3%. Enabling additional WORK electrodes increases the combined current drain by less than 2 uA with the WORK electrode current of 25 nA.

With the ASIC programmed to the potentiostat configuration with the diagnostic function enabled to measure the impedance of one of the WORK electrodes with respect to the COUNTER electrode, the ASIC is configured to meet the following:
(i) Test frequencies: 0.1, 0.2, 0.3, 0.5 Hz, 1.0, 2.0, 5.0, 10, 100, 1000 and 4000 Hz.
(ii) The measurement of the above frequencies is not to exceed 50 seconds.
(iii) The total charge supplied to the ASIC is less than 8 millicoulombs.

Environment

In preferred embodiments of the invention, the ASIC:
(i) Operates and meets all specifications in the commercial temperature range of 0 to 70° C.
(ii) Functionally operates between −20° C. and 80° C. but may do so with reduced accuracy.
(iii) Is expected to operate after being stored in a temperature range of −30 to 80° C.

(iv) Is expected to operate in the relative humidity range of 1% to 95%.

(v) ESD protection is greater than ±2 KV, Human Body Model on all pins when packaged in a TBD package, unless otherwise specified.

(vi) Is configured such that the WORK1-WORK5, COUNTER, RE, TX_EXT_OD, and nRX_EXT pads withstand greater than ±4 KV Human Body Model.

(vii) Is configured such that the leakage current of the WORK1-WORK5 and RE pads is less than 0.05 nA at 40° C.

In embodiments of the invention, the ASIC may be fabricated in 0.25-micron CMOS process, and backup data for the ASIC is on DVD disk, 916-TBD.

As described in detail hereinabove, the ASIC provides the necessary analog electronics to: (i) support multiple potentiostats and interface with multi-terminal glucose sensors based on either Oxygen or Peroxide; (ii) interface with a microcontroller so as to form a micropower sensor system; and (iii) implement EIS diagnostics based on measurement of EIS-based parameters. The measurement and calculation of EIS-based parameters will now be described in accordance with embodiments of the inventions herein.

As mentioned previously, the impedance at frequencies in the range from 0.1 Hz to 8 kHz can provide information as to the state of the sensor electrodes. The AFE IC circuitry incorporates circuitry to generate the measurement forcing signals and circuitry to make measurements used to calculate the impedances. The design considerations for this circuitry include current drain, accuracy, speed of measurement, the amount of processing required, and the amount of on time required by a control microprocessor.

In a preferred embodiment of the invention, the technique the AFE IC uses to measure the impedance of an electrode is to superimpose a sine wave voltage on the dc voltage driving an electrode and to measure the phase and amplitude of the resultant AC current. To generate the sine wave, the AFE IC incorporates a digitally-synthesized sine wave current. This digital technique is used because the frequency and phase can be precisely controlled by a crystal derived timebase and it can easily generate frequencies from DC up to 8 kHz. The sine wave current is impressed across a resistor in series with a voltage source in order to add the AC component to the electrode voltage. This voltage is the AC forcing voltage. It is then buffered by an amplifier that drives a selected sensor electrode.

The current driving the electrode contains the resultant AC current component from the forcing sine wave and is converted to a voltage. This voltage is then processed by multiplying it by a square wave that has a fixed phase relative to the synthesized sine wave. This multiplied voltage is then integrated. After the end of a programmable number of integration intervals—an interval being an integral number of ½ periods of the driving sine wave—the voltage is measured by the ADC. By calculations involving the values of the integrated voltages, the real and imaginary parts of the impedance can be obtained.

The advantage of using integrators for the impedance measurement is that the noise bandwidth of the measurement is reduced significantly with respect to merely sampling the waveforms. Also, the sampling time requirements are significantly reduced which relaxes the speed requirement of the ADC.

Figure 45:
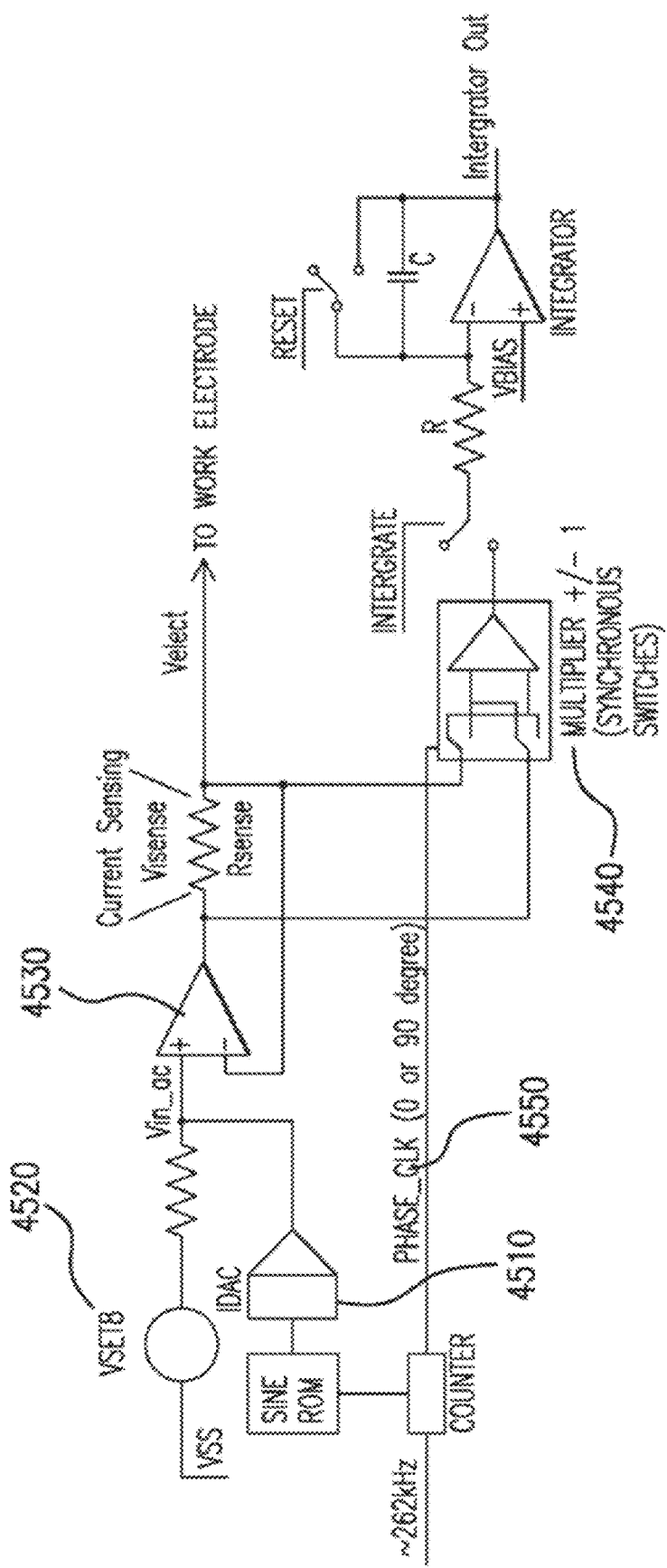
FIG. 45 shows some of the main blocks of the EIS circuitry in the analog front end IC of a glucose sensor in accordance with embodiments of the invention.
Figure 46A:
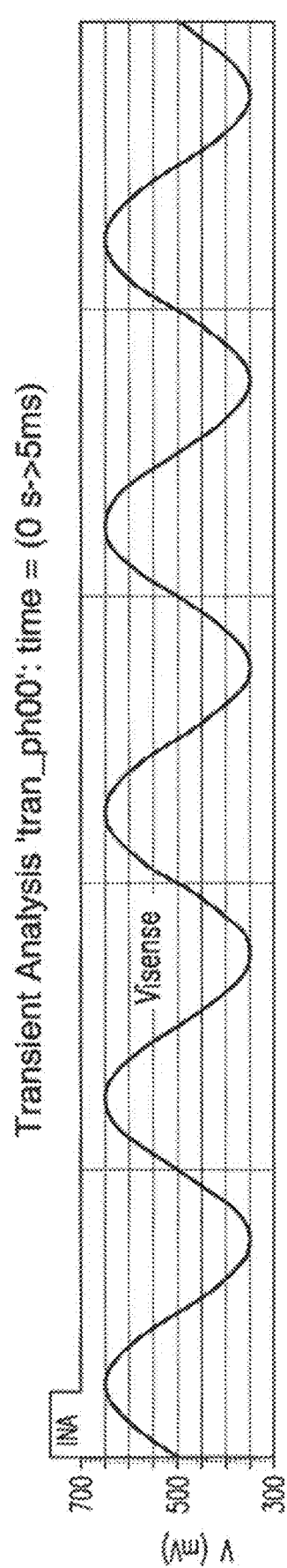
FIGS. 46A-46F show a simulation of the signals of the EIS circuitry shown in FIG. 45 for a current of 0-degree phase with a 0-degree phase multiply.
Figure 46B:
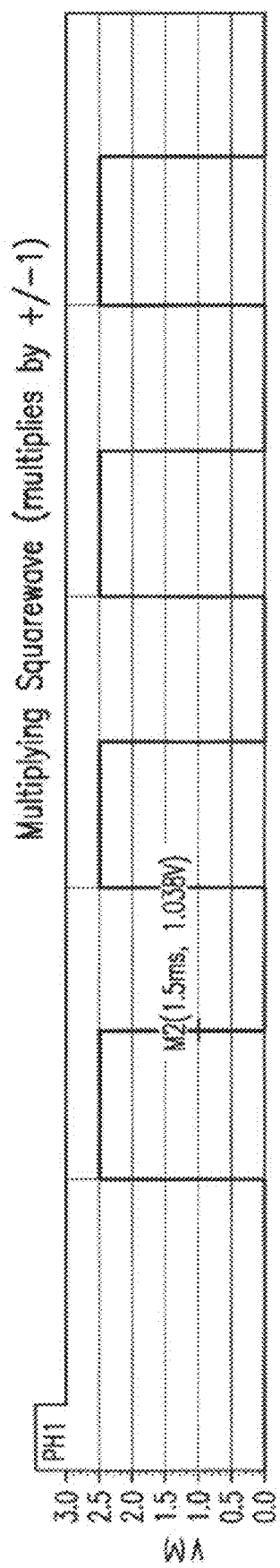
Figure 46C:
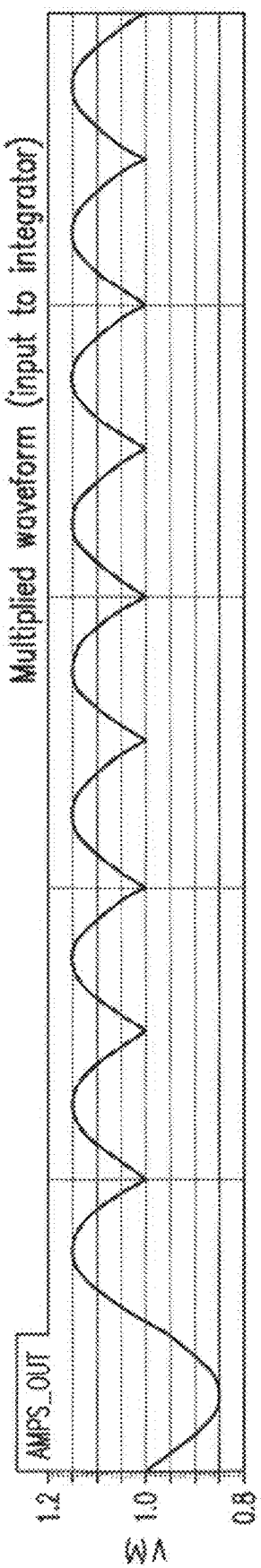
Figure 46D:
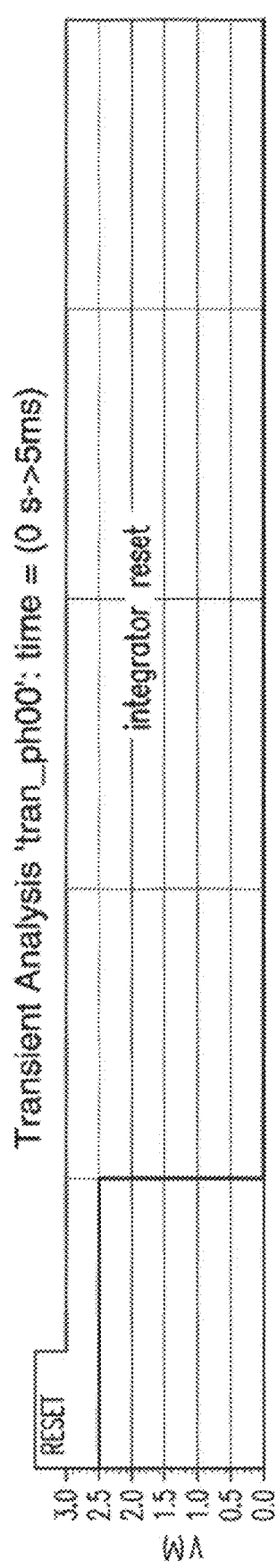
Figure 46E:
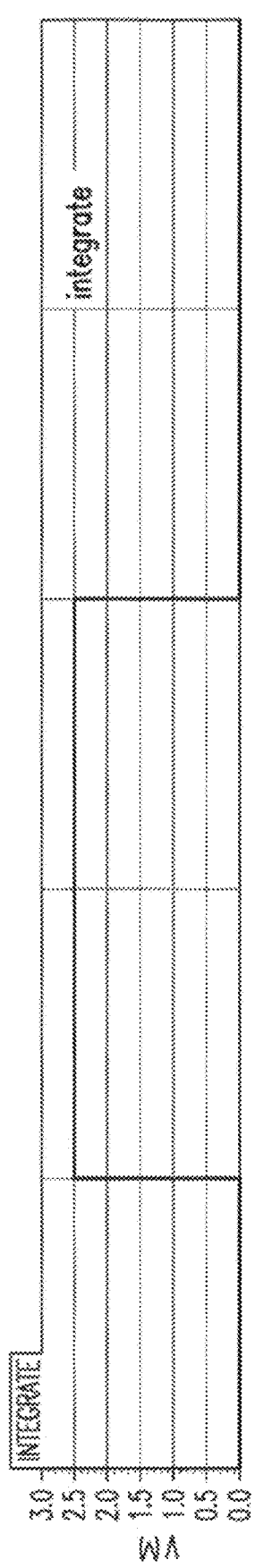
Figure 46F:
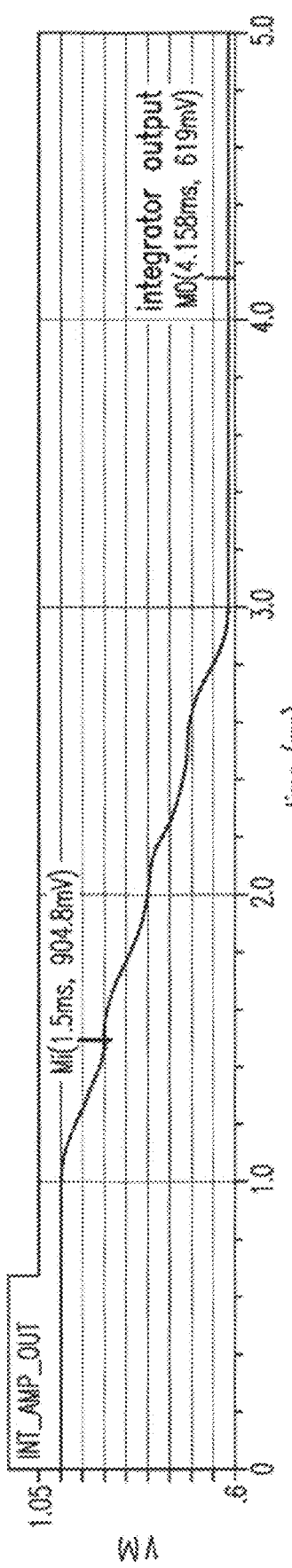
Figure 47A:
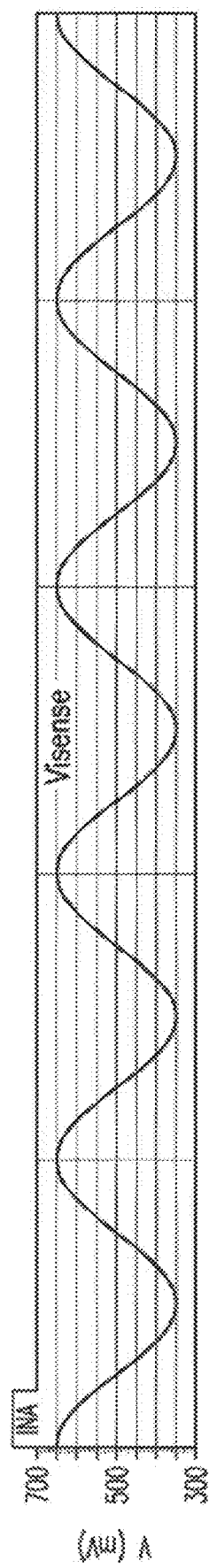
FIGS. 47A-47F show a simulation of the signals of the EIS circuitry shown in FIG. 45 for a current of 0-degree phase with a 90-degree phase multiply.
Figure 47B:
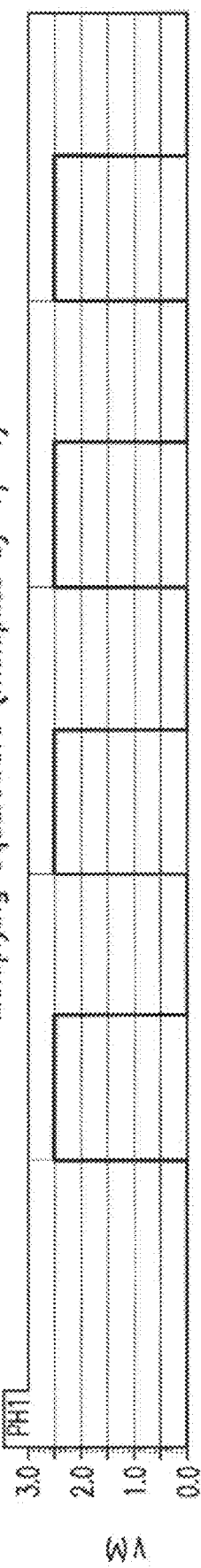
Figure 47C:
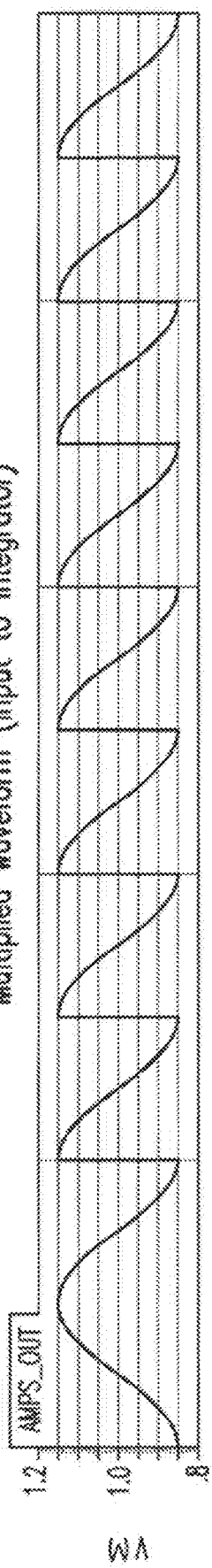
Figure 47D:
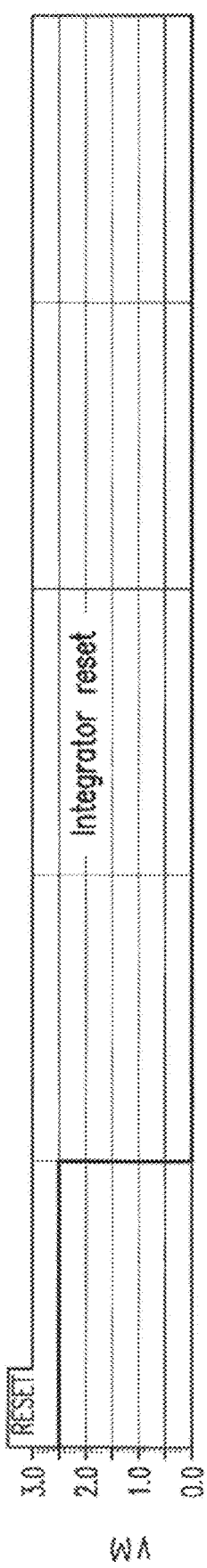
Figure 47E:
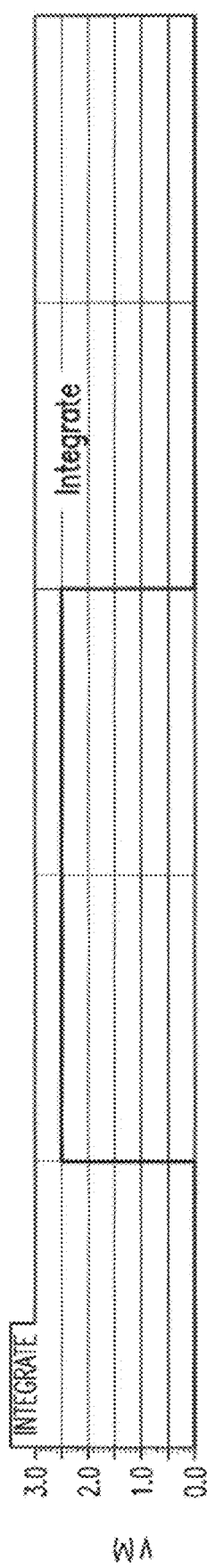
Figure 47F:
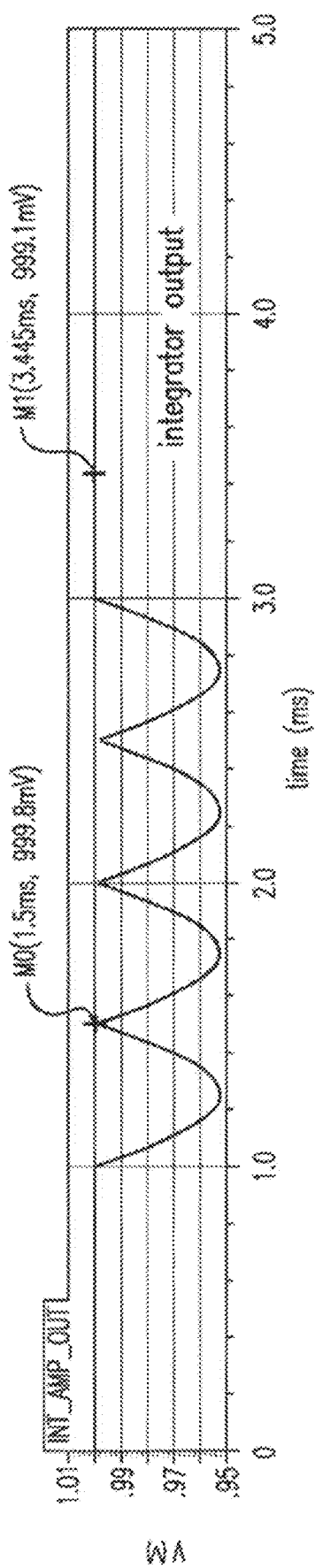

FIG. 45 shows the main blocks of the EIS circuitry in the AFE IC (designated by reference numeral 4255 in FIG. 42B). The IDAC 4510 generates a stepwise sine wave in synchrony with a system clock. A high frequency of this system clock steps the IDAC through the lookup table that contains digital code. This code drives the IDAC, which generates an output current approximating a sine wave. This sine wave current is forced across a resistor to give the AC component, Vin_ac, with the DC offset, VSET8 (4520). When the IDAC circuit is disabled, the DC output voltage reverts to VSET8, so the disturbance to the electrode equilibrium is minimized. This voltage is then buffered by an amplifier 4530 that drives the electrode through a resistor in series, Rsense. The differential voltage across Rsense is proportional to the current. This voltage is presented to a multiplier 4540 that multiplies the voltage by either +1 or −1. This is done with switches and a differential amplifier (instrumentation amplifier). The system clock is divided to generate the phase clock 4550 which controls the multiply function and can be set to 0, 90, 180 or 270 degrees relative to the sine wave.

The plots in FIGS. 46A-46F and 47A-47F show a simulation of the signals of the circuit shown in FIG. 45 to a current that has 0-degree phase shift, which represents a real resistance. For these example simulations, the simulation input values were selected to give the current sense voltage equal to 0.150V. To obtain enough information to derive the impedance and phase, two integrations are required: one with a 0-degree phase multiply (FIGS. 46A-46F) and one with a 90-degree phase multiply (FIGS. 47A-47F).

Calculation of Impedance

The equations describing the integrator output are provided below. For simplicity, only ½ of a sine wave period is considered. As can be seen from the plots of FIGS. 46A-46F and 47A-47F, total integrator output will be approximately the integrated value of a ½ sine wave cycle multiplied by the number of ½ cycles integrated. It is noted that the multiplying switches in relation with the integrate time perform a "gating" function of the signal to the integrator; this can be viewed as setting the limits of integration. The multiplying signal has a fixed phase to the generated sine wave. This can be set to 0, 90, 180, or 270 degrees with software. If the sine wave is in phase (0-degree shift) with respect to the multiply square wave, the limits of integration will be π(180°) and 0 (0°). If the sine wave is shifted by 90 degrees, the limits of integration can be viewed as ¾π(270°) and ¼π (90°).

The formulas with the multiplying square wave in-phase (0°) with respect to the driving sine wave are shown below. This will yield a voltage that is proportional to the real component of the current. It is noted that Φ is the phase shift of the sine wave relative to the multiplying square wave; Vout is the integrator output, and Aampl is the current sine wave amplitude. Also, the period of the sine wave is 1/f, and RC is the time constant of the integrator.

$$V_{out0} = \int_0^{\frac{1}{2f}} \frac{V_{in}}{RC} \partial t = \frac{A_{ampl}}{RC} \int_0^{\frac{1}{2f}} \sin[2\pi f \partial t + \phi] = -\frac{A_{ampl}}{2\pi fRC} \cos[2\pi ft + \phi]\Big|_0^{\frac{1}{2f}}$$

$$V_{out0} = -\frac{A_{ampl}}{2\pi fRC}[\cos[\pi + \phi] - \cos[\phi]]$$

$$\cos(\phi + \varphi) = \cos(\phi)\cos(\varphi) - \sin(\phi)\sin(\varphi); \cos(\pi + \phi) = -\cos(\phi);$$

$$\cos(-\phi) = \cos(\phi)$$

-continued $$v_{out0} = \frac{-A_{ampl}}{2\pi fRC}[\cos(\pi + \phi) - \cos(\phi)] = \frac{A_{ampl}}{2\pi fRC}[\cos(\phi) + \cos(\phi)] = \frac{A_{ampl}}{\pi fRC}\cos(\phi)$$

If $\Phi = 0$, $v_{out0} = \frac{A_{ampl}}{\pi fRC}$.

This corresponds to the real part of the current.

For the multiplying square wave quadrature phase (90°) with respect to the driving sine wave to yield an output proportional to the imaginary component of the current:

$$v_{out90} =$$

$$\int_{\frac{1}{4f}}^{\frac{3}{4f}} \frac{V_{in}}{RC} \partial t = \frac{A_{ampl}}{RC} \int_{\frac{1}{4f}}^{\frac{3}{4f}} \sin[2\pi f \partial t + \phi] = -\frac{A_{ampl}}{2\pi fRC}\cos[2\pi ft + \phi]\Big|_{\frac{1}{4f}}^{\frac{3}{4f}}$$

$$v_{out90} = -\frac{A_{ampl}}{2\pi fRC}\left[\cos\left[\frac{3}{2}\pi + \phi\right] - \cos\left[\frac{1}{2}\pi + \phi\right]\right]$$

$$\cos(\phi + \varphi) = \cos(\phi)\cos(\varphi) - \sin(\phi)\sin(\varphi);$$

$$\cos\left[\frac{3}{2}\pi + \phi\right] = \sin(\phi);$$

$$\cos\left[\frac{1}{2}\pi + \phi\right] = -\sin(\phi)$$

$$v_{out90} =$$

$$\frac{-A_{ampl}}{2\pi fRC}[\sin(\phi) + \sin(\phi)] = \frac{-A_{ampl}}{2\pi fRC}[\sin(\phi) + \sin(\phi)] = \frac{-A_{ampl}}{\pi fRC}\sin(\phi)$$

If $\Phi = 0$, $v_{out90} = \frac{A_{ampl}}{\pi fRC}\sin(\phi) = 0$.

This corresponds to the imaginary part of the current.

In the first example plot shown in FIGS. 46A-46F, $A_{ampl}$ is 0.150 v, the frequency is 1 kHz, $\Phi=0$, the RC for the integrator is 20M ohm and 25 pF which gives RC=0.5 msec. Plugging in those numbers into the equations, gives 0.09549 v, which favorably compares to the integrator output of the plot in FIG. 46. It is noted that the integrator output over the period of integration is the delta voltage from the start of integration to the measurement.

For the 90° square wave multiply, the result should be 0 since sin(0)=0. The simulation result is close to this value.

To calculate the phase: since $$\frac{v_{out90}}{v_{out0}} = \frac{\sin(\phi)}{\cos(\phi)},$$

it follows:

$$\phi = \arctan\frac{\sin(\phi)}{\cos(\phi)} = \arctan\frac{v_{out90}}{v_{out0}}$$

where $V_{out90}$ is the integrator output with the 90° phase shift for the multiply, and $V_{out0}$ is the integrator output for the 0° phase shift. The $V_{out90}$ and $V_{out0}$ outputs must be integrated for the same number of ½ cycles or normalized by the number of cycles. It is important to note that, in the actual software (e.g., ASIC) implementation, only integral cycles (360°) are allowed because an integral number of cycles compensates for any offset in the circuitry before the multiplier.

The magnitude of the current can be found from $$|I| = \frac{A_{ampl}}{R_{sense}} \text{ and}$$

$$A_{ampl} = \frac{v_{out\_90}\pi fRC}{\sin(\phi)} \text{ or}$$

$$A_{ampl} = \frac{v_{out\_0}\pi fRC}{\cos(\phi)}, \text{ or}$$

$$A_{ampl} = \pi fRC\sqrt{V_{out\_0}^2 + V_{out\_90}^2}.$$

This current has the phase angle as calculated above.

The above analysis shows that one can determine the current amplitude and its phase with respect to the multiplying signal. The forcing voltage is generated in a fixed phase (0, 90, 180 or 270 degrees) with respect to the multiplying signal—this is done digitally so that it is precisely controlled. But there is at least one amplifier in the path before the forcing sine wave is applied to the electrode; this will introduce unwanted phase shift and amplitude error. This can be compensated for by integrating the forcing sine wave signal obtained electrically near the electrode. Thus, the amplitude and any phase shift of the forcing voltage can be determined. Since the path for both the current and voltage waveform will be processed by the same circuit, any analog circuit gain and phase errors will cancel.

Since the variable of interest is the impedance, it may not be necessary to actually calculate the $A_{ampl}$. Because the current waveform and the voltage waveform are integrated through the same path, there exists a simple relationship between the ratio of the current and the voltage. Calling the integrated current sense voltage $V_{I\_out}$ and the integrated electrode voltage as $V_{V\_out}$ with the additional subscript to describe the phase of the multiplying function:

$$I = \frac{A_{I\_ampl}}{R_{sense}} \angle \phi = \frac{V_{I\_out\_0}\pi fRC}{\cos(\phi)R_{sense}} \angle \phi;$$

$$V = A_{V\_ampl} \angle \theta = \frac{V_{V\_out\_0}\pi fRC}{\cos(\theta)} \angle \theta$$

The impedance will be the voltage divided by the current. Thus, $$Z = \frac{|V|\angle\theta}{|I|\angle\phi} = \frac{\frac{V_{V\_out\_0}\pi fRC\angle\theta}{\cos(\theta)}}{\frac{V_{I\_out\_0}\pi fRC\angle\phi}{\cos(\phi)R_{sense}}} = R_{sense} * \frac{V_{V\_out\_0}\cos(\phi)}{V_{I\_out\_0}\cos(\theta)} \angle(\theta - \phi)$$

The magnitudes of the voltage and the current can also be obtained from the square root of the squares of the 0 and 90 degree phase integration voltages. As such, the following may also be used:

$$Z = \frac{|V|\angle\theta}{|I|\angle\phi} =$$

$$\frac{\sqrt{V_{V\_out\_0}^2 + V_{V\_out\_90}^2} \angle\theta}{\sqrt{V_{I\_out\_0}^2 + V_{I\_out\_90}^2} \angle\phi} = R_{sense} * \frac{\sqrt{V_{V\_out\_0}^2 + V_{V\_out\_90}^2}}{\sqrt{V_{I\_out\_0}^2 + V_{I\_out\_90}^2}} \angle(\theta - \phi)$$

The integration of the waveforms may be done with one hardware integrator for the relatively-higher frequencies, e.g., those above about 256 Hz. The high frequencies require four measurement cycles: (i) one for the in-phase sensor current; (ii) one for the 90 degree out of phase sensor current; (iii) one for the in-phase forcing voltage; and (iv) one for the 90 degree out of phase forcing voltage.

Two integrators may be used for the relatively-lower frequencies, e.g., those lower than about 256 Hz, with the integration value consisting of combining integrator results numerically in the system microprocessor. Knowing how many integrations there are per cycle allows the microprocessor to calculate the 0 and 90 degree components appropriately.

Synchronizing the integrations with the forcing AC waveform and breaking the integration into at least four parts at the lower frequencies will eliminate the need for the hardware multiplier as the combining of the integrated parts in the microprocessor can accomplish the multiplying function. Thus, only one integration pass is necessary for obtaining the real and imaginary current information. For the lower frequencies, the amplifier phase errors will become smaller, so below a frequency, e.g., between 1 Hz and 50 Hz, and preferably below about 1 Hz, the forcing voltage phase will not need to be determined. Also, the amplitude could be assumed to be constant for the lower frequencies, such that only one measurement cycle after stabilization may be necessary to determine the impedance.

As noted above, whereas one hardware integrator is used for the relatively-higher frequencies, for the relatively-lower frequencies, two integrators may be used. In this regard, the schematic in FIG. 45 shows the EIS circuitry in the AFE IC as used for the relatively-higher EIS frequencies. At these frequencies, the integrator does not saturate while integrating over a cycle. In fact, multiple cycles are integrated for the highest frequencies as this will provide a larger output signal which results in a larger signal to noise ratio.

For the relatively-lower frequencies, such as, e.g., those below about 500 Hz, the integrator output can saturate with common parameters. Therefore, for these frequencies, two integrators are used that are alternately switched. That is, while a first integrator is integrating, the second integrator is being read by the ADC and then is reset (zeroed) to make it ready to integrate when the integration time for first integrator is over. In this way, the signal can be integrated without having gaps in the integration. This would add a second integrator and associated timing controls to the EIS circuitry shown in FIG. 45.

Stabilization Cycle Considerations

The above analysis is for steady state conditions in which the current waveform does not vary from cycle to cycle. This condition is not met immediately upon application of a sine wave to a resistor-capacitor (RC) network because of the initial state of the capacitor. The current phase starts out at 0 degrees and progresses to the steady state value. However, it would be desirable for the measurement to consume a minimum amount of time in order to reduce current drain and also to allow adequate time to make DC sensor measurements (Isigs). Thus, there is a need to determine the number of cycles necessary to obtain sufficiently accurate measurements.

The equation for a simple RC circuit—with a resistor and capacitor in series—is $$v_{ac} = R*I(t) + \frac{1}{C}\int I(t)\partial t$$

Solving the above for I(t) gives:

$$I(t) = \frac{-1}{RC}\left[V_{c0}C + \frac{\omega V_m}{R\left[\omega^2 + \frac{1}{R^2C^2}\right]}\right]e^{\frac{-t}{RC}} +$$

$$\frac{V_m}{R}\left[\frac{1}{\left[\omega^2 + \frac{1}{R^2C^2}\right]}\right]\left[\omega^2\sin(\omega t) + \frac{\omega}{RC}\cos\omega t\right]$$

where $V_{c0}$ is the initial value of the capacitor voltage, $V_m$ is the magnitude of the driving sine wave, and ω is the radian frequency (2πf).

The first term contains the terms defining the non-steady state condition. One way to speed the settling of the system would be to have the first term equal 0, which may be done, e.g., by setting $$V_{cinit}C = \frac{\omega V_m}{R\left[\omega^2 + \frac{1}{R^2C^2}\right]} \text{ or } V_{cinit} = \frac{RC\omega V_m}{[R^2C^2\omega^2 + 1]}$$

While this may not be necessary in practice, it is possible to set the initial phase of the forcing sine wave to jump immediately from the DC steady state point to $V_{cinit}$. This technique may be evaluated for the specific frequency and anticipated phase angle to find the possible reduction in time.

The non-steady state term is multiplied by the exponential function of time. This will determine how quickly the steady state condition is reached. The RC value can be determined as a first order approximation from the impedance calculation information. Given the following:

$$X_c = \frac{1}{\omega C} = Z\sin\phi \text{ and } R = Z\cos\phi,$$

it follows that $$RC = \frac{Z\cos\phi}{\omega Z\sin\phi} = \frac{1}{\omega\tan\phi}$$

For a sensor at 100 Hz with a 5 degree phase angle, this would mean a time constant of 18.2 msec. For settling to less than 1%, this would mean approximately 85 msec settling time or 8.5 cycles. On the other hand, for a sensor at 0.10 Hz with a 65 degree phase angle, this would mean a time constant of 0.75 sec. For settling to less than 1%, this would mean approximately 3.4 sec settling time.

Thus, in embodiments of the invention as detailed hereinabove, the ASIC includes (at least) 7 electrode pads, 5 of which are assigned as WORK electrodes (i.e., sensing electrodes, or working electrodes, or WEs), one of which is labeled COUNTER (i.e., counter electrode, or CE), and one that is labeled REFERENCE (i.e., reference electrode, or RE). The counter amplifier 4321 (see FIG. 42B) may be programmably connected to the COUNTER, the REFERENCE, and/or any of the WORK assigned pads, and in any combination thereof. As has been mentioned, embodiments of the invention may include, e.g., more than five WEs. In this regard, embodiments of the invention may also be directed to an ASIC that interfaces with more than 5 working electrodes.

It is important to note that, with the ASIC as described herein, each of the above-mentioned five working electrodes, the counter electrode, and the reference electrode is individually and independently addressable. As such, any one of the 5 working electrodes may be turned on and measure Isig (electrode current), and any one may be turned off. Moreover, any one of the 5 working electrodes may be operably connected/coupled to the EIS circuitry for measurement of EIS-related parameters, e.g., impedance and phase. In other words, EIS may be selectively run on any one or more of the working electrodes. In addition, the respective voltage level of each of the 5 working electrodes may be independently programmed in amplitude and sign with respect to the reference electrode. This has many applications, such as, e.g., changing the voltage on one or more electrodes in order to make the electrode(s) less sensitive to interference.

In embodiments where two or more working electrodes are employed as redundant electrodes, the EIS techniques described herein may be used, e.g., to determine which of the multiplicity of redundant electrodes is functioning optimally (e.g., in terms of faster start-up, minimal or no dips, minimal or no sensitivity loss, etc.), so that only the optimal working electrode(s) can be addressed for obtaining glucose measurements. The latter, in turn, may drastically reduce, if not eliminate, the need for continual calibrations. At the same time, the other (redundant) working electrode(s) may be: (i) turned off, which would facilitate power management, as EIS may not be run for the "off" electrodes; (ii) powered down; and/or (iii) periodically monitored via EIS to determine whether they have recovered, such that they may be brought back on line. On the other hand, the non-optimal electrode(s) may trigger a request for calibration. The ASIC is also capable of making any of the electrodes—including, e.g., a failed or off-line working electrode—the counter electrode. Thus, in embodiments of the invention, the ASIC may have more than one counter electrode.

While the above generally addresses simple redundancy, wherein the redundant electrodes are of the same size, have the same chemistry, the same design, etc., the above-described diagnostic algorithms, fusion methodologies, and the associated ASIC may also be used in conjunction with spatially distributed, similarly sized or dissimilarly sized, working electrodes as a way of assessing sensor implant integrity as a function of implant time. Thus, in embodiments of the invention, sensors may be used that contain electrodes on the same flex that may have different shapes, sizes, and/or configurations, or contain the same or different chemistries, used to target specific environments.

For example, in one embodiment, one or two working electrodes may be designed to have, e.g., considerably better hydration, but may not last past 2 or 3 days. Other working electrode(s), on the other hand, may have long-lasting durability, but slow initial hydration. In such a case, an algorithm may be designed whereby the first group of working electrode(s) is used to generate glucose data during early wear, after which, during mid-wear, a switch-over may be made (e.g., via the ASIC) to the second group of electrode(s). In such a case, the fusion algorithm, e.g., may not necessarily "fuse" data for all of the WEs, and the user/patient is unaware that the sensing component was switched during mid-wear.

In yet other embodiments, the overall sensor design may include WEs of different sizes. Such smaller WEs generally output a lower Isig (smaller geometric area) and may be used specifically for hypoglycemia detection/accuracy, while larger WEs—which output a larger Isig—may be used specifically for euglycemia and hyperglycemia accuracy. Given the size differences, different EIS thresholds and/or frequencies must be used for diagnostics as among these electrodes. The ASIC, as described hereinabove, accommodates such requirements by enabling programmable, electrode-specific, EIS criteria. As with the previous example, signals may not necessarily be fused to generate an SG output (i.e., different WEs may be tapped at different times).

As was noted previously, the ASIC includes a programmable sequencer 4266 that commands the start and stop of the stimulus and coordinates the measurements of the EIS-based parameters for frequencies above about 100 Hz. At the end of the sequence, the data is in a buffer memory, and is available for a microprocessor to quickly obtain (values of) the needed parameters. This saves time, and also reduces system power requirements by requiring less microprocessor intervention.

For frequencies lower than about 100 Hz, the programmable sequencer 4266 coordinates the starting and stopping of the stimulus for EIS, and buffers data. Either upon the end of the measurement cycle, or if the buffer becomes close to full, the ASIC may interrupt the microprocessor to indicate that it needs to gather the available data. The depth of the buffer will determine how long the microprocessor can do other tasks, or sleep, as the EIS-based parameters are being gathered. For example, in one preferred embodiment, the buffer is 64 measurements deep. Again, this saves energy as the microprocessor will not need to gather the data piecemeal. It is also noted that the sequencer 4266 also has the capability of starting the stimulus at a phase different from 0, which has the potential of settling faster.

The ASIC, as described above, can control the power to a microprocessor. Thus, for example, it can turn off the power completely, and power up the microprocessor, based on detection of sensor connection/disconnection using, e.g., a mechanical switch, or capacitive or resistive sensing. Moreover, the ASIC can control the wakeup of a microprocessor. For example, the microprocessor can put itself into a low-power mode. The ASIC can then send a signal to the microprocessor if, e.g., a sensor connect/disconnect detection is made by the ASIC, which signal wakes up the processor. This includes responding to signals generated by the ASIC using techniques such as, e.g., a mechanical switch or a capacitive-based sensing scheme. This allows the microprocessor to sleep for long periods of time, thereby significantly reducing power drain.

It is important to reiterate that, with the ASIC as described hereinabove, both oxygen sensing and peroxide sensing can be performed simultaneously, because the five (or more) working electrodes are all independent, and independently addressable, and, as such, can be configured in any way desired. In addition, the ASIC allows multiple thresholds for multiple markers, such that EIS can be triggered by various factors—e.g., level of $V_{cntr}$, capacitance change, signal noise, large change in Isig, drift detection, etc.—each having its own threshold(s). In addition, for each such factor, the ASIC enables multiple levels of thresholds.

In yet another embodiment of the invention, EIS may be used as an alternative plating measurement tool, wherein the impedance of both the working and counter electrodes of the sensor substrate may be tested, post-electroplating, with respect to the reference electrode. More specifically, existing systems for performing measurements of the sensor substrate which provide an average roughness of the electrode surface sample a small area from each electrode to determine the average roughness (Ra) of that small area. For example, currently, the Zygo Non-contact Interferometer is used to quantify and evaluate electrode surface area. The Zygo interferometer measures a small area of the counter and working electrodes and provides an average roughness value. This measurement correlates the roughness of each sensor electrode to their actual electrochemical surface area. Due to the limitations of systems that are currently used, it is not possible, from a manufacturing throughput point of view, to measure the entire electrode surface, as this would be an extremely time-consuming endeavor.

In order to measure the entire electrode in a meaningful and quantitative manner, an EIS-based methodology for measuring surface area has been developed herein that is faster than current, e.g., Zygo-based, testing, and more meaningful from a sensor performance perspective. Specifically, the use of EIS in electrode surface characterization is advantageous in several respects. First, by allowing multiple plates to be tested simultaneously, EIS provides a faster method to test electrodes, thereby providing for higher efficiency and throughput, while being cost-effective and maintaining quality.

Second, EIS is a direct electrochemical measurement on the electrode under test, i.e., it allows measurement of EIS-based parameter(s) for the electrode and correlates the measured value to the true electrochemical surface area of the electrode. Thus, instead of taking an average height difference over a small section of the electrode, the EIS technique measures the double layer capacitance (which is directly related to surface area) over the whole electrode surface area and, as such, is more representative of the properties of the electrode, including the actual surface area. Third, EIS testing is non-destructive and, as such, does not affect future sensor performance. Fourth, EIS is particularly useful where the surface area to be measured is either fragile or difficult to easily manipulate.

For purposes of this embodiment of the invention, the EIS-based parameter of interest is the Imaginary impedance (Zim), which may be obtained, as discussed previously, based on measurements of the impedance magnitude (|Z|) in ohms and the phase angle ($\Phi$) in degrees of the electrode immersed in an electrolyte. It has been found that, in addition to being a high-speed process, testing using the electrochemical impedance of both the Counter Electrode (CE) and the WE is an accurate method of measuring the surface area of each electrode. This is also important because, although the role of electrode size in glucose sensor performance is dictated, at least in part, by the oxidation of the hydrogen peroxide produced by the enzymatic reaction of glucose with GOX, experiments have shown that an increased WE surface area reduces the number of low start-up events and improves sensor responsiveness—both of which are among the potential failure modes that were previously discussed at some length.

Returning to the imaginary impedance as the EIS-based parameter of interest, it has been found that the key parameters that drive the electrode surface area, and consequently, its imaginary impedance values are: (i) Electroplating conditions (time in seconds and current in micro Amperes); (ii) EIS frequency that best correlates to surface area; (iii) the number of measurements conducted on a single electrode associated to the electrolyte used in the EIS system; and (iv) DC Voltage Bias.

In connection with the above parameters, experiments have shown that using Platinum plating solution as the electrolyte presents a poor correlation between the imaginary impedance and surface area across the entire spectrum. However, using Sulfuric Acid (H2SO4) as the electrolyte presents very good correlation data, and using Phosphate Buffered saline Solution with zero mg/ml of Glucose (PBS-0) presents even better correlation data, between imaginary impedance and Surface Area Ratio (SAR), especially between the relatively-lower frequencies of 100 Hz and 5 Hz. Moreover, fitted regression analysis using a cubic regression model indicates that, in embodiments of the invention, the best correlation may occur at a frequency of 10 Hz. In addition, it has been found that reducing the Bias voltage from 535 mV to zero dramatically reduces the day-to-day variability in the imaginary impedance measurement.

Using the above parameters, the limits of acceptability of values of imaginary impedance can be defined for a given sensor design. Thus, for example, for the Comfort Sensor manufactured by Medtronic Minimed, the imaginary impedance measured between the WE and the RE (Platinum mesh) must be greater than, or equal to, −100 Ohms. In other words, sensors with an imaginary impedance value (for the WE) of less than −100 Ohms will be rejected. For the WE, an impedance value of greater than, or equal to, −100 Ohms corresponds to a surface area that is equal to, or greater than, that specified by an equivalent Ra measurement of greater than 0.55 um.

Similarly, the imaginary impedance measured between the CE and the RE (Platinum mesh) must be greater than, or equal to, −60 Ohms, such that sensors with an imaginary impedance value (for the CE) of less than −60 Ohms will be rejected. For the CE, an impedance value of greater than, or equal to, −60 Ohms corresponds to a surface area that is equal to, or greater than, that specified by an equivalent Ra measurement greater than 0.50 um.

Figure 48:
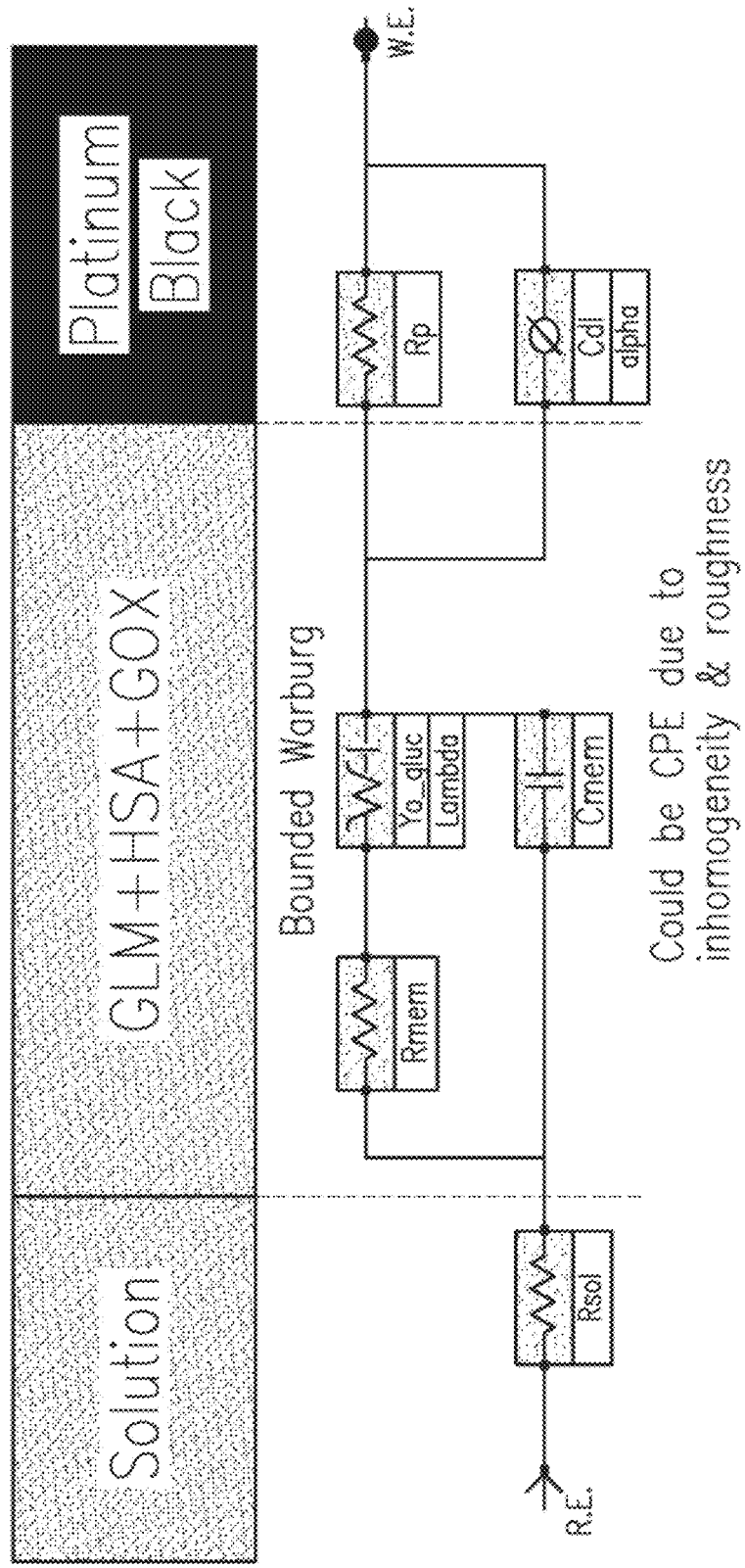
FIG. 48 shows a circuit model in accordance with embodiments of the invention.

In accordance with embodiments of the invention, an equivalent circuit model as shown in FIG. 48 may be used to model the measured EIS between the working and reference electrodes, WE and RE, respectively. The circuit shown in FIG. 48 has a total of six (6) elements, which may be divided into three general categories: (i) reaction-related elements; (ii) Membrane-related elements; and (iii) solution-related elements. In the latter category, Rsol is the solution resistance, and corresponds to the properties of the environment external to the sensor system (e.g., interstitial fluid in vivo).

The reaction-related elements include $R_p$, which is the polarization resistance (i.e., resistance to voltage bias and charge transfer between the electrode and electrolyte), and Cdl, which is the double layer capacitance at the electrode-electrolyte interface. It is noted that, while, in this model, the double layer capacitance is shown as a constant phase element (CPE) due to inhomogeneity of the interface, it can also be modeled as a pure capacitance. As a CPE, the double layer capacitance has two parameters: Cdl, which denotes the admittance, and $\alpha$, which denotes the constant phase of the CPE (i.e., how leaky the capacitor is). The frequency-dependent impedance of the CPE may be calculated as $$Z_{CPE} = \frac{1}{Cdl(j\omega)^\alpha}.$$

Thus, the model includes two (2) reaction-related elements—$R_p$ and Cdl—which are represented by a total of three (3) parameters: $R_p$, Cdl, and $\alpha$.

The membrane-related elements include Rmem, which is the membrane resistance (or resistance due to the chemistry layer), and Cmem, which is the membrane capacitance (or capacitance due to the chemistry layer). Although Cmem is shown in FIG. 48 as a pure capacitance, it can also be modeled as a CPE in special cases. As shown, W is the bounded Warburg element, and has two parameters: $Y_0$, which denotes the admittance of the Warburg element due to glucose/$H_2O_2$ diffusion within the chemistry layer, and $\lambda$, which denotes the diffusion time constant of the Warburg element. It is noted that Warburg may also be modeled in other ways (e.g., unbounded). The frequency-dependent impedance of the bounded Warburg element may be calculated as $$Z_W = \frac{1}{Y_0 \sqrt{j\omega}} \times \coth(\lambda \sqrt{j\omega})$$

Thus, the model includes three (3) membrane-related elements—Rmem, Cmem, and W—which are represented by a total of four (4) parameters: Rmem, Cmem, $Y_0$, and $\lambda$.

The top portion of FIG. 48 shows the overall structure of a sensor in accordance with embodiments of the invention, where Platinum Black refers to the electrode. Here, it is important to note that, while a single electrode is depicted, this is by way of illustration only, and not limitation, as the model may be applied to sensors having a greater number of layers, and a larger number of electrodes, than the illustrative 3-layer, single-electrode structure shown in FIG. 48. As described previously herein, GLM is the sensor's glucose limiting membrane, HSA is human serum albumin, GOX is glucose oxidase enzyme (used as the catalyst), and Solution refers to the environment in which the electrode is disposed, such as, e.g., a user's bodily fluid(s).

Figure 49A:
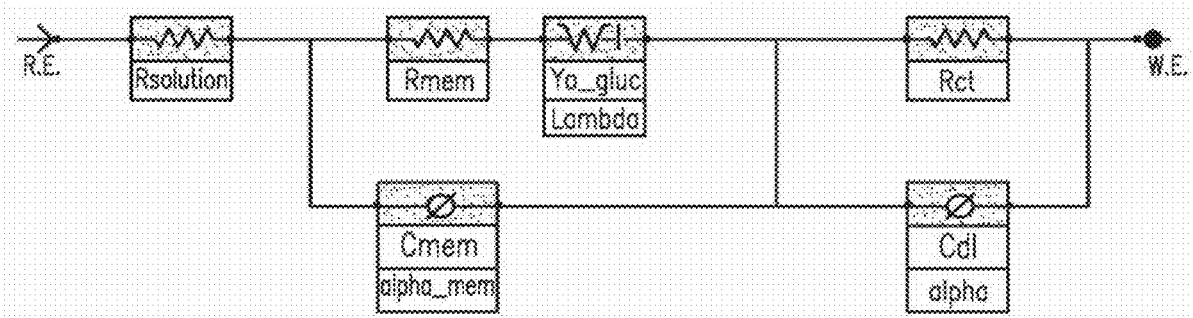
FIGS. 49A-49C show illustrations of circuit models in accordance with alternative embodiments of the invention.
Figure 49B:
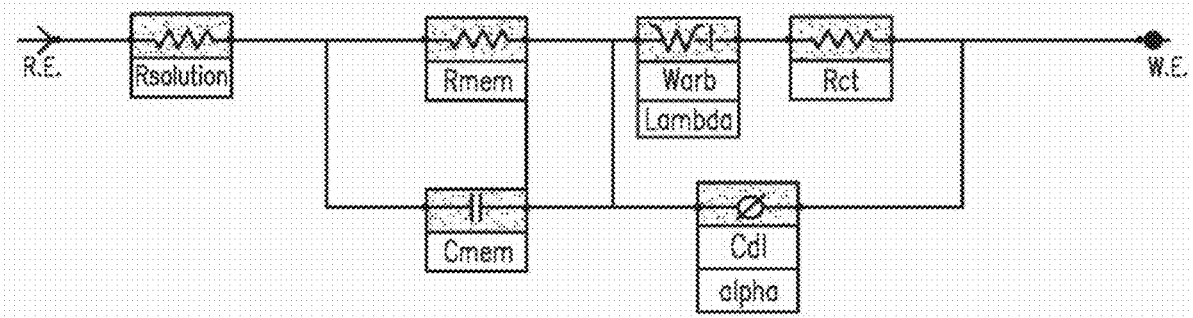
Figure 49C:
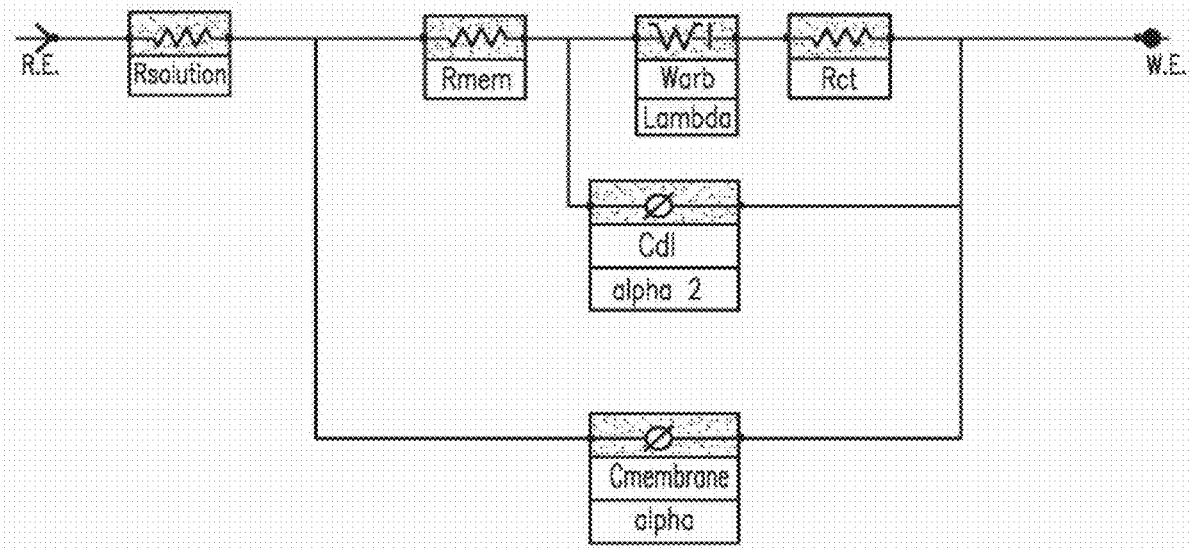
Figure 50A:
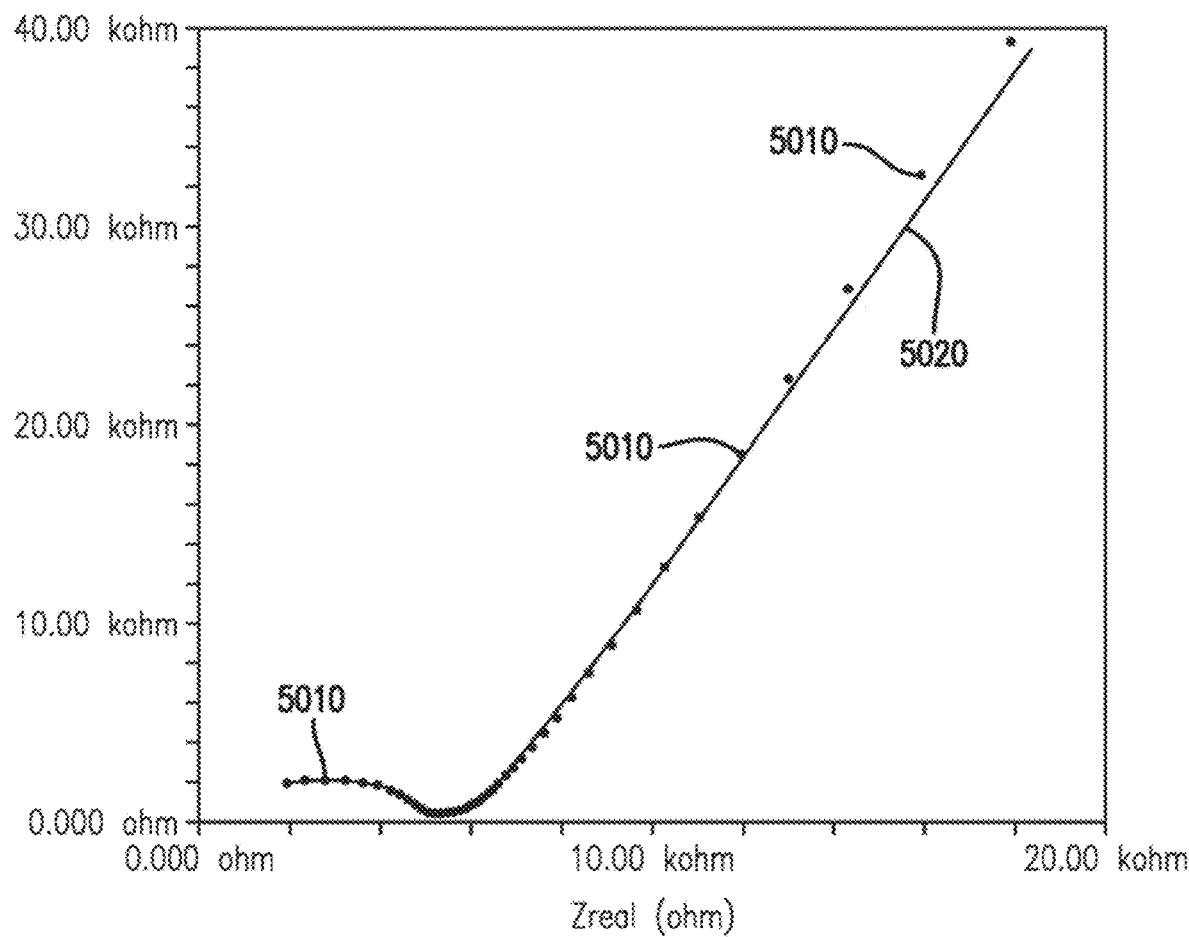
FIG. 50A is a Nyquist plot overlaying an equivalent circuit simulation in accordance with embodiments of the invention.
Figure 50B:
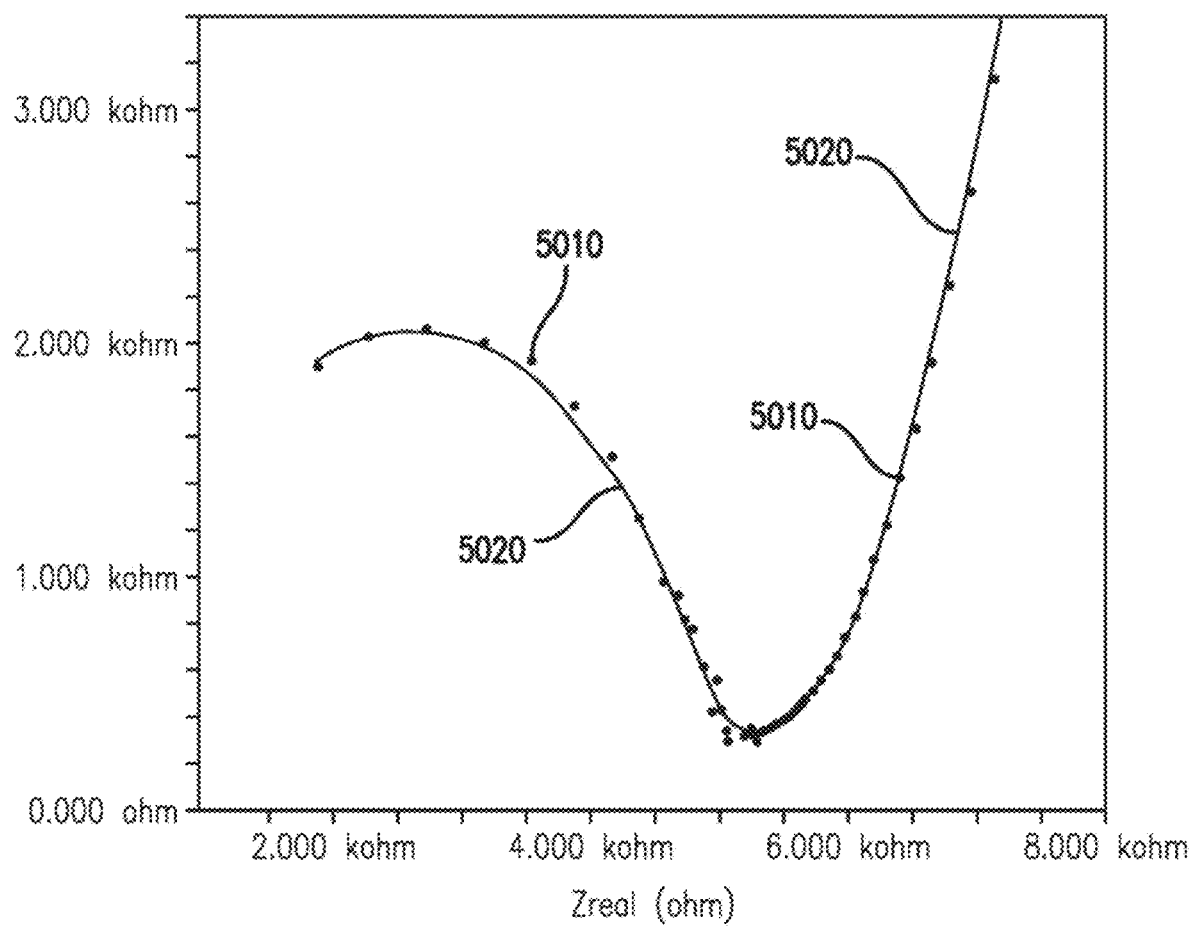
FIG. 50B is an enlarged diagram of the high-frequency portion of FIG. 50A.

In the ensuing discussion, the equivalent circuit model of FIG. 48 will be used to explain some of the physical properties of the sensor behavior. Nevertheless, it should be mentioned that, depending on how the glucose diffusion is modeled, other circuit configurations may also be possible. In this regard, FIGS. 49A-49C show illustrations of some additional circuit models, some of which include a larger number of elements and/or parameters. For purposes of the invention, however, it has been discovered that the circuit model of FIG. 48, wherein the mass transport limitation—i.e., the Warburg component—is attributed to glucose diffusion through the membrane, provides the best fit vis-à-vis empirical data. FIG. 50A is a Nyquist plot showing that the equivalent circuit simulation 5020 fits the empirical data 5010 very closely. FIG. 50B is an enlarged diagram of the high-frequency portion of FIG. 50A, showing that the simulation tracks the actual sensor data quite accurately in that region as well.

Figure 51:
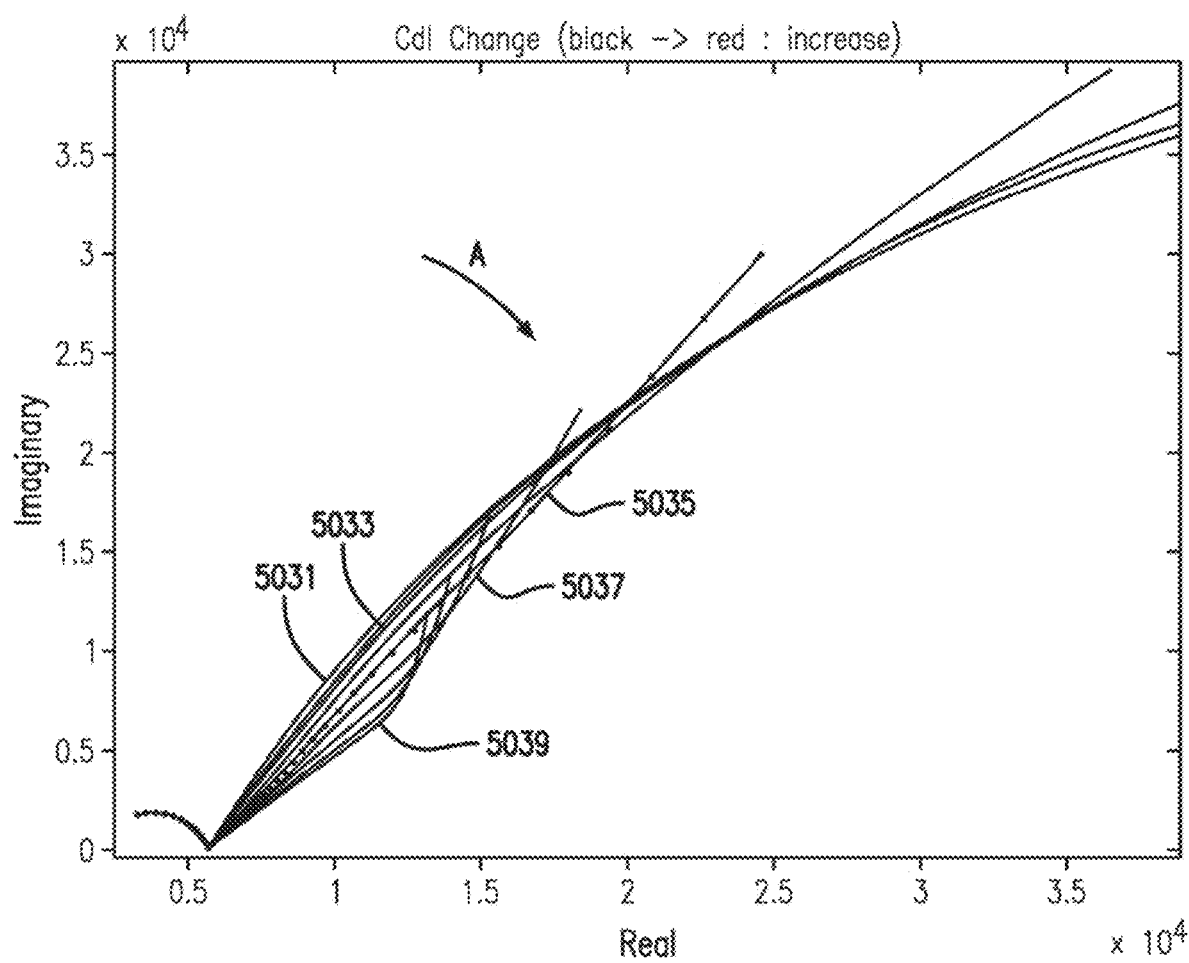
FIG. 51 shows a Nyquist plot with increasing Cdl in the direction of Arrow A, in accordance with embodiments of the invention.

Each of the above-described circuit elements and parameters affects the EIS output in various ways. FIG. 51 shows a Nyquist plot, wherein Cdl increases in the direction of Arrow A. As can be seen, as the value of Cdl increases, the length of the (lower frequency) Nyquist plot decreases, and its slope increases. Thus, the length of the Nyquist plot decreases from plot 5031 to plot 5039, with each of plots 5033, 5035, and 5037 having respective lengths that progressively decrease as Cdl increases from plot 5031 to plot 5039. Conversely, the slope of the Nyquist plot increases from plot 5031 to plot 5039, with each of plots 5033, 5035, and 5037 having respective slopes that progressively increase as Cdl increases from plot 5031 to plot 5039. The higher-frequency region of the Nyquist plot, however, is generally not affected.

Figure 52:
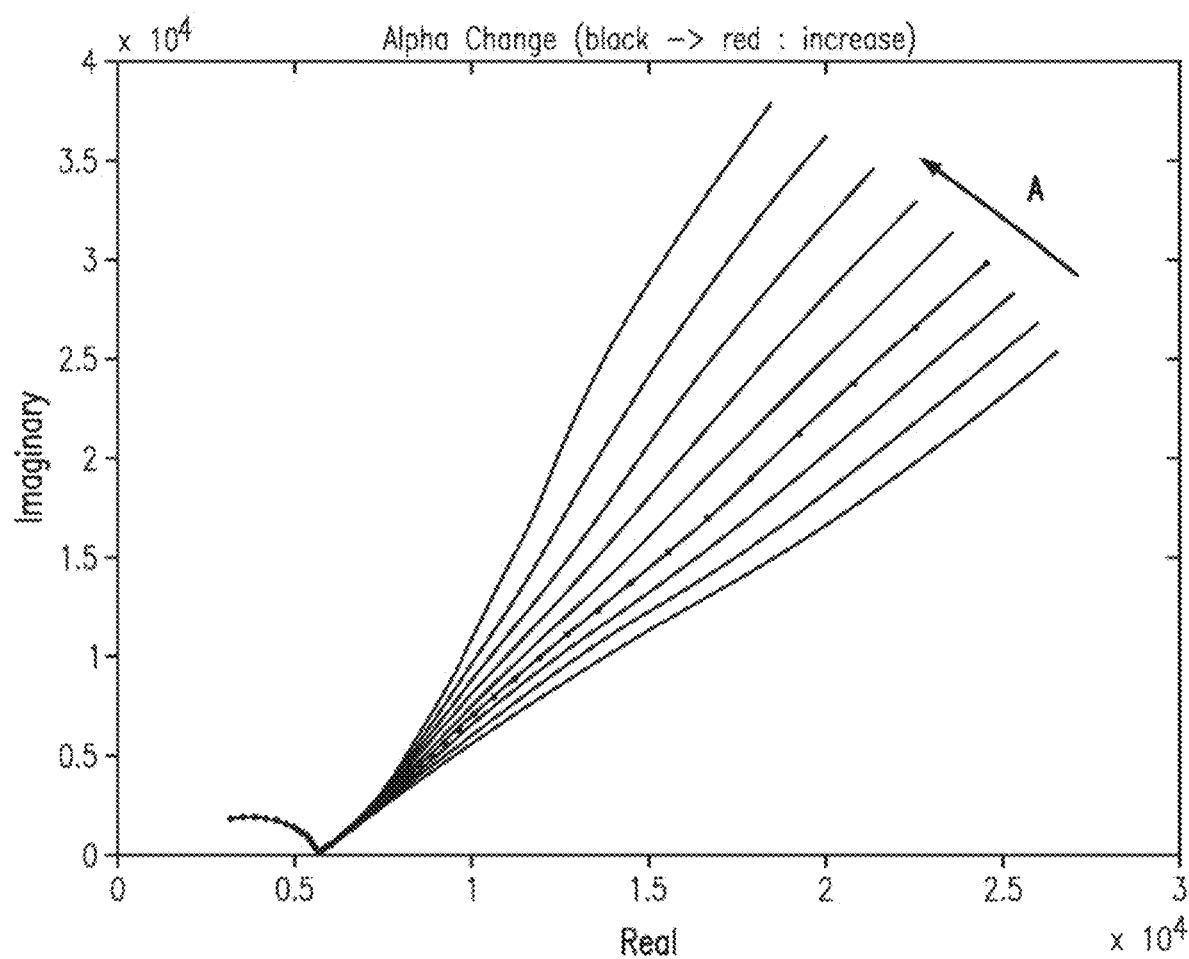
FIG. 52 shows a Nyquist plot with increasing $\alpha$ in the direction of Arrow A, in accordance with embodiments of the invention.
Figure 53:
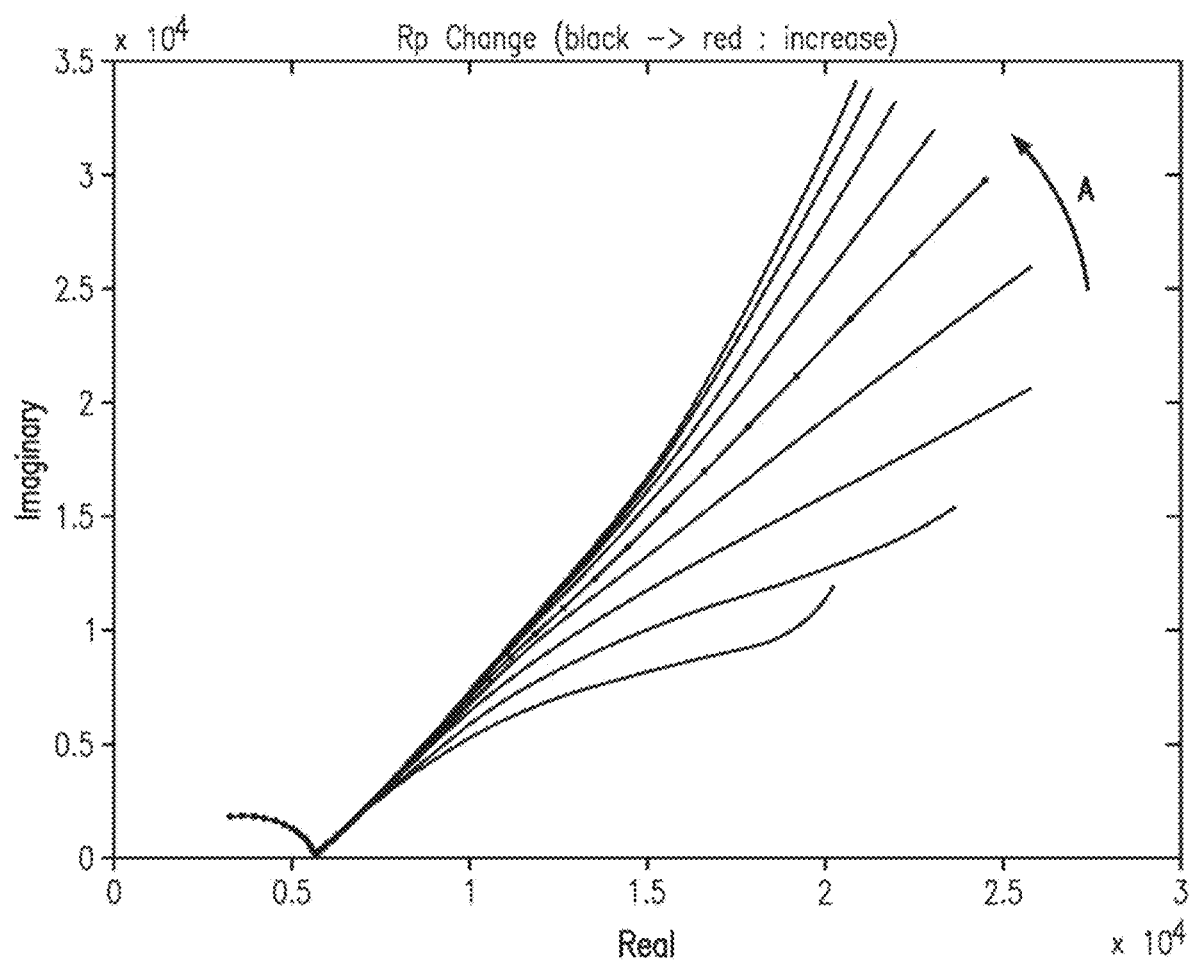
FIG. 53 shows a Nyquist plot with increasing Rp in the direction of Arrow A, in accordance with embodiments of the invention.

FIG. 52 shows a Nyquist plot, wherein a increases in the direction of Arrow A. Here, as α increases, the slope of the Nyquist plot increases in the lower frequency region. In FIG. 53, as $R_p$ increases in the direction of Arrow A, the length and the slope of the lower-frequency Nyquist plot increase. The higher the Rp, the higher the amount of resistance to the chemical reaction and, therefore, the slower the rate of electron and ion exchange. Thus, phenomenologically, FIG. 53 shows that the length and the slope of the lower-frequency Nyquist plot increase as the electron-ion exchange rate decreases—i.e., as the resistance to the chemical reaction increases, which, in turn, means a lower current (Isig) output. Again, there is minimal to no effect on the higher-frequency region of the Nyquist plot.

Figure 54:
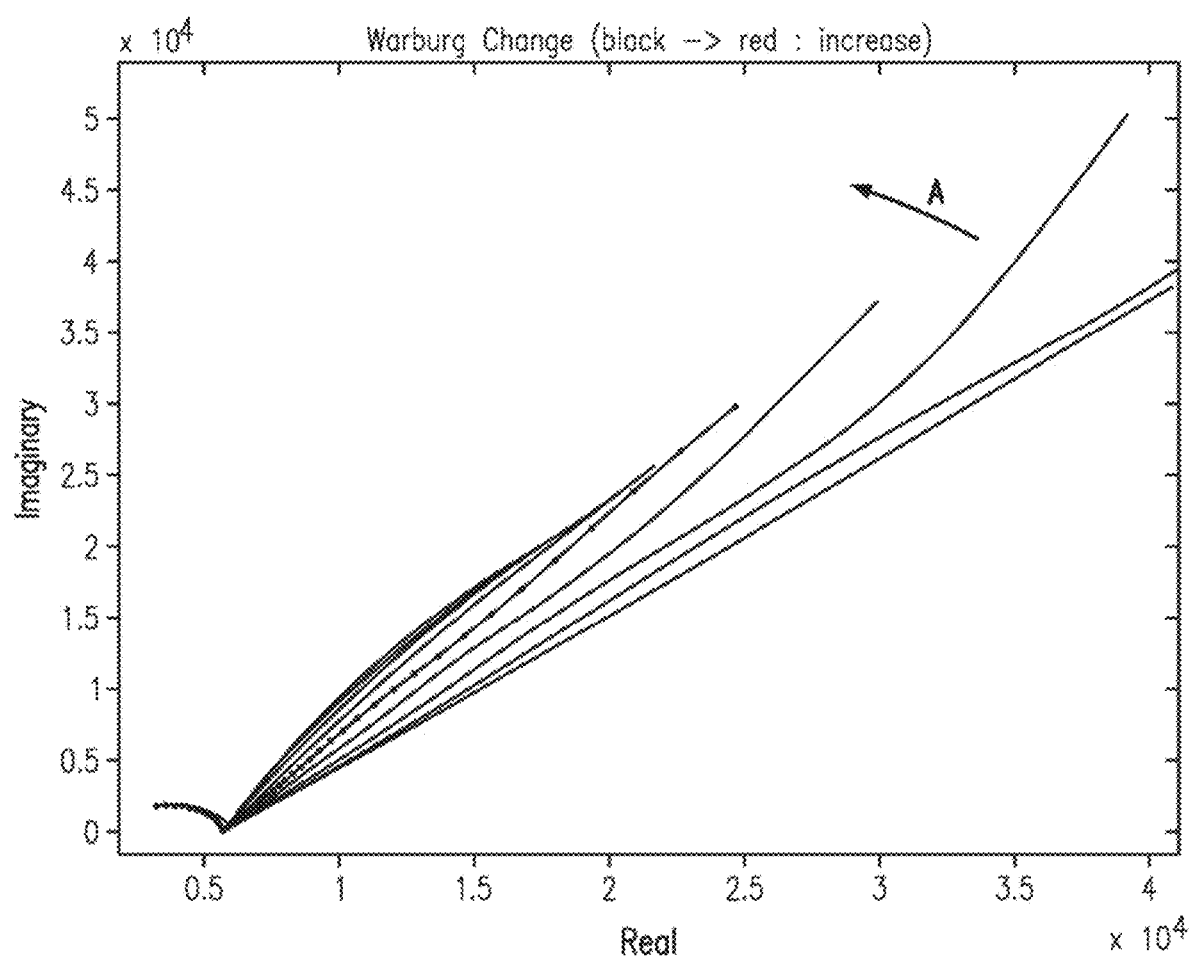
FIG. 54 shows a Nyquist plot with increasing Warburg admittance in the direction of Arrow A, in accordance with embodiments of the invention.
Figure 55:
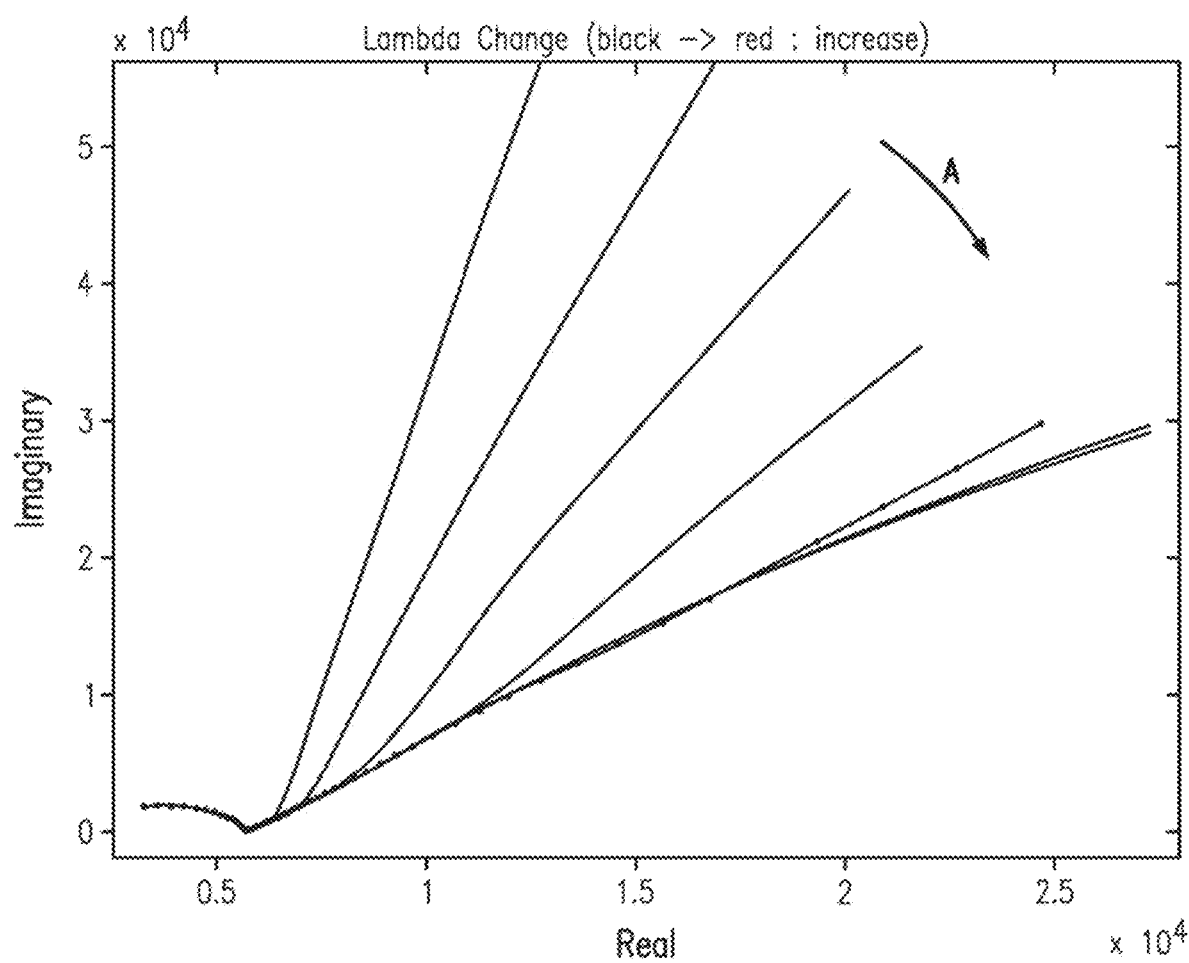
FIG. 55 shows a Nyquist plot with increasing $\lambda$ in the direction of Arrow A, in accordance with embodiments of the invention.

The effect of change in the Warburg admittance is shown in FIG. 54. As the Warburg admittance increases in the direction of Arrow A, both the length and the slope of the lower-frequency Nyquist plot increase. Phenomenologically, this means that the length and the slope of the lower-frequency Nyquist plot tend to increase as the influx of the reactant increases. In FIG. 55, as $\lambda$ increases in the direction of Arrow A, the slope of the Nyquist plot decreases.

Figure 56:
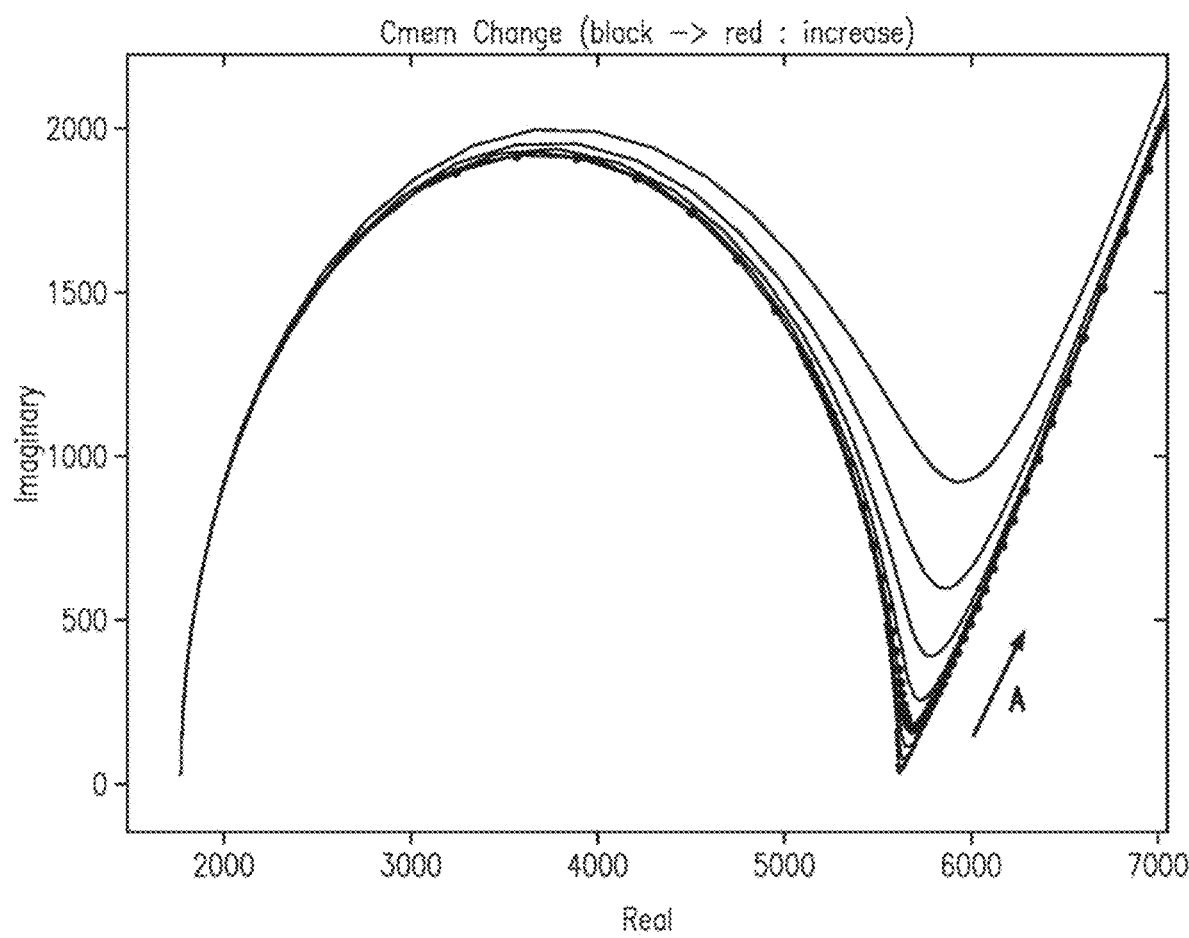
FIG. 56 shows the effect of membrane capacitance on the Nyquist plot, in accordance with embodiments of the invention.
Figure 57:
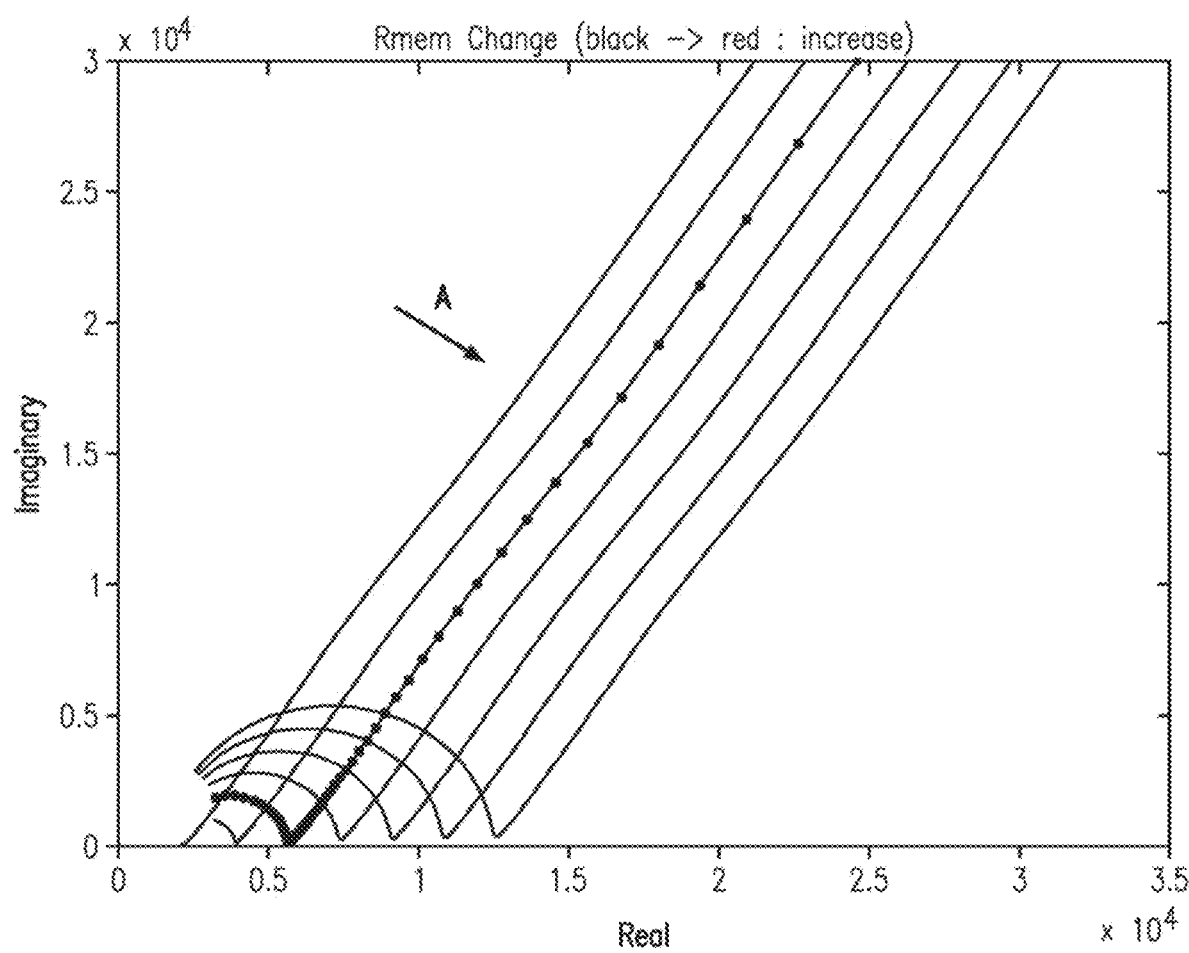
FIG. 57 shows a Nyquist plot with increasing membrane resistance in the direction of Arrow A, in accordance with embodiments of the invention.
Figure 58:
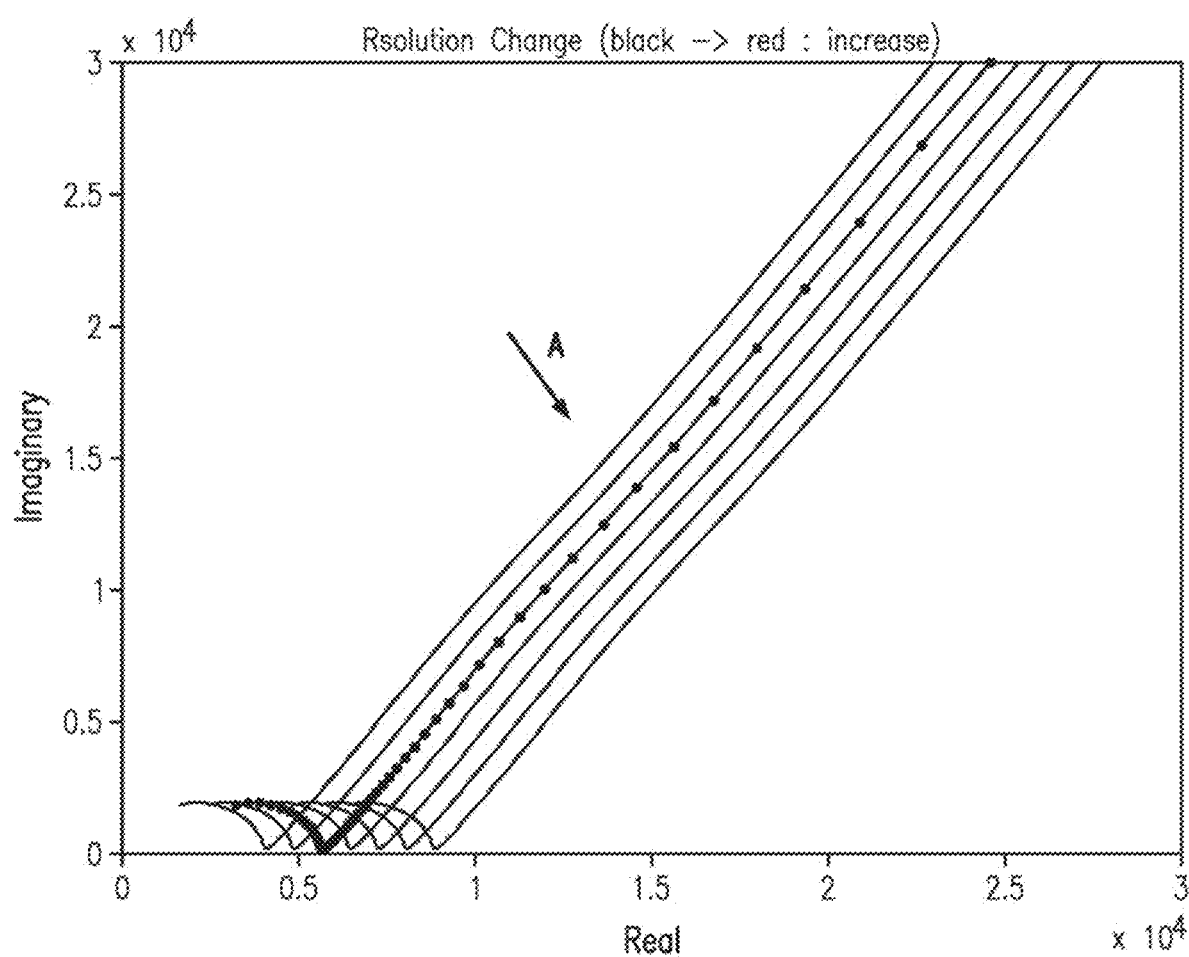
FIG. 58 shows a Nyquist plot with increasing Rsol in the direction of Arrow A, in accordance with embodiments of the invention.

In contrast to the above-described elements and parameters, the membrane-related elements and parameters generally affect the higher-frequency region of the Nyquist plot. FIG. 56 shows the effect of the membrane capacitance on the Nyquist plot. As can be seen from FIG. 56, changes in Cmem affect how much of the high-frequency region's semi-circle is visible. Thus, as membrane capacitance increases in the direction of Arrow A, progressively less of the semi-circle can be seen. Similarly, as shown in FIG. 57, as the membrane resistance increases in the direction of Arrow A, more of the high-frequency region semi-circle becomes visible. In addition, as Rmem increases, the overall Nyquist plot shifts from left to right. The latter parallel-shifting phenomenon also holds true for Rsol, as shown in FIG. 58.

The above discussion in connection with the equivalent circuit model of FIG. 48 may be summarized as follows. First, Cdl, α, Rp, Warburg, and $\lambda$ generally control the low frequency response. More specifically, the lower-frequency Nyquist slope/Zimag primarily depends on Cdl, α, Rp, and $\lambda$, and the lower-frequency length/Zmagnitude primarily depends on Cdl, Rp, and Warburg Admittance. Second, Rmem and Cmem control the higher-frequency response. In particular, Rmem determines the high frequency semi-circle diameter, and Cmem determines the turning point frequency, having minimal overall effect on the Nyquist plot. Lastly, changes in Rmem and Rsol cause parallel shifts in the Nyquist plot.

Figure 59A:
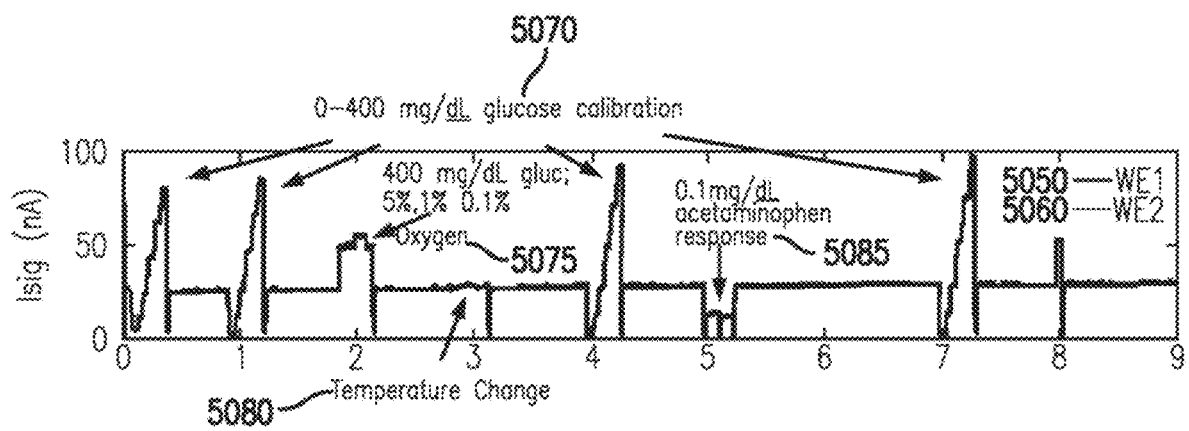
FIGS. 59A-59C show changes in EIS parameters relating to circuit elements during start-up and calibration in accordance with embodiments of the invention.
Figure 59B:
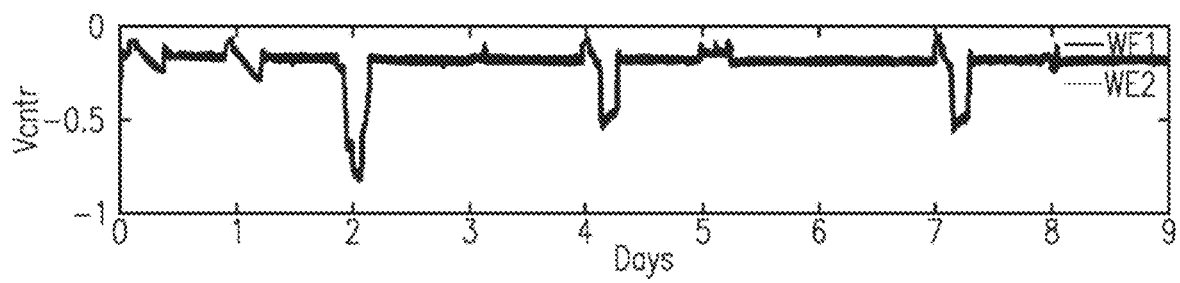
Figure 59C:
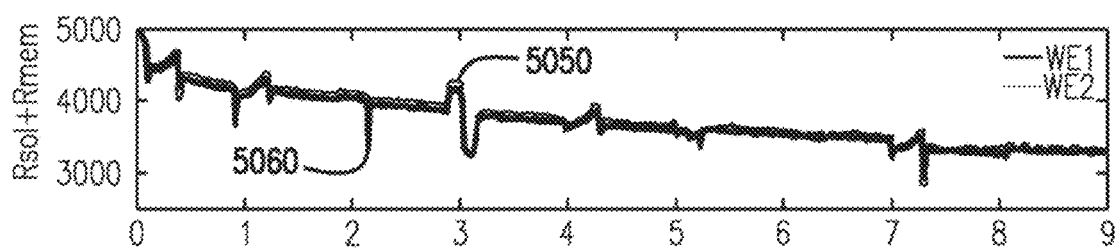
Figure 60A:
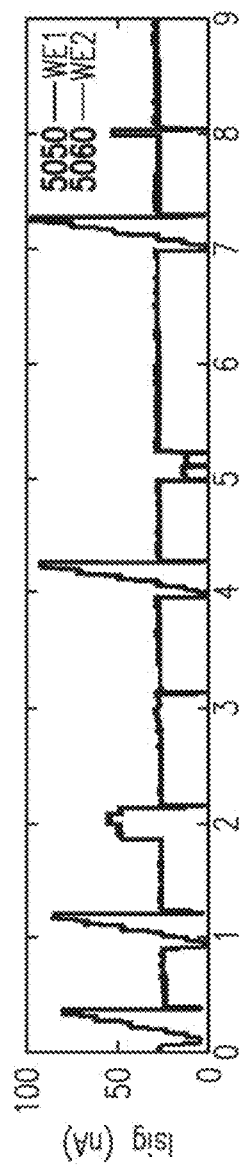
FIGS. 60A-60C show changes in a different set of EIS parameters relating to circuit elements during start-up and calibration in accordance with embodiments of the invention.
Figure 60B:
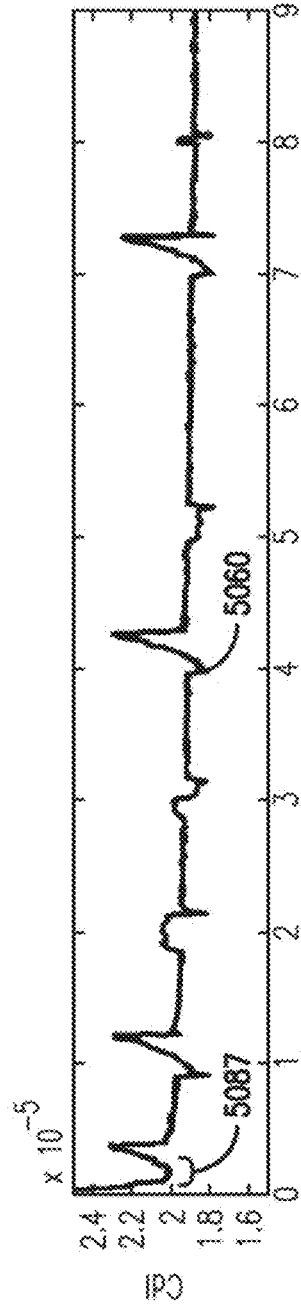
Figure 60C:
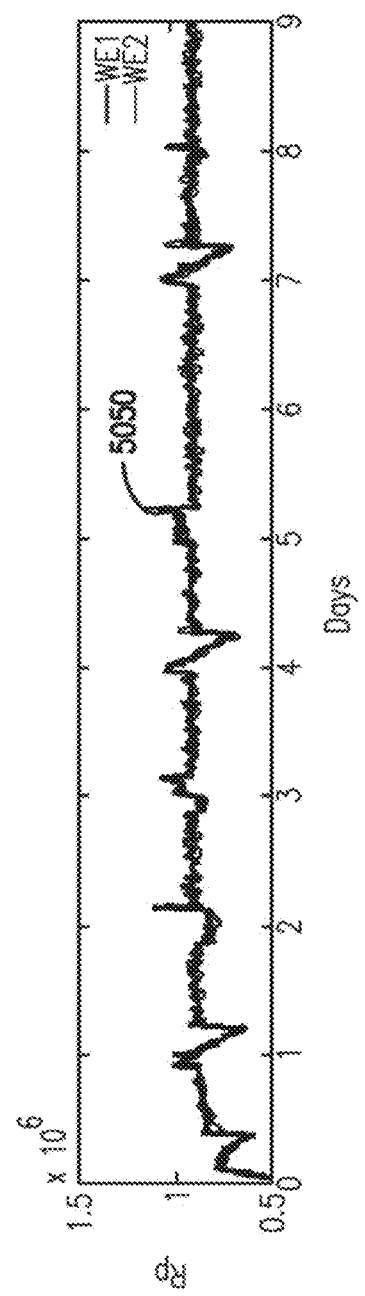
Figure 61A:
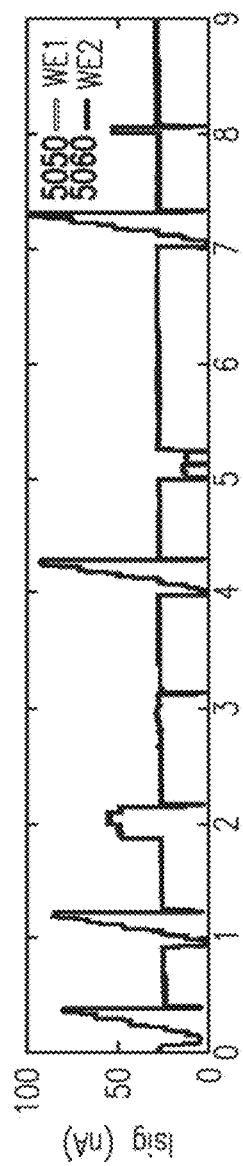
FIGS. 61A-61C show changes in yet a different set of EIS parameters relating to circuit elements during start-up and calibration in accordance with embodiments of the invention.
Figure 61B:
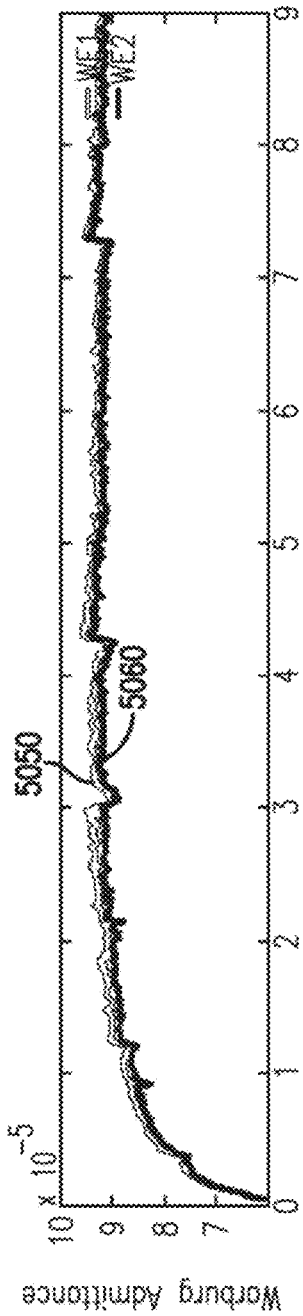

FIGS. 59A-59C, 60A-60C, and 61A-61C show results of in-vitro experiments for changes in the above-described circuit elements during sensor start-up and calibration. FIGS. 59A, 60A, and 61A are identical. As shown in FIG. 59A, the experiments were generally run with two redundant working electrodes 5050, 5060, and for a period of (between 7 and) 9 days. A baseline glucose amount of 100 mg/dL was used, although the latter was changed between zero and 400 mg/dL at various points throughout the experiment (5070). In addition, the effects of a (solution) temperature change between 32° C. and 42° C. (5080) and a 0.1 mg/dL acetaminophen response (5085) were explored. Lastly, the experiments included an Oxygen stress test, where the supply of Oxygen dissolved in the solution was varied (i.e., limited) between 0.1% and 5% (5075). For purposes of these experiments, a full EIS sweep (i.e., from 0.1 Hz-8 kHz) was run, and the output data was recorded (and plotted) about once every 30 minutes. However, shorter or longer intervals may also be used.

In FIG. 59C, the sum of Rsol and Rmem—which, again, may be estimated by the magnitude of real impedance at the inflection point of the Nyquist plot—displays a general downwards trend as a function of time. This is due primarily to the fact that the membrane takes time to hydrate, such that, as time passes by, it will become less resistant to the electrical charges. A slight correlation can also be seen between the plot for Isig (FIG. 59A) and that for Rsol+Rmem (FIG. 59C).

Figure 61C:
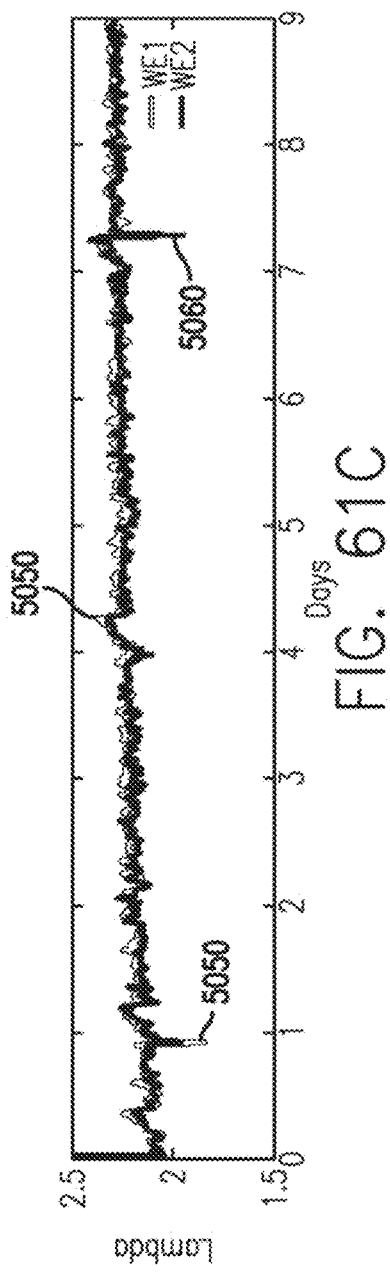
Figure 62:
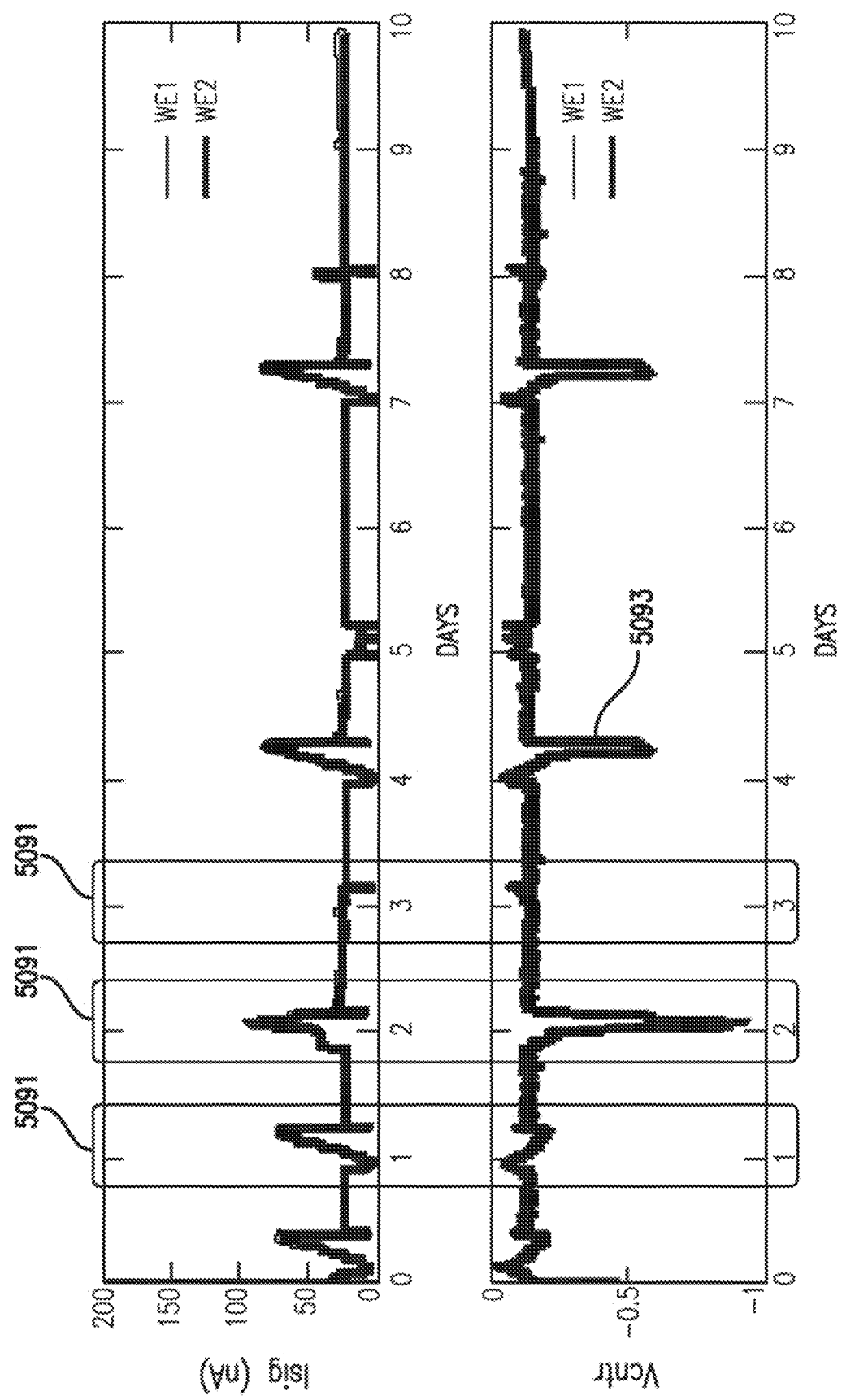
FIG. 62 shows the EIS response for multiple electrodes in accordance with embodiments of the invention.

FIG. 60B shows the EIS output for Cdl. Here, there is initially a relatively rapid drop (5087), over a period of several hours, due to the sensor activation/sensor charge-up process. Thereafter, however, Cdl remains fairly constant, exhibiting a strong correlation with Isig (FIG. 60A). Given the latter correlation, Cdl data, as an EIS parameter, may be less useful in applications where glucose independence is desired. As shown in FIG. 60C, the trend for Rp may be generally described as a mirror image of the plot for Cdl. As the membrane becomes more hydrated, the influx increases, which is reflected in the plot of Warburg admittance in FIG. 61B. As shown in FIG. 61C, λ remains generally constant throughout.

Figure 63:
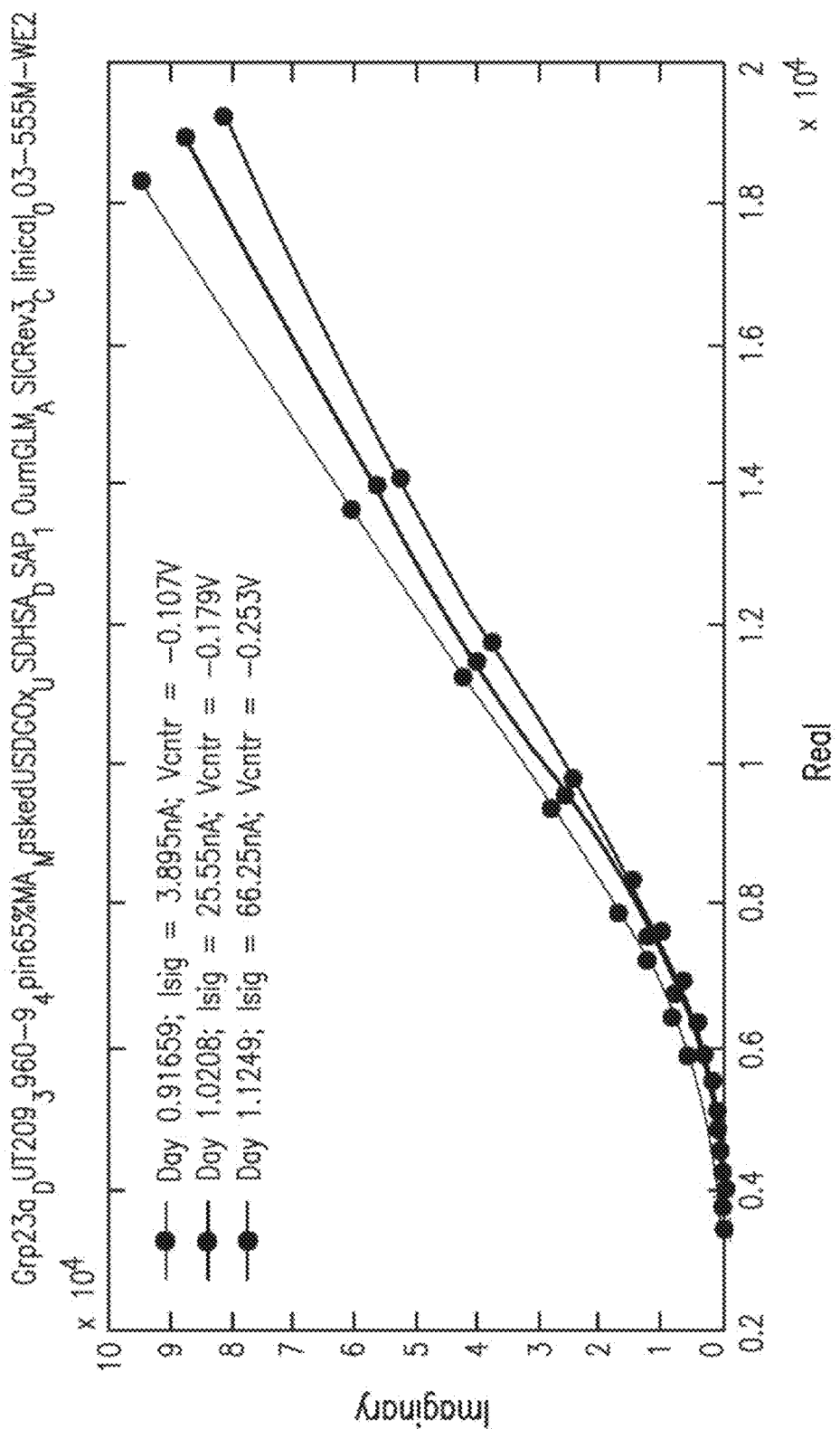
FIG. 63 is a Nyquist plot showing the effect of Isig calibration via an increase in glucose in accordance with embodiments of the invention.
Figure 64:
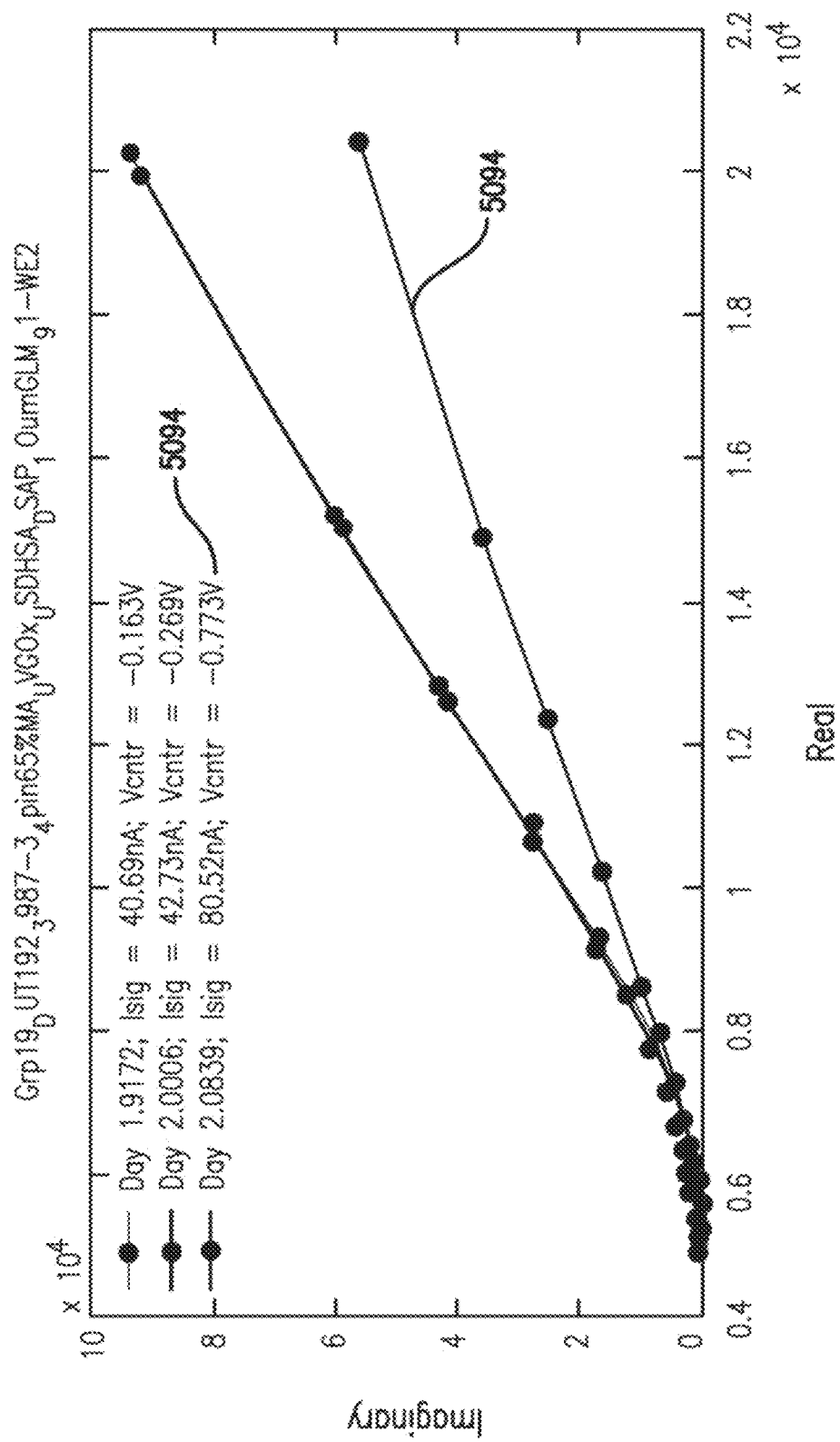
FIG. 64 shows the effect of oxygen (Vcntr) response on the Nyquist plot, in accordance with embodiments of the invention.
Figure 65:
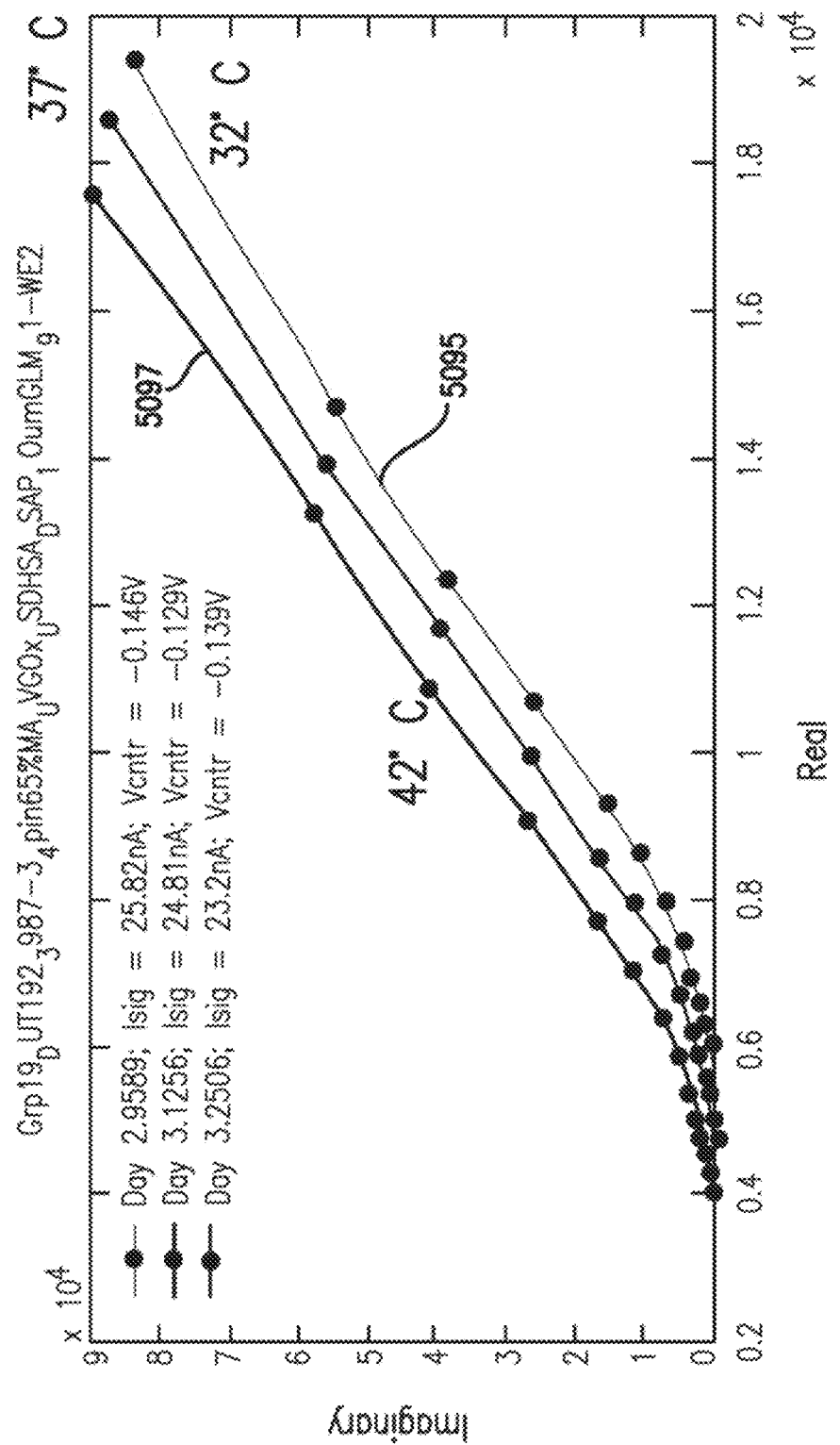
FIG. 65 shows a shift in the Nyquist plot due to temperature changes, in accordance with embodiments of the invention.

FIGS. 62-65 show the actual EIS response for various parts of the above-described experiments. Specifically, the changes that were made during the first 3 days—i.e., glucose changes, Oxygen stress, and temperature changes, as shown in FIGS. 59A, 60A, and 61A—are boxed (5091) in FIG. 62, with the Vcntr response 5093 being shown in the bottom portion of this Figure and in FIG. 59B. FIG. 63 shows that an Isig calibration via an increase in glucose caused the slope and length of the Nyquist plot to decrease. In FIG. 64, the Oxygen (or Vcntr) response is shown in Day 2, where Vcntr becomes more negative as the Oxygen content is decreased. Here, the Nyquist plot becomes shorter in length, and its slope decreases (5094), indicating a large decrease in imaginary impedance. The plot length depends primarily on Cdl and Rp, and is strongly correlated to Vcntr which, in turn, responds to changes in glucose and Oxygen. In FIG. 65, the Isig changes negligibly from Day 2 to Day 3. Nevertheless, the Nyquist plot shifts horizontally (from the plot at 37° C.) for data taken at 32° C. (5095) and at 42° C. (5097). However, there is no significant impact on Nyquist plot length, slope, or Isig.

Putting the above-described EIS output and signature information together, it has been discovered that, during sensor start-up, the magnitude of Rmem+Rsol decreases over time, corresponding to a shift from right to left in the Nyquist plot. During this period, Cdl decreases, and Rp increases, with a corresponding increase in Nyquist slope. Finally, Warburg admittance also increases. As noted previously, the foregoing is consistent with the hydration process, with EIS plots and parameter values taking on the order of 1-2 days (e.g., 24-36 hours) to stabilize.

Embodiments of the invention are directed to real-time self-calibration, and more particularly, to in-vivo self-calibration of glucose sensors based on EIS data. Any calibration algorithm, including self-calibration algorithms, must address sensitivity loss. As discussed previously, two types of sensitivity loss may occur: (1) Isig dip, which is a temporary loss of sensitivity, typically occurring during the first few days of sensor operation; and (2) permanent sensitivity loss, occurring generally at the end of sensor life, and sometimes correlated with the presence of a Vcntr rail.

It has been discovered that sensitivity loss can manifest itself as an increase in Rsol or Rmem (or both), which can be observed in the Nyquist plot as a parallel shift to the right, or, if Rmem changes, a more visible start to a semicircle at the higher frequencies (resulting in an increase in high-frequency imaginary impedance). In addition to, or instead of, Rsol and Rmem, there could be an increase in Cmem only. This can be observed as changes in the high-frequency semicircle. Sensitivity loss will be accompanied by a change in Cdl (by way of a longer tail in the lower-frequency segment of the Nyquist plot). The foregoing signatures provide a means for determining how different changes in EIS output can be used to compensate for changes in sensitivity.

Figure 66:
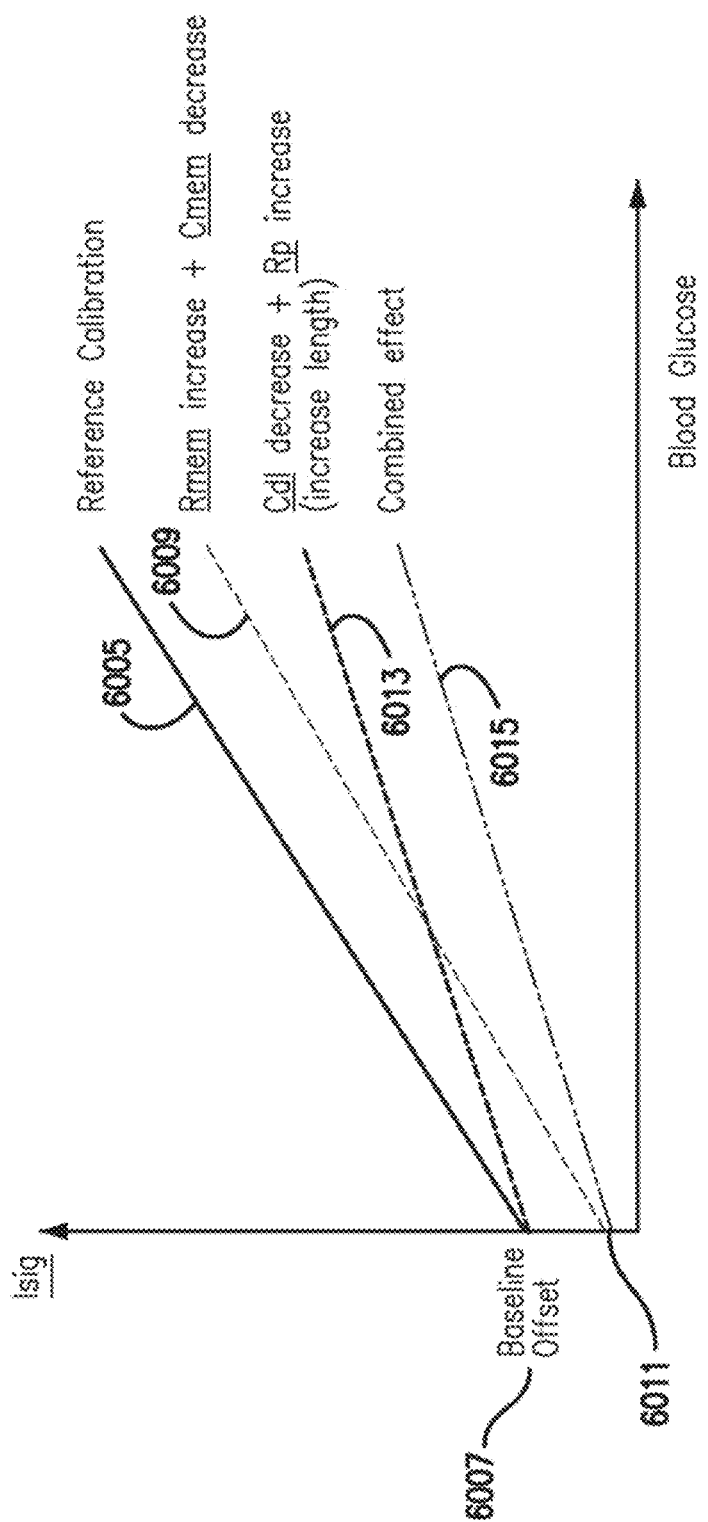
FIG. 66 shows the relationship between Isig and blood glucose in accordance with embodiments of the invention.

For a normally operating glucose sensor, there is a linear relationship between blood glucose (BG) and the sensor's current output (Isig). Thus, $$BG = CF \times (Isig + c)$$

where "CF" is the Cal Factor, and "c" is the offset. This is shown in FIG. 66, where the calibration curve is as shown by line 6005, and "c" is the baseline offset 6007 (in nA). However, when there is an increase in Rmem and/or a decrease in Cmem, then c will be affected. Thus, line 6009 depicts a situation in which Rmem increases and Cmem decreases—which signifies changes in the membrane properties—thereby causing the offset "c" to move to 6011, i.e., a downward shift of the calibration curve. Similarly, when there are (non-glucose related) changes in Cdl and increases in Rp—with a resultant increase in the length of the (lower-frequency) Nyquist plot—then the slope will be affected, where the slope=1/CF. Thus, in FIG. 66, line 6013 has a different (smaller) slope that line 6005. Combined changes can also occur, which is illustrated by line 6015, indicating sensitivity loss.

The length of the lower-frequency segment of the Nyquist plot ($L_{nyquist}$)—which, for simplicity, may be illustratively estimated as the length between 128 Hz and 0.105 Hz (real) impedance—is highly correlated with glucose changes. It has been discovered, through model fitting, that the only parameter that changes during glucose changes is the double layer capacitance Cdl, and specifically the double layer admittance. Therefore, the only Isig-dependent—and, by extension, glucose-dependent—parameter in the equivalent circuit model of FIG. 48 is Cdl, with all other parameters being substantially Isig-independent.

In view of the above, in one embodiment of the invention, changes in Rmem and Cmem may be tracked to arrive at a readjustment of the Cal Factor (BG/Isig) and, thereby, enable real-time self-calibration of sensors without the need for continual finger-stick testing. This is possible, in part, because changes in Rmem and Cmem result in a change in the offset (c), but not in the slope, of the calibration curve. In other words, such changes in the membrane-related parameters of the model generally indicate that the sensor is still capable of functioning properly.

Graphically, FIG. 67A shows actual blood glucose (BG) data 6055 that is being recorded, overlaid by the Isig output 6060 from the working electrode. Comparing the data from a first period (or time window) comprising approximately days 1-4 (6051) with the data from a second period comprising approximately days 6-9 (6053), FIG. 67A shows that the sensor is drifting generally downwards during the second time period, indicating perhaps a moderate sensitivity loss in the sensor. There is also an increase in Vcntr during the second time period, as shown in FIG. 67B.

Figure 68:
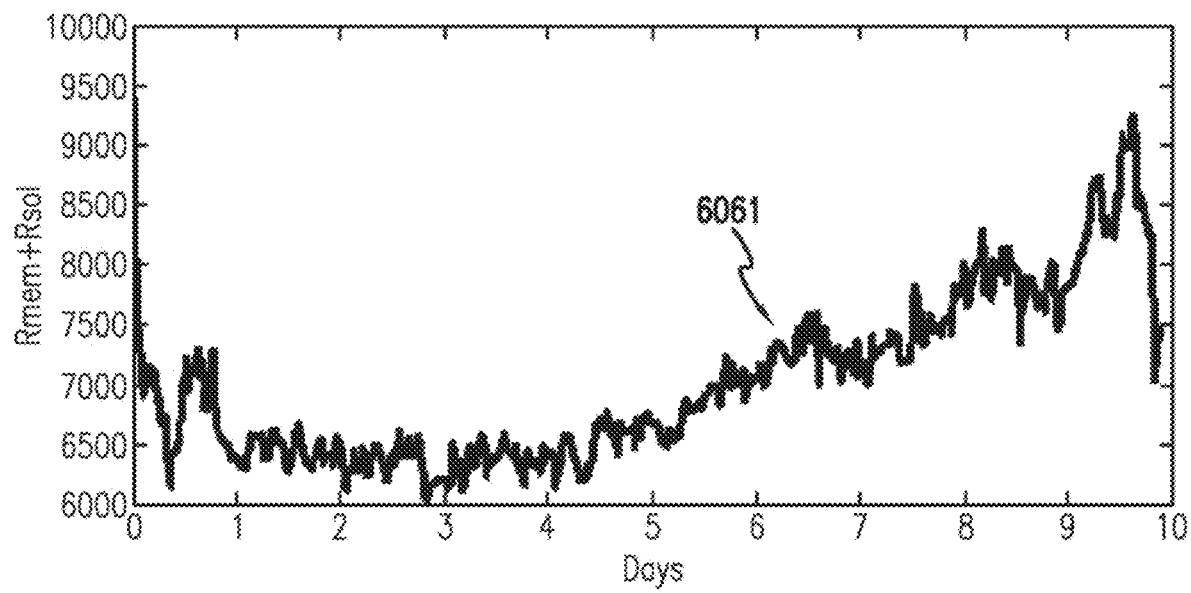
FIG. 68 shows an increase in membrane resistance during sensitivity loss, in accordance with embodiments of the invention.
Figure 69:
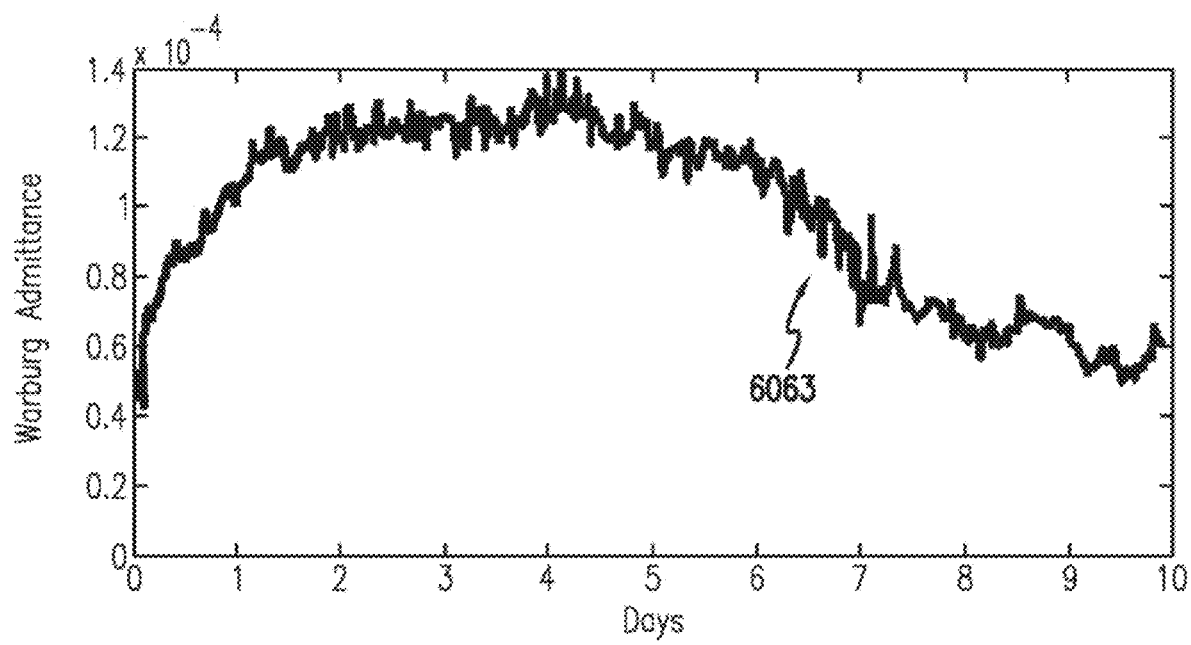
FIG. 69 shows a drop in Warburg Admittance during sensitivity loss, in accordance with embodiments of the invention.
Figure 70:
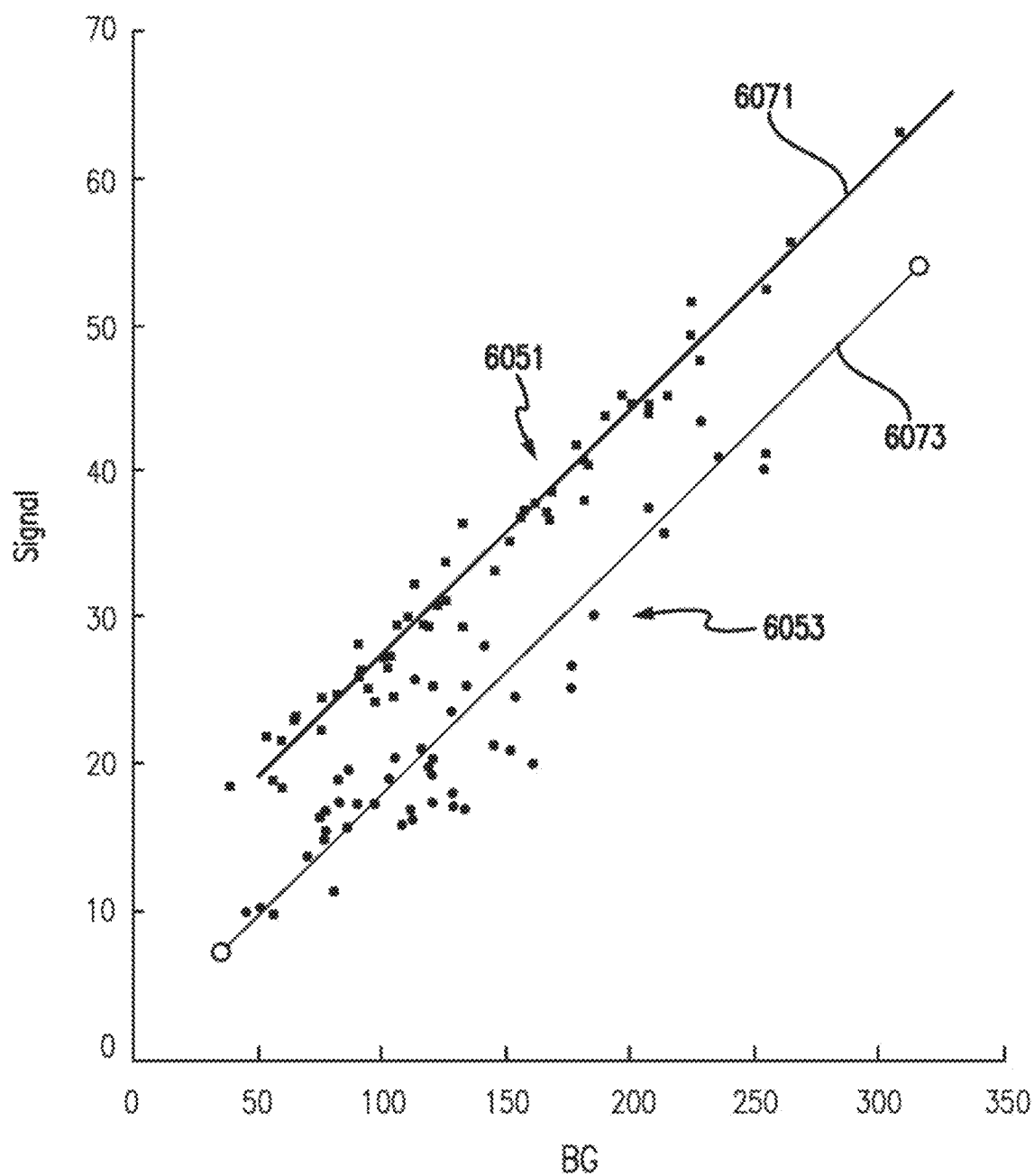
FIG. 70 shows calibration curves in accordance with embodiments of the invention.
Figure 71:
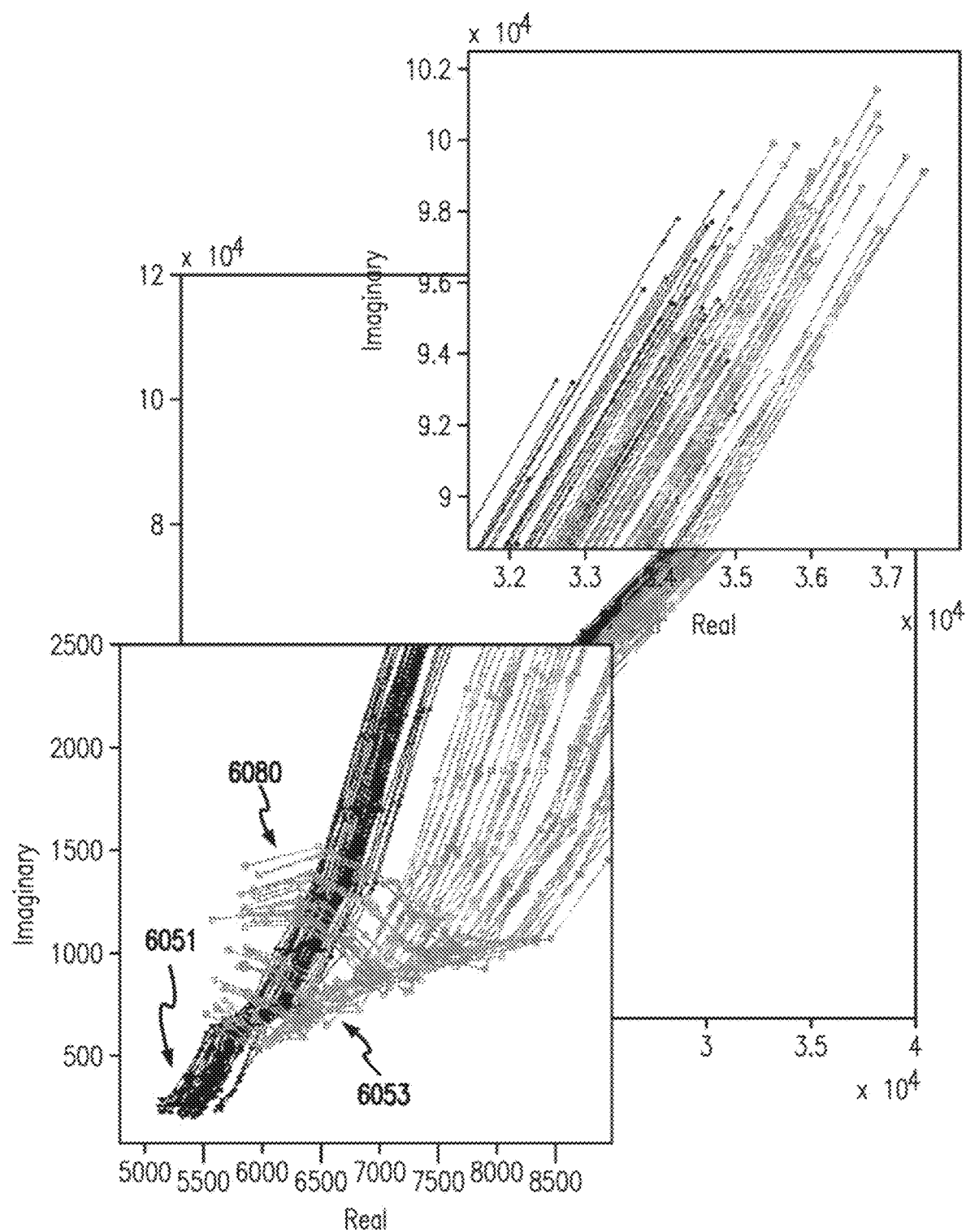
FIG. 71 shows a higher-frequency semicircle becoming visible on a Nyquist plot in accordance with embodiments of the invention.

With reference to FIGS. 68 and 69, it can be seen that the sensitivity loss is clearly shown by a rather significant increase in membrane resistance 6061, as well as a corresponding drop in Warburg Admittance 6063, during the second time period between days 6 and 9. Accordingly, FIG. 70 shows that the calibration curve 6073 for the second time period 6053 is parallel to, but shifted down from, the calibration curve 6071 for the first time period 6051. Also, as discussed hereinabove in connection with FIG. 57, as the membrane resistance (Rmem) increases, overall Nyquist plot shifts from left to right, and more of the high-frequency region semi-circle becomes visible. For the data of FIGS. 67A-70, this phenomenon is shown in FIG. 71, where the enlarged higher-frequency region of the Nyquist plot shows that the data from the second time period 6053 moves the plot from left to right as compared with the data from the first time period 6051, and that the semi-circle becomes more and more visible (6080) as the shift in the Nyquist plot progresses from left to right. In addition, the enlarged lower-frequency region of the plot shows that there is no significant change in $L_{nyquist}$.

Changes in Cdl and Rp, on the other hand, generally indicate that the electrode(s) may already be compromised, such that recovery may no longer be possible. Still, changes in Cdl and Rp may also be tracked, e.g., as a diagnostic tool, to determine, based on the direction/trend of the change in these parameters, whether, the drift or sensitivity loss has in fact reached a point where proper sensor operation is no longer recoverable or achievable. In this regard, in embodiments of the invention, respective lower and/or upper thresholds, or ranges of thresholds, may be calculated for each of Cdl and Rp, or for the change in slope, such that EIS output values for these parameters that fall outside of the respective threshold (range) may trigger, e.g., termination and/or replacement of the sensor due to unrecoverable sensitivity loss. In specific embodiments, sensor-design and/or patient-specific ranges or thresholds may be calculated, wherein the ranges/thresholds may be, e.g., relative to the change in Cdl, Rp, and/or slope.

Figure 72A:
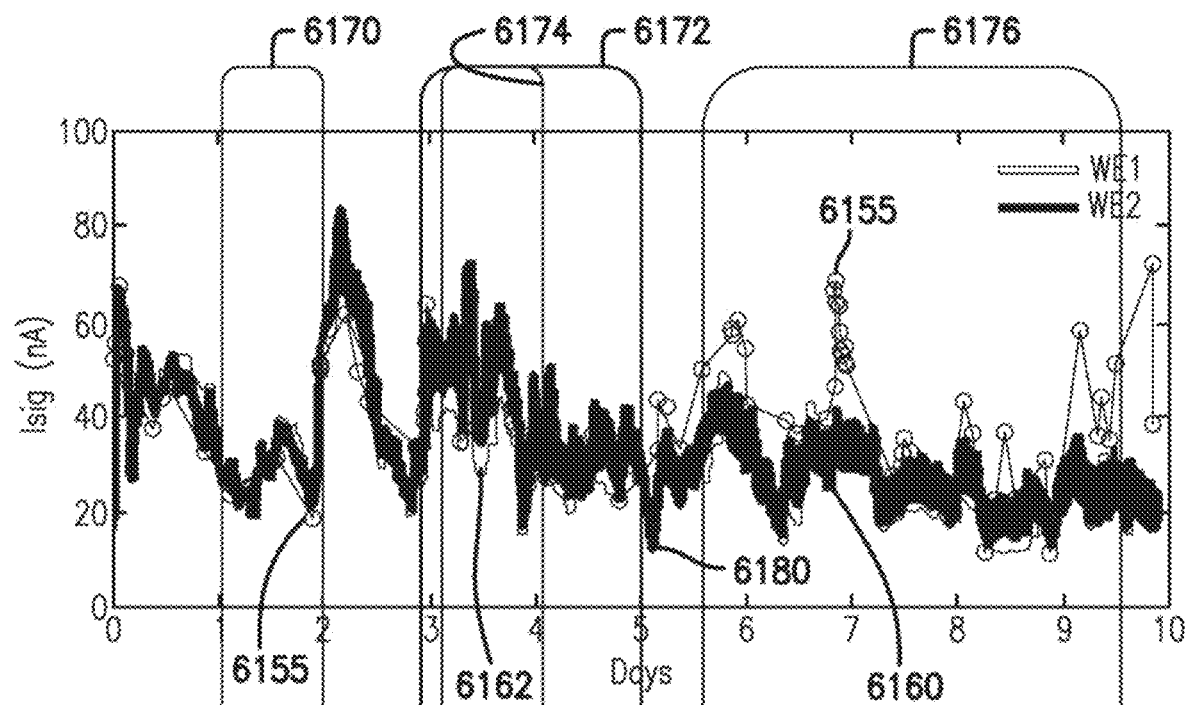
FIGS. 72A and 72B show Vcntr rail and Cdl decrease in accordance with embodiments of the invention.
Figure 72B:
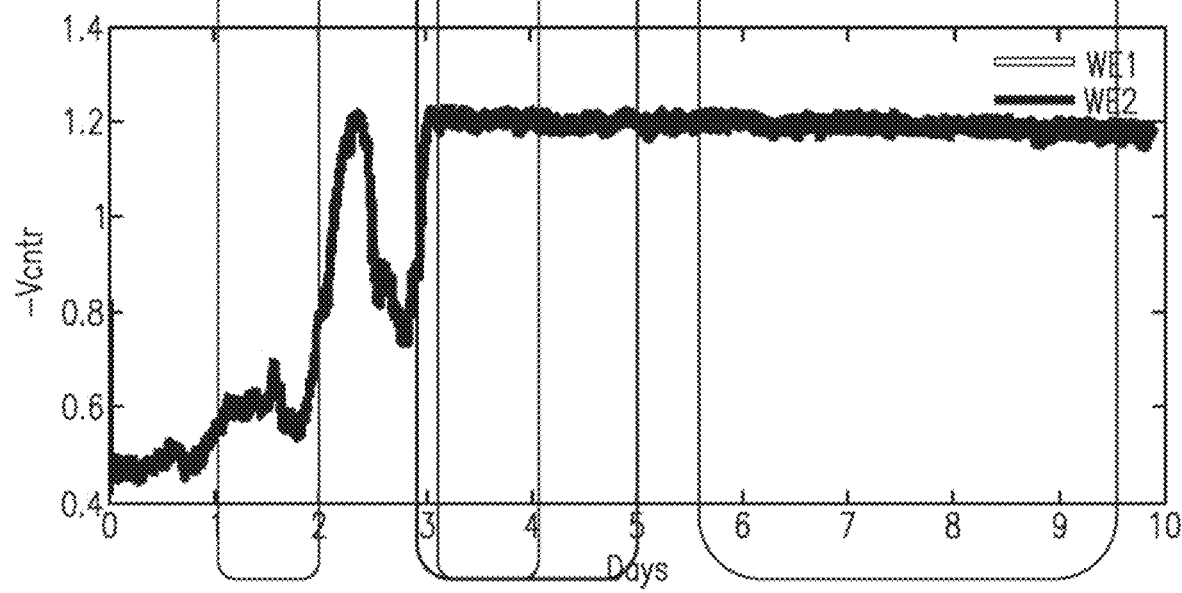
Figure 73:
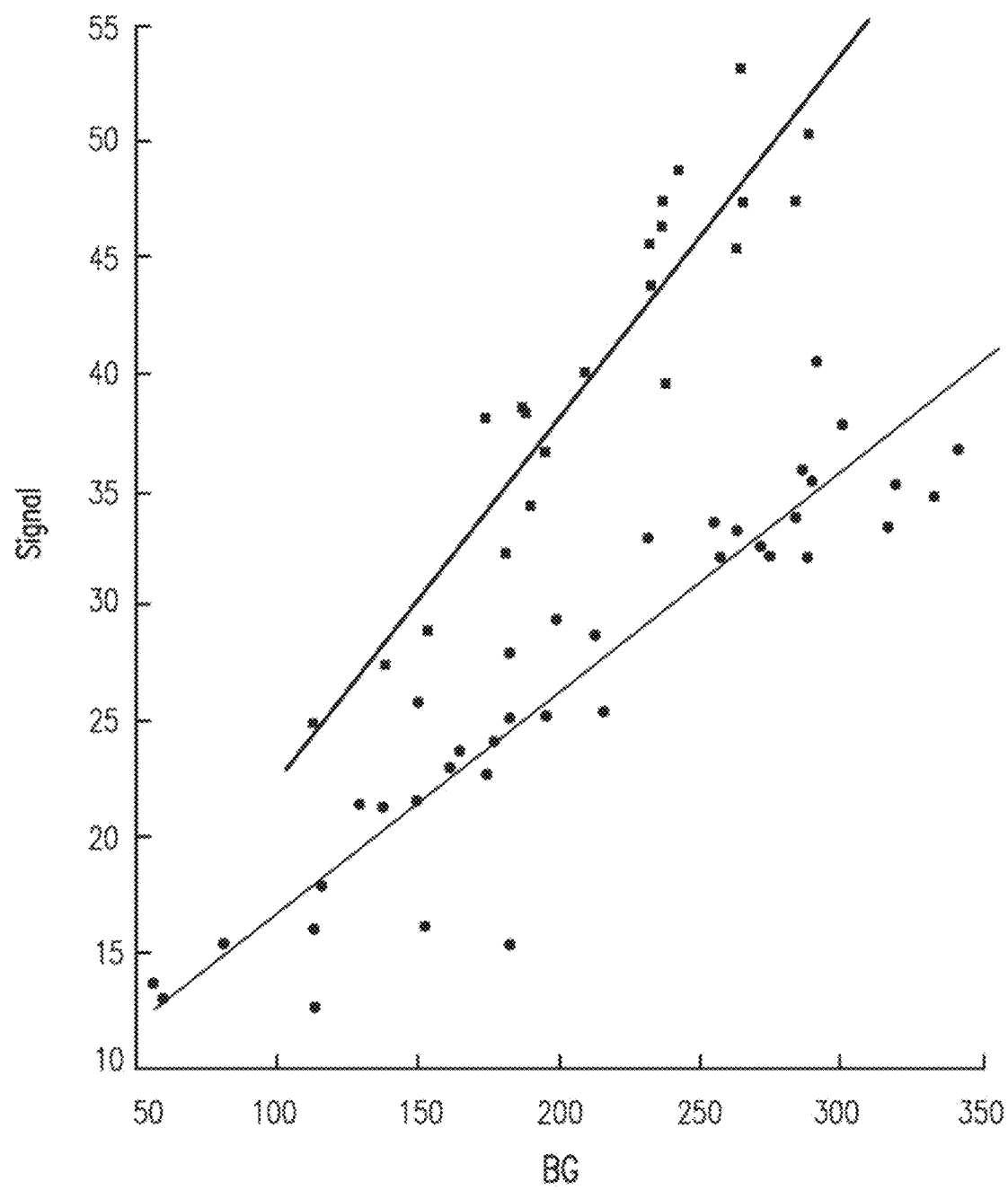
FIG. 73 shows the changing slope of calibration curves in accordance with embodiments of the invention
Figure 74:
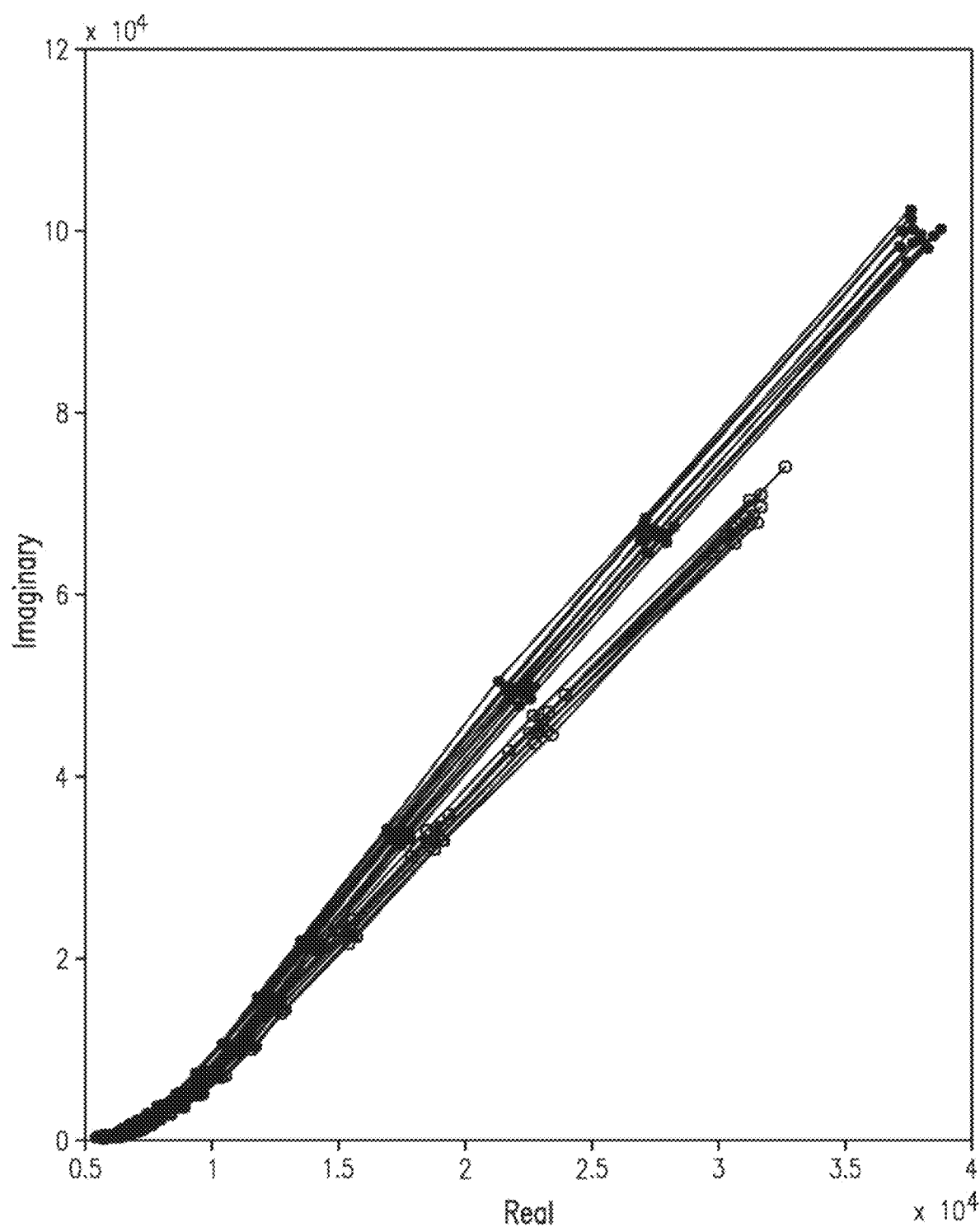
FIG. 74 shows the changing length of the Nyquist plot in accordance with embodiments of the invention.
Figure 75:
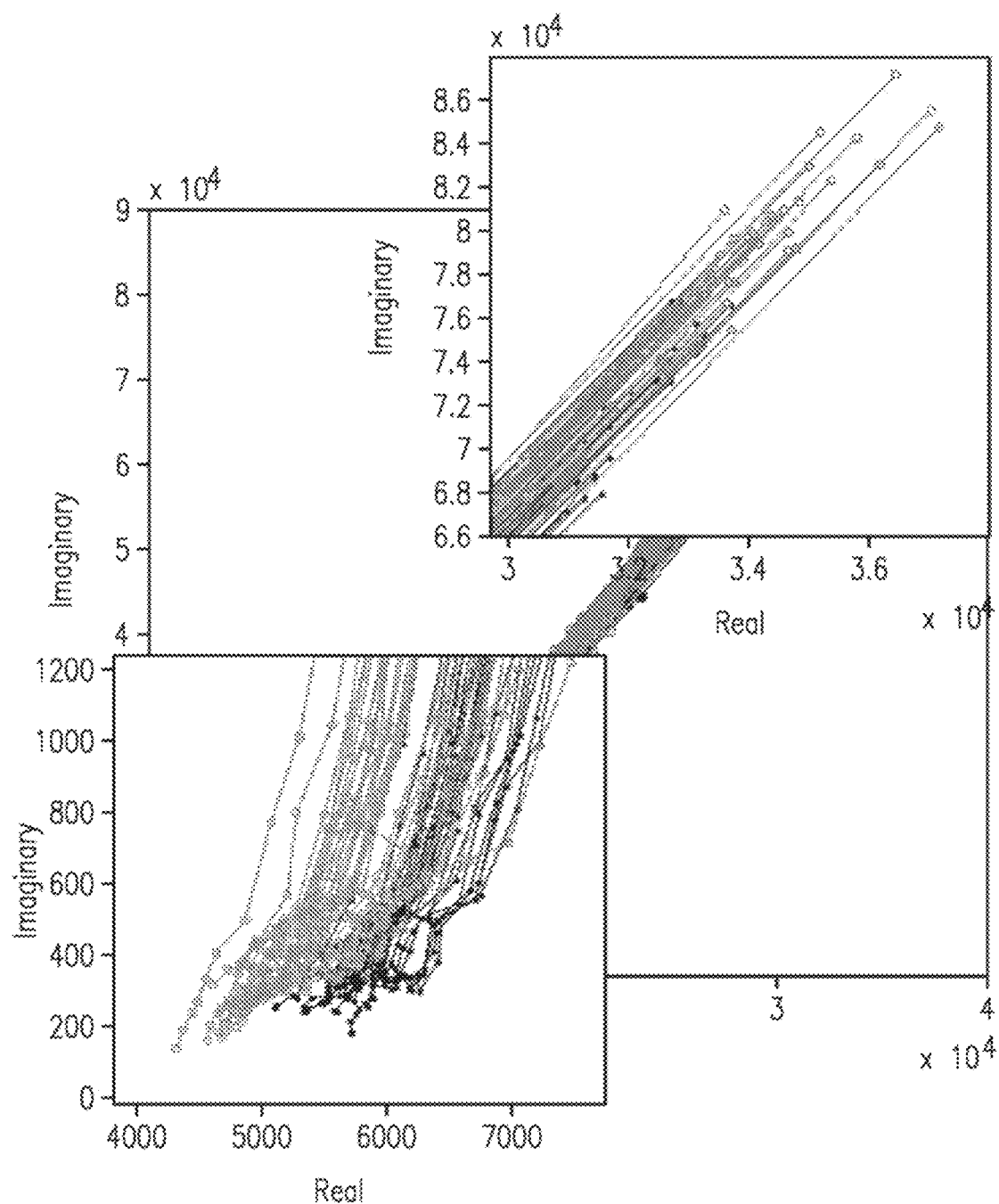
FIG. 75 shows enlarged views of the lower-frequency and the higher-frequency regions of the Nyquist plot of FIG. 74.

Graphically, FIG. 72A shows actual blood glucose (BG) data 6155 that is being recorded, overlaid by the Isig output from two working electrodes, WE16160 and WE26162. The graphs show data from a first-time window for day 1 (6170), a second time window for days 3-5 (6172), a third time window for day 3 (6174), and a fourth time window for days 5½ to 9½ (6176). Starting on Day 3, FIG. 72B shows that Vcntr rails at 1.2 volts. However, the decrease in sensitivity occurs from about Day 5 or so (6180). Once the Vcntr rails, the Cdl increases significantly, with a corresponding decrease in Rp, signifying a higher resistance to the overall electrochemical reaction. As expected, the slope of the calibration curve also changes (decreases), and $L_{nyquist}$ becomes shorter (see FIGS. 73-75). It is noted that, in embodiments of the invention, the occurrence of a Vcntr rail may be used to trigger termination of a sensor as unrecoverable.

Figure 76:
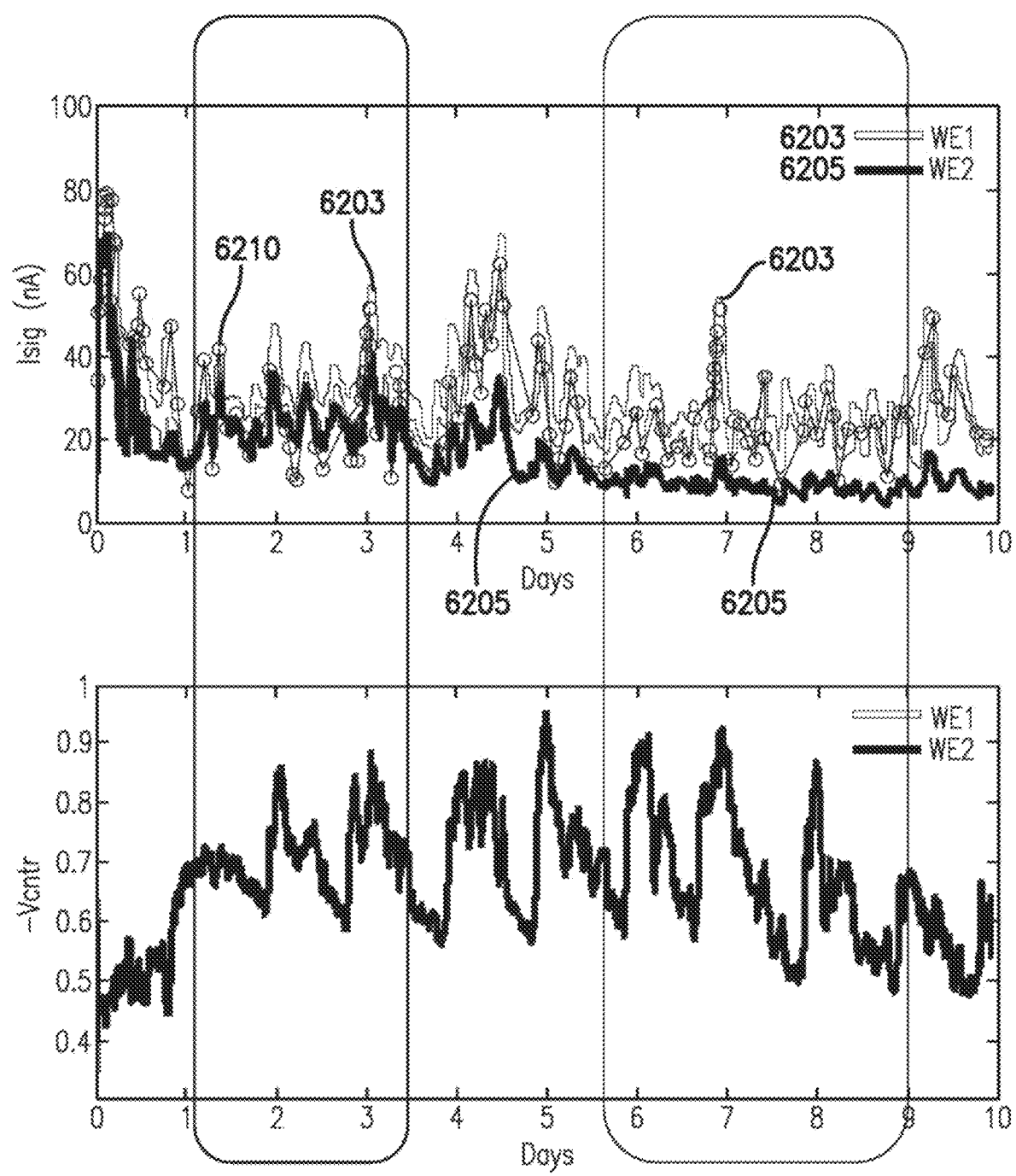
FIGS. 76A and 76B show the combined effect of increase in membrane resistance, decrease in Cdl, and Vcntr rail in accordance with embodiments of the invention.
Figure 77:
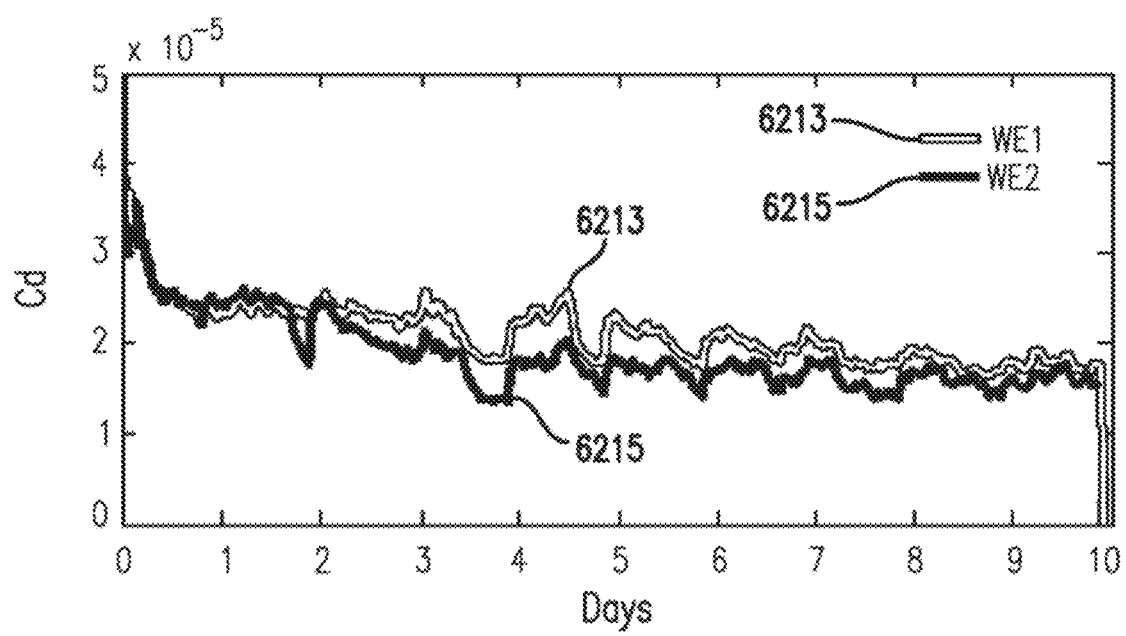
FIG. 77 shows relative Cdl values for two working electrodes in accordance with embodiments of the invention.
Figure 78:
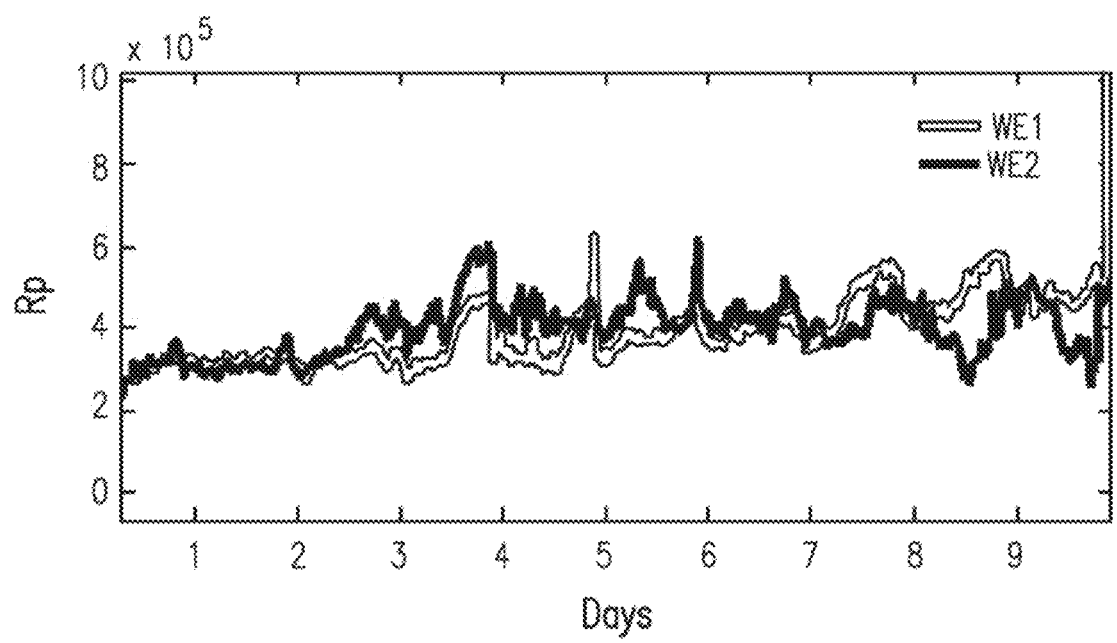
FIG. 78 shows relative Rp values for two working electrodes in accordance with embodiments of the invention.

The combined effect of the increase in membrane resistance, the decrease in Cdl, and Vcntr rail is shown in FIGS. 76A-76B and 77-80. In FIG. 76A, actual blood glucose (BG) data 6210 is overlaid by the Isig output from two working electrodes, WE16203 and WE26205. As can be seen, WE1 generally tracks the actual BG data 6210—i.e., WE1 is functioning normally. The Isig from WE2, on the other hand, appears to start at a lower point, and continues a downwards trend all the way from the beginning to Day 10, thus signifying a gradual loss of sensitivity. This is consistent with the Cdl for WE2 (6215) being lower than that for WE1 (6213), as shown in FIG. 77, even though the Cdl for both working electrodes generally exhibits a downward trend.

Figure 79:
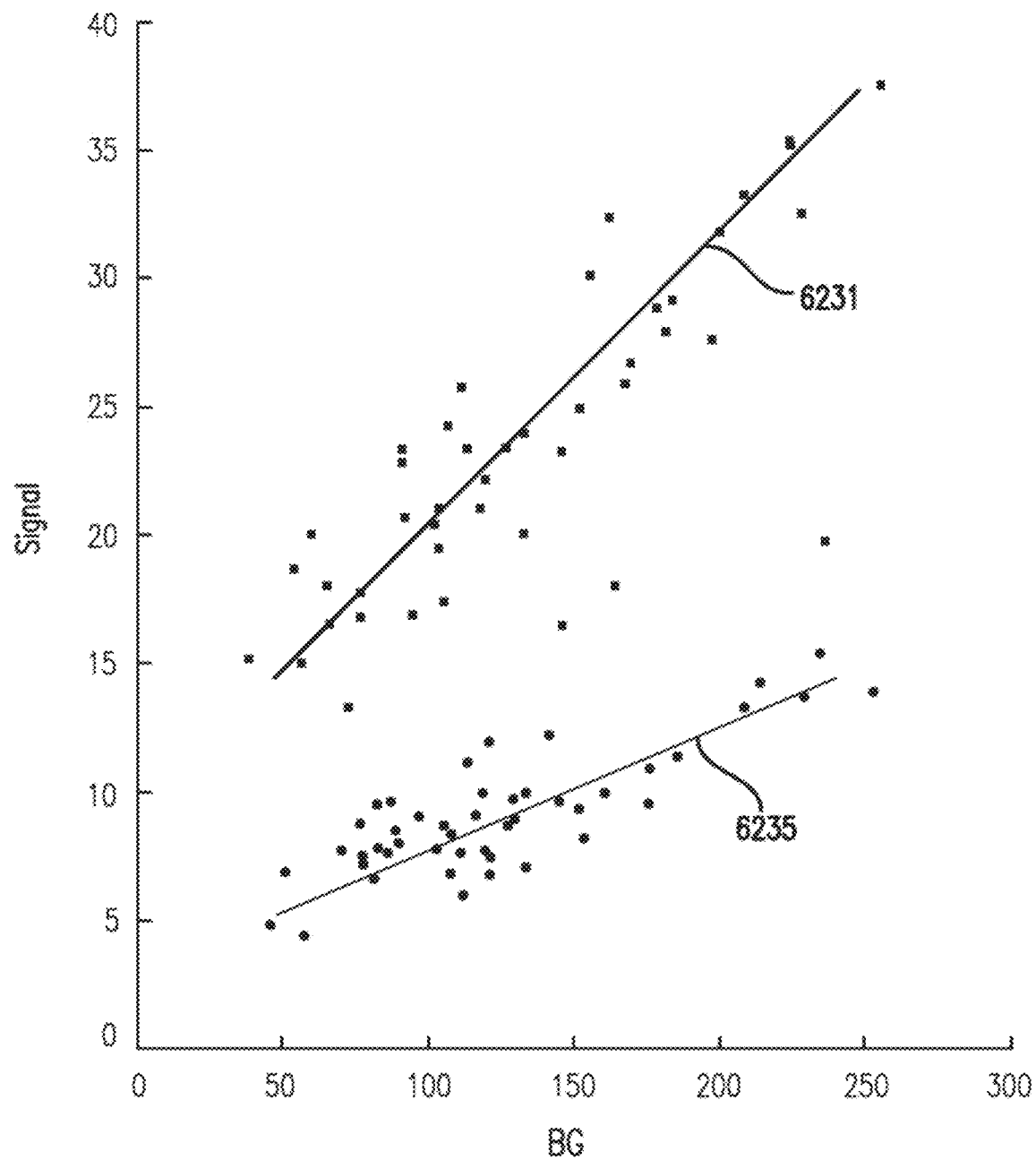
FIG. 79 shows the combined effect of changing EIS parameters on calibration curves in accordance with embodiments of the invention.
Figure 80:
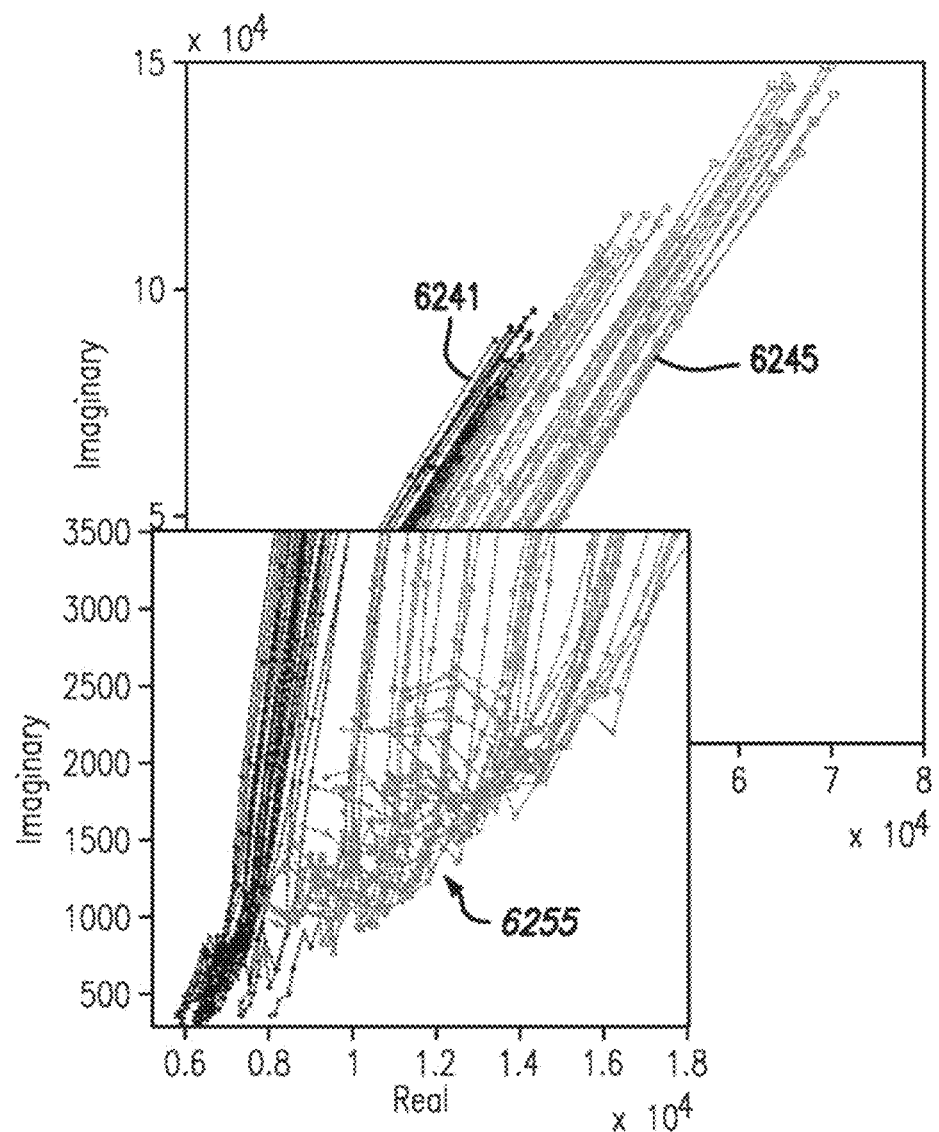
FIG. 80 shows that, in accordance with embodiments of the invention, the length of the Nyquist plot in the lower-frequency region is longer where there is sensitivity loss.

FIG. 79 shows the combined effect on the calibration curve, where both the offset and the slope of the linear fit for the period of sensitivity loss (6235) change relative to the calibration curve 6231 for the normally-functioning time windows. In addition, the Nyquist plot of FIG. 80 shows that, in the lower-frequency region, the length of the Nyquist plot is longer where there is sensitivity loss (6245), as compared to where the sensor is functioning normally (6241). Moreover, near the inflection point, the semicircles (6255) become more and more visible where there is loss of sensitivity. Importantly, where there is sensitivity loss, the Nyquist plot of FIG. 80 shifts horizontally from left to right as a function of time. In embodiments of the invention, the latter shift may be used as a measure for compensation or self-correction in the sensor.

Thus, it has been discovered that, as an EIS signature, a temporary dip may be caused by increased membrane resistance (Rmem) and/or local Rsol increase. An increase in Rmem, in turn, is reflected by increased higher-frequency imaginary impedance. This increase may be characterized by the slope at high frequencies, ($S_{nyquist}$)—which, for simplicity, may be illustratively estimated as the slope between 8 kHz and 128 Hz. In addition, Vcntr railing increases Cdl and decrease Rp, such that the length and slope decrease; this may be followed by gradual Cdl decrease and Rp increase associated with sensitivity loss. In general, a decrease in Cdl, combined with an increase in Rp (length increase) and in Rmem may be sufficient to cause sensitivity loss.

Figure 81:
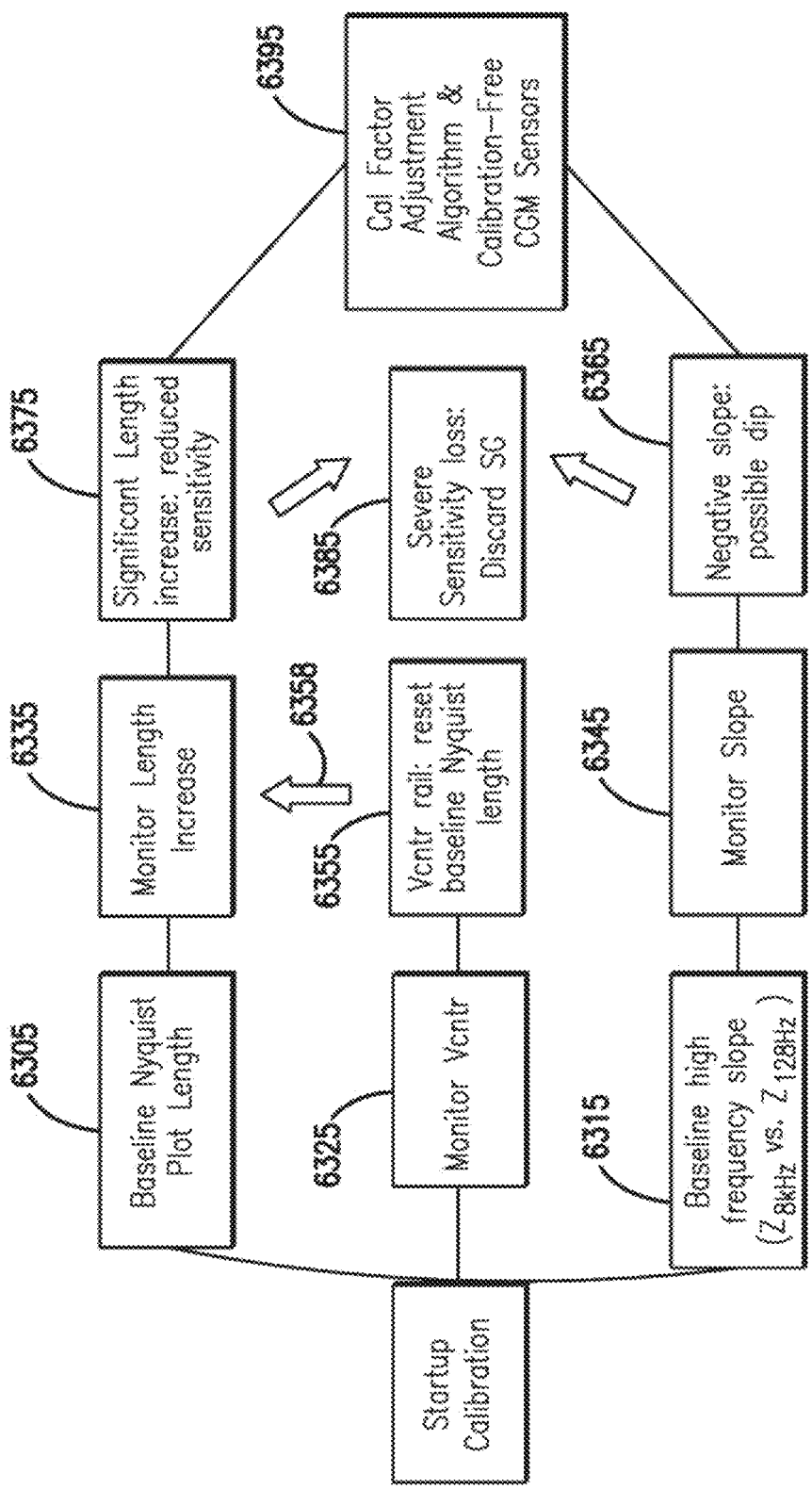
FIG. 81 is a flow diagram for sensor self-calibration based on the detection of sensitivity change in accordance with embodiments of the invention.

In accordance with embodiments of the invention, an algorithm for sensor self-calibration based on the detection of sensitivity change and/or loss is shown in FIG. 81. At blocks 6305 and 6315, a baseline Nyquist plot length ($L_{nyquist}$) and a baseline higher frequency slope, respectively, are set, so as to be reflective of the EIS state at the beginning of sensor life. As noted, the Nyquist plot length is correlated to the Cdl, and the higher frequency Nyquist slope is correlated to the membrane resistance. The process then continues by monitoring the Nyquist plot length (6335) and the higher frequency slope (6345), as well as the Vcntr value (6325). When the Vcntr rails, the baseline $L_{nyquist}$ is adjusted, or reset 6355, as the railing of the Vcntr changes the Cdl significantly. There is therefore a feedback loop 6358 to accommodate real-time changes in the monitored EIS parameters.

As shown in block 6375, as the length of the Nyquist plot is monitored, a significant increase in that length would indicate reduced sensitivity. In specific embodiments, sensor-design and/or patient-specific ranges or thresholds may be calculated, wherein the ranges/thresholds may be, e.g., relative to the change in the length of the Nyquist plot. Similarly, a more negative higher-frequency slope $S_{nyquist}$ corresponds to an increased appearance of the high-frequency semicircle and would be indicative of a possible dip 6365. Any such changes in $L_{nyquist}$ and $S_{nyquist}$ are monitored, e.g., either continuously or periodically and, based on the duration and trend of the reduction in sensitivity, a determination is made as to whether total (i.e., severe) sensitivity loss has occurred, such that specific sensor glucose (SG) value(s) should be discarded (6385). In block 6395, the Cal Factor may be adjusted based on the monitored parameters, so as to provide a "calibration-free" CGM sensor. It is noted that, within the context of the invention, the term "calibration-free" does not mean that a particular sensor needs no calibration at all. Rather, it means that the sensor can self-calibrate based on the EIS output data, in real time, and without the need for additional finger-stick or meter data. In this sense, the self-calibration may also be referred to as "intelligent" calibration, as the calibration is not performed based on a predetermined temporal schedule, but on an as-needed basis, in real-time.

Figure 82:
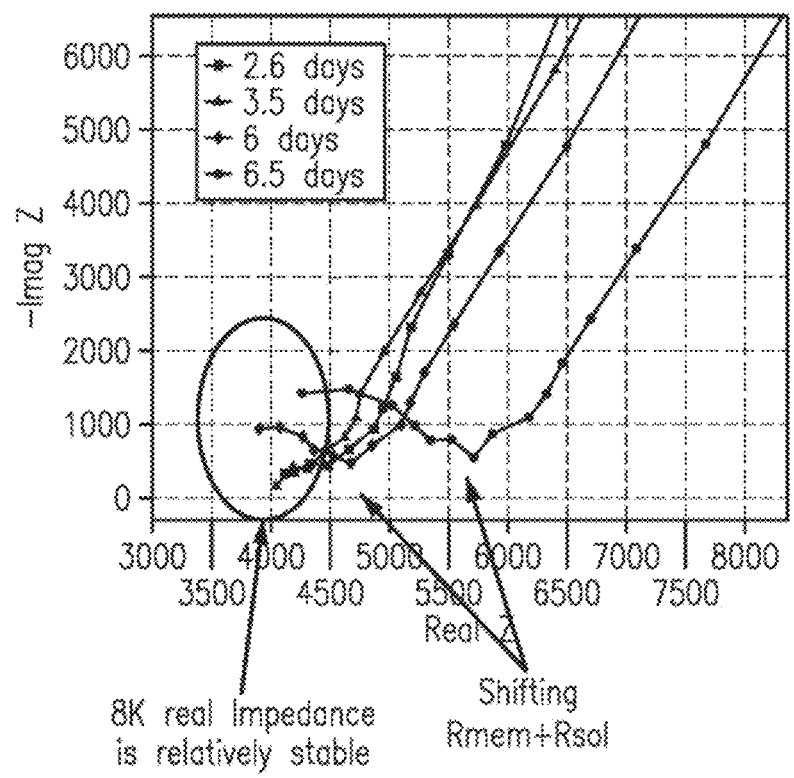
FIG. 82 illustrates a horizontal shift in Nyquist plot as a result of sensitivity loss, in accordance with embodiments of the invention.

In embodiments of the invention, algorithms for adjustment of the Cal Factor (CF) and/or offset may be based on the membrane resistance which, in turn, may be estimated by the sum of Rmem and Rsol. As membrane resistance is representative of a physical property of the sensor, it generally cannot be estimated from EIS data run for a single frequency. Put another way, it has been observed that no single frequency will consistently represent membrane resistance, since frequencies shift depending on sensor state. Thus, FIG. 82, e.g., shows that, when there is some sensitivity loss, there is a horizontal shift in the Nyquist plot, and therefore, a shift in the inflection point that estimates the value of Rmem+Rsol. In this case, the shift in the real component of impedance is actually quite large. However, if only the high-frequency (e.g., at 8 kHz) real impedance is monitored, there is little to no shift at all, as indicated by the encircled region in FIG. 82.

Figure 83:
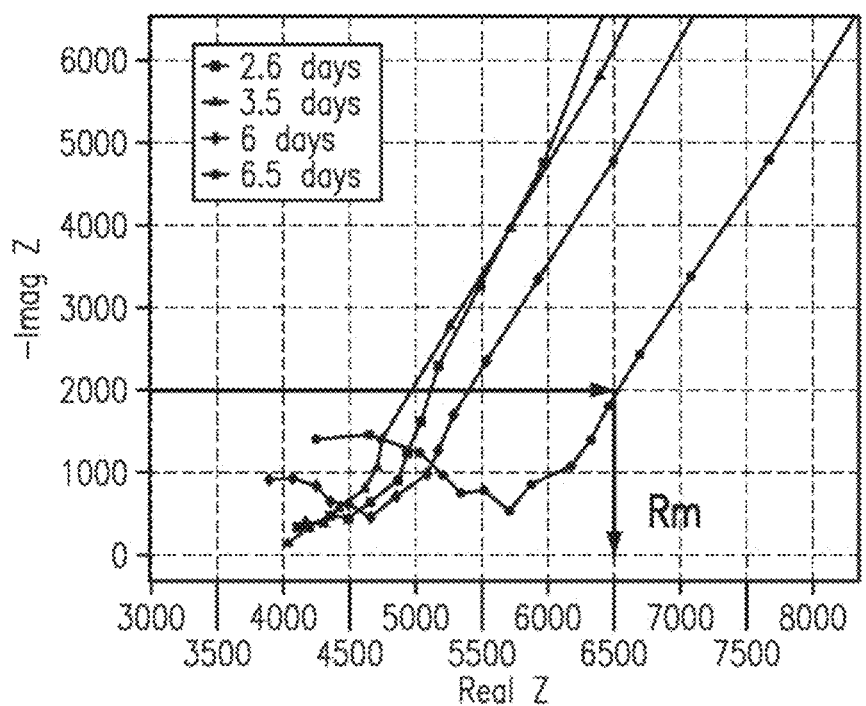
FIG. 83 shows a method of developing a heuristic EIS metric based on a Nyquist plot in accordance with embodiments of the invention.

There is therefore a need to track membrane resistance in a physically meaningful way. Ideally, this may be done through model fitting, where Rmem and Rsol are derived from model fitting, and Rm is calculated as Rm=Rmem+Rsol. However, in practice, this approach is not only computationally expensive, as it may take an unpredictably long amount of time, but also susceptible to not converging at all in some situations. Heuristic metrics may therefore be developed to approximate, or estimate, the value of Rm=Rmem+Rsol. In one such metric, Rmem+Rsol is approximated by the value of the real-impedance intercept at a fairly stable imaginary impedance value. Thus, as shown in FIG. 83, for example, a region of general stability for the imaginary impedance (on the Y axis) may be identified at about 2000Ω. Taking this as a reference value and traveling across, parallel to the X axis, a value proportional to Rm may then be approximated as the real-impedance value of where the reference line crosses the Nyquist plot. An interpolation between frequencies may be performed to estimate ΔRm ∝Δ(Rmem+Rsol).

Figure 84:
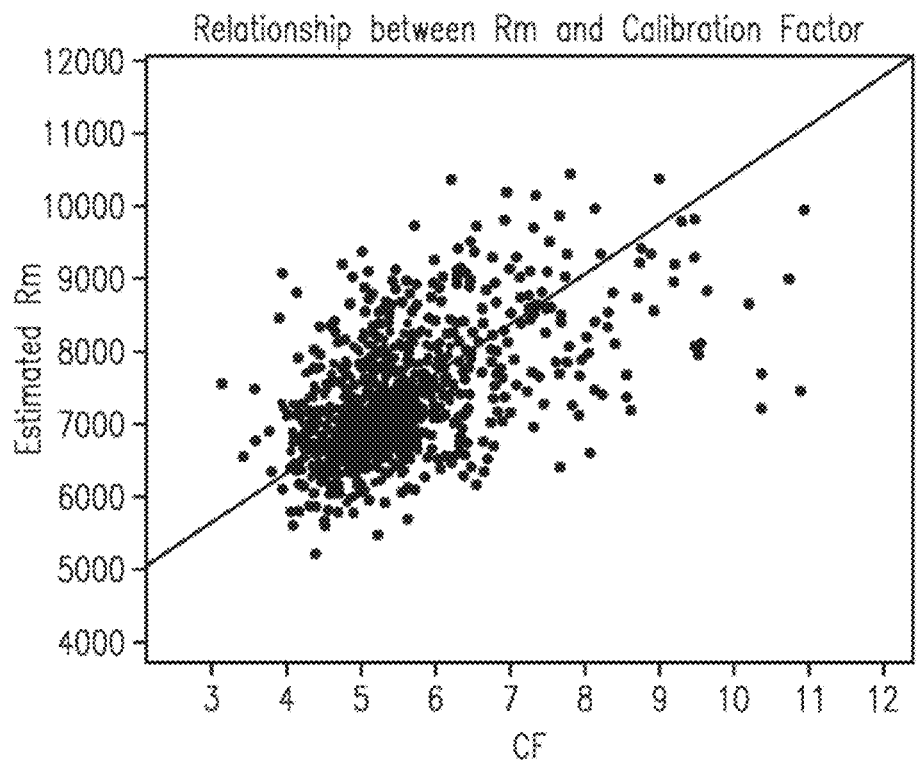
FIG. 84 shows the relationship between Rm and Calibration Factor in accordance with embodiments of the invention.
Figure 85:
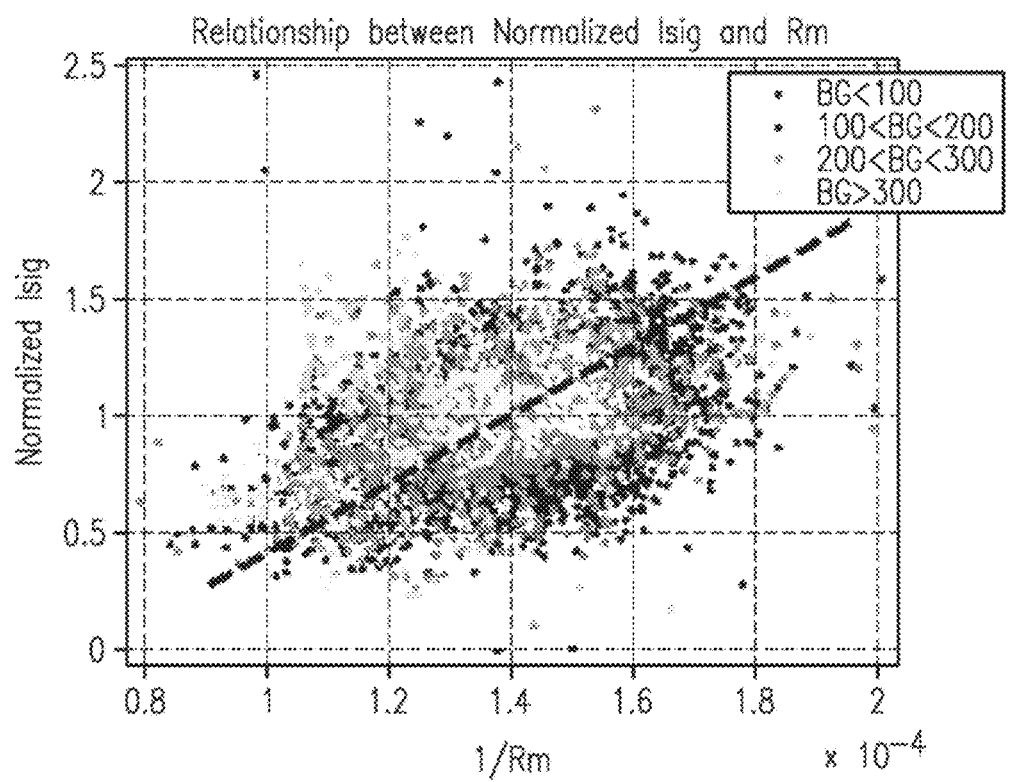
FIG. 85 shows the relationship between Rm and normalized Isig in accordance with embodiments of the invention.

Having estimated the value of Rm as discussed above, the relationship between Rm and the Cal Factor (CF) and/or Isig may then be explored. Specifically, FIG. 84 shows the relationship between the estimated Rm and CF, wherein the former is directly proportional to the latter. The data points for purposes of FIG. 84 were derived for steady state sensor operation. FIG. 85 shows a plot of normalized Isig vs. 1/Rm, where Isig has been normalized by the BG range (of the Isig). As can be seen from the figure, Isig can be adjusted based on changes in Rm. Specifically, an increase in 1/Rm (i.e., reduced membrane resistance) will lead to a proportional increase in Isig, as there is a linear relationship between Isig and 1/Rm.

Thus, in one embodiment, an algorithm for adjustment of the Cal Factor would entail monitoring the change in membrane resistance based on a reference Cal Factor, and then modifying the Cal Factor proportionally based on the correlation between Rm and CF. In other words:

$$\frac{d(CF)}{dt} \propto \frac{d(Rm)}{dt}$$

$$\Rightarrow \text{Adjusted } CF \propto \left(\frac{d(Rm)}{dt}\right) \times CF$$

In another embodiment, a Cal Factor adjustment algorithm may entail modification of Isig based on proportional changes in 1/Rm, and independently of CF calculations. Thus, for purposes of such an algorithm, the adjusted Isig is derived as $$\text{Adjusted } Isig \propto \left(\frac{d\left(\frac{1}{R_m}\right)}{dt}\right) \times Isig$$

Experiments have shown that the most dramatic CF changes occur in first 8 hours of sensor life. Specifically, in one set of in-vitro experiments, Isig was plotted as a function of time, while keeping various glucose levels constant over the life of the sensor. EIS was run every 3 minutes for the first 2 hours, while all model parameters were estimated and tracked over time. As noted previously, given a limited spectrum EIS, Rmem and Rsol cannot be (independently) estimated robustly. However, Rm=Rmem+Rsol can be estimated.

Figure 86:
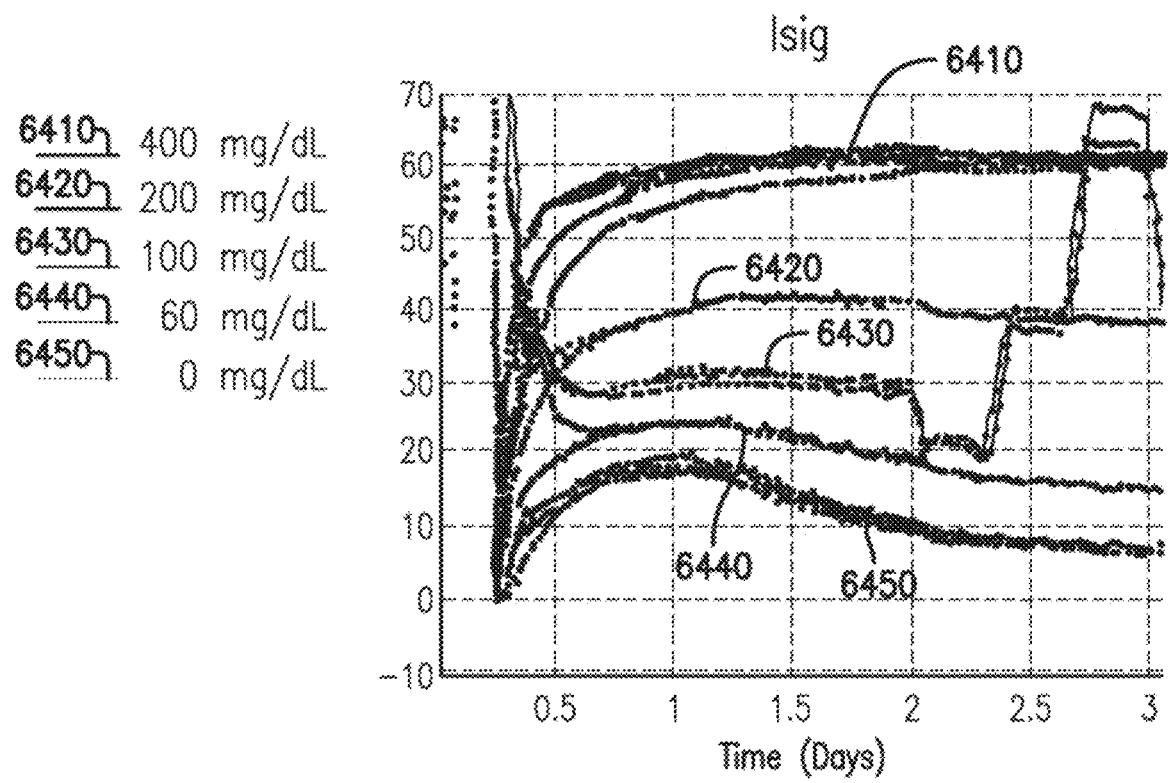
FIG. 86 shows Isig plots for various glucose levels as a function of time, in accordance with embodiments of the invention.
Figure 87:
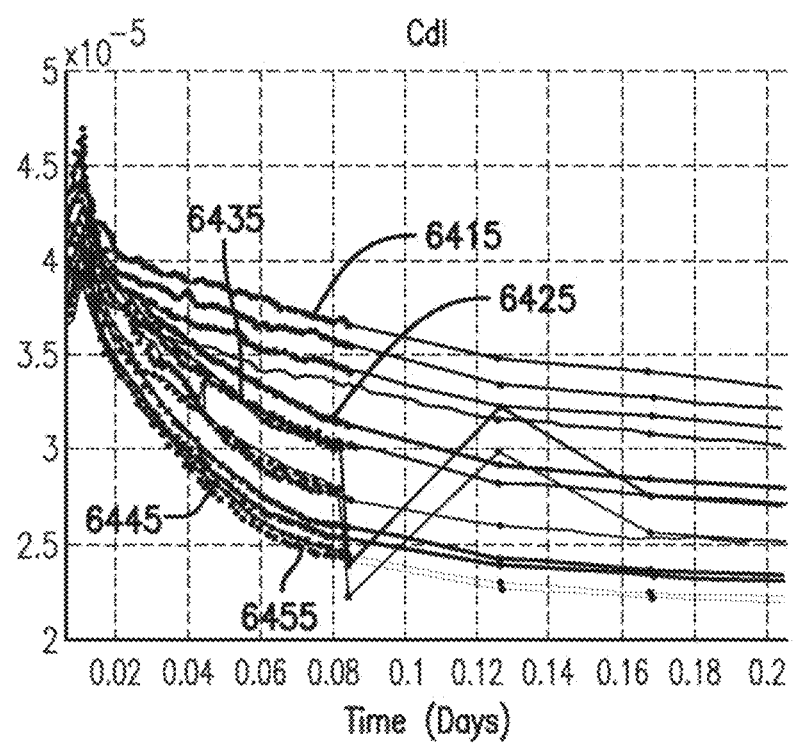
FIG. 87 shows Cdl plots for various glucose levels as a function of time, in accordance with embodiments of the invention.

FIG. 86 shows the plots for Isig over time for various glucose levels, including 400 mg/dL (6410), 200 mg/dL (6420), 100 mg/dL (6430), 60 mg/dL (6440), and 0 mg/dL (6450). At startup, generally dramatic changes appear in all parameters. One example is shown in FIG. 87, where Cdl is plotted as a function of time, with plot 6415 corresponding to 400 mg/dL glucose, plot 6425 corresponding to 200 mg/dL glucose, plot 6435 corresponding to 100 mg/dL glucose, plot 6445 corresponding to 60 mg/dL glucose, and plot 6455 corresponding to 0 mg/dL glucose. As is the case in the illustrative example of FIG. 87, most parameters correlate well with changes in the first 0.5 hour, but generally may not account for changes in timeframes >0.5 hour.

Figure 88:
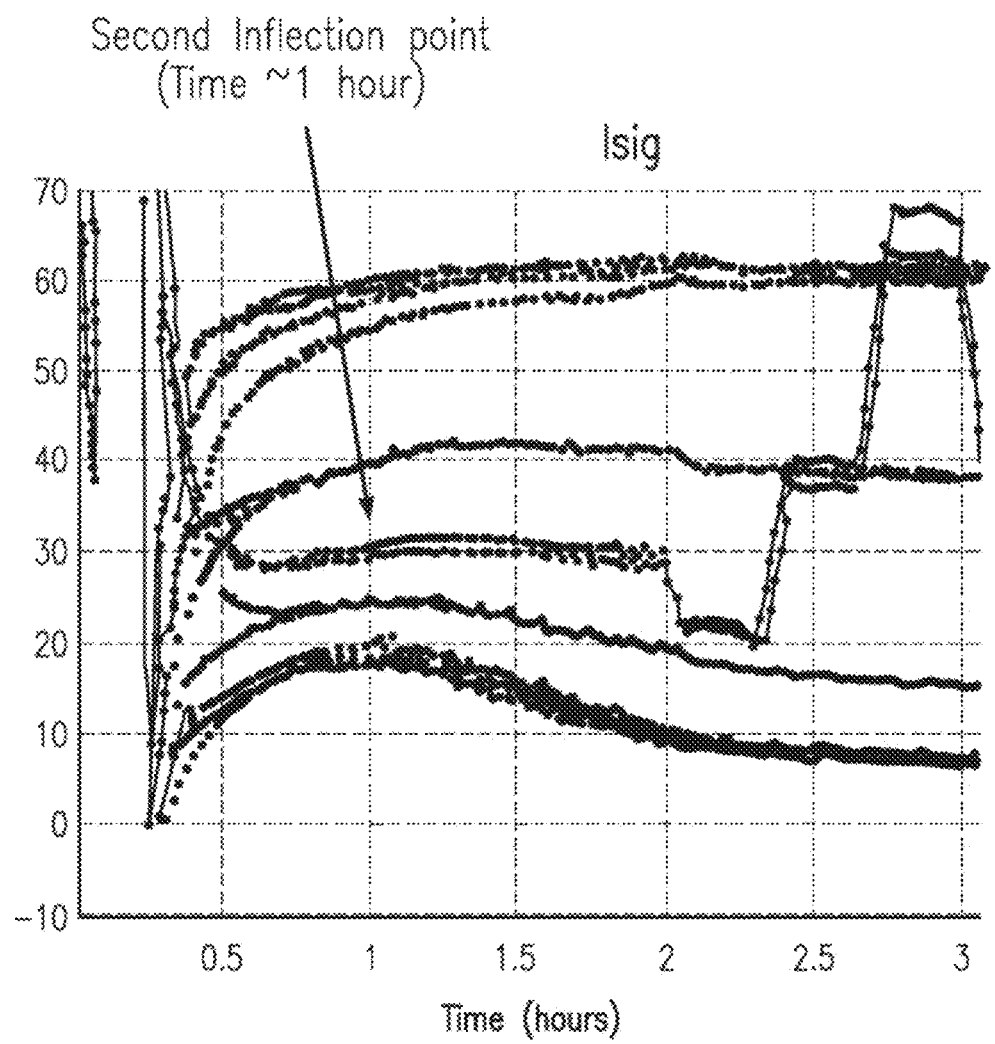
FIG. 88 shows a second inflection point for the plots of FIG. 86, in accordance with embodiments of the invention.
Figure 89:
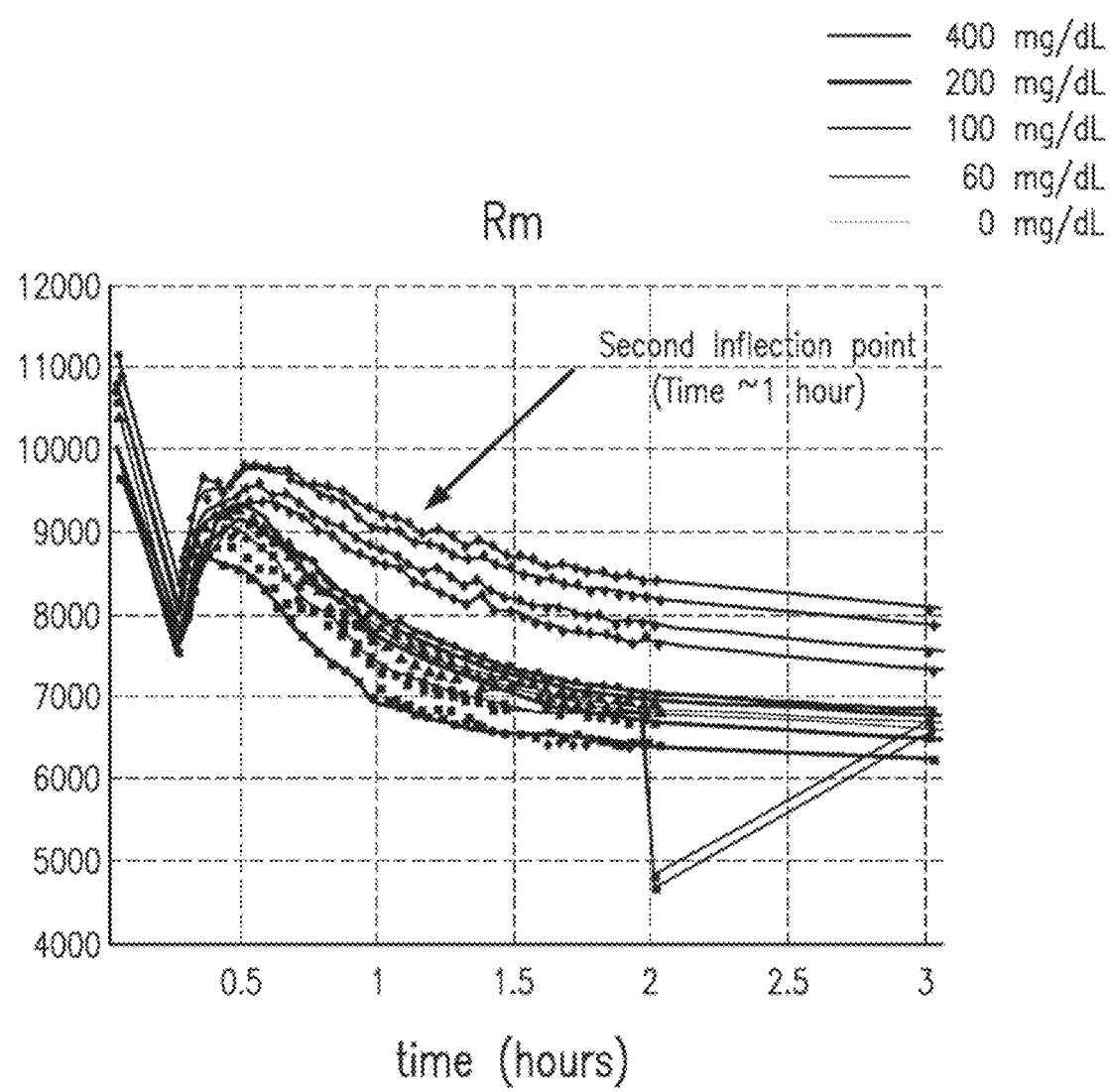
FIG. 89 shows a second inflection point for Rm corresponding to the peak in FIG. 88, in accordance with embodiments of the invention.

It has been discovered, however, that Rm=Rmem+Rsol is the only parameter that can account for changes in Isig over a similar startup time frame. Specifically, FIG. 88 shows the same graph as in FIG. 86, except for an indication that there is a peak, or second inflection point, that occurs at about T=1 hour, especially at low glucose levels, e.g., 100 mg/dL and lower. However, of all the EIS parameters that were studied, membrane resistance was the only one that exhibited a relationship to this change in Isig; the other parameters generally tend to proceed fairly smoothly to steady state. Thus, as shown in FIG. 89, Rm also exhibits a second inflection point at about T=1 hour that corresponds to the peak in Isig at the same time.

Figure 90:
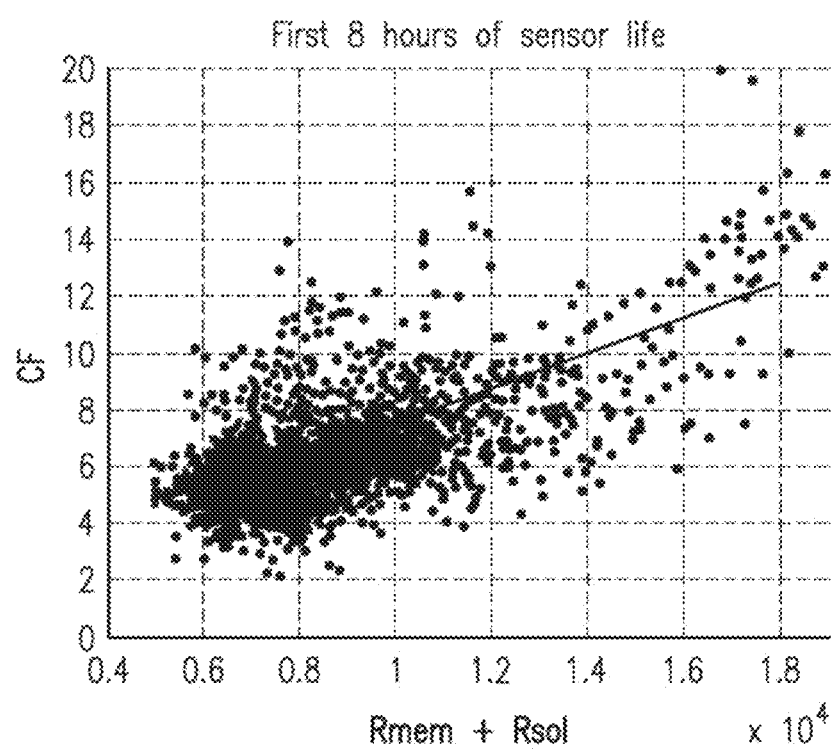
FIG. 90 shows one illustration of the relationship between Calibration Factor (CF) and Rmem+Rsol in accordance with embodiments of the invention.
Figure 92A:
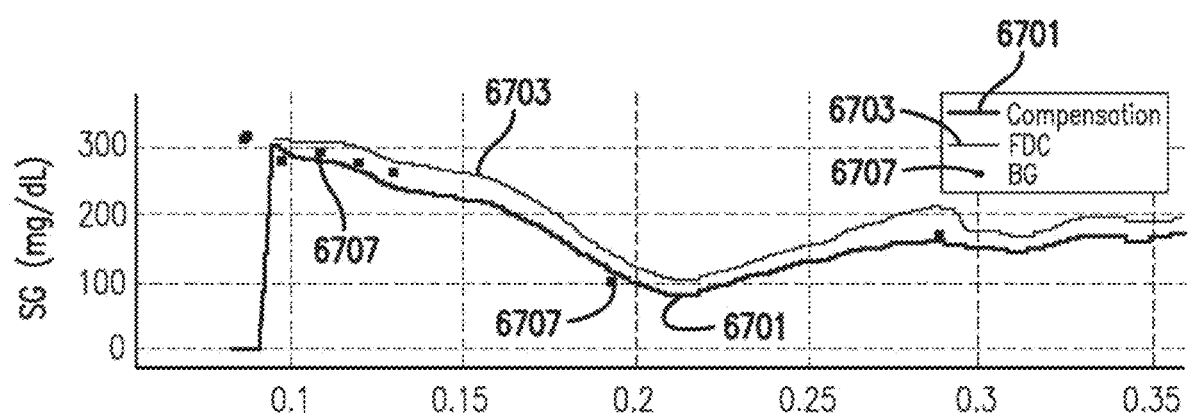
FIGS. 92A-92C show Calibration Factor adjustment in accordance with embodiments of the invention.
Figure 92B:
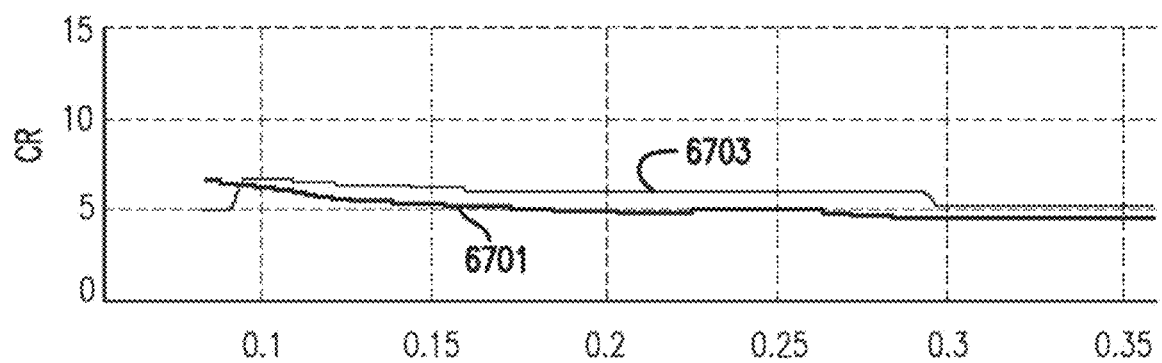
Figure 92C:
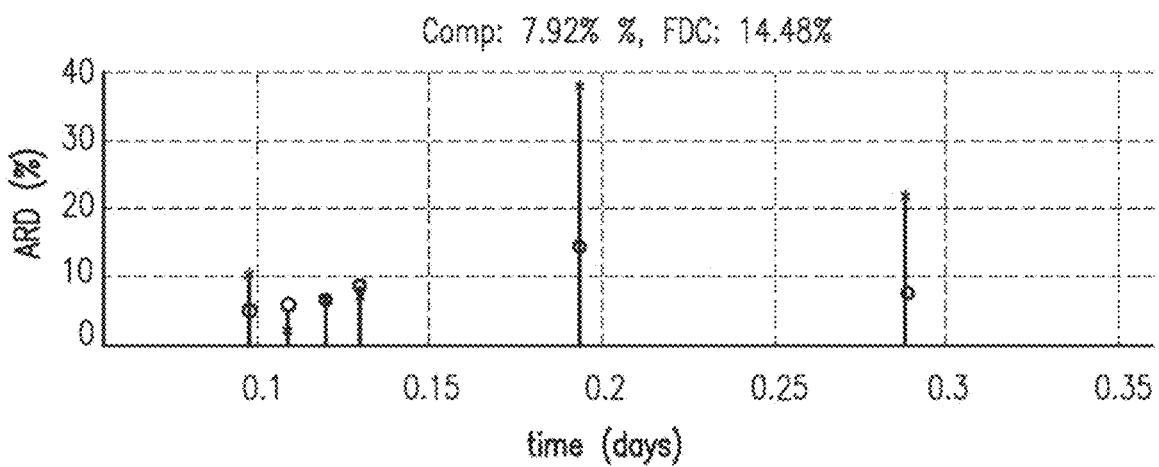
Figure 93A:
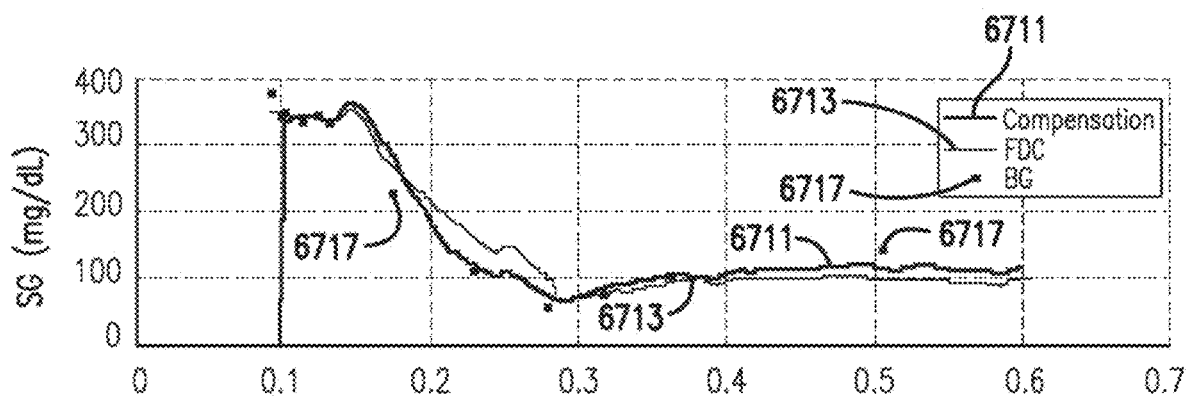
FIGS. 93A-93C show Calibration Factor adjustment in accordance with embodiments of the invention.
Figure 93B:
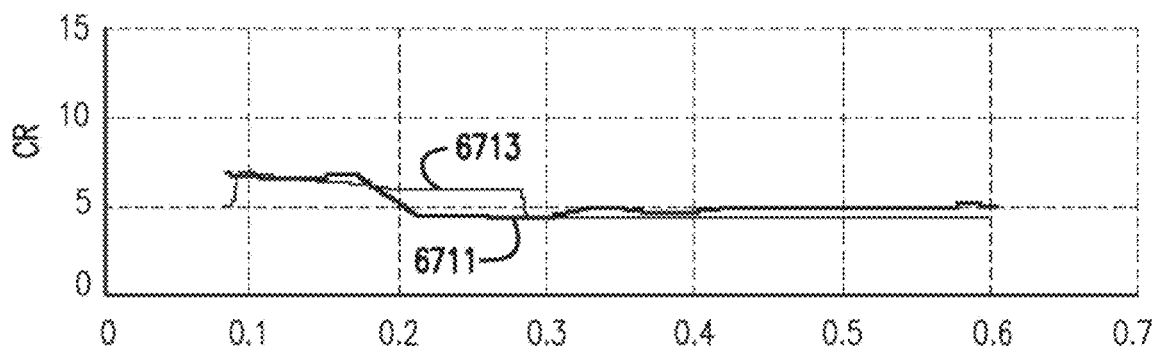
Figure 93C:
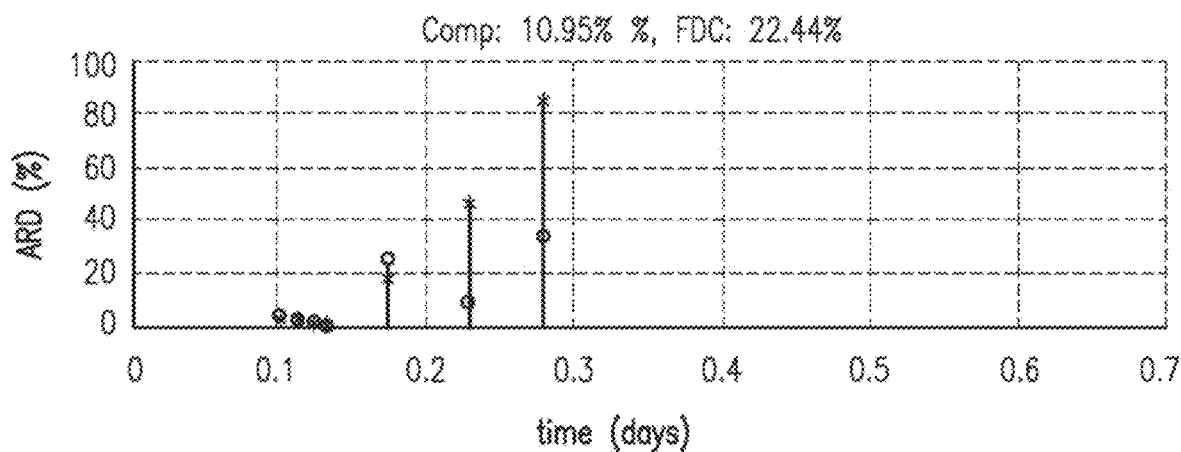
Figure 94A:
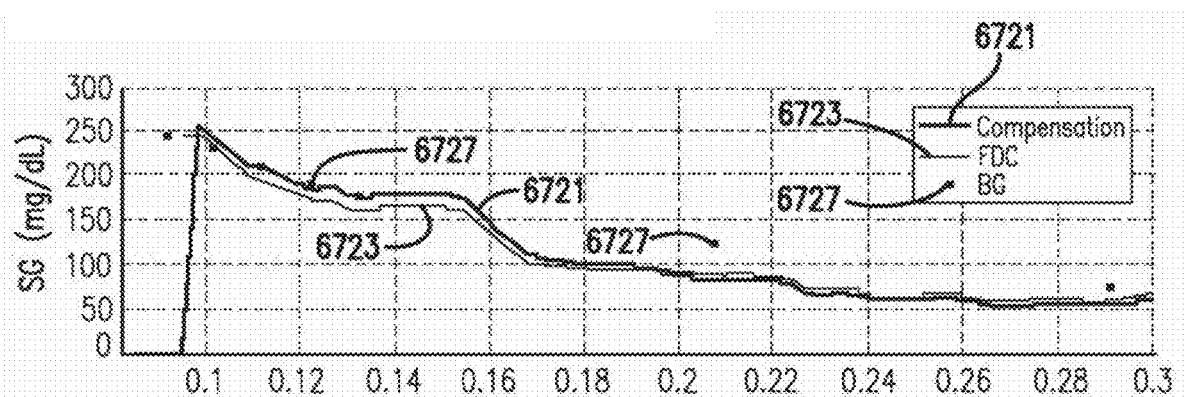
FIGS. 94A-94C show Calibration Factor adjustment in accordance with embodiments of the invention.
Figure 94B:
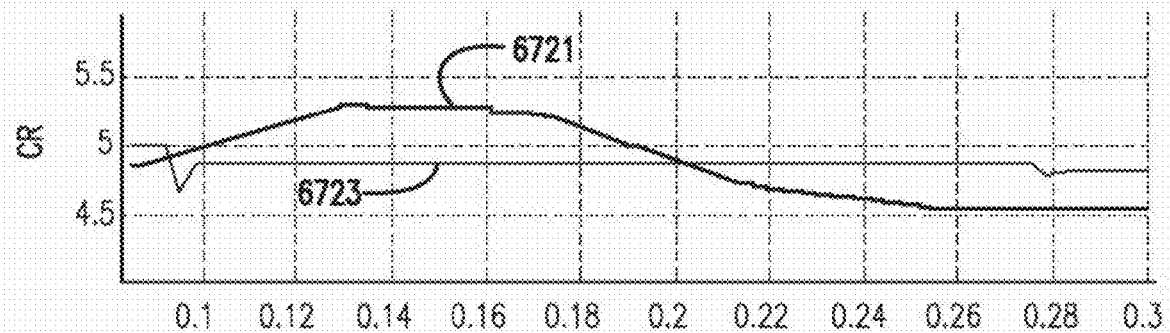
Figure 94C:
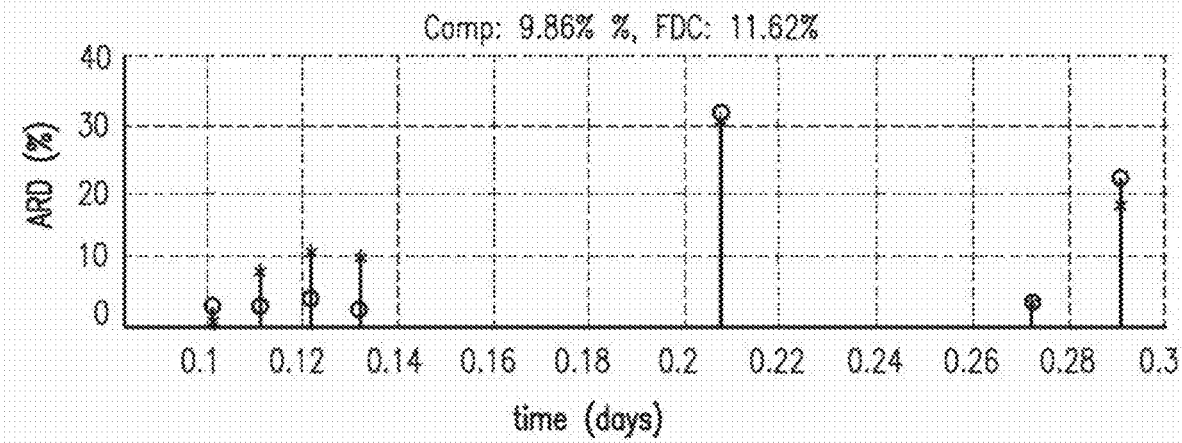

FIG. 90 shows the relationship between Cal Factor and Rm for in-vivo data during the first 8 hours of sensor operation. Here, EIS was run about once every 30 minutes at startup and interpolated for periods in between. As can be seen, Rm=Rmem+Rsol correlates with Cal Factor (CF) during the first 8 hours of sensor operation. For purposes of the diagram in FIG. 90, the baseline offset was assumed to be 3 nA.

As noted above in connection with FIGS. 83-85, in one embodiment of the invention, an algorithm for adjustment of the Cal Factor at start up may include selecting a reference value for the calibration factor ($CF_{reference}$), estimating the value of membrane resistance ($R_{reference}$) for $CF=CF_{reference}$, monitoring the change in membrane resistance ($Rm=Rmem+Rsol$), and based on the magnitude of that change, adjusting the calibration factor in accordance with the relationship shown in FIG. 90. Thus $$CF(t)=CF_{reference}-m(R_{reference}-R_m(t))$$

where m is the gradient of the correlation in FIG. 90. It is noted that, for purposes of the above algorithm, the value of $CF_{reference}$ is sensor-specific, to account for the differences between sensors.

In another embodiment, the Cal Factor adjustment algorithm may be modified by using a limited range of $R_m$ over which adjustment occurs. This can help with small differences once $R_m$ is smaller than $-7000\Omega$, as may happen due to noise. The limited $R_m$ range can also help when $R_m$ is very large, as may happen due to very slow sensor hydration/stabilization. In yet another embodiment, the range of allowable CF may be limited, such as, e.g., by setting a lower limit of 4.5 for CF.

FIG. 91A is a chart showing in-vivo results for MARD over all valid BGs in approximately the first 8 hours of sensor life. A single (first) calibration is performed with the first BG at either 1 hour, 1.5 hours, or 2 hours after startup. As can be seen, without any Cal Factor adjustment, the MARD for calibration at 1 hour is much higher than that for calibration performed at 2 hours (22.23 vs. 19.34). However, with adjustment, or modified adjustment, as described above, the difference between the respective MARD numbers becomes smaller. Thus, for example, with adjustment, the MARD for calibration at 1 hour is 16.98, as compared to 15.42 for calibration performed at 2 hours. In addition, the MARD with adjustment for calibration at 1 hour is much less than the MARD without adjustment for calibration performed at 2 hours (16.98 vs. 19.34). As such, in accordance with embodiments of the invention, Cal Factor adjustments (and modified adjustments) may be used to elongate the useable life of a sensor—e.g., by starting the sensor one hour earlier, in this example—while maintaining, or improving, the MARD. The chart in FIG. 91B provides median ARD numbers over all valid BGs in approximately the first 8 hours.

FIGS. 92A-92C, 93A-93C, and 94A-94C show examples of when the above-described Cal Factor adjustment algorithms work better than some current, non-EIS based, methods. In one such method, generally referred to as "First Day Compensation" (or FDC), a first Cal Factor is measured. If the measured Cal Factor falls outside of a predetermined range, a constant linear decay function is applied to bring the Cal Factor back to within normal range at a projected time determined by the rate of the decay. As can be seen from FIGS. 92A-94C, the Cal Factor adjustment algorithms of the invention (referred to in the diagrams as "Compensation") 6701, 6711, 6721 produce results that are closer to the actual blood glucose (BG) measurements 6707, 6717, 6727 than results obtained by the FDC method 6703, 6713, 6723.

Given the complexities of estimating the value of EIS-related parameters, some of the current methods, including FDC, may be computationally less complex than the EIS Cal Factor adjustment algorithms described herein. However, the two approaches may also be implemented in a complementary fashion. Specifically, there may be situations in which FDC may be augmented by the instant Cal Factor adjustment algorithms. For example, the latter may be used to define the rate of change of the FDC, or to identify the range for which FDC should be applied (i.e., other than using CF alone), or to reverse the direction of FDC in special cases.

In yet other embodiments, the offset, rather than the Cal Factor, may be adjusted. In addition, or instead, limits may be imposed on applicable ranges of $R_m$ and CF. In a specific embodiment, absolute, rather than relative, values may be used. Moreover, the relationship between Cal Factor and membrane may be expressed as multiplicative, rather than additive. Thus, $$\frac{CF(t)}{CF_{reference}} = -m\left(\frac{R(t)}{R_{reference}}\right)$$

In an embodiment using EIS-based dynamic offset, the total current that is measured may be defined as the sum of the Faradaic current and the non-Faradaic current, wherein the former is glucose-dependent, while the latter is glucose-independent. Thus, mathematically, $$i_{total} = i_{Faradaic} + i_{non-Faradaic}$$

Ideally, the non-Faradaic current should be zero, with a fixed working potential, such that $$i_{total} = i_{faradaic} = A \times \text{Diffusivity} \times \frac{\partial C_{peroxide}}{\partial n}$$

where A is the surface area, and $$\frac{\partial C_{peroxide}}{\partial n}$$

is the gradient of Peroxide.

However, when the double layer capacitance in changing, the non-Faradaic current cannot be ignored. Specifically, the non-Faradaic current may be calculated as $$q_{non-Faradaic} = V \times C = \int_{t_0}^{t_0 + \Delta t} i_{non-Faradaic} dt$$

$$\frac{d}{dt} q_{non-Faradaic} = i_{non-Faradaic} = \frac{d(V \times C)}{dt} = C\frac{dV}{dt} + V\frac{dC}{dt}$$

where q is the charge, V is the voltage, C is (double layer) capacitance. As can be seen from the above, when both voltage (V) and capacitance (C) are constant, both time-derivative values on the right-hand side of the equation are equal to zero, such that $i_{non-Faradaic} = 0$. In such an ideal situation, the focus can then turn to diffusion and reaction.

When V and C are both functions of time (e.g., at sensor initialization), $$i_{non-Faradaic} = \frac{d(V \times C)}{dt} = C\frac{dV}{dt} + V\frac{dC}{dt}$$

On the other hand, when V is constant, and C is a function of time, $$i_{non-Faradaic} = V\frac{dC}{dt}$$

Figure 95:
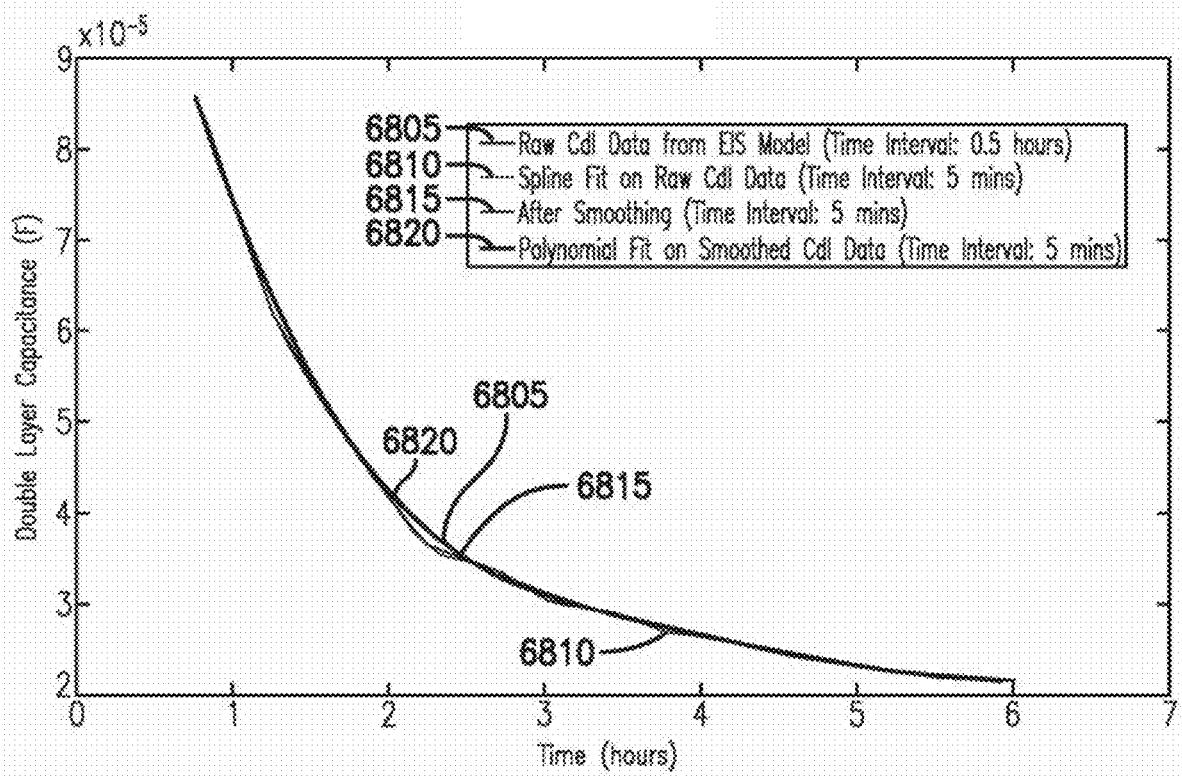
FIG. 95 shows an illustrative example of initial decay in Cdl in accordance with embodiments of the invention.

Such conditions are present, for example, on day 1 of sensor operation. FIG. 95 shows an example of a typical (initial) decay in double layer capacitance during day 1, in this case, the first 6 hours after sensor insertion. As indicated on the graph, plot 6805 shows raw Cdl data based on EIS data obtained at half-hour intervals, plot 6810 shows a spline fit on the raw Cdl data for 5-minute time intervals, plot 6815 shows the smoothed curve for 5-minute time intervals, and plot 6820 shows a polynomial fit on the smoothed Cdl data for 5-minute time intervals.

It is noted that the Cdl decay is not exponential. As such, the decay cannot be simulated with an exponential function. Rather, it has been found that a $6^{th}$-order polynomial fit (6820) provides a reasonable simulation. Thus, for the purposes of the above-mentioned scenario, where V is constant, and C is a function of time, $i_{non-Faradaic}$ may be calculated if the polynomial coefficients are known. Specifically, $$C = P(1)t^6 + P(2)t^5 + P(3)t^4 + P(4)t^3 + P(5)t^2 + P(6)t^1 + P(7)$$

where P is the polynomial coefficient array, and t is time. The non-Faradaic current can then be calculated as:

$$i_{non-Faradaic} = V\frac{dC}{dt} = V(6P(1)t^5 + 5P(2)t^4 + 4P(3)t^3 + 3P(4)t^2 + 2P(5)t^1 + P(6))$$

Finally, since $i_{total} = i_{Faradaic} + i_{non-Faradaic}$, the non-Faradaic component of the current can be removed by rearranging, such that $$i_{Faradaic} = i_{total} - i_{non-Faradaic}$$

Figure 96:
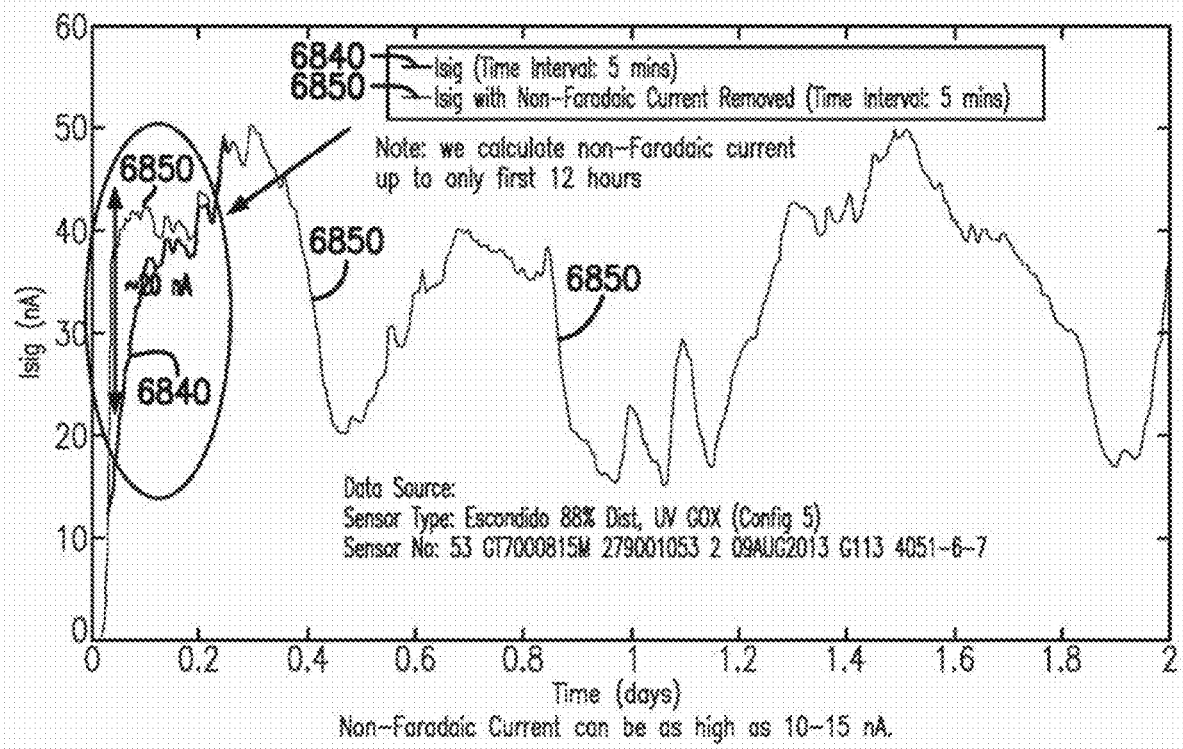

FIG. 96 shows Isig based on the total current (6840), as a function of time, as well as Isig after removal of the non-Faradaic current based on the capacitance decay (6850). The non-Faradaic component of the current may be as high as 10-15 nA. As can be seen from the figure, removal of the non-Faradaic current helps remove a large majority of the low start-up Isig data at the beginning of sensor life.

It has been found that the above approach can be used to reduce the MARD, as well as adjust the Cal Factor right at the beginning of sensor life. With regard to the latter, FIG. 97A shows the Cal Factor before removal of the non-Faradaic current for a first working electrode (WE1) 6860, and a second working electrode (WE2) 6870. FIG. 97B, on the other hand, shows the Cal Factor for WE1 (6862) and WE2 (6872) after removal of the non-Faradaic current. Comparing the Cal Factor for WE1 in FIG. 97A (6860) to that for WE1 in FIG. 97B (6862), it can be seen that, with removal of the non-Faradaic component, the Cal Factor (6862) is much closer to the expected range.

Figure 98A:
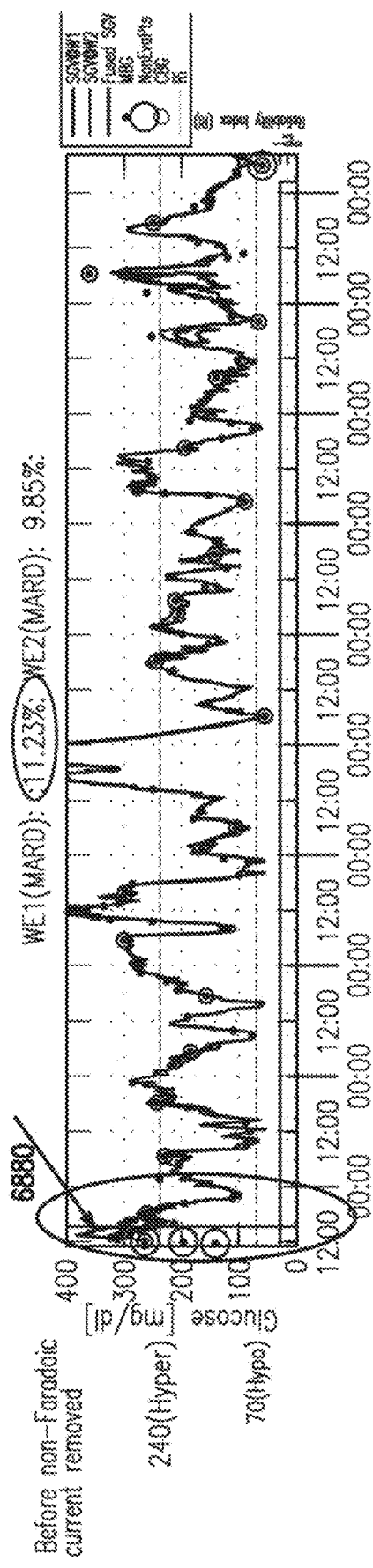
Figure 98B:
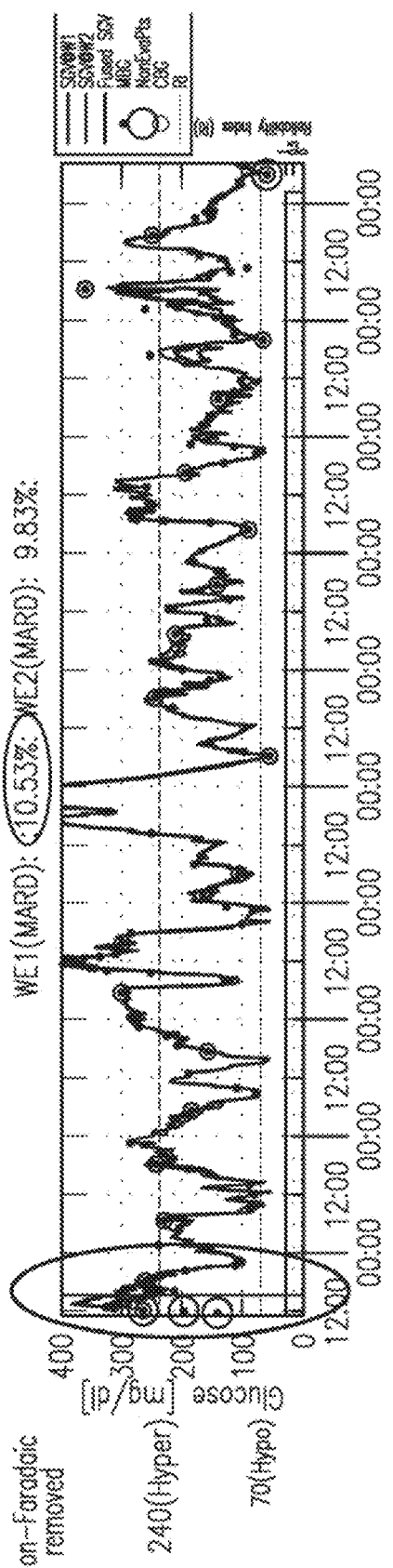

In addition, the reduction in MARD can be seen in the example shown in FIGS. 98A and 98B, where sensor glucose values are plotted over time. As shown in FIG. 98A, before removal of the non-Faradaic current, calibration at low startup causes significant sensor over-reading at WE1 (6880), with a MARD of 11.23%. After removal of the non-Faradaic current, a MARD of 10.53% is achieved for WE1. It is noted that, for the illustrative purposes of FIGS. 97A-98B, the non-Faradaic current was calculated and removed in pre-processing using the relation $$i_{non-Faradaic} = V\frac{dC}{dt} = V(6P(1)t^5 + 5P(2)t^4 + 4P(3)t^3 + 3P(4)t^2 + 2P(5)t^1 + P(6)),$$

where P is the polynomial coefficient (array) used to fit the double layer capacitance curve.

Figure 99:
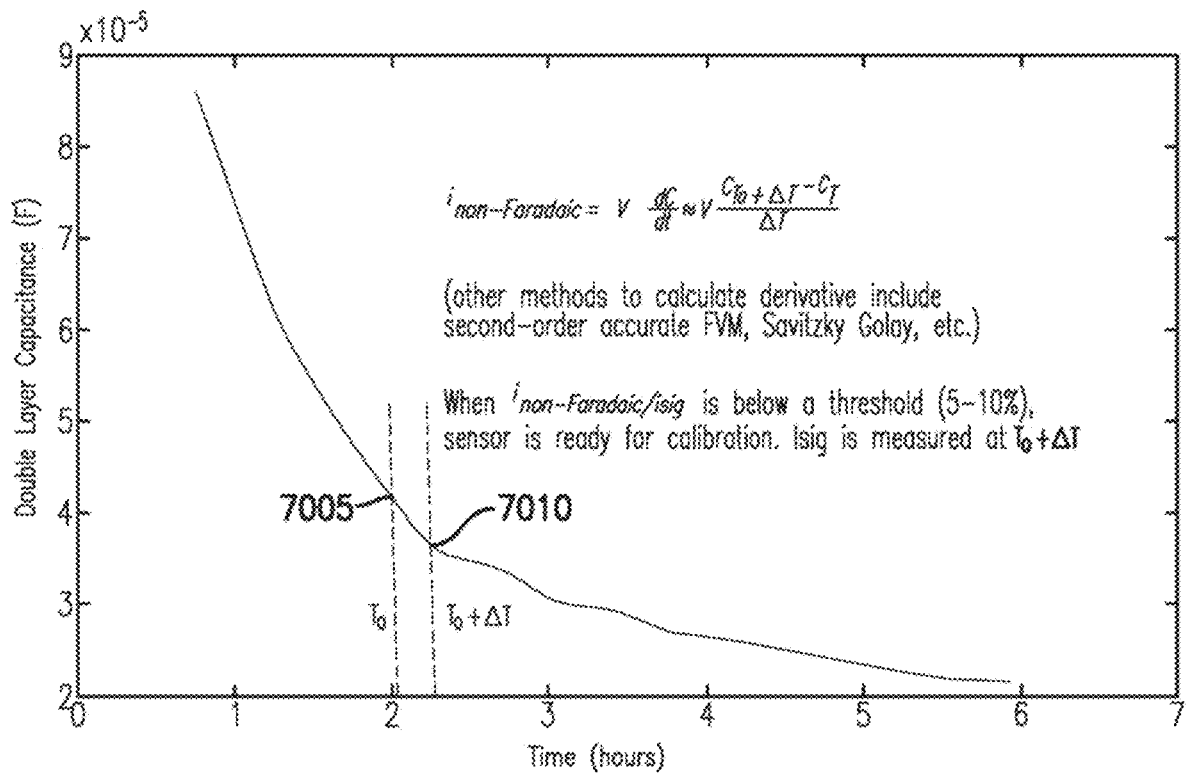

In real-time, separation of the Faradaic and non-Faradaic currents may be used to automatically determine the time to conduct the first calibration. FIG. 99 shows the double layer capacitance decay over time. Specifically, over the constant time interval ΔT, the double layer capacitance undergoes a change from a first value $C_{T_0+\Delta T}$ (7005) to a second value $C_T$ (7010). A first-order time difference method, e.g., can then be used to calculate the non-Faradaic current as $$i_{non-Faradaic} = V\frac{dC}{dt} \approx V\frac{C_{T_0+\Delta T} - C_T}{\Delta T}$$

Other methods may also be used to calculate the derivative $$\frac{dC}{dt},$$

such as, e.g., second-order accurate finite value method (FVM), Savitzky-Golay, etc.

Next, the percentage of the total current, i.e., Isig, that is comprised of the non-Faradaic current may be calculated simply as the ratio $i_{non-Faradaic}$/Isig. Once this ratio reaches a lower threshold, a determination can then be made, in real-time, as to whether the sensor is ready for calibration. Thus, in an embodiment of the invention, the threshold may be between 5% and 10%.

In another embodiment, the above-described algorithm may be used to calculate an offset value in real-time, i.e., an EIS-based dynamic offset algorithm. Recalling that $$i_{non-Faradaic} = V\frac{dC}{dt} = V(6P(1)t^5 + 5P(2)t^4 + 4P(3)t^3 + 3P(4)t^2 + 2P(5)t^1 + P(6))$$

and that sensor current Isig is the total current, including the Faradaic and non-Faradaic components $$i_{total} = i_{Faradaic} + i_{non-Faradaic}$$

the Faradaic component is calculated as $$i_{Faradaic} = i_{total} - i_{non-Faradaic}$$

Thus, in an embodiment of the invention, the non-Faradaic current, $i_{non-Faradaic}$, can be treated as an additional offset to Isig. In practice, when double layer capacitance decreases, e.g., during the first day of sensor life, $i_{non-Faradaic}$ is negative and decreases as a function of time. Therefore, in accordance with this embodiment of the invention, a larger offset—i.e., the usual offset as calculated with current methods, plus $i_{non-Faradaic}$—would be added to the Isig at the very beginning of sensor life and allowed to decay following the $5^{th}$-order polynomial curve. That is, the additional offset $i_{non-Faradaic}$ follows a $5^{th}$-order polynomial, the coefficient for which must be determined. Depending on how dramatic the change in double layer capacitance is, the algorithm in accordance with this embodiment of the invention may apply to the first few hours, e.g., the first 6-12 hours, of sensor life.

The polynomial fit may be calculated in various ways. For example, in an embodiment of the invention, coefficient P may be pre-determined based upon existing data. Then, the dynamic offset discussed above is applied, but only when the first Cal Factor is above normal range, e.g., ~7. Experiments have shown that, generally, this method works best when the real-time double layer capacitance measurement is less reliable than desired.

In an alternative embodiment, an in-line fitting algorithm is used. Specifically, an in-line double layer capacitance buffer is created at time T. P is then calculated based on the buffer, using a polynomial fit at time T. Lastly, the non-Faradaic current (dynamic offset) at time T+ΔT is calculated using P at time T. It is noted that this algorithm requires double layer capacitance measurements to be more frequent than their current level (every 30 mins), and that the measurements be reliable (i.e., no artifacts). For example, EIS measurements could be taken once every 5 minutes, or once every 10 minutes, for the first 2-3 hours of sensor life.

In developing a real-time, self-calibrating sensor, the ultimate goal is to minimize, or eliminate altogether, the reliance on a BG meter. This, however, requires understanding of the relationships between EIS-related parameters and Isig, Cal Factor (CF), and offset, among others. For example, in-vivo experiments have shown that there is a correlation between Isig and each of Cdl and Warburg Admittance, such that each of the latter may be Isig-dependent (at least to some degree). In addition, it has been found that, in terms of factory calibration of sensors, Isig and Rm (=Rmem+Rsol) are the most important parameters (i.e., contributing factors) for the Cal Factor, while Warburg Admittance, Cdl, and Vcntr are the most important parameters for the offset.

In in-vitro studies, metrics extracted from EIS (e.g., Rmem) tend to exhibit a strong correlation with Cal Factor. However, in-vivo, the same correlation can be weak. This is due, in part, to the fact that patient-specific, or (sensor) insertion-site-specific, properties mask the aspects of the sensor that would allow use of EIS for self-calibration or factory calibration. In this regard, in an embodiment of the invention, redundant sensors may be used to provide a reference point that can be utilized to estimate the patient-specific response. This, in turn, would allow a more robust factory calibration, as well as help identify the source of sensor failure mode(s) as either internal, or external, to the sensor.

In general, EIS is a function of electric fields that form between the sensor electrodes. The electric field can extend beyond the sensor membrane and can probe into the properties of the (patient's) body at the sensor insertion site. Therefore, if the environment in which the sensor is inserted/disposed is uniform across all tests, i.e., if the tissue composition is always the same in-vivo (or if the buffer is always the same in-vitro), then EIS can be correlated to sensor-only properties. In other words, it may be assumed that changes in the sensor lead directly to changes in the EIS, which can be correlated with, e.g., the Cal Factor.

However, it is well known that the in-vivo environment is highly variable, as patient-specific tissue properties depend on the composition of the insertion site. For example, the conductivity of the tissue around the sensor depends on the amount of fat around it. It is known that the conductivity of fat is much lower than that of pure interstitial fluid (ISF), and the ratio of local fat to ISF can vary significantly. The composition of the insertion site depends on the site of insertion, depth of insertion, patient-specific body composition, etc. Thus, even though the sensor is the same, the Rmem that is observed from EIS studies varies much more significantly because the reference environment is rarely, if ever, the same. That is, the conductivity of the insertion site affects the Rmem of the sensor/system. As such, it may not be possible to use the Rmem uniformly and consistently as a reliable calibration tool.

As described previously, EIS can also be used as a diagnostic tool. Thus, in embodiments of the invention, EIS may be used for gross failure analysis. For example, EIS can be used to detect severe sensitivity loss which, in turn, is useful for determining whether, and when, to block sensor data, deciding on optimal calibration times, and determining whether, and when, to terminate a sensor. In this regard, it bears repeating that, in continuous glucose monitoring and analysis, two major types of severe sensitivity loss are typically considered: (1) Temporary sensitivity loss (i.e., an Isig dip), which typically occurs early in sensor life, and is generally believed to be a consequence of external sensor blockage; and (2) Permanent sensitivity loss, which typically occurs at the end of sensor life, and never recovers, thus necessitating sensor termination.

Figure 100:
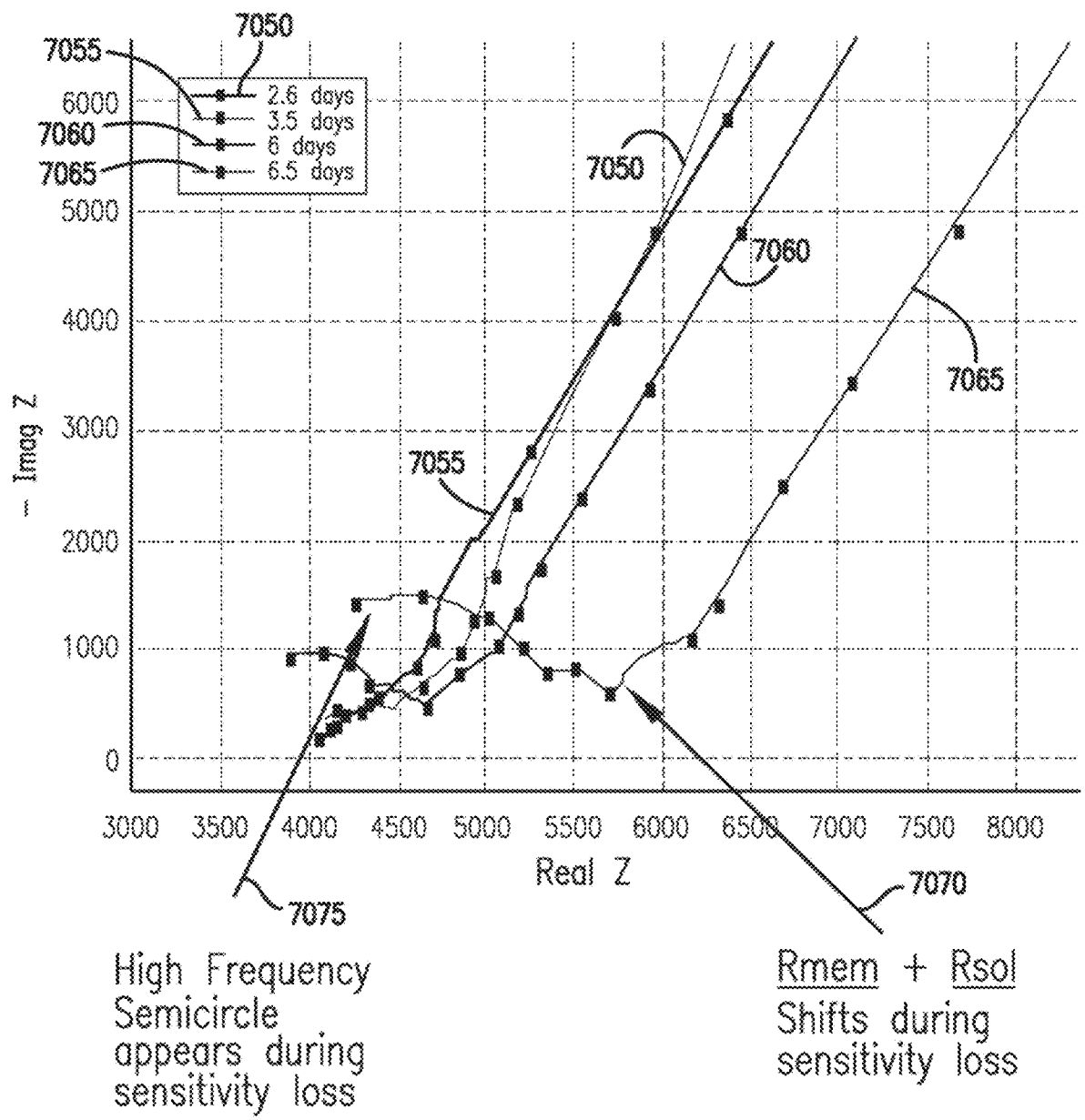

Both in-vivo and in-vitro data show that, during sensitivity loss and Isig dips, the EIS parameters that change may be any one or more of Rmem, Rsol, and Cmem. The latter changes, in turn, manifest themselves as a parallel shift in the higher-frequency region of the Nyquist plot, and/or an increased appearance of the high-frequency semicircle. In general, the more severe the sensitivity loss, the more pronounced these symptoms are. FIG. 100 shows the higher-frequency region of the Nyquist plot for data at 2.6 days (7050), 3.5 days (7055), 6 days (7060), and 6.5 days (7065). As can be seen, there may be a horizontal shift, i.e., Rmem+Rsol shifts, from left to right, during sensitivity loss (7070), indicating an increase in membrane resistance. In addition, the plot for 6 days, and especially that for 6.5 days (7065), clearly show the appearance of the higher frequency semicircle during sensitivity loss (7075), which is indicative of a change in membrane capacitance. Depending on the circumstances and the severity of the sensitivity loss, either or both of the above-mentioned manifestations may appear on the Nyquist plot.

With specific regard to the detection of Isig dips, as opposed to permanent sensitivity loss, some current methodologies use the Isig only to detect Isig dips by, e.g., monitoring the rate at which Isig may be dropping, or the degree/lack of incremental change in Isig over time, thereby indicating that perhaps the sensor is not responsive to glucose. This, however, may not be very reliable, as there are instances when Isig remains in the normal BG range, even when there is an actual dip. In such a situation, sensitivity loss (i.e., the Isig dip) is not distinguishable from hypoglycemia. Thus, in embodiments of the invention, EIS may be used to complement the information that is derived from the Isig, thereby increasing the specificity and sensitivity of the detection method.

Permanent sensitivity loss may generally be associated with Vcntr rails. Here, some current sensor-termination methodologies rely solely on the Vcntr rail data, such that, e.g., when Vcntr rails for one day, the sensor may be terminated. However, in accordance with embodiments of the invention, one method of determining when to terminate a sensor due to sensitivity loss entails using EIS data to confirm whether, and when, sensitivity loss happens after Vcntr rails. Specifically, the parallel shift in the higher-frequency region of the Nyquist plot may be used to determine whether permanent sensitivity loss has actually occurred once a Vcntr rail is observed. In this regard, there are situations in which Vcntr may rail at, e.g., 5 days into sensor life, but the EIS data shows little to shift at all in the Nyquist plot. In this case, normally, the sensor would have been terminated at 5-6 days. However, with EIS data indicating that there was, in fact, no permanent sensitivity loss, the sensor would not be terminated, thereby saving (i.e., using) the remainder of the sensor's useful life.

As mentioned previously, detection of sensitivity loss may be based on change(s) in one or more EIS parameters. Thus, changes in membrane resistance (Rm=Rmem+Rsol), for example, may manifest themselves in the mid-frequency (~1 kHz) real impedance region. For membrane capacitance (Cmem), changes may be manifested in the higher-frequency (~8 kHz) imaginary impedance because of increased semicircle. The double layer capacitance (Cdl) is proportional to average Isig. As such, it may be approximated as the length of lower-frequency Nyquist slope $L_{nyquist}$. Because Vcntr is correlated to oxygen levels, normal sensor behavior typically entails a decrease in Vcntr with decreasing Isig. Therefore, an increase in Vcntr (i.e., more negative), in combination with a decrease in Isig may also be indicative of sensitivity loss. In addition, average Isig levels, rates of change, or variability of signal that are low or physiologically unlikely may be monitored.

The EIS parameters must, nevertheless, be first determined. As described previously in connection with Cal Factor adjustments and related disclosure, the most robust way of estimating the EIS parameters is to perform model fitting, where the parameters in model equations are varied until the error between the measured EIS and the model output are minimized. Many methods of performing this estimate exist. However, for a real time application, model fitting may not be optimal because of computational load, variability in estimation time, and situations where convergence is poor. Usually, the feasibility will depend on the hardware.

When the complete model fitting noted above is not possible, in one embodiment of the invention, one method for real-time application is through use of heuristic methodologies. The aim is to approximate the true parameter values (or a corresponding metric that is proportional to trends shown by each parameter) with simple heuristic methods applied to the measured EIS. In this regard, the following are implementations for estimating changes in each parameter.

Double Layer Capacitance (Cdl)

Generally speaking, a rough estimate of Cdl can be obtained from any statistic that measures the length of the lower-frequency Nyquist slope (e.g., frequencies lower than ~128 Hz). This can be done, for example, by measuring $L_{nyquist}$ (the Cartesian distance between EIS at 128 Hz and 0.1 Hz in the Nyquist plot). Other frequency ranges may also be used. In another embodiment, Cdl may be estimated by using the amplitude of the lower-frequency impedance (e.g., at 0.1 Hz).

Membrane Resistance (Rmem) and Solution Resistance (Rsol)

As has been discussed hereinabove, on the Nyquist plot, Rmem+Rsol corresponds to the inflection point between the lower-frequency and the higher-frequency semicircles. Thus, in one embodiment, Rmem+Rsol may be estimated by localizing the inflection point by detecting changes in directionality of the Nyquist slope (e.g., by using derivatives and/or differences). Alternatively, a relative change in Rmem+Rsol can be estimated by measuring the shift in the Nyquist slope. To do this, a reference point in the imaginary axis can be chosen (see FIG. 83) and interpolation can be used to determine the corresponding point on the real axis. This interpolated value can be used to track changes in Rmem+Rsol over time. The chosen reference should lie within a range of values that, for a given sensor configuration, are not overly affected by large changes in the lower-frequency part of the Nyquist slope (for example, because of Vcntr Rail). Typical values may be between 1 kΩ and 3 kΩ. In another embodiment, it may be possible to use the real component of a single high frequency EIS (e.g., 1 kHz, 8 kHz). In certain sensor configurations, this may simulate Rmem the majority of the time, though it is noted that a single frequency may not be able to represent Rmem exactly in all situations.

Membrane Capacitance (Cmem)

Increases in Cmem manifest as a more pronounced (or the more obvious appearance of) a higher-frequency semicircle. Changes in Cmem can therefore be detected by estimating the presence of this semicircle. Thus, in one embodiment, Cmem may be estimated by tracking the higher-frequency imaginary component of impedance. In this regard, a more negative value corresponds to the increased presence of a semicircle.

Alternatively, Cmem may be estimated by tracking the highest point in the semicircle within a frequency range (e.g., 1 kHz-8 kHz). This frequency range can also be determined by identifying the frequency at which the inflection point occurs and obtaining the largest imaginary impedance for all frequencies higher than the identified frequency. In this regard, a more negative value corresponds to an increased presence of the semicircle.

In a third embodiment, Cmem may be estimated by measuring the Cartesian distance between two higher-frequency points in the Nyquist plot, such as, e.g., 8 kHz and 1 kHz. This is the high frequency slope ($S_{nyquist}$) defined previously in the instant application. Here, a larger absolute value corresponds to an increased semicircle, and a negative slope (with negative imaginary impedance on the y axis, and positive real impedance on the x) corresponds to the absence of a semicircle. It is noted that, in the above-described methodologies, there may be instances in which some of the detected changes in the semicircle may also be attributed to changes in Rmem. However, because changes in either are indicative of sensitivity loss, the overlap is considered to be acceptable.

Non-EIS Related Metrics

For context, it is noted that, prior to the availability of EIS metrics, sensitivity loss was by and large detected according to several non-EIS criteria. By themselves, these metrics are not typically reliable enough to achieve perfect sensitivity and specificity in the detection. They can, however, be combined with EIS-related metrics to provide supporting evidence for the existence of sensitivity loss. Some of these metrics include: (1) the amount of time that Isig is below a certain threshold (in nA), i.e., periods of "low Isig"; (2) the first order or second order derivatives of Isig leading to a state of "low Isig", used as an indication of whether the changes in Isig are physiologically possible or induced by sensitivity loss; and (3) the variability/variance of Isig over a "low Isig" period, which can be indicative of whether the sensor is responsive to glucose or is flat lining.

Sensitivity-Loss Detection Algorithms

Embodiments of the invention are directed to algorithms for detection of sensitivity loss. The algorithms generally have access to a vector of parameters estimated from EIS measurements (e.g., as described hereinabove) and from non-EIS related metrics. Thus, e.g., the vector may contain Rmem and or shift in horizontal axis (of the Nyquist plot), changes in Cmem, and changes in Cdl. Similarly, the vector may contain data on the period of time Isig is in a "low" state, variability in Isig, rates of change in Isig. This vector of parameters can be tracked over time, wherein the aim of the algorithm is to gather robust evidence of sensitivity loss.

In this context, "robust evidence" can be defined by, e.g., a voting system, a combined weighted metric, clustering, and/or machine learning.

Specifically, a voting system may entail monitoring of one or more of the EIS parameters. For example, in one embodiment, this involves determining when more than a predetermined, or calculated, number of the elements in the parameter vector cross an absolute threshold. In alternative embodiments, the threshold may be a relative (%) threshold. Similarly, the vector elements may be monitored to determine when a particular combination of parameters in the vector crosses an absolute or a relative threshold. In another embodiment, when any of a subset of elements in the vector crosses an absolute or a relative threshold, a check on the remainder of the parameters may be triggered to determine if enough evidence of sensitivity loss can be obtained. This is useful when at least one of a subset of parameters is a necessary (but perhaps insufficient) condition for sensitivity loss to be reliably detected.

A combined weighted metric entails weighing the elements in the vector according to, for example, how much they cross a predetermined threshold by. Sensitivity loss can then be detected (i.e., determined as occurring) when the aggregate weighted metric crosses an absolute or a relative threshold.

Machine learning can be used as more sophisticated "black box" classifiers. For example, the parameter vector extracted from realistic in-vivo experimentation can be used to train artificial neural networks (ANN), support vector machines (SVM), or genetic algorithms to detect sensitivity loss. A trained network can then be applied in real time in a very time-efficient manner.

Figure 101A:
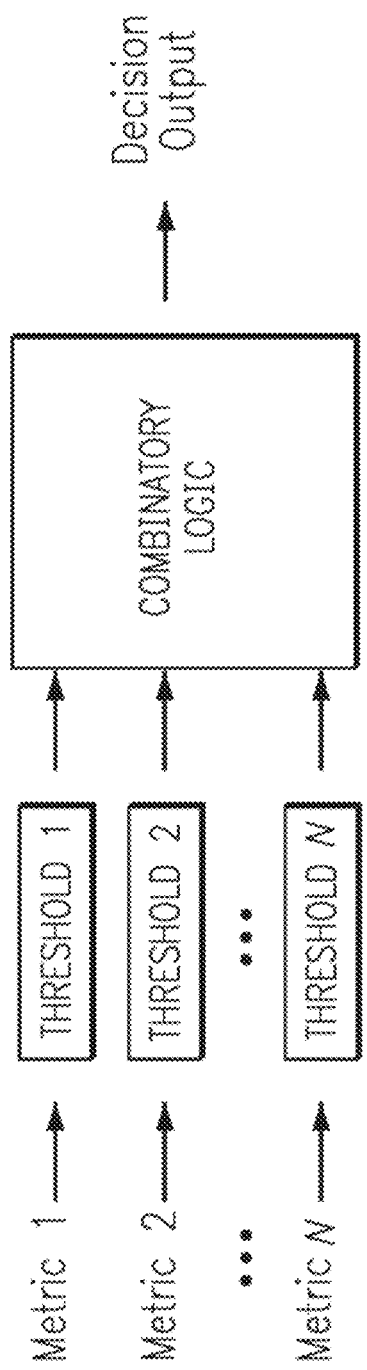
Figure 101B:
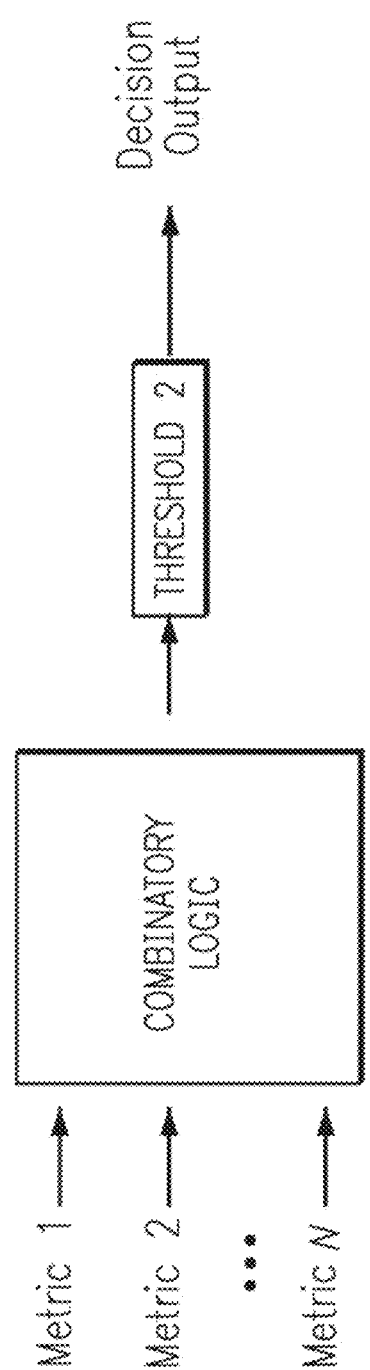

FIGS. 101A and 101B show two illustrative examples of flow diagrams for sensitivity-loss detection using combinatory logic. As shown, in both methodologies, one or more metrics 1-N may be monitored. In the methodology of FIG. 101A, each of the metrics is tracked to determine if and when it crosses a threshold and described hereinabove. The output of the threshold-determination step is then aggregated via a combinatory logic, and a decision regarding sensitivity loss is made based on the output of the combinatory logic. In FIG. 101B, values of the monitored metrics 1–N are first processed through a combinatory logic, and the aggregate output of the latter is then compared to a threshold value(s) to determine whether sensitivity loss has occurred.

Additional embodiments of the invention are also directed to using EIS in intelligent diagnostic algorithms. Thus, in one embodiment, EIS data may be used to determine whether the sensor is new, or whether it is being re-used (in addition to methodologies presented previously in connection with re-use of sensors by patients). With regard to the latter, it is important to know whether a sensor is new or is being re-used, as this information helps in the determination of what type of initialization sequence, if any, should be used. In addition, the information allows prevention of off-label use of a sensor, as well as prevention of sensor damage due to multiple reinitializations (i.e., each time a sensor is disconnected and then re-connected, it "thinks" that it is a new sensor, and therefore tries to reinitialize upon re-connection). The information also helps in post-processing of collected sensor data.

Figure 102:
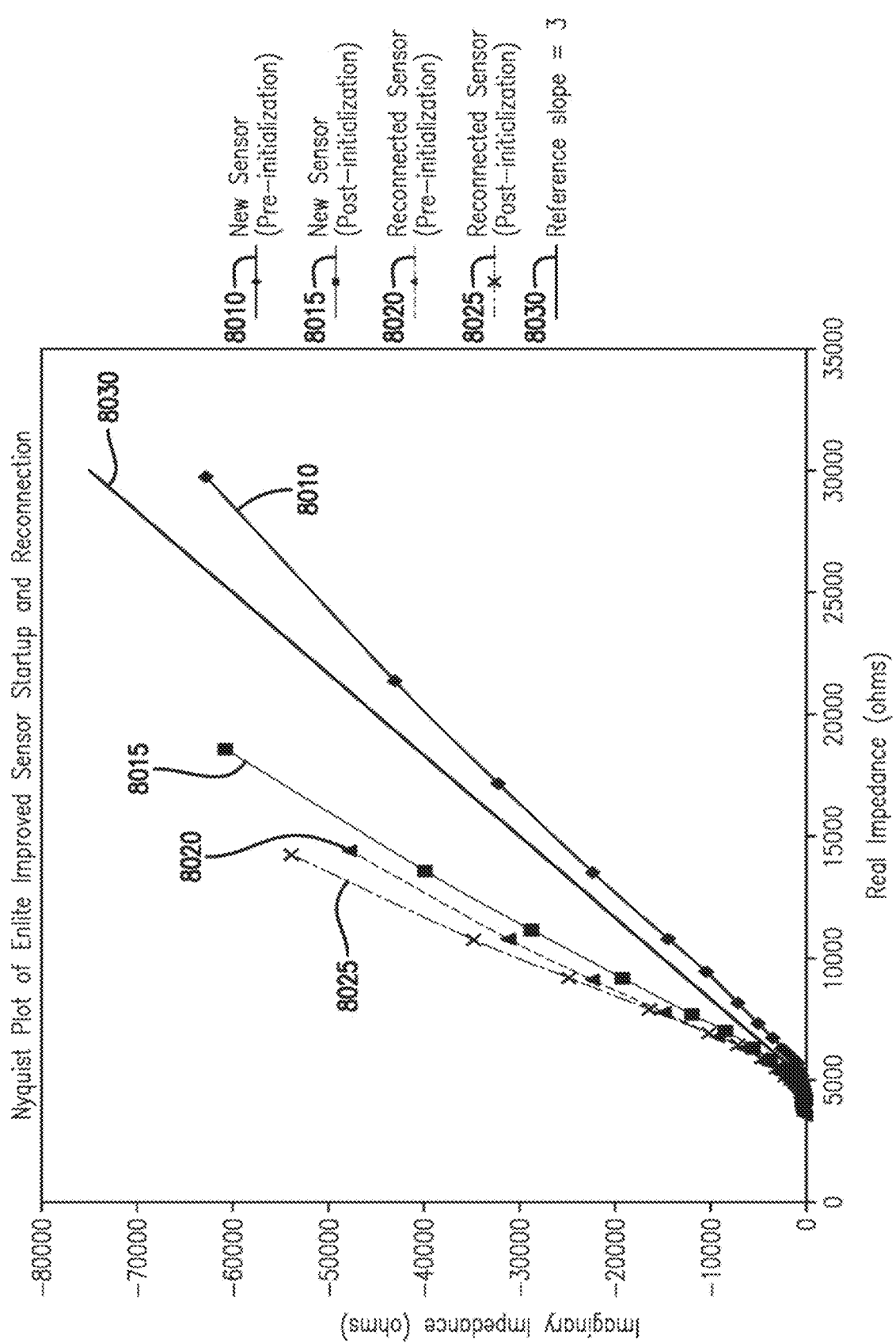

In connection with sensor re-use and/or re-connection, it has been discovered that the lower-frequency Nyquist slope for a new sensor before initialization is different from (i.e., lower than) the lower-frequency Nyquist slope for a sensor that has been disconnected, and then reconnected again. Specifically, in-vitro experiments have shown that the Nyquist slope is higher for a re-used sensor as opposed to a newly-inserted one. The Nyquist slope, therefore, can be used as a marker to differentiate between new and used (or re-used) sensors. In one embodiment, a threshold may be used to determine, based on the Nyquist slope, whether a specific sensor is being re-used. In embodiments of the invention, the threshold may be a Nyquist slope=3. FIG. 102 shows the low-frequency Nyquist plot with a reference slope=3 (8030), as well as the plots for a new sensor (pre-initialization) 8010, a new sensor (post-initialization) 8015, a reconnected sensor (pre-initialization) 8020, and a reconnected sensor (post-initialization) 8020. As noted, the slope for a new sensor (pre-initialization) 8010 is lower than the reference, or threshold (8030), while that for a reconnected sensor (pre-initialization) 8020 is higher than the threshold (8030).

Equivalently, lower-frequency phase measurements may be used to detect sensors that have been previously initialized. Here, the pre-initialization phase angle at 0.105 Hz, e.g., may be used to differentiate between new and used (or re-used) sensors. Specifically, a threshold may be set at a phase angle of about −70°. Thus, if the pre-initialization phase angle at 0.105 Hz is less than the threshold, then the sensor is considered to be an old (i.e., previously-initialized) sensor. As such, no further initialization pulses will be applied to the sensor.

In another embodiment, EIS data may be used to determine the type of sensor being used. Here, it has been discovered that, if the sensor designs are significantly different, the respective EIS outputs should also be significantly different, on average. Different sensor configurations have different model parameters. It is therefore possible to use identification of these parameters at any point during the sensor life to determine the sensor type currently inserted. The parameters can be estimated, e.g., based on methods described hereinabove in connection with gross failure/sensitivity-loss analysis. Identification can be based on common methods to separate values, for example, setting thresholds on specific (single or multiple) parameters, machine learning (ANN, SVM), or a combination of both methods.

This information may be used, e.g., to change algorithm parameters and initialization sequences. Thus, at the beginning of the sensor life, this can be used to have a single processing unit (GST, GSR) to set optimal parameters for the calibration algorithm. Offline (non real-time), the identification of sensor type can be used to aid analysis/evaluation of on-the-field sensor performance.

Figures 103A, 103B:
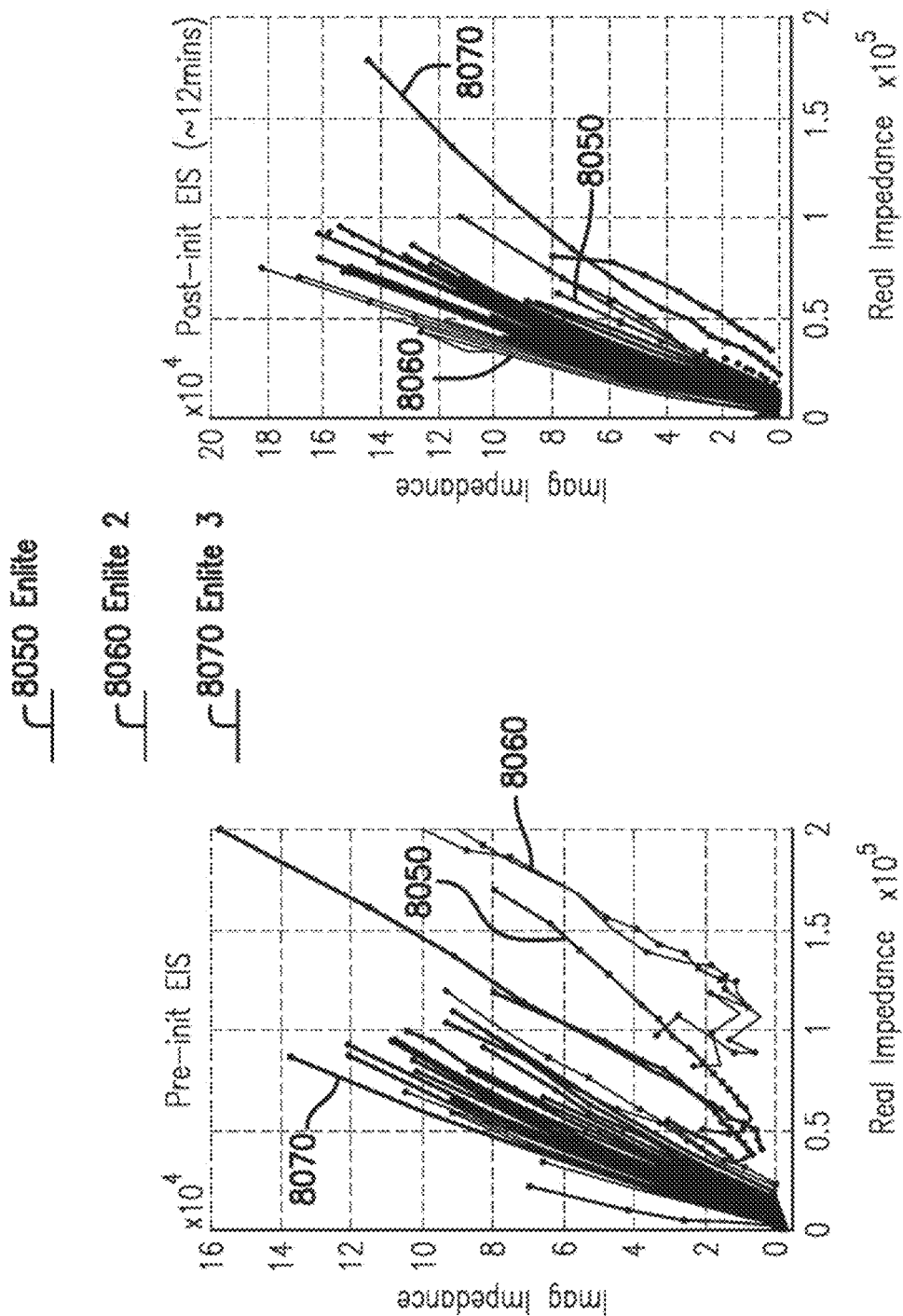
Figure 103C:
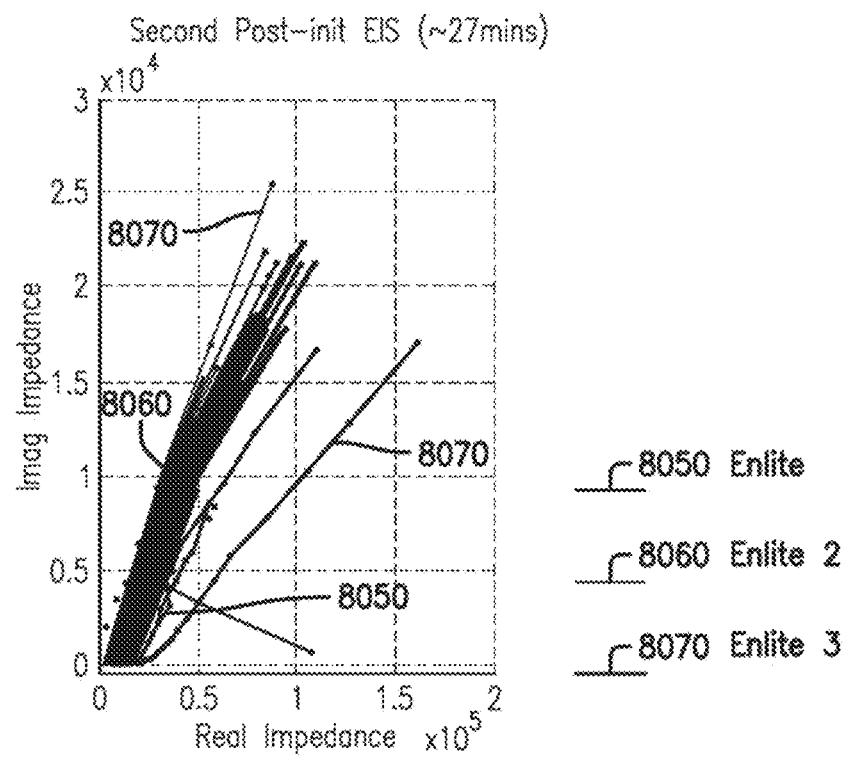
Figure 104:
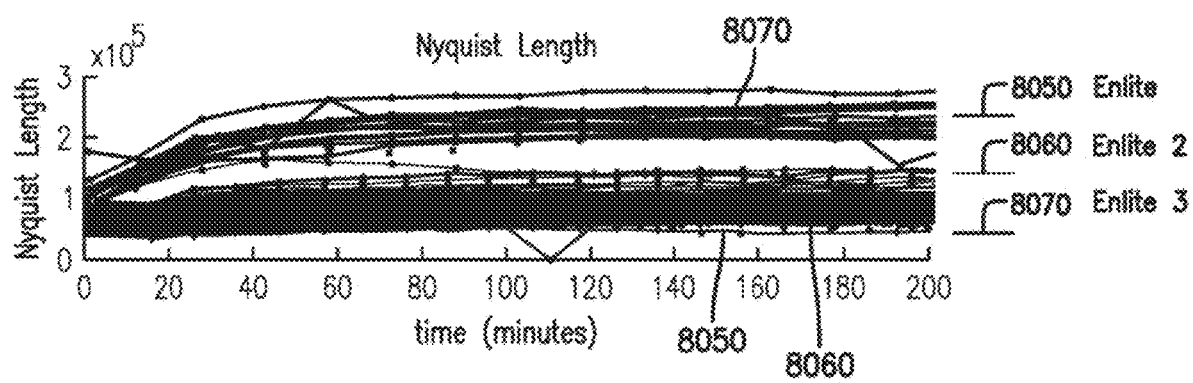

It has also been discovered that the length of the lower-frequency Nyquist slope may be used to differentiate between different sensor types. FIGS. 103A-103C show Nyquist plots for three different sensors (i.e., different sensor configurations), identified as Enlite (8050), Enlite 2 (i.e., "Enlite Enhanced") (8060), and Enlite 3 (8070), all of which are manufactured by Medtronic Minimed (Northridge, Calif.). As can be seen, for various stages, including pre-initialization, post-initialization, and second post-initialization (FIGS. 103A-103C, respectively), the Enlite sensor has the shortest lower-frequency Nyquist slope length (8050), followed by the Enlite 2 (8060), and the Enlite 3 (8070), which has the longest length. The latter are also shown on FIG. 104, where Nyquist (slope) length, computed as the Cartesian distance between EIS at 0.105 Hz and 1 Hz, is plotted against time.

Embodiments of the invention are also directed to using diagnostic EIS measurements as a guide in determining the type of initialization that should be performed. As noted previously, initialization sequences can be varied based on detected sensor type (EIS-based or other), and/or detection of whether a new or old sensor is inserted (EIS-based). In addition, however, EIS-based diagnostics may also be used in determining a minimal hydration state prior to initialization (e.g., by tracking Warburg impedance), or in determining when to terminate initialization (e.g., by tracking reaction-dependent parameter, such as, e.g., Rp, Cdl, Alpha, etc.), so as to properly minimize sensor initialization time.

More specifically, to minimize initialization response time, additional diagnostics are required to control the processes that occur during initialization. In this regard, EIS may provide for the required additional diagnostics. Thus, for example, EIS may be measured between each initialization pulse to determine if further pulsing is required. Alternatively, or in addition, EIS may be measured during high pulses, and compared to the EIS of optimal initialization state to determine when the sensor is sufficiently initialized. Lastly, as noted above, EIS may be used in estimating a particular model parameter—most likely one or more reaction-dependent parameters, such as Rp, Cdl, Alpha, etc.

As has been noted, sensor calibration in general, and real-time sensor calibration in particular, is central to a robust continuous glucose monitoring (CGM) system. In this regard, calibration algorithms are generally designed such that, once a BG is received by taking a fingerstick, the new BG value is used to either generate an error message, or update the calibration factor which, in turn, is used to calculate sensor glucose. In some previous algorithms, however, a delay of 10-20 minutes may exist between the time when a fingerstick is entered, and the time when the user is notified of either the fingerstick being accepted or a new fingerstick being required for calibration. This is burdensome, as the user is left not knowing whether he/she will need his/her BG meter again in a few minutes.

In addition, in some situations, the presence of older BG values in the calibration buffer causes either perceived system delay, due to the newest BG value carrying less than 100% weight, or inaccuracy in the calculated SG (due to the older BG values no longer being representative of the current state of the system). Moreover, erroneous BG values are sometimes entered, but not caught by the system, which may lead to large inaccuracies until the next calibration.

In view of the above, embodiments of the invention seek to address potential shortcomings in prior methodologies, especially with regard to sensor performance for use with closed-loop systems. For example, in order to make the system more predictable, calibration errors may be notified only when the fingerstick (BG value) is received by the transmitter (i.e., entered), rather than, e.g., 10-15 minutes later. Additionally, in contrast to some existing systems, where a constant calibration error (CE) threshold is used, embodiments of the invention may utilize variable calibration error thresholds when higher errors are expected (e.g., either due to lower reliability of the sensor, or high rates of change), thereby preventing unnecessary calibration error alarms and fingerstick requests. Thus, in one aspect, when the sensor is in FDC mode, Isig dip calibration mode, or undergoing a high rate of change (e.g., when 2-packet rate of change×CF>1.5 mg/dL/min.), a limit corresponding to 50% or 50 mg/dL may be used.

On the other hand, when low error is expected, the system may use a tighter calibration error limit, such as, e.g., 40% or 40 mg/dL. This reduces the likelihood that erroneous BG values may be used for calibration, while also allowing the status of the calibration attempt to be issued immediately (i.e., accepted for calibration, or a calibration error). Moreover, in order to handle situations where newer Isig values would cause a calibration error, a check at calibration time (e.g., 5-10 minutes after fingerstick) may select the most appropriate filtered Isig (fIsig) value to use for calibration.

In connection with the aforementioned issues involving BG values and the BG buffer, embodiments of the invention aim to reduce the delay, and the perceptions of delay, by assigning higher weighting to the newer BG value than was assigned in previous algorithms, and by ensuring that the early calibration update occurs more frequently. In addition, in situations where there is a confirmed sensitivity change (as confirmed, e.g., by the Smart Calibration logic mentioned previously and to be explored hereinbelow, and by recent calibration BG/Isig ratios), the calibration buffer may undergo partial clearing. Lastly, whereas prior algorithms may have employed an expected calibration factor (CF) weight which was a constant, embodiments of the invention provide for a variable CF value based on sensor age.

In short, embodiments of the invention provide for variable calibration error thresholds based on expectation of error during calibration attempt, as well as issuance of calibration error message(s) without waiting for additional sensor data, less delay in calibrating (e.g., 5-10 minutes), updated expected calibration factor value based on sensor age, and partial clearing of the calibration buffer as appropriate. Specifically, in connection with First Day Compensation (FDC), embodiments of the invention provide for requesting additional calibrations when higher Cal Factor thresholds are triggered in order to more expeditiously correct sensor performance. Such higher CF thresholds may be set at, e.g., between 7 and 16 mg/dL/nA, with the latter serving as the threshold for indication of calibration error in embodiments of the invention.

Thus, in one aspect, if a high CF threshold is triggered after the first calibration, the system requires that the next calibration be performed in 3 hours. However, if a high CF threshold is triggered after the second, or subsequent, calibration, the system requires that the next calibration be performed in 6 hours. The foregoing procedure may be implemented for a period of 12 hours from sensor connection.

In another aspect, the expected Cal Factor, which is used during calibration to calculate the Cal Factor, is increased over time so as to reduce the likelihood of under-reading. By way of background, existing methodologies may use a fixed expected Cal Factor throughout the sensor life, without accounting for possible shifts in sensor sensitivity. In such methodologies, the expected Cal Factor may be weighted in calculating the final Cal Factor, and used to reduce noise.

In embodiments of the present invention, however, the expected CF is calculated as a function of time, expressed in terms of the age of the sensor. Specifically, $$\text{Expected } CF = SensorAge \times \frac{0.109 \text{ mg/dL/nA}}{\text{day}} + 4.730 \text{ mg/dL/nA}$$

where Sensor Age is expressed in units of days. In further embodiments, the expected Cal Factor may be calculated as a function of the existing CF and impedance, such that any changes in sensitivity may be reflected in the expected CF. In addition, in aspects of the invention, expected CF may be calculated on every Isig packet, rather than doing so only at a BG entry, so as to gradually adjust the Cal Factor between calibrations.

In connection with calibration buffer and calibration error calculations, embodiments of the invention provide for modification of calibration buffer weights and/or clearing of the calibration buffer. Specifically, when impedance measurements (e.g., through EIS) indicate that the Cal Factor might have changed, and a calibration attempt indicates that a change might have occurred, the change in Cal Ratio (CR) is checked by comparing the CR of the current BG to the most recent CR in the calibration buffer. Here, such a change may be verified by, e.g., values of the 1 kHz impedance, as detailed previously in connection with related EIS procedures. In addition, weights may be added in the calibration buffer calculation based on reliability indices, the direction in which the Cal Factor is expected to change, and/or the rate of change of calibration. In the latter situation, e.g., a lower weight may be assigned, or CF only temporarily updated, if calibration is on a high rate of change.

In embodiments of the invention, selection of filtered Isig (fIsig) values for the calibration buffer may be initiated on the second Isig packet after BG entry. Specifically, the most recent of the past three (3) fIsig values that would not cause a calibration error may be selected. Then, once accepted for calibration, the calibration process will proceed without a calibration error being issued. Such calibration error may be caused, e.g., by an invalid Isig value, a Cal Ratio range check, a percentage error check, etc.

In other embodiments, values of fIsig may be interpolated to derive a one-minute resolution. Alternatively, fIsig values may be selected from recent values based on the rate of change in the values (and accounting for delays). In yet another alternative embodiment, fIsig values may be selected based on a value of CR that is closest to a predicted CR value. The predicted CR value, in turn, is closest to the current value of the Cal Factor, unless the latter, or EIS data, indicate that CF should change.

Figure 105:
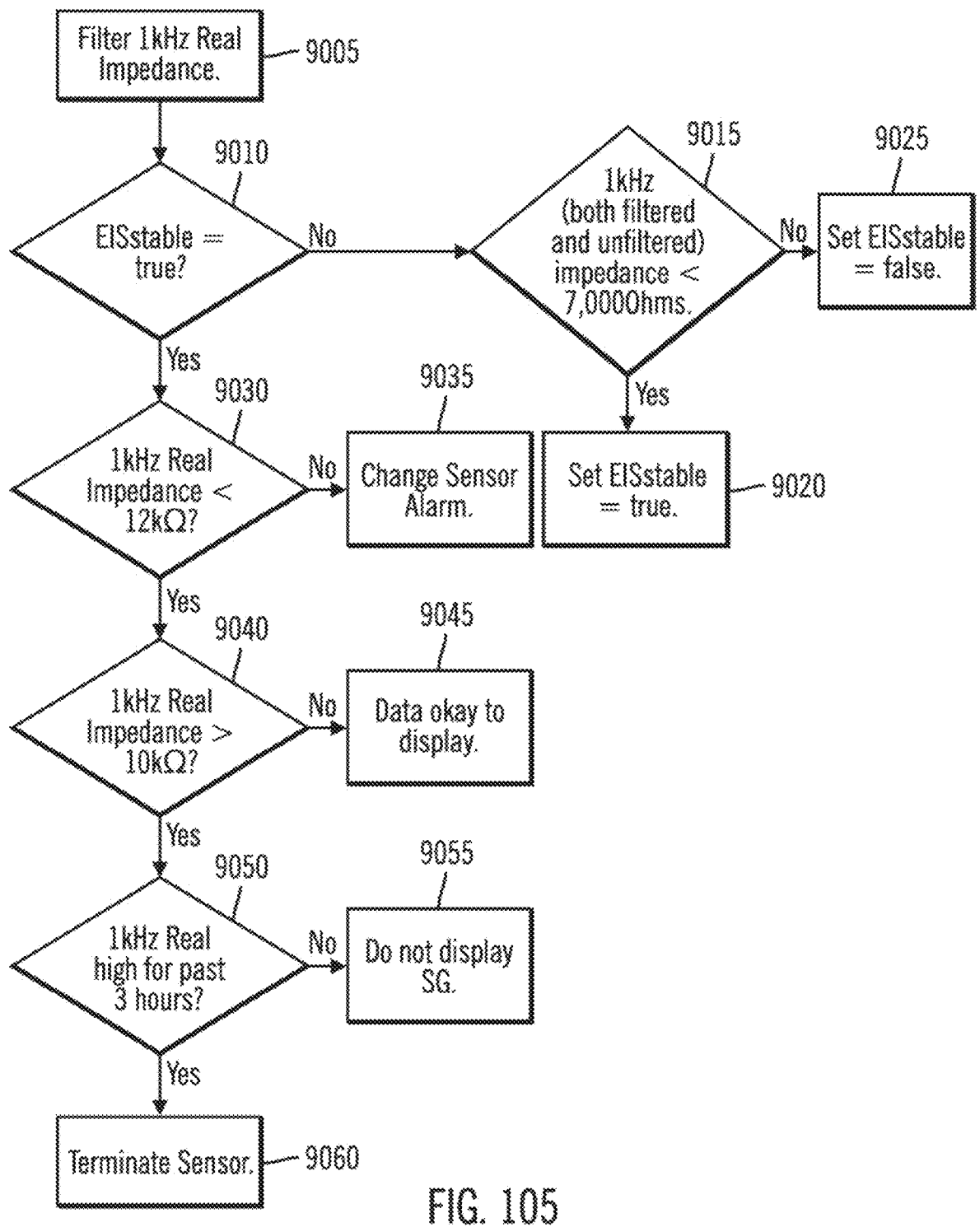

As noted previously, in connection with FIGS. 24 and 34, e.g., values for 1 kHz real impedance provide information on potential occlusion(s) that may exist on the sensor membrane surface, which occlusion(s) may temporarily block passage of glucose into the sensor and thus cause the signal to dip. More broadly, the 1 kHz real impedance measurement may be used to detect sensor events that are typically sudden and may indicate that the sensor is no longer fully inserted. In this regard, FIG. 105 shows a flow chart for a method of blanking sensor data or terminating the sensor in accordance with an embodiment of the invention.

The methodology starts at block 9005, where 1 kHz real impedance values are filtered using, e.g., a moving average filter, and, based thereon, a determination is made as to whether the EIS-derived values are stable (9010). If it is determined that the EIS-derived values are not stable, the methodology proceeds to block 9015, wherein a further determination is made based on the magnitude of the 1 kHz impedance. Specifically, if both the filtered and unfiltered values of 1 kHz real impedance are less than 7,000Ω, then EIS is set as stable (9020). If, on the other hand, both the filtered and unfiltered values of 1 kHz real impedance are not less than 7,000Ω, then EIS is set as unstable (9025). It is noted that the above-described 7,000Ω threshold prevents data blanking or sensor termination for sensors that have not stabilized.

When EIS is stable, the algorithm proceeds to block 9030. Here, if the 1 kHz real impedance is less than 12,000Ω (9030), and also less than 10,000Ω (9040), the algorithm determines that the sensor is within normal operating range and, as such, allows sensor data to continue to be displayed (9045). If, on the other hand, the 1 kHz real impedance value is greater than 10,000Ω (i.e., when the 1 kHz real impedance is between 10 kΩ and 12 kΩ), the logic determines whether the 1 kHz real impedance value has been high (i.e., greater than 10 kΩ) for the past 3 hours (9050). If it is determined that the 1 kHz real impedance value has been high for the past 3 hours, then the sensor is terminated at 9060, as the sensor is assumed to have pulled out, rendering sensor data invalid. Otherwise, the sensor is not terminated, as the sensor signal may be simply drifting, which, as discussed previously, may be a recoverable phenomenon. Nevertheless, the sensor data is blanked (9055) while the sensor is given a chance to recover.

It is noted that, in further embodiments, in determining whether data should be blanked, or the sensor terminated, the logic may also consider, in addition to the above-mentioned thresholds, sudden increases in impedance by, e.g., comparing impedance derivatives to historical derivatives. Moreover, the algorithm may incorporate noise-based blanking or termination, depending on the duration of high noise-low sensor signal combination. In this regard, prior methodologies included termination of the sensor after three (3) consecutive 2-hour windows of high noise and low sensor signal. However, in order to prevent unreliable data from being displayed to the user, embodiments of the invention employ noise-based blanking, wherein the algorithm stops calculating SG values after 2 consecutive 2-hour windows (i.e., at the start of the third consecutive window) involving high noise and low signal. In further aspects, the algorithm may allow further calculation and display of the calculated SG values after one hour of blanking, rather than two hours, where the sensor signal appears to have recovered. This is an improvement over methodologies that blank otherwise reliable data for longer periods of time.

Whereas 1 kHz real impedance may be used to detect sudden sensor failures, measurements of imaginary impedance at higher frequencies (e.g., 8 kHz) may be used to detect more gradual changes, where sensor sensitivity has drifted significantly from its typical sensitivity. In this regard, it has been discovered that a large shift in 8 kHz imaginary impedance typically signifies that the sensor has experienced a large change in glucose sensitivity or is no longer stable.

FIG. 106 shows a flow diagram for a method of sensor termination in accordance with an embodiment of the invention. As shown in FIG. 106, the algorithm employs a reference at 1.5 days (since sensor start), as doing so provides for a more robust logic, and ensures that the logic focuses on long-term sensitivity changes. Thus, if the sensor has not been operating for at least 1.5 days (9002), no action is taken, and the algorithm "waits" (9012), i.e., it periodically loops back to step 9002. Once the condition in block 9002 is met, a determination is made as to whether a reference imaginary impedance value is set (9022). If a reference value has not been previously set, the algorithm proceeds to set one by assigning the minimum 8 kHz imaginary impedance value since sensor initialization as the reference value (9032), clipped within the range −1,000Ω-800Ω. With the reference value set, a change value is calculated as the absolute value of the difference between the reference value and the current value of the 8 kHz imaginary impedance (9052). In block 9062, the algorithm determines whether the change value is greater than 1,200Ω for two consecutive measurements, as well as whether the Cal Ratio is larger than 14. If at least one of the latter inquiries is answered in the negative, then the sensor is allowed to continue operating and display SG values (9072). However, if the change value is greater than 1,200Ω for two consecutive measurements, and the Cal Ratio is larger than 14, then the sensor is terminated at block 9082.

Embodiments of the invention are also directed to assessment of reliability of sensor glucose values, as well as estimation of sensor-data error direction, in order to provide users and automated insulin delivery systems—including those in closed-loop systems—an indicator of how reliable the system is when SG is displayed to the user. Depending on the reliability of sensor data, such automated systems are then able to assign a corresponding weight to the SG and make a determination as to how aggressively treatments should be provided to users. Additionally, the direction of error can also be used to inform users and/or the insulin delivery system in connection with SG being a "false low" or a "false high" value. The foregoing may be achieved by, e.g., detecting dips in sensor data during the first day (EIS dip detection), detecting sensor lag, and lower-frequency (e.g., 10 Hz) impedance changes.

Specifically, in accordance with an embodiment of the invention, it has been discovered that a Cal Factor (CF) of above about 9 mg/dL/nA may be indicative of low sensor reliability and, as such, a predictor of higher error. Thus, CF values outside of this range may be generally indicative of one or more of the following: abnormal glucose sensitivity; calibrations that occurred during a dip in signal; delay in entering BG information, or high rate of change when calibrating; BG error when calibrating; and sensor with a transient change in glucose sensitivity.

FIG. 107 shows a flow diagram for a signal dip detection methodology in accordance with an embodiment of the invention, where increases in unfiltered real 1 kHz impedance may be used in combination with low Isig values to identify the start of a dip. As shown in the diagram, at block 9102, the logic determines whether sensor data is currently being blanked due to signal dip. If data is not being blanked, then the logic determines whether less than 4 hours have passed since sensor start (9104). If more than 4 hours have elapsed since sensor start, the logic then determines whether more than 12 hours have passed since sensor start (9106), in which case there will be no dip detection or blanking of data (9108). Thus, in this regard, the methodology is directed to identifying transient dips during the first 12 hours of sensor data.

Returning to block 9106, if less than 12 hours have passed since sensor start, then an inquiry is made regarding the recent EIS, Isig, and SG values. Specifically, in block 9110, if the two most-recent real impedance values (at 1 kHz) have been increasing, Isig<18 nA, and SG<80 mg/dL, then the algorithm determines that the start of a dip has been detected and notifies the system to stop displaying SG values (9112). On the other hand, if all of the foregoing conditions are not met, then there will be no dip detection or data blanking (9108).

When it is determined, at block 9104, that less than 4 hours have passed since sensor start, then a sensor dip event may still be encountered. Specifically, if the two most-recent EIS (i.e., 1 kHz impedance) values are increasing, and Isig<25 nA, then the algorithm determines that the start of a dip has been detected and notifies the system to stop displaying SG values (9114, 9116). If, however, the two most-recent 1 kHz impedance values are not increasing, or Isig is not less than 25 nA, then there will be no dip detection or data blanking (9108), as before.

Returning to block 9102, if it is determined that data is currently being blanked due to a dip, there is still a possibility that data will nevertheless be shown. That is, if Isig is greater than about 1.2 times Isig at the start of the dip event (9118), then it is determined that Isig has recovered, i.e., the dip event is over, and data display will resume (9122). On the other hand, if Isig is not greater than about 1.2 times Isig at the start of the dip event (9118), then it is determined that Isig has not yet recovered, i.e., the dip event is not over, and the system will continue to blank sensor data (9120).

In accordance with embodiments of the invention, the direction of error in SG (under-reading or over reading), in general, may be determined by considering one or more factors related to under- and/or over-reading. Thus, it has been discovered that under-reading in sensors may occur when: (1) Vcntr is extreme (e.g., Vcntr<−1.0 V); (2) CF is high (e.g., CF>9); (3) lower frequency impedance (e.g., at 10 Hz) is high (e.g., real 10 Hz impedance>10.2 kΩ); (4) FDC is in low CF mode; (5) sensor lag suggests under-reading; (6) lower frequency impedance (e.g., at 10 Hz) increases (e.g., 10 Hz impedance increases over 700Ω); and/or (7) EIS has detected a dip. Over-reading, on the other hand, may occur when: (1) lower frequency impedance (e.g., 10 Hz) decreases (e.g., lower frequency impedance<−200Ω); (2) sensor lag suggests over-reading; and/or (3) FDC when CF is in extreme mode.

Such under-reading or over-reading, especially in closed-loop systems, can have a profound impact on patient safety. For example, over-reading near the hypoglycemic range (i.e., <70 mg/dL) may cause an overdose of insulin to be administered to the patient. In this regard, several indicators of error direction have been identified, which may be used as test criteria, including: (1) low sensitivity indicators; (2) sensor lag; (3) FDC mode; and (4) loss/gain in sensitivity since calibration.

Two such low sensitivity indicators are high (lower-frequency) real impedance (e.g., >10 kΩ) and high Vcntr (e.g., Vcntr<−1.0V), both of which are, in general, indicative of loss of sensitivity. FIG. 108A shows an example in which Vcntr 9130 gradually increases (i.e., become more negative) as a function of time. At about 115 hours, shown by line 9135, Vcntr crosses−1.0V, as indicated by line 9137, and continues to increase (i.e., Vcntr<−1.0V) to about −1.2V. As shown, prior to about 115 hours, the Isig trend 9132 generally follows the Vcntr trend. However, once Vcntr passes the threshold (i.e., to the right of line 9135), the Isig departs from Vcntr, and continues to drop. At the same time, as shown in FIG. 108B, glucose 9134 also has a generally downward trend, with Cal errors 9136 being indicated at about 130 hours and about 165 hours.

As discussed previously, (EIS) sensor dips are also indicative of temporary sensitivity loss. Similarly, a high Cal Factor is indicative of the sensor's attempt to compensate for reduced sensitivity. In one example shown in FIGS. 109A and 109B, the Cal Factor 9140 increases steadily as a function of time. At about 120 hours (9145), the Cal Factor 9140 crosses a threshold value of 9 (9147). As shown in FIG. 109B, once the Cal Factor crosses the threshold, the glucose values 9142 show more frequent departures from BG values, with several errors 9144 occurring between about 135 hours and 170 hours.

As mentioned previously, sensor lag is another indicator of error direction. Accordingly, in an embodiment of the invention, the error that is caused by sensor lag is compensated for by approximating what the glucose value will be. Specifically, in an embodiment of the invention, the error from sensor lag may be approximated by defining:

$$sg(t+h) = sg(t) + hsg'(t) + \frac{1}{2}h^2 sg''(t)$$

where sg(t) is the sensor glucose function, and "h" is the sensor lag. The error may then be calculated as $$\text{Error} = \frac{sg(t+h) - sg(t)}{sg(t)} = \frac{\left(hsg'(t) + \frac{1}{2}h^2 sg''(t)\right)}{sg(t)}$$

or $$\text{Error} = \frac{k(C_1 sg'(t) + C_2 sg''(t))}{sg(t)}.$$

First day calibration (FDC) occurs when the Cal Factor (CF) is not within the expected range. The CF is set to the value indicated by the calibration, and then ramps up or down to the expected range, as shown, e.g., in FIGS. 110A and 110B. During this time, usually high, but generally predictable, errors may exist, resulting in potential over-reads or under-reads. As can be seen from FIGS. 110A and 110B, the CF changes at a generally constant slope as it rises or falls, and then settles, in this case at 4.5 or 5.5.

Lastly, post-calibration sensitivity change, i.e., loss/gain in sensitivity since calibration, is also an indicator of error/ error direction. Under normal circumstances, and except for first day calibration as discussed hereinabove, the Cal Factor remains generally constant until a new calibration is performed. Shifts in sensitivity after calibration, therefore, can cause over-reads and under-reads which, in turn, may be reflected by values of lower-frequency (e.g., 10 Hz) real impedance.

Specifically, it has been discovered that a drop in lower-frequency real impedance causes over-reading, with the direction of error being indicated by the real impedance curve. Conversely, lower-frequency real-impedance increases cause under-reading, with the direction of error also being indicated by the real impedance curve. However, current directionality tests may be unable to readily decipher points at peaks and valleys of the glucose profile. Thus, in one embodiment, the degree of sharpness of such peaks and valleys may be reduced by filtering, such as, e.g., by deconvolution with lowpass filtering.

As described previously in connection with FIG. 81, e.g., sensitivity change and/or loss may be used to inform proper sensor calibration. In this regard, in a further aspect of the invention, changes in sensor sensitivity may be predicted based on the previous calibration factor or on impedance so as to enable implementation of "smart calibrations", which help address continued generation and/or display of inaccurate glucose data when, e.g., sensor sensitivity has changed.

It is known that, in some existing continuous glucose monitoring systems (CGMS), calibration fingersticks are required every twelve hours. The calibration allows the CGMS to update the function used to convert the measured sensor current into a displayed glucose concentration value. In such systems, the 12-hour calibration interval is selected as a balance between reducing the user burden (of performing too many fingersticks) and using an interval that is sufficient to adjust for changes in sensor sensitivity before inaccuracies can cause too large of a problem. However, while this interval may be appropriate in general, if the sensor sensitivity has changed, 12 hours can be too long to wait if a high level of accuracy (in support of closed loop insulin delivery) is expected.

Embodiments of the invention, therefore, address the foregoing issues by using the previous calibration factor (see discussion of FDC below), or impedance (see discussion of EIS-based "smart calibrations" below), to predict if sensitivity has changed. Aspects of the invention also use time limits to maintain predictability for users, as well as include steps (in the associated methodology) to ensure that detection is robust to variations between sensors.

FIG. 111 shows a flow diagram in accordance with an embodiment of the invention for First Day Calibration (FDC). Starting at block 9150, if FDC is not on after successful calibration, there is simply no smart calibration request (9151). However, if FDC is on, a determination is made at block 9153 as to whether this is the first calibration and, if it is not, then a smart calibration request is made, with the timer set for 6 hours, i.e., it is requested that an additional calibration be made in 6 hours (9155). If, on the other hand, this is the first calibration, then block 9157 determines whether the Cal Ratio is less than 4, or greater than 7. If the condition in block 9157 is not met, then the logic proceeds to block 9155 where, as noted above, a smart calibration request is made, with the timer set for 6 hours. However, if the criterion in block 9157 is not met, then a smart calibration request is made, with the timer set for 3 hours, i.e., it is requested that an additional calibration be made in 3 hours (9159). Thus, in order to improve accuracy for sensors which need calibration adjusted, additional (smart) calibrations are requested which, in turn, limit the amount of time where the adjustment is incorrect.

In contrast with FDC mode, EIS-based smart calibration mode provides for additional calibrations if impedance changes. Thus, in an embodiment of the invention shown in FIG. 112, an allowed range relating to impedance values (and as defined hereinbelow) is set in the hour after calibration and, following the calibration, a request for additional calibrations is made if impedance is outside of range. Thus, if not within one hour since calibration, a determination is made as to whether the filtered 1 kHz imaginary impedance value is outside of range (9160, 9162). If the impedance value is not outside of range, then no change is made (9164). However, if the filtered 1 kHz imaginary impedance value is outside of range, then the calibration timer is updated so that calibration is requested to be performed at 6 hours from the previous calibration (9168). It is noted that, while higher-frequency imaginary impedance tends to better identify changes in glucose sensitivity, towards the higher end of the frequency spectrum, measurements are generally noisier and, as such, may require filtering.

Returning to block 9160, if it is determined that less than one hour has passed since calibration, then the range for impedance values may be updated (9166). Specifically, in one embodiment, the impedance range calculation is performed on the last EIS measurement 1 hour after calibration. In a preferred embodiment, the range is defined as $$\text{range} = 3 \times \text{median}(|x_i - x_j|)$$

where j is the current measurement, and i are the most recent 2 hours of values. In addition, the range may be limited to be values between 50Ω and 100Ω. It is noted that the range as defined above allows for 3 times median value. The latter has been discovered to be more robust than the 2-standard-deviation approach used in some prior algorithms, which allowed noise and outliers to cause inconsistencies.

As has been discussed in detail herein, most continuous glucose sensor monitoring (CGM) systems require fingerstick blood glucose measurements for calibration. For real-time systems, it can be difficult to determine changes in sensor behaviors, such as sensitivity or sensor anomaly, at the time of the data output. Therefore, calibration using a finger-stick measurement is needed to assure sensor accuracy. Calibration using fingersticks, however, is not only painful, but also cumbersome for the user. Embodiments, therefore, have been directed to retrospective calibration-free algorithms for continuous sensor recorders, including use of the ASIC previously described in detail herein. In this regard, as was noted previously in connection with EIS-related algorithms and calibration, within the context of the instant description, the term "calibration-free" does not mean that a particular sensor needs no calibration at all. Rather, it means that the sensor can self-calibrate based on the data that is stored in the sensor recorders, without the need for additional finger-stick or meter data. Thus, the need for finger-stick measurements to provide a reference can be eliminated for retrospective systems.

Retrospective sensor systems have the ability to have the entire traces of raw signals available for use by an algorithm before processing and converting to glucose values. Specifically, sensor recorders may record the raw signals, such as, e.g., Isig and Vcntr, as well as EIS data for diagnostics. As shown in FIG. 113, the retrospective algorithm may comprise several processing components, including: (1) raw Isig signal processing (9205, 9210); (2) discrete wavelet decomposition of the raw Isig signal (9215); (3) raw EIS signal processing (9230, 9235); (4) generating sensor glucose (SG) based on different models from machine learning methods (9240, 9245); (5) fusion of the SG values from different models (9250); (6) selective filtering (9263); and (7) blanking of SG (9255, 9260).

The processing of the raw Isig signal may use a unified and simplified function to handle several anomalies such as artifacts and noisy signals. In addition, signal smoothing (9220) may be accomplished by using a polynomial model for local regression with weighted linear least squares. Effects of outliers are reduced by assigning less weight. Retrospective processing allows local regression to be done with forward and backward data, with the smoothing having no phase delay as seen in most real-time filtering. Following the smoothing, noise calculation is performed. Noise calculation (9225) is based on evaluating the difference between the raw and smoothed signal and calculating the percentage of data within a defined window that has high noise-to-signal ratio. EIS data may also be smoothed using a similar retrospective smoothing function (9235). After smoothing of the EIS data, the EIS data may then be interpolated to generate EIS data that match the timestamps of the Isig data.

In one embodiment, discrete wavelet transform may be applied on the raw Isig signals (9215). The transform operation decomposes the Isig signal into several predefined levels. At each level, the algorithm generates the coefficients for approximation and detail signals, where the approximations are the high-scale, low-frequency components of the signal, and the details are the low-scale, high-frequency components of the signal. For the approximation signals, the lower level approximation captures the short-term variations and the higher-level approximation captures the long-term trend. Discrete wavelet transform may also be used as a valuable tool in identifying regions with sensitivity loss in the signal.

Machine learning techniques may be used, e.g., for generating the models for converting signals into SG values (9240) as a function of measured signals (e.g., Isig, Vcntr, EIS, etc.). In embodiments, three specific techniques may be used, including genetic programming (GP), artificial neural network (NN), and regression decision tree (DT). To generate the training data set, blood glucose (BG) measurement values and the associated Isig, Vcntr, wavelet and EIS data points are extracted. Preprocessing of the data can also be done to improve the model being generated. Preprocessing steps include reducing the number of data points that are close in time, adjusting the distribution of points within a certain glycemic range to reduce overemphasis at that (BG) range, and removing outliers to reduce/eliminate BG points with high variations.

Genetic programming (GP) is based on rules that imitate biological evolution. Combining basis functions, inputs, and constants creates an initial model population. The models are structured in a tree-like fashion, with basis functions linking nodes of inputs. In each generation (iteration) of the algorithm, relatively successful individuals are selected as "parents" for the next generation and form a reproduction pool. New generations of solutions evolve, using one of three possible operators: crossover, mutation, and permutation. The procedure is repeated until a stopping criterion is attained. In one embodiment, examples of training results may include:

$$sg=(u2\cdot^*-0.083513-0.48779\cdot^*((u1+0.11432\cdot^*u6)\cdot^*u33))-0.30892 \quad \text{GP1:}$$

$$sg=(u4\cdot^\wedge 2-0.55328*u4-0.46565*u45-1.5951*u2)*0.13306+0.88185*u1-0.40782 \quad \text{GP2:}$$

$$sg=((u4\cdot^\wedge 2)\cdot^\wedge 2-7.8567*(u2+0.33071*u43))*0.02749+0.88109*u1-0.38492 \quad \text{GP3:}$$

where
u1: Isig
u2: Vcntr
u4: 4 KHz Real
u6: 1 KHz Real
u9: 128 Hz Real
u33: 40 Hz Imag
u43: 0.4 Hz Imag
u45: 0.16 Hz Imag Neural networks are composed of simple elements operating in parallel. These elements are inspired by biological nervous systems. As in nature, the connections between elements largely determine the network function. A neural network model is trained to perform a particular function by adjusting the values of the connections (weights) between elements. The back propagation (BP) neural network algorithm, a multi-layer feedforward network trained according to error back propagation algorithm, may be used, with inputs including, e.g., Isig, Vcntr, EIS, wavelets, duration (i.e., time since sensor insertion), etc., to produce a BG output.

In a decision tree, the model is comprised of several nodes in which splitting of the population occurs and the output is comprised of several regression models. For a numeric prediction, a regression tree may be used which, in turn, uses measured inputs (including, e.g., Isig, Vcntr, EIS, wavelets, etc.), to produce a BG as output in the training. Initially, a starting tree is built from top down. At each node, a decision is made on a variable and split into subsets. Splitting is based on maximizing the purity of each node. The results at the bottom are the leaves, wherein each leaf is a linear model relating the SG with the input variables. Pruning can be done to reduce the number of splits.

FIG. 114 shows an example of a decision tree. Starting with measured Isig in block 9302, a determination (i.e., decision) is made as to whether the measured Isig value is ≤34.58 nA (9304), or >34.58 nA (9306). If the latter is true, then a further decision is made as to whether the Isig value is ≤48.82 nA (9304), or >48.82 nA. If the former is true, then the SG may be calculated according to a Linear Model (LM5), as shown in block 9320. If, on the other hand, Isig is >48.82 nA, then SG may be calculated according to a different Linear Model (LM6), as shown in block 9322.

Returning to block 9304, when Isig is ≤34.58 nA, a further decision is made as to whether Isig is ≤19.975 nA (9308). If it is, then, if Vcntr≤−0.815V, then a first Linear Model (LM1) is employed (9312). Otherwise (i.e., if Vcntr>−0.815V), then a second Linear Model (LM2) is used (9314). If, on the other hand, Isig>19.975 nA, then a further decision is made at block 9310. Here, if wavelet10 (w10)≤27.116, then a third Linear Model (LM3) is used (9316). However, if wavelet10>27.116, then a fourth Linear Model (LM4) is used to calculate SG (9318).

Fusion of the SGs may be performed to generate a single output SG. As has been discussed hereinabove, fusion may be done by assigning weights to each of the SGs based on various inputs, and then combining the outputs. In preferred embodiments of the invention, such inputs may include EIS, Isig, duration, and wavelets. Other methods for signal fusion may also be utilized.

In embodiments of the invention, blanking of the data may be performed on the final SG to prevent displaying of unreliable signals. Blanking based on noise is done by setting thresholds on the noise level and blanking the data above the threshold. Blanking based on EIS, Isig, Vcntr, wavelets, as well as other factors, may also be performed. A decision tree may also be used to generate blanking models that combine the various inputs. For example, a decision tree may be used to identify "good" or "bad" points in a training set. In an embodiment of the invention, a threshold may be set on Cal Ratio (as a good indicator of sensitivity loss), with points having a Cal Ratio above the threshold identified as "bad" points.

FIG. 115 shows an example of training results with Isig, Vcntr, and two wavelets (w7 and w10) as inputs. If w7 is less than or equal to a first threshold, and Vcntr is greater than a second threshold, then the signal may be shown (9350, 9352, 9356). However, if Vcntr is less than or equal to the second threshold, then the signal will be blanked (9354). As shown on the right-hand side of the decision tree, if w7 is greater than the first threshold, and w10 is greater than a third threshold, then the signal may be shown (9358, 9362). Similarly, if w10 is not greater than the third threshold, but the Isig is greater than a fourth threshold, then the signal may still be shown (9360, 9366). Moreover, if w10 is not greater than the third threshold, and Isig is not greater than the fourth threshold, but Vcntr is greater than a fifth threshold, then the signal may still be shown (9360, 9364, 9370). However, if Vcntr is less than or equal to the fifth threshold, then the signal will be blanked (9368).

In embodiments herein, an outlier detection algorithm may be used as a diagnostic tool, including fusion, selective filtering, and blanking of data. Specifically, the fusion algorithm may fuse sensor glucose values from, e.g., a decision tree (DT) algorithm and genetic programming (GP), based on approximated error difference. Selective filtering entails filtering of the fused SG values and spike removal. A blanking algorithm may be based on approximated error prediction.

More particularly, the above-mentioned fusion algorithm may include examining the difference between decision tree Absolute Relative Difference (ARD) and genetic programming ARD at each BG point, as each of DT and GP has respective areas with better performance. The difference is then fit by a linear regression combination of parameters, inputs, and functions of parameters, including, e.g., SG, CR, imaginary impedance, real impedance, noise, rate of change, sensor gain, cumulative Vcntr rail time, etc. Thus, e.g.:

$$ARD_{DT} - ARD_{GP} = \Sigma weight_n \times param_n$$

where the parameter list and weights are updated with every iteration of DT and GP. The parameters are automatically pruned one by one based on removing the lowest sensitivity, until a final set of parameters and coefficients is obtained. The expected difference is then transformed into a weight ([0,1]) for DT and GP for generating a weighted average of SG values:

$$w(ARD_{diff}) = \frac{1}{1 + e^{kARD_{diff}}}$$

Selective sensor glucose (SG) filtering allows noisy segments of SG to be smoothed, rather than blanked, so that SG display may continue without disruption. Thus, selected sections may be smoothed using a filter that turns on at high noise. In this regard, in one embodiment, spikes in SG may be detected by the second derivative and removed, with SG selectively smoothed by, e.g., a 12-point, low-pass infinite impulse response (IIR) filter on low signal-to-noise ratio (SNR) points.

As noted, a blanking algorithm may be based on approximated error prediction, i.e., model prediction of error at each point. In this regard, coefficient weights may be generated by fitting the model to ARD at each BG point in training data. Thus:

$$ARD_{expected} = C_0 + \sum_{n=1}^{N} C(n)param(n) + abs\left(\sum_{m=1}^{M} C(m)Param(m)\right)$$

where SG is blanked when expected ARD is above a threshold. FIG. 116 shows examples of parameters that may be used in a blanking algorithm based on approximated error prediction. As shown in FIG. 117, diagnostic steps progressively decrease MARD and increase consensus while, at the same time, ensuring that sensor display times remain high at about 98% after blanking.

In some embodiments, the foregoing algorithms may also be applied to real-time systems, where real-time information (e.g., Isig, Vcntr, real-time EIS with zeroth-order hold, etc.) may be used as inputs. In contrast to the retrospective algorithms, real-time algorithms may be generated that do not use interpolated EIS or wavelets.

As noted hereinabove, to reduce the computational burden of glucose value estimation, glucose sensing systems aim to create a linear relationship between blood glucose (BG) and sensor current (Isig) values such that their ratio yields a constant calibration factor (CF), for all glucose levels of interest, expressed as $$CF = BG/(Isig + offset)$$

Here "offset" is an assumed constant sensor bias. When glucose sensing is based on measurements from interstitial fluids, the cumulative effect of the lag in the translation of glucose from blood to interstitial fluid and spurious sensor measurement noise leads to a time-varying calibration factor and "offset" and a more complex sensor sensitivity relationship that may be linearly approximated as $$SG = CF(Isig + offset) + \varepsilon_s$$

where SG is the sensor glucose value, and $\varepsilon_s$ represents the random time-varying sensor error. A reference BG level is usually measured using a finger stick procedure. In general, this measurement differs from the SG value implied by a linear relationship between BG and Isig by a prediction error value ($\varepsilon_P$). That is, $$BG=SG+\varepsilon_P.$$

There is also a first order lag between SG and the physical sensor current output, Isig. Thus:

$$\dot{SG} = -\frac{1}{\tau}(SG) + \frac{1}{\tau}(Isig),$$

where $\tau$ is a dynamic time variable that characterizes the dynamic relationship between SG and Isig. It should be noted that $\tau$ is not known precisely as it can vary by sensor type, patient physiology, sensor insertion location, wear time, and other variables.

Embodiments of the inventions herein may use modeling algorithms, including logic that combines values of Isig, electrochemical impedance spectroscopy (EIS), counter electrode voltage (Vcntr), and wear time, as well as their trending values to model $\tau$ and the prediction error value $\varepsilon_P$. The estimate of the prediction error $\varepsilon_P$ produced by the modeling process is called the model estimated error, or $\varepsilon_M$. The difference between the prediction error $\varepsilon_P$ and the model estimated error $\varepsilon_M$ is the residual error, or $\varepsilon_R$. The residual error is the portion of the prediction error $\varepsilon_P$ that is not captured by the modeling process and not incorporated into $\varepsilon_M$. In other words, $$\varepsilon_P=\varepsilon_M+\varepsilon_R.$$

The better the modeling process is at estimating $\varepsilon_P$, the lower the value of residual error $\varepsilon_R$, and the more accurate the prediction models obtained will be. So typically, $$\varepsilon_R<<\varepsilon_P.$$

Success in modeling SG can be measured by the attained success in reducing $\varepsilon_R$. When choosing between a plurality of modeling options, preference is given to models that produce relatively lower $\varepsilon_R$ as they are likely to provide a better correction for dynamic changes in sensor sensitivity and systemic sensing biases due to manufacturing and use variability.

In embodiments herein, the error reduction may be achieved through various mechanisms. As described in more detail hereinbelow, in one embodiment, e.g., a plurality of independent sensor glucose calculation units—e.g., four—may be used, wherein each unit may implement a distinct dynamic model of interstitial glucose sensing that variously accounts for nonlinearities in glucose sensing response caused by such factors as bio-fouling, foreign body response, nonlinear sensor response curves, particularly during hypoglycemia, and variations in chemistry layer stabilization and settling times. In embodiments, an external calibration module may be used to determine whether external physiological measures (PM) and/or environmental measures (EM) are available for use in calibrating the glucose sensor, and, when available, to convert the PM and/or EM into a modification factor that may be incorporated into the calculation of the SG value. Thus, embodiments of the inventions herein enable adjustment of SG calculation to account for changes in a user's environment and physiology in real time.

FIG. 118 shows an embodiment in which the aforementioned modification factor from an external calibration module may be applied individually to independent sensor glucose calculating units prior to SG calculation and subsequent fusion, wherein each of the sensor glucose calculating units may include a respective model for SG calculation. FIG. 119, on the other hand, shows another embodiment, in which individual SG values are first fused into a final (fused) SG value, after which a modification factor from an external calibration module is applied to the fused SG. It is noted that the SG values may be fused using any one or more of the fusion algorithms discussed previously herein.

More specifically, as shown in FIG. 118, at Block 9401, raw data received from sensor electronics are first preprocessed to extract information including, e.g., electrochemical impedance spectroscopy (EIS) measurements, Isig values, and counter electrode voltage (Vcntr) values, as well as their trending information. One or more (calibration-free, SG-predictive) models 9405-9408 are then used to calculate SG values based on the outputs of Block 9401. It is noted that, although four such models are shown in the figures herein, fewer or more models may be used.

As shown in FIG. 118, each of the four models may use, as an input, a calibration factor 9403 that is obtained from external physiological and/or environmental factors to calculate respective SG values via each of the plurality of models 9405-9408. At Block 9411, the plurality of individual SG values is fused to generate a final, calibrated, single (fused) SG value. In Block 9413, diagnostics are performed on the fused SG to detect and, where possible, correct errors before the (corrected) final SG may be displayed (e.g., to a user of the glucose sensor) and/or transmitted (e.g., to a receiving device) to be used for therapy, in Block 9415. Where correction is not possible, however, the fused SG value may be blanked, so that it is not shown to the user and/or not used for therapy. FIG. 119 is similar to FIG. 118, except that, now, the calibration factor that is obtained from external physiological and/or environmental factors (Block 9417) is applied during the fusion process in Block 9416. Moreover, in embodiments, a filter may be applied to the fused SG value prior to calculating calibrated SG value.

FIG. 120 describes the concept, implementation, and key assumptions behind each of four models used in embodiments of the inventions herein. In some embodiments, the glucose sensitivity map, representing the relationship between BG and Isig across various glycemic and wear time ranges, is expected to be non-linear. Thus, modeling the sensitivity includes developing algorithms to reduce residual error components that may arise from estimating the sensor sensitivity map, $\varepsilon_S$, implementing the sensing models, $\varepsilon_I$, and overcoming the lack of representativeness of the training samples used to tune the model parameters, $\varepsilon_T$. The residual error from the modeling process, $\varepsilon_R$, may then be described as a function of these errors:

$$\varepsilon_R=f(\varepsilon_S,\varepsilon_I,\varepsilon_T)$$

In embodiments of the inventions herein, the dynamic sensing models were chosen to be different from each other and yet to each yield approximately the same value of residual error, $\varepsilon_R$, and exhibit unique patterns of strengths and weaknesses. The strengths of the models therefore augment each other and mitigate potential weaknesses of the group.

For a randomly chosen sensor, FIG. 121 shows an annotated sensor plot indicating regions where each of the four models performs best. As discussed above in connection with FIGS. 118 and 119, the respective outputs of the sensing units (e.g., sensors) may be blended to provide a final, fused sensor glucose value in blocks 9411 and 9416, and a measure of confidence in the calculated value in block 9413.

In embodiments herein, confidence in the fused sensor glucose value, or $C_{SG}$, may be calculated through various mechanisms within blocks 9411, 9416, and/or 9413. As described in more detail hereinbelow, in one embodiment, the measure of confidence is obtained from the relation between the absolute range of the SG values produced by the respective sensing units, or $R_{SG}$, and an experimentally determined threshold value $T^R$, e.g., $$C_{SG} = \begin{cases} 0, & \text{if } R_{SG} > T^R \\ 1 - R_{SG}/T^R, & \text{if } R_{SG} < T^R \end{cases}.$$

In one preferred embodiment, the threshold may be set as 10 mg/dL. In a different embodiment, the experimentally determined threshold may not be a fixed value for all glucose ranges, but a fraction, e.g., 10%, of the magnitude of the absolute mean of the values produced by the respective sensing units.

In another embodiment, described in more detail herein, the measure of confidence may be obtained in two steps. In the first step, a measure of the dispersion of the values produced by the respective sensing units, e.g., their standard deviation, absolute range, inter-quartile range, etc. is divided by the mean of the individual values to obtain a generalized normalized dispersion ratio, or $D_{SG}$. In the second step, the confidence value, or $C_{SG}$, is produced from the relation between $D_{SG}$ and a threshold value $T^D$, e.g., as $$C_{SG} = \begin{cases} 0, & \text{if } D_{SG} > T^D \\ 1 - D_{SG}/T^D, & \text{if } D_{SG} < T^D \end{cases}.$$

In a preferred embodiment, $D_{SG}$ was the coefficient of variation (the standard deviation of the values produced by the sensing units divided by their mean value) and the threshold value was set to 15% for mean values less than 70 mg/dL and 20% for mean values greater than 70 mg/dL.

FIG. 122 shows an embodiment of the logic flow for operationalizing the optional external calibration algorithm, such as that for, e.g., Blocks 9403 and 9417 discussed previously in connection with FIGS. 118 and 119, respectively. The algorithm receives physiological (9430) and/or environmental (9450) measurements, when they are available, and uses them to generate a modification factor, MF, that can be used to calibrate a glucose sensor at various points in its glucose estimation logic. Specifically, at 9432, if it is determined (e.g., by a microcontroller) that the received raw physiological measurement (RPM) is not valid, then physiological factors are ignored in generating the external calibration estimations (9434). If, on the other hand, it is determined that the RPM is valid, then a physiological calibration factor (PCF)—or, when a plurality of PCFs are present, then their aggregate—is calculated (9436). Thus, the algorithm calculates a physiological calibration factor from one or more valid physiological data received and ignores the data if none of it is valid. Similarly, at 9456, the algorithm calculates an environmental calibration factor (ECF) from one or more valid raw environmental measurements (REM) received. However, if it is determined, at 9452, that the ECF is not valid, then the latter is ignored in generating the external calibration estimations (9454).

In one preferred embodiment, RPM and REM values are determined to be valid if they satisfy two conditions: (1) they are "regular" or fall within experimentally determined normal ranges; and (2) they are "actionable" or indicated by the system and/or user as informative enough that variations in their value could be expected to affect sensor glucose value estimation. Information on which supported RPM and REM values are "actionable" is input into the system through a user interface, e.g., a touchscreen of a pump, a graphical user interface, a glucose monitoring mobile application, etc.

For instance, using the heart rate measurement obtained from a wearable device, experiments have shown that RPM values associated with heart rate measurements outside of the range 75 to 155 beats per minute are invalid and RPM values associated with body temperature measurements outside of the range 33 to 38 degrees Celsius are invalid as well. Other experiments have shown that REM values associated with ambient temperature outside of the range 10 to 50 degrees Celsius obtained from a wearable device are invalid. In this case, temperatures outside of the stated range appeared to interfere with the proper working of the electronics of the sensor system.

In embodiments, aggregation of RPM and REM values may comprise two steps. In the first step, the values are normalized (e.g., by a microcontroller) using a normalization function, e.g., subtracting each value from its minimum expected amount (e.g., 75 beats per minute for heart rate, 33 degrees Celsius for body temperature, and 10 degrees Celsius for ambient temperature) and dividing the result by the magnitude of its expected range (e.g., 155-75 beats per minute for heart rate, 38-33 degrees Celsius for body temperature, and 50-10 degrees Celsius for ambient temperature). In the second step, the normalized values are scaled using scaling functions, such as, e.g., FIG. 125 and FIG. 126, specific to the environmental or physiological factor under consideration, and the scaled values are combined to generate an aggregate value. In one embodiment, the combination may be obtained by multiplying the different scaled values together. In other embodiments, the aggregation may be achieved by determining a mean value or selecting the maximum of the available values.

Returning to FIG. 122, at 9438 and 9458, respectively, it is determined whether each of the PCF and ECF is valid. In a preferred embodiment, the PCF and ECF values may be determined to be valid if they fall within experimentally determined upper threshold $T_U^{CF}$ and lower threshold $T_L^{CF}$ calibration factor values, e.g., 0.6 and 1.5, respectively. In each case, if either the PCF and/or the ECF is found not to be valid, then it is ignored in the external calibration estimation (9434, 9454). For the physiological and environmental calibration factors that are valid, their respective values are fused to generate a modification factor MF (9442). Next, it is determined whether the calculated MF is valid (9444). If the MF is determined to be invalid, then it is ignored at 9446. However, when it is determined that the MF is valid, it is applied in the overall algorithm (9448) as discussed, e.g., in connection with FIGS. 118 and 119. In a embodiments, the MF values are determined to be valid if they fall between experimentally determined upper threshold, or $T_U^{MF}$, and lower threshold, or $T_U^{MF}$, values, e.g., 0.8 and 1.2, respectively. In this case, the maximum allowed adjustment to SG values due to environmental and physiological factors of about 20%.

In one embodiment, the fusion process (9442) between the PCF and ECF values to calculate the modification factor, MF, may comprise a simple multiplication of the respective factors. Thus, for this embodiment, MF may be defined as follows:

MF=PCF×ECF.

In another embodiment, the combination may comprise selecting the maximum value between the respective factors. Here, MF=max(PCF,ECF).

In yet another embodiment, the combination may comprise selecting the average of the two factors, such that MF is defined as follows:

MF=(PCF+ECF)×0.5.

FIGS. 123 and 124 show the details for generating each of the PFC and EFC, respectively. Specifically, in FIG. 123A, external physiological measurements, including, by way of illustration, one or more of activity level or exercise status information (9460), heart rate status information (9470), blood pressure status information (9480), and body temperature status information (9490) are received. Once received, each of the physiological measurements is separately evaluated for validity and, if valid, is eventually converted into its own unique factor, such as, e.g., an activity level factor, a heart rate factor, a blood pressure factor, and a body temperature factor. The factors from all valid measurements are then combined to generate a physiological calibration factor (PCF). See FIG. 123B. In one embodiment, this combination is achieved by multiplying the values of all valid physiological factors. In other embodiments, the combination may be achieved by selecting the mean or maximum of the values of all the valid physiological factors.

More specifically, the value of each obtained (raw) physiological measurement is first compared to a normal range or, alternatively, to a threshold value (9462, 9472, 9482, 9492). For example, in embodiments, the experimentally determined normal range for body temperature may be 33 to 38 degrees Celsius as measured by wearable device. Similarly, the normal range for heart rate may be 75 to 155 beats per minute as measured by a wearable device. If the obtained value is found to be valid based on this comparison, then the respective value is used to generate a factor for the respective physiological measurement (9463, 9473, 9483, 9493). If the obtained value fails the latter test, then it is determined whether the value is nevertheless actionable (9465, 9475, 9485, 9495), in which case the value is still used in generating the respective factor. A value may be considered to be actionable if, e.g., by user interface selections, it is indicated by the system and/or user to be informative enough that variations in its value could be expected to affect sensor glucose value estimation. However, if the obtained value is determined not to be actionable, then a factor is not generated for that specific physiological parameter (9467, 9477, 9487, 9497). Finally, as noted above, all of the valid measurements are then combined at 9499 to generate a physiological calibration factor (PCF).

Similarly, as shown in FIG. 124A, environmental measurements including, by way of illustration, one or more of ambient temperature status (9510), ambient pressure status (9520), relative altitude status (9530), and ambient humidity status (9530) are received. Once received, each of the environmental measurements is separately evaluated for validity and, if valid, is eventually converted into its own unique factor, such as, e.g., a temperature factor, a heart pressure factor, a blood altitude factor, and a body humidity factor. The factors from all valid measurements are then combined to generate an environmental calibration factor (ECF). See FIG. 124B. In one embodiment, this combination is achieved by multiplying the values of all valid environmental factors. In other embodiments, the combination is achieved by selecting the mean or maximum of the values of all the valid environmental factors.

More specifically, the value of each obtained (raw) environmental measurement is first compared to a normal range or, alternatively, to a threshold value. (9512, 9522, 9532, 9542). For example, in embodiments, the experimentally determined normal range for ambient temperature may be 10 to 50 degrees Celsius as measured by wearable device. If the obtained value is found to be valid based on this comparison, then the respective value is used to generate a factor for the respective environmental measurement (9513, 9523, 9533, 9543). If the obtained value fails the latter test, then it is determined whether the value is nevertheless actionable (9515, 9525, 9535, 9545), in which case the value is still used in generating the respective factor. A value may be considered to be actionable if, e.g., by user action (e.g., through a graphical user interface on a glucose pump system or a software application), it is indicated by the system and/or user to be informative enough that variations in its value could be expected to affect sensor glucose value estimation. However, if the obtained value is determined not to be actionable, then a factor is not generated for that specific environmental parameter (9517, 9527, 9537, 9547). Finally, as noted above, all of the valid measurements are then combined at 9549 to generate an environmental calibration factor (ECF).

In embodiments of the invention, the conversion scale may include either boosting or suppressing. In this regard, FIG. 125 shows an idealized boosting conversion scale for physiological and environmental factors. In this context, a boosting conversion scale amplifies values that fall below the typical range for a specific physiological or environmental factor, while suppressing values that fall above the range. This is useful for physiological and environmental measures that may artificially increase the observed measurement recorded by a glucose sensor. In embodiments of the inventions herein, body temperature, ambient temperature, and ambient pressure are some of the factors that may benefit from such conversion.

FIG. 126 shows an idealized suppression conversion scale for physiological and environmental factors. Unlike a boosting conversion scale, a suppression conversion scale suppresses values that fall below the typical range for a specific physiological or environmental factor, while boosting values that fall above the range. This may be useful for physiological and environmental measures, such as, e.g., relative altitude, that may artificially decrease the observed measurement recorded by a glucose sensor.

In embodiments, the external calibration is a measure of blood glucose concentration obtained from continuous glucose monitoring systems that may be similar to, or dissimilar from, the systems described herein. An example of a system that is different from that described herein would be importing SG measurements from the Abbott FreeStyle Libre Professional CGM. Here, the SG reading is used as an externally calibrated BG value and either used to calibrate each of the SG generating units or integrated into the aggregated SG calculation, by, for example, adjusting the variance estimate of each SG generating unit. The variance estimate of the output of an SG generating unit is an estimate of the expected accuracy variation with which the SG calculating unit is expected to predict SG values (e.g., within a specified glucose range on a specified sensor wear day) obtained from analyzing the SG calculating unit's past performance predicting SG values under similar conditions.

Figure 127B:
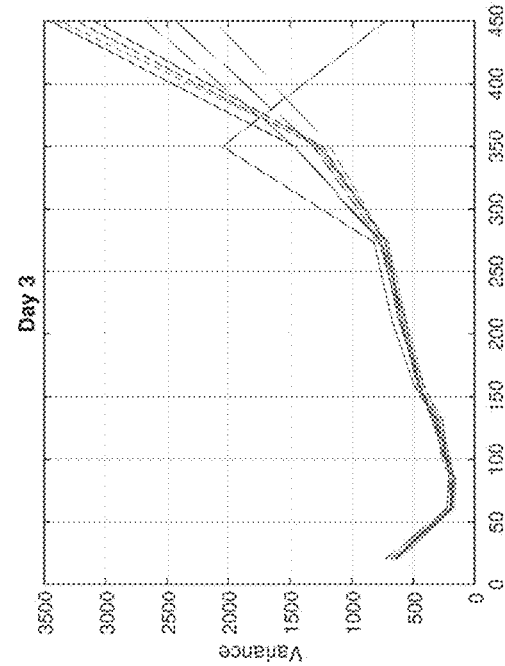
Figure 127D:
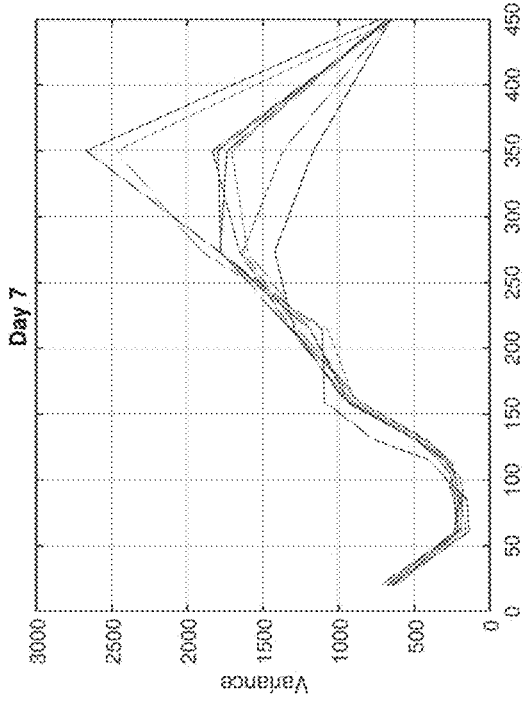
Figure 127A:
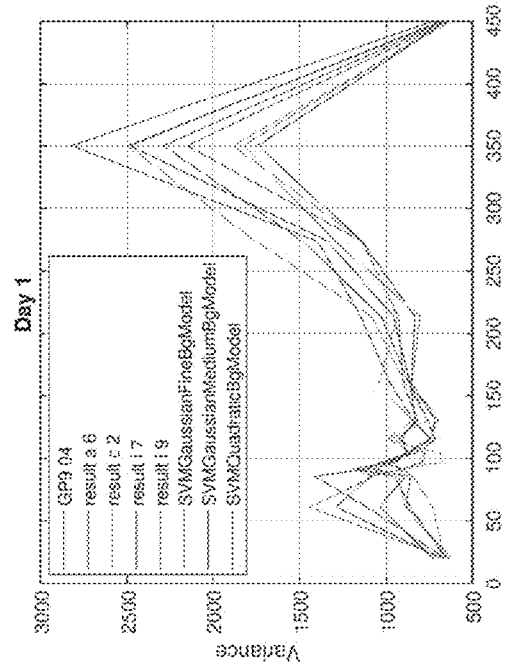
Figure 127C:
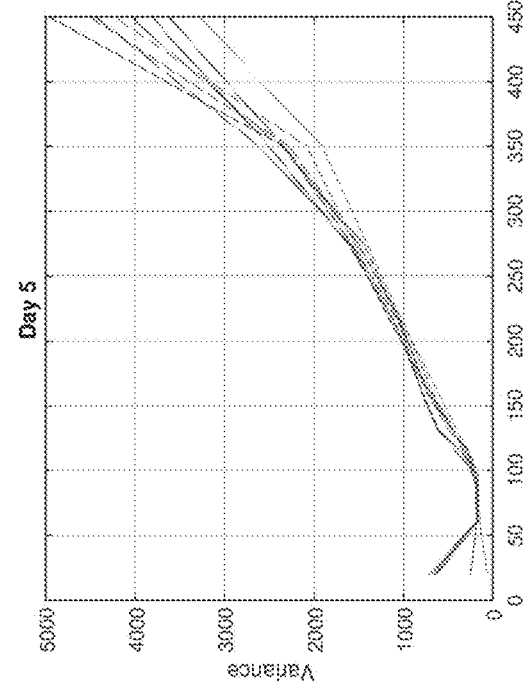

In embodiments, the first step in calculating variance estimates for SG calculating units is to obtain distributions of SG predictions over a large glycemic range and across multiple days of sensor wear using, e.g., past clinical study data input. Within each bin, comprising, e.g., a sensor wear range and a glycemic range, the mean of the square difference between the SG produced by the SG calculating unit and the BG supplied by a reference method is determined. FIG. 127A shows a plot of variance estimates for various glucose ranges for eight distinct SG calculating units for the first 24 hours, or Day 1, of sensor wear for a group of 1821 sensors worn by 537 different subjects. FIG. 127B shows a similar plot for Day 3 of sensor wear. FIG. 127C shows the variance estimates for Day 5 of sensor wear and FIG. 127D shows the estimates for Day 7 of sensor wear.

On the other hand, an example of using external calibration measures from a device that is similar to those described herein may involve, e.g., overlapping two sensors, inserted into the body at different times, in such a way that the second sensor is inserted towards the end of life of the first sensor, so that the first sensor reaches its end of life by the time the second sensor is warmed up and ready for normal operation. In this embodiment, the first sensor is the primary source of SG values to a third device, such as a glucose pump system or hand-held glucose monitor device, until the second sensor is warmed up, at which time the second sensor becomes the primary source of SG values to a third device. This arrangement could be used to prevent loss of SG values to the third device due to downtime during sensor warm up. The SG value is handled similar to the embodiment with the Abbott FreeStyle Libre Professional CGM.

Embodiments of the inventions herein may be implemented in connection with hybrid closed-loop (HCL) systems, while other embodiments allow for use in standalone CGM systems. In the former, the system may have transmitters that communicate with an insulin pump supporting a HCL algorithm via a proprietary radio-frequency protocol. In the latter embodiment, the communication protocol may be Bluetooth Low Energy Technology supported through a mobile device display application. When supporting an HCL system, the transmitter may include logic to ensure sensor values reliably support insulin dosing.

Embodiments of the inventions herein are also directed to methods and systems for correcting for manufacturing batch variations in sensor parameters in sensor glucose modeling. Specifically, the manufacture of sensors used in continuous glucose monitoring (CGM) devices adheres to fixed tolerances to ensure that sensors produced are of consistent quality and exhibit similar performance. In practical applications, differences in performance between sensor batches still exist. This is often evident when the performance of batches of sensors are compared over extended time periods. This variability in performance due to variations in manufacturing parameters/processes often means that algorithms for sensor glucose estimation are designed and tested on sensor batches that may have different performance profiles from those of future (i.e., subsequently-manufactured/tested) sensors to which the algorithm may be applied in the field. This, in turn, could lead to systemic bias, as well as hard-to-track errors in sensor glucose estimation.

FIGS. 128A-C show data for a typical sensor trace-set. Here, the sensor performance is standard with a consistent sensor sensitivity profile during a 7-day wear. Two very different sensor algorithms, i.e., "C-alg", which is an algorithm that requires two blood glucose (BG) calibrations per day, and "Zeus", which is a more advanced optional BG calibration algorithm that works with and without BG calibrations, were used to analyze the sensor data obtained and produced nearly identical results.

Specifically, FIG. 128A shows the sensor current (Isig) and counter voltage (Vcntr) traces over the 7-day wear period. FIG. 128B shows the calibration factor used to generate the sensor glucose (SG) values for the two algorithms mentioned hereinabove, where plot 9601 is indicative of the calibration ratio (the after-the-fact imputed ratio between Isig and SG) for the Zeus algorithm, and plot 9603 is indicative of the calibration factor (the before-estimate determined ratio between Isig and SG) for the C-alg algorithm. In FIG. 128C, the calculated SG value for the Zeus algorithm is shown by plot 9605, and that for the C-alg algorithm is shown by the plot 9607.

FIGS. 129A-C show a sensor trace-set for a sensor that exhibits a decrease in sensitivity during the 7-day sensor wear, as indicated by the decrease in the average Isig level over time. In this case, the "Zeus" algorithm does a better job of correcting for the sensitivity change than the "C-alg". FIGS. 130A-C, in contrast, show a sensor trace-set for a sensor that exhibits sensitivity increase during a 7-day sensor wear, as indicated by the increase in the average Isig level over time. This type of sensitivity change is atypical of the training set of sensors used to generate both algorithms, but not necessarily atypical of later batches of sensors destined for use in the field with the algorithms. The algorithms were not previously exposed to this type of data. As a result, the "Zeus" algorithm was only able to correctly compensate for the change when external calibration using BG values was allowed. Thus, plot 9609 shows the calibration factor used to generate the SG values for the Zeus algorithm with no calibrations, while plot 9611 shows the calibration factor used to generate the SG values for the Zeus algorithm with one calibration per day.

As noted previously, calibration-free sensors provide users with better sensor wear experiences, reduce discomfort associated with using CGM devices, and reduce errors that may be introduced by using BGs to augment the performance of CGMs. In this regard, embodiments of the inventions herein provide methods, including systems and algorithms, for correcting for manufacturing batch variations in sensor parameters in sensor glucose modeling using factory calibration techniques. As shown in FIG. 131, in embodiments, this is achieved by characterizing the performance characteristics of the sensors used to build the glucose estimation algorithm (9620), using, e.g., batch-sampling metrics that become standard metrics (9622), and then, for each sensor batch produced afterwards: (1) determining their equivalent performance characteristics (9624); (2) determining deviations from the standard metrics (9626); and (3) determining correction parameters to be applied to mitigate the effect of the deviation and assign the correction parameters to sensors in the batch as factory calibration for each sensor (9628).

In embodiments, the factory calibration focuses on determining a correction factor for each of three key input signals: 1 kHz real impedance, 1 kHz imaginary impedance, and counter voltage (or Vcntr). In embodiments, the population distributions of the three features are determined by characterizing the output of 1821 sensors worn by 537 subjects. The mean, standard deviation and interquartile variances of each distribution is obtained and provided as reference (or standard) metrics (9622). Similar distribution metrics are obtained for each sensor batch that is to be factory calibrated. The factory calibration procedure, in embodiments, involves calculating for each of the three input signals: (a) the difference between the mean of the batch distribution and the mean of the reference distribution; (b) determining the ratio between the batch distribution standard deviation and the reference distribution standard deviation; (c) determining the difference between the interquartile ranges of the batch and reference distributions; and (d) determining the ratios between the interquartile ranges of the batch and reference distributions. These difference and ratio values are the correction parameters that, when applied to inputs from sensors from the sensor batch, can transform them to their equivalent values in the reference distribution.

In embodiments, the four correction factors obtained from each of the key input signals may be together treated as a four-dimensional index of a bin in a 4-by-4-by-4-by-4 matrix, where each dimension corresponds to each correction factor and the bin boundaries are obtained by evenly dividing the experimentally determined maximum and minimum values of each correction factor. For example, the correction factor quartet of 15:0.89:12:0.93 may become: 2:1:2:3. This means that there are at most 16 different configurations of correction factors that can be assigned to sensor batches, and only sixteen correction equations need to be determined for transforming signals from each sensor batch into their equivalent reference signal value. It should be understood that though the indexing structure used in this illustration was a 4-by-4-by-4-by-4 matrix, other indexing structures with more or fewer dimensions and bins per dimension are also possible.

FIG. 132 shows an embodiment in which various modules (shown as blocks) of an algorithm, in accordance with an embodiment of the invention, are designed to correct for the time-varying change in sensor sensitivity using an optional factory calibration mechanism. Step 1B indicates the placement of the logic implementing the mechanism in the algorithm in relation to other modules (9630). In this embodiment, in a pre-processing step, Step 1A (9632), the factory calibration factors from Step 1B are applied to the input sensor current (Isig), the electrochemical impedance spectroscopy (EIS) values, and/or the counter voltage values (Vcntr) that are input to the four SG calculating units shown as Steps 2A, 2B, 2C, and 2D (9634, 9635, 9636, 9637).

At Block 9639, the plurality of individual (factory calibrated) SG values are fused to generate a final, single (fused) SG value. In Block 9641, diagnostics are performed on the fused SG to detect and, where possible, correct errors before the (corrected) final SG may be displayed (e.g., to a user of the glucose sensor) and/or transmitted (e.g., to a receiving device) to be used for therapy, in Block 9643. Where correction is not possible, however, the fused SG value may be blanked, so that it is not shown to the user and/or not used for therapy. It is noted that, although four SG calculating units are shown in FIG. 132, fewer or more units/models may be used. In addition, in Block 9639, the SG values may be fused using any one or more of the fusion algorithms discussed previously herein.

FIG. 133 shows the logic flow within the optional factory calibration block 9630. When a factory calibration value is obtained, the first step involves determining if the calibration factor is valid (9650). In embodiments, this determination is made by checking to see that the factory calibration value falls within an acceptable range of values. In embodiments, the factory calibration code is designed to have additional properties, e.g., be a multiple of a prime number, such that checking for validity involves checking to see if the encoded number is divisible by a predetermined prime number, and if so, checking to see if the result of that division yields a number within an expected range of values. If valid, the factor is converted into a weight metric that is specific to the features used by the glucose estimation algorithm (9652). In embodiments, the conversion to a weight metric is accomplished by using calibration scales such as those depicted, e.g., in FIGS. 125 and 126. Thus, each of, e.g., Isig, EIS values, and Vcntr will have a respective weight metric associated therewith (see Block 9632 in FIG. 132). Next, for each input sensor feature, the feature is weighted by the respective weight metric (9654), that is, those from block 9652, and the resulting value is clamped to a pre-defined acceptable correction range (9656). In embodiments, acceptable correction ranges are defined so that applying the factory calibration weight metric to the input features does not result in feature values beyond the natural range of the input features, and the result is sent to the one or more glucose estimation modules implemented by the algorithm (9658). For example, the median value of an input feature, in embodiments, was experimentally observed to be 0.52, with a range of 0.4 to 0.6, but SG producing units could work within a range of 0.25 to 0.95. In embodiments, the acceptable correction range may be a multiplication factor between 1.0 and 1.58 to reduce the chance of a calibration producing a feature value outside the device range.

In an embodiment of the invention, the activation sequence of the sensor involves pairing the glucose estimation algorithm with the factory parameters. In another embodiment, the factory parameters are auto-encoded into the sensor's transmitter and automatically activated upon activation of the sensor prior to use.

In one embodiment, the generation of the factory calibration metrics involves analyzing all the input sensor characteristic features to the SG calculation for fitness. From sensor data collected from a plurality of sensors, pairs of points separated by: (a) a single measurement period (e.g., five minutes in this case); (b) a single day; and (c) up to 5 days may be selected and their differences evaluated.

FIG. 134 shows histograms of the differences in sensor values obtained for each of the above-mentioned time periods, where 9661 is the plot for data collected over a period of up to 5 days, 9663 is the plot for data collected over a single day, and 9665 is the plot for data collected for a plurality of single measurements over successive time periods, e.g., every five minutes. The results for this sensor characteristic feature show that the histograms (i.e., plots) all share the same median value. This indicates that the values may originate from a consistent probability distribution and that the feature shows consistent performance and may be a good candidate for use as a factory calibration metric. FIG. 135 shows the corresponding histograms for a sensor characteristic feature whose distributions are not uniform, where 9671 is the plot for data collected over a period of up to 5 days, 9673 is the plot for data collected over a single day, and 9675 is the plot for data collected for a plurality of single measurements over successive time periods. As can be seen, it is unlikely that the values originate from the same probability distribution in this case, such that the feature here would not be a good candidate for use as a factory calibration metric.

In a preferred embodiment of the invention, feature selection is limited to features with acceptable histograms. Each feature may further be put through a perturbation analysis, as shown in FIG. 136. Here, the input sensor signal 9680 may be combined with a noise value 9682 that is derived from a distribution of possible noise values retrospectively observed from signals collected, e.g., from a clinical study. The combined signal 9684, and in parallel to it the original signal, are independently passed through blocks that implement the SG calculation, i.e., the sensor algorithm. The outputs from the two separate blocks are subtracted and the difference 9686 is the observed signal response to input perturbation.

FIG. 137 shows an idealized response to perturbation, while FIG. 138 shows an actual perturbation response plot obtained for an example set of sensor characteristic features. The features are ranked according to the span of the graph below a fixed performance threshold. In a preferred embodiment, the threshold may be set, e.g., at 0.2. The threshold is set at a level that represents the maximum expected range of noise that is expected to be naturally present in the sensing system.

Specifically, FIG. 137 shows the normalized response to perturbation for typical sensor characteristic features used as factory calibration input, including, e.g., signal in (Isig) 9711, Vcntr 9713, and 1 kHz real impedance 9715. It has been discovered that features that are robust to manufacturing variability and, as such, require a relatively lesser degree of tighter controls, tend to have large spans below the threshold 9710. In this regard, they are best suited for use as factory calibration metrics. Thus, in FIG. 137, whereas 1 kHz real impedance 9715, e.g., exhibits less of a need for tighter controls, Isig 9711 exhibits more of a need for tighter controls. FIG. 138 shows an actual set of results of perturbation analysis for determining the best features to be used for factory calibration, including the following features: Isig 9717; 128 Hz real impedance 9719; 1 kHz imaginary impedance 9721; Vcntr 9723; and Isig moving average 9725. In this example, the 1 kHz imaginary impedance is the best feature to use for factory calibration because it displays the least amount of change across the signal change (due to input perturbation) range.

In a preferred embodiment, the means and standard deviations of the best ranked features may be set as the standard metric for the factory calibration. Determining the batch sampling metric involves a similar process as determining the standard metrics. Generating factory calibration data involves determining a mathematical transformation that can modify the histograms of data generated from each batch to make them similar to the histograms of the data used to generate the standard metric. Application of the standard metric involves applying this transformation to the data generated when the sensor is in operation.

In embodiments of the invention, the algorithm may be implemented on existing CGM platforms. An embodiment allows for use with hybrid closed-loop (HCL) systems. Another embodiment allows for use in stand-alone CGM systems. In the former embodiment, the system may have transmitters that communicate with an insulin pump supporting a HCL algorithm via a proprietary radio-frequency protocol. In the latter embodiment, the communication protocol may be, e.g., Bluetooth Low Energy Technology that is supported through a mobile device display application. When supporting an HCL system, the transmitter may include logic to ensure sensor values reliably support insulin dosing.

As has been previously discussed, in a normally operating glucose sensor, measured current, Isig is designed to be proportional to measured glucose concentration (SG), thus Measured Glucose=Calibration Factor×(Measured Current+offset)

and

Calibration Factor=Base Calibration Factor×Baseline Adjustment.

As will be explored further hereinbelow, a theory-based glucose sensor model based on sensor fundamentals can be built piece-by-piece from learnings from in-vitro and in-vivo experimentation with sensors focused on deciphering the components of the base calibration factor, the baseline adjustment and the offset component. In contrast to some of the models based on machine learning methods previously described, the analytical optimization model that results from the piecewise evaluation of the effect of various processes on sensor chemistry and subject physiology is comprehensible, modularized, easier to explain to regulatory bodies and complements models developed through machine learning and other approaches.

The underlying assumption is that the role of input features such as the full suite of real and imaginary impedance values and counter voltage values is to correct for errors from the expected linear glucose/current relationship that is due to physiology, bio-fouling, sensitivity loss, sensor variation and other aberrant processes. Thus, a methodology for estimating the output sensor glucose value of a glucose sensor by analytically optimizing input sensor signals including sensor current, electrochemical impedance spectroscopy measurements, counter voltage and sensor age, measured as time from sensor insertion or another sensor wear milestone, may be described to accurately correct for changes in sensitivity, run-in time, glucose current dips, and other variable sensor wear effects, thereby helping to achieve the goal of improved accuracy and reliability without the need for blood-glucose calibration.

In embodiments, the base calibration factor is the primary estimate of the sensor sensitivity, modeled by medium frequency real impedance input features. Literature indicates that this frequency range may be disproportionately affected by differences in sensor coatings and tissue properties, depending on the specific sensor design. In general, Base Calibration Factor=$c_1 \times \ln(real128) + c_2$, where real128 is the real component of the 128 Hz frequency input and $c_1$ and $c_2$ are experimentally determined calibration coefficients that vary across sensor lots. For example, in one preferred embodiment, $c_1$ may be 3.7 mg/dL/nA/ohm, and $c_2$ may be −26.4 mg/dL/nA.

FIG. 139 shows a schematic of the components of the calibration factor component of embodiments of the analytical optimization model. In a preferred embodiment, this component is comprised of modules that correct for: foreign body response, oxygen, hypoglycemia and day one stabilization.

The foreign body response correction was done through high frequency impedance adjustments, as discovered through analysis of post-explant sensors whose performance before and after implantation were compared. The theory was also based on literature studies of various sensor chemistries. Specifically Foreign body response=$c_1 \times e^{imag1000 \times c_2} + c_3$, where imag1000 is the imaginary 1000 Hz frequency input and $c_1$, $c_2$ and $c_3$ are experimentally determined calibration coefficients. In one preferred embodiment, e.g., $c_1$ may be −1.4, $c_2$ may be 0.008, and, $c_3$ may be 1.3. In embodiments, the maximum indicated adjustment due to foreign body response may be 30%.

The oxygen response adjustment was primarily by changes to the counter voltage values. The rationale for this is that hydrogen peroxide concentration gradient is affected by oxygen gradient and the counter voltage is a proxy for oxygen concentration. Specifically $$\text{Oxygen response} = c_1 \times \text{Vcntr}^2 + c_2 \times \text{Vcntr} + c_3,$$

where Vcntr is the counter voltage input and $c_1$, $c_2$ and $c_3$ are experimentally determined calibration coefficients. In one preferred embodiment, $c_1$ may be 2.0/V, $c_2$ may be 2.0, and $c_3$ may be 2.0V. In embodiments, the maximum adjustment due to foreign body response may be 12%.

Sensor current dips and hypoglycemia correction was driven by adjustments to long term sensor current trends. The rationale for this is that unexpected dips in sensor current (dips not apparent from sensor current trends) may be due to hypoglycemia. Specifically $$\text{Dip adjustment} = c_1 \times e^{\text{IsigTrend} \times c_2} + c_3,$$

where IsigTrend is the long-term sensor current trend input and $c_1$, $c_2$ and $c_3$ are experimentally determined calibration coefficients that vary slightly across sensor lots. In one preferred embodiment, $c_1$ may be 4.68, $c_2$ may be $-0.21$, and $c_3$ may be 0.97. In embodiments, the long-term sensor current trend is variously implemented, e.g., as 6, 12, 18, 24, and 48-hour average sensor current values. In embodiments, the input feature is represented by outputs of Butterworth filtering of sensor current values over, e.g., 24 and 48-hour windows. In embodiments, the maximum adjustment due to current dip response may be 5%.

Upon sensor insertion the sensor is stabilized for wear. As previously discussed, the rate at which a sensor stabilizes is affected by sensor chemistry, insertion location, physiology, and insertion process, amongst other factors. In embodiments of the analytical optimization SG calculation model, the stabilization of the sensor is estimated and corrected for chiefly by the counter voltage input. The rationale is that platinum oxidation and capacitance relationship plays key roles both in first day performance and counter voltage values. Specifically $$\text{Stabilization response} = c_1 \times \text{Vcntr} + c_2,$$

where Vcntr is the counter voltage input and $c_1$ and $c_2$ are experimentally determined calibration coefficients. In one preferred embodiment, e.g., $c_1$ may be 0.48/V, and $c_2$ may be 1.24. The maximum adjustment due to foreign body response was set at 5% in preferred embodiments.

FIG. 140 shows a schematic of the components of the offset adjustment of embodiments of the analytical optimization model. In a preferred embodiment, this component includes two adjustments: for stabilization time and for non-linear sensor response.

The stabilization time adjustment was driven by implant age based on studies of in-vivo data and confirmed through in-vitro studies. Specifically $$\text{Stabilization time adjustment} = c_1 \times e^{\text{age} \times c_2} + c_3,$$

where age is the sensor age, which in a preferred embodiment, is measured from the completion of sensor warm-up. In another embodiment, the sensor age may be measured from sensor insertion. $c_1$, $c_2$ and $c_3$ are experimentally determined calibration coefficients. In one preferred embodiment, $c_1$ may be $-5.4$, $c_2$ may be $-0.50$, and $c_3$ may be $-1.5$ nA. In one embodiment, the value of this term was not found to be limited, though a limit of 50% was imposed.

The non-linear sensor response was driven by sensor current values and sensor age as backed by in-vivo data studies and confirmed from in-vitro observations. Specifically $$\text{Non linear response adjustment} = c_1 + (\text{age} \times c_2 + c_3) \times \text{Isig},$$

where Isig is the sensor current, age is sensor age and $c_1$, $c_2$, and $c_3$ are experimentally determined calibration coefficients. In one preferred embodiment, $c_1$ may be 13.8 nA, $c_2$ may be $-0.1$/day, and $c_3$ may be $-0.7$. As with the stabilization time adjustment, embodiments utilized various measures of sensor age including: time from sensor insertion, time from sensor warm up and time from the completion of sensor calibration. In one embodiment, the sensor current may be filtered sensor current values, with the adjustment limited to values between $-1$ nA and 10 nA.

While the description above refers to particular embodiments of the present inventions, it will be understood that many modifications may be made without departing from the spirit thereof. Additional steps and changes to the order of the algorithms can be made while still performing the key teachings of the present inventions. Thus, the accompanying claims are intended to cover such modifications as would fall within the true scope and spirit of the present inventions. The presently disclosed embodiments are, therefore, to be considered in all respects as illustrative and not restrictive, the scope of the inventions being indicated by the appended claims rather than the foregoing description. All changes that come within the meaning of, and range of, equivalency of the claims are intended to be embraced therein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method for using factory calibration to correct for manufacturing batch variations in one or more sensor parameters of a glucose sensor used for measuring the level of glucose in the body of a user, said sensor including physical sensor electronics, a microcontroller, and a working electrode, the method comprising:
- periodically measuring, by the physical sensor electronics, electrode current (Isig) signal values for the working electrode;
- performing, by the microcontroller, an Electrochemical Impedance Spectroscopy (EIS) procedure to generate values of one or more EIS-related parameters for the working electrode;
- measuring, by the physical sensor electronics, values of counter voltage (Vcntr) for the sensor;
- applying, by said microcontroller, a factory calibration factor to said Isig, EIS parameter, and Vcntr values to generate respective modified Isig, EIS parameter, and Vcntr values;
- based on the modified Isig, EIS parameter, and Vcntr values and a plurality of calibration-free sensor glucose (SG)-predictive models, calculating, by the microcontroller, a respective SG value for each of the SG-predictive models;
- fusing, by the microcontroller, the respective SG values to calculate a single, fused SG value;
- performing, by the microcontroller, error detection diagnostics on said calibrated, fused SG value to determine whether a correctable error exists in the calibrated, fused, SG value;
- correcting, by the microcontroller, said correctable error; and
- displaying a corrected, calibrated, fused SG value to the user.

2. The method of claim 1, wherein, when it is determined that an error in the calibrated, fused SG value is not correctable, the calibrated, fused SG value is blanked to the user.

3. The method of claim 1, wherein said plurality of calibration-free SG-predictive models include at least two of a genetic programming model, an analytical model, a bag of trees model, and a decision tree model.

4. The method of claim 1, wherein said plurality of calibration-free SG-predictive models include a genetic programming model, an analytical model, a bag of trees model, and a decision tree model.

5. The method of claim 1, wherein said factory calibration factor is a correction parameter that mitigates deviations in sensor performance characteristics between sensors of a prior batch and sensors of a subsequent batch.

6. The method of claim 5, wherein said correction parameter is a weighting factor that is multiplied by said Isig, EIS parameter, and Vcntr values.

7. The method of claim 6, wherein said weighting factor has a first value that is applied to the Isig values, a second value that is applied to the EIS parameter values, and a third value that is applied to the Vcntr values.

8. The method of claim 7, wherein each of said first, second, and third values of the weighting factor is determined by using one or more calibration scales.

9. The method of claim 8, wherein said Isig value is weighted by said first value of the weighting factor, said EIS parameter value is weighted by said second value of the weighting factor, and said Vcntr value is weighted by said third value of the weighting factor.

10. The method of claim 9, wherein the each of the weighted Isig value, the weighted EIS parameter value, and the weighted Vcntr value is clamped to respective pre-defined acceptable range.

11. The method of claim 1, wherein said factory calibration factor is determined for each of said Isig, EIS parameter, and Vcntr values based on respective reference values for a previously-manufactured sensor batch.

12. The method of claim 1, wherein said one or more EIS-related parameters includes 1 kHz real impedance.

13. The method of claim 1, wherein said one or more EIS-related parameters includes 1 kHz imaginary impedance.

14. The method of claim 1, further comprising applying, by the microcontroller, a filter to the single, fused SG value.

15. The method of claim 1, wherein the glucose sensor is used in a hybrid closed-loop (HCL) glucose monitoring system.

* * * * *